US011304954B2

(12) United States Patent
Bonner et al.

(10) Patent No.: US 11,304,954 B2
(45) Date of Patent: Apr. 19, 2022

(54) LIPID PRODRUGS OF MYCOPHENOLIC ACID AND USES THEREOF

(71) Applicants: PureTech LYT, Inc., Boston, MA (US); Monash University, Clayton (AU)

(72) Inventors: Daniel Kenneth Bonner, Sharon, MA (US); Ketki Karanam, Newton, MA (US); Sifei Han, Clayton (AU); Luojuan Hu, Clayton (AU); Christopher John Hamilton Porter, Clayton (AU); Tim Quach, Clayton (AU); Rishab R. Shyam, Arlington, MA (US); Jamie Simpson, Chestnut Hill, MA (US); Natalie Trevaskis, Clayton (AU)

(73) Assignees: PureTech LYT, Inc., Boston, MA (US); Monash University, Clayton (AU)

( * ) Notice: Subject to any disclaimer, the term of this patent is extended or adjusted under 35 U.S.C. 154(b) by 0 days.

(21) Appl. No.: 16/955,162

(22) PCT Filed: Dec. 19, 2018

(86) PCT No.: PCT/US2018/066585
§ 371 (c)(1),
(2) Date: Jun. 18, 2020

(87) PCT Pub. No.: WO2019/126378
PCT Pub. Date: Jun. 27, 2019

(65) Prior Publication Data
US 2020/0390777 A1    Dec. 17, 2020

Related U.S. Application Data

(60) Provisional application No. 62/768,583, filed on Nov. 16, 2018, provisional application No. 62/724,274, filed on Aug. 29, 2018, provisional application No. 62/607,749, filed on Dec. 19, 2017.

(51) Int. Cl.
C07D 413/12 (2006.01)
A61K 31/5377 (2006.01)
A61K 47/54 (2017.01)
A61P 37/06 (2006.01)

(52) U.S. Cl.
CPC ........ *A61K 31/5377* (2013.01); *A61K 47/542* (2017.08); *A61P 37/06* (2018.01); *C07D 413/12* (2013.01)

(58) Field of Classification Search
CPC .................................................. C07D 413/12
See application file for complete search history.

(56) References Cited

U.S. PATENT DOCUMENTS

| | | | |
|---|---|---|---|
| 4,958,046 A | 9/1990 | Rosenberg et al. |
| 5,962,440 A | 10/1999 | Sulsky |
| 6,013,665 A | 1/2000 | DeMichele et al. |
| 6,054,591 A | 4/2000 | Aono et al. |
| 6,417,191 B1 | 7/2002 | Barry et al. |
| 6,552,065 B2 | 4/2003 | Remiszewski et al. |
| 7,390,799 B2 | 6/2008 | Bruncko et al. |
| 7,557,210 B2 | 7/2009 | Singh et al. |
| 7,635,690 B2 | 12/2009 | Schinazi et al. |
| 8,138,347 B2 | 3/2012 | Knight et al. |
| 8,338,439 B2 | 12/2012 | Singh et al. |
| 8,455,510 B2 | 6/2013 | Nan et al. |
| 2007/0191415 A1 | 8/2007 | Kumar et al. |
| 2009/0023805 A1 | 1/2009 | Marrast et al. |
| 2009/0297533 A1 | 12/2009 | Lighter et al. |
| 2010/0298560 A1 | 11/2010 | Choi et al. |
| 2011/0213028 A1 | 9/2011 | Milne et al. |
| 2011/0243884 A1 | 10/2011 | O'Shea et al. |
| 2014/0081016 A1 | 3/2014 | Felzmann et al. |
| 2014/0234418 A1 | 8/2014 | Coulter et al. |
| 2014/0328793 A1 | 11/2014 | Gavegnano et al. |
| 2017/0326103 A1 | 11/2017 | Porter et al. |
| 2018/0243425 A1 | 8/2018 | Forter et al. |
| 2018/0258094 A1 | 9/2018 | Long et al. |
| 2018/0318318 A1 | 11/2018 | Wang et al. |
| 2019/0105299 A1 | 4/2019 | Porter et al. |

FOREIGN PATENT DOCUMENTS

| | | |
|---|---|---|
| JP | 200312691 A | 1/2003 |
| WO | WO-1994009010 A1 | 4/1994 |
| WO | WO-2001042246 A2 | 6/2001 |

(Continued)

OTHER PUBLICATIONS

Alouane et al., "Self-immolative spacers: kinetic aspects, structure-property relationships, and applications," Angew. Chem. Int. Ed. Engl. 2015; 54(26):7492-509.

Alouane et al., "Self-immolative spacers: kinetic aspects, structure-property relationships, and applications," Supporting Information, Angew. Chem. Int. Ed. Engl. 2015;(10 pages).

Amory et al., "Oral testosterone-triglyceride conjugate in rabbits: single-dose pharmacokinetics and comparison with oral testosterone undecanoate," J. Androl. 2003;24(5):716-20.

Amsberry et al., "Amine prodrugs which utilize hydroxy amide lactonization. II. A potential esterase-sensitive amide prodrug," Pharm. Res. 1991; 8(4):455-61.

(Continued)

*Primary Examiner* — Paul V Ward
(74) *Attorney, Agent, or Firm* — Womble Bond Dickinson (US) LLP; Danielle L. Herritt; Mark R. Deluca

(57) ABSTRACT

The present invention provides lymphatic system-directing lipid prodrugs, pharmaceutical compositions thereof, methods of producing such prodrugs and compositions, and methods of improving the bioavailability or other properties of a therapeutic agent that comprises part of the lipid prodrug. The present invention also provides methods of treating a disease, disorder, or condition such as those disclosed herein, comprising administering to a patient in need thereof a disclosed lipid prodrug or a pharmaceutical composition thereof.

20 Claims, 18 Drawing Sheets

(56) References Cited

FOREIGN PATENT DOCUMENTS

| | | |
|---|---|---|
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005112919 A2 | 12/2005 |
| WO | WO-2005113554 A2 | 12/2005 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008048611 A1 | 4/2008 |
| WO | WO-2008109943 A1 | 9/2008 |
| WO | WO-2008118802 A1 | 10/2008 |
| WO | WO-2009114512 A1 | 9/2009 |
| WO | WO-2009143295 A1 | 11/2009 |
| WO | WO-2011051967 A2 | 5/2011 |
| WO | WO-2011090760 A1 | 7/2011 |
| WO | WO-2011120044 A1 | 9/2011 |
| WO | WO-2015116904 A1 | 8/2015 |
| WO | WO-2016023082 A1 | 2/2016 |
| WO | WO-2017041139 A1 | 3/2017 |
| WO | WO-2018237282 A1 | 12/2018 |
| WO | WO-2019046478 A1 | 3/2019 |
| WO | WO-2019046491 A1 | 3/2019 |

OTHER PUBLICATIONS

Andréen et al., "Sex steroid induced negative mood may be explained by the paradoxical effect mediated by GABAA modulators," Psychoneuroendocrinology. 2009;34(8):1121-32.

Bitran et al., "Anxiolytic effect of progesterone is mediated by the neurosteroid allopregnanolone at brain GABAA receptors," J. Neuroendocrinol. 1995;7(3):171-7.

Blencowe et al., "Self-immolative linkers in polymeric delivery systems," Polym. Chem. 2011, 2:773-790.

Bourgeois et al., "Application of thermal analysis to the study of lipidic prodrug incorporation into nanocarriers," J.Therm. Anal. Calorim. 2009;98:65-71.

Braile-Fabris et al., "Controlled clinical trial of IV cyclophosphamide versus IV methylprednisolone in severe neurological manifestations in systemic lupus erythematosus," Ann. Rheum. Dis. 2005;64(4):620-25.

Brand et al., "Collagen-induced arthritis," Nat. Protoc. 2007;2(5):1269-75.

Charette et al., "Practical and Highly Regio- and Stereoselective Synthesis of 2-Substituted Dihydropyridines and Piperidines:? Application to the Synthesis of (−)-Coniine," J. Am. Chem. Soc. 2001; 123(47):11829-11830.

Chowdhury and Ghosh, "Highly Regio- and Enantioselective Organocatalytic Conjugate Addition of Alkyl Methyl Ketones to a ?-Silylmethylene Malonate," Org. Lett. 2009;11(15):3270-3273.

Codelli et al., "Second-Generation Difluorinated Cyclooctynes for Copper-Free Click Chemistry," J. Am. Chem. Soc. 2008; 130(34):11486-11493.

Coutinho and Chapman, "The anti-inflamatory and immunosuppressive effects of glucocorticoids, recent developments and mechanistic insights," Mol. Cell. Endrocrinol. 2011;335(1):2-13.

Cyr et al., "Recent progress on nuclear receptor ROR? modulators," Bioorg. Med. Chem. Lett. 2016; 26(18):4387-4393.

D'yakova et al., "Lymphotropic prodrugs based on 2',3'-didehydro-3'-deoxythymidine. Synthesis and sensitivity to hydrolysis," Russian Journal of Bioorganic Chemistry. 2011;47(10):1588-1593.

Deverre et al., "In-vitro evaluation of filaricidal activity of GABA and 1,3-dipalmitoyl-2-(4-aminobutyryl)glycerol HCI: a diglyceride prodrug," J. Pharm. Pharmacol. 1989; 41(3):191-3.

DeWolf and Sykes, "Alloimmune T cells in transplantation ," J. Clin. Invest. 2017;127(7):2473-2481.

Dommerholt et al., "Readily accessible bicyclononynes for bioorthogonal labeling and three-dimensional imaging of living cells," Angew. Chem. Int. Ed. Engl. 2010; 49(49):9422-5.

Edwards et al., "Animal models for the study of intestinal lymphatic drug transport," Adv. Drug. Deliv. Rev. 2001;50(1-2):45-60.

Freitag et al., "Gliadin-primed CD4+CD45RBlowCD25− T cells drive gluten-dependent small intestinal damage after adoptive transfer into lymphopenic mice," Gut. 2009;58(12):1597-605.

Frye and Duncan, "Progesterone metabolites, effective at the GABAA receptor complex, attenuate pain sensitivity in rats," Brain Res. 1994:643(1-2):194-203.

Frye and Waif, "Changes in progesterone metabolites in the hippocampus can modulate open field and forced swim test behavior of proestrous rats," Horm. Behav. 2002;41(3):306-15.

Garzon-Aburbeh et al., "1,3-Dipalmitoylglycerol ester of chlorambucil as a lymphotropic, orally administrable antineoplastic agent," J. Med. Chem. 1983; 26(8):1200-1203.

Garzon-Aburbeh et al., "A lymphotropic prodrug of L-dopa: synthesis, pharmacological properties and pharmacokinetic behavior of 1,3-dihexadecanoyl-2-[(S)-2-amino-3-(3,4-dihydroxyphenyl)propanoyl]propane-1,2,3-triol," J. Med. Chem. 1986; 29(5):687-691.

Goodin, "Glucocorticoid treatment of multiple sclerosis," Handb. Clin. Neurol. 2014;122:455-64.

Gossauer and Kühne, "Synthesen von Gallenfarbstoffen, V. Stereospezifische Totalsynthesen diastereomerer Mesobilirhodine und Isomesobilirhodine," Justus Liebigs Annalender Chemie. 1977;4:664-686.

Grainge et al., "Case series reporting the effectiveness of mycophenolate mofetil in treatment-resistant asthma," Eur. Respir. J. 2013;42(4):1134-7.

Griffin et al., "Niemann-Pick type C disease involves disrupted neurosteroidogenesis and responds to allopregnanolone," Nat. Med. 2004;10(7):704-11.

Guo et al., "Rheumatoid arthritis: pathological mechanisms and modern pharmacologic therapies," Bone Res. 2018;6:15.

Gupta et al., "Dexamethasone cyclophosphamide pulse therapy in systemic lupus erythematosus: a case report," J. Dermatolg. Treat. 2009;20(1):55-8.

Han et al., "Lymphatic Transport and Lymphocyte Targeting of a Triglyceride Mimetic Prodrug Is Enhanced in a Large Animal Model: Studies in Greyhound Dogs," Mol. Pharm. 2016; 13(10):3351-3361.

Han et al., "Targeted delivery of a model immunomodulator to the lymphatic system: comparison of alkyl ester versus triglyceride mimetic lipid prodrug strategies," J. Control Release. 2014; 177:1-10.

Hu et al., "Glyceride?Mimetic Prodrugs Incorporating Self? Immolative Spacers Promote Lymphatic Transport, Avoid First? Pass Metabolism, and Enhance Oral Bioavailability," Angew. Chem. Int. Ed. Engl. 2016;55(44):13700-13705.

Huvelle et al., "Syntheses and kinetic studies of cyclisation-based self-immolative spacers," Org. Biomol. Chem. 2017; 15(16):3435-3443.

Irwin and Diaz Brinton, "Allopregnanolone as regenerative therapeutic for Alzheimer's disease: translational development and clinical promise," Prog. Neurobiol. 2014;113:40-55.

Irwin et al., "Frontiers in therapeutic development of allopregnanolone for Alzheimer's disease and other neurological disorders," Front. Cell. Neurosci. 2014;8:203.

Iwaszkiewicz-Grzes et al., "Synthesis and biological activity of mycophenolic acid-amino acid derivatives," Eur. J. Med. Chem. 2013;69:863-71.

Janossy and Greaves, "Lymphocyte activation: I. Response of T and B lymphocytes to phytomitogens," Clin. Exp. Immunol. 1971;9(4):483-498.

(56) References Cited

OTHER PUBLICATIONS

Jeong et al., "Dose optimization of tacrolimus for improving survival time of PEGylated islets in a rat-to-mouse xenograft model," Macromolecular Research. 2016;24(12):1047-1054.
Jew et al., "Asymmetric synthesis of (R)-(+)-etomoxir," Tetrahedron: Asymmetry. 1997; 8(8):1187-1192.
Jewett et al., "Rapid Cu-free click chemistry with readily synthesized biarylazacyclooctynones," J. Am. Chem. Soc. 2010; 132(11):3688-90.
Kai et al., "Structure-activity relationship study of flowering-inducer FN against Lemna paucicostata," Tetrahedron. 2008; 64(28):6760-6769.
Kanes et al., "Brexanolone (SAGE-547 injection) in post-partum depression: a randomised controlled trial," Lancet. 2017;390(10093):480-489.
Kihel et al., "Synthesis and evaluation of the anti-inflammatory effects of niflumic acid lipophilic prodrugs in brain edema," Arzneimittelforschung. 1996;46(11):1040-4.
Kim et al., "Convenient Synthesis of Electron Deficient Dienes via Pd(0) Catalyzed Coupling," Synlett. 1998; 1998(10):1059-1060.
Kim et al., "The Anti-Inflammatory Effects of Oral-Formulated Tacrolimus in Mice with Experimental Autoimmune Encephalomyelitis," J. Korean Med. Sci. 2017;32(9):1502-1507.
Koboziev et al., "Gut-associated lymphoid tissue, T cell trafficking, and chronic intestinal inflammation," Ann. NY. Acad. Sci. 2010;1207(Suppl 1):E86-E93.
Kratz et al., "Prodrug strategies in anticancer chemotherapy," ChemMedChem. 2008; 3(1):20-53.
Lalanne et al., "Metabolism evaluation of biomimetic prodrugs by in vitro models and mass spectrometry," Int. J. Pharm. 2009;379(2):235-43.
Lalanne et al., "Synthesis and biological evaluation of two glycerolipidic prodrugs of didanosine for direct lymphatic delivery against HIV," Bioorg. Med. Chem. Lett. 2007;17(8):2237-40.
Levine and Raines, "Trimethyl lock: a trigger for molecular release in chemistry, biology, and pharmacology," Chem. Sci. 2012; 3(8):2412-2420.
Li et al., "Mycophenolate mofetil or tacrolimus compared with intravenous cyclophosphamide in the induction treatment for active lupus nephritis," Nephrol. Dial. Transplant. 2012;27(4):1467-72.
Ling and Luster, "Allergen-Specific CD4+ T Cells in Human Asthma," Ann. Am. Thorac. Soc. 2016;13(Suppl 1):S25-S30.
Ling et al., C1q restrains autoimmunity and viral infection by regulating CD8+ T cell metabolism; Science. 2018;360(6388):558-563.
Liénard et al., "Structural basis for the broad-spectrum inhibition of metallo-beta-lactamases by thiols," Org. Biomol. Chem. 2008;6(13):2282-94.
Loiseau et al., "Lymphotropic antifilarial agents derived from closantel and chlorambucil," Int. J. Parasitol. 1997;27(4):443-7.
Lonshakov et al., "Synthesis and properties of 3?-azido-3?-deoxythymidine derivatives of glycerolipids," Pharm. Chem. J. 2011;44(10):557-563.
Lui et al., "Effect of mycophenolate mofetil on severity of nephritis and nitric oxide production in lupus-prone MRL/lpr mice," Lupus. 2002;11(7):411-8.
Lv et al., "Mycophenolate Mofetil Modulates Differentiation of Th1/Th2 and the Secretion of Cytokines in an Active Crohn's Disease Mouse Model," Int. J. Mol. Sci. 2015;16(11):26654-66.
Maria and Davidson, "Emerging areas for therapeutic discovery in SLE," Curr. Opin. Immunol. 2018;55:1-8.
Mattarei et al., "Novel lipid-mimetic prodrugs delivering active compounds to adipose tissue," Eur. J. Med. Chem. 2017;135:77-88.
Meliambro et al., "Therapy for Proliferative Lupus Nephritis," Rheum. Dis. Clin. North Am. 2018;44(4):545-560.
Mergen et al., "Antiepileptic activity of 1,3-dihexadecanoylamino-2-valproyl-propan-2-ol, a prodrug of valproic acid endowed with a tropism for the central nervous system," J. Pharm. Pharmacol. 1991; 43(11):815-6.
Michel et al., "Mycophenolate mofetil in multiple sclerosis: a multicentre retrospective study on 344 patients," J. Neurol. Neurosurg. Psychiatry. 2014;85(3):279-83.
Miller et al., "Experimental autoimmune encephalomyelitis in the mouse," Curr. Protoc. Immunol. 2007;Chapter 15:Unit 15.1.
Minard-Colin et al., "Lymphoma depletion during CD20 immunotherapy in mice is mediated by macrophage Fc?RI, Fc?RIII, and Fc?RIV," Blood. 2008;112(4):1205-1213.
Miyamoto et al., "A novel prodrug strategy for extremely hydrophobic agents: conjugation to symmetrically branched glycerol trimer improves pharmacological and pharmacokinetic properties of fenofibrate," Mol. Pharm. 2013;10(7):2723-9.
Mok, "Mycophenolate mofetil for lupus nephritis: an update," Expert Rev. Clin. Immunol. 2015;11(12):1353-64.
Nakajima, et al., "Effectiveness of tacrolimus in comparison with methotrexate or biologies in propensity score-matched patients with rheumatoid arthritis," Mod. Rheumatol. 2016;26(6):836-843.
Nash et al., "Phase 3 study comparing methotrexate and tacrolimus with methotrexate and cyclosporine for prophylaxis of acute graft-versus-host disease after marrow transplantation from unrelated donors," Blood. 2000;96:2062-2068.
Negi and Das, "CNS: Not an immunoprivilaged site anymore but a virtual secondary lymphoid organ," Int. Rev.Immunol. 2018;37(1):57-68.
Nieschlag et al., "Testosterone replacement therapy: current trends and future directions," Hum. Reprod. Update. 2004;10(5):409-19.
Ning et al., "Visualizing metabolically labeled glycoconjugates of living cells by copper-free and fast huisgen cycloadditions," Angew. Chem. Int. Ed. Engl. 2008; 47(12):2253-5.
Okayama et al., "Mast cells are involved in the pathogenesis of indomethacin-induced rat enteritis," J. Gastroenterol. 2009;44(Suppl 19):35-9.
Osborne et al., "Lower allopregnanolone during pregnancy predicts postpartum depression: An exploratory study," Psychoneuroendocrinology. 2017;79:116-121.
Pallet et al., "Impact of Immunosuppressive Drugs on the Metabolism of T Cells ," Int. Rev. Cell. Mol. Biol. 2018;341:169-200.
Paris et al., "Glycerides as prodrugs. 1. Synthesis and antiinflammatory activity of 1,3-bis(alkanoyl)-2-(O-acetylsalicyloyl)glycerides (aspirin triglycerides).," J. Med. Chem. 1979; 22(6):683-7.
Paris et al., "Glycerides as prodrugs. 2. 1,3-Dialkanoyl-2-(2-methyl-4-oxo-1,3-benzodioxan-2-yl)glycerides (cyclic aspirin triglycerides) as antiinflammatory agents," J. Med. Chem. 1980;23(1):79-82.
Paris et al., "Glycerides as prodrugs. 3. Synthesis and antiinflammatory activity of [1-(p-chlorobenzoyl)-5-methoxy-2-methylindole-3-acetyl]glycerides (indomethacin glycerides)," J. Med. Chem. 1980;23(1):9-13.
PCT International Search Report and Written Opinion from PCT/AU2015/050460 dated Oct. 15, 2015.
PCT International Search Report and Written Opinion from PCT/AU2016/050845 dated Oct. 27, 2016.
PCT International Search Report and Written Opinion from PCT/US2018/048642 dated Dec. 11, 2018.
PCT International Search Report and Written Opinion from PCT/US2018/066580 dated Apr. 24, 2019.
PCT International Search Report and Written Opinion from PCT/US2018/066585 dated Apr. 30, 2019.
PCT International Search Report and Written Opinion from PCT/US2019/044877 dated Oct. 24, 2019.
PCT International Search Report and Written Opinion from PCT/US2020/020387 dated Jun. 24, 2020.
PCT International Search Report and Written Opinion from PCT/US2020/020398 dated Jul. 20, 2020.
PCT International Search Report and Written Opinion from PCT/US2020/020433 dated Jun. 26, 2020.
Perché et al., "Prenatal testosterone treatment potentiates the aggression-inhibiting effect of the neurosteroid dehydroepiandrosterone in female mice," Agress. Behav. 2001;27(2):130-8.
Pesu et al., "Jak3, severe combined immunodeficiency, and a new class of immunosuppressive drugs," Immunol. Rev. 2005;203:127-42.

(56) References Cited

OTHER PUBLICATIONS

Ple et al., "Natural killer cells accumulate in lung-draining lymph nodes and regulate airway eosinophilia in a murine model of asthma," Scand. J. Immunol. 2010;72(2):118-27.
Pond and Tozer, "First-pass elimination. Basic concepts and clinical consequences," Clin. Pharmacokinet. 1984;9(1):1-25.
Pouton, "Formulation of poorly water-soluble drugs for oral administration: physicochemical and physiological issues and the lipid formulation classification system," Eur. J. Pharm. Sci. 2006; 29(3-4):278-87.
Pouton, "Lipid formulations for oral administration of drugs: non-emulsifying, self-emulsifying and 'self-microemulsifying' drug delivery systems," Eur. J. Pharm. Sci. 2000; 11(Suppl 2):S93-8.
Powell et al., "The immunomodulatory drugs cyclosporin A, mycophenolate mofetil, and sirolimus (rapamycin) inhibit allergen-induced proliferation and IL-5 production by PBMCs from atopic asthmatic patients," J. Allergy. Clin. Immunol. 2001;108(6):915-7.
Pubmed Compound Summary for CID 132121512, '1-O-[3R,5S,8S,9S,10S,13S,14S,17S)-17-Acetyl-10,13-dimethyl-11-oxo-1,2,3,4,5,6,7,8,9,12,14,15,16,17-tetradecahydrocyclopenta[a]phenanthren-3-yl] 3-O-[1,3-di(hexadecanoyloxy)propan-2-yl]propanedioate', U.S. National Library of Medicine, Jan. 29, 2018 (https://pubchem.ncbi.nlm.nih.gov/compound/132131512).
Renna et al., "Optimization of the treatment with immunosuppressants and biologics in inflammatory bowel disease," World J. Gastroenterol. 2014;20(29):9675-9690.
Rodriguez-Lago et al., "Previous exposure to biologies and C-reactive protein are associated with the response to tacrolimus in inflammatory bowel disease," Rev. Esp. Enferm. Dig. 2016;108(9):550-7.
Rogawski et al., "Neuroactive steroids for the treatment of status epilepticus," Epilepsia. 2013;54(Suppl 6):93-8.
Rupprecht, "Neuroactive steroids: mechanisms of action and neuropsychopharmacological properties," Psychoneuroendocrinology. 2003;20(2):139-68.
Sagiv-Barfi et al., "Ibrutinib enhances the antitumor immune response induced by intratumoral injection of a TLR9 ligand in mouse lymphoma," Blood. 2015;125(13):2079-86.
Schüle et al., "The role of allopregnanolone in depression and anxiety," Prog. Neurobiol. 2014;113:79-87.
Scriba et al., "Bioavailability of Phenytoin Following Oral Administration of Phenytoin-lipid Conjugates to Rats," J. Pharm. Pharmacol. 1995; 47(11):945-948.
Scriba, "Synthesis and in vitro degradation of testosterone-lipid conjugates," Arch. Pharm. (Weinheim). 1995; 328(3):271-6.
Shastina et al., "Synthesis, properties, and Anti-HIV activity of new lipophilic 3'-azido-3'-deoxythymidine conjugates containing functional phosphoric linkages," Russian Journal of Bioorganic Chemistry. 2013;39:161-169.
Siebert et al., "New Analogues of Mycophenolic Acid," Mini Rev. Med. Chem. 2017;17(9):734-745.
Silverman, "Chapter 8—Prodrugs and Drug Delivery Systems," in The Organic Chemistry of Drug Design and Drug Action (Second Edition), 2004 (pp. 497-557, 520-525).
Silverman, "Chapter 9—Prodrugs and Drug Delivery Systems," in The Organic Chemistry of Drug Design and Drug Action (Third Edition), 2014 (pp. 423-486).
Skanji et al., "A new nanomedicine based on didanosine glycerolipidic prodrug enhances the long term accumulation of drug in a HIV sanctuary," Int.J. Pharm. 2011;414(1-2):285-97.
Smith and Cooper, "Mycophenolate mofetil therapy in the management of inflammatory bowel disease—a retrospective case series and review," J. Crohns Colitis. 2014;8(8):890-7.
Smith et al., "Modular assembly of macrocyclic organo-peptide hybrids using synthetic and genetically encoded precursors," Angew. Chem. Int. Ed. Engl. 2011;50(22):5075-80.
Sobczak, "Synthesis and characterization of polyester conjugates of ciprofloxacin," Eur. J. Med. Chem. 2010;45(9):3844-9.
Stadnyk et al., "Neutrophil migration into indomethacin induced rat small intestinal injury is CD11a/CD18 and CD11b/CD18 co-dependent," Gut. 2002;50(5):629-635.
Stump et al., "Lymphatic Changes in Respiratory Diseases: More than Just Remodeling of the Lung?" Am. J. Respir. Cell Mol. Biol. 2017;57(3):272-279.
Subba Reddy et al., "A Concise and Convergent Total Synthesis of Two Novel Cytotoxic Hydroquinones, Lanneaquinol and (R)-2'-Hydroxylanneaquinol," Helv. Chim. Acta. 2013; 96(10):1983-1990.
Sugihara et al., "Studies on intestinal lymphatic absorption of drugs. I. Lymphatic absorption of alkyl ester derivatives and alpha-monoglyceride derivatives of drugs," J. Pharmacobiodyn. 1988; 11(5):369-76.
Sugihara et al., "Studies on intestinal lymphatic absorption of drugs. II. Glyceride prodrugs for improving lymphatic absorption of naproxen and nicotinic acid," J. Pharmacobiodyn. 1988;11(8):555-62.
Takada et al., "Conversion of a novel 5-fluorouracil (5-FU) derivative to 5-FU in rats," Res. Commun. Chem. Pathol. Pharmacol. 1983;40(1):99-108.
Takagi et al., "The synthesis of enantiomerically pure novel liquid crystal compounds containing the bis(trifluoromethyl)alkanediol moiety," Tetrahedron Asymmetry. 2004;15(17):2591-2594.
Tan and Lawrence, "Use of mycophenolate mofetil in inflammatory bowel disease," World J. Gastroenterol. 2009;15(13):1594-1599.
Tanaka et al., "Structure of FK506, a novel immunosuppressant isolated from Streptomyces," J. Am. Chem. Soc. 1987;109(16):5031-5033.
Taniguchi et al., "A Case of Severe Bronchial Asthma Controlled with Tacrolimus," J. Allergy (Cairo). 2011;201:479129.
Taylor and Ryan, "Understanding mechanisms of hypertension in systemic lupus erythematosus," Ther. Adv. Cardiovasc. Dis. 2017;11(1):20-32.
Tohda et al., "Establishment of a novel B-cell lymphoma cell line with suppressed growth by gamma-secretase inhibitors," Leuk. Res. 2006;30(11):1385-90.
Tranoy-Opalinski et al., "Design of self-immolative linkers for tumour-activated prodrug therapy," Anticancer Agents Med. Chem. 2008;8(6):618-37.
Trevaskis et al., "Bile increases intestinal lymphatic drug transport in the fasted rat," Pharm. Res. 2005;22(11):1863-1870.
Trevaskis et al., "From sewer to saviour—targeting the lymphatic system to promote drug exposure and activity," Nature Review Drug Discovery. 2015;14:781-803.
Van Bruggen et al., "Attenuation of murine lupus nephritis by mycophenolate mofetil," J. Am. Soc. Nephrol. 1998;9(8):1407-15.
Van Dieren et al., "Local application of tacrolimus in distal colitis: feasible and safe," Inflamm. Bowel Dis. 2009;15(2):193-8.
Wagner et al., "Selective epimerization and skeletal resection in the ascomycin framework: A study of the biological consequences of lactam rotamer selection," Tetrahedron. 1996;52(29):9643-9654.
Warren et al., "Evaluation of the Structural Determinants of Polymeric Precipitation Inhibitors Using Solvent Shift Methods and Principle Component Analysis," Mol. Pharmaceutics. 2013;10(8):2823-2848.
Weyand and Goronzy, "Immunometabolism in early and late stages of rheumatoid arthritis," Nat. Rev. Rheumatol. 2017;13(5):291-301.
Wiebe and Kavaliers, "Analgesic effects of the putative FSH-suppressing gonadal steroid, 3 alpha-hydroxy-4-pregnen-20-one: possible modes of action," Brain Res. 1988;461(1):150-7.
Wirtz et al., "Chemically induced mouse models of acute and chronic intestinal inflammation," Nat. Protoc. 2017;12(7):1295-1309.
Wittman et al., "Synthesis and antitumor activity of novel paclitaxel-chlorambucil hybrids," Bioorg. Med. Chem. Lett. 2001;11(6):811-814.
Wolbers et al., "Viability study of HL60 cells in contact with commonly used microchip materials," Electrophoresis. 2006;27(24):5073-80.
Young and Kerr, "Total Synthesis of (+)-Nakadomarin A," J. Am. Chem. Soc. 2007;129(5):1465-1469.

(56) References Cited

OTHER PUBLICATIONS

Zgair et al., "Oral administration of cannabis with lipids leads to high levels of cannabinoids in the intestinal lymphatic system and prominent immunomodulation," Scientific Report. 2017;7(14542):1-2.

Mean ± range: 0.3 ± 0.1%

Mean ± SD 11.9 ± 6.7%

Mean ± SD: 43.2 ± 17.5%

Mean ± SD: 6.8 ± 3.4%

LIPID PRODRUGS OF MYCOPHENOLIC ACID AND USES THEREOF

CROSS-REFERENCE TO RELATED APPLICATIONS

This application is a National Phase Application of International Application no. PCT/US2018/066585 filed on Dec. 19, 2018, which claims the benefit of U.S. Provisional Patent Application No. 62/607,749, filed Dec. 19, 2017; U.S. Provisional Patent Application No. 62/724,274, filed Aug. 29, 2018; and U.S. Provisional Patent Application No. 62/768,583, filed Nov. 16, 2018; the entire contents of each of which is hereby incorporated by reference.

TECHNICAL FIELD

The present invention relates to compounds in the form of prodrugs, in particular, compounds that promote transport of a pharmaceutical agent to the lymphatic system and subsequently enhance release of the parent drug. The present invention also relates to compositions and methods of using such prodrugs.

BACKGROUND OF THE INVENTION

Mycophenolic acid (MPA) is an antibiotic agent with immunosuppressive and antiproliferative properties, selectively active on immune cells. MPA is a potent inhibitor of inosine-5'-monophosphate dehydrogenase (IMPDH), an enzyme essential to the de novo synthesis of guanosine-5'-monophosphate (GMP) from inosine-5'-monophosphate (IMP). IMPDH inhibition particularly affects lymphocytes, since they rely almost exclusively on de novo purine synthesis of purines, as opposed to salvage pathways employed by other cell types. Thus, use of mycophenolic acid leads to a relatively selective inhibition of DNA replication in T- and B-lymphocytes, consequently suppressing proliferation, priming and activation. Mycophenolic acid has also been shown to inhibit antibody formation by B-lymphocytes and is thought to prevent the glycosylation of lymphocyte and monocyte glycoproteins important for adhesion to endothelial cells, and as such may inhibit recruitment of lymphocytes and monocytes to inflammation sites and to sites of graft rejection.

MPA is widely used as an immunosuppressive drug for the prevention of acute and chronic transplant rejection, often in combination with calcineurin inhibitors such as tacrolimus. It is also used off label in inflammatory autoimmune disorders, such as lupus erythematosus and lupus nephritis. Moreover, MPA has the potential to be applied to other disorders characterized by excessive inflammation. However, MPA and its derivatives, mycophenolate mofetil and mycophenolate sodium, have significant side effects (Siebert et al., New Analogues of Mycophenolic Acid; Mini-Reviews in Medicinal Chemistry, 2017, 17, 734-745). Undesired effects of immunosuppressive drugs are related to the consequences of immunodeficiency and to the toxicity to other tissues (Pallet et al., Impact of Immunosuppressive Drugs on the Metabolism of T Cells; Int Rev Cell Mol Biol. 2018; 341:169-200). For MPA, side effects include gastrointestinal, vomiting, abdominal pain, diarrhea, and leucopenia. Moreover, the intensity of immunosuppression (rather than MPA itself) can lead to opportunistic infection (BK virus nephropathy, CMV or EBV reactivations) and cancer (e.g., posttransplantation lymphoproliferative disease or cutaneous neoplasia).

These adverse effects are an especially important consideration in cases where an immunosuppression strategy is used to induce remission and then maintenance immunosuppression is continued for several years to avoid relapses, e.g., as in the treatment of autoimmune diseases, such as systemic lupus erythematosus. Prevention of allograft rejection is also based on the use of induction strategy followed by a long-term maintenance therapy. These drawbacks in vivo limit the use of these compounds as pharmaceuticals. Therefore, there is still a need for forms of MPA, which maintain efficacy, while being more tolerable over time.

The lymphatic system consists of a specialized network of vessels, nodes and lymphoid tissues that are distributed throughout the body in close proximity to the vascular system. The lymphatic system plays a number of key roles in immune response, fluid balance, nutrient absorption, lipid homeostasis, and tumor metastasis. Due to the unique anatomical and physiological characteristics of the lymphatic system, targeted drug delivery to and through the lymphatic system has been suggested as a means to improve both pharmacokinetic and pharmacodynamic profiles.

Lymphatic drug transport has the potential to enhance oral bioavailability through avoidance of first pass metabolism, to alter systemic drug disposition, and to enhance efficacy against lymph or lymphocyte mediated pathologies such as lymphoma, leukemia, lymphatic tumor metastasis, autoimmune disease, lymph resident infections and transplant rejection. In order for drugs to access the intestinal lymph, they must first associate with intestinal lymph lipoproteins that are assembled in intestinal absorptive cells (enterocytes) in response to lipid absorption. Association with these lipoproteins subsequently promotes drug transport into the lymph since their size precludes ready diffusion across the vascular endothelium lining the blood capillaries that drain the small intestine. Instead, these large colloidal structures enter the lymphatic capillaries since the lymphatic endothelium is considerably more permeable than that of the vascular endothelium.

Historically, drugs with high lymphatic transport have been highly lipophilic in order to promote physical association with lipoproteins (usually, but not exclusively, log D>5 and solubility in long chain triglyceride of >50 mg/g). Therefore, highly lipophilic analogues of drugs have been envisaged as one way to promote lymphatic drug transport. However, chemical modification of a parent drug can result in a reduction in potency and, in many cases, significant increases in lipophilicity have been correlated with increases in toxicity.

Compounds in the form of lipophilic prodrugs provide a means to temporarily increase lipophilicity and lipoprotein affinity of a pharmaceutical compound, thereby increasing lymphatic targeting. Having been transported via the lymphatic system, the prodrug is cleaved, thereby releasing the parent drug in order to be active at its target site.

Lipophilic esters of drugs have been explored as more bioavailable versions of existing drugs. For example, testosterone undecanoate is a marketed drug for hypogonadism and other conditions. Oral administration of testosterone itself is problematic because of its extensive first pass metabolism in the liver and resulting very low bioavailability. The undecanoate ester of testosterone redirects a small proportion of the absorbed dose into the lymphatic system, thereby avoiding hepatic first pass metabolism and increasing the oral bioavailability of testosterone. However, this process is still very inefficient, and the bioavailability of testosterone after oral administration of the undecanoate ester is thought to be <5%.

Accordingly, there exists a need to develop novel lipid-pharmaceutical agent conjugates that facilitate stable transport of the pharmaceutical agent, such as MPA, to the intestinal lymph and allow the agent, e.g., MPA, to be released in its active form. The compounds, methods, and uses described herein address this need and provide other related advantages.

SUMMARY OF THE INVENTION

In one aspect, the present invention provides a compound of Formula VI:

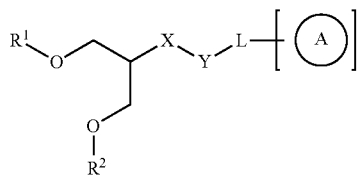

VI or a pharmaceutically acceptable salt thereof, wherein each variable is as defined herein.

In another aspect, the present invention provides a method of treating a disease, disorder, or condition such as one of those disclosed herein, comprising administering to a patient in need thereof an effective amount of a disclosed compound, such as a compound of Formula VI, or a pharmaceutically acceptable salt thereof.

DETAILED DESCRIPTION OF THE INVENTION

Figure 1:
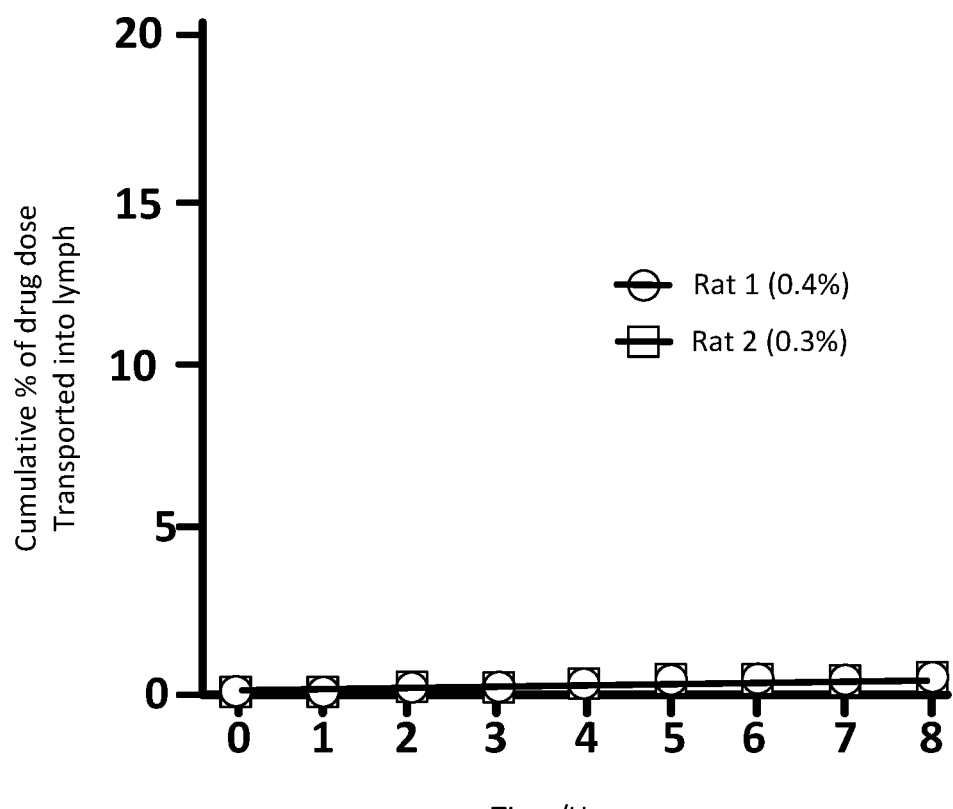
FIG. 1 shows lymphatic transport data for mycophenolic acid prodrug I-17 in rats.

1. General Description of Certain Aspects of the Invention

Lymphatic System-Directing Prodrugs

One approach to ameliorating the problems with previously known mycophenolic acid and its analogs, e.g., as described in the instant disclosure, is administration of a prodrug tailored to more specifically target MPA to its site of action. Lymphatic vessels are critical to host immune function. Antigens (foreign or autoantigens), and dendritic cells presenting such antigens, migrate through afferent lymphatic vessels and reach the draining lymph nodes. Antigen presentation in the draining lymph nodes results in priming, activation, polarization, and expansion to activate T cells, initiating an inflammatory response, e.g., against the foreign or self antigen. B cells are also activated, leading to antibody production against the foreign or self-antigen. Accordingly, targeting MPA to the lymphatic system allows localized immune suppression at the initiation site of the immune response, consequently allowing improved delivery, greater efficacy, and/or administration of the drug effectively at lower doses. Targeting the lymphatics has the potential to decrease the levels of MPA in the blood stream, and as such, has the potential to reduce off-target side effects. Accordingly, targeting MPA directly to the lymph provides a strategy to allow new treatment options for diseases currently being treated with MPA and/or permits the application of MPA to additional diseases, for which limited treatment options currently exist.

Compounds of the present invention, and compositions thereof, are useful in promoting transport of a therapeutic agent to the lymphatic system and in subsequently enhancing release of the parent drug, i.e. the therapeutic agent. In some embodiments, the therapeutic agent is mycophenolic acid or a derivative, analogue, or prodrug thereof, e.g. a $C_{1-6}$ aliphatic ester thereof or mycophenolate mofetil.

In one aspect, the present invention provides a compound of Formula I:

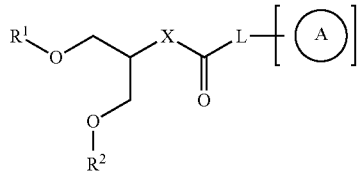

or a pharmaceutically acceptable salt thereof, wherein:

$R^1$ and $R^2$ are each independently hydrogen, a lipid, or —C(O)$R^3$;

each $R^3$ is independently a saturated or unsaturated, straight or branched, optionally substituted $C_{2-37}$ hydrocarbon chain;

X is —O—, —NR—, or —S—;

each R is independently hydrogen or an optionally substituted $C_{1-4}$ aliphatic;

L is a covalent bond or a saturated or unsaturated, straight or branched, optionally substituted bivalent $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

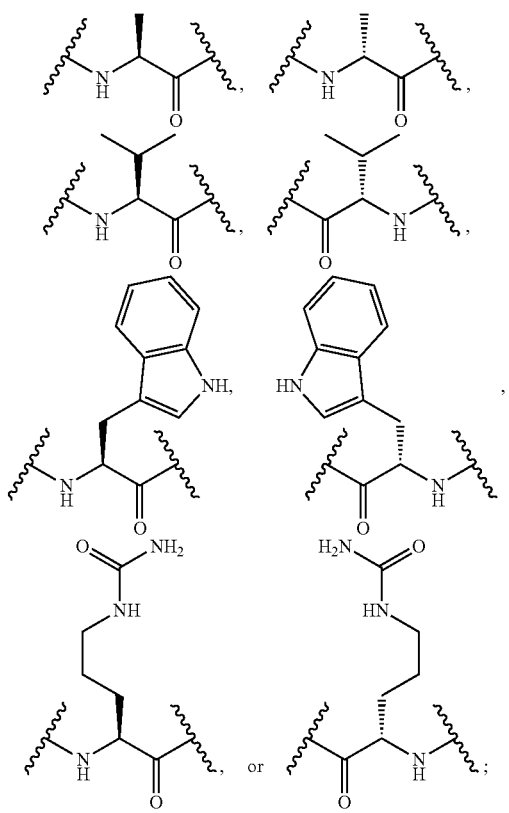

and wherein 1 methylene unit of L is optionally replaced with -M-; or

L is

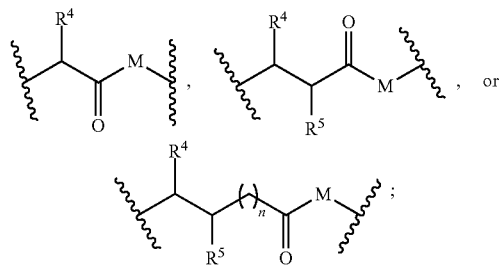

each -Cy- is independently an optionally substituted 5-6 membered bivalent saturated, partially unsaturated, or aromatic ring having 0-4 heteroatoms independently selected from nitrogen, oxygen, or sulfur;

$R^4$ and $R^5$ are each independently hydrogen or $C_{1-4}$ aliphatic optionally substituted with 1, 2, 3, 4, 5, or 6 deuterium or halogen atoms;

-M- is a self-immolative group;

n is 1-18; and

A is mycophenolic acid or a prodrug thereof.

In another aspect, the present invention provides a compound of Formula VI:

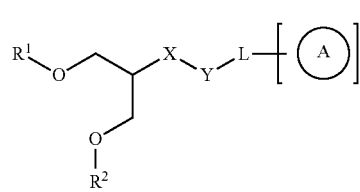

or a pharmaceutically acceptable salt thereof, wherein:

$R^1$ and $R^2$ are each independently hydrogen, an acid-labile group, a lipid, or —C(O)$R^3$;

each $R^3$ is independently a saturated or unsaturated, straight or branched, optionally substituted $C_{1-37}$ hydrocarbon chain;

X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;

L is a covalent bond or a saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

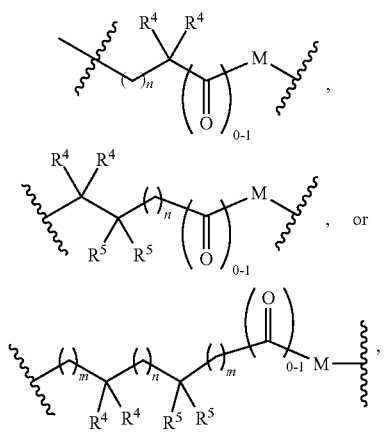

wherein either the right-hand side or left-hand side of L is attached to A;

each -Cy- is independently an optionally substituted 3-6 membered bivalent saturated, partially unsaturated, or aromatic ring having 0-4 heteroatoms independently selected from nitrogen, oxygen, or sulfur;

each $R^4$ and $R^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

-M- is a self-immolative group;

n is 0-18;

each m is independently 0-6; and

A is a therapeutic agent selected from mycophenolic acid or a derivative, analogue, or prodrug thereof.

In another aspect, the present invention provides a method of treating a disease, disorder, or condition in a patient in need thereof, comprising administering to the patient a disclosed lipid prodrug, such as a compound of Formula I or VI, or a pharmaceutically acceptable salt thereof.

It is understood that a disclosed lipid prodrug may exist in the form of a pharmaceutically acceptable salt. Thus, a reference to a "lipid prodrug" is also a disclosure of "lipid prodrug or a pharmaceutically acceptable salt thereof." It follows that such a lipid prodrug or pharmaceutically acceptable salt thereof may be used in a pharmaceutical composition and a method of use, such as those disclosed herein.

One approach to directing drugs into the lymphatic transport system is to employ prodrugs that participate in endogenous pathways that control the absorption, transport (including passive transport), and metabolism of dietary lipids. In one aspect, the present invention provides a lipid prodrug comprising a therapeutic agent conjugated to a glycerol-based moiety comprising two fatty acids or other lipids. Without wishing to be bound by theory, it is believed that such a prodrug mimics a dietary triglyercide, such that it participates in triglyceride processing and metabolism in the GI tract. Where appropriate, certain lipid prodrug scaffolds may be modified from the literature for use in accordance with the present disclosure. For example, certain drug-lipid conjugates and lipid prodrug scaffolds are disclosed in WO 2017/041139 and WO 2016/023082, each of which is hereby incorporated by reference in its entirety. Further examples of drug-lipid conjugates where the parent drug contains an available carboxylic acid group and has been directly conjugated to a glyceride backbone are described in Paris, G. Y. et al., J. Med. Chem. 1979, 22, (6), 683-687; Garzon Aburbeh, A. et al., J. Med. Chem. 1983, 26, (8), 1200-1203; Deverre, J. R; et al., J. Pharm. Pharmacol. 1989, 41, (3), 191-193; Mergen, F. et al, J. Pharm. Pharmacol. 1991, 43, (11), 815-816; Garzon Aburbeh, A. et al, J. Med. Chem. 1986, 29, (5), 687-69; and Han, S. et al. J. Control. Release 2014, 177, 1-10.

Further examples have used a short linker where the drug does not contain an available carboxylic acid (Scriba, G. K. E., Arch. Pharm. (Weinheim) 1995, 328, (3), 271-276; and Scriba, G. K. E. et al, J. Pharm. Pharmacol. 1995, 47, (11), 945-948). Other examples have utilized an ester linkage to the drug and an ether linkage to the glyceride (Sugihara, J. et al., J. Pharmacobiodyn. 1988, 11, (5), 369-376; and Sugihara, J. et al., J. Pharmacobiodyn. 1988, 11, (8), 555-562).

Typical use of prodrug strategies to improve a therapeutic agent's (active pharmaceutical agent's) pharmacokinetic properties relies on cleavage in vivo of the parent agent via non-specific degradation or enzymatic cleavage, thus allowing the agent to exert its biological activity. The present invention, in one aspect, provides modified glyceride-based compounds (lipid prodrugs) that direct lymphatic transport of a therapeutic agent and improve cleavage of the lipid prodrug to the therapeutic agent.

Dietary lipids, including triglycerides, follow a particular metabolic pathway to gain access to the lymph (and ultimately the systemic circulation) that is entirely distinct from that of other nutrients such as proteins and carbohydrates. After ingestion, dietary triglycerides are hydrolyzed by lipases in the lumen to release one monoglyceride and two fatty acids for each molecule of triglyceride. The monoglyceride and two fatty acids are subsequently absorbed into enterocytes and re-esterified to triglycerides.

Resynthesised triglycerides are assembled into intestinal lipoproteins, primarily chylomicrons. After formation, chylomicrons are exocytosed from enterocytes and subsequently gain preferential access to the intestinal lymphatics. Once within the lymphatic system, chylomicrons containing packaged triglycerides drain through a series of capillaries, nodes and ducts to join the systemic circulation at the junction of the left subclavian vein and internal jugular vein. Following entry into blood circulation, triglycerides in chylomicrons are preferentially and efficiently taken up by tissues with high expression levels of lipoprotein lipases, such as adipose tissue, the liver, and potentially certain types of tumor tissues.

Lipid prodrugs are expected to behave similarly to natural triglycerides and to be transported to and through the lymphatic system to reach the systemic circulation without interacting with the liver. In some embodiments, the lipid prodrugs are cleaved, releasing the therapeutic agent, after the prodrugs have reached the systemic circulation, or after reaching a target tissue. In some embodiments, the lipid prodrugs release the therapeutic agent by destruction of a self-immolative linker that attaches the therapeutic agent to the glyercol-derived group, or by enzymatic cleavage of a linker. In this way, the pharmacokinetic and pharmacodynamic profiles of the parent therapeutic agent may be manipulated to enhance access to the lymph and lymphoid tissues, thereby promoting oral bioavailability via avoidance of first-pass metabolism (and potentially intestinal efflux). Accordingly, in some embodiments, the disclosed lipid prodrug has improved oral bioavailability, reduced first-pass metabolism, reduced liver toxicity, or improved other pharmacokinetic properties as compared with the parent therapeutic agent. In some embodiments, the disclosed lipid prodrug has increased drug targeting (as compared with the parent therapeutic agent) to sites within the lymph, lymph nodes and lymphoid tissues, and to sites of high lipid utilization and lipoprotein lipase expression such as adipose tissue, liver and some tumors. In some embodiments, a disclosed lipid prodrug is delivered to the central nervous system (CNS) or crosses the blood-brain barrier (BBB) via the lymphatic system.

In certain aspects, the present invention provides methods of modulating the delivery, distribution, or other properties of a therapeutic agent. In one aspect, the present invention provides a method of delivering a therapeutic agent to the systemic circulation of a patient in need thereof, wherein the therapeutic agent partially, substantially, or completely bypasses first-pass liver metabolism in the patient, comprising the step of administering to the patient a disclosed lipid prodrug of the therapeutic agent. In another aspect, the present invention provides a method of modifying a therapeutic agent to partially, substantially, or completely bypass first-pass liver metabolism in a patient after administration of the therapeutic agent, comprising the step of preparing a disclosed lipid prodrug of the therapeutic agent. In some embodiments, the lipid prodrug is administered orally. In some embodiments, preparing the lipid prodrug comprises the step of conjugating a therapeutic agent to a glycerol-based scaffold comprising two fatty acids or other lipids, thereby providing the lipid prodrug.

In another aspect, the present invention provides a method of improving oral bioavailability of a therapeutic agent, enhancing gut absorption of a therapeutic agent, or decreasing metabolism, decomposition, or efflux in the gut of a therapeutic agent, comprising the step of preparing a disclosed lipid prodrug of the therapeutic agent.

In another aspect, the present invention provides a method of modifying, e.g., improving, delivery of a therapeutic agent to a target tissue, comprising the step of preparing a disclosed lipid prodrug of the therapeutic agent. In some embodiments, the target tissue is the lymph, a lymph node (such as a mesenteric lymph node), adipose tissue, liver, or a tumor, such as a lymph node site of metastasis. In some embodiments, the target tissue is the brain or CNS.

Lipid prodrugs that readily convert to parent therapeutic agent after transport via the systemic circulation have reduced free drug concentrations in the gastrointestinal (GI) tract, which may provide benefits in reducing gastrointestinal irritation or toxicity, and/or in increased drug solubility in intestinal bile salt micelles (due to similarities to endogenous monoglycerides).

Disclosed lipid prodrugs may also in certain embodiments have increased passive membrane permeability (due to greater lipophilicity compared with the parent therapeutic agent). In some embodiments, the lipid prodrug has greater solubility in lipid formulations or vehicles comprising either lipids alone or mixtures of lipids with surfactants and/or cosolvents, allowing for the use of lipophilic formulations for otherwise highly hydrophilic therapeutic agents.

Lipid Prodrugs of Mycophenolic Acid and Related Compounds

In one aspect, the present invention provides a compound of Formula I:

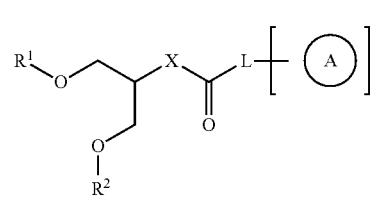

or a pharmaceutically acceptable salt thereof, wherein:
$R^1$ and $R^2$ are each independently hydrogen, a lipid, or —C(O)$R^3$;
each $R^3$ is independently a saturated or unsaturated, straight or branched, optionally substituted $C_{2-37}$ hydrocarbon chain;
X is —O—, —NR—, or —S—;
each R is independently hydrogen or an optionally substituted $C_{1-4}$ aliphatic;
L is a covalent bond or a bivalent, saturated or unsaturated, straight or branched, optionally substituted $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

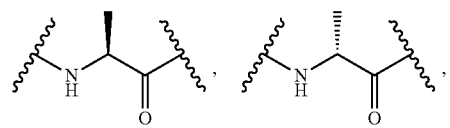

-continued

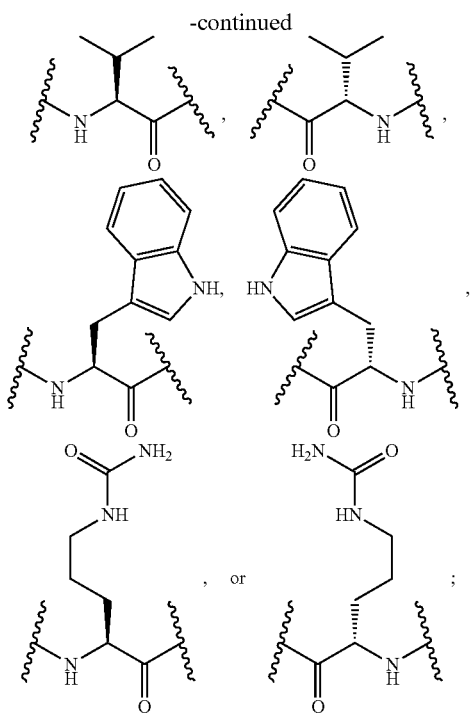

, or and wherein 1 methylene unit of L is optionally replaced with -M-; or
L is

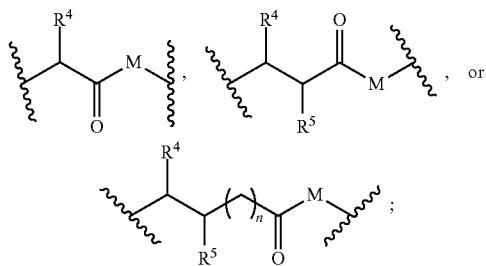

, or ;

each -Cy- is independently an optionally substituted 5-6 membered bivalent saturated, partially unsaturated, or aromatic ring having 0-4 heteroatoms independently selected from nitrogen, oxygen, or sulfur;
$R^4$ and $R^5$ are each independently hydrogen or $C_{1-4}$ aliphatic optionally substituted with 1, 2, 3, 4, 5, or 6 deuterium or halogen atoms;
M- is a self-immolative group;
n is 1-18; and A is mycophenolic acid, or a prodrug thereof.

As defined above and described herein, $R^1$ and $R^2$ are each independently hydrogen, a lipid such as a fatty acid, or —C(O)$R^3$.

In some embodiments, $R^1$ is hydrogen. In some embodiments, $R^1$ is a lipid. In some embodiments, $R^1$ is a fatty acid. In some embodiments, $R^1$ is —C(O)$R^3$. In some embodiments, $R^1$ is selected from those depicted in Table 1, below.

In some embodiments, $R^2$ is hydrogen. In some embodiments, $R^2$ is a lipid. In some embodiments, $R^2$ is a fatty acid. In some embodiments, $R^2$ is —C(O)$R^3$. In some embodiments, $R^2$ is selected from those depicted in Table 1, below.

As defined above and described herein, each $R^3$ is independently a saturated or unsaturated, straight or branched, optionally substituted $C_{2-37}$ hydrocarbon chain.

In some embodiments, $R^3$ is a saturated, straight, optionally substituted $C_{2-37}$ hydrocarbon chain. In some embodiments, $R^3$ is an unsaturated, straight, optionally substituted $C_{2-37}$ hydrocarbon chain. In some embodiments, $R^3$ is a saturated, branched, optionally substituted $C_{2-37}$ hydrocarbon chain. In some embodiments, $R^3$ is an unsaturated, branched, optionally substituted $C_{2-37}$ hydrocarbon chain. In some embodiments, $R^3$ is selected from those depicted in Table 1, below.

As defined above and described herein, X is —O—, —NR—, or —S—.

In some embodiments, X is —O—. In some embodiments, X is —NR—. In some embodiments, X is —S—. In some embodiments, X is selected from those depicted in Table 1, below.

As defined above and described herein, each R is independently hydrogen or an optionally substituted $C_{1-4}$ aliphatic.

In some embodiments, R is hydrogen. In some embodiments, R is an optionally substituted $C_{1-4}$ aliphatic. In some embodiments, R is selected from those depicted in Table 1, below.

As defined above and described herein, L is a covalent bond or a bivalent, saturated or unsaturated, straight or branched, optionally substituted $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

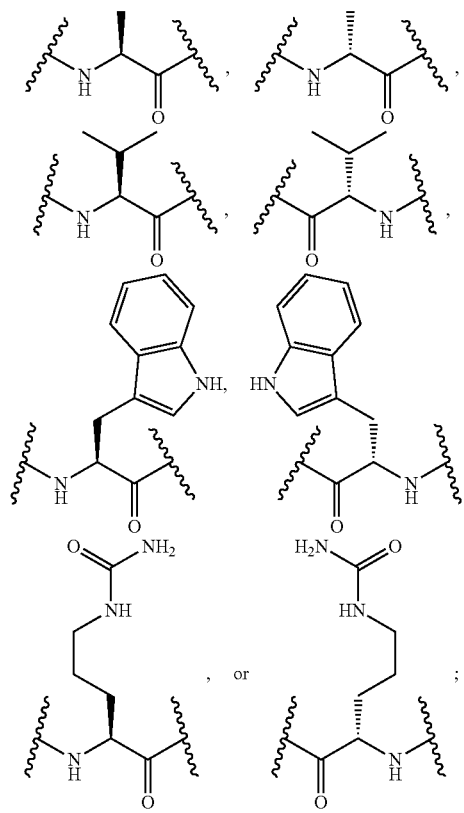

, or ;

wherein 1 methylene unit of L is optionally replaced with -M-.

In some embodiments, L is a covalent bond. In some embodiments, L is a bivalent, saturated or unsaturated, straight or branched, optionally substituted $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

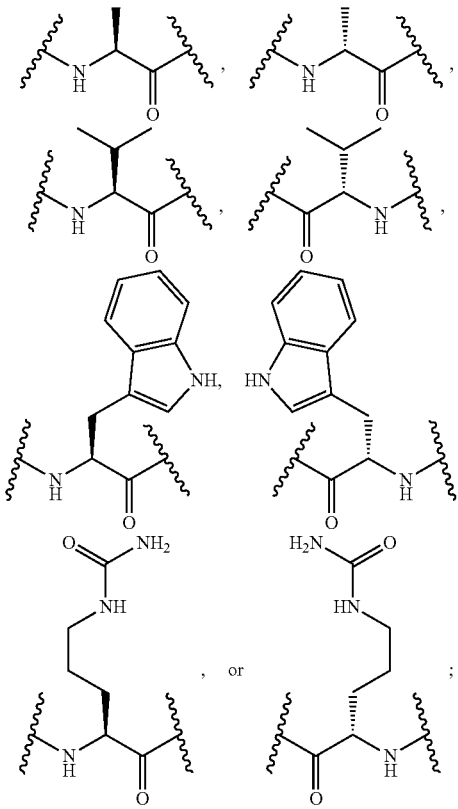

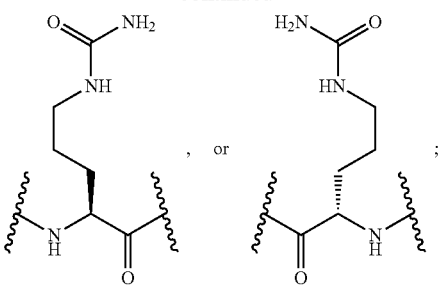

and 1 methylene unit of L is optionally replaced with -M-. In some embodiments, L is a bivalent, unsaturated, straight $C_{1-20}$, $C_{1-16}$, $C_{1-12}$, $C_{1-10}$ or $C_{1-8}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

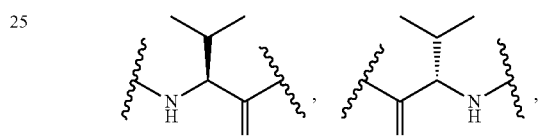

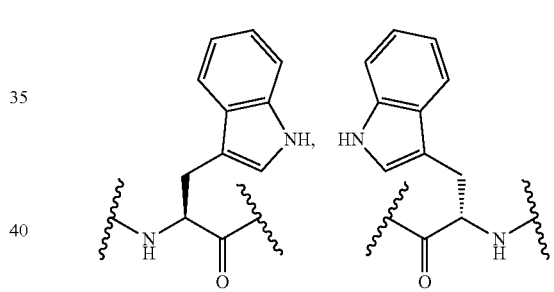

and 1 methylene unit of L is optionally replaced with -M-. In some embodiments, L is a bivalent, saturated, branched $C_{1-20}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

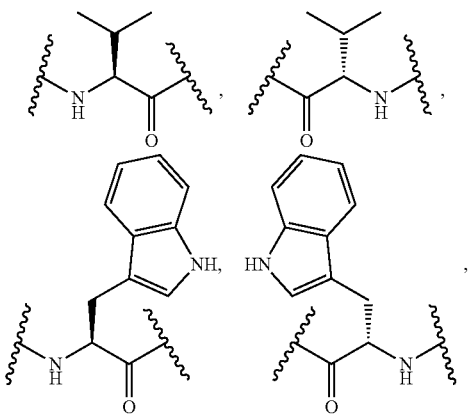

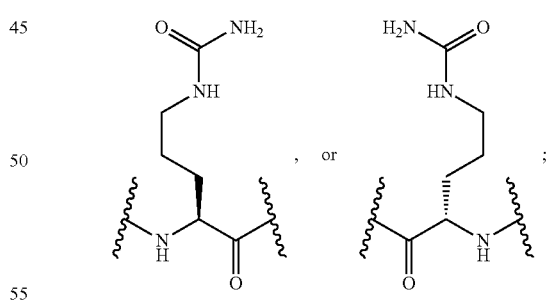

and 1 methylene unit of L is optionally replaced with -M-. In some embodiments, L is a bivalent, unsaturated, branched $C_{1-20}$, $C_{1-16}$, $C_{1-12}$, $C_{1-10}$ or $C_{1-6}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—; and 1 methylene unit of L is optionally replaced with -M-.

In some embodiments, L comprises
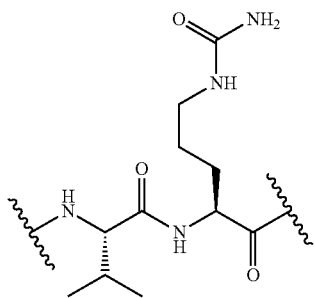
In some embodiments, L comprises
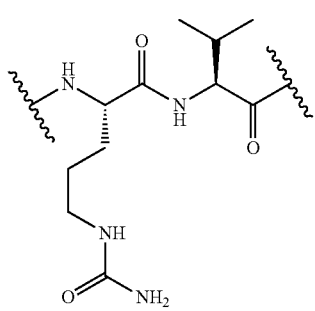
In some embodiments, L comprises
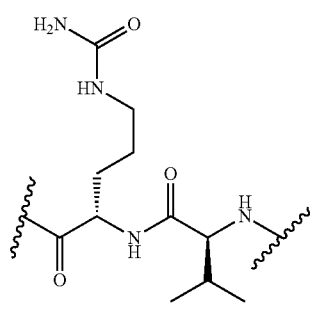
In some embodiments, L comprises
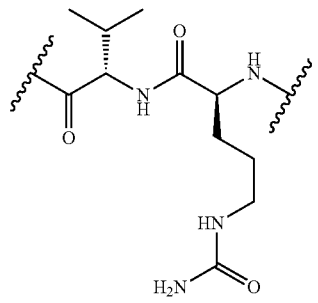
In some embodiments, L comprises
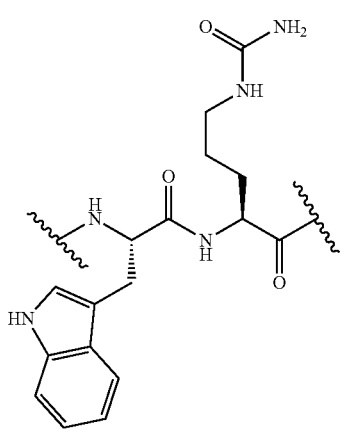
In some embodiments, L comprises
In some embodiments, L comprises
In some embodiments, L comprises In some embodiments, L comprises

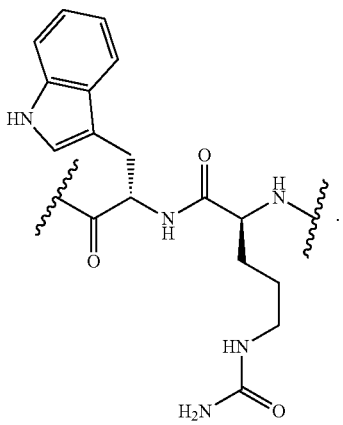 [SMILES: *N[C@@H](CCCNC(N)=O)C(=O)N[C@@H](Cc1c[nH]c2ccccc12)C(*)=O]

In some embodiments, 1 methylene unit of L is replaced with -M-. In some embodiments, L is selected from those depicted in Table 1, below.

As defined above and described herein, L may also be selected from

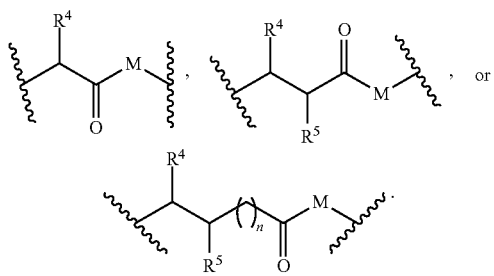

In some embodiments, L is

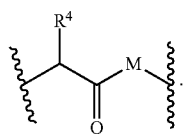

In some embodiments, L is

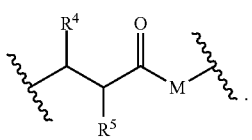

In some embodiments, L is

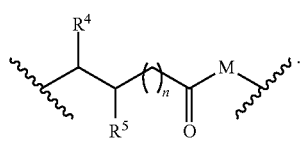

As defined above and described herein, each -Cy- is independently an optionally substituted 5-6 membered bivalent saturated, partially unsaturated, or aromatic ring having 0-4 heteroatoms independently selected from nitrogen, oxygen, or sulfur.

In some embodiments, -Cy- is an optionally substituted 5-6 membered bivalent saturated ring having 0-4 heteroatoms independently selected from nitrogen, oxygen, or sulfur. In some embodiments, -Cy- is an optionally substituted 5-membered bivalent saturated, partially unsaturated, or aromatic ring having 0-4 heteroatoms independently selected from nitrogen, oxygen, or sulfur. In some embodiments, -Cy- is an optionally substituted 6-membered bivalent saturated, partially unsaturated, or aromatic ring having 0-4 heteroatoms independently selected from nitrogen, oxygen, or sulfur. In some embodiments, -Cy- is selected from those depicted in Table 1, below.

As defined above and described herein, $R^4$ and $R^5$ are each independently hydrogen or $C_{1-4}$ aliphatic optionally substituted with 1, 2, 3, 4, 5, or 6 deuterium or halogen atoms.

In some embodiments, $R^4$ is hydrogen. In some embodiments, $R^4$ is $C_{1-4}$ aliphatic. In some embodiments, $R^4$ is methyl. In some embodiments, $R^4$ is ethyl. In some embodiments, $R^4$ is n-propyl. In some embodiments, $R^4$ is isopropyl. In some embodiments, $R^4$ is cyclopropyl or cyclobutyl. In some embodiments, $R^4$ is n-butyl. In some embodiments, $R^4$ is sec-butyl. In some embodiments, $R^4$ is isobutyl. In some embodiments, $R^4$ is tert-butyl. In some embodiments, $R^4$ is selected from those depicted in Table 1, below.

In some embodiments, $R^5$ is hydrogen. In some embodiments, $R^5$ is $C_{1-4}$ aliphatic. In some embodiments, $R^5$ is methyl. In some embodiments, $R^5$ is ethyl. In some embodiments, $R^5$ is n-propyl. In some embodiments, $R^5$ is isopropyl. In some embodiments, $R^4$ is cyclopropyl or cyclobutyl. In some embodiments, $R^5$ is n-butyl. In some embodiments, $R^5$ is sec-butyl. In some embodiments, $R^5$ is isobutyl. In some embodiments, $R^5$ is tert-butyl. In some embodiments, $R^4$ is selected from those depicted in Table 1, below.

As defined above and described herein, -M- is a self-immolative group.

In some embodiments, -M- is

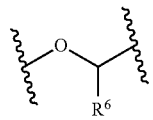

or another self-immolative group.

In some embodiments, -M- is

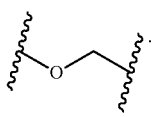

In some embodiments, -M- is

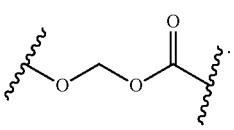 [SMILES: *OCOC(*)=O]

In some embodiments, -M- is

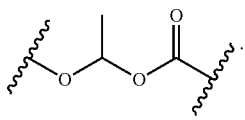 [SMILES: *OC(C)OC(*)=O]

In some embodiments, -M- is

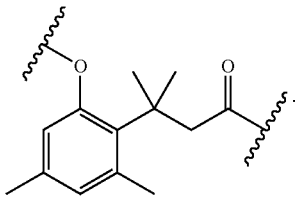 [SMILES: *Oc1cc(C)cc(C)c1C(C)(C)CC(*)=O]

In some embodiments, -M- is

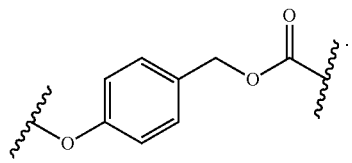 [SMILES: *Oc1ccc(COC(*)=O)cc1]

In some embodiments, -M- is

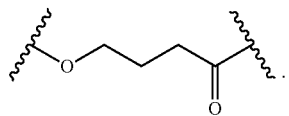 [SMILES: *OCCCC(*)=O]

In some embodiments, -M- is selected from those depicted in Table 1, below.

As defined above and described herein, n is 1-18.

In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 1-16, 1-14, 1-12, 1-10, 1-8, 1-6, 1-3, 2-16, 2-14, 2-12, 2-10, 2-8, 2-6, 3-12, 3-8, 3-6, 4-10, 4-8, 4-6, 5-10, 5-8, 5-6, 6-10, 6-8, or 8-12.

As defined above and described herein, $R^6$ is hydrogen or $C_{1-4}$ aliphatic.

In some embodiments, $R^6$ is hydrogen. In some embodiments, $R^6$ is $C_{1-4}$ aliphatic. In some embodiments, $R^6$ is methyl. In some embodiments, $R^6$ is ethyl. In some embodiments, $R^6$ is n-propyl. In some embodiments, $R^6$ is isopropyl. In some embodiments, $R^6$ is n-butyl. In some embodiments, $R^6$ is isobutyl. In some embodiments, $R^6$ is tert-butyl.

In some embodiments, $R^6$ is selected from those depicted in Table 1, below.

As defined above, A is mycophenolic acid, or a prodrug thereof. In some embodiments, A is mycophenolic acid, or a pharmaceutically acceptable salt thereof. In some embodiments, A is a derivative or analogue of mycophenolic acid (MPA). Exemplary MPA derivatives include, without limitation, MPAs with modified side chains, MPA substituted at the phenolic OH group, MPA prodrugs (e.g., mycophenolate mofetil), and the like. More specific examples of MPA derivatives may include, without limitation, euparvic acid, RS-97613, F01 1358B, F01 1358A, F13459, mycophenolic acid-amino acid conjugates (see, e.g., Iwaszkiewicz-Grzes, D. et al., European Journal of Medicinal Chemistry Volume 69, November 2013, Pages 863-871), mycophenolic acids with adenine dinucleotides, C2-mycophenolic adenine dinucleotide, C4-mycophenolic adenine dinucleotide, C6-mycophenolic adenine dinucleotide, mycophenolic acid glucuronide, beta-methylene-mycophenolic adenine dinucleotide, mycophenolic adenine dinucleotide, mycophenolate mofetil, dextran T70-mycophenolic acid conjugate, ethyl 0-(N-(4 carboxyphenyl]carbamoyl) mycophenolate, carbamoyl mycophenolic acid ethyl ester, and combinations thereof.

In other embodiments, A is a prodrug of mycophenolic acid. In some embodiments, A is mycophenolate mofetil. In some embodiments, A is a pharmaceutically acceptable salt of mycophenolic acid, such as the sodium salt. In some embodiments, A is an ester of mycophenolic acid, such as a methyl, ethyl, phenyl, isopropyl, or $C_{1-6}$ aliphatic ester.

One of ordinary skill in the art will appreciate that the therapeutic agent mycophenolic acid may be in the form of a prodrug. For example, mycophenolate mofetil is a prodrug of a mycophenolic acid. Thus, it will be appreciated that a lipid prodrug moiety of the present invention is attached to the mycophenolic acid prodrug (e.g. mycophenolate mofetil) or the active form thereof. For the purpose of clarity, and by way of example, it will be understood that a provided lipid prodrug moiety is attached at any modifiable oxygen, sulfur, or nitrogen atom of either mycophenolate mofetil or its active agent mycophenolic acid, or a derivative or prodrug of mycophenolic acid.

As used herein, depiction of brackets around a therapeutic agent, A,

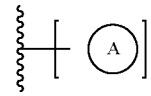

means that the

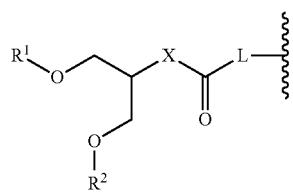

moiety is covalently attached to A at any available modifiable nitrogen, oxygen, or sulfur atom of A.

In some embodiments, the present invention provides a compound of any of Formula I-a, I-b, or I-c:

I-a
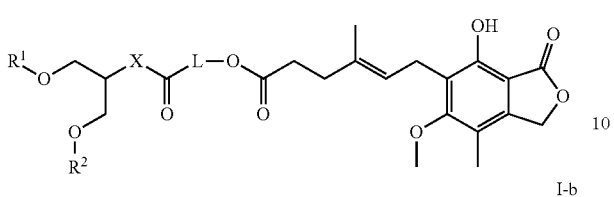

I-b
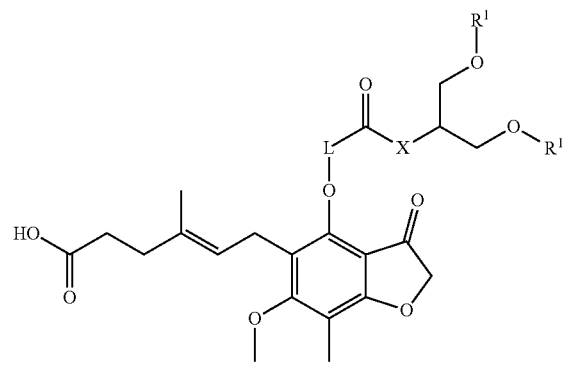

I-c
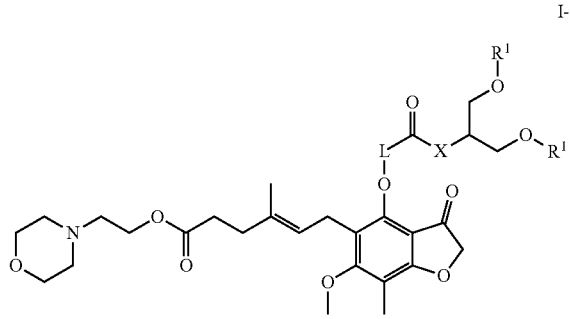

or a pharmaceutically acceptable salt thereof, wherein each variable is as defined above and described herein in embodiments, both singly and in combination.

In certain embodiments, the present invention provides a compound of formula I, wherein L is

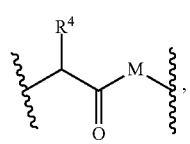

thereby forming a compound of Formula II:

II
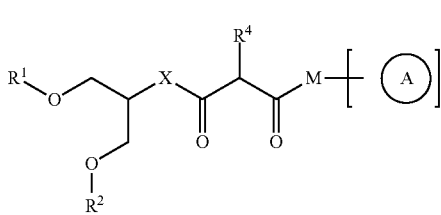

or a pharmaceutically acceptable salt thereof, wherein each of $R^1$, $R^2$, $R^4$, X, M and A is as defined above and described in embodiments herein, both singly and in combination.

In certain embodiments, the present invention provides a compound of Formula I, wherein L is

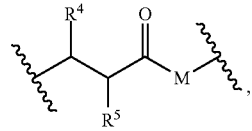

thereby forming a compound of formula III:

III
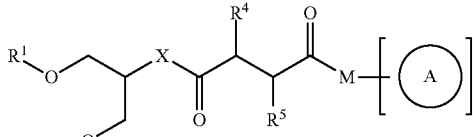

or a pharmaceutically acceptable salt thereof, wherein each of $R^1$, $R^2$, $R^4$, $R^5$, X, M and A is as defined above and described in embodiments herein, both singly and in combination.

In certain embodiments, the present invention provides a compound of Formula I, wherein L is

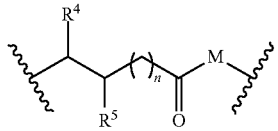

and -M- is

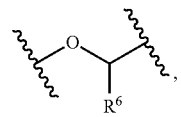

thereby forming a compound of Formula IV:

IV
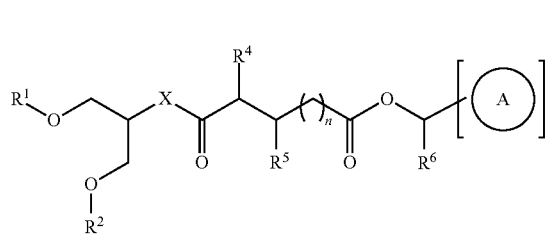

or a pharmaceutically acceptable salt thereof, wherein each of $R^1$, $R^2$, $R^4$, $R^5$, $R^6$, X, and A is as defined above and described in embodiments herein, both singly and in combination.

In other embodiments, the present invention provides a compound of Formula V:

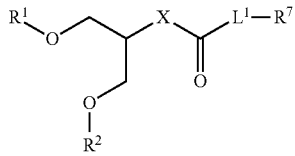

or a pharmaceutically acceptable salt thereof, wherein:
$R^1$ and $R^2$ are each independently hydrogen or —C(O)$R^3$;
each $R^3$ is independently a saturated or unsaturated, straight or branched $C_{2-37}$ hydrocarbon chain;
X is —O—, —NR—, or —S—;
each R is independently hydrogen or an optionally substituted $C_{1-4}$ aliphatic;
$L^1$ is a covalent bond or a bivalent, saturated or unsaturated, straight or branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O) NR—, or —NRC(O)O—, wherein:
each -Cy- is independently an optionally substituted 5-6 membered bivalent aryl ring having 0-4 heteroatoms independently selected from nitrogen, oxygen, or sulfur; and
$R^7$ is a moiety suitable for click chemistry or metal-free click chemistry.

$R^1$, $R^2$, $R^3$, X, R, and -Cy- are as defined above and described herein.

As defined above and described herein, $L^1$ is a covalent bond or a bivalent, saturated or unsaturated, straight or branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—.

In some embodiments, $L^1$ is a covalent bond. In some embodiments, $L^1$ is a bivalent, saturated, straight $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, saturated, branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, unsaturated, straight $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—. In some embodiments, $L^1$ is a bivalent, unsaturated, branched $C_{1-20}$ hydrocarbon chain, wherein 0-6 methylene units of $L^1$ are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—.

As defined above and described herein, $R^7$ is a moiety suitable for click chemistry or metal-free click chemistry.

In some embodiments, $R^7$ is a moiety suitable for click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction.

In some embodiments, $R^7$ is a moiety suitable for metal-free click chemistry. As used herein, the phrase "a moiety suitable for metal-free click chemistry" refers to a functional group capable of dipolar cycloaddition without use of a metal catalyst. Such moieties include an activated alkyne (such as a strained cyclooctyne), an oxime (such as a nitrile oxide precursor), or oxanorbornadiene, for coupling to an azide to form a cycloaddition product (e.g., triazole or isoxazole).

In some embodiments, $R^7$ is —$N_3$. In some embodiments, $R^7$ is

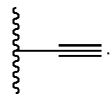

In some embodiments, $R^7$ is

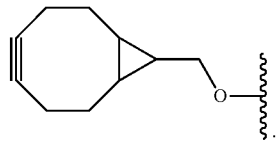 [SMILES: *OCC1C2CCC#CCCC21]

In some embodiments, $R^7$ is

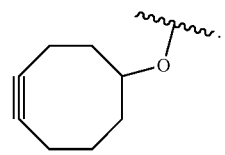 [SMILES: *OC1CCC#CCCC1]

In some embodiments, $R^7$ is

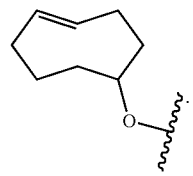 [SMILES: *OC1CC/C=C/CCC1]

In some embodiments, $R^7$ is

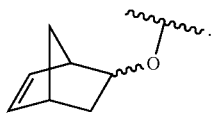 [SMILES: *OC1CC2C=CC1C2]

In some embodiments,

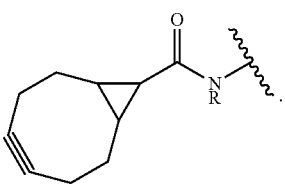

In some embodiments, $R^7$ is

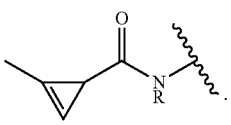

In some embodiments, $R^7$ is

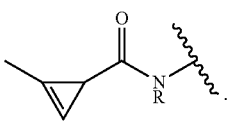

In some embodiments, $R^7$ is

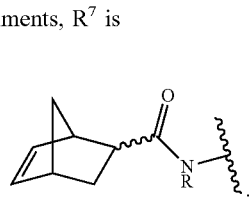

In some embodiments, $R^7$ is

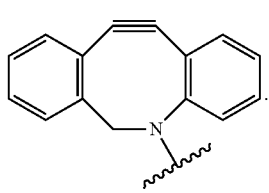 [SMILES: *N1Cc2ccccc2C#Cc2ccccc21]

In some embodiments, $R^7$ is

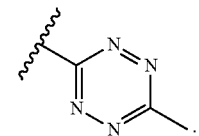 [SMILES: *c1nnc(C)nn1]

In some embodiments, $R^7$ is

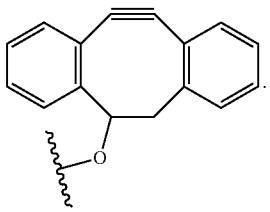 [SMILES: *OC1Cc2ccccc2C#Cc2ccccc21]

In some embodiments, $R^7$ is

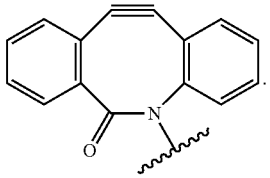 [SMILES: *N1C(=O)c2ccccc2C#Cc2ccccc21]

In some embodiments, $R^7$ is

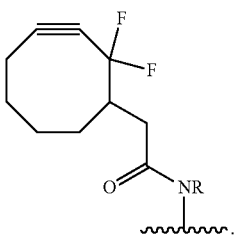

One of ordinary skill in the art would appreciate that compounds of formula V are suitable for covalently modifying the therapeutic agent, mycophenolic acid, or a prodrug thereof (e.g. mycophenolate mofetil), via click chemistry. Thus, it will be appreciated that the present invention further contemplates derivatives of mycophenolic acid, or a prodrug thereof (e.g. mycophenolate mofetil), that are suitable for reacting with a provided compound of formula V via a click reaction.

In each of the above embodiments, A is covalently attached to the remainder of the formula at any chemically feasible attachment point of A, such as a chemically modifiable oxygen, nitrogen, or sulfur atom. For example, in some embodiments, A is attached to the remainder of the formula as shown below:

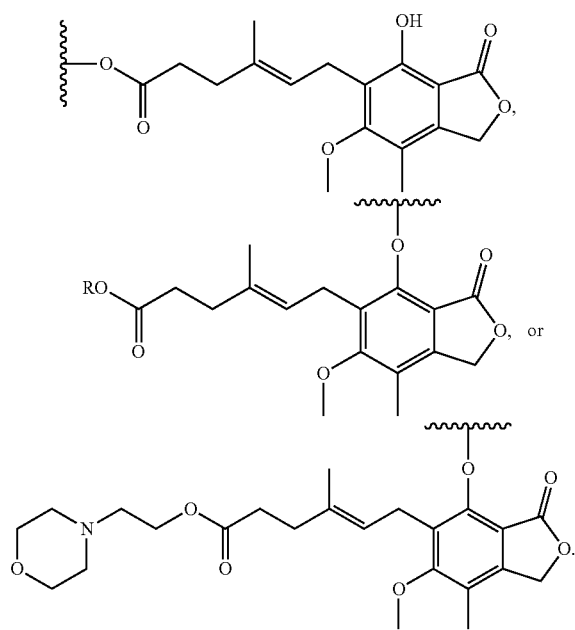

In one aspect, the present invention provides a compound of Formula VI:

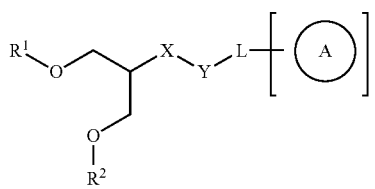

or a pharmaceutically acceptable salt thereof, wherein:
R$^1$ and R$^2$ are each independently hydrogen, an acid-labile group, a lipid, or —C(O)R$^3$;
each R$^3$ is independently a saturated or unsaturated, straight or branched, optionally substituted C$_{1-37}$ hydrocarbon chain;
X is —O—, —NR—, —S—, —O(C$_{1-6}$ aliphatic)-O—, —O(C$_{1-6}$ aliphatic)-S—, —O(C$_{1-6}$ aliphatic)-NR—, —S(C$_{1-6}$ aliphatic)-O—, —S(C$_{1-6}$ aliphatic)-S—, —S(C$_{1-6}$ aliphatic)-NR—, —NR(C$_{1-6}$ aliphatic)-O—, —NR(C$_{1-6}$ aliphatic)-S—, or —NR(C$_{1-6}$ aliphatic)-NR—, wherein 0-2 methylene units of the C$_{1-6}$ aliphatic group are independently and optionally replaced with —O—, —NR—, or —S— and the C$_{1-6}$ aliphatic group is independently and optionally substituted with 1, 2, or 3 deuterium or halogen atoms;
each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;
L is a covalent bond or a bivalent, saturated or unsaturated, straight or branched, optionally substituted bivalent C$_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-;
or
L is

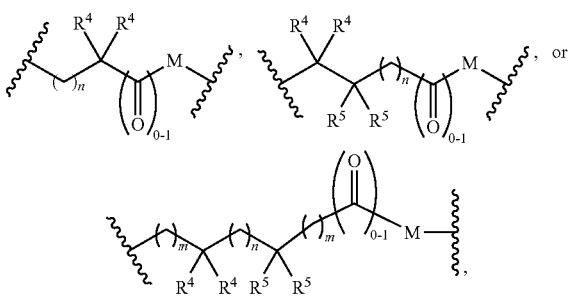

wherein either the right-hand side or left-hand side of L is attached to A;
each -Cy- is independently an optionally substituted 3-6 membered bivalent saturated, partially unsaturated, or aromatic ring having 0-4 heteroatoms independently selected from nitrogen, oxygen, or sulfur;
each R$^4$ and R$^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a C$_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the C$_{1-6}$ aliphatic is optionally substituted with 1, 2, 3, 4, 5, or 6 deuterium or halogen atoms; or two instances of R$^4$ or R$^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

-M- is a self-immolative group;
n is 0-18;
each m is independently 0-6; and
A is a therapeutic agent selected from mycophenolic acid or a derivative, analogue, or prodrug thereof.

As defined above and described herein, $R^1$ and $R^2$ are each independently hydrogen, an acid-labile group, a lipid such as a fatty acid, or —C(O)$R^3$.

In some embodiments, $R^1$ is hydrogen. In some embodiments, $R^1$ is an acid-labile group. In some embodiments, $R^1$ is a lipid. In some embodiments, $R^1$ is a fatty acid. In some embodiments, $R^1$ is —C(O)$R^3$. In some embodiments, $R^1$ is selected from those depicted in Table 1, below.

In some embodiments, $R^2$ is hydrogen. In some embodiments, $R^2$ is an acid-labile group. In some embodiments, $R^2$ is a lipid. In some embodiments, $R^2$ is a fatty acid. In some embodiments, $R^2$ is —C(O)$R^3$. In some embodiments, $R^2$ is selected from those depicted in Table 1, below.

In some embodiments, each of $R^1$ and $R^2$ is independently a fatty acid, phosphatide, phospholipid, or analogue thereof, such as those described in detail below. In some embodiments, each fatty acid is independently a saturated or unsaturated medium-chain or long-chain fatty acid.

In some embodiments, each fatty acid independently has a $C_2$-$C_{40}$ chain. In some embodiments, each fatty acid independently has a $C_6$-$C_{20}$, $C_8$-$C_{20}$, $C_{10}$-$C_{20}$, $C_{10}$-$C_{18}$, $C_{12}$-$C_{18}$, $C_{14}$-$C_{18}$, $C_{16}$-$C_{18}$, or $C_{10}$-$C_{16}$ chain. In some embodiments, each fatty acid is independently selected from oleic acid, palmitic acid, EPA, or DHA.

In some embodiments, $R^1$ and $R^2$ are each independently selected from an acid labile group such as tert-butoxycarbonyl (Boc), an amino acid, PEG group, —C(O)OR, —C(O)NR$_2$, —CH$_2$OR, —C(NR)R, or —P(O)$_2$OR.

As defined above and described herein, each $R^3$ is independently a saturated or unsaturated, straight or branched, optionally substituted $C_{1-37}$ hydrocarbon chain.

In some embodiments, $R^3$ is a saturated, straight, optionally substituted $C_{1-37}$ hydrocarbon chain. In some embodiments, $R^3$ is an unsaturated, straight, optionally substituted $C_{1-37}$ hydrocarbon chain. In some embodiments, $R^3$ is a saturated, branched, optionally substituted $C_{1-37}$ hydrocarbon chain. In some embodiments, $R^3$ is an unsaturated, branched, optionally substituted $C_{1-37}$ hydrocarbon chain. In some embodiments, $R^3$ is selected from those depicted in Table 1, below.

As defined above and described herein, X is —O—, —NR—, —S—, —O(C$_{1-6}$ aliphatic)-O—, —O(C$_{1-6}$ aliphatic)-S—, —O(C$_{1-6}$ aliphatic)-NR—, —S(C$_{1-6}$ aliphatic)-O—, —S(C$_{1-6}$ aliphatic)-S—, —S(C$_{1-6}$ aliphatic)-NR—, —NR(C$_{1-6}$ aliphatic)-O—, —NR(C$_{1-6}$ aliphatic)-S—, or —NR(C$_{1-6}$ aliphatic)-NR—, wherein 0-2 methylene units of the C$_{1-6}$ aliphatic group are independently and optionally replaced with —O—, —NR—, or —S— and the C$_{1-6}$ aliphatic group is independently and optionally substituted with 1, 2, or 3 deuterium or halogen atoms.

In some embodiments, X is —O—. In some embodiments, X is —NR—. In some embodiments, X is —S—. In some embodiments, X is —O(C$_{1-6}$ aliphatic)-O—. In some embodiments, X is —O(C$_{1-6}$ aliphatic)-S—. In some embodiments, X is —O(C$_{1-6}$ aliphatic)-NR—. In some embodiments, X is —S(C$_{1-6}$ aliphatic)-O—. In some embodiments, X is —S(C$_{1-6}$ aliphatic)-S—. In some embodiments, X is —S(C$_{1-6}$ aliphatic)-NR—. In some embodiments, X is —NR(C$_{1-6}$ aliphatic)-O—. In some embodiments, X is —NR(C$_{1-6}$ aliphatic)-S—. In some embodiments, X is —NR(C$_{1-6}$ aliphatic)-NR—. In any of the foregoing embodiments, 0-2 methylene units of the bivalent C$_{1-6}$ aliphatic group are independently and optionally replaced with —O—, —NR—, or —S— and the bivalent C$_{1-6}$ aliphatic group is independently and optionally substituted with 1, 2, or 3 deuterium or halogen atoms. In some embodiments, X is selected from those depicted in Table 1, below.

As defined above and described herein, Y is absent or is —C(O)—, —C(NR)—, or —C(S)—.

In some embodiments, Y is absent. In some embodiments, Y is —C(O)—. In some embodiments, Y is —C(NR)—. In some embodiments, Y is —C(S)—. In some embodiments, Y is selected from those depicted in Table 1, below.

As defined above and described herein, L is a covalent bond or a bivalent, saturated or unsaturated, straight or branched, optionally substituted bivalent C$_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

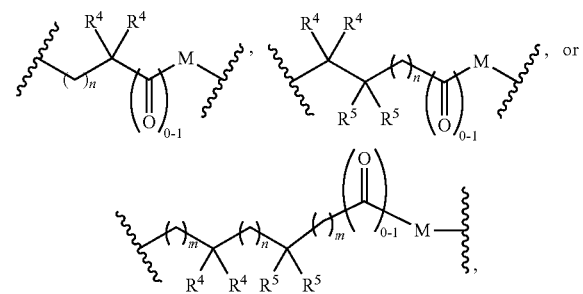

wherein either the right-hand side or left-hand side of L is attached to A.

In some embodiments, L is a covalent bond. In some embodiments, L is a bivalent, saturated or unsaturated, straight or branched, optionally substituted bivalent C$_{1-30}$ (e.g., C$_{3-30}$, C$_{5-30}$, C$_{7-30}$, C$_{3-25}$, C$_{5-25}$, C$_{7-25}$, C$_{3-20}$, C$_{5-20}$, C$_{7-20}$, C$_{8-18}$, C$_{6-18}$, C$_{7-17}$, C$_{5-16}$, C$_{5-15}$, C$_{8-14}$, C$_{7-13}$, C$_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-. In some embodiments, L is

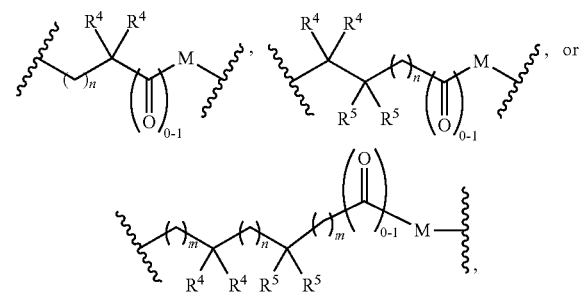

wherein either the right-hand side or left-hand side of L is attached to A.

In some embodiments, L is a covalent bond or a bivalent, saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, $C_{7-20}$, $C_{8-18}$, $C_{6-18}$, $C_{7-17}$, $C_{5-16}$, $C_{5-15}$, $C_{5-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid selected from

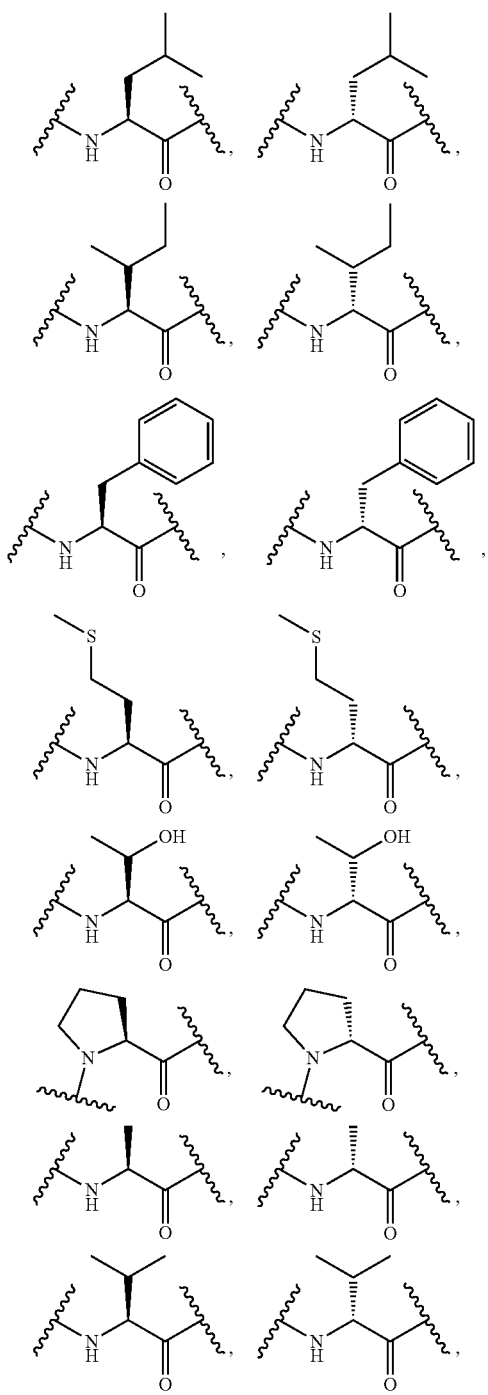

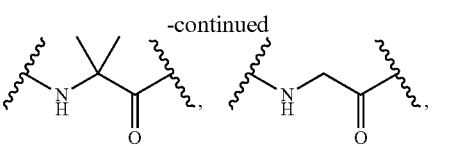

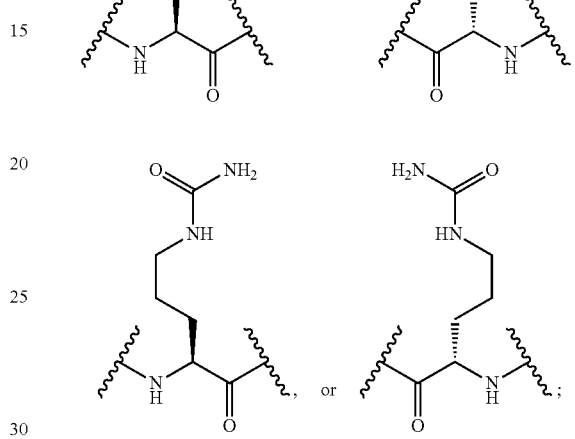

and wherein 1 methylene unit of L is optionally replaced with -M-; or

L is

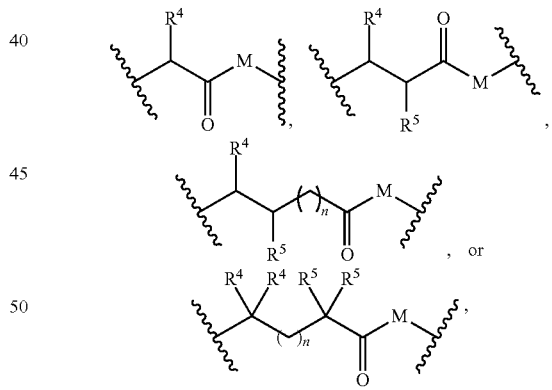

wherein either the right-hand side or left-hand side of L is attached to A.

In some embodiments, L is a bivalent, saturated or unsaturated, straight or branched, optionally substituted bivalent $C_{1-20}$ (e.g., $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or a naturally-occurring amino acid such as

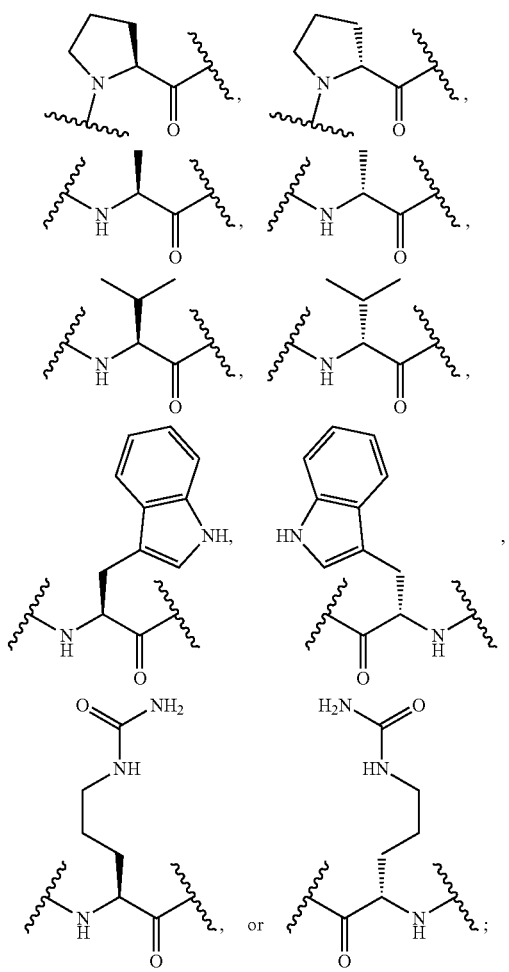

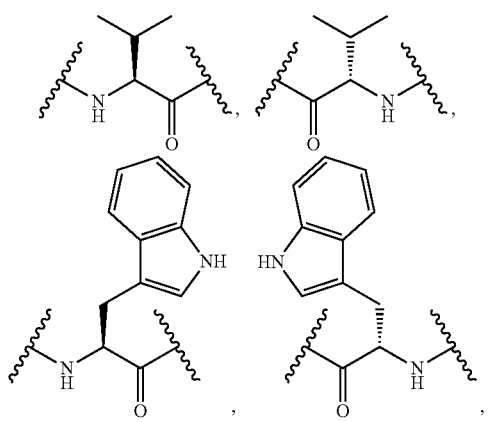

and wherein 1 methylene unit of L is optionally replaced with -M-. In some embodiments, L is a covalent bond or a bivalent, saturated or unsaturated, straight or branched $C_{3-16}$, $C_{5-12}$, $C_{8-16}$ or $C_{6-16}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—,

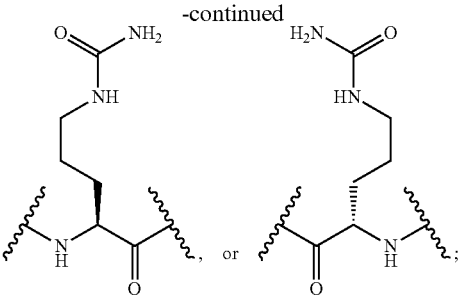

and 1 methylene unit of L is optionally replaced with -M-. In some embodiments, L is a bivalent, saturated, straight $C_{3-20}$, $C_{5-16}$, $C_{6-12}$, $C_{7-20}$, $C_{5-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, or —NRC(O)O—; and 1 methylene unit of L is optionally replaced with -M-. In some embodiments, L is a bivalent, saturated, straight $C_{3-20}$, $C_{5-16}$, $C_{6-12}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by —O—, —NR—, —S—, —OC(O)—, —C(O)O—, —C(O)—, —S(O)—, —S(O)$_2$—, or —C(S)—; and 1 methylene unit of L is optionally replaced with -M-.

In some embodiments, L is a bivalent, saturated $C_{3-30}$, $C_{5-25}$, $C_{6-20}$, $C_{8-20}$, $C_{10-18}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain optionally substituted with 1, 2, 3, or 4 $R^4$ groups, wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{1-25}$, $C_{5-25}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain optionally substituted with 1, 2, 3, or 4 groups each independently selected from deuterium, halogen, —CN, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

In some embodiments, L comprises (—OCH$_2$CH$_2$-)$_{1-8}$ (i.e., 1-8 polyethylene glycol (PEG) units). In some embodiments, L comprises 1, 2, 3, 4, 5, 6, 7, or 8 PEG units.

In some embodiments, 0-6 units of L are independently replaced by —O—, —S—, —OC(O)—, —C(O)O—, —C(O)—, or —C(S)—; and 1 methylene unit of L is optionally replaced with -M-.

In some embodiments, L comprises
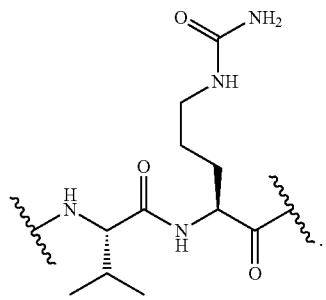 [SMILES: *N[C@H](C(=O)N[C@@H](CCCNC(N)=O)C(*)=O)C(C)C]
In some embodiments, L comprises
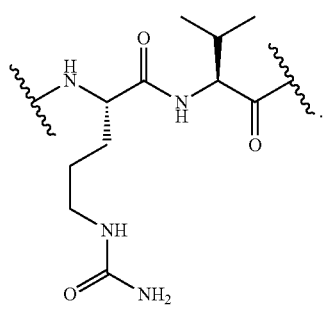 [SMILES: *N[C@@H](CCCNC(N)=O)C(=O)N[C@H](C(*)=O)C(C)C]
In some embodiments, L comprises
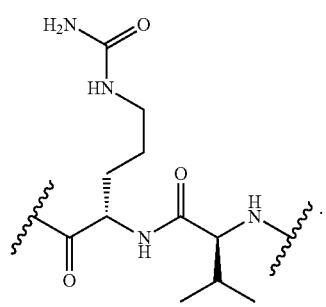 [SMILES: *N[C@H](C(=O)N[C@@H](CCCNC(N)=O)C(*)=O)C(C)C]
In some embodiments, L comprises
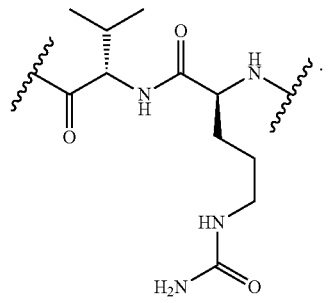 [SMILES: *N[C@@H](CCCNC(N)=O)C(=O)N[C@H](C(*)=O)C(C)C]
In some embodiments, L comprises
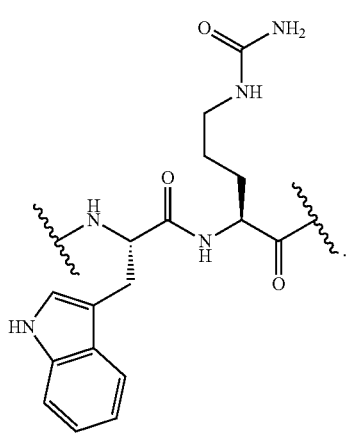 [SMILES: *N[C@@H](Cc1c[nH]c2ccccc12)C(=O)N[C@@H](CCCNC(N)=O)C(*)=O]
In some embodiments, L comprises
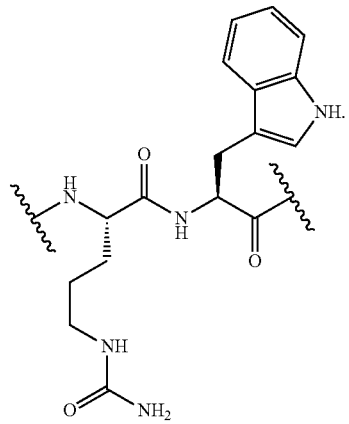 [SMILES: *N[C@@H](CCCNC(N)=O)C(=O)N[C@@H](Cc1c[nH]c2ccccc12)C(*)=O]
In some embodiments, L comprises
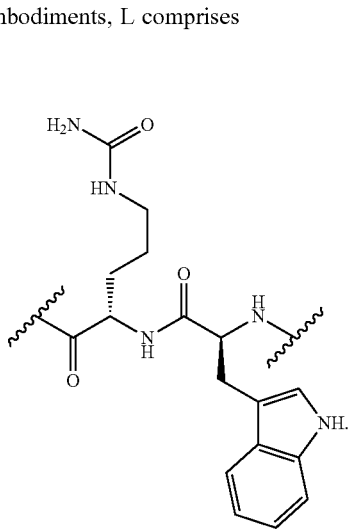

In some embodiments, L comprises

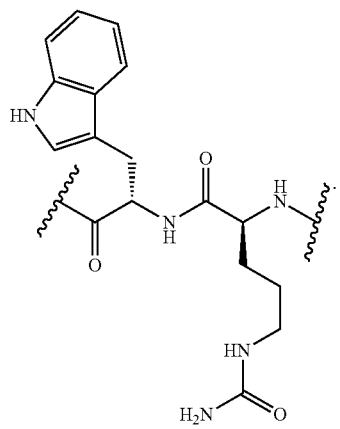 [SMILES: *N[C@@H](CCCNC(N)=O)C(=O)N[C@@H](Cc1c[nH]c2ccccc12)C(*)=O]

In some embodiments, 1 methylene unit of L is replaced with -M-.

In some embodiments, 1, 2, 3, or 4 available hydrogen atoms of L are replaced with an $R^4$ group, i.e., L is optionally substituted with 1, 2, 3, or 4 $R^4$ groups.

In some embodiments, a methylene unit of L is replaced with an amino acid. The amino acid may be naturally-occurring or non-naturally occurring. In some embodiments, the amino acid is selected from a non-polar or branched chain amino acid (BCAA). In some embodiments, the amino acid is selected from valine, isoleucine, leucine, methionine, alanine, proline, glycine, phenylalanine, tyrosine, tryptophan, histidine, asparagine, glutamine, serine threonine, lysine, arginine, histidine, aspartic acid, glutamic acid, cysteine, selenocysteine, or tyrosine. In some embodiments, the amino acid is an L-amino acid. In some embodiments, the amino acid is a D-amino acid.

In some embodiments, L is selected from those depicted in Table 1, below.

As defined above and described herein, each -Cy- is independently an optionally substituted 3-6 membered bivalent saturated, partially unsaturated, or aromatic ring having 0-4 heteroatoms independently selected from nitrogen, oxygen, or sulfur.

In some embodiments, -Cy- is an optionally substituted 3-6 membered bivalent saturated ring having 0-4 heteroatoms independently selected from nitrogen, oxygen, or sulfur. In some embodiments, -Cy- is an optionally substituted 5-membered bivalent saturated, partially unsaturated, or aromatic ring having 0-4 heteroatoms independently selected from nitrogen, oxygen, or sulfur. In some embodiments, -Cy- is an optionally substituted 6-membered bivalent saturated, partially unsaturated, or aromatic ring having 0-4 heteroatoms independently selected from nitrogen, oxygen, or sulfur. In some embodiments, -Cy- is selected from those depicted in Table 1, below.

As defined above and described herein, each $R^4$ and $R^5$ is independently hydrogen, deuterium, halogen, —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, $R^4$ is hydrogen. In some embodiments, $R^4$ is deuterium. In some embodiments, $R^4$ is halogen. In some embodiments, $R^4$ is —CN. In some embodiments, $R^4$ is —OR. In some embodiments, $R^4$ is —$NR_2$. In some embodiments, $R^4$ is —SR. In some embodiments, $R^4$ is a 3-8 membered saturated or partially unsaturated monocyclic carbocyclic ring. In some embodiments, $R^4$ is phenyl. In some embodiments, $R^4$ is an 8-10 membered bicyclic aromatic carbocyclic ring. In some embodiments, $R^4$ is a 4-8 membered saturated or partially unsaturated monocyclic heterocyclic ring having 1-2 heteroatoms independently selected from nitrogen, oxygen, or sulfur. In some embodiments, $R^4$ is a 5-6 membered monocyclic heteroaromatic ring having 1-4 heteroatoms independently selected from nitrogen, oxygen, or sulfur. In some embodiments, $R^4$ is an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with 1, 2, 3, 4, 5, or 6 deuterium or halogen atoms. In some embodiments, two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^4$ is independently hydrogen, deuterium, halogen, —CN, or $C_{1-4}$ aliphatic optionally substituted with 1, 2, 3, 4, 5, or 6 deuterium or halogen atoms; or two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^4$ is not hydrogen.

In some embodiments, $R^4$ is $C_{1-4}$ aliphatic optionally substituted with 1, 2, 3, 4, 5, or 6 deuterium or halogen atoms. In some embodiments, $R^4$ is $C_{1-4}$ alkyl optionally substituted with 1, 2, or 3 deuterium or halogen atoms. In some embodiments, $R^4$ is methyl optionally substituted with 1, 2, or 3 deuterium or halogen atoms. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is isobutyl. In some embodiments, $R^4$ is tert-butyl. In some embodiments, $R^4$ is selected from those depicted in Table 1, below.

In some embodiments, $R^5$ is hydrogen. In some embodiments, $R^5$ is deuterium. In some embodiments, $R^5$ is halogen. In some embodiments, $R^5$ is —CN. In some embodiments, $R^5$ is —OR. In some embodiments, $R^5$ is —NR$_2$. In some embodiments, $R^5$ is —SR. In some embodiments, $R^5$ is a 3-8 membered saturated or partially unsaturated monocyclic carbocyclic ring. In some embodiments, $R^5$ is phenyl. In some embodiments, $R^5$ is an 8-10 membered bicyclic aromatic carbocyclic ring. In some embodiments, $R^5$ is a 4-8 membered saturated or partially unsaturated monocyclic heterocyclic ring having 1-2 heteroatoms independently selected from nitrogen, oxygen, or sulfur. In some embodiments, $R^5$ is a 5-6 membered monocyclic heteroaromatic ring having 1-4 heteroatoms independently selected from nitrogen, oxygen, or sulfur. In some embodiments, $R^5$ is an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with 1, 2, 3, 4, 5, or 6 deuterium or halogen atoms. In some embodiments, two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^5$ is independently hydrogen, deuterium, halogen, —CN, or $C_{1-4}$ aliphatic optionally substituted with 1, 2, 3, 4, 5, or 6 deuterium or halogen atoms; or two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^5$ is not hydrogen.

In some embodiments, $R^5$ is $C_{1-4}$ aliphatic optionally substituted with 1, 2, 3, 4, 5, or 6 deuterium or halogen atoms. In some embodiments, $R^5$ is methyl optionally substituted with 1, 2, or 3 deuterium or halogen atoms. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is isobutyl. In some embodiments, $R^5$ is tert-butyl. In some embodiments, $R^5$ is selected from those depicted in Table 1, below.

As defined above and described herein, -M- is a self-immolative group.

In some embodiments, -M- is an acetal, an obenzylalcohol, a p-benzylalcohol, a styryl group, a coumarin, or a group that self-immolates via a cyclization reaction. In some embodiments, -M- is selected from a disulfide, hydrazone, acetal self-immolative group, carboxyacetal self-immolative group, carboxy(methylacetal) self-immolative group, p-hydroxybenzyl self-immolative group, para-hydroxybenzyl carbonyl self-immolative group, flipped ester self-immolative group, trimethyl lock, or 2-hydroxyphenyl carbamate (2-HPC) self-immolative group.

In some embodiments, -M- is:

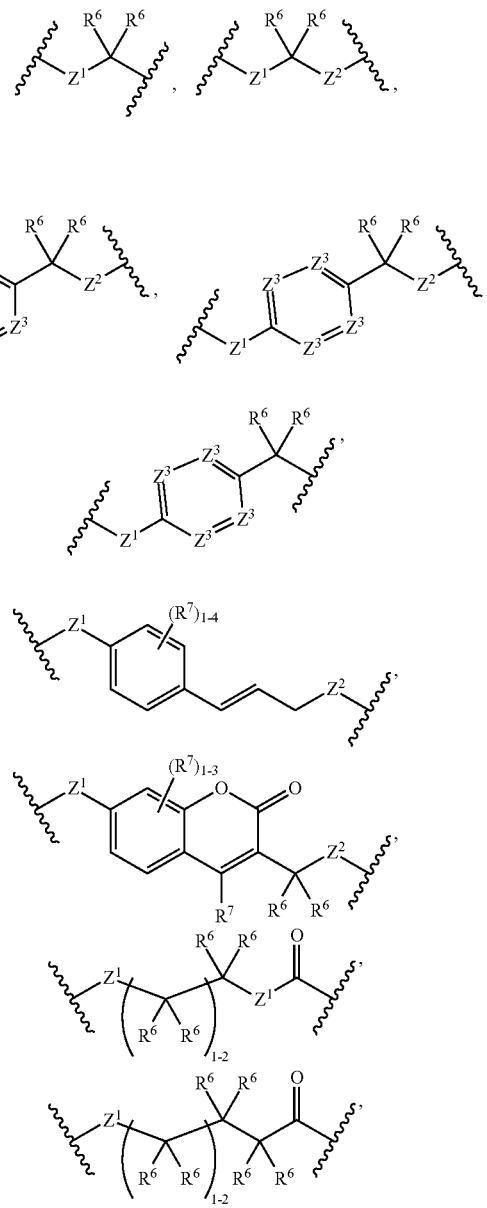

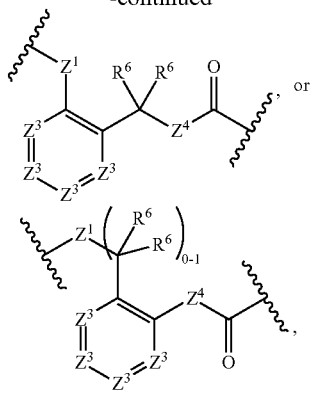

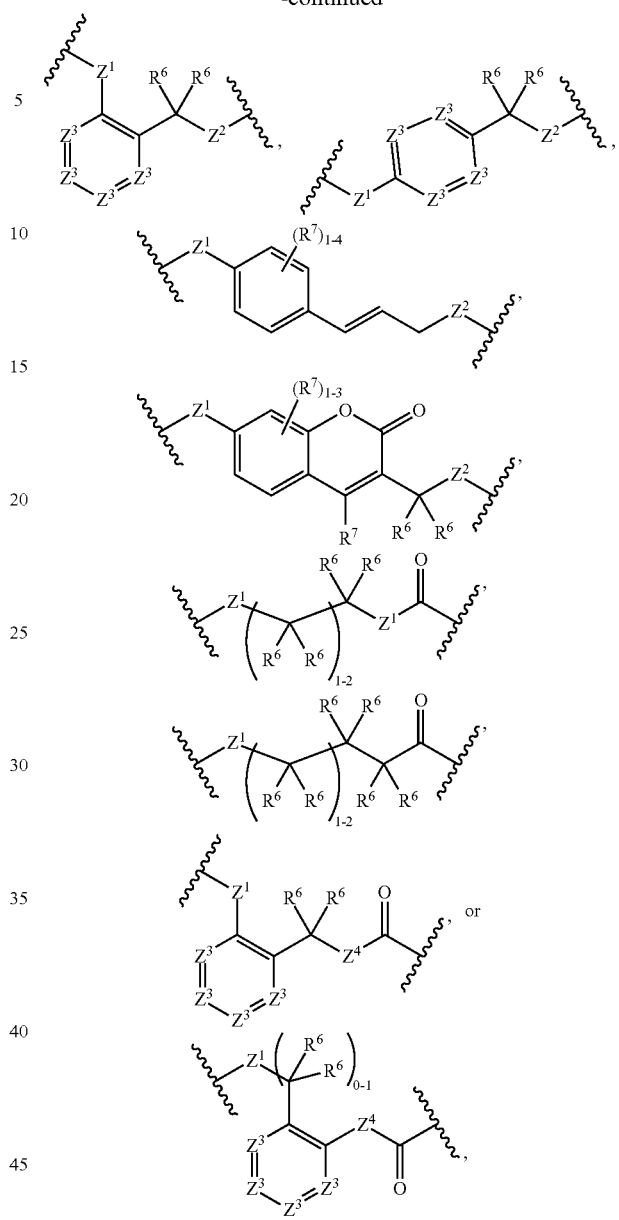

wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C(R$^7$)—; and each $Z^4$ is independently selected from —O—, —NR—, —S—, —C(R$^6$)$_2$—, or a covalent bond.

In some embodiments, -M- is selected from one of the following:

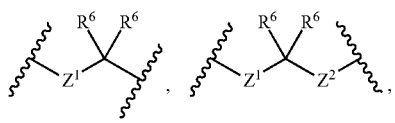

wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C($R^7$)—; and each $Z^4$ is independently selected from —O—, —NR—, —S—, —C($R^6$)$_2$—, or a covalent bond.

As defined generally above and described herein, each $R^6$ is independently selected from hydrogen, deuterium, $C_{1-10}$ aliphatic, halogen, or —CN. In some embodiments, $R^6$ is hydrogen. In some embodiments, $R^6$ is deuterium. In some embodiments, $R^6$ is $C_{1-5}$ aliphatic. In some embodiments, $R^6$ is halogen. In some embodiments, $R^6$ is —CN.

In some embodiments, $R^6$ is hydrogen, $C_{1-5}$ alkyl, halogen, or —CN. In some embodiments, $R^6$ is hydrogen or $C_{1-3}$ alkyl. In some embodiments, $R^6$ is hydrogen or methyl.

In some embodiments, each instance of $R^6$ in the above formulae is the same. In some embodiments, each $R^6$ is different. In some embodiments, one $R^6$ is hydrogen. In some embodiments, one $R^6$ is $C_{1-5}$ aliphatic. In some embodiments, each $R^6$ is hydrogen. In some embodiments, each $R^6$ is $C_{1-5}$ aliphatic. In some embodiments, $R^6$ is selected from those depicted in Table 1, below.

As defined generally above and described herein, each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic group is optionally substituted with 1, 2, 3, 4, 5, or 6 deuterium or halogen atoms.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —NR$_2$. In some embodiments, $R^7$ is —NO$_2$. In some embodiments, $R^7$ is —SR. In some embodiments, $R^7$ is a 3-8 membered saturated or partially unsaturated monocyclic carbocyclic ring. In some embodiments, $R^7$ is phenyl. In some embodiments, $R^7$ is an 8-10 membered bicyclic aromatic carbocyclic ring. In some embodiments, $R^7$ is a 4-8 membered saturated or partially unsaturated monocyclic heterocyclic ring having 1-2 heteroatoms independently selected from nitrogen, oxygen, or sulfur. In some embodiments, $R^7$ is a 5-6 membered monocyclic heteroaromatic ring having 1-4 heteroatoms independently selected from nitrogen, oxygen, or sulfur. In some embodiments, $R^7$ is or an 8-10 membered bicyclic heteroaromatic ring having 1-5 heteroatoms independently selected from nitrogen, oxygen, or sulfur. In some embodiments, $R^7$ is or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^7$ is a $C_{1-6}$ aliphatic group optionally substituted with 1, 2, 3, 4, 5, or 6 deuterium or halogen atoms.

In some embodiments, $R^7$ is hydrogen, deuterium, halogen, —CN, —OR, —NR$_2$, —NO$_2$, —SR, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with —CN, —OR, —NR$_2$, —SR, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-6}$ aliphatic group is optionally substituted with 1, 2, 3, 4, 5, or 6 deuterium or halogen atoms. In some embodiments, $R^7$ is hydrogen, deuterium, halogen, —CN, a 3-6 membered saturated or partially unsaturated monocyclic carbocyclic ring, phenyl, a 5-6 membered monocyclic heteroaromatic ring having 1-4 heteroatoms independently selected from nitrogen, oxygen, or sulfur, or a $C_{1-4}$ alkyl group optionally substituted with —CN, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-4}$ alkyl group is optionally substituted with 1, 2, 3, 4, 5, or 6 deuterium or halogen atoms. In some embodiments, $R^7$ is hydrogen, halogen, —CN, —OR, or $C_{1-4}$ alkyl.

In some embodiments, R is hydrogen or $C_{1-4}$ alkyl.

In some embodiments, $R^7$ is selected from those depicted in Table 1, below.

As defined generally above and described herein, each $Z^1$ is independently selected from —O—, —NR—, or —S—. In some embodiments, $Z^1$ is —O—. In some embodiments, $Z^1$ is —NR—. In some embodiments, $Z^1$ is —S. In some embodiments, $Z^1$ is —NH— or —NMe-.

In some embodiments, $Z^1$ is selected from those depicted in Table 1, below.

As defined generally above and described herein, each $Z^2$ is independently selected from —O—, —NR—, —S—, —OC(O)—, —NRC(O)O—, or —OC(O)NR—.

In some embodiments, $Z^2$ is —O—. In some embodiments, $Z^2$ is —NR—. In some embodiments, $Z^2$ is —S—. In some embodiments, $Z^2$ is —OC(O)—. In some embodiments, $Z^2$ is —NRC(O)O—. In some embodiments, $Z^2$ is —OC(O)NR—.

In some embodiments, each $Z^2$ is independently selected from —O—, —NH—, —NMe-, —S—, —OC(O)—, —NHC(O)O—, —NMeC(O)O—, —OC(O)NH—, or —OC(O)NMe-.

In some embodiments, $Z^2$ is covalently bound to A. In some embodiments, $Z^2$ is —O— or —OC(O)O—.

In some embodiments, $Z^2$ is selected from those depicted in Table 1, below.

In some embodiments, $Z^1$ is —O— and $Z^2$ is —O— or —OC(O)O—.

As defined generally above and described herein, each $Z^3$ is independently selected from =N— or =C($R^7$)—. In some embodiments, $Z^3$ is =N—. In some embodiments, $Z^3$ is =C($R^7$)—.

In some embodiments, $Z^3$ is selected from those depicted in Table 1, below.

As defined generally above and described herein, each $Z^4$ is independently selected from —O—, —NR—, —S—, —C($R^6$)$_2$—, or a covalent bond. In some embodiments, $Z^4$ is —O—. In some embodiments, $Z^4$ is —NR—. In some embodiments, $Z^4$ is —S—. In some embodiments, $Z^4$ is —C($R^6$)$_2$—. In some embodiments, $Z^4$ is a covalent bond.

In some embodiments, $Z^4$ is selected from those depicted in Table 1, below.

In some embodiments, -M- is

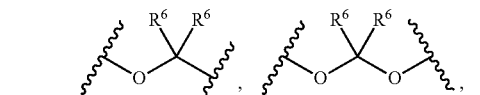

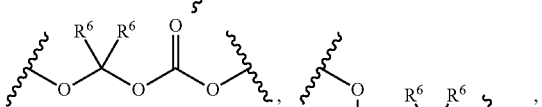

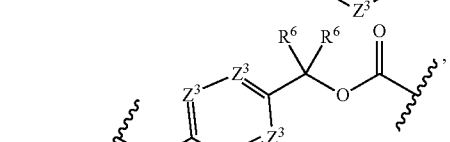

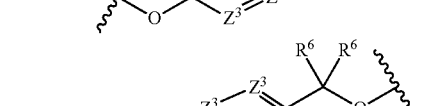

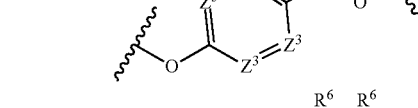

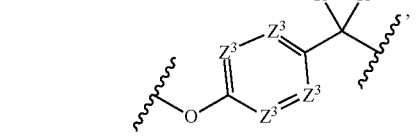

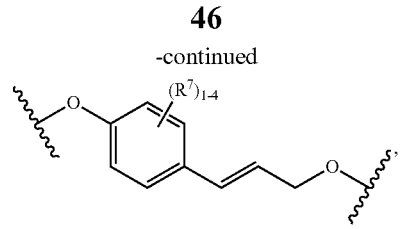

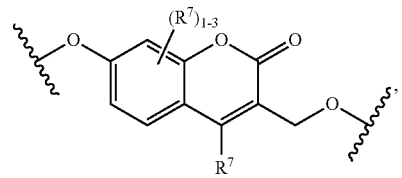

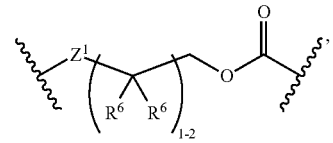

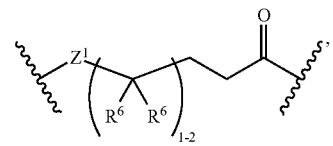

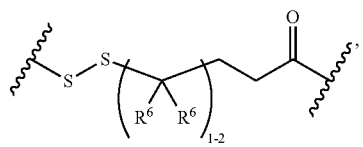

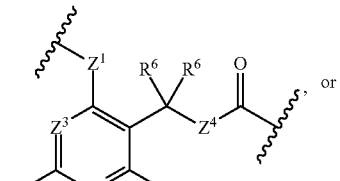

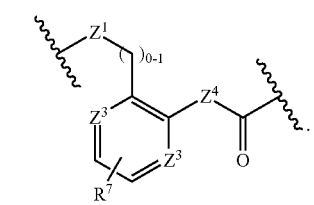

In some embodiments, -M- is selected from one of the following:

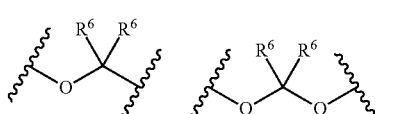

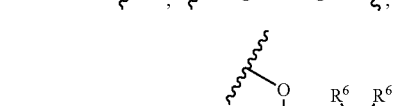

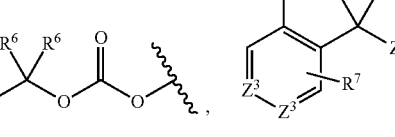

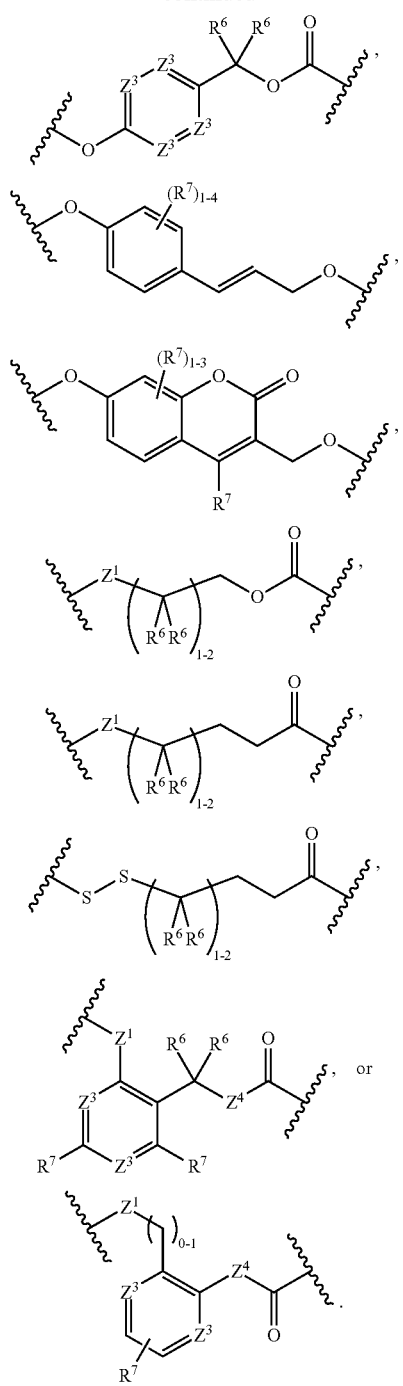
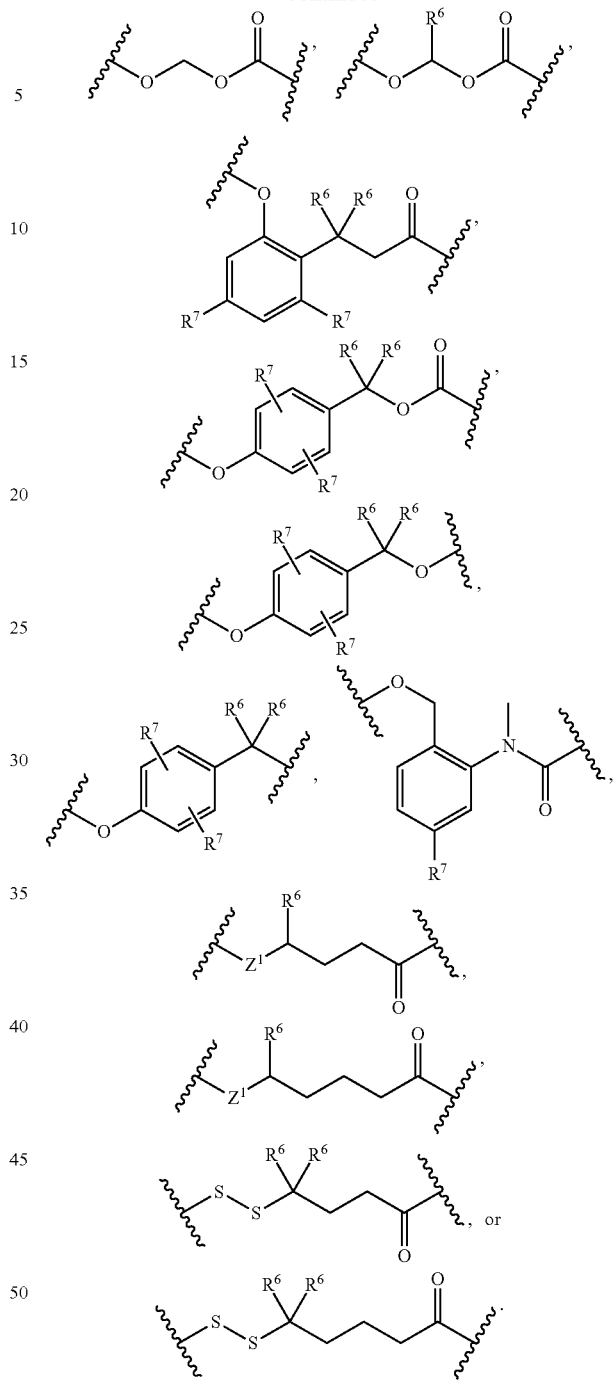
In some embodiments, -M- is
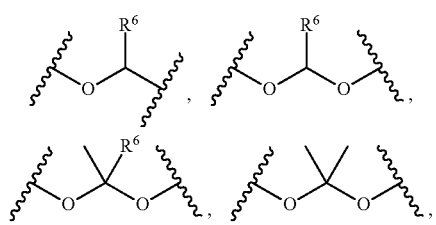
In some embodiments, -M- is selected from
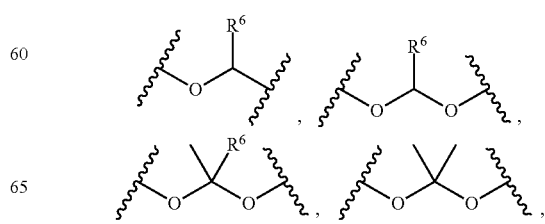

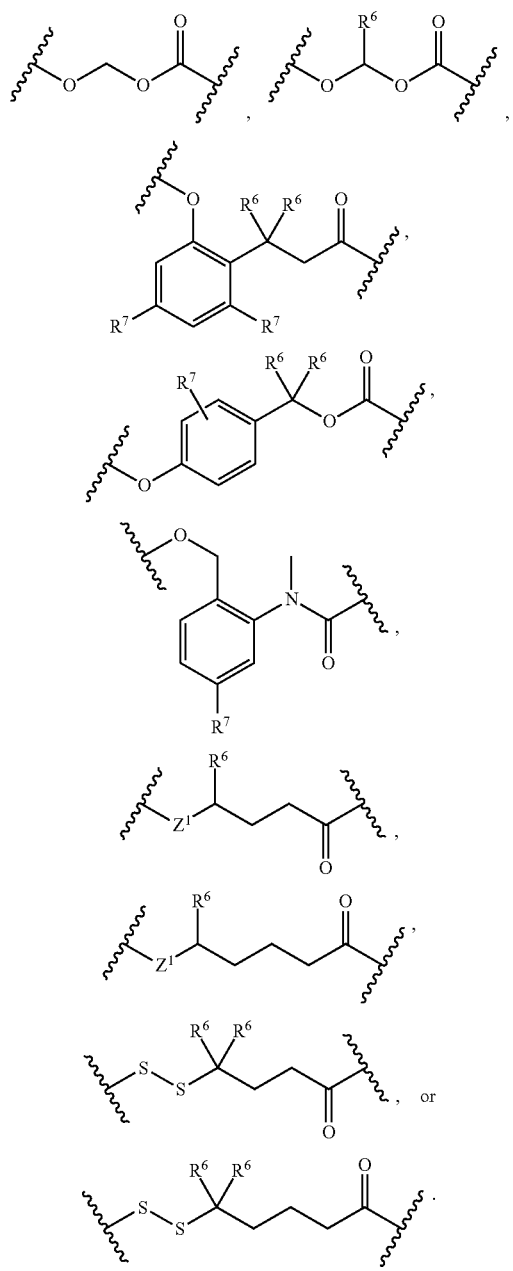
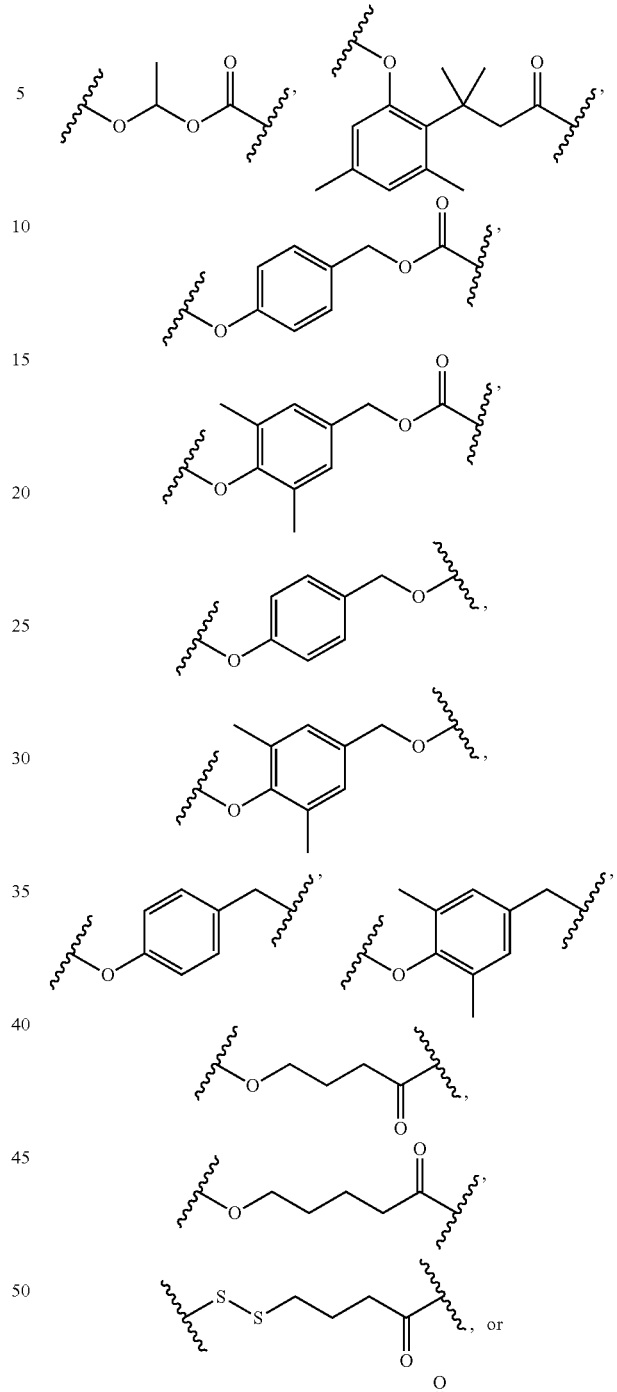
In some embodiments, -M- is
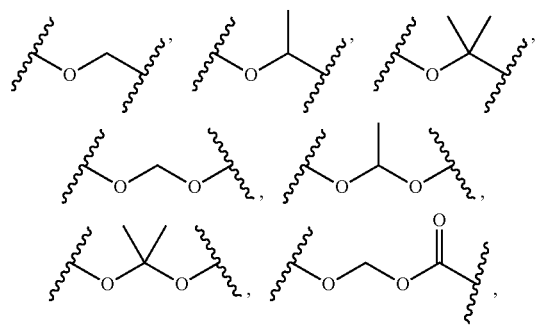
In some embodiments, -M- is selected from
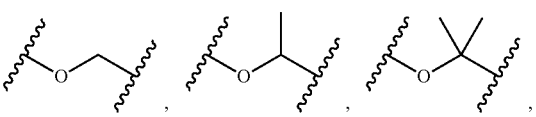

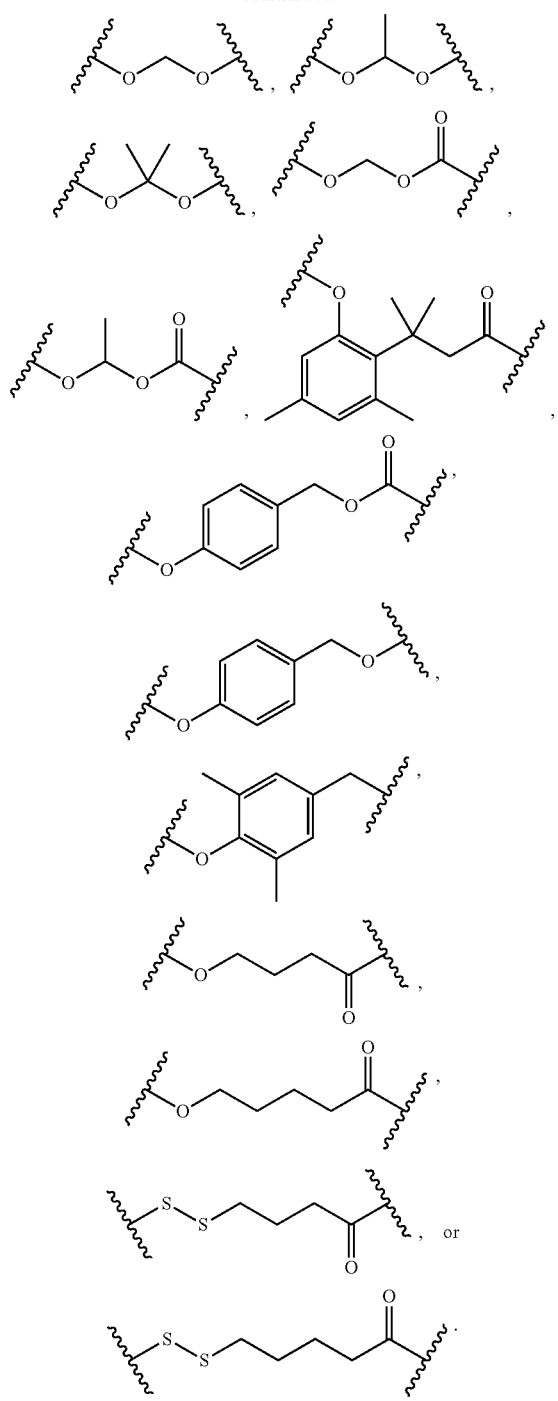

In some embodiments, -M- is selected from

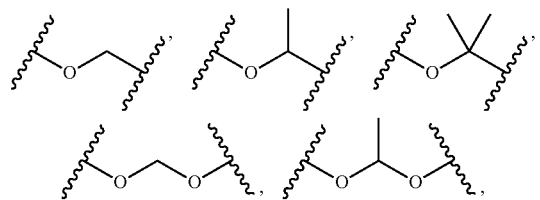

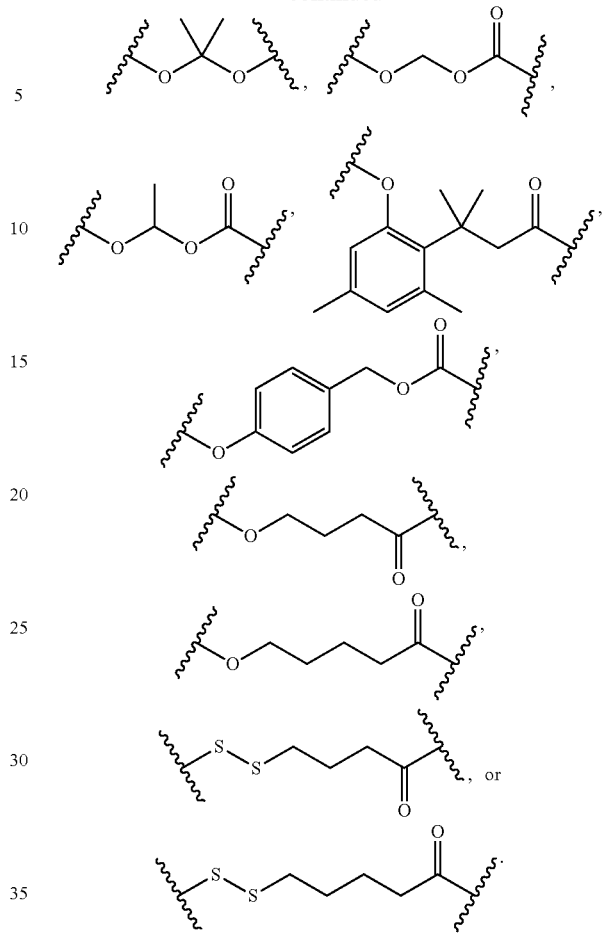

In some embodiments, -M- is selected from those depicted in Table 1, below.

As defined above and described herein, n is 0-18.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 1-16, 1-14, 1-12, 1-10, 1-8, 1-6, 1-3, 2-16, 2-14, 2-12, 2-10, 2-8, 2-6, 3-12, 3-8, 3-6, 4-10, 4-8, 4-6, 5-10, 5-8, 5-6, 6-18, 6-10, 6-8, 8-12, 5-18, 5-13, 8-18, 8-17, 8-16, 8-15, 8-16, or 6-16.

As defined above and described herein, each m is independently 0-6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, each m is independently 0, 1, or 2. In some embodiments, each m is independently 1, 2, 3, or 4.

As defined above and described herein, A is mycophenolic acid or a derivative, analogue, or prodrug thereof.

In some embodiments, A is mycophenolic acid, or a pharmaceutically acceptable salt thereof. Mycophenolic acid has the following structure:

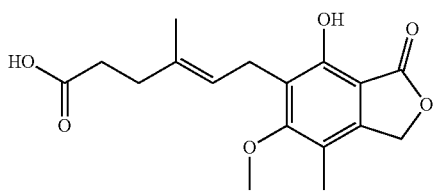 [SMILES: COc1c(C)c2c(c(O)c1C/C=C(\C)CCC(=O)O)C(=O)OC2]

In some embodiments, A is a derivative or analogue of mycophenolic acid (MPA). An MPA "derivative" as used herein generally refers to an MPA molecule that has been functionalized or chemically altered. Exemplary MPA derivatives include, without limitation, MPA with a modified side chain, MPA substituted at the phenolic OH group, and the like. More specific examples of MPA derivatives include, without limitation, euparvic acid, RS-97613, F01 1358B, F01 1358A, F13459, mycophenolic acid-amino acid conjugates (see, e.g., Iwaszkiewicz-Grzes, D. et al., European Journal of Medicinal Chemistry Volume 69, November 2013, Pages 863-871), mycophenolic acid modified with an adenine dinucleotide, C2-mycophenolic adenine dinucleotide, C4-mycophenolic adenine dinucleotide, C6-mycophenolic adenine dinucleotide, mycophenolic acid glucuronide, beta-methylene-mycophenolic adenine dinucleotide, mycophenolic adenine dinucleotide, mycophenolate mofetil, dextran T70-mycophenolic acid conjugate, ethyl 0-(N-(4 carboxyphenyl)carbamoyl) mycophenolate, carbamoyl mycophenolic acid ethyl ester, an ester of MPA, and combinations thereof.

In other embodiments, A is a prodrug of mycophenolic acid. In some embodiments, A is mycophenolate mofetil (MMF). Mycophenolate mofetil has the following structure:

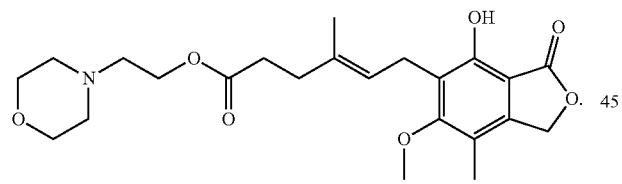

In some embodiments, A is a pharmaceutically acceptable salt of mycophenolic acid, such as the sodium salt. In some embodiments, A is an ester of mycophenolic acid, such as a methyl, ethyl, phenyl, isopropyl, allyl, $C_{1-6}$ alkyl, or $C_{1-12}$ aliphatic ester.

As used herein, depiction of brackets around a therapeutic agent, A,

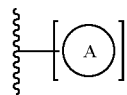

means that the

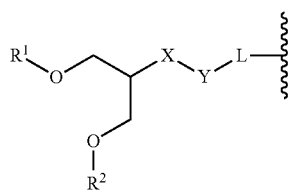

moiety is covalently attached to A at any available modifiable nitrogen, oxygen, or sulfur atom.

In some embodiments, A is

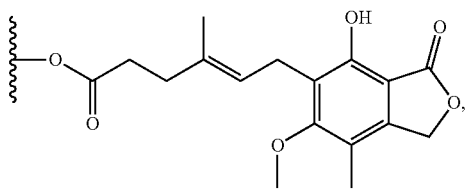

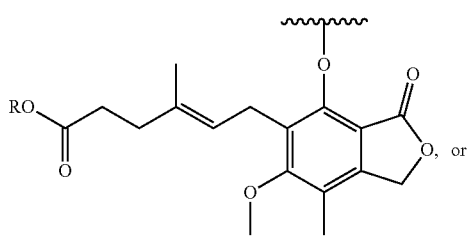

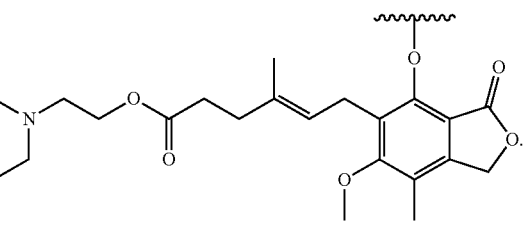

In some embodiments, the present invention provides a compound of Formula VI-a, VI-b, or VI-c:

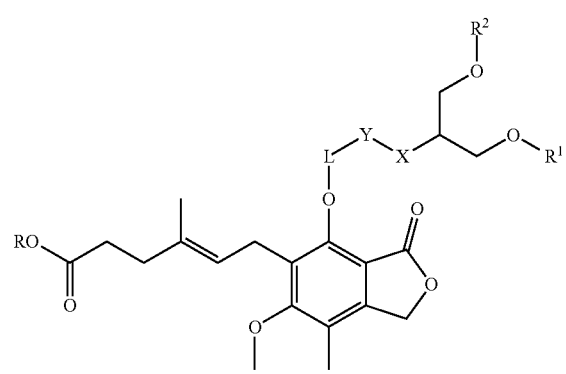

VI-a

-continued

VI-b

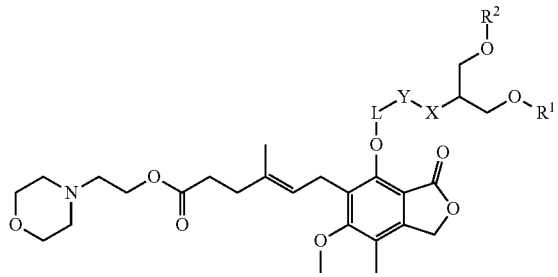

VI-c

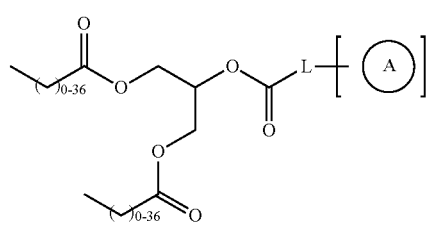

or a pharmaceutically acceptable salt thereof, wherein each of L, $R^1$, $R^2$, R, X, and A is as defined above and described in embodiments herein, both singly and in combination.

In some embodiments, the present invention provides a compound of Formula VII-a or VII-b:

VII-a

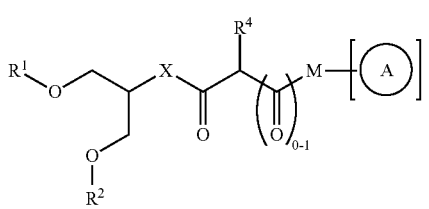

VII-b

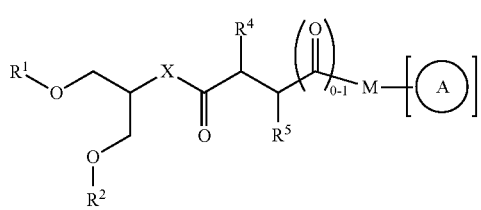

or a pharmaceutically acceptable salt thereof, wherein each of $R^1$, $R^2$, $R^4$, $R^5$, X, M, and A is as defined above and described in embodiments herein, both singly and in combination.

In some embodiments, the present invention provides a compound of Formula VIII-a or VIII-b:

VIII-a

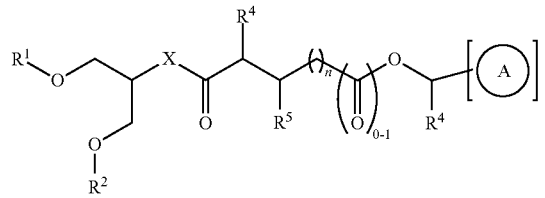

VIII-b

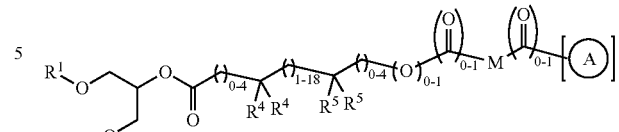

or a pharmaceutically acceptable salt thereof, wherein each of $R^1$, $R^2$, $R^4$, $R^5$, X, n, and A is as defined above and described in embodiments herein, both singly and in combination.

In some embodiments, the present invention provides a compound of Formula IX:

IX

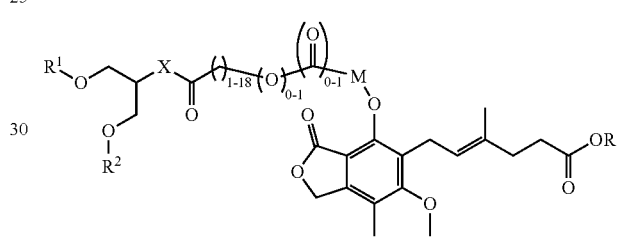

or a pharmaceutically acceptable salt thereof, wherein each of $R^1$, $R^2$, R, X, and -M- is as defined above and described in embodiments herein, both singly and in combination.

In some embodiments, the present invention provides a compound of Formula X:

X

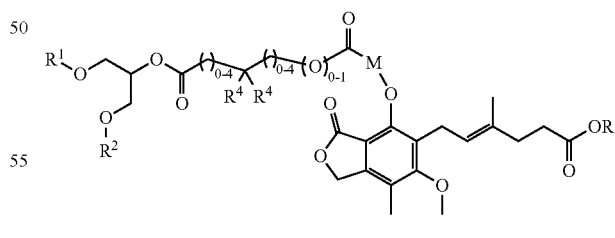

or a pharmaceutically acceptable salt thereof, wherein each of $R^1$, $R^2$, $R^4$, R, and -M- is as defined above and described in embodiments herein, both singly and in combination.

In some embodiments, the present invention provides a compound of Formula XI-a, XI-b, XI-c, XI-d, XI-e, XI-f, or XI-g:

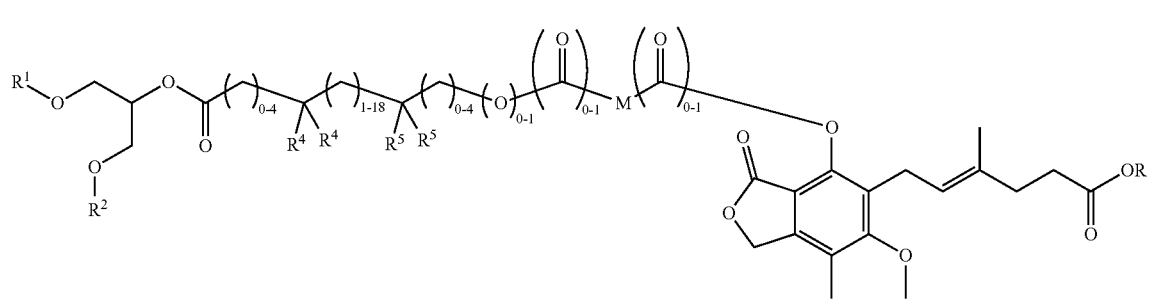
XI-a
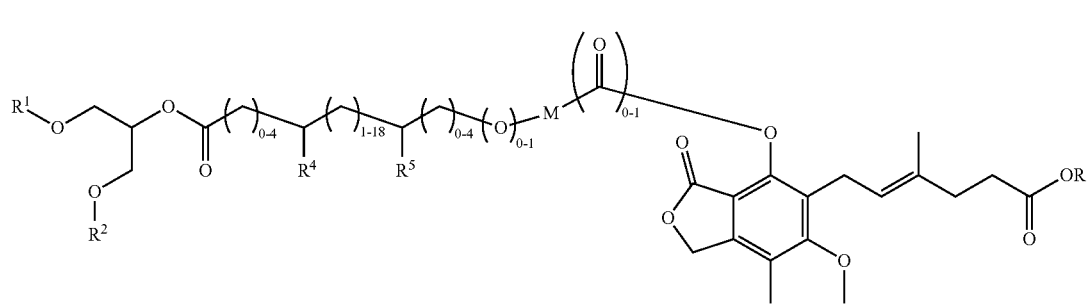
XI-b
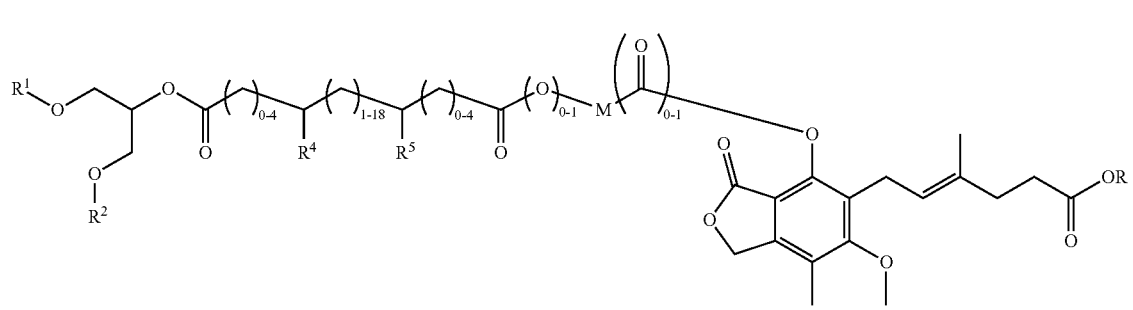
XI-c
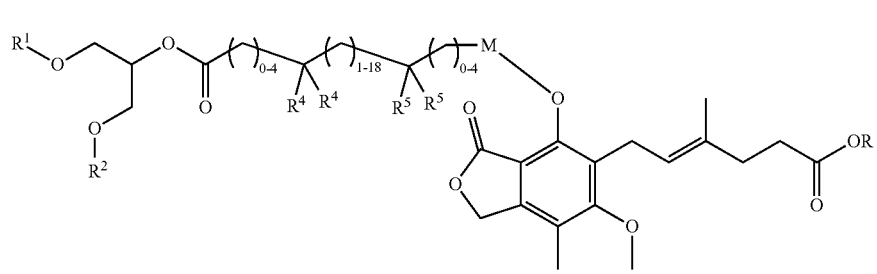
XI-d
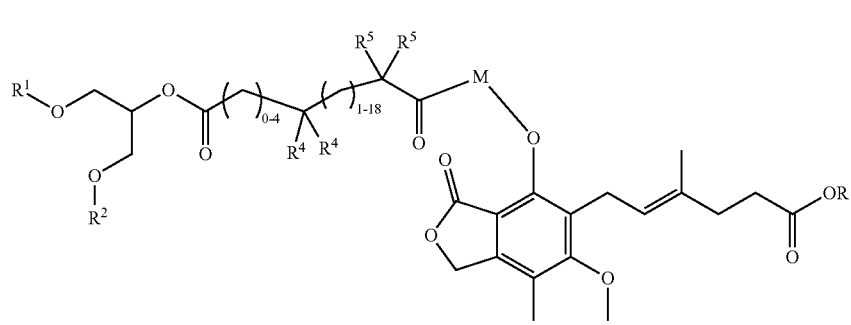
XI-e -continued XI-f
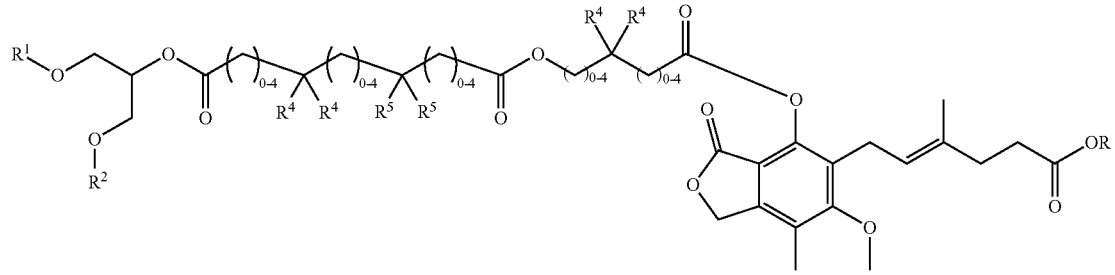

XI-g
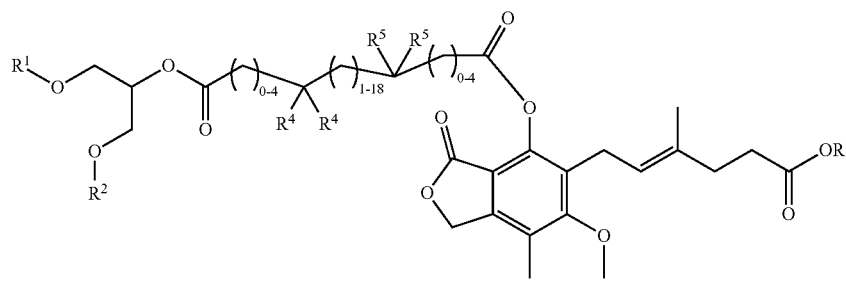

or a pharmaceutically acceptable salt thereof, wherein each of $R^1$, $R^2$, $R^4$, $R^5$, R, and -M- is as defined above and described in embodiments herein, both singly and in combination.

In some embodiments, the present invention provides a compound of Formula XII-a or XII-b:

XII-a
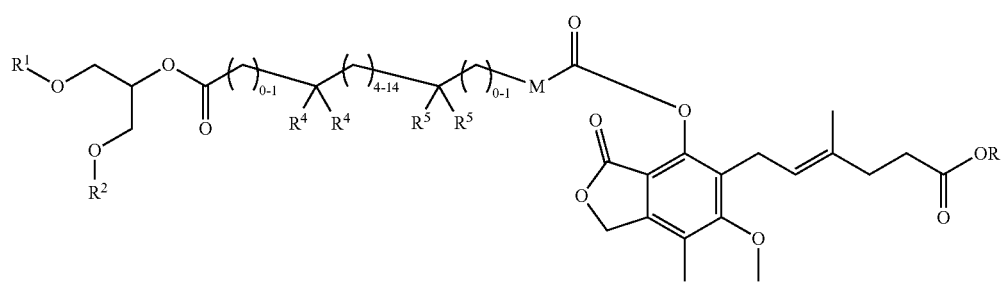

XII-b
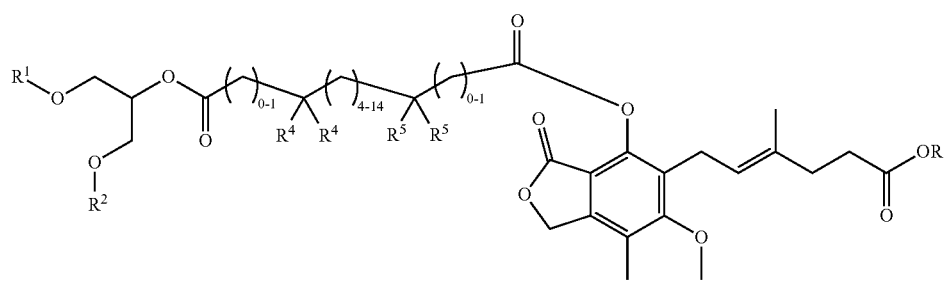

or a pharmaceutically acceptable salt thereof, wherein each of $R^1$, $R^2$, $R^4$, $R^5$, R, and -M- is as defined above and described in embodiments herein, both singly and in combination.

In the above formulae, when a range of numbers, such as 0-4 or 1-18, is disclosed, individual integers within the range are also specifically disclosed. Thus, the above range of 0-4 includes 0, 1, 2, 3, and 4. The range 1-18 includes 1, 2, 3, 4, 5, 6, 7, 8, 9, 10, 11, 12, 13, 14, 15, 16, 17, and 18 as well as ranges in between such as 6-18 and 8-18. The range 0-1 includes 0 and 1, i.e. the group is optionally present. Where more than one range is disclosed in a formula, each range is independently and optionally selected from the disclosed range. For example, in Formula XI-c above, each 0-4 and 0-1 range is varied independently of the others.

In one aspect, the present invention provides a lipid prodrug compound, shown in Table 1, or a pharmaceutically acceptable salt thereof:

TABLE 1
Exemplary Compounds
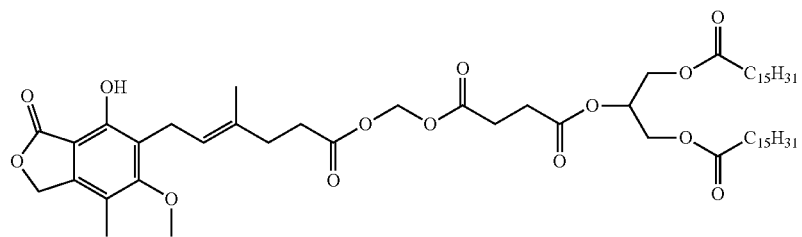
I-1
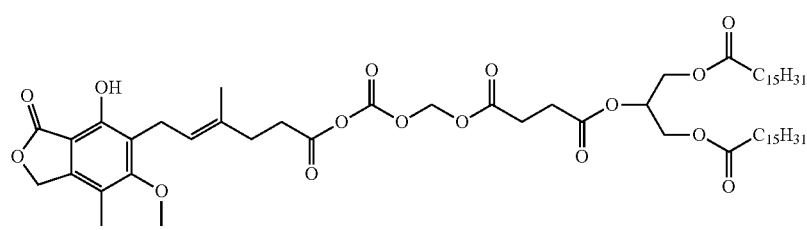
I-2
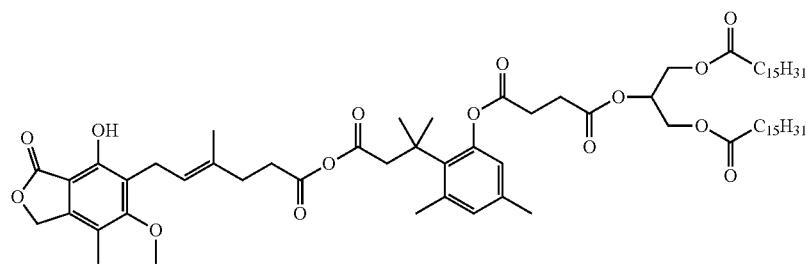
I-3
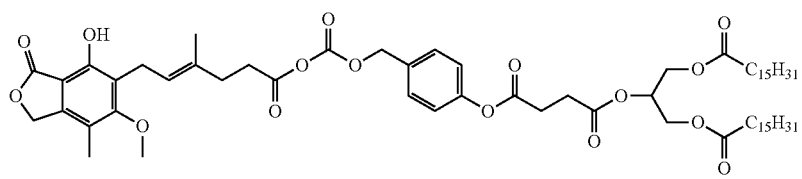
I-4
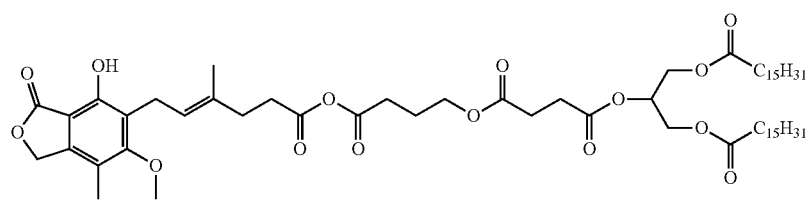
I-5
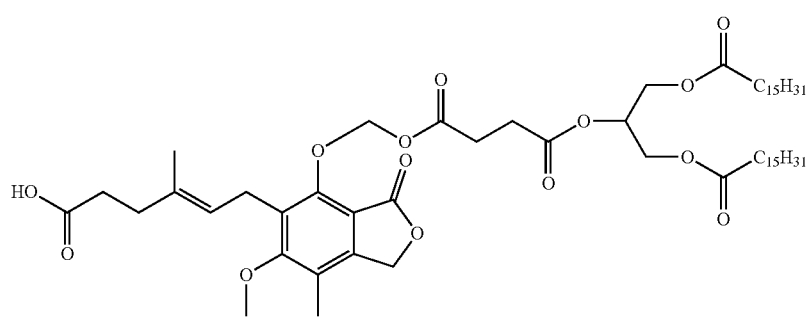
I-6

TABLE 1-continued
Exemplary Compounds
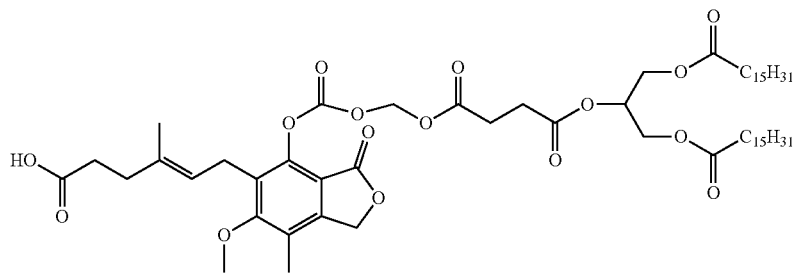
I-7
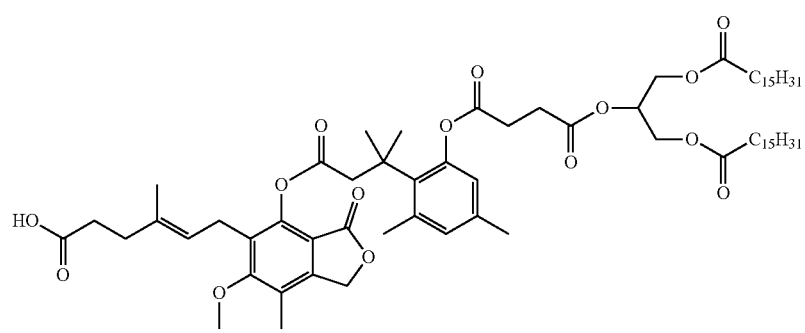
I-8
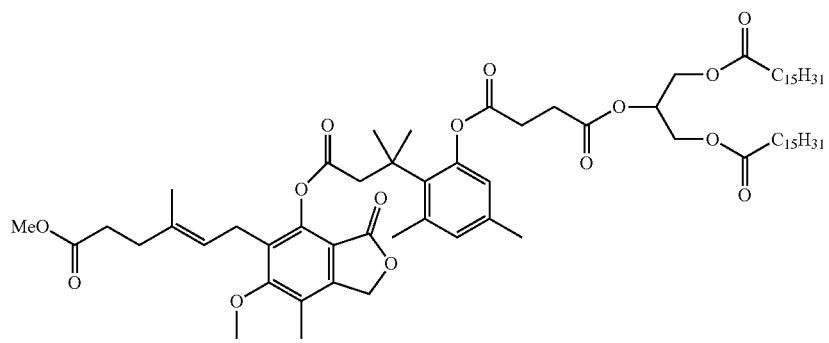
I-8'
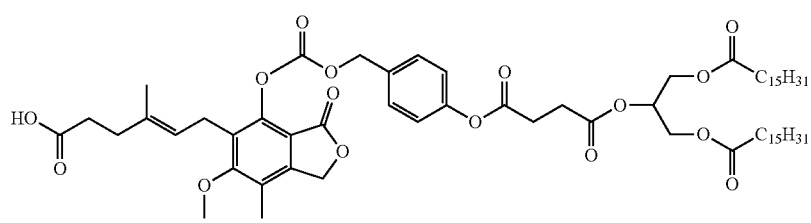
I-9
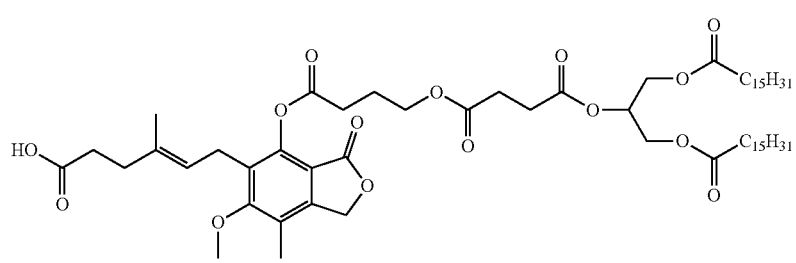
I-10

TABLE 1-continued
Exemplary Compounds
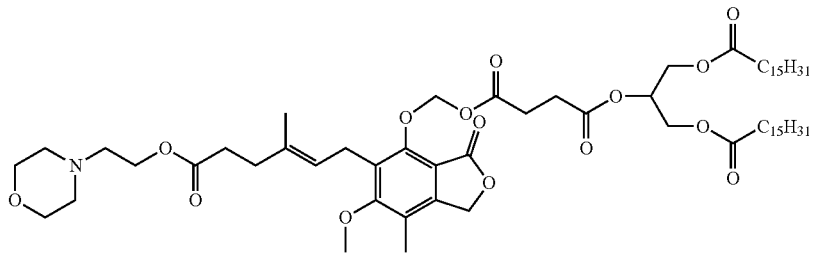
I-11
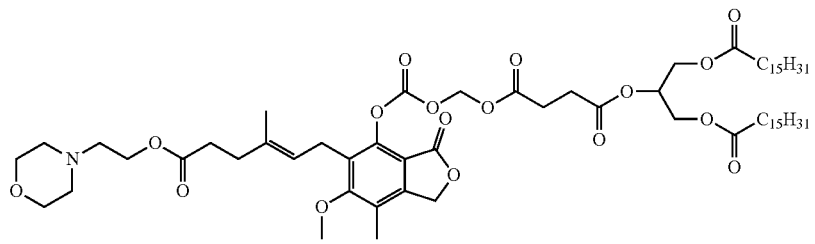
I-12
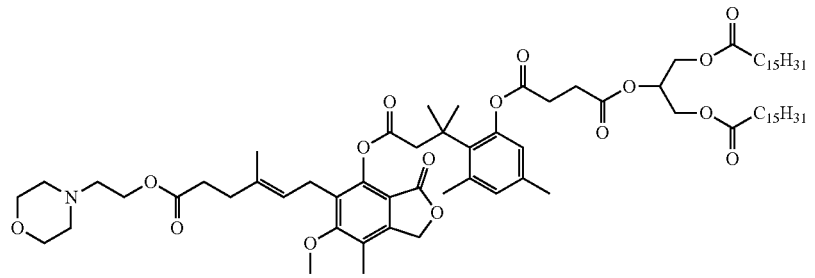
I-13
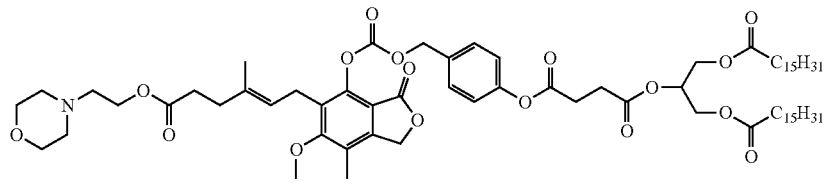
I-14
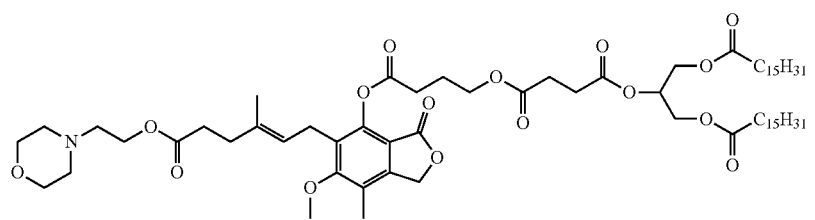
I-15

TABLE 1-continued
Exemplary Compounds
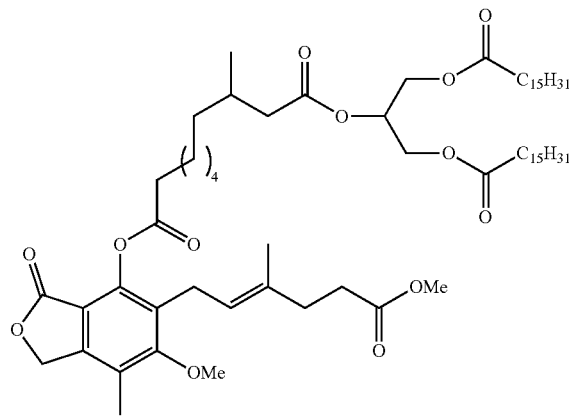
I-16
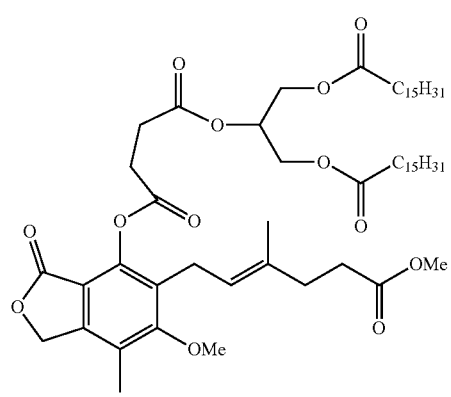
I-17
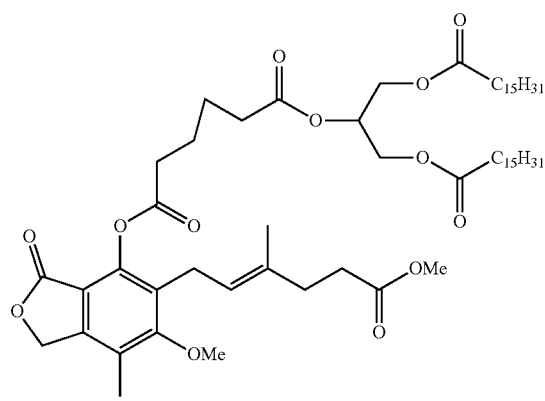
I-18
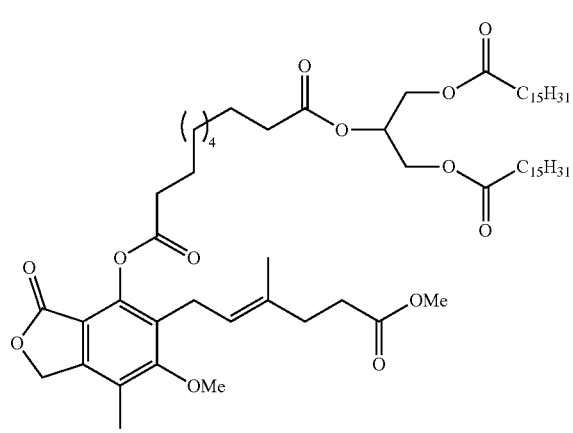
I-19

TABLE 1-continued
Exemplary Compounds
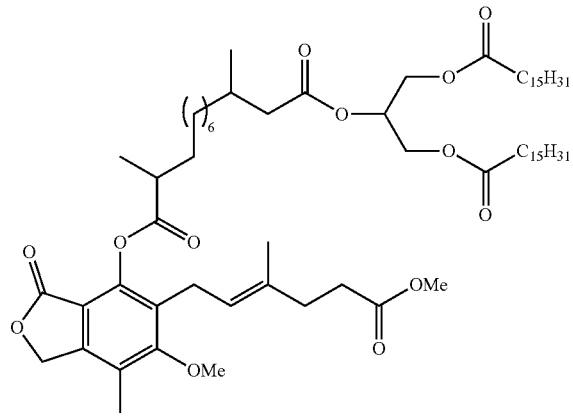
I-20
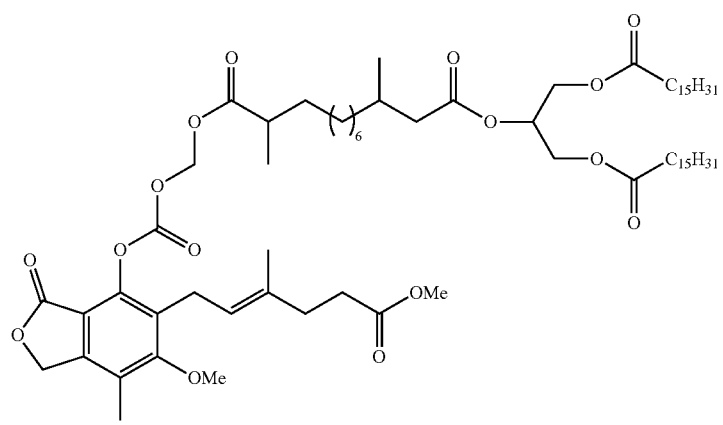
I-21
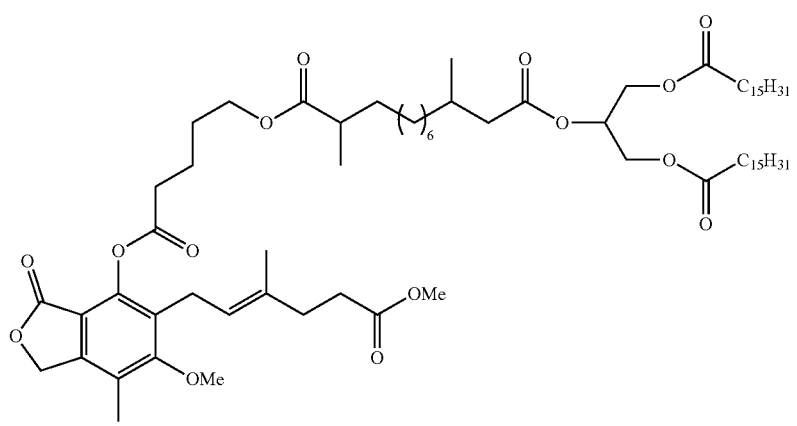
I-22
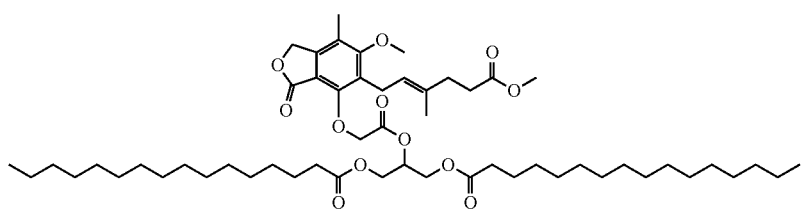 [SMILES: CCCCCCCCCCCCCCCC(=O)OCC(COC(=O)CCCCCCCCCCCCCCC)OC(=O)COc1c(C/C=C(\C)CCC(=O)OC)c(OC)c(C)c2c1C(=O)OC2]
I-23

TABLE 1-continued
Exemplary Compounds
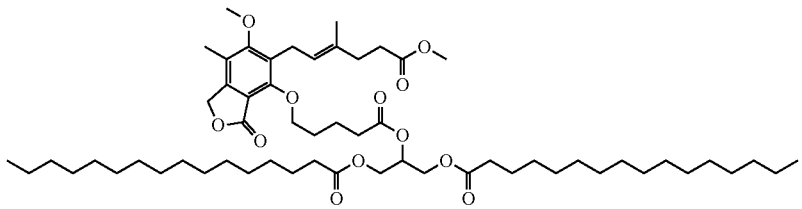 [SMILES: CCCCCCCCCCCCCCCC(=O)OCC(COC(=O)CCCCCCCCCCCCCCC)OC(=O)CCCCOc1c(C/C=C(\C)CCC(=O)OC)c(OC)c(C)c2c1C(=O)OC2]
I-24
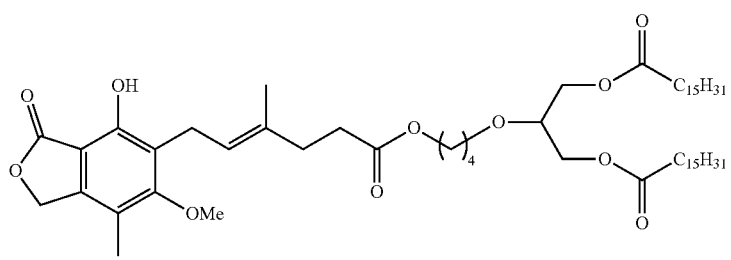
I-25
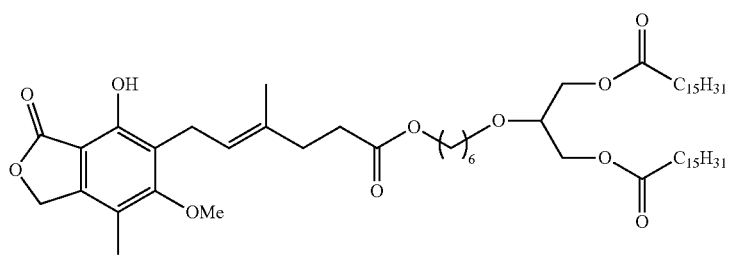
I-26
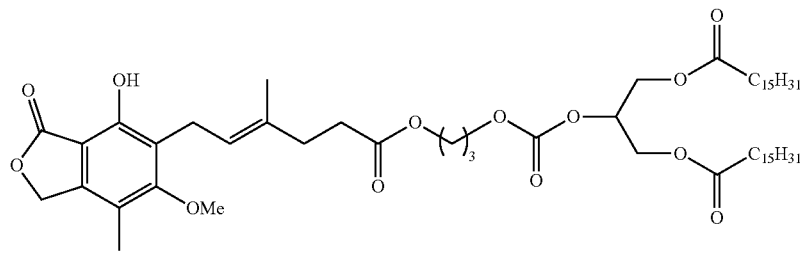
I-27
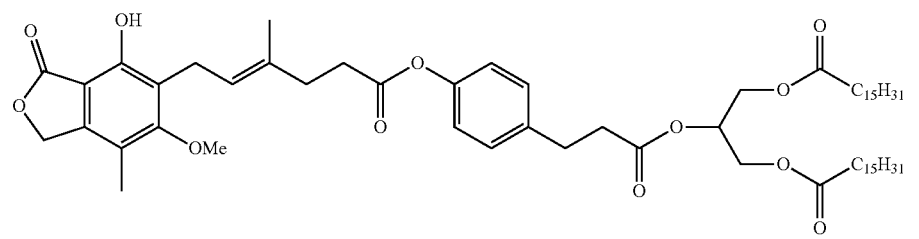
I-28

TABLE 1-continued
Exemplary Compounds
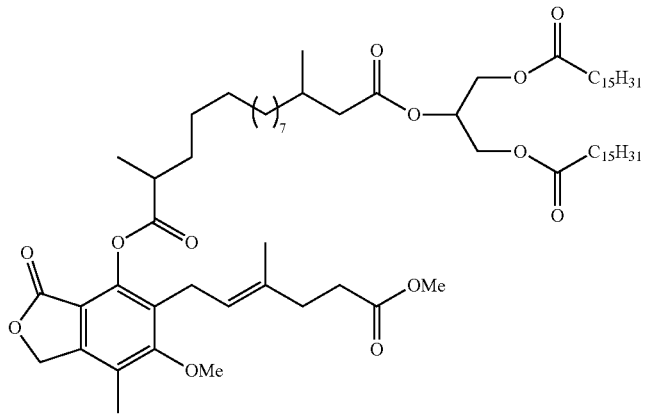
I-29
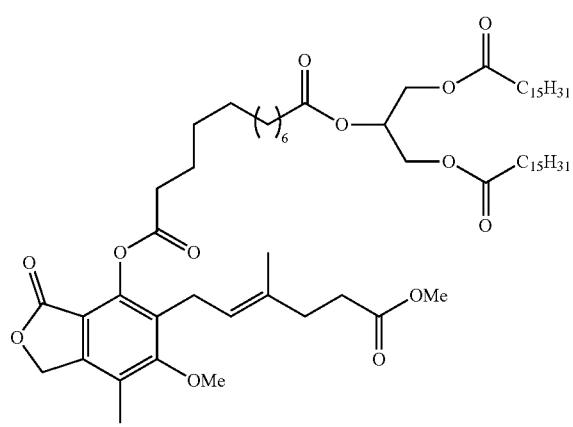
I-30
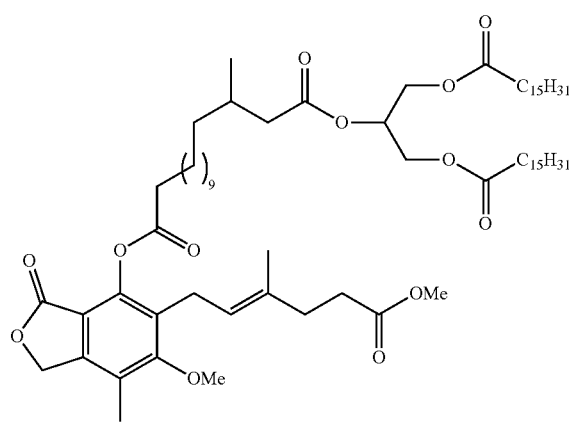
I-31
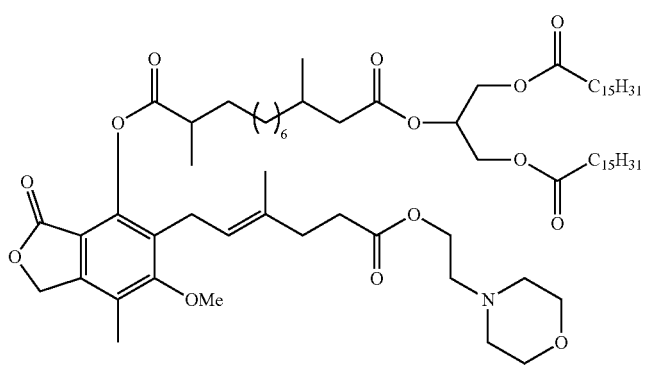
I-32

TABLE 1-continued
Exemplary Compounds
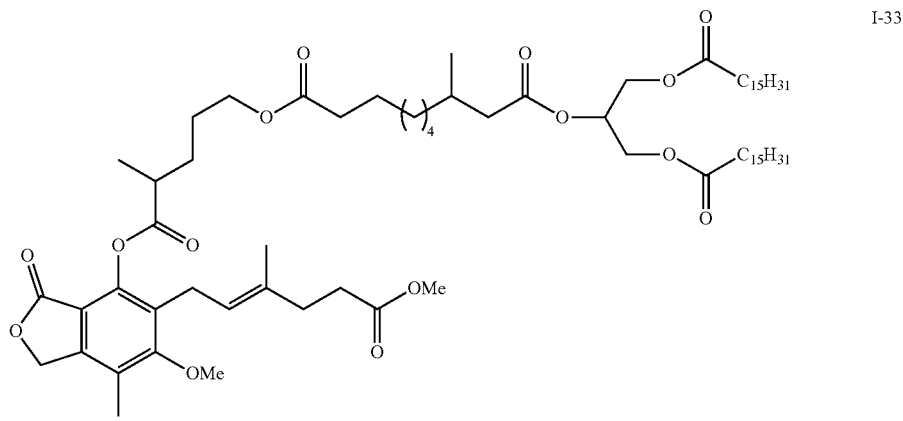
I-33
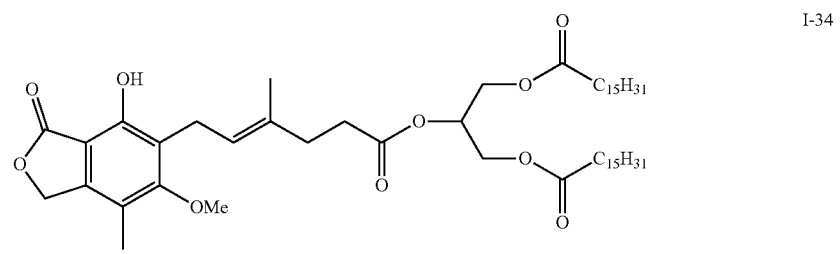
I-34
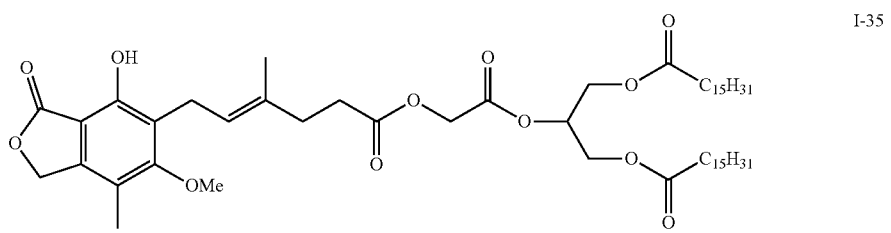
I-35
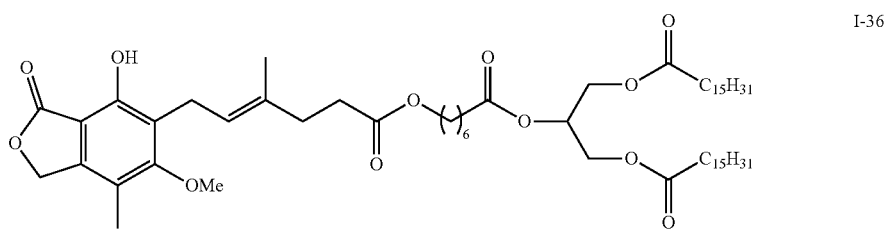
I-36
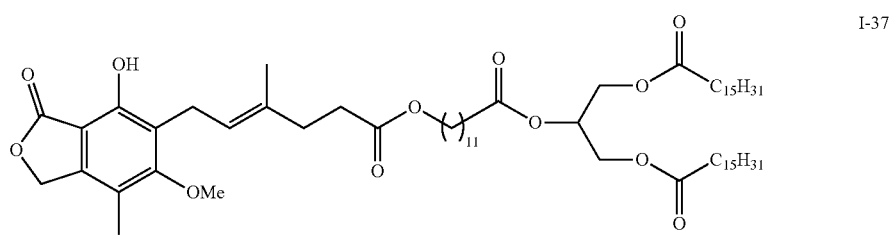
I-37

TABLE 1-continued

Exemplary Compounds

I-38

I-39

I-40

I-41

I-42

TABLE 1-continued
Exemplary Compounds
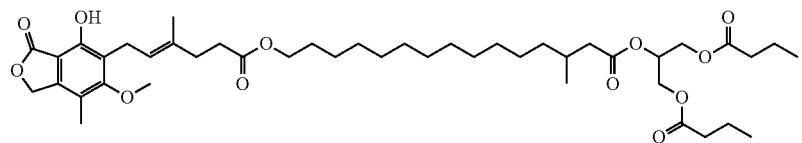 [SMILES: CCCC(=O)OCC(COC(=O)CCC)OC(=O)CC(C)CCCCCCCCCCCCOC(=O)CC/C(C)=C/Cc1c(O)c2c(c(C)c1OC)COC2=O]
I-43
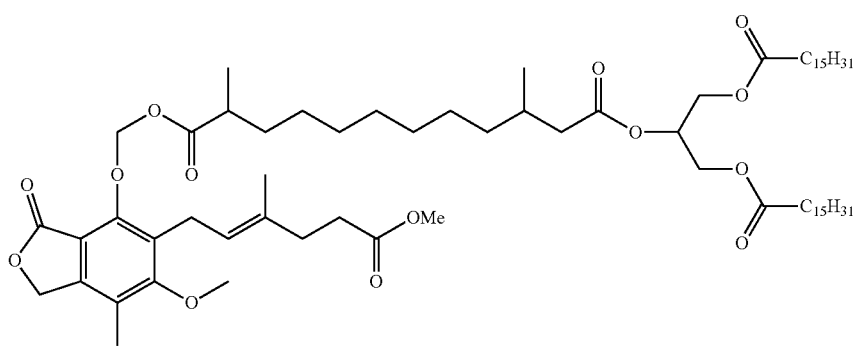
I-44
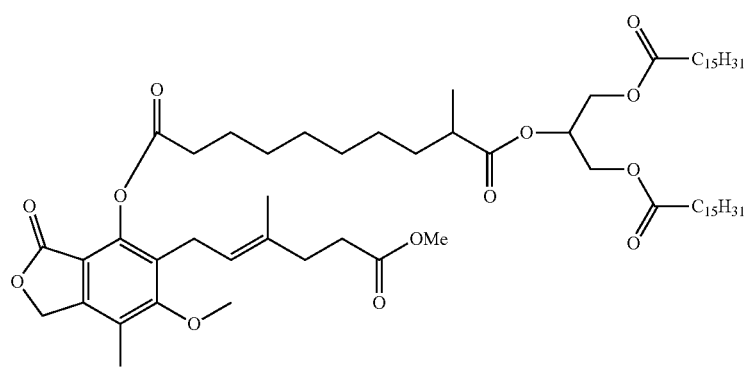
I-45
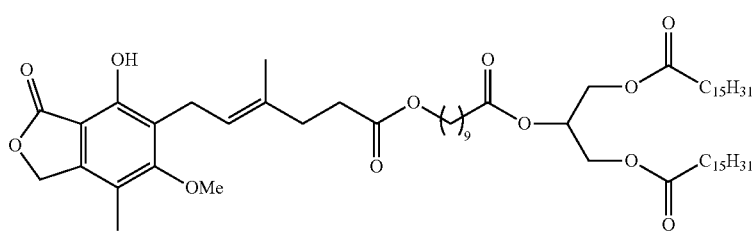
I-46
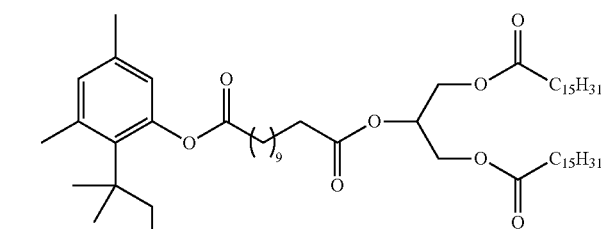
I-47
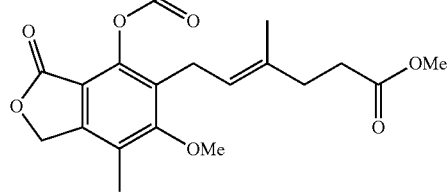

TABLE 1-continued

Exemplary Compounds

I-48

I-49

I-50

I-51

I-52

TABLE 1-continued
Exemplary Compounds
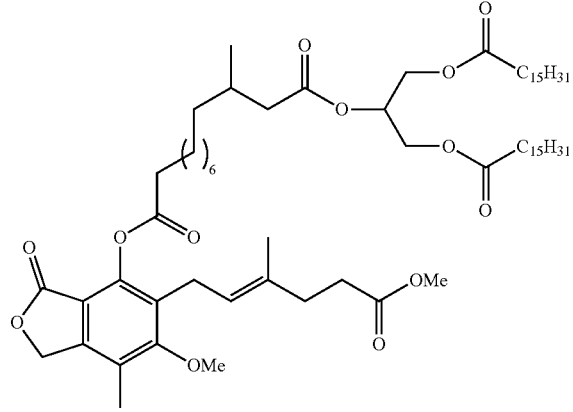
I-53
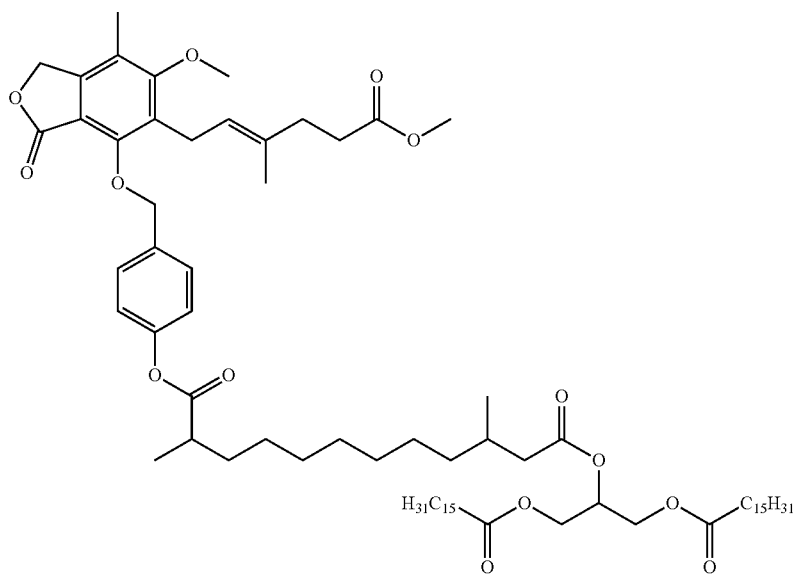
I-54
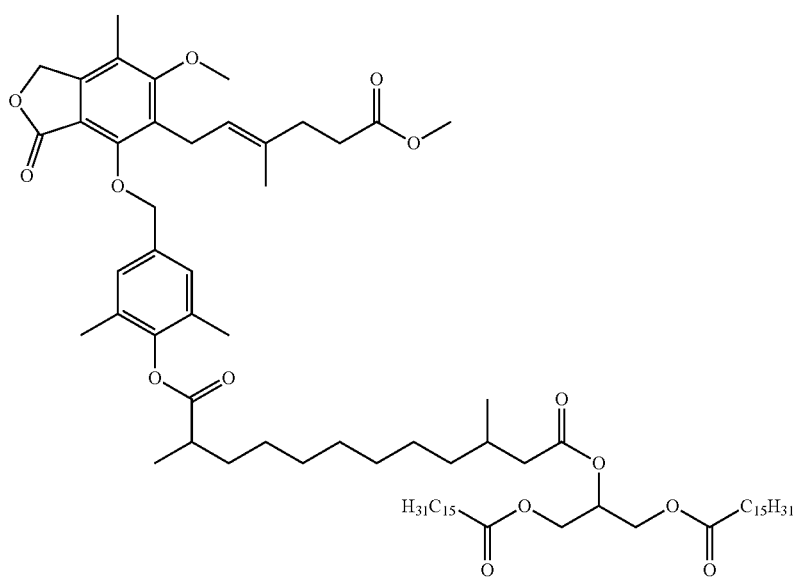
I-55

TABLE 1-continued
Exemplary Compounds
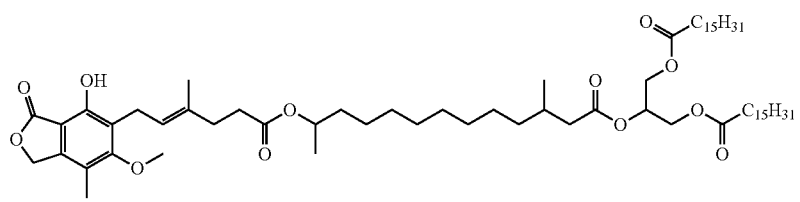
I-56
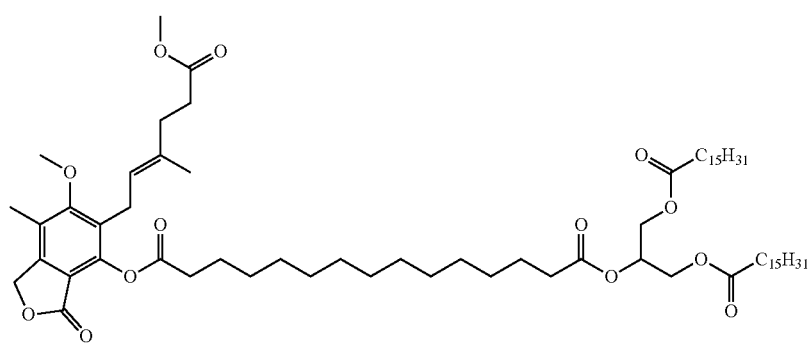
I-57
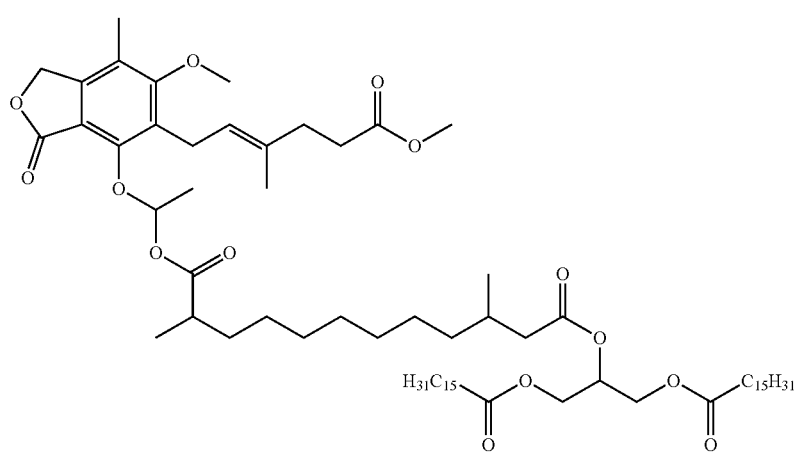
I-58
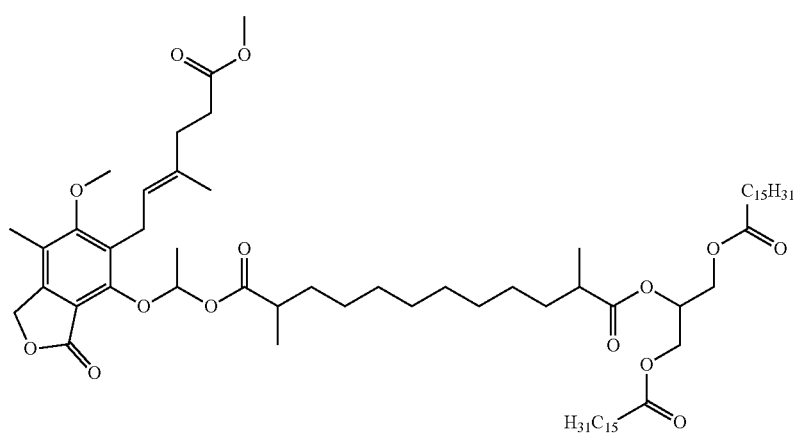
I-59

TABLE 1-continued
Exemplary Compounds
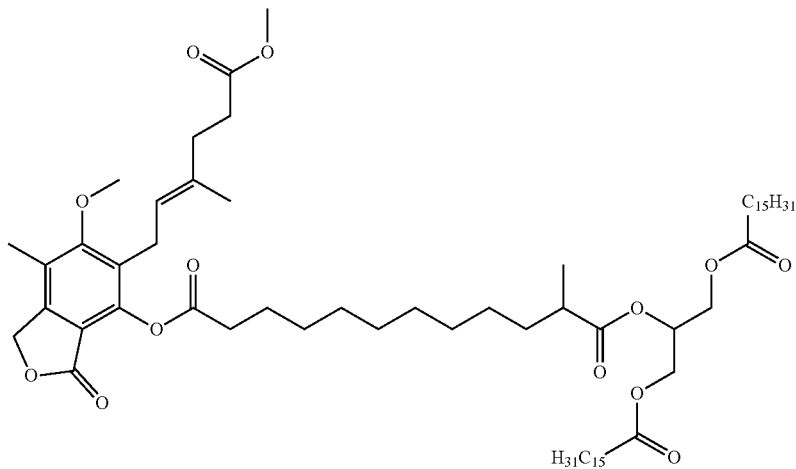
I-60
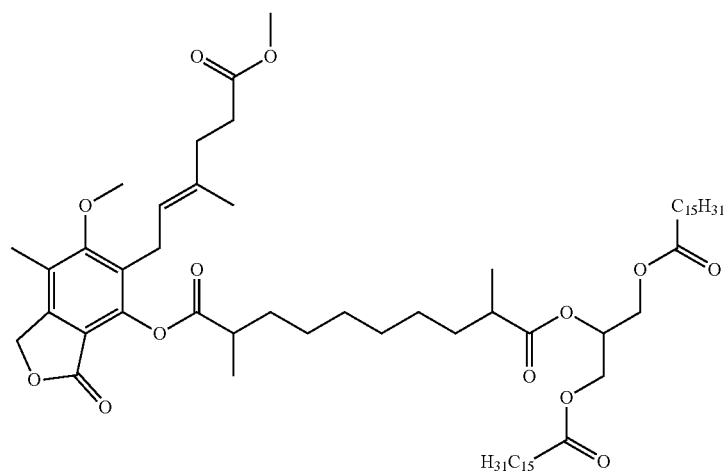
I-61
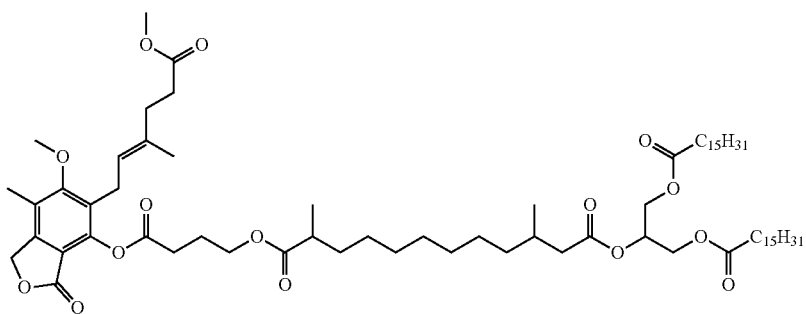
I-62

TABLE 1-continued
Exemplary Compounds
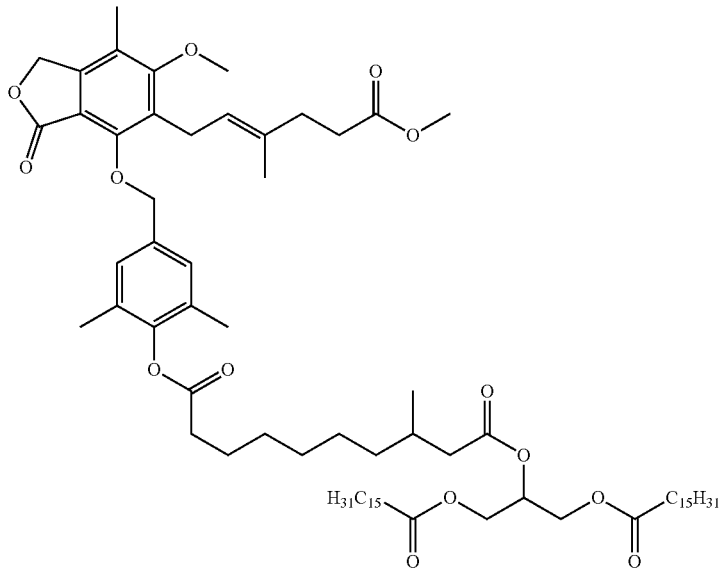
I-63
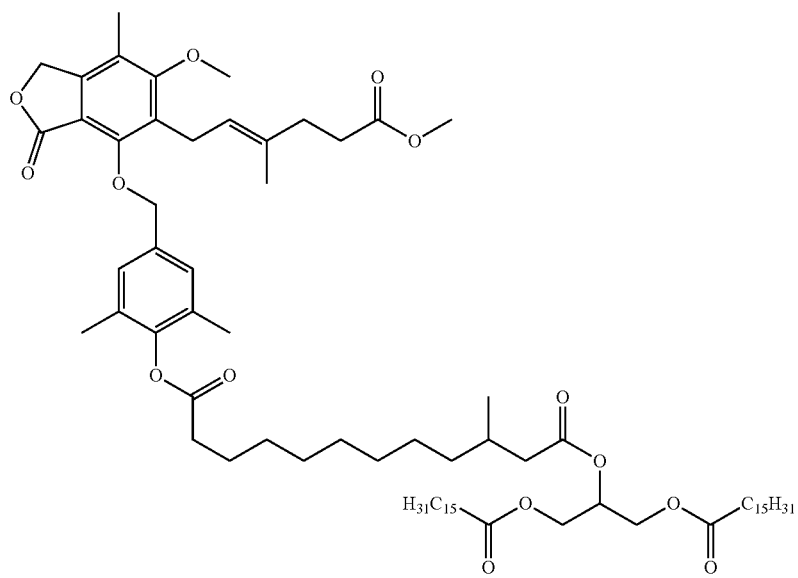
I-64
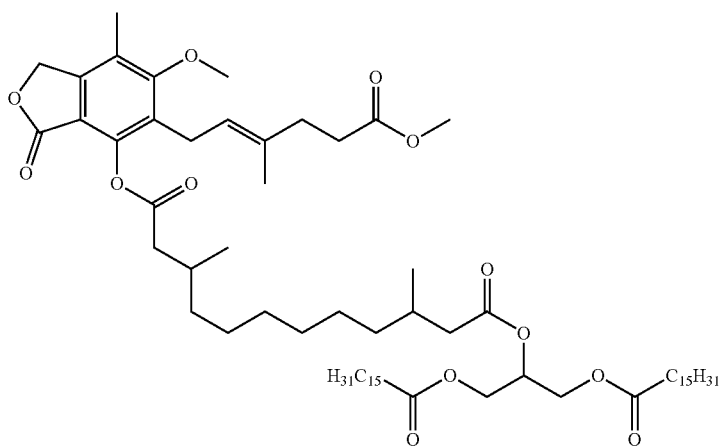
I-65

TABLE 1-continued
Exemplary Compounds
I-66
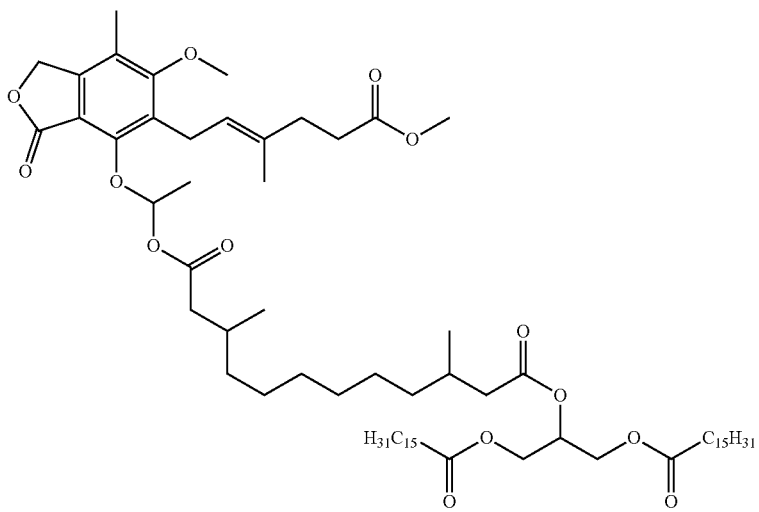
I-67
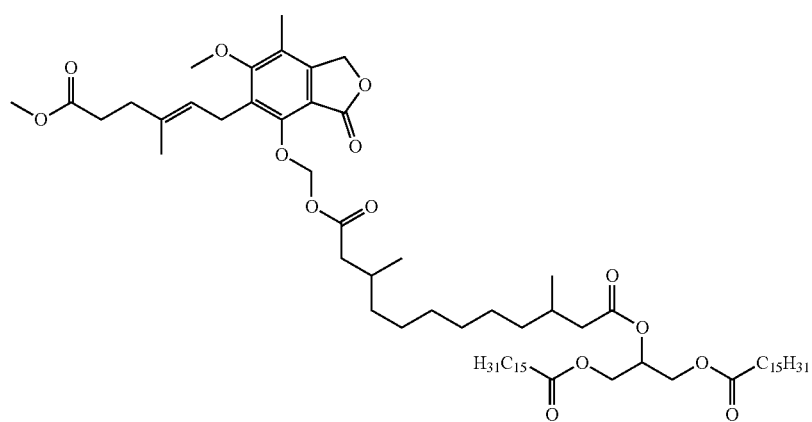
I-68
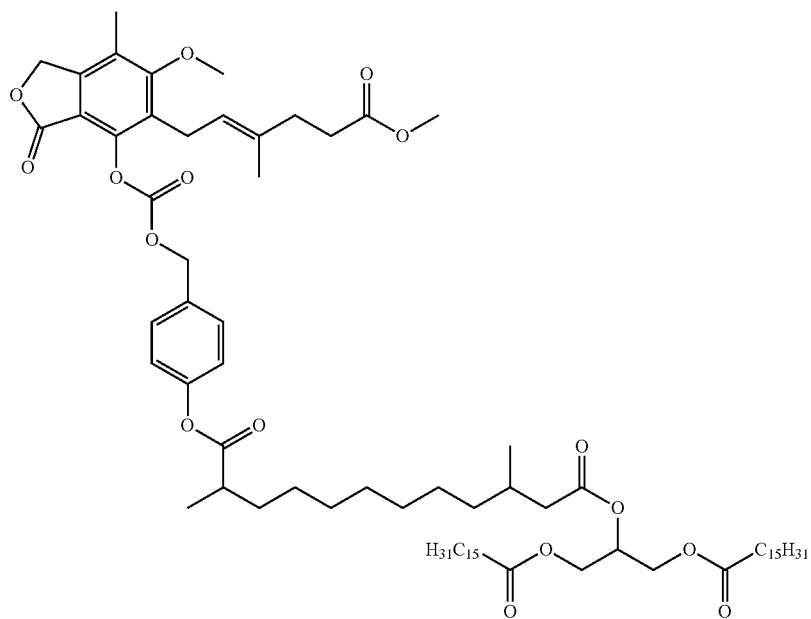

TABLE 1-continued
Exemplary Compounds
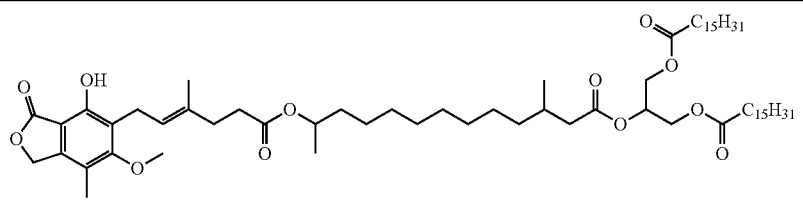
I-69
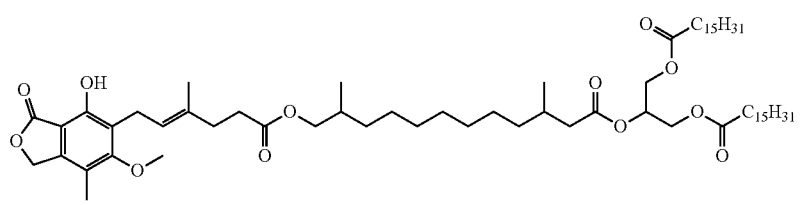
I-70
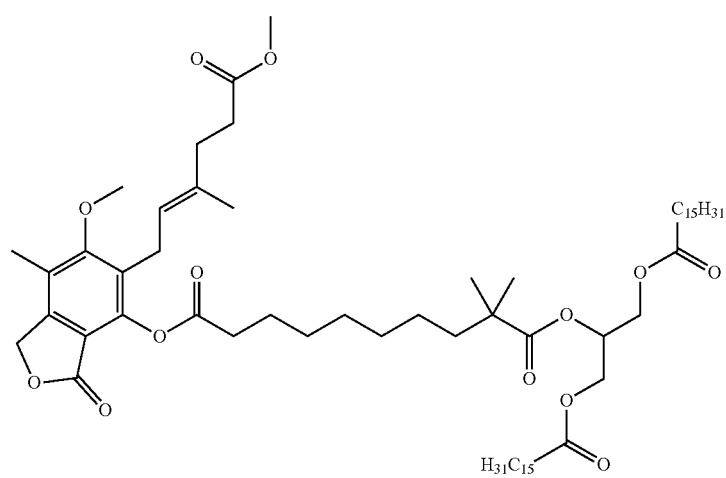
I-71
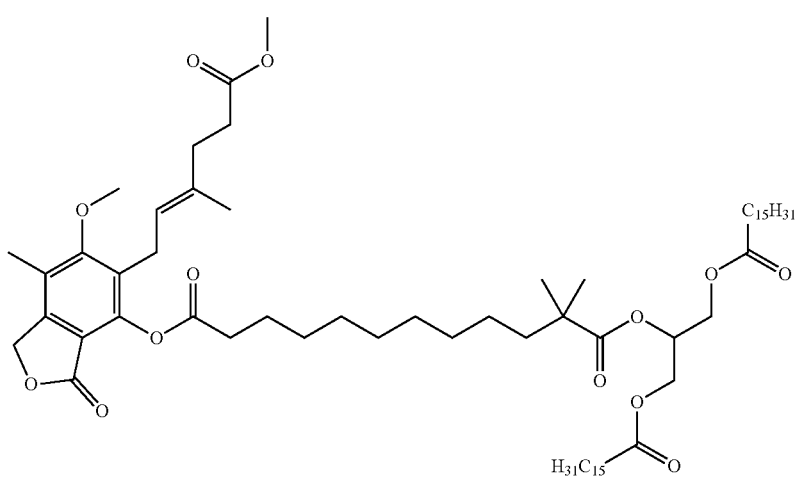
I-72

TABLE 1-continued
Exemplary Compounds
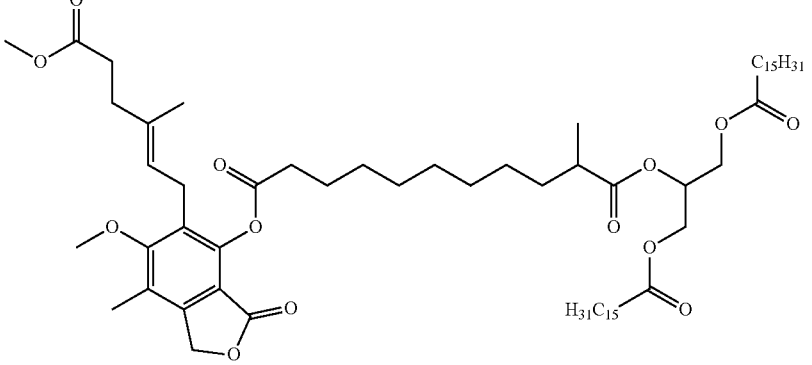
I-73
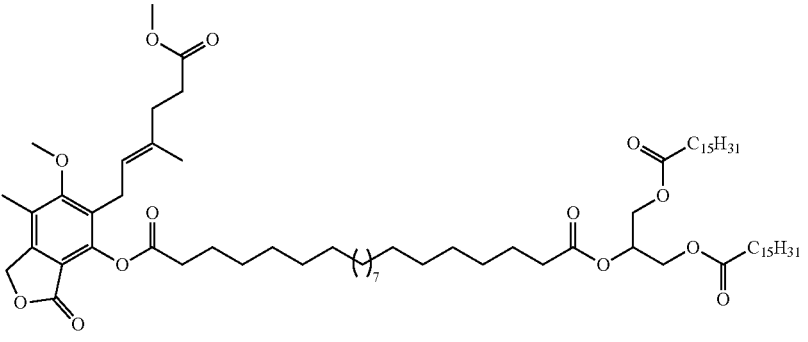
I-74
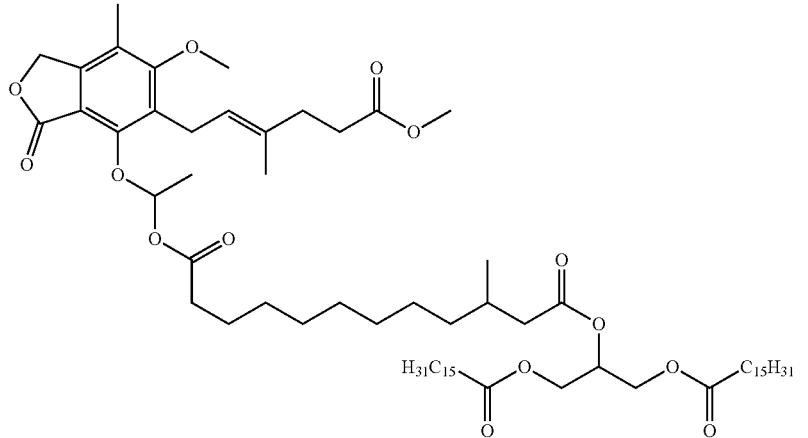
I-75
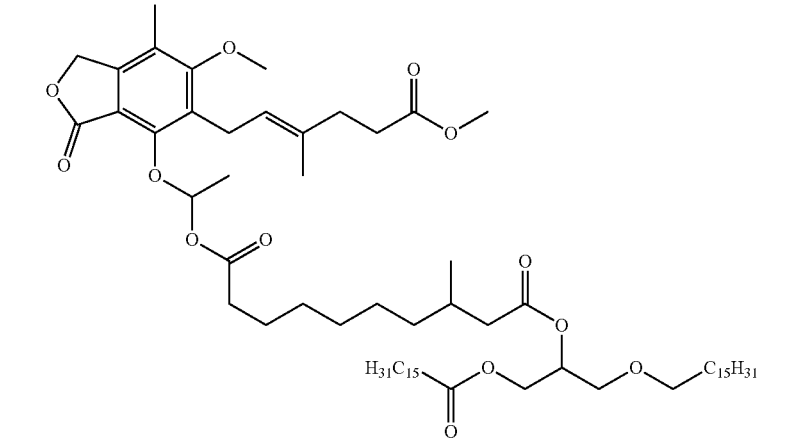
I-76

TABLE 1-continued
Exemplary Compounds
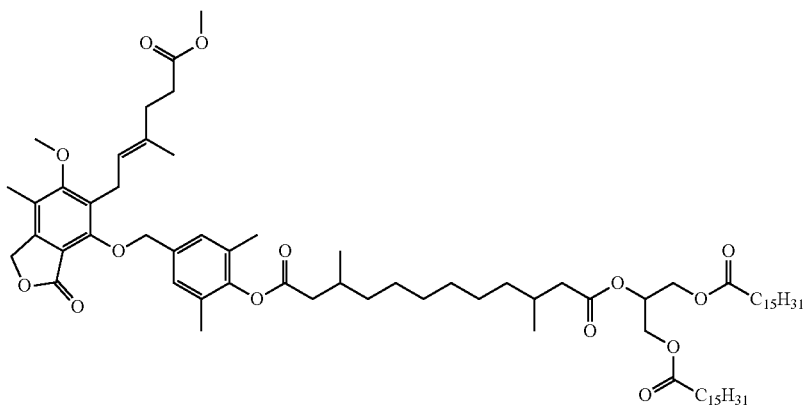
I-77
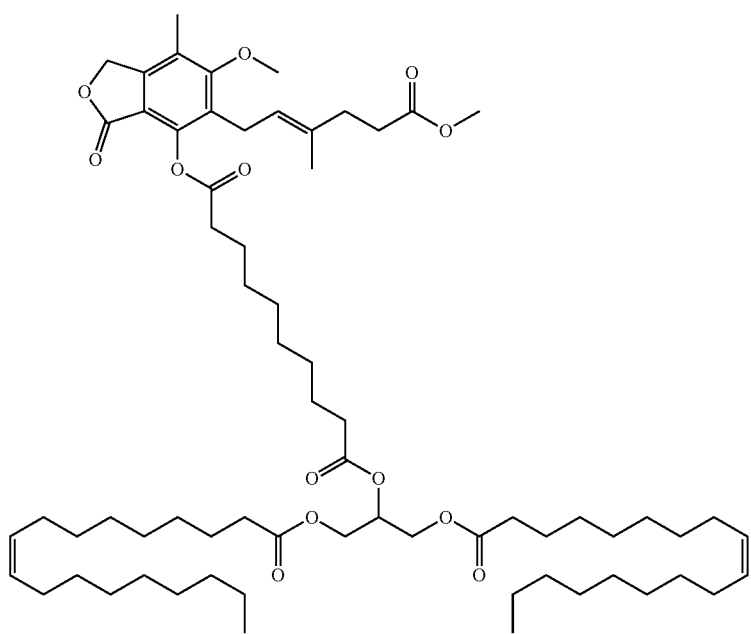 [SMILES: CCCCCCCC/C=C\CCCCCCCC(=O)OCC(COC(=O)CCCCCCC/C=C\CCCCCCCC)OC(=O)CCCCCCCCC(=O)Oc1c(C/C=C(\C)CCC(=O)OC)c(OC)c(C)c2c1C(=O)OC2]
I-78

TABLE 1-continued
Exemplary Compounds
I-79
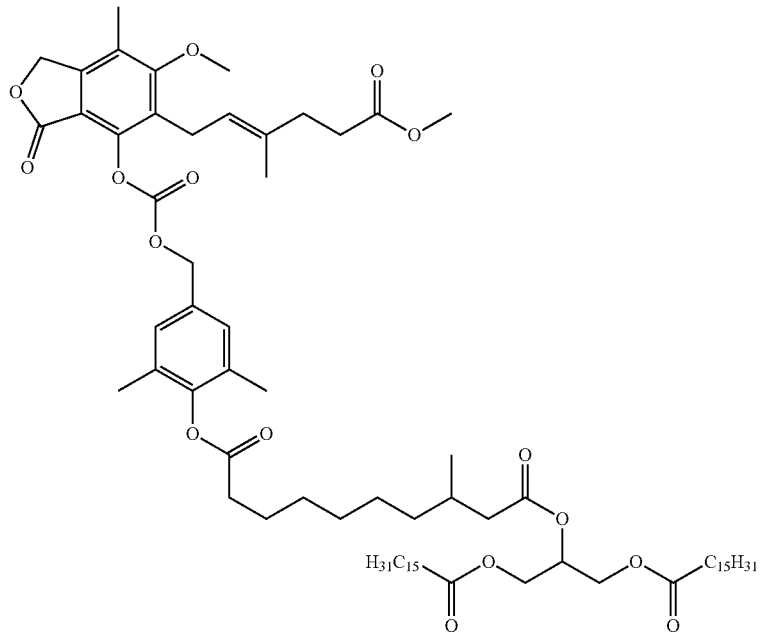
I-80
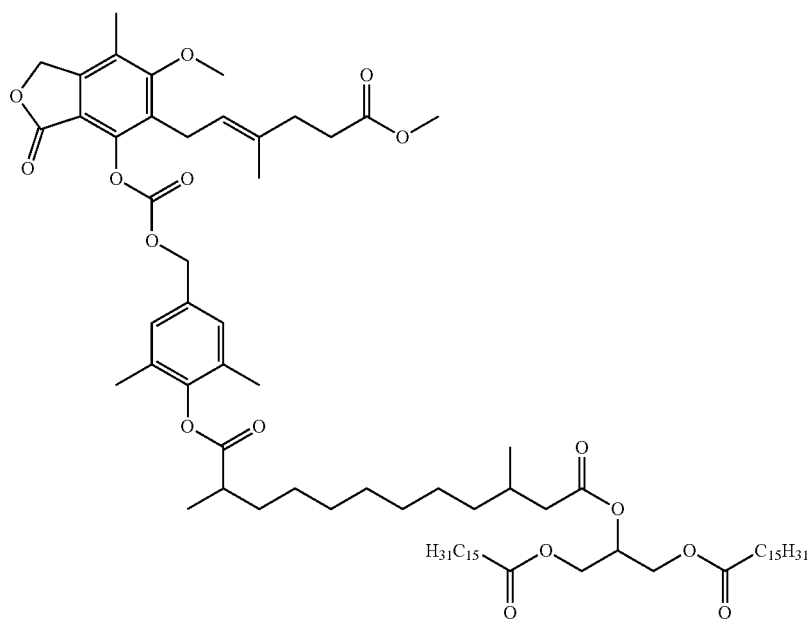

TABLE 1-continued
Exemplary Compounds
I-81
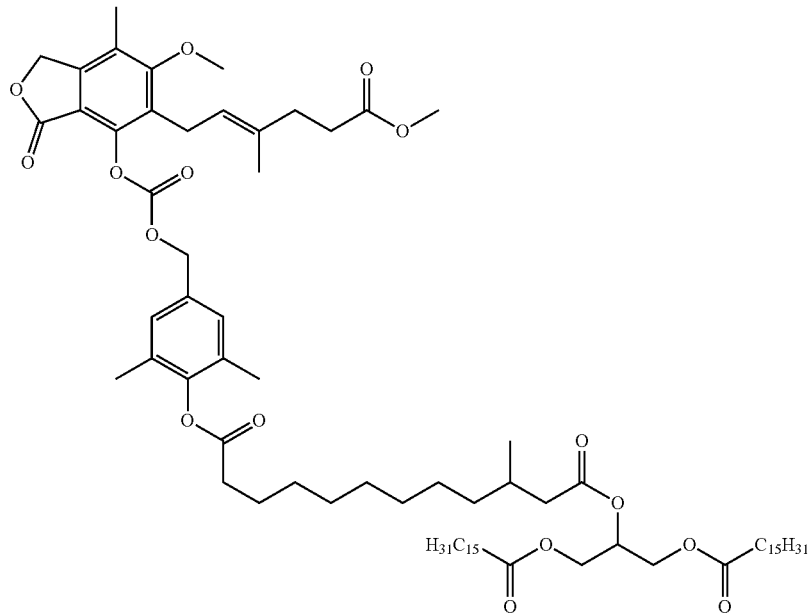
I-82
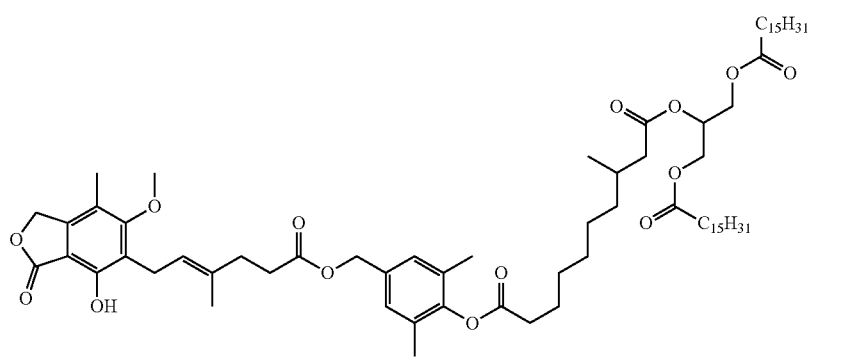
I-83
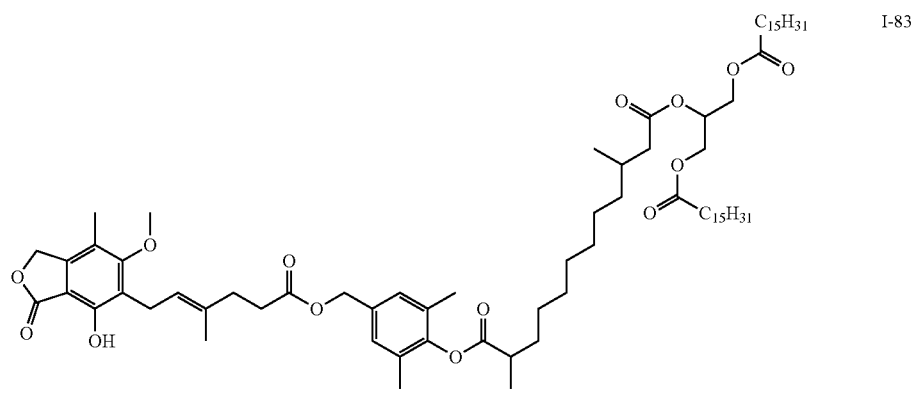

TABLE 1-continued

Exemplary Compounds

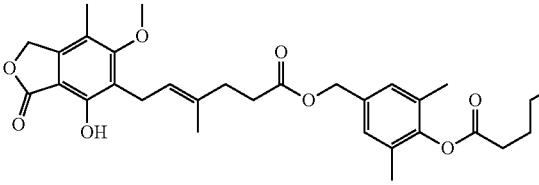

I-84

In some embodiments, the present invention provides a compound as depicted in Table 1, above, or a pharmaceutically acceptable salt thereof.

Lipids, Including Fatty Acids, Phospholipids, Lipid-Processing Mimetics, and Mixtures Thereof, for Use in Disclosed Livid Prodrugs Lipid prodrugs according to the present disclosure mimic the lipid-processing that takes place in the human body.

A variety of lipids are suitable for use in lipid prodrugs of the present disclosure. In some embodiments, the lipid prodrug comprises a fatty acid, phosphatide, phospholipid, or analogue thereof (e.g. phophatidylcholine, lecithin, phosphatidylethanolamine, cephalin, or phosphatidylserine or analogue or portion thereof, such as a partially hydrolyzed portion thereof), or other lipid-processing mimetic (e.g., a group cleaved by lipases, other digestive enzymes, or other mechanisms in the GI tract that enables the lipid prodrug to mimic dietary lipid processing).

In some embodiments, the fatty acid is a short-chain, medium-chain, or long-chain fatty acid. In some embodiments, the fatty acid is a saturated fatty acid. In some embodiments, the fatty acid is an unsaturated fatty acid. In some embodiments, the fatty acid is a monounsaturated fatty acid. In some embodiments, the fatty acid is a polyunsaturated fatty acid, such as an ω-3 (omega-3) or ω-6 (omega-6) fatty acid. In some embodiments, the lipid, e.g., fatty acid, has a $C_2$-$C_{60}$ chain. In some embodiments, the lipid, e.g., fatty acid, has a $C_2$-$C_{28}$ chain. In some embodiments, the lipid, e.g., fatty acid, has a $C_2$-$C_{40}$ chain. In some embodiments, the lipid, e.g., fatty acid, has a $C_2$-$C_{12}$ or $C_4$-$C_{12}$ chain. In some embodiments, the lipid, e.g., fatty acid, has a $C_4$-$C_{40}$ chain. In some embodiments, the lipid, e.g., fatty acid, has a $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_8$-$C_{24}$, $C_{10}$-$C_{24}$, $C_2$-$C_{22}$, $C_4$-$C_{22}$, $C_6$-$C_{22}$, $C_8$-$C_{22}$, $C_{10}$-$C_{22}$, $C_2$-$C_{20}$, $C_4$-$C_{20}$, $C_6$-$C_{20}$, $C_8$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_8$-$C_{16}$, $C_{10}$-$C_{16}$, $C_{12}$-$C_{16}$, $C_{14}$-$C_{16}$, $C_2$-$C_{15}$, $C_4$-$C_{15}$, $C_6$-$C_{15}$, $C_8$-$C_{18}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_8$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_8$-$C_{13}$, $C_9$-$C_{13}$, $C_{10}$-$C_{13}$, $C_{10}$-$C_{13}$, $C_{11}$-$C_{13}$, $C_2$-$C_{12}$, $C_4$-$C_{12}$, $C_6$-$C_{12}$, $C_7$-$C_{12}$, $C_8$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_8$-$C_{11}$, $C_9$-$C_{12}$, $C_2$-$C_{10}$, $C_4$-$C_{10}$, $C_2$-$C_9$, $C_4$-$C_9$, $C_2$-$C_8$, $C_4$-$C_8$, $C_2$-$C_7$, $C_4$-$C_7$, $C_2$-$C_6$, or $C_4$-$C_6$, chain. In some embodiments, the lipid, e.g., fatty acid, has a $C_2$, $C_3$, $C_4$, $C_5$, $C_6$, $C_7$, $C_8$, $C_9$, $C_{10}$, $C_{11}$, $C_{12}$, CD, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, or $C_{60}$ chain. In some embodiments, the lipid prodrug comprises two fatty acids, each of which is independently selected from a fatty acid having a chain with any one of the foregoing ranges or numbers of carbon atoms. In some embodiments, one of the fatty acids is independently a fatty acid with a $C_6$-$C_{12}$ chain and one is independently a fatty acid with a $C_{12}$-$C_{36}$ chain. In some embodiments, each fatty acid independently has a chain of 11, 12, 13, 14, 15, 16, or 17 carbon atoms.

In some embodiments, the lipid prodrug comprises two lipids. In some embodiments, the two lipids, e.g. fatty acids, taken together have 6-80 carbon atoms (an equivalent carbon number (ECN) of 6-80). In some embodiments, the lipids, e.g., fatty acids, have an ECN of 6-80, 8-80, 10-80, 12-80, 14-80, 16-80, 18-80, 20-80, 22-80, 24-80, 26-80, 28-80, 30-80, 4-76, 6-76, 8-76, 10-76, 12-76, 14-76, 16-76, 18-76, 20-76, 22-76, 24-76, 26-76, 28-76, 30-76, 6-72, 8-72, 10-72, 12-72, 14-72, 16-72, 18-72, 20-72, 22-72, 24-72, 26-72, 28-72, 30-72, 6-68, 8-68, 10-68, 12-68, 14-68, 16-68, 18-68, 20-68, 22-68, 24-68, 26-68, 28-68, 30-68, 6-64, 8-64, 10-64, 12-64, 14-64, 16-64, 18-64, 20-64, 22-64, 24-64, 26-64, 28-64, 30-64, 6-60, 8-60, 10-60, 12-56, 14-56, 16-56, 18-56, 20-56, 22-56, 24-56, 26-56, 28-56, 30-56, 6-52, 8-52, 10-52, 12-52, 14-52, 16-52, 18-52, 20-52, 22-52, 24-52, 26-52, 28-52, 30-52, 6-48, 8-48, 10-48, 12-48, 14-48, 16-48, 18-48, 20-48, 22-48, 24-48, 26-48, 28-48, 30-48, 6-44, 8-44, 10-44, 12-44, 14-44, 16-44, 18-44, 20-44, 22-44, 24-44, 26-44, 28-44, 30-44, 6-40, 8-40, 10-40, 12-40, 14-40, 16-40, 18-40, 20-40, 22-40, 24-40, 26-40, 28-40, 30-40, 6-36, 8-36, 10-36, 12-36, 14-36, 16-36, 18-36, 20-36, 22-36, 24-36, 26-36, 28-36, 30-36, 6-32, 8-32, 10-32, 12-32, 14-32, 16-32, 18-32, 20-32, 22-32, 24-32, 26-32, 28-32, or 30-32.

Suitable fatty acids include saturated straight-chain fatty acids, saturated branched fatty acids, unsaturated fatty acids, hydroxy fatty acids, and polycarboxylic acids. In some embodiments, such fatty acids have up to 32 carbon atoms.

Examples of useful saturated straight-chain fatty acids include those having an even number of carbon atoms, such as butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, and heptacosanoic acid.

Examples of suitable saturated branched fatty acids include isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.). Suitable saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid.

Examples of suitable unsaturated fatty acids include 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid, and the like.

Examples of suitable hydroxy fatty acids include α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid and the like.

Examples of suitable poly carboxylic acids include oxalic acid, malonic acid, succinic acid, glutaric acid, adipic acid, pimelic acid, suberic acid, azelaic acid, sebacic acid, D,L-malic acid, and the like.

In some embodiments, each fatty acid is independently selected from Propionic acid, Butyric acid, Valeric acid, Caproic acid, Enanthic acid, Caprylic acid, Pelargonic acid, Capric acid, Undecylic acid, Laurie acid, Tridecylic acid, Myristic acid, Pentadecylic acid, Palmitic acid, Margaric acid, Stearic acid, Nonadecylic acid, arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, geddic acid, ceroplastic acid, hexatriacontylic acid, heptatriacontanoic acid, or octatriacontanoic acid.

In some embodiments, each fatty acid is independently selected from α-linolenic acid, stearidonic acid, eicosapentaenoic acid, docosahexaenoic acid, linoleic acid, gamma-linoleic acid, dihomo-gamma-linoleic acid, arachidonic acid, docosatetraenoic acid, palmitoleic acid, vaccenic acid, paullinic acid, oleic acid, elaidic acid, gondoic acid, eurcic acid, nervonic acid, mead acid, adrenic acid, bosseopentaenoic acid, ozubondo acid, sardine acid, herring acid, docosahexaenoic acid, or tetracosanolpentaenoic acid, or another monounsaturated or polyunsaturated fatty acid.

In some embodiments, one or both of the fatty acids is an essential fatty acid. In view of the beneficial health effects of certain essential fatty acids, the therapeutic benefits of disclosed lipid prodrugs may be increased by including such fatty acids in the lipid prodrug. In some embodiments, the essential fatty acid is an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3 acid, or docosahexaenoic acid.

In some embodiments, each fatty acid is independently selected from all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid, or lipoic acid. In other embodiments, the fatty acid is selected from eicosapentaenoic acid, docosahexaenoic acid, or lipoic acid. Other examples of fatty acids include all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid). In some embodiments, the fatty acid is a medium-chain fatty acid such as lipoic acid.

Fatty acid chains differ greatly in the length of their chains and may be categorized according to chain length, e.g. as short to very long.

Short-chain fatty acids (SCFA) are fatty acids with chains of about five or less carbons (e.g. butyric acid). In some embodiments, each of the fatty acids is independently a SCFA. In some embodiments, one of the fatty acids is independently a SCFA.

Medium-chain fatty acids (MCFA) include fatty acids with chains of about 6-12 carbons, which can form medium-chain triglycerides. In some embodiments, each of the fatty acids is independently a MCFA. In some embodiments, one of the fatty acids is independently a MCFA.

Long-chain fatty acids (LCFA) include fatty acids with chains of 13-21 carbons. In some embodiments, each of the fatty acids is independently a LCFA. In some embodiments, one of the fatty acids is independently a LCFA.

Very long chain fatty acids (VLCFA) include fatty acids with chains of 22 or more carbons, such as 22-60, 22-50, or 22-40 carbons. In some embodiments, each of the fatty acids is independently a VLCFA. In some embodiments, one of the fatty acids is independently a VLCFA.

In some embodiments, one of the fatty acids is independently a MCFA and one is independently a LCFA.

Therapeutic Agents and Exemplary Associated Diseases

In accordance with the present invention, a variety of therapeutic agents may be covalently conjugated to the lymphatic system-directing lipids, e.g. triglyceride scaffolds, described herein. In some embodiments, by conjugating a therapeutic agent to a lymphatic system-directing lipid, the present invention provides enhanced desirable properties of the therapeutic agent such as improving oral bioavailability, minimizing destruction of the agent in the gut, avoiding liver first-pass effect, improving therapeutic agent delivery to a target tissue, or increasing the solubility and stability of the therapeutic agents, including the solubility and stability of the agents in vivo.

Mycophenolic acid and related derivatives, analogues, prodrugs, and pharmaceutically acceptable salts such as those described herein are broad-spectrum acting drugs having antiviral, antifungal, antibacterial, anti cancer, and antiinflammatory properties. Such compounds are also used to treat autoimmune disorders, as well as other disorders described herein such as transplant rejection and graft-versus-host disease. Mycophenolic acid (sold, e.g., under the trade name Myfortic®) and prodrugs thereof (e.g., mycophenolate mofetil, sold under the trade name CellCept®) are indicated for the prevention of organ transplant rejection and treatment of autoimmune diseases, disorders, or conditions. Disclosed lipid prodrugs are therefore useful in treating the foregoing and other diseases, disorders, or conditions, such as those disclosed herein.

In some embodiments, a disclosed lipid prodrug, e.g., an MPA lipid prodrug disclosed herein, modulates the immune system of a patient after administration. Without wishing to be bound by theory, it is believed that mycophenolic acid effects immunosuppression by inhibiting purine synthesis. Purines can either be synthesized de novo using ribose 5-phosphate or they can be salvaged from free nucleotides. Mycophenolic acid is a potent, reversible, non-competitive inhibitor of inosine-5'-monophosphate dehydrogenase (IMPDH), an enzyme essential to the de novo synthesis of guanosine-5'-monophosphate (GMP) from inosine-5'-monophosphate (IMP). IMPDH inhibition particularly affects lymphocytes since they rely almost exclusively de novo purine synthesis. In contrast, many other cell types use both pathways, and some cells, such as terminally differentiated neurons, depend completely on purine nucleotide salvage. Thus, use of mycophenolic acid leads to a relatively selective inhibition of DNA replication in T cells and B cells.

In some embodiments, a disclosed lipid prodrug, e.g., an MPA lipid prodrug disclosed herein, is taken up selectively into the lymphatic system of a patient after oral administration. In some embodiments, once in the lymphatic system, the lipid prodrug interacts with immune cells in the lymphatic system. In some embodiments, a disclosed lipid prodrug is delivered selectively to B or T lymphocytes. In some embodiments, a disclosed lipid prodrug modulates the activity of B or T lymphocytes. In some embodiments, a disclosed lipid prodrug modulates the activity of one or more of B cells, dendritic cells, granulocytes, innate lymphoid cells (ILCs), megakaryocytes, monocytes/macrophages, myeloid-derived suppressor cells (MDSC), natural killer (NK) cells, platelets, red blood cells (RBCs), T cells, or thymocytes. In some embodiments, a disclosed lipid prodrug, e.g., an MPA lipid prodrug disclosed herein, exhibits increased delivery at a given dose or more selective delivery at a given dose to B or T lymphocytes as compared with a corresponding dose of a non-lipid prodrug form of mycophenolic acid, or a derivative, analogue, or prodrug thereof. In some embodiments, a given dose of a disclosed lipid prodrug more effectively modulates the activity of one or more of B cells, dendritic cells, granulocytes, innate lymphoid cells (ILCs), megakaryocytes, monocytes/macrophages, myeloid-derived suppressor cells (MDSC), natural killer (NK) cells, platelets, red blood cells (RBCs), T cells, or thymocytes, as compared with a corresponding dose of a non-lipid prodrug form of mycophenolic acid, or a derivative, analogue, or prodrug thereof.

In some embodiments, the present invention provides a method of treating an autoimmune disease, disorder, or condition in a patient in need thereof, comprising administering to the patient an effective amount of a disclosed lipid prodrug. In some embodiments, the present invention provides a method of treating an autoimmune disease, disorder, or condition in a patient in need thereof, comprising administering to the patient an effective amount of a disclosed lipid prodrug, e.g., an MPA lipid prodrug. In some embodiments, the MPA lipid prodrug is a compound of formula I or VI, or a pharmaceutically acceptable salt thereof. In some embodiments, the MPA lipid prodrug is a compound depicted in Table 1, or a pharmaceutically acceptable salt thereof. In some embodiments, the autoimmune disease, disorder, or condition is selected from Behget's disease, pemphigus vulgaris, refractory incomplete systemic lupus erythematosus, retroperitoneal fibrosis, idiopathic thrombocytopenic purpura (ITP), scleroderma (systemic sclerosis or SSc), pemphigus vulgaris, granulomatosis with polyangiitis, immunoglobulin A nephropathy, small vessel vasculitis, retroperitoneal fibrosis, and psoriasis. In some embodiments, the autoimmune disease is systemic lupus erythematosus (SLE) and/or lupus nephritis (LN). In some embodiments, the autoimmune disease is celiac disease. In some embodiments, the autoimmune disease is inflammatory bowel disease (IBD; e.g. Crohn's disease, ulcerative colitis). In some embodiments, the autoimmune disease is a neurodegenerative disorder. In some embodiments, the neurodegenerative disorder is multiple sclerosis.

In some embodiments, the present invention provides a method of treating or preventing organ transplant rejection, graft-versus-host disease, or implant rejection, comprising administering to a patient in need thereof an effective amount of a disclosed lipid prodrug. In some embodiments, the present invention provides a method of treating or preventing organ transplant rejection, graft-versus-host disease, or implant rejection, comprising administering to a patient in need thereof an effective amount of a disclosed lipid prodrug e.g., an MPA lipid prodrug. In some embodiments, the MPA lipid prodrug is a compound of formula I or VI, or a pharmaceutically acceptable salt thereof. In some embodiments, the MPA lipid prodrug is a compound depicted in Table 1, or a pharmaceutically acceptable salt thereof. In some embodiments, the organ transplant is selected from a skin, liver, heart, kidney, pancreas, thymus, small intestine, large intestine, uterus, a vascularized composite allograft (VCA) such as face or hand, bone marrow, allogenic blood and marrow transplant (BMT), cornea, and lung transplant. In some embodiments, the organ transplant rejection is acute or chronic transplant rejection.

In some embodiments, the present invention provides a method of treating a disease, disorder, or condition in a patient in need thereof, comprising administering to the patient a disclosed lipid prodrug such as a compound of formula I or VI, or a pharmaceutically acceptable salt thereof, wherein the disease, disorder, or condition is selected from retroperitoneal fibrosis, idiopathic thrombocytopenic purpura (ITP), scleroderma (systemic sclerosis or SSc), pemphigus vulgaris, granulomatosis with polyangiitis, refractory incomplete systemic lupus erythematosus, inflammatory disease, Abdominal cavity inflammation, Peritonitis, Mesenteritis, Perihepatitis, Salpingoperitonitis, Auto inflammatory disease, Cryopyrin associated periodic syndrome, CINCA syndrome, Familial cold auto inflammatory syndrome, Muckle Wells syndrome, Cardiovascular inflammation, Carditis, Endocarditis, Bacterial endocarditis, Infectious endocarditis, Non infectious endocarditis, Thromboendocarditis, Pericarditis, Chylopericarditis, Dressier syndrome, Pleuropericarditis, Vasculitis, Arteritis, Aortitis, Takayasus arteritis, Endarteritis, HIV associated arteritis, Kawasaki disease, Periarteritis, Polyarteritis nodosa, Temporal arteritis, Extracranial temporal arteritis, Intracranial temporal arteritis, Churg-Strauss syndrome, Cutaneous vasculitis, Perivasculitis, Phlebitis, Lymphangiophlebitis, Thrombophlebitis, Mondor disease, Thromboangiitis, Thromboangiitis obliterans, Thrombophlebitis, Dermatitis, Acrodermatitis, Angiodermatitis, Drug eruption, Erythema multiforme, Serum sickness, Stevens Johnson syndrome, Toxic epidermal necrolysis, Intertrigo, Skin allergy, Atopic dermatitis, Contact dermatitis, Eczema, Fibrosis, Cicatrix, Tissue adhesions, Pulmonary fibrosis, Idiopathic pulmonary fibrosis, Renal fibrosis, Gastrointestinal inflammation, Anusitis, Biliary tract inflammation, Hepatocholangitis, Cholecystitis, Esophagitis, Eosinophilic esophagitis, Gastritis, Gastroduodenitis, Gastroenteritis, Hypertrophic gastritis, Hepatitis, Enterohepatitis, Hepatitis virus infection, Hepatitis A virus infection, Hepatitis B virus infection, Hepatitis C virus infection, Hepatitis D virus infection, Hepatitis E virus infection, Hepatitis F virus infection, Hepatitis G virus infection, Hepatocholangitis, Non-viral hepatitis, Alcoholic hepatitis, Autoimmune hepatitis, Perihepatitis, Steatohepatitis, Non-alcoholic steatohepatitis, Inflammatory bowel disease, Colitis, Diverticulitis, Meckel's diverticulitis, Enterocolitis, Acute enterocolitis, Necrotizing enterocolitis, Ileocecitis, Pseudomembranous colitis, Sigmoiditis, Rectosigmoiditis, Ulcerative colitis, Crohns disease, Enteritis, Enterocolitis, Acute enterocolitis, Necrotizing enterocolitis, Enterohepatitis, Hemorrhagic enteritis, Ileitis, Ileocecitis, Pouchitis, Jejunitis, Mucositis, Pancreatitis, Balser necrosis, Necrotizing acute pancreatitis, Peritonitis, Mesenteritis, Perihepatitis, Salpingoperitonitis, Proctitis, Rectosigmoiditis, Ulcerative proctitis, Genitourinary tract inflammation, Genital tract inflammation, Female genital tract inflammation, Endometriosis, Parametritis, Pelvic inflammatory disease, Salpingitis, Vaginitis, Atrophic vaginitis, Bartholinitis, Vulvovaginitis, Vulvitis, Vulvovaginitis, Male genital tract inflammation, Balanitis, Epididymitis, Epididymo-orchitis, Orchitis, Epididymo-orchitis, Periorchitis, Prostatitis, Urinary tract inflammation, Nephritis, Alport syndrome, Glomerulonephritis, Focal segmental glomerulosclerosis, IgA nephropathy, Membranoproliferative glomerulonephritis, Membranous glomerulonephritis, Wegener granulomatosis, Lupus nephritis, Pyelitis, Pyelocystitis, Pyelonephritis, Granulomatosis, Allergic granulomatosis, Sarcoidosis, Mastitis, Mouth inflammation, Gingivitis, Pericoronitis, Pharyngitis, Rhinopharyngitis, Sialadenitis, Musculoskeletal system inflammation, Arthritis, Behcets disease, Chondrocalcinosis, Gout, Infectious arthritis, Osteoarthritis, Periarthritis, Psoriatic arthritis, Reiter syndrome, Rheumatoid arthritis, Adult onset Stills disease, Felty syndrome, Juvenile rheumatoid arthritis, Bursitis, Dactylitis, Myositis, Dermatomyositis, Inclusion body myositis, Hereditary inclusion body myositis, Sporadic inclusion body myositis, Polymyositis, Pyomyositis, Nervous system inflammation, Meningitis, Arachnoiditis, Aseptic meningitis, Infectious meningitis, Bacterial meningitis, *Neisseria meningitidis* meningitis, Fungal meningitis, *Cryptococcus neoformans* meningitis, Parasitic meningitis, Viral meningitis, Neoplastic meningitis, Pachymeningitis, Neuritis, Neuromyelitis optica, Poliovirus infection, Postpoliomyelitis syndrome, Ocular and orbital inflammation, Ocular inflammation, Chorioretinitis, Conjunctivitis, Allergic conjunctivitis, Blepharoconjunctivitis, Keratoconjunctivitis, Infectious keratoconjunctivitis, Ophthalmia neonatorum, Trachoma, Uveitis, Intermediate uveitis, Pars planitis, Orbital inflammatory disease, Idiopathic orbital inflammation, Respiratory tract inflammation, Lower respiratory tract inflammation, Bronchitis, Lung inflammation, Asthma, Asthma attack, Exercise induced asthma, Nocturnal asthma, Occupational asthma, Status asthmaticus, Pleurisy, Upper respiratory tract inflammation, Pharyngitis, Rhinopharyngitis, Rhinitis, Allergic rhinitis, Perennial allergic rhinitis, Seasonal allergic rhinitis, Rhinopharyngitis, Sinusitis, Acute sinusitis, Chronic sinusitis, Ethmoiditis, Kartagener syndrome, Pansinusitis, Serositis, Familial mediterranean fever, Systemic inflammatory response syndrome, Immune disorder, Allergy, Delayed hypersensitivity, Contact dermatitis, Hypersensitivity, Immediate hypersensitivity, Food hypersensitivity, Egg hypersensitivity, Milk hypersensitivity, Oral allergy syndrome, Peanut hypersensitivity, Wheat hypersensitivity, Fungal allergy, Immune complex disease, Arthus reaction, Immediate type hypersensitivity, Respiratory tract allergy, Allergic rhinitis, Perennial allergic rhinitis, Seasonal allergic rhinitis, Asthma, Asthma attack, Exercise induced asthma, Nocturnal asthma, Occupational asthma, Status asthmaticus, Skin allergy, Contact dermatitis, eczema, autoimmune disease, antiphospholipid syndrome, Autoimmune hemolytic anemia, aplastic anemia, cold agglutinin disease, autoimmune hepatitis, autoimmune nervous system disease, autoimmune demyelinating nervous system disease, Stiff person syndrome, Lambert-Eaton syndrome, Behcet's disease, Crohn's disease, Cutaneous lupus erythematosus, Discoid lupus erythematosus, Evans syndrome, Goodpasture syndrome, Graves' disease, Guillain-Barre syndrome, Hashimoto's disease, Henoch Schonlein purpura, lupus nephritis, multiple sclerosis (MS), myasthenia gravis, paroxysmal nocturnal hemoglobinuria, primary biliary cirrhosis, painful bladder syndrome, psoriasis, Parapsoriasis, Psoriatic arthritis, rheumatoid arthritis, Adult onset Stills disease, Felty syndrome, Juvenile rheumatoid arthritis, Sjögren's syndrome, systemic lupus erythematosus (SEE), Temporal arteritis, Extracranial temporal arteritis, Intracranial temporal arteritis, ulcerative colitis, Vitiligo, Non segmental vitiligo, Segmental vitiligo, graft-versus-host disease, Transplant rejection, Bone marrow transplant rejection, Cell transplant rejection, Corneal transplant rejection, Heart transplant rejection, Kidney transplant rejection, Liver transplant rejection, Lung transplant rejection, organ transplant rejection, intestine transplantation, large intestine transplantation, small intestine transplantation, pancreas transplant rejection, islet cell transplant rejection, skin transplant rejection, tissue transplant rejection, immune deficiency, Agammaglobulinemia, Brutons disease, combined immunodeficiency, HIV, acquired immune deficiency syndrome (AIDS), AIDS related complex, Nezelof syndrome, severe combined immunodeficiency syndrome, adenosine deaminase deficiency, common variable immunodeficiency, DiGeorge syndrome, dysgammaglobulinemia, Immunoglobulin A deficiency, Immunoglobulin G deficiency, phagocyte bactericidal disorder, Chediak Higashi syndrome, chronic granulomatous disease, Job syndrome, Wiskott-Aldrich syndrome, immunoadsorption, lymphatic system disease, adenoid disease, adenoid hypertrophy, adenoid tumor, adenoiditis, lymphadenopathy, Kawasaki disease, lymphadenitis, lymphangiophlebitis, lymphangitis, lymphatic system tumor, Castleman's disease, lymphangioma, cystic hygroma, lymphangiomyoma, interstitial cystitis, a neuromyelitis optica spectrum disorder, juvenile neuronal ceroid lipofuscinosis, autoimmune bullous dermatose, nephrotic syndrome (e.g. including idiopathic nephrotic syndrome or minimal change nephropathy), idiopathic membranous nephropathy, congenital urological abnormality, chronic inflammatory demyelinating polyradiculopathy, immune thrombocytopenia, microscopic polyangiitis, MPO-ANCA vasculitis, Takayasu arteritis, hyperkalemia, Bronchiolitis Obliterans, polycystic liver disease, polyomavirus infection, amyotrophic lateral sclerosis (AES), familial lipoprotein lipase deficiency, Hurler Syndrome, Fanconi Anemia, Glanzmann Thrombasthenia, severe congenital neutropenia, leukocyte adhesion deficiency, Shwachman-Diamond Syndrome, Diamond-Blackfan Anemia, Dyskeratosis-congenita, Chediak-Higashi Syndrome, histiocytosis, DOCKS deficiency, uremia (e.g., uremia due to renal transplantation), Epidermolysis Bullosa, Amegakaryocytic Thrombocytopenia, Kostmann Syndrome, Lysosomal Storage Disease, Peroxisomal Disorder, mastocytosis, and Henoch-Schoenlein Purpura Nephritis.

In some embodiments, the present invention provides a method of treating a disease, disorder, or condition in a patient in need thereof, comprising administering to the patient a disclosed lipid prodrug such as a compound of formula I or VI, or a pharmaceutically acceptable salt thereof, wherein the disease, disorder, or condition is selected from end stage renal disease (ESRD), allogeneic peripheral haematopoietic stem cell transplant, neuroepithelial tumor, multiple myeloma, agnogenic myeloid metaplasia, leukemia, malignant lymphoma, Smith-Magenis Syndrome, a congenital haemoglobinopathy, a sickle cell disorder, a thalassemic disorder such as beta-thalassemia, type 1 diabetes, severe systemic sclerosis, a myelodysplastic syndrome or neoplasm, antibody-mediated rejection, accelerated phase chronic myelogenous leukemia, adult acute lymphoblastic leukemia, adult acute myeloid leukemia with 11q23 (MEL) abnormalities, adult acute myeloid leukemia with Del(5q), adult nasal type extranodal NK/T-Cell lymphoma, anaplastic large cell lymphoma, angioimmunoblastic T-cell lymphoma, blastic phase chronic myelogenous leukemia, childhood acute lymphoblastic leukemia, Burkitt lymphoma, chronic myelogenous leukemia, diffuse large cell lymphoma, immunoblastic large cell lymphoma, nasal type extranodal NK/T-cell lymphoma, chronic myelomonocytic leukemia, chronic phase chronic myelogenous leukemia, cutaneous B-cell non-Hodgkin lymphoma, essential thrombocythemia (ET), extranodal marginal zone B-cell lymphoma of mucosa-associated lymphoid tissue, hepatosplenic T-cell lymphoma, intraocular lymphoma, juvenile myelomonocytic leukemia, nodal marginal zone B-cell lymphoma, noncutaneous extranodal lymphoma, peripheral T-Cell Lymphoma (PTCL), polycythemia vera (PV), post-transplant lymphoproliferative disorder, primary myelofibrosis, recurrent adult diffuse large cell lymphoma, recurrent adult diffuse mixed cell lymphoma, recurrent adult diffuse small cleaved cell lymphoma, recurrent adult grade III lymphomatoid granulomatosis, Hodgkin's lymphoma, recurrent adult immunoblastic large cell lymphoma, recurrent adult lymphoblastic lymphoma, recurrent adult T-cell leukemia/lymphoma, recurrent childhood or adult acute myeloid leukemia, recurrent childhood anaplastic large cell lymphoma, recurrent childhood grade III lymphomatoid granulomatosis, recurrent childhood large cell lymphoma, recurrent childhood lymphoblastic lymphoma, recurrent childhood small noncleaved cell lymphoma, recurrent cutaneous T-cell non-Hodgkin lymphoma, recurrent grade 1 follicular lymphoma, recurrent grade 2 follicular lymphoma, recurrent grade 3 follicular lymphoma, mantle cell lymphoma, marginal Zone Lymphoma, mycosis fungoides/Sezary Syndrome, small lymphocytic lymphoma, non-small cell lung cancer, recurrent/refractory childhood Hodgkin lymphoma, refractory anemia with excess blasts, refractory cytopenia with multilineage dysplasia, hairy cell leukemia, refractory multiple myeloma, relapsing chronic myelogenous leukemia, secondary acute myeloid leukemia, small intestine lymphoma, splenic marginal zone lymphoma, T-cell large granular lymphocyte leukemia, testicular lymphoma, Waldenstrom's Macroglobulinemia (WM), acute myeloid leukaemia (in remission), aplastic anemia (AA), chronic myelomonocytic leukemia, indolent Non-Hodgkin's Lymphoma, acute myeloid leukemia (AML), Hodgkin's Lymphoma, a myeloproliferative neoplasm, plasma cell myeloma, refractory anemia, refractory anemia with excess blasts, refractory anemia with ring sideroblasts, refractory cytopenia with multi lineage dysplasia, refractory cytopenia with multilineage dysplasia and ring sideroblasts, uveitis, renal interstitial fibrosis, interstitial lung disease, chronic kidney disease, cytomegalovirus infection, antibody-mediated rejection, hepatocellular carcinoma, pancreatic cancer, sarcoma, Ewing's tumor, and hypodiploidy.

In some embodiments, the lipid prodrug is administered in combination with one or more additional immunomodulatory (e.g., immunosuppressive) agents or other co-administered agents such as tacrolimus, everolimus, sirolimus, a steroid such as prednisone, prednisolone, or dexamethasone, cyclophosphamide, azathioprine, methotrexate, or the like. In some embodiments, the lipid prodrug, e.g., a MPA lipid prodrug disclosed herein, is administered in combination with one or more additional immunomodulatory (e.g., immunosuppressive) agents or other co-administered agents such as tacrolimus, everolimus, sirolimus, a steroid such as prednisone, prednisolone, or dexamethasone, cyclophosphamide, azathioprine, methotrexate, or the like. In some embodiments, the one or more immunomodulatory (e.g., immunosuppressive) agents or other co-administered agents such as tacrolimus, everolimus, sirolimus, a steroid such as prednisone, prednisolone, or dexamethasone, cyclophosphamide, azathioprine, methotrexate, or the like are administered as a lipid prodrug form. In some embodiments, the lipid prodrug form is prepared according to a method described herein. In some embodiments, the lipid prodrug is administered in combination with a calcineurin inhibitor (such as ciclosporin or tacrolimus) and/or prednisolone. In some embodiments, the calcineurin inhibitor (such as ciclosporin or tacrolimus) and/or prednisolone are administered as a lipid prodrug form. In some embodiments, the lipid prodrug form is prepared according to a method described herein. In some embodiments, the lipid prodrug is administered in combination with an antibacterial, antifungal, or antiviral agent, such as ribavirin. In some embodiments, the antibacterial, antifungal, or antiviral agent, such as ribavirin, are administered as a lipid prodrug form. In some embodiments, the lipid prodrug form is prepared according to a method described herein.

2. Definitions

While the terms used herein are believed to be well understood by one of ordinary skill in the art, definitions are set forth herein to facilitate explanation of the presently-disclosed subject matter.

As used herein, the term "about," when referring to a numerical value or range of a parameter such as mass, weight, volume, time, concentration, biological activity, clogP, or percentage, is meant to encompass variations of, e.g., ±20%, in some embodiments ±10%, in some embodiments ±5%, in some embodiments ±1%, in some embodiments ±0.5%, and in some embodiments ±0.1% from the specified value or range.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "lipid," as used herein, refers to natural and non-natural hydrophobic and/or lipophilic fats, oils, polymers, hydrocarbons, and other such materials. In some embodiments, suitable lipids, when incorporated into a lipid prodrug, are processed or metabolized similarly to triglyercides in the GI tract or mimic such processing or metabolism. The term "glyceride" refers to an ester of glycerol (1,2,3-propanetriol) with acyl radicals of fatty acids or other lipids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides" (or "LCT") means both a simple and mixed triglyceride containing fatty acids with more than 12 carbon atoms (long chain fatty acids, "LCFA"), whereas the term "medium chain triglycerides" (or "MCT") means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECNs of 24-30 typically contain predominately medium chain fatty acids, while triacylglycerols with ECNs of greater than 43 typically contain predominantly long chain fatty acids. Triacylglycerols having an ECNs of 32-42 typically contain one or two MCFA in combination with one or two LCFAs to "fill" the triglyceride. Triacylglycerols with ECNs in the range of greater than 30 to less than 48 typically represent mixed triacylglycerol species that are absent from or are present in significantly lower concentrations in physical mixtures. The fatty acids that occur in foods usually contain an even number of carbon atoms in an unbranched chain, e.g., lauric or dodecanoic acid.

The term "self-immolative group," as used herein, refers to a bivalent chemical moiety that comprises a covalent, scissile bond as one of its bivalent bonds and a stable, covalent bond with a therapeutic agent as its other bivalent bond, wherein the bond with the therapeutic agent becomes labile upon cleavage of the scissile bond. Examples of self-immolative groups include, but are not limited to, disulfide groups, hydrazones, acetal self-immolative groups, carboxyacetal self-immolative groups, carboxy(methylacetal) self-immolative groups, p-hydroxybenzyl self-immolative groups, para-hydroxybenzyl carbonyl self-immolative groups, flipped ester self-immolative groups, and trimethyl lock, or 2-hydroxyphenyl carbamate (2-HPC) self-immolative groups. A number of other suitable self-immolative groups are known in the art as described, for example, in C. A. Blencowe et al., Polym. Chem. 2011, 2, 773-790 and F. Kratz et al., ChemMedChem. 2008, 3(1), 20-53; Huvelle, S. et al., Org. Biomol. Chem. 2017, 75(16), 3435-3443; and Alouane, A. et al., Angewandte Chemie international lidilion 2015, 54 (26), 7492-7509; and Levine, M. N. et al., Chem. Sci. VL-IS-3 (8), 2412-2420; each of which is hereby incorporated by reference in its entirety.

In some embodiments, the therapeutic agent is covalently attached to the lymphatic drug-release moiety (i.e., the remaining portion of the lipid prodrug besides the therapeutic agent) by the use of "click" chemistry. The term "click-ready group" refers to a chemical moiety capable of undergoing a click reaction, such as an azide or alkyne.

Click reactions tend to involve high-energy ("spring-loaded") reagents with well-defined reaction coordinates that give rise to selective bond-forming events of wide scope. Examples include nucleophilic trapping of strained-ring electrophiles (epoxide, aziridines, aziridinium ions, episulfonium ions), certain carbonyl reactivity (e.g., the reaction between aldehydes and hydrazines or hydroxylamines), and several cycloaddition reactions. The azide-alkyne 1,3-dipolar cycloaddition and the Diels-Alder cycloaddition are two such reactions.

Such click reactions (i.e., dipolar cycloadditions) are associated with a high activation energy and therefore require heat or a catalyst. Indeed, use of a copper catalyst is routinely employed in click reactions. However, in certain instances where click chemistry is particularly useful (e.g., in bioconjugation reactions), the presence of copper can be detrimental (See Wolbers, F. et al.; Electrophoresis 2006, 27, 5073). Accordingly, methods of performing dipolar cycloaddition reactions were developed without the use of metal catalysis. Such "metal free" click reactions utilize activated moieties in order to facilitate cycloaddition. Therefore, the present invention provides click-ready groups suitable for metal-free click chemistry.

Certain metal-free click moieties are known in the literature. Examples include 4-dibenzocyclooctynol (DIBO)

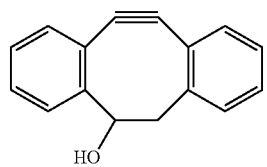 [SMILES: OC1Cc2ccccc2C#Cc2ccccc21]

(from Ning et al; *Angew Chem Int Ed,* 2008, 47, 2253); gem-difluorinated cyclooctynes (DIFO or DFO)

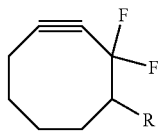

(from Codelli, et al.; *J Am. Chem. Soc.* 2008, 130, 11486-11493.); biarylazacyclooctynone (BARAC)

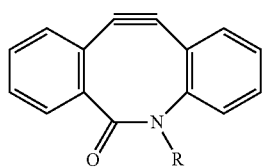

(from Jewett et al.; *J. Am. Chem. Soc.* 2010, 132, 3688.); or bicyclononyne (BCN) (From Dommerholt, et al.; *Angew Chem Int Ed,* 2010, 49, 9422-9425).

As used herein, the phrase "a moiety suitable for metal-free click chemistry" refers to a functional group capable of dipolar cycloaddition without use of a metal catalyst. Such moieties include an activated alkyne (such as a strained cyclooctyne), an oxime (such as a nitrile oxide precursor), or oxanorbornadiene, for coupling to an azide to form a cycloaddition product (e.g., triazole or isoxazole).

As used here in, the term "therapeutic agent," "active pharmaceutical agent," "active agent," or "pharmaceutical agent" includes any therapeutic agent or imaging (contrasting) agent which would benefit from transport via the intestinal lymphatic system, for example, to enable oral administration (e.g. of an intravenously administered therapeutic agent), to avoid first pass metabolism, avoid liver toxicity or other toxicity, or for targeted delivery within the lymphatic system.

Lipid prodrug compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, Handbook of Chemistry and Physics, 98th Ed. Additionally, general principles of organic chemistry are described in "Organic Chemistry," Thomas Sorrell, University Science Books, Sausalito: 1999, and *March's Advanced Organic Chemistry: Reactions, Mechanisms, and Structure*, M. B. Smith and J. March, 7th Edition, John Wiley & Sons, 2013, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphonates and phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

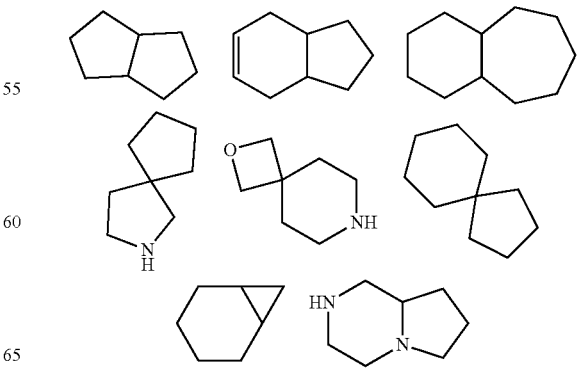

Exemplary bridged bicyclics include:

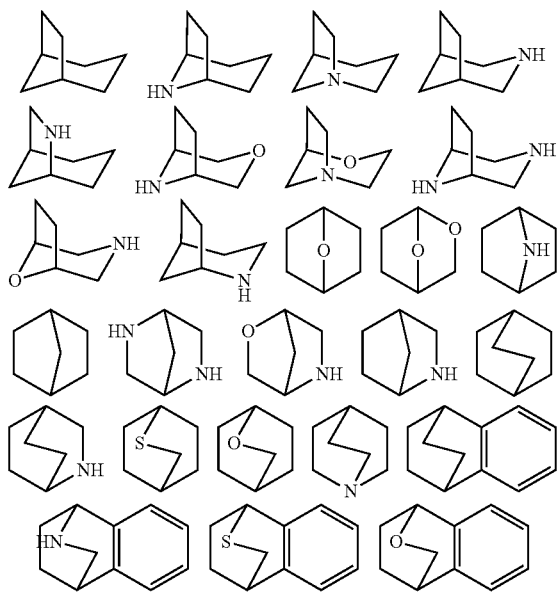

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of boron, oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain" refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinvl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in TV-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical,"

are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)(NR^\circ)R^\circ$; $-S(O)_2N=C(NR^\circ_2)_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$.

Each $R^\circ$ is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from $=O$ and $=S$; or each $R^\circ$ is optionally substituted with a monovalent substituent independently selected from halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ Straight or branched alkylene)$C(O)OR^\bullet$, or $-SSR^\bullet$.

Each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, or a divalent substituent bound to vicinal substitutable carbons of an "optionally substituted" group is $-O(CR^*_2)_{2-3}O-$, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^e$ is unsubstituted or where preceded by halo is substituted only with one or more halogens.

An optional substituent on a substitutable nitrogen is independently $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic, unsubstituted $-OPh$, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, $-R^\bullet$, -(halo$R^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group (or other basic group) formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Uses, Formulation and Administration

Uses of Lymphatic-Directing Livid Prodrugs

Disclosed herein are lymphatic-directing lipid prodrugs, as well as pharmaceutically acceptable compositions comprising a disclosed lipid prodrug, and a pharmaceutically acceptable excipient, diluent, or carrier, are useful for treating a variety of diseases, disorders or conditions. Such diseases, disorders, or conditions include those described herein.

One of ordinary skill in the art will recognize and appreciate that each of the therapeutic agents described herein are known to be associated with treatment of one or more diseases, disorders, or conditions. Accordingly, it will be appreciated that, in certain embodiments, the present invention provides a method of treating a disease, disorder, or condition in a patient in need thereof comprising administering to said patient a disclosed lipid prodrug. In certain embodiments, the present invention provides a method of treating a disease, disorder, or condition in a patient in need thereof comprising administering to said patient a disclosed lipid prodrug, e.g., a lipid prodrug form of MPA.

The presently disclosed lipid prodrugs, e.g., lipid prodrug forms of MPA, are useful for the stable transport of pharmaceutical agents to the intestinal lymph and release of the pharmaceutical agents in the lymph, lymphocytes, lymphoid tissues, tissues with high lipase activity such as adipose tissue, certain cancers, the liver, or in the systemic circulation. Disclosed lipid prodrugs, e.g., lipid prodrug forms of MPA, are particularity useful for the transport and release of pharmaceutical agents that benefit from avoidance of first pass metabolism, for example, therapeutic agents that exhibit greater than about 50% first pass metabolism when administered orally. In some embodiments, the therapeutic agent exhibits greater than about 60% first pass metabolism when administered orally. In some embodiments, the therapeutic agent exhibits greater than about 20%, 25%, 30%, 40%, 50%, 60%, 70%, 80%, or 90% first pass metabolism when administered orally.

The presently disclosed lipid prodrugs are also useful for the targeted release of the therapeutic agent within the lymphatic system, for example, in the lymph, lymphocytes and lymphoid tissues, as well as in tissues with high lipase activity such as adipose tissue, certain cancers, or the liver. In some embodiments, the therapeutic agent exhibits poor lymphatic transport when administered orally. In some embodiments, the therapeutic exhibits less than 70%, 60%, 50%, 40%, 30%, 20%, 15%, 10%, 8%, 5%, 4%, 3%, 2%, 1%, 0.5%, 0.25%, 0.2%, 0.15%, or 0.1% lymphatic transport when administered orally. In contrast, the present invention provides for improved lymphatic transport of such therapeutic agents. In some embodiments, a disclosed lipid prodrug exhibits at least 1%, 5%, 7.5%, 10%, 12.5%, 15%, 20%, 25%, 30%, 35%, 40%, or 50% lymphatic transport when administered orally. In some embodiments, a disclosed lipid prodrug exhibits about 1-50%, 5-40%, 10-30%, 15-25%, or about 50%, 40%, 30%, 25%, 20%, 15%, 12.5%, 10%, 7.5%, 5%, 2.5%, or 1% lymphatic transport when administered orally, as measured by either w/w % of the lipid prodrug administered or w/w % of the therapeutic agent in its lipid prodrug form vs. the unmodified therapeutic agent.

In some embodiments, a disclosed lipid prodrug, e.g., the MPA lipid prodrug, is delivered to the central nervous system (CNS) or crosses the blood-brain barrier (BBB) via the lymphatic system.

In some embodiments, the present disclosure provides a method of modulating an immune response, comprising administering to a patient in need thereof an effective amount of a disclosed lipid prodrug that comprises an immunomodulatory therapeutic agent. In some embodiments, the immunomodulatory therapeutic agent is MPA. In some embodiments, the immune response includes one or more immune responses mediated by the lymphatic system, or mediated by immune cells in the lymphatic system. In some embodiments, the present disclosure provides a method of modulating an immune response, e.g., modulating, e.g., inhibiting or reducing the activation of B and/or T lymphocytes, or eliminating or reducing the production of activated B and/or T lymphocytes, comprising administering to a patient in need thereof an effective amount of a disclosed lipid prodrug form of MPA.

In some embodiments, the present disclosure provides a method of increasing transport of an immune suppressant, e.g., of MPA, to the lymph, the method comprising administering to a patient in need thereof an effective amount of a disclosed lipid prodrug form of MPA. In some embodiments, the compositions described herein comprising a prodrug form of MPA are useful for increasing transport of an immune suppressant, e.g., of MPA, to the lymph.

In some embodiments, the present disclosure provides a method of reducing the first pass metabolism observed with MPA, the method comprising administering to a patient in need thereof an effective amount of a disclosed lipid prodrug form of MPA. In some embodiments, the compositions described herein comprising a prodrug form of MPA are useful for reducing the first pass metabolism observed with MPA.

In some embodiments, the present disclosure provides a method of administering MPA, wherein the adverse side effects observed with MPA are reduced, the method comprising administering to a patient in need thereof an effective amount of a disclosed lipid prodrug form of MPA. In some embodiments, the compositions described herein comprising a prodrug form of MPA are useful for reducing the adverse side effects observed with administration of MPA In some embodiments, the present disclosure provides a method of reducing the activation of macrophages, or eliminating or reducing the production of activated macrophages, the method comprising administering to a patient in need thereof an effective amount of a disclosed lipid prodrug form of MPA. In some embodiments, the present disclosure provides a method of suppressing antibody formation by E-lymphocytes, the method comprising administering to a patient in need thereof an effective amount of a disclosed lipid prodrug form of MPA. In some embodiments, the present disclosure provides a method for reducing infiltration of circulating monocytes and lymphocytes to a site of inflammation, the method comprising administering to a patient in need thereof an effective amount of a disclosed lipid prodrug form of MPA. Any of the MPA lipid prodrugs described herein can be used in any of the methods described herein. In some embodiments, the MPA lipid prodrug is a compound of formula I or VI, or a pharmaceutically acceptable salt thereof, or combinations thereof. In some embodiments, the MPA lipid prodrug is selected from the compounds depicted in Table 1 or a pharmaceutically acceptable salt thereof, or combinations thereof. Non-limiting examples of such MPA lipid prodrugs include, for example, MPA-2-TG (I-34) or MPA-(O-C10bMe-2-TG)-OMe (I-16) or a pharmaceutically acceptable salt thereof. Such lipid prodrugs can be used for treating diseases associated with hyperinflammation.

In some embodiments, the patient is suffering from a hyperproliferative disease, disorder, or condition such as cancer. In some embodiments, the patient is suffering from an autoimmune disease, disorder, or condition.

The present disclosure provides pharmaceutical compositions comprising at least one lipid prodrug form of MPA, e.g., as described herein, and uses of such for inhibiting or reducing the activation of B and/or T lymphocytes, or eliminating or reducing the production of activated B and/or T lymphocytes. In some embodiments, the compositions described herein comprising a prodrug form of MPA, are useful for reducing the activation of macrophages, or eliminating or reducing the production of activated macrophages. In some embodiments, the compositions described herein are useful for suppressing antibody formation by B-lymphocytes. In some embodiments, the compositions comprising at least on lipid prodrug form of MPA are capable of reducing infiltration of circulating monocytes and lymphocytes to a site of inflammation. Any of the MPA lipid prodrugs described herein are used in any of the methods described herein. In some embodiments, the MPA lipid prodrug is a compound of formula I or VI, or a pharmaceutically acceptable salt thereof, or combinations thereof. In some embodiments, the MPA lipid prodrug is selected from the compounds depicted in Table 1, or a pharmaceutically acceptable salt thereof, or combinations thereof. Non-limiting examples of such MPA lipid prodrugs include for example MPA-2-TG (I-34) or MPA-(O-C10bMe-2-TG)-OMe (I-16) or a pharmaceutically acceptable salt thereof.

In some aspects, the invention provides a method of treating a disease, disorder, or condition selected from inflammatory disorders, autoimmune disorders, auto inflammatory diseases (such as IBD), metabolic disease, neurological disorders, transplant rejection and/or graft-versus-host disease and others described herein, comprising administering to a patient in need thereof an effective amount of a disclosed lipid prodrug. In some embodiments, the present disclosure provides methods for reducing, ameliorating, or eliminating one or more symptom(s) associated with inflammatory disorders, autoimmune disorders, auto inflammatory diseases (such as IBD), metabolic disease, neurological disorders, transplant rejection and/or graft-versus-host disease and others described herein, comprising administering to a patient in need thereof an effective amount of a disclosed lipid prodrug.

In some embodiments, the disclosure provides a method for treating, reducing, ameliorating, or eliminating one or more symptom(s) associated with inflammatory disorders, autoimmune disorders, autoinflammatory diseases (such as IBD), metabolic disease, neurological disorders, transplant rejection and/or graft-versus-host disease, and others described herein in a patient, comprising administering to a patient in need thereof an effective amount of a disclosed lipid prodrug. In some embodiments, the disclosure provides a method for treating inflammatory disorders, including autoimmune disorders, autoinflammatory diseases (such as IBD), metabolic disease, neurological disorders, transplant rejection and/or graft-versus-host disease, and others described herein in a patient, comprising administering to a patient in need thereof an effective amount of a disclosed lipid prodrug. The present disclosure provides pharmaceutical compositions comprising at least one lipid prodrug form of MPA, e.g., as described herein and uses of such for treating, reducing, ameliorating, or eliminating one or more symptom(s) associated with inflammatory disorders, autoimmune disorders, autoinflammatory diseases (such as IBD), metabolic disease, neurological disorders, transplant rejection and/or graft-versus-host disease, and others described herein in a patient. In some embodiments, the MPA lipid prodrug is selected from a compound of formula I or VI, or a pharmaceutically acceptable salt thereof. In some embodiments, the MPA lipid prodrug is selected from a compound depicted in Table 1 or a pharmaceutically acceptable salt thereof.

In some embodiments, the inflammatory disorder is selected from one or more diseases listed herein under "Therapeutic Agents and Exemplary Associated Diseases." In some embodiments, the disease is an autoimmune disease. In some embodiments, the inflammatory disorder is, or is related to, transplant rejection and/or graft-versus-host disease. In some embodiments, the disorder is a metabolic, and/or a neurological disorder, and/or viral infection. In some embodiments, the disease or disorder is an auto inflammatory disorder. The method may comprise preparing a pharmaceutical composition with an MPA lipid prodrug described herein, and administering the pharmaceutical composition to a subject in a therapeutically effective amount.

The inflammatory bowel diseases (IBD; e.g., Crohn's disease, ulcerative colitis) are chronic idiopathic intestinal inflammatory disorders. Symptoms associated with the aforementioned diseases and conditions include, but are not limited to, one or more of diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, inflammation of the skin, inflammation of the eyes, inflammation of the joints, inflammation of the liver, and inflammation of the bile ducts. Such diseases and conditions associated with gut inflammation include, but are not limited to, auto inflammatory diseases, inflammatory bowel diseases, diarrheal diseases, and related diseases. "Inflammatory bowel diseases" and "IBD" are used interchangeably herein to refer to a group of diseases associated with gut inflammation, which include, but are not limited to, Crohn's disease, ulcerative colitis, collagenous colitis, lymphocytic colitis, diversion colitis, Behcet's disease, and indeterminate colitis. As used herein, "diarrheal diseases" include, but are not limited to, acute watery diarrhea, e.g., cholera; acute bloody diarrhea, e.g., dysentery; and persistent diarrhea. As used herein, related diseases include, but are not limited to, short bowel syndrome, ulcerative proctitis, proctosigmoiditis, left-sided colitis, pancolitis, and fulminant colitis.

IBD is characterized by dysregulated immune responses, leading to abnormal cytokine production and cellular inflammation, and consequently injury to the distal small intestine and the colonic mucosa. A large amount of evidence points to involvement of T cell and T cell trafficking to the gut and associated lymphoid tissue as a key part in disease pathogenesis. Chronic gut inflammation in IBD is a consequence of dysregulated immune response to commensal gut bacteria. To mount a protective immune response to pathogenic bacteria in the gut, intravascular naive T cells must home to the inductive sites of the intestinal tract, the gut-associated lymphoid tissue (GALT) and the gut-draining MLNs, where they undergo antigen-driven priming, activation, polarization, and expansion to yield Th1 and/or Th17 effector cells. Next, the effector cells leave the lymphoid tissue through the efferent lymphatics, enter the systemic circulation, and then arrive at the gut, where they help to destroy the pathogenic bacteria. These same events may occur in response to commensal bacteria resulting in induction of chronic intestinal inflammation directed against bacterial antigens, (see e.g., Kobziev et al., Gut-associated lymphoid tissue, T cell trafficking, and chronic intestinal inflammation; Ann N Y Acad Sci. 2010 October; 1207 (Suppl 1): E86-E93, and references therein).

Furthermore, it has been shown that MPA derivative mycophenolate mofetil improves experimental colitis and induced inflammatory response remission of Crohn's disease and have demonstrated efficacy in the management of difficult IBD (Lv, et al., Mycophenolate Mofetil Modulates Differentiation of Th1/Th2 and the Secretion of Cytokines in an Active Crohn's Disease Mouse Model; Int J Mol Sci. 2015 November; 16(11): 26654-26666). Additionally results from clinical trials suggest that mycophenolate mofetil may represent a promising treatment for inducing and maintaining remission in IBD patients, including ulcerative colitis in particular, where few alternative therapies are available (Smith and Cooper, Mycophenolate mofetil therapy in the management of inflammatory bowel disease—a retrospective case series and review; J Crohns Colitis. 2014 August; 8(8): 890-7; Tan and Lawrence, Use of mycophenolate mofetil in inflammatory bowel disease; World J Gastroenterol. 2009 Apr. 7; 15(13): 1594-9).

Accordingly, without wishing to be bound by theory, targeting MPA to the MEN, e.g., using a lipid prodrug of MPA, e.g., as described herein, may provide benefit in the treatment of IBD and other autoinflammatory diseases of the gut, by allowing proximity to the site of T cell activation, e.g., may allow greater efficacy of the treatment and/or alternate, lower MPA dosing regimens helping to reduce negative side effects of MPA, and increase patient compliance.

Accordingly, in some embodiments, the disclosure provides a method for treating or reducing, ameliorating, or eliminating symptoms for diseases and conditions associated with gut inflammation in a subject. In some embodiments, the disclosure provides a method for treating a disease associated with gut inflammation in a subject, the method comprising administering to a subject in need thereof an effective amount of an MPA lipid prodrug described herein, e.g., a compound of formula I or VI, or a pharmaceutically acceptable salt thereof, including but not limited to, a compound depicted in Table 1 or a pharmaceutically acceptable salt thereof. In some embodiments, the disease associated with gut inflammation is ulcerative colitis.

In some embodiments, the disclosure provides the use of an MPA lipid prodrug as a medicament for the treatment of diseases and conditions associated with gut inflammation, wherein the MPA lipid prodrug is any of the compounds described herein, e.g., a compound of formula I or VI, or a pharmaceutically acceptable salt thereof, including but not limited to, a compound depicted in Table 1 or a pharmaceutically acceptable salt thereof. In some embodiments, the disclosure provides the use of an MPA lipid prodrug as a medicament for the treatment of diseases and conditions associated with gut inflammation, wherein the MPA lipid prodrug is MPA-2-TG (I-34) or MPA-(O-C10bMe-2-TG)-OMe (I-16).

In certain embodiments, administering a disclosed lipid prodrug or pharmaceutically acceptable salt or pharmaceutical composition thereof to the subject reduces inflammation, e.g., in the lining of the gut. In some embodiments, symptoms are ameliorated. In some embodiments, administering the lipid prodrug or composition results in complete response, partial response, reduced severity, or stable disease. Disease severity (mild, moderate, or severe) may be assessed as follows: (1) impact of the disease on the patient (clinical symptoms, quality of life, fatigue, and disability); (2) measurable inflammatory burden (C-reactive protein, other inflammatory markers known in the art, mucosal lesions, upper gastrointestinal involvement, and disease extent), and disease course (including structural damage, history/extension of intestinal resection, perianal disease, number of flares, and extraintestinal manifestations). In some embodiments, the disease associated with gut inflammation is Crohn's disease. In some embodiments, the disease associated with gut inflammation is ulcerative colitis.

Celiac disease (CD) is an autoimmune disorder in which the immune system is abnormally sensitive to gluten. CD is triggered by exposure to oral gluten (the storage proteins of wheat and related cereals) in the gut and is characterized by a dysregulation of gluten specific T cell responses. Adaptive immunity plays a key role in CD pathogenesis. Celiac patients have gluten-specific intestinal CD4+ T cells and there is a strong correlation between human leukocyte antigen (HLA)-DQ2 and HLA-DQ8 genes and celiac disease. Small intestinal lesions in CD are defined by mucosal infiltration with lymphocytes, crypt hyperplasia and villus atrophy and are thought to be induced by the secretion of interferon (IFN)-γ from these gluten-specific T cells (Freitag et al., Gliadin-primed CD4+CD45RBlowCD25− T cells drive gluten dependent small intestinal damage after adoptive transfer into lymphopenic mice; Gut. 2009 December; 58(12): 1597-1605). Accordingly, given that celiac is an inflammatory disorder of the gut involving priming and activation of gliadin-specific T cells in the GALT and/or MSN, treatment with MPA or a lymph targeting lipid prodrug thereof may provide a means to ameliorate or reduce inflammation. Without wishing to be bound by theory, lipid prodrugs of MPA described herein, which are predominantly targeted to the lymphatic system, may provide further benefit in the treatment of celiac disease over MPA alone, e.g., by reducing side effects and increasing efficacy, as described herein.

Accordingly, in some embodiments, the disclosure provides a method for the treatment of celiac disease in a subject, the method comprising administering to a subject in need thereof an effective amount of an MPA lipid prodrug described herein.

In some embodiments, the disclosure provides the use of an MPA lipid prodrug as a medicament for the treatment of an autoimmune disorder, wherein the MPA lipid prodrug is any of the compounds described herein and wherein the autoimmune disorder is celiac disease.

Systemic lupus erythematosus (SLE) is a chronic multisystem autoimmune disorder that can affect almost all organ systems including the kidneys, skin, joints, and central nervous system. Lupus nephritis (LN) is an immune complex-mediated glomerulonephritis that affects nearly 50% of patients with systemic lupus erythematosus (SLE). B cells, defects in the naïve B cell tolerance, and the production of autoantibodies have long been known to play a critical part in the pathogenesis of SLE. However, T cells are also major contributors to the disease processes-SLE T cells are abnormal in several ways. For example, in CD4 T cells from active SLE patients T cell calcium flux is faster and cellular signaling is altered (Maria and Davidson, Emerging areas for therapeutic discovery in SLE; Current Opinion in Immunology 2018, 55:1-8, and references therein). More recently, a role for CD8+ T cells is also described (Ling et al., C1q restrains autoimmunity and viral infection by regulating CD8+ T cell metabolism; Science. 2018 May 4; 360(6388): 558-563).

Many recently developed experimental therapeutics have focused on either eliminating or limiting the activity of these immune cells. The treatment of SLE often uses an immunosuppression strategy to induce remission and to avoid relapses using maintenance immunosuppression, usually for years. Immunosuppressive agents are used to treat the renal-immune-complex-mediated injuries responsible for the occurrence of immune complex-mediated glomerulonephritis, lupus nephritis flares (LN), (characterized by reduced renal function, hematuria, and proteinuria; Meliambro et al., Therapy for Proliferative Lupus Nephritis; Rheum Dis Clin N Am 44 (2018) 545-560).

MMF has been shown to be safe and effective in treatment of lupus nephritis. Several clinical trials have been conducted in which MMF is compared to other immunosuppressants, including cyclophosphamide, as induction agents. The results have shown that MMF is at least as effective as cyclophosphamide and may be advantageous over cyclophosphamide (Li et al., Mycophenolate mofetil or tacrolimus compared with intravenous cyclophosphamide in the induction treatment for active lupus nephritis; Nephrology Dialysis Transplantation, Volume 27, Issue 4, 1 Apr. 2012, Pages 1467-1472, and references therein). Without wishing to be bound by theory, targeting MPA to the lymphatic system, e.g., by using a lipid prodrugs of MPA as described herein, may provide further benefit in the treatment of SLE and LN over MPA alone.

In some embodiments, the disclosure provides the use of an MPA lipid prodrug as a medicament for the treatment of SLE and/or LN, wherein the MPA lipid prodrug is any of the compounds described herein, and wherein the autoimmune disorder is SLE and/or LN.

Multiple sclerosis (MS) is the paradigmatic autoimmune inflammatory disorder of the CNS characterized by chronic inflammation, primary demyelination, axonal damage, perivascular infiltration of lymphocytes, and plasma cells in the white substance of the brain and spinal cord, loss of blood brain barrier integrity as well as astrocyte and microglia activation (Negi and Das, CNS: Not an immunoprivilaged site anymore but a virtual secondary lymphoid Organ; International Reviews Of Immunology 2017, Vol. 0, No. 0, 1-12, and references therein). The DCs and macrophages presenting myelin antigens leave the CNS and reach the cervical lymph nodes (LNs) where they present the myelin antigen to auto-reactive T and B lymphocytes, which then differentiate into effector cells. Once activated, these auto-reactive lymphocytes home in the CNS and begin the inflammatory process.

Immunosuppressive therapy, such as cyclophosphamide, is commonly used in the treatment of MS. Several studies suggest that MPA could find an application as a first line disease modifying drug in MS (Michel et al., Mycophenolate mofetil in multiple sclerosis: a multicentre retrospective study on 344 patients. J Neurol Neurosurg Psychiatry. 2014 March; 85(3):279-83). Accordingly, targeting MPA to the lymphatic system using a lipid prodrug form of MPA described herein may provide further benefit in the treatment of MS over MPA alone.

Accordingly, in some embodiments, the disclosure provides a method for treating a neurodegenerative disease in a subject, the method comprising administering to a subject in need thereof an effective amount of an MPA lipid prodrug described herein or antigen binding fragment thereof. In some embodiments, the neurodegenerative disease is multiple sclerosis.

In some embodiments, the disclosure provides the use of an MPA lipid prodrug as a medicament for the treatment of a neurodegenerative disorder, wherein the MPA lipid prodrug is any of the compounds described herein, and wherein the neurodegenerative disease is multiple sclerosis.

Rheumatoid arthritis (RA) is an immune-inflammatory disorder that mainly targets the synovium of diarthrodial joints. Cell-cell and cytokine networks established within the inflamed RA synovium promote disease chronicity, amplify autoimmune responses and cause cartilage and bone destruction (Guo et al., Rheumatoid arthritis: pathological mechanisms and modern pharmacologic therapies Bone Res. 2018; 6: 15). Several clinical observations implicate the lymphatic system in RA pathogenesis. RA takes several years to develop, and the early steps of the disease process in RA occur in lymphoid organs, where lymphocytes are primed and differentiate into effector and memory cells. Next, auto-reactive T cells and B cells are continuously activated and proliferate, resulting in the production of cytokines and autoantibodies. Then, the T cells and B cells invade the synovium, by forming novel lymphoid structures and producing defective repair mechanisms. New blood vessels formed as a result of inflammation allow the immune cells to easily migrate into the synovial lesion. The longevity of the pathologic immune response depends on the specific interactions between the immune cells and the non-lymphoid cells, and determines the level of tissue damage associated with RA (as reviewed in Weyand and Goronzy, "Immunometabolism in early and late stages of rheumatoid arthritis," Nature Reviews Rheumatology, 13(5), 291-301 (2017)).

Accordingly, targeting the lymphoid organs with an agent that can suppress the activation of immune cells within the lymphoid tissue, such as the lipid prodrugs described herein may be useful for the treatment of RA, in particular in the early stages of RA.

In some embodiments, the disclosure provides a method for treating rheumatoid arthritis in a subject, the method comprising administering to a subject in need thereof an effective amount of an MPA lipid prodrug described herein.

In some embodiments, the disclosure provides the use of an MPA lipid prodrug as a medicament for the treatment of an immune-inflammatory disorder, wherein the MPA lipid prodrug is any of the compounds described herein and wherein the immune-inflammatory disorder is rheumatoid arthritis.

Asthma is an inflammatory disease characterized by reversible, and at times irreversible, airflow obstruction and pulmonary symptoms of variable severity. Chronic inflammation in patients with asthma leads to mucosal edema, subepithelial fibrosis, and alterations in the extracellular matrix (Stump et al., Lymphatic Changes in Respiratory Diseases: More than Just Remodeling of the Lung?; Am J Respir Cell Mol Biol. 2017 September; 57(3): 272-279.). Allergen-specific CD4+ T cells play a key role in asthma (reviewed in Ling and Luster, Allergen-Specific CD4+ T Cells in Human Asthma; Ann Am Thorac Soc. 2016 March; 13(Suppl 1): S25-S30). MMF has ben proposed as a potential treatment option for asthma in a number of studies. In one study, MMF reduced IL-5 generation in animal models of asthma and also in peripheral blood mononuclear cells from asthmatics in vitro (Powell et al. The immunomodulatory drugs cyclosporin A, mycophenolate mofetil, and sirolimus (rapamycin) inhibit allergen-induced proliferation and IL-5 production by PBMCs from atopic asthmatic patients. J Allergy Clin Immunol 2001; 108: 915-917). Moreover, MMF improved many measures of asthma control, including ACQ6, FEV1 and exacerbation rates in a clinical trial in patients with long-standing asthma (Grainge, et al. Case series reporting the effectiveness of mycophenolate mofetil in treatment-resistant asthma; Eur Respir J. 2013 October; 42(4):1134-7).

In some embodiments, the disclosure provides a method for treating asthma in a subject, the method comprising administering to a subject in need thereof an effective amount of an MPA lipid prodrug described herein.

In some embodiments, the disclosure provides the use of an MPA lipid prodrug as a medicament for the treatment of an immune-inflammatory disorder, wherein the MPA lipid prodrug is any of the compounds described herein and wherein the immune-inflammatory disorder is asthma.

Transplantation provides lifesaving organs to patients with end-stage organ failure and lifesaving hematopoietic cell grafts to individuals with malignant or nonmalignant hematologic disorders. Alloimmune T cells are the key component of the human adaptive immune response to transplants of organs, cells, and tissues from other humans, which are referred to as allogeneic. This alloimmune response is the central immune response in solid organ transplantation and hematopoietic stem cell transplantation (HSCT), in both host-versus-graft and graft-versus-host responses (DeWolf and Sykes Alloimmune T cells in transplantation; J Clin Invest. 2017 Jun. 30; 127(7): 2473-2481). The success of HSCT is dependent on potent nonspecific immunosuppressive therapy to prevent graft rejection and graft-versus-host disease (GVHD).

The most common use of mycophenolate is to prevent organ rejection after solid organ transplantation. It is extensively used after kidney transplant, but is also used after heart, lung, heart-lung and liver transplantation. Mycophenolate is used in combination with other immunosuppressant medications, especially with the calcineurin inhibitors cyclosporine and tacrolimus. It is also used as an adjunct therapy in patients receiving bone marrow transplant, for graft versus host disease (GVHD).

In some embodiments, the disclosure provides a method for providing immunosuppressive therapy to prevent transplant rejection in a subject, the method comprising administering to a subject in need thereof an effective amount of an MPA lipid prodrug described herein. In some embodiments the transplant is a heart, lung, heart-lung, or liver transplant. In some embodiments, the disclosure provides a method for providing immunosuppressive therapy to prevent graft-versus-host disease in a subject, the method comprising administering to a subject in need thereof an effective amount of an MPA lipid prodrug described herein or antigen binding fragment thereof. In some embodiments, the disclosure provides a method for providing immunosuppressive therapy to prevent host-versus-graft-disease in a subject, the method comprising administering to a subject in need thereof an effective amount of an MPA lipid prodrug described herein or antigen binding fragment thereof. In some embodiments the transplant is a heart, lung, heart-lung or liver transplant. In some embodiments, the transplant is a hematopoietic stem cell transplant.

In some embodiments, the disclosure provides the use of an MPA lipid prodrug as a medicament to prevent transplant rejection in a subject, wherein the MPA lipid prodrug is any of the compounds described herein, and wherein the transplant is selected from a heart, lung, heart-lung or liver transplant.

In some embodiments, the disclosure provides the use of an MPA lipid prodrug as a medicament to prevent graft-versus-host disease in a subject, wherein the MPA lipid prodrug is any of the compounds described herein, and wherein the transplant is a hematopoietic stem cell transplant.

In some embodiments, the disclosure provides the use of an MPA lipid prodrug as a medicament to prevent host-versus-graft disease in a subject, wherein the MPA lipid prodrug is any of the compounds described herein, and wherein the transplant is a hematopoietic stem cell transplant.

In some embodiments of any of the methods described above, the MPA lipid prodrug is a compound of formula I or VI, or a pharmaceutically acceptable salt thereof, or wherein the MPA lipid prodrug is selected from the compounds depicted in Table 1, or a pharmaceutically acceptable salt thereof. In some embodiments, the MPA lipid prodrug is MPA-2-TG (I-34) or MPA-(O-C10bMe-2-TG)-OMe (I-16).

Measurement of T Cell Populations and Inflammation Status

Activated T cells express surface receptors or co-stimulatory molecules, such as CD25+(IL2RA), CD69+, CD95+ (FasR), CD 134+(OX40), CD137+(4-1BB), CD 154+ (CD40L), Ki-67+, and/or KLRG1+. Both surface marker expression and cell proliferation are assessed by flow cytometry.

Inflammatory status can be measured by determining levels of cytokines such as IFN-gamma and/or TNF-alpha, CD44, ICOS granzymeB, Perforin, IL2 (upregulation); CD26L and IL-10 (downregulation)). In some embodiments, inflammatory markers may be measured in plasma or blood. In some embodiments, inflammatory markers are measured in lymphoid fluid.

Inflammatory markers include measurement of CD8+ and CD4+(conventional) T-cell activation (in an in vitro or in vivo assay, e.g., by measuring inflammatory cytokine levels, e.g., IFNgamma, TNFalpha, CD44, ICOS granzymeB, Perforin, IL2 (upregulation); CD26L and IL-10 (downregulation))

Pharmaceutically Acceptable Compositions

According to another embodiment, the present invention provides a composition comprising a lipid prodrug of the present disclosure and a pharmaceutically acceptable carrier, adjuvant, or vehicle. The amount of lipid prodrug in the composition is an amount effective to treat the relevant disease, disorder, or condition in a patient in need thereof (an "effective amount"). In some embodiments, a composition of the present disclosure is formulated for oral administration to a patient.

The term "pharmaceutically acceptable carrier, adjuvant, or vehicle" refers to a nontoxic carrier, adjuvant, or vehicle that does not destroy the pharmacological activity of the agent with which it is formulated. Pharmaceutically acceptable carriers, adjuvants or vehicles that may be used in the disclosed compositions include, but are not limited to, ion exchangers, alumina, stearates such as aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the composition is formulated as a lipophilic mixture, such as a lipid-based composition.

Compositions of the present invention may be administered orally, parenterally, enterally, intracisternally, intraperitoneally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition is administered orally, intraperitoneally, or intravenously. In some embodiments, the composition is a transmucosal formulation. In some embodiments, the composition is injected directly into the lymphatic system. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

To aid in delivery of the composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, the pharmaceutically acceptable composition is formulated for oral administration. Such formulations may be administered with or without food. In some embodiments, the pharmaceutically acceptable composition is administered without food. In other embodiments, the pharmaceutically acceptable composition is administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Therapeutic agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the lipid prodrug is formulated as an orally administerable, lipid-based formulation. Lipid-based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., *Eur. J. Pharm. Sci.* 11 (Supp 2), S93-S98, 2000; Pouton, C. W., *Eur. J. Pharm. Sci.* 29 278-287, 2006).

Lipid vehicles, and the resulting lipid formulations, may contain oil/lipids and/or surfactants, optionally with co-solvents. In the LFCS terminology, Type I formulations include oils or lipids which require digestion, such as mono, di and tri-glycerides and combinations thereof. Type II formulations are water-insoluble self emulsifying drug delivery systems (SEDDS) which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type IIIa) or a greater proportion of water-soluble components (Type IIIb). Type IV formulations contain predominantly hydrophilic surfactants and co-solvents (e.g. PEG, propylene glycol and diethylene glycol monoethyl ether) and are useful for drugs which are poorly water soluble but not lipophilic. Any such lipid formulation (Type I-IV) is contemplated herein for use with a disclosed lipid prodrug or pharmaceutical composition thereof.

In some embodiments, the lipid vehicle contains one or more oils or lipids, without additional surfactants, co-surfactants or co-emulsifiers, or co-solvents, i.e. it consists essentially of one or more oils or lipids. In some further embodiments, the lipid vehicle contains one or more oils or lipids together with one or more water-insoluble surfactants, optionally together with one or more co-solvents. In some embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_{8-12}$ fatty acid chains, medium chain triglycerides containing primarily $C_{8-12}$ fatty acid chains, long chain triglycerides containing primarily $>C_{12}$ fatty acid chains, modified triglycerides, fractionated triglycerides, and mixtures thereof.

Examples of mono and diglycerides which may be used in such formulations include glycerol mono- and diesters having fatty acid chains from 8 to 40 carbon atoms, including hydrolysed coconut oils (e.g. Capmul® MCM), hydrolysed corn oil (e.g. Maisine™35-1). In some embodiments, the monoglycerides and diglycerides are mono- or di- saturated fatty acid esters of glycerol having fatty acid chains of 8 to 18 carbon chain length (e.g. glyceryl monostearate, glyceryl distearate, glyceryl monocaprylate, glyceryl dicaprylate, glyceryl monocaprate and glyceryl dicaprate). Mixtures of fatty acids ("structured glycerides") adapted for enhancing the absorption and transport of lipid soluble compounds are disclosed in, e.g., U.S. Pat. No. 6,013,665, which is hereby incorporated by reference.

Suitable surfactants for use in the lipid formulations include propylene glycol mono- and di-esters of $C_{8-22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, and sucrose stearate; sorbitan fatty acid esters such as, but not limited to, sorbitan laurate, sorbitan palmitate, and sorbitan oleate; polyoxyethylene sorbitan fatty acid esters such as, but not limited to, polysorbate 20, polysorbate 40, polysorbate 60, polysorbate 80, and polysorbate 85; polyoxyethylene mono- and di-fatty acid esters including, but not limited to, polyoxyl 40 stearate and polyoxyl 40 oleate; a mixture of polyoxyethylene mono- and di-esters of $C_{8-22}$ fatty acids and glyceryl mono-, di-, and tri-esters of $C_{8-22}$ fatty acids as sold under tradenames such as Labrasol®, Gelucire® 44/14, Gelucire® 50/13, and Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® REMO, and Cremophor®/Kolliphor® RH60; polyoxyethylene alkyl ethers including, but not limited to, polyoxyl 20 cetostearyl ether and polyoxyl 10 oleyl ether; DL-α-tocopheryl polyethylene glycol succinate; glyceryl mono-, di-, and tri-esters; glyceryl mono-, di-, and tri-esters of $C_{8-22}$ fatty acids; sucrose mono-, di-, and tri-esters; sodium dioctylsulfosuccinate; polyoxyethylene-polyoxypropylene copolymers such as, but not limited to poloxamer 124, poloxamer 188, and poloxamer 407; polyoxyethylene ethers of $C_{8-22}$ fatty alcohols including, but not limited to, polyoxyethylenelauryl alcohol, polyoxyethylenecetyl alcohol, polyoxyethylene stearyl alcohol, polyoxyethyleneoleyl alcohol, as sold under tradenames such as Brij® 35, Brij® 58, Brij® 78, Brij® 98, or a mixture of any two or more thereof.

A co-emulsifier, or co-surfactant, may be used in the formulation. A suitable ω-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid, and caproic acid.

Suitable solvents/co-solvents include ethanol, propylene glycol, polyethylene glycol, diethylene glycol monoethyl ether, and glycerol.

A polymer may also be used in the formulation to inhibit drug precipitation or to alter the rate of drug release. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone, or others as described in, e.g. Warren et al., *Mol. Pharmaceutics* 2013, 10, 2823-2848.

Formulations may be chosen specifically to provide for sustained release of the active in the gastrointestinal (GI) tract in order to control the rate of absorption. Many different approaches may be used to achieve these ends including the use of high melting point lipids that disperse/erode slowly in the GI tract, or polymers that form a matrix that slowly erodes. These formulations may take the form of large monolithic dose forms or may be present as micro or nano-particulate matrices as described in, for example, in Mishra, *Handbook of Encapsulation and Controlled Release*, CRC Press, Boca Raton, (2016) ISBN 978-1-4822-3234-9, Wilson and Crowley, *Controlled Release in Oral Drug Delivery*, Springer, NY, ISBN 978-1-4614-1004-1 (2011) or Wise, *Handbook of Pharmaceutical Controlled Release Technology*, Marcel Dekker, NY, ISBN 0-82467-0369-3 (2000).

Formulations may also contain materials commonly known to those skilled in the art to be included in lipid based formulations, including antioxidants, for example, butylated hydroxyanisole (BHA) or butylated hydroxytoluene (BHT) and solidifying agents such as microporous silica, for example magnesium alumino-metasilicate (Neusilin).

In some embodiments, the lipid prodrug may be co-administered orally with an enzyme inhibitor to increase stability of the prodrug in the gastrointestinal tract or enterocyte. In certain embodiments, the enzyme inhibitor inhibits pancreatic lipases, examples of which include, but are not limited to, Alii® (orlistat). In other embodiments it is envisaged that the enzyme inhibitor will inhibit cellular lipase enzymes such as monoacylglycerol lipase, an example of which includes, but is not limited to, JZL184 (4-nitrophenyl-4- [bis(l, 3-benzodioxol-5-yl)(hydroxy)methyl]piperidine-1-carboxylate).

Combination Therapies

A provided lipid prodrug, or pharmaceutically acceptable composition thereof, may be administered to a patient in need thereof in combination with one or more additional therapeutic agents and/or therapeutic processes. A provided lipid prodrug, e.g., any MPA lipid prodrug described herein, or pharmaceutically acceptable composition thereof, may be administered to a patient in need thereof in combination with one or more additional therapeutic agents and/or therapeutic processes.

The lipid prodrug or pharmaceutically acceptable composition thereof can be administered alone or in combination with one or more other therapeutic compounds, possible combination therapy taking the form of fixed combinations or the administration of the lipid prodrug or composition and one or more other therapeutic compounds being staggered or given independently of one another, or the combined administration of fixed combinations and one or more other therapeutic compounds. A disclosed lipid prodrug or composition can besides or in addition be administered especially for tumor therapy in combination with chemotherapy, radiotherapy, immunotherapy, phototherapy, surgical intervention, or a combination of these. In some embodiments, any of the disclosed MPA prodrugs described herein are combined with one or more additional lipid prodrug(s). In some embodiments, the one or more lipid prodrug(s) are an immune suppressant. Long-term therapy is equally possible as is adjuvant therapy in the context of other treatment strategies, as described above. Other possible treatments are therapy to maintain the patient's status after tumor regression, or even chemopreventive therapy, for example in patients at risk. In some embodiments, the therapy maintains disease severity after a treatment, e.g., in patients with an inflammatory and/or autoimmune disorder described herein.

Such additional agents may be administered separately from a provided lipid prodrug or composition, as part of a multiple dosage regimen. Alternatively, those agents may be part of a single dosage form, mixed together with a disclosed lipid prodrug in a single composition. If administered as part of a multiple dosage regime, the two active agents may be submitted simultaneously, sequentially or within a period of time from one another.

As used herein, the term "combination," "combined," and related terms refers to the simultaneous or sequential administration of therapeutic agents in accordance with the present disclosure. For example, a disclosed lipid prodrug may be administered with another therapeutic agent simultaneously or sequentially in separate unit dosage forms or together in a single unit dosage form. Accordingly, the present disclosure provides a single unit dosage form comprising a disclosed lipid prodrug, an additional therapeutic agent, and a pharmaceutically acceptable carrier, adjuvant, or vehicle. In some embodiments, the additional agent is formulated in a separate composition from the lipid prodrug.

The amount of both a disclosed lipid prodrug and additional therapeutic agent (in those compositions which comprise an additional therapeutic agent as described above) that may be combined with the carrier materials to produce a single dosage form will vary depending upon the patient treated and the particular mode of administration. In certain embodiments, compositions of this invention should be formulated so that a dosage of between 0.01-100 mg/kg body weight/day of a disclosed lipid prodrug can be administered.

In those compositions which comprise an additional therapeutic agent, that additional therapeutic agent and the disclosed lipid prodrug may act synergistically. Therefore, the amount of additional therapeutic agent in such compositions will be less than that required in a monotherapy utilizing only that therapeutic agent. In such compositions, a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Examples of agents with which the lipid prodrugs of this invention may be combined include, without limitation: treatments for Alzheimer's Disease such as Aricept® and Excelon®; treatments for HIV such as ritonavir; treatments for Parkinson's Disease such as L-DOPA/carbidopa, entacapone, ropinirole, pramipexole, bromocriptine, pergolide, trihexyphendyl, and amantadine; agents for treating multiple sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), agents for treating immunodeficiency disorders such as gamma globulin, and agents for treatment of auto-immune disorders such as idiopathic thrombocytopenic purpura (ITP), systemic lupus erythematosus (SEE), scleroderma (systemic sclerosis or SSc), and pemphigus vulgaris (PV).

In certain embodiments, combination therapies of the present invention include a monoclonal antibody or a siRNA therapeutic.

In another embodiment, the present invention provides a method of treating an inflammatory disease, disorder or condition by administering to a patient in need thereof a disclosed lipid prodrug and one or more additional therapeutic agents. Such additional therapeutic agents may be small molecules or a biologic and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), JAK inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a disclosed lipid prodrug and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating an autoimmune disease such as rheumatoid arthritis comprising administering to a patient in need thereof a disclosed lipid prodrug and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a disclosed lipid prodrug and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a disclosed lipid prodrug and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a disclosed lipid prodrug and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a disclosed lipid prodrug and one or more additional therapeutic agents selected from Singulair®, beta-2 agonists such as albuterol (Ventolin® HFA, Proventil® UFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a disclosed lipid prodrug and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, and combinations thereof.

In some embodiments, the present invention provides a method of treating HIV comprising administering to a patient in need thereof a disclosed lipid prodrug and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a Bcl-2 inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a Bcl-2 inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a disclosed lipid prodrug and a Hedgehog (Hh) signaling pathway inhibitor. In some embodiments, the hematological malignancy is DLBCL.

In another embodiment, the present invention provides a method of treating diffuse large B-cell lymphoma (DLBCL) comprising administering to a patient in need thereof a disclosed lipid prodrug and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a disclosed lipid prodrug and one or more additional therapeutic agents selected from bortezomib (Velcade®), and dexamethasone (Decadron®), a hedgehog signaling inhibitor, a Bcl-2 inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenstrom's macroglobulinemia comprising administering to a patient in need thereof a disclosed lipid prodrug and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a Bcl-2 inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheimer's disease comprising administering to a patient in need thereof a disclosed lipid prodrug and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a disclosed lipid prodrug and one or more additional therapeutic agents selected from a steroid, cyclosporin, FK506, rapamycin, a hedgehog signaling inhibitor, a Bcl-2 inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a disclosed lipid prodrug and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, myasthenia gravis, Hashimoto's thyroiditis, Ord's thyroiditis, Graves' disease, autoimmune thyroiditis, Sjögren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, Fanconi Anemia, autoimmune hepatitis, autoimmune gastritis, pernicious anemia, celiac disease, Goodpasture's syndrome, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, caused by HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjögren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, atopic dermatitis, degenerative joint disease, vitiligo, autoimmune hypopituitarism, Behcet's disease, scleraderma, mycosis fungoides, acute inflammatory responses (such as acute respiratory distress syndrome and ischemia/reperfusion injury), and Graves' disease.

In some embodiments the present invention provides a method of treating or lessening the severity of a disease comprising administering to a patient in need thereof a disclosed lipid prodrug and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or a solid tumor.

In another embodiment, the present invention provides a method of treating or lessening the severity of a disease comprising administering to a patient in need thereof a disclosed lipid prodrug and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a disclosed lipid prodrug and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

A disclosed lipid prodrug of the current invention may also be used to advantage in combination with an antiproliferative compound. Such antiproliferative compounds include, but are not limited to, aromatase inhibitors; anti estrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycm, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Fetrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Penfosme; Ilmofosme; RO 318220 and RO 320432; GO 6976; Isis 3521; LY333531/LY379196; isochinoline compounds; FTIs; PD 184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-10}33$, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYE-719, dactolisib, XL-147, XL-765, and idelalisib; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYE-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogues thereof), dual Bcl-2/Bcl-xL inhibitors (Infinity Pharmaceuticals/N ovartis Pharmaceuticals), Genasense (G3139), HA14-1 (and analogues thereof; see WO2008118802), navitoclax (and analogues thereof, see U.S. Pat. No. 7,390,799), NH-1 (Shenayng Pharmaceutical University), obatoclax (and analogues thereof, see WO 2004/106328, hereby incorporated by reference), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with a disclosed lipid prodrug include, but are not limited to, bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term "cyclooxygenase inhibitor" as used herein includes, but is not limited to, Cox-2 inhibitors, 5-alkyl substituted 2-arylaminophenylacetic acid and derivatives, such as celecoxib (Celebrex™), etoricoxib, valdecoxib or a 5-alkyl-2- arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™.

Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase enzyme, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AGS340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HD AC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), a disclosed lipid prodrug can be used in combination with standard leukemia therapies, especially in combination with therapies used for the treatment of AML. In particular, a disclosed lipid prodrug can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analogue, which is the 2'-alpha-hydroxy ribose (arabinoside) derivative of deoxycytidine. Also included is the purine analogue of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Heilman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogues including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474;

SU5416; SU6668; bevacizumab; or anti-VEGF antibodies or anti-VEGF receptor antibodies, such as rhuMAb and RETUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxy corticosterone, testosterone, estrone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

Disclosed lipid prodrugs are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A disclosed lipid prodrug may be mixed with the other drug substance in a fixed pharmaceutical composition or it may be administered separately, before, simultaneously with or after the other drug substance. Accordingly the invention includes a combination of a disclosed lipid prodrug as hereinbefore described with an anti-inflammatory, bronchodilatory, antihistamine or anti-tussive drug substance, said disclosed lipid prodrug and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of disclosed lipid prodrugs with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

In some embodiments, the additional therapeutic agent is selected from Abacavir, Abiraterone, Acetylcysteine, acyclovir, adefovir dipivoxil, Alatrofloxacin, Albendazole, albuterol, Alendronic acid, Altropane, Amifostine, Aminolevulinic acid, amiodarone (e.g. cosolvent-free), Amisulpride, amitriptyline, amprenavir, anastrozole, Apomorphine, apremilast, Arbutamine, Argatroban, Arsenic trioxide, aspirin, Atazanavir/cobicistat, Atorvastatin, Avibactam/ceftazidime, Azacitidine, azathioprine, Azithromycin, Belinostat, bendamustine, Bexarotene, Biapenem, Bicalutamide, Bortezomib, Bosentan, bosutinib, Bromfenac, Buprenorphine, Bupropion, Busulfan, C1 esterase inhibitor, Caffeine, calcium levofolinate, Cangrelor, capecitabine, capsaicin, Carfilzomib, Carvedilol, Cefepime, Ceftaroline fosamil, Ceftazidime, Ceftibuten, Ceftolozane/tazobactam, celecoxib, Celgosivir, chlorambucil, Cidofovir, Ciprofloxacin, Cladribine, Clazosentan, Clofarabine, Clopidogrel, cyclophosphamide, cytarabine, danazol, Dantrolene, dasatinib, Daunorubicin, Decitabine, Deferiprone, delavirdine, Deoxycholic acid, deoxythymidine, Dexamethasone, Dexmedetomidine, Dexrazoxane, Diclofenac, Didanosine, diethylcarbamazine, Docetaxel, Dolasetron, Doripenem, Doxapram, Doxercalciferol, Doxorubicin, doxycycline, Efavirenz, Eflapegrastim, elvitegravir, emtricitabine, Entacapone, Epacadostat, epinephrine, epitiostanol, Epoprostenol, ergotamine, Eribulin, Esomeprazole, estradiol, estrogen, etonogestrel, Ezetimibe, Ezetimibe/simvastatin, Fasudil, Fenoldopam, Fentanyl, Ferric carboxymaltose, Finasteride, Fingolimod, Florbenazine F18, Florbetaben F 18, florbetapir F 18, Fludarabine, Fluorine 18 AV 1451, fluorouracil, Fluoxymesterone, Flurpiridaz F-18, Flutafuranol F 18, Flutemetamol F 18, Fomepizole, Fosaprepitant, Fosphenytoin, Fospropofol, fulvestrant, Furosemide, Gadobenic acid, Gadobutrol, Gadoversetamide, Gadoxetate disodium, gemcitabine, Glimepiride, Granisetron, Guadecitabine, hydroxychloroquine, Ibandronic acid, ibuprofen, imatinib, Imiquimod, Iobenguane 1-123, Ioflupane 1231, Ioxilan, Irinotecan, Isavuconazonium, isosorbidedinitrate, ivermectin, ixabepilone, labelalol, Facosamide, lamivudine, Famotrigine, Fansoprazole, Fapatinib, F-dopa, leflunomide, Fetermovir, Fetrozole, Fevetiracetam, Fevofloxacin, Fevothyroxine, Fidocaine, lidocaine, Finezolid, Fobaplatin, Fomitapide, lopinavir, maraviroc, Meloxicam, melphalan, mercaptopurine, Meropenem, Mesna, methotrexate, Methylnaltrexone, Methylphenidate, metoprolol, midazolam, Minocycline IV, Mitoxantrone, Moxifloxacin, Mycophenolate mofetil, naloxone, naltrexone, naproxen, Nefazodone, nelarabine, nelfinavir, Nevirapine, nilotinib, Nilutamide, nitrosoureas, nortriptyline, Omacetaxine mepesuccinate, Omadacycline, Omeprazole, an opioid such as codeine, meperidine, fentanyl, morphine, oxycodone, hydrocodone, hydromorphone, or methadone, Oxaliplatin, oxprenolol, Oxybutynin, Oxymetholone, paclitaxel (Taxol®), Palonosetron, Pantoprazole, Paracetamol, Pemetrexed, pentazocine, Pentostatin, Phenylephrine, Pirmenol, platinum, Plazomicin, Plerixafor, ponatinib, pralatrexate, predisone, prednisolone, Propofol, propranolol, Quinapril, Radium-223 chloride, Raloxifene, raltegravir, Raltitrexed, Ramatroban, Regadenoson, Remifentanil, Remimazolam besylate, rilpivirine, rinotecan, Risperidone, Ritonavir, Rivastigmine, rofecoxib, Romidepsin, Ropeginterferon alfa-2b, Rotigotine, salbutamol, Salmeterol, Samarium 153 lexidronam, saquinavir, Selegiline, Sertraline, Sildenafil, Simvastatin, Sorivudine, Stavudine, sulfasalazine, Sulfur hexafluoride, Sumatriptan, Sunitinib, Tacrine, tamoxifen, Technetium Tc 99m trofolastat, Tedizolid, Temozolomide, tenofovir, Terbinafine, Testosterone propionate, thiotepa, Tianeptine, Tigecycline, Tizanidine, Topiramate, Topotecan, toremifene, Treprostinil, Tretinoin, Triciribine, verapamil, Verteporfin, Vinorelbine, Vismodegib, Voglibose, zalcitabine, zidovudine, Zileuton, or Zoledronic acid; or a pharmaceutically acceptable salt thereof.

The structure of the active compounds identified by code numbers, generic or trade names may be taken from the actual edition of the standard compendium "The Merck Index" or from databases, e.g. Patents International (e.g. IMS World Publications).

A disclosed lipid prodrug may also be used in combination with known therapeutic processes, for example, the administration of hormones or radiation. In certain embodiments, a disclosed lipid prodrug is used as a radiosensitizer, especially for the treatment of tumors which exhibit poor sensitivity to radiotherapy.

The disclosed lipid prodrugs and compositions, and any co-administered additional therapeutic agents, according to the method of the present invention, may be administered using any amount and any route of administration effective for treating or lessening the severity of a disease, disorder, or condition such as cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Disclosed lipid prodrugs are preferably formulated in dosage unit form for ease of administration and uniformity of dosage. The expression "dosage unit form" as used herein refers to a physically discrete unit of agent appropriate for the patient to be treated. It will be understood, however, that the total daily usage of a disclosed lipid prodrug or composition thereof and any co-administered additional therapeutic agents will be decided by the attending physician within the scope of sound medical judgment. The specific effective dose level for any particular patient or organism will depend upon a variety of factors including the disorder being treated and the severity of the disorder; the activity of the specific lipid prodrug employed; the specific composition employed; the age, body weight, general health, sex and diet of the patient; the time of administration, route of administration, and rate of excretion of the specific lipid prodrug or composition; the duration of the treatment; drugs used in combination or coincidental with the specific lipid prodrug or composition employed, and like factors well known in the medical arts. The term "subject" or "patient," as used herein, means an animal, preferably a mammal, and most preferably a human.

4. Methods of Making Livid Prodrugs

General Methods for Making Livid Prodrugs

The lipid prodrug compounds of this invention may be prepared or isolated in general by synthetic and/or semi-synthetic methods known to those skilled in the art for analogous compounds and by methods described in detail in the Examples, herein.

The therapeutic agents comprised in disclosed lipid prodrugs (e.g., conjugated to a glyceride-based prodrug) may be purchased commercially or prepared by organic synthesis, semi-synthesis, fermentation (e.g. with viral vectors), and like methods known in the art.

In some embodiments, protecting groups (as defined below) can be used to manipulate therapeutic agents in preparation for conjugation to the remainder of the lipid prodrug structure, for example, to prevent undesired side reactions from taking place.

In the synthesis methods described herein, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry*: Reactions, Mechanisms, and Structure, M. B. Smith and J. March, $7^{th}$ Edition, John Wiley & Sons, 2013, *Comprehensive Organic Transformations*, R. C. Larock, $3^{rd}$ Edition, John Wiley & Sons, 2018, and *Protective Groups in Organic Synthesis*, P. G. M. Wuts, $5^{th}$ edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, $5^{th}$ edition, John Wiley & Sons, 2014, and Philip Kocienski, in *Protecting Groups*, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in*

*Organic Synthesis*, P. G. M. Wuts, 5th edition, John Wiley & Sons, 2014, and Philip Kocienski, in Protecting Groups, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxy carbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, *March's Advanced Organic Chemistry: Reactions, Mechanisms, and Structure*, M. B. Smith and J. March, 7th Edition, John Wiley & Sons, 2013, *Comprehensive Organic Transformations*, R. C. Larock, 3rd Edition, John Wiley & Sons, 2018, the entirety of each of which is incorporated herein by reference. Such inter conversions may require one or more of the aforementioned techniques, and certain methods for synthesizing compounds of the invention are described below.

As a general strategy, compounds of the present invention may be synthesized via one of the following routes:

Scheme 1. Synthesis of compounds of formula iii.

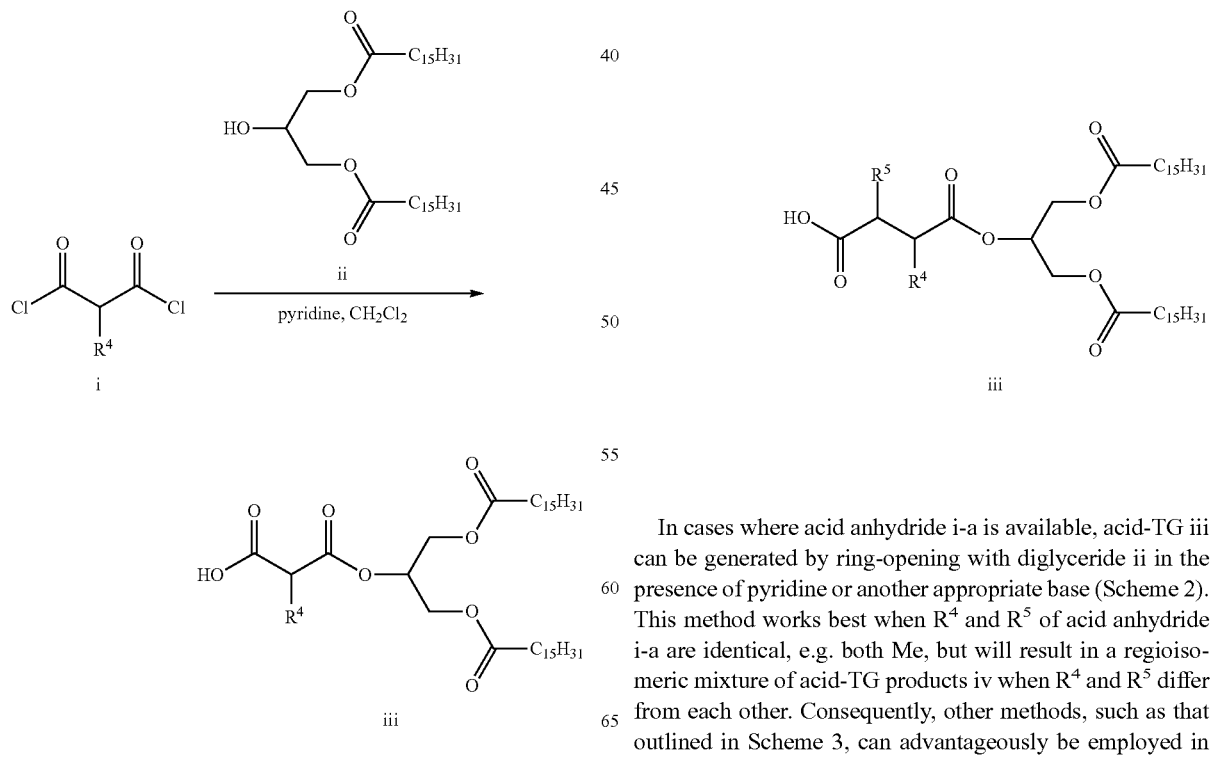

Diacid chlorides i, which are readily available from the corresponding malonic acids, can be reacted with a diglyceride such as ii in the presence of pyridine or another appropriate base to give acid-triglyceride (acid-TG) iii (see Scheme 1). Formula iii is shown with $C_{15}H_{31}$ fatty acid side chains, but other fatty acids (such as those described above) can be substituted in this and other Formulas described below.

Scheme 2. Synthesis of compounds of formula iii.

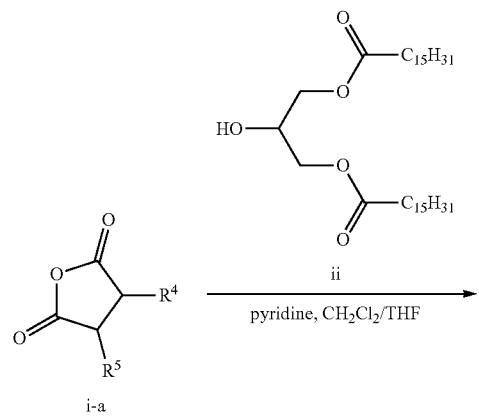

In cases where acid anhydride i-a is available, acid-TG iii can be generated by ring-opening with diglyceride ii in the presence of pyridine or another appropriate base (Scheme 2). This method works best when $R^4$ and $R^5$ of acid anhydride i-a are identical, e.g. both Me, but will result in a regioisomeric mixture of acid-TG products iv when $R^4$ and $R^5$ differ from each other. Consequently, other methods, such as that outlined in Scheme 3, can advantageously be employed in this circumstance.

Scheme 3. Synthesis of compounds of formula iv where $R^4$ = Me, Alkyl, etc. and $R^5$ = H.

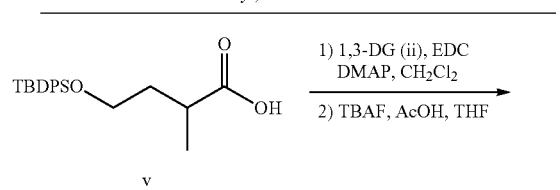

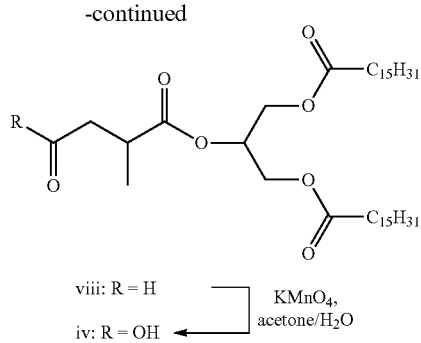

To obtain acid-TG iv as a single regioisomer in the specific example where $R^4$=Me or other alkyl or substitution and $R^5$=H, the known carboxylic acid v (Lienard, B. M. R. et al., *Org. Biomol. Chem.* 2008, 6, (13), 2282-2292) can be used as a starting point (see Scheme 3). Coupling of acid v with 1,3-DG ii under standard conditions produces TBDPS protected triglyceride vi, which can be treated with appropriate conditions such as TBAF and AcOH to afford alcohol vii. A two-step oxidation process (for example, PCC, then $KMnO_4$) can then be used to transform alcohol vii into the desired acid-TG iv via the intermediate aldehyde viii.

Scheme 4. Synthesis of compounds of formula x wherein ―M― is an acetal self-immolative (ASI) group.

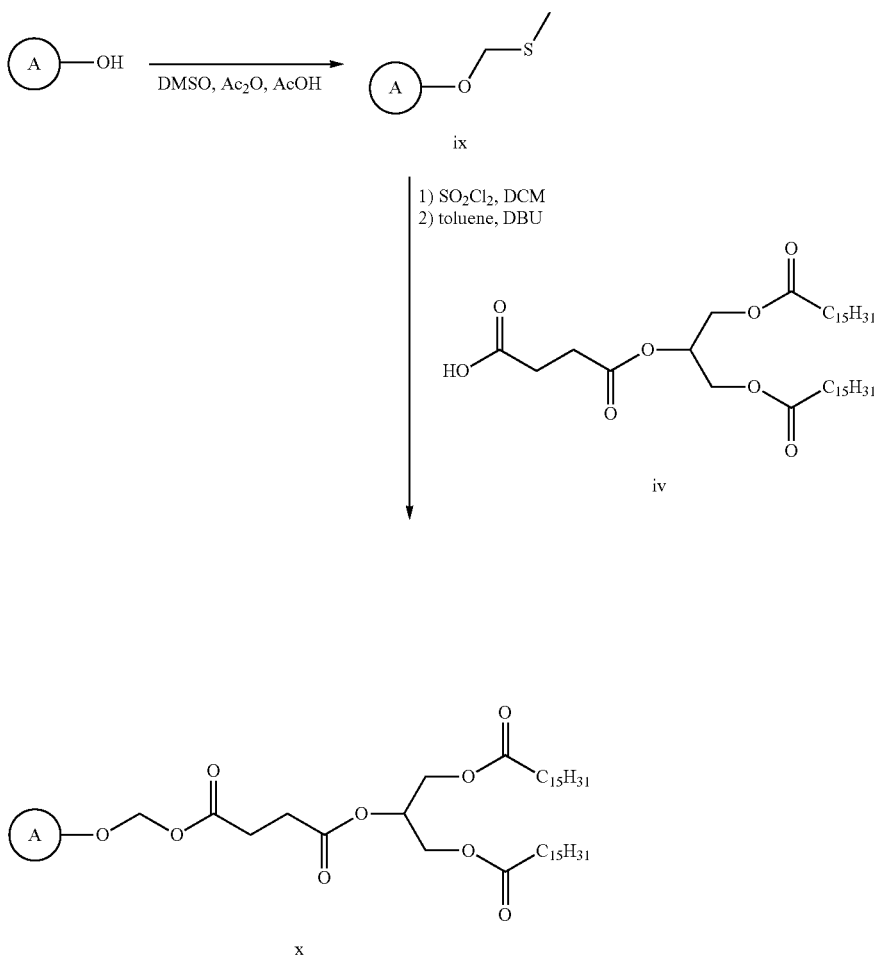

For the synthesis of compounds containing an acetal self-immolative (ASI) group between the pharmaceutical agent and the alkyl spacer, the alcohol-bearing parent molecule must be functionalized and activated prior to conjugation with acid-triglyceride iii as outlined above in Scheme 4. Treatment of an alcohol with DMSO in a mixture of acetic anhydride and acetic acid results in the formation of (methylthio)methyl (MTM) ether ix. Activation of MTM ether ix using sulfuryl chloride forms a presumed sulfoxide species that can react with the carboxylate of acid-triglyceride iv to give the target compound x.

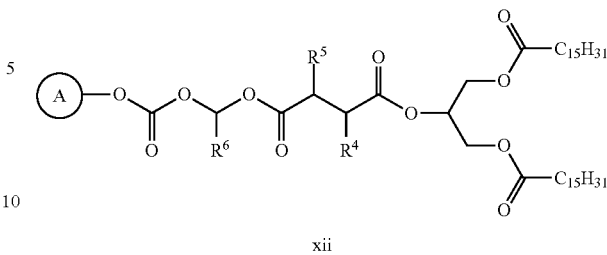

xii

In cases where the pharmaceutical agent contains an alcohol, phenol or amine (primary or secondary) functional group, a modified version of the acetal self-immolative group can be used where an additional carboxy group is included. Reaction of the parent drug with a chloroalkyl chloroformate gives chloroalkyl carbonates (shown) or carbamates xi (see Scheme 5). Displacement of the halide leaving group is then accomplished by treatment with the carboxylate derived from acid-TG iv in an appropriate solvent such as refluxing toluene to afford the target compound xii.

Scheme 5. Synthesis of compounds of formula xii wherein —M— is a carboxyacetal (CASI) or carboxy(methylacetal) (CMSI) self-immolative group.

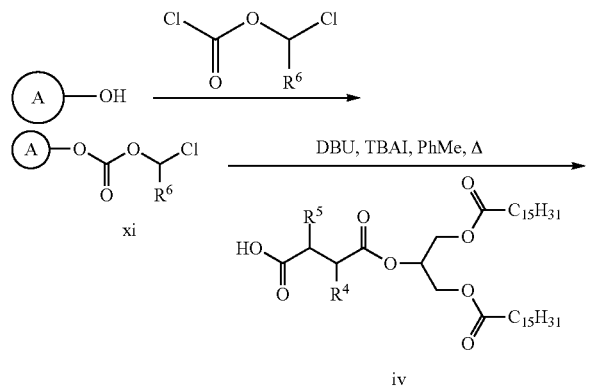

Scheme 6. Synthesis of compounds of formula xviii wherein —M— is a trimethyl-lock (TML) self-immolative group.

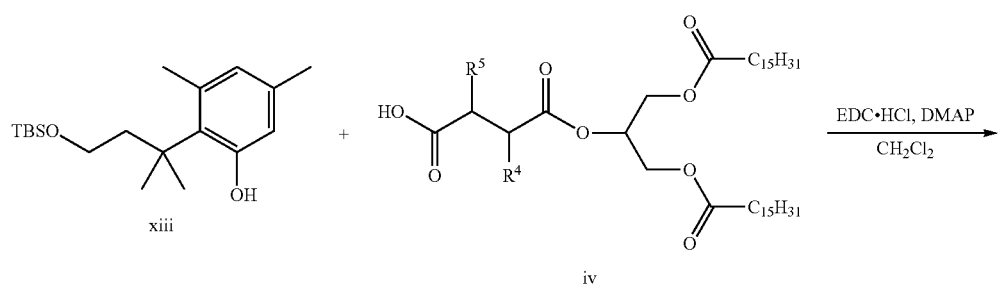

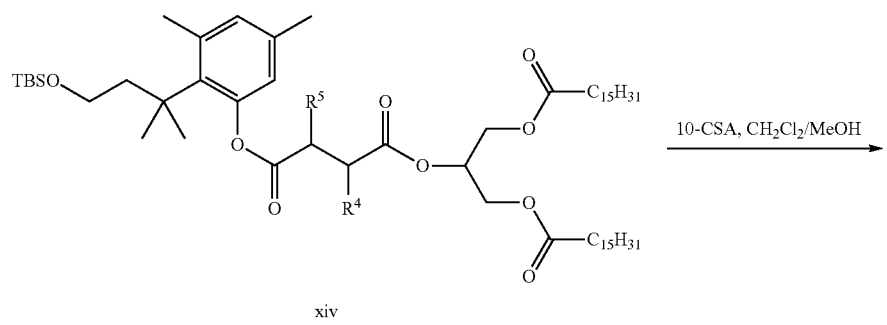

-continued

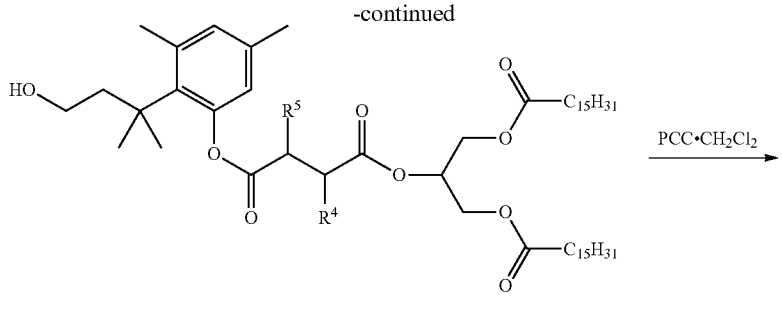

xv

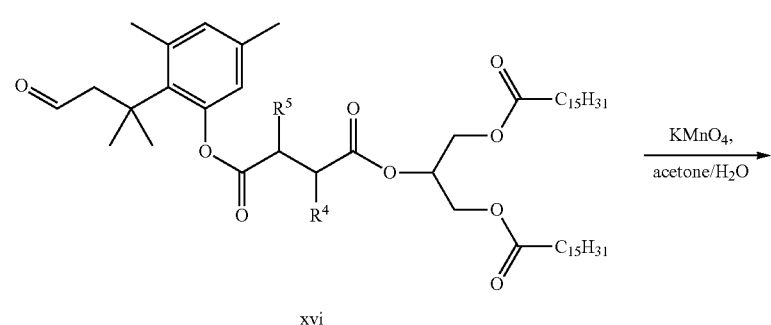

xvi

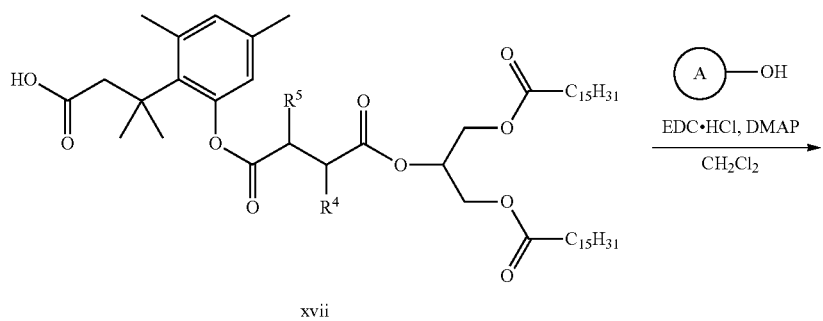

xvii

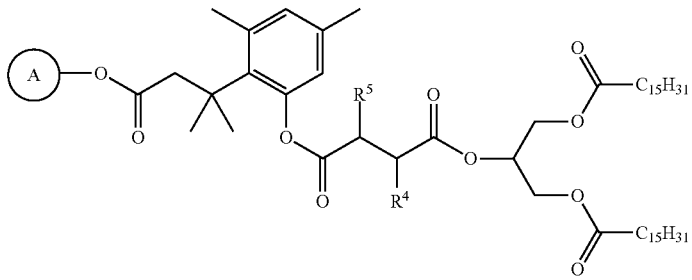

xviii

For the synthesis of prodrugs containing a trimethyl lock (TML) self-immolative group (Levine, M. N.; Raines, R. T. Chem. Sci. 2012, 3, 2412-2420, hereby incorporated by reference) between the pharmaceutical agent and the alkyl spacer to facilitate systemic release of the parent molecule, the acid- triglyceride iv must be functionalized with the TML moiety prior to conjugation with a pharmaceutical agent as outlined in Scheme 6. Coupling of acid-TG iv with TML phenol xiii under standard conditions gives triglyceride xiv, which can be deprotected under acidic conditions (10-camphorsulfonic acid) to give alcohol xv. Sequential oxidation of alcohol xv firstly to aldehyde xvi and then acid xvii, followed by coupling to either an alcohol (shown), amine or sulfonamide-containing pharmaceutical agent under standard conditions can give the target compound xviii.

Scheme 7. Synthesis of compounds of formula xxiv wherein —M— is a p-hydroxybenzyl carbonyl (PHB) self-immolative group.

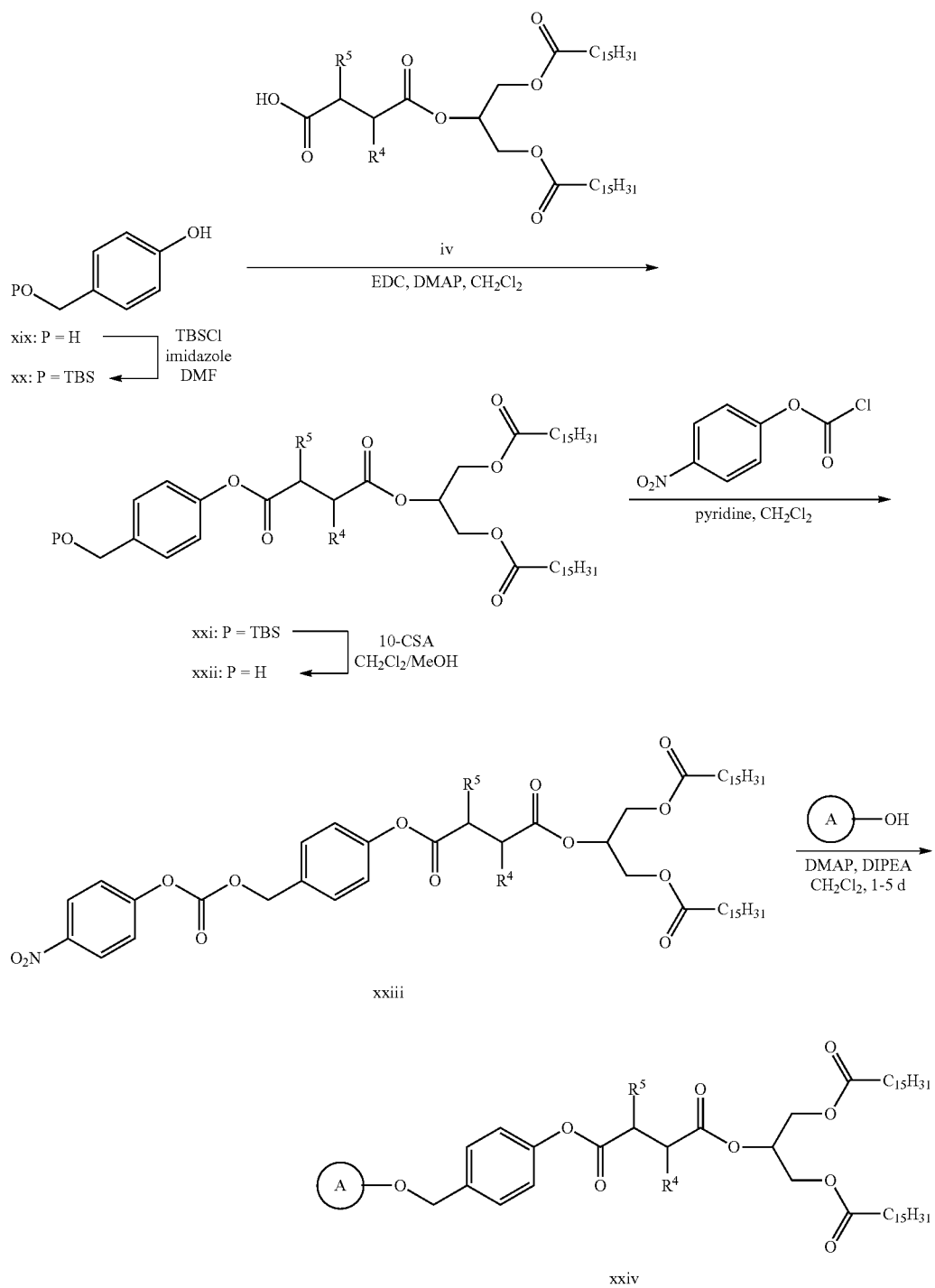

For the synthesis of compounds containing a p-hydroxybenzyl (PHB) carbonyl self-immolative group, the primary hydroxyl group of p-hydroxybenzyl alcohol (xix) is first protected as a silyl ether and the free phenolic hydroxyl group coupled with acid-TG iv to give PHB triglyceride xxi (see Scheme 7). After removal of the silicon protecting group, primary alcohol xxii can be activated by treatment with p-nitrophenyl (PNP) chloroformate to give PNP carbonate xxiii. Displacement of the PNP group is then achieved by reaction with a pharmaceutical agent (A-OH shown) under basic conditions to give the desired compound xxiv.

Scheme 8. Synthesis of compounds of formula III wherein —M— is a flipped-ester self-immolative (FSI) group.

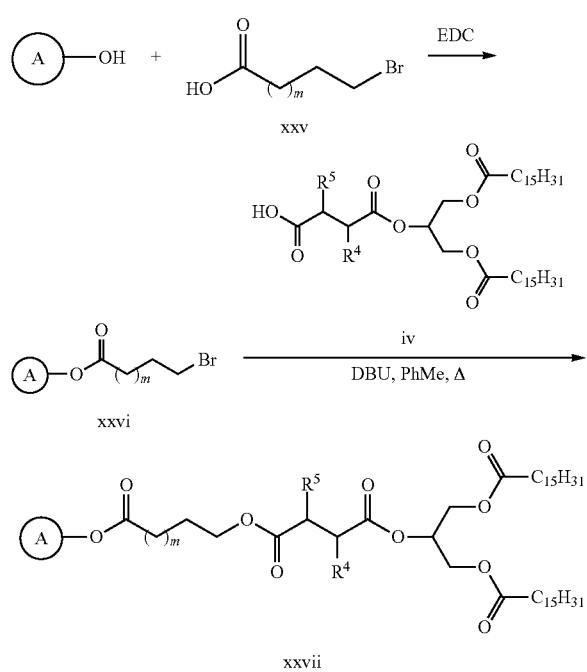

Without wishing to be bound by theory, it is believed that the flipped-ester self-immolative (FSI) group can liberate the free pharmaceutical agent by a cyclization mechanism, resulting in loss of either a four-carbon (FSI-4) or five-carbon (FSI-5) lactone. Alternatively, liberation of the agent may occur by a chemical or enzymatic mechanism in vivo. FSI prodrugs can be synthesized by coupling the pharmaceutical agent (A-OH shown) with either 4-bromobutyric acid (m=1) or 5-bromovaleric acid (m=2) (xxv) to give bromide xxvi (see Scheme 8). Displacement of bromide xxvi using the carboxylate derived from acid-TG iv generates the desired ester bond in target compound xxvii.

EXEMPLIFICATION

Example 1: Synthesis of Intermediates

List of Abbreviations equiv or eq: molar equivalents
rt or RT: room temperature
UV: ultraviolet
HPLC: high pressure liquid chromatography
Rt: retention time
LCMS or LC-MS: liquid chromatography-mass spectrometry
NMR: nuclear magnetic resonance
TLC: thin layer chromatography
sat: saturated
aq: aqueous
Ac: acetyl
BINAP: (±)-2,2'-Bis(diphenylphosphino)-1,1'-binaphthalene
Bn: Benzyl
DBU: 1,8-Diazabicyclo[5.4.0]undec-7-ene
DCC: N,N'-Dicyclohexylcarbodiimide
DCM: Diehloromethane
DCE: Dichloroethane
DEA: Diethylamine
DIPA: Diisopropylamine
DMF: N,N-dimethylformamide
DMSO: dimethylsulfoxide
DMPU: N,N'-D imethylpropyleneurea
ACN orMeCN: acetonitrile
DIPEA: diisopropylethylamine
EA or EtOAc: ethyl acetate
EDCI, EDC, or ED AC: 1-Ethyl-3-(3-dimethylaminopropyl) carbodiimide
TEA: triethylamine
THF: tetrahydrofuran
TBS: tert-butyldimethylsilyl
KHMDS: potassium hexamethyl disilylazide
Tf: trifluoromethanesulfonate
Ms: methanesulfonyl
MBS: N-bromosuccinimide
PCC: Pyridinium chlorochromate
PE: petroleum ether
TEA: trifluoroacetic acid
MMPP: magnesium monoperoxyphthalate
HATU: 1-[Bis(dimethylamino)methylene]-1H-1,2,3-triazolo[4,5-b-]pyridinium 3-oxid Hexafluorophosphate
Cy: cyclohexyl
Tol: toluene
DMP: Dess-Martin periodinane
IBX: 2-iodoxybenzoic acid
PMB: p-methoxybenzyl
SEM: [2-(Trimethylsilyl)ethoxy]methyl
1,3-DG (Int-2):

Scheme 9. Synthesis of Int-2.

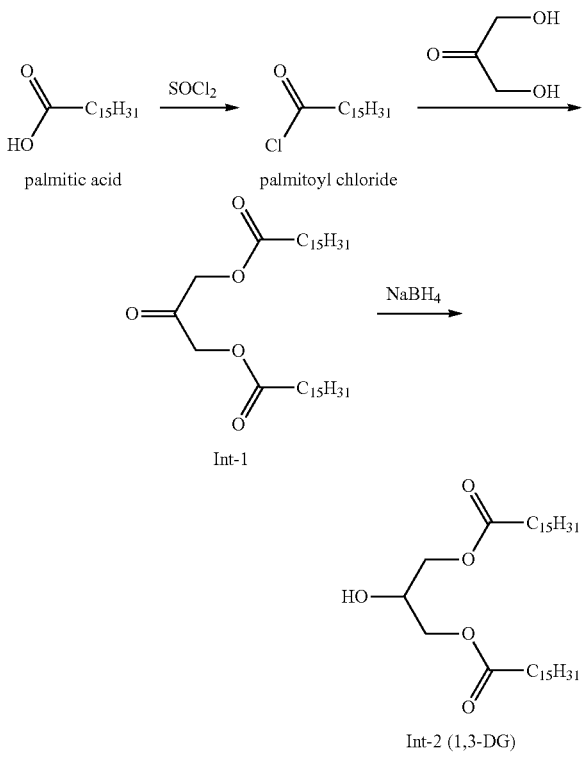

DMF (1 mL, 13.7 mmol) was added into a mixture of palmitic acid (433 g, 1.69 mol) in thionyl chloride (500 mL, 6.3 mol) at room temperature. The resultant reaction mixture was heated under reflux for 3 h. It was concentrated to dryness to afford palmitoyl chloride (453 g, 1.64 mol, 97% yield) as a yellowish oil, which was used in the next step without further purification.

To a mixture of 1,3-dihydroxypropan-2-one (77 g, 0.855 mol) and anhydrous pyridine (140 g, 1.76 mol) in anhydrous dichloromethane (2500 mL) under nitrogen at room temperature, was added with palmitic chloride (453 g, 1.64 mol). The mixture was stirred at room temperature for 16 h. It was diluted with MeOH (1000 mL) and water (2000 mL) and stirred for 30 min. The precipitate was collected by filter and dried to afford Int-1 (462 g, 0.815 mmol, 95% yield) as a white solid.

Int-1 (220 g, 388 mmol) was dissolved in a solution of THF (3000 mL) and water (200 mL) at 0° C. Sodium borohydride (22 g, 579 mmol) was added portion wise. After addition, the mixture was filtered to afford a cake, which was dried to afford compound Int-2 (1,3-DG) (177 g, 311 mmol, 80% yield) as a white solid. LC-MS: MS m/z=591 (M+Na+), RT=4.39 min; NMR (400 MHz, chloroform-d) δ 4.20-4.05 (m, 5H), 2.35 (t, J=7.6 Hz, 4H), 1.62 (t, J=7.6 Hz, 4H), 1.25 (s, 48H), 0.88 (t, J=6.6 Hz, 6H).

C5βMe-acid-2-TG (Int-4):

was added to acid chloride Int-3 (80.4 mg, 0.439) in dichloromethane (1.5 mL) and the mixture heated at reflux for two hours. The reaction was cooled to room temperature, diluted with ethyl acetate (15 mL) and 1 M HCl (5 mL) and the organic phase separated. The aqueous layer was further extracted with ethyl acetate (2×20 mL) and the combined organic extracts washed with 1 M HCl (20 mL) and brine (2×30 mL), dried (MgSO$_4$) and concentrated under reduced pressure to give the crude product. Purification by silica gel chromatography (20% to 45% ethyl acetate/hexanes) gave Int-4 (54.0 mg, 88%) as a colorless solid. $^1$H NMR (400 MHz, CDCl$_3$) δ 5.27 (m, 1H), 4.311 (dd, J=11.9, 4.2 Hz, 1H), 4.305 (dd, J=11.9, 4.2 Hz, 1H), 4.14 (dd, j=11.9, 5.6 Hz, 2H), 2.52-2.39 (m, 3H), 2.36-2.24 (m, 6H), 1.66-1.55 (m, 4H), 1.37-1.17 (m, 48H), 1.06 (d, J=6.3 Hz, 3H), 0.88 (t, j=6.8 Hz, 6H); $^{13}$C NMR (101 MHz, CDCl$_3$) δ 178.1 (C), 173.5 (2C; C), 171.4 (C), 69.3 (CH), 62.2 (2C; CH$_2$), 40.7 (CH$_2$), 40.4 (CH$_2$), 34.1 (2C; CH$_2$), 32.1 (2C; CH$_2$), 29.82 (6C; CH$_2$), 29.78 (4C; CH$_2$), 29.74 (2C; CH$_2$), 29.6 (2C; CH$_2$), 29.5 (2C; CH$_2$), 29.4 (2C; CH$_2$), 29.2 (2C; CH$_2$), 27.3 (CH), 25.0 (2C; CH$_2$), 22.8 (2C; CH$_2$), 19.8 (CH$_3$), 14.2 (2C; CH$_3$); ESI-HRMS: calcd. for C$_{41}$H$_{76}$NaO$_8$ [M+Na$^+$] 719.5432; found 719.5451.

Alternate Procedure (Larger Scale):

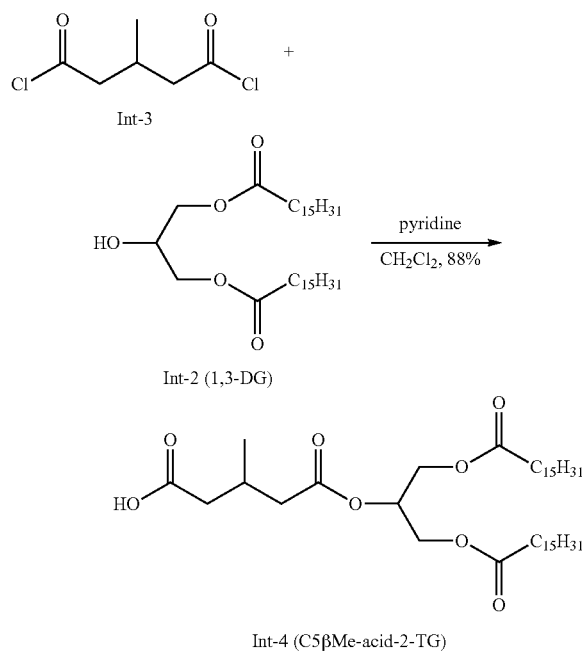

Scheme 10. Synthesis of Int-4.

Int-4 (C5βMe-acid-2-TG)

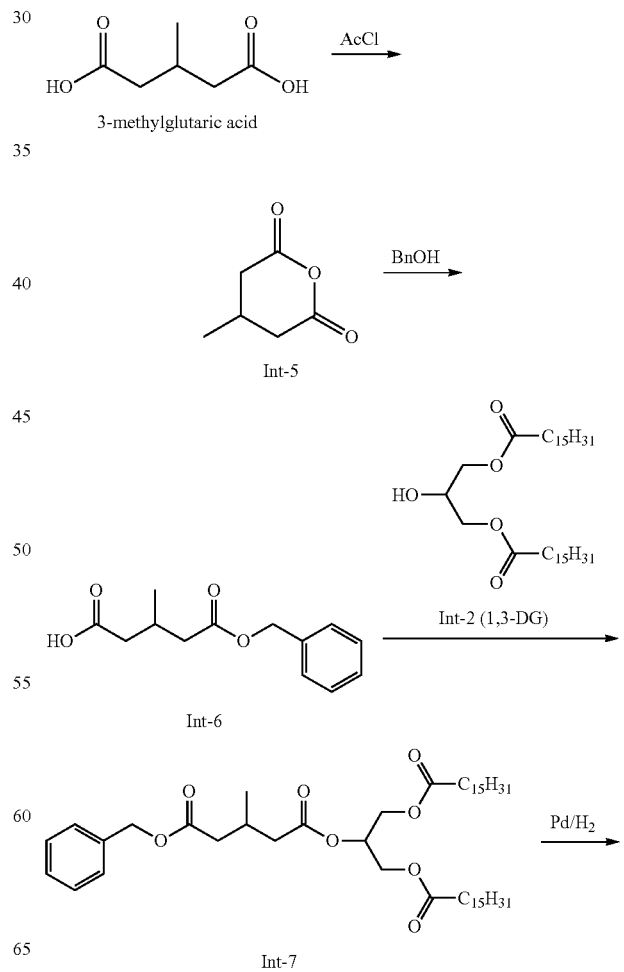

Scheme 11. Alternate Synthesis of Int-4.

A mixture of 3-methylglutaric acid (500 mg, 3.42 mmol) and DMF (two drops) in thionyl chloride (2.48 mL, 34.2 mmol) was heated at reflux for two hours. The reaction was cooled to room temperature, diluted with toluene (5 mL) and concentrated under reduced pressure to give diacid chloride Int-3 (584 mg, 83%) as a yellow oil that was used without purification. $^1$H NMR (400 MHz, CDCl$_3$) δ 3.02 (dd, J=17.3, 6.1 Hz, 2H), 2.89 (dd, J=17.3, 7.2 Hz, 2H), 2.61 (m, 1H), 1.13 (d, J=6.8 Hz, 2H).

A solution of Int-2 (1,3-DG) (50.0 mg, 0.0879 mmol) and pyridine (71.1 μL, 0.879 mmol) in dichloromethane (2 mL)

-continued

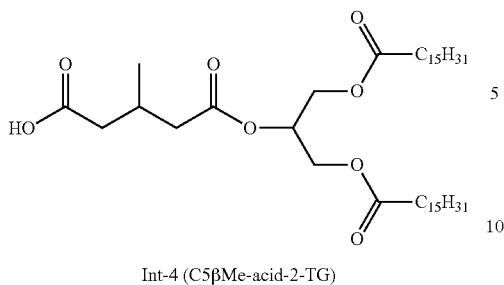

Int-4 (C5βMe-acid-2-TG)

A mixture of 3-methylglutaric acid (100 g, 685 mmol) and acetyl chloride (250 mL, 3.53 mol) was heated under reflux for 16 h, then concentrated to dryness before adding into a solution of pyridine (270 g, 3.4 mol) and benzyl alcohol (100 g, 926 mmol) in dichloromethane (1500 mL) at room temperature. The mixture was stirred for 72 h. The reaction was concentrated and the residue was purified by silica column chromatography, eluting with from 0 to 50% ethyl acetate in petroleum ether to afford Int-6 (70 g, 297 mmol, 43% yield) as a yellowish oil. $^1$H NMR (400 MHz, chloroform-d) δ 7.39-7.30 (m, 5H), 5.12 (s, 2H), 2.52-2.25 (m, 5H), 1.04 (d, J=6.6 Hz, 3H).

To a mixture of Int-6 (70 g, 297 mmol) and Int-2 (1,3-DG) (80 g, 140 mmol) in dichloromethane (1500 mL) was added EDCI (115 g, 600 mmol) and DMAP (3.66 g, 30 mmol). Triethylamine (100 mL, 719 mmol) was added drop wise at 0° C. The mixture was stirred at room temperature for 72 h. The reaction was concentrated to dryness and the residue was purified by silica column chromatography, eluting with ethyl acetate in petroleum ether from 0 to 50% to afford Int-7 (68 g, 86.5 mmol, 29% yield) as a white solid. $^1$H NMR (400 MHz, chloroform-d) δ 7.40-7.32 (m, 5H), 5.30-5.24 (m, 1H), 5.12 (s, 2H), 4.31-4.27 (m, 2H), 4.17-4.10 (m, 2H), 2.50-2.38 (m, 3H), 2.34-2.28 (m, 6H), 1.61-1.55 (m, 4H), 1.35-1.20 (m, 48H), 1.02 (d, J=6.4 Hz, 3H), 0.88 (t, J=6.6 Hz, 6H).

Int-7 (68 g, 86.5 mmol) and palladium on carbon (3 g) were suspended in THF (400 mL). The mixture was hydrogenated under hydrogen atmosphere at 30° C. for 16 h, then filtered and concentrated to dryness. The residue was further purified by trituration with hexane to afford Int-4 (C5βMe-acid-2-TG) (51 g, 73.2 mmol, 84% yield) as a white solid. LC-MS: MS m/z=719 (M+Na+), RT=3.83 mm. $^1$H NMR (400 MHz, chloroform-d) δ 5.31-5.25 (m, 1H), 4.34-4.29 (m, 2H), 4.16-4.12 (m, 2H), 2.49-2.40 (m, 3H), 2.33-2.28 (m, 6H), 1.62-1.57 (m, 4H), 1.35-1.20 (m, 48H), 1.06 (d, j=6.4 Hz, 3H), 0.88 (t, J=6.6 Hz, 6H).

C10-acid-2-TG:

Scheme 12. Synthesis of Int-9.

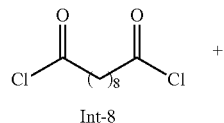

Int-8

-continued

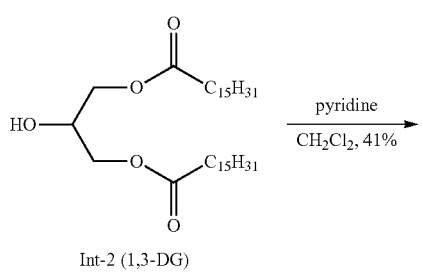

Int-2 (1,3-DG)

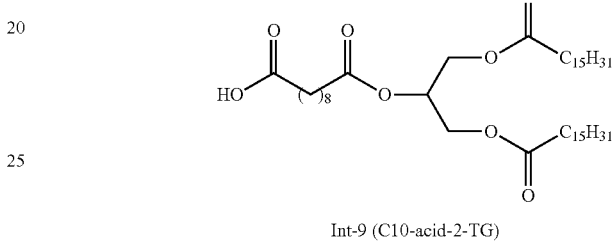

Int-9 (C10-acid-2-TG)

A mixture of sebacic acid (88.0 mg, 0.435 mmol) and DMF (one drop) in thionyl chloride (316 μL, 4.35 mmol) was heated at reflux for 1.5 hours. The reaction was cooled to RT, diluted with toluene (5 mL) and concentrated under reduced pressure to give diacid chloride Int-8 (104 mg, quant.) as a yellow oil that was used without purification. $^1$H NMR (400 MHz, chloroform-d) δ 2.88 (t, J=7.3 Hz, 4H), 1.76-1.66 (m, 4H), 1.42-1.26 (m, 8H).

A solution of Int-2 (1,3-DG) (45.0 mg, 0.0791 mmol) and pyridine (64.0 μL, 0.791 mmol) in dichloromethane (1.5 mL) was added to diacid chloride Int-8 (104 mg, 0.435 mmol) in dichloromethane (1.5 mL) and the mixture stirred at rt for 1.5 hours. The reaction was diluted with ethyl acetate (5 mL), water (10 mL) and 1 M HCl (3 mL) and the aqueous layer extracted with ethyl acetate (3×15 mL). The combined organic extracts were washed with 1 M HCl (30 mL) and brine (30 mL), dried (MgSO$_4$) and concentrated under reduced pressure to give the crude product. Purification by silica gel chromatography (20% to 50% ethyl acetate/hexanes) gave Int-9 (C10-acid-2-TG) (24.3 mg, 41%) as a pale yellow solid. $^1$H NMR (400 MHz, CDCl$_3$) δ 5.26 (m, 1H), 4.29 (dd, J=11.9, 4.4 Hz, 2H), 4.14 (dd, J=11.9, 5.9 Hz, 2H), 2.37-2.27 (m, 8H), 1.70-1.53 (m, 8H), 1.39-1.19 (m, 56H), 0.87 (t, J=6.9 Hz, 6H); $^{13}$C NMR (101 MHz, CDCl$_3$) δ 178.6 (C), 173.5 (2C; C), 173.0 (C), 69.0 (CH), 62.2 (CH$_2$), 34.3 (CH$_2$), 34.2 (2C; CH$_2$), 33.9 (CH$_2$), 32.01 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 29.2 (2C; CH$_2$), 29.11 (CH$_2$), 29.10 (CH$_2$), 25.00 (2C; CH$_2$), 24.95 (CH$_2$), 24.8 (CH$_2$), 22.8 (2C; CH$_2$), 14.3 (2C; CH$_3$).

Alternate Procedure (Larger Scale):
Scheme 13. Synthesis of Int-9.
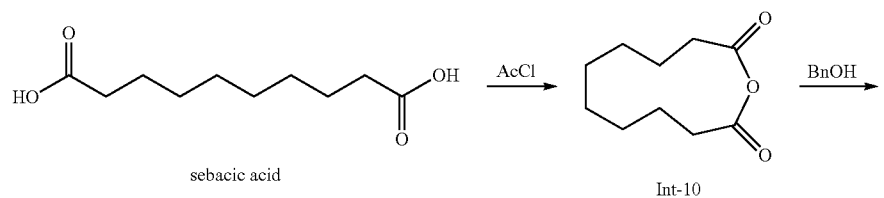
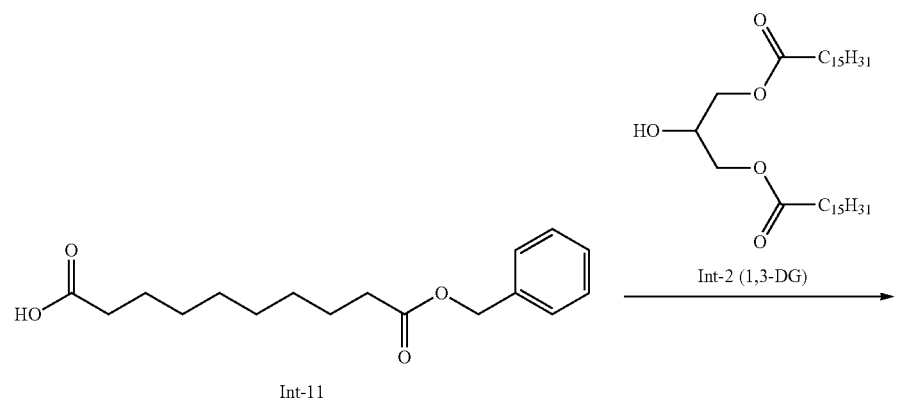
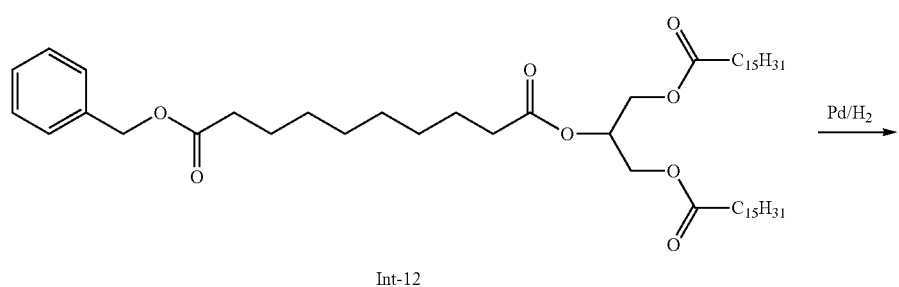
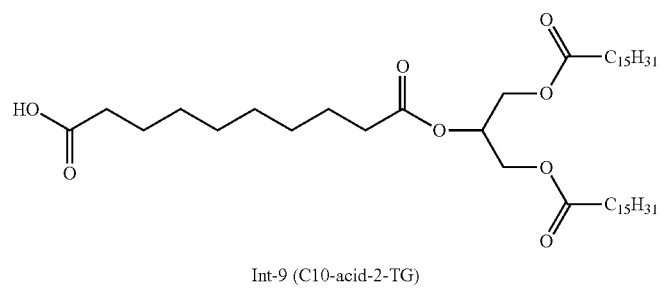

A mixture of sebacic acid (100 g, 495 mmol) and acetyl chloride (250 mL, 3.53 mol) was heated under reflux for 16 h, then cooled and concentrated to dryness. It was added into a solution of pyridine (270 g, 3.4 mol) and benzyl alcohol (100 g, 926 mmol) in dichloromethane (1500 mL) at room temperature and the mixture was stirred for 72 h. The reaction was concentrated and the residue was purified by column chromatography, eluting with from 0 to 50% ethyl acetate in petroleum ether to afford Int-11 (82 g, 281 mmol, 57% yield) as a yellowish oil. LC-MS: MS m/z=293 (M+H+), RT=1.45 mm.

To a mixture of Int-11 (82 g, 281 mmol) and Int-2 (1,3-DG) (80 g, 140 mmol) in dichloromethane (1500 mL) was added EDCI (115 g, 600 mmol) and DMAP (3.66 g, 30 mmol). Then triethylamine (100 mL, 719 mmol) was added drop wise at 0° C. The mixture was stirred at room temperature for 72 h. The reaction was concentrated to dryness and the residue was purified by column chromatography, eluting with ethyl acetate in petroleum ether from 0 to 50% to afford Int-12 (65 g, 77 mmol, 27% yield) as a white solid. $^1$H NMR (400 MHz, chloroform-d) δ 7.38-7.29 (m, 5H), 5.27-5.25 (m, 1H), 5.11 (s, 2H), 4.31-4.27 (m, 2H), 4.17-4.12 (m, 2H), 2.37-2.29 (m, 8H), 1.65-1.57 (m, 8H), 1.35-1.20 (m, 56H), 0.88 (t, J=6.6 Hz, 6H).

Int-12 (65 g, 77 mmol) and palladium on carbon (3 g) were suspended in THF (400 mL). The mixture was hydrogenated under hydrogen atmosphere at 30° C. for 16 h, then it was filtered and the filtrate concentrated to dryness and then further purified by trituration with hexane to afford Int-9 (C10-acid-2-TG) (50 g, 66.4 mmol, 86% yield) as a white solid. LC-MS: MS m/z=775 (M+Na+), RT=5.95 mm; $^1$H NMR (400 MHz, chloroform-d) δ 5.29-5.24 (m, 1H), 4.31-4.27 (m, 2H), 4.19-4.12 (m, 2H), 2.37-2.39 (m, 8H), 1.65-1.58 (m, 8H), 1.35-1.20 (m, 56H), 0.88 (t, J=6.6 Hz, 6H).

Int-120 was prepared using similar methods:

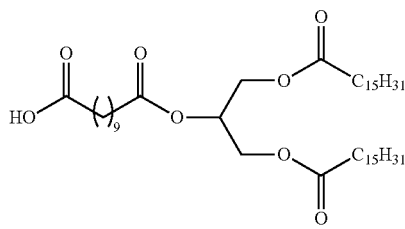

$^1$H NMR (401 MHz, CDCl$_3$) δ 5.25 (m, 1H), 4.28 (dd, J=11.9, 4.3 Hz, 2H), 4.13 (dd, J=11.9, 5.9 Hz, 2H), 2.35-2.26 (m, 8H), 1.65-1.54 (m, 8H), 1.35-1.18 (m, 58H), 0.86 (t, J=6.9 Hz, 6H); $^{13}$C NMR (101 MHz, CDCl$_3$) δ 179.9 (C), 173.4 (2C; C), 173.0 (C), 69.0 (CH), 62.2 (2C; CH$_2$), 34.3 (CH$_2$), 34.2 (2C; CH$_2$), 34.1 (CH$_2$), 32.0 (2C; CH$_2$), 29.81 (6C; CH$_2$), 29.77 (4C; CH$_2$), 29.74 (2C; CH$_2$), 29.59 (2C; CH$_2$), 29.48 (2C; CH$_2$), 29.38 (2C; CH$_2$), 29.36 (CH$_2$), 29.31 (2C; CH$_2$), 29.22 (2C; CH$_2$), 29.15 (CH$_2$), 29.13 (CH$_2$), 25.0 (3C; CH$_2$), 24.8 (CH$_2$), 22.8 (2C; CH$_2$), 14.2 (2C; CH$_3$). ESI-HRMS: calcd. for C$_{46}$H$_{86}$NaO$_8$ [M+Na$^+$] 789.6215; found 789.6218.

C12α'βMe-acid-2-TG (Int-23 and Int-27):

Scheme 14. Synthesis of Int-23 and Int-27.

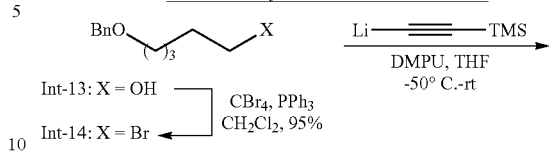

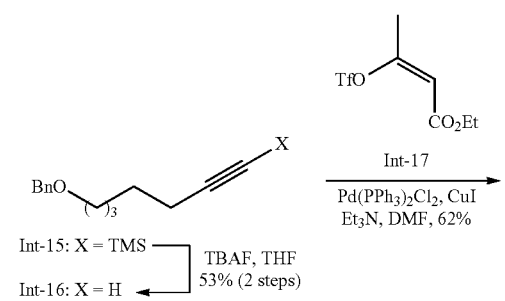

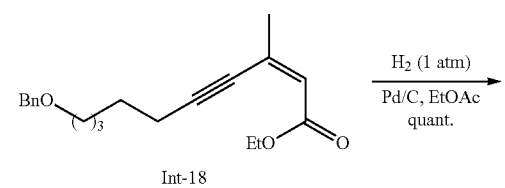

Scheme 14 (Continued).

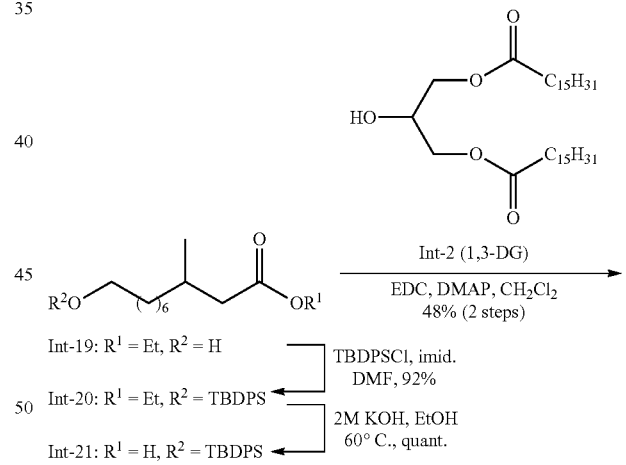

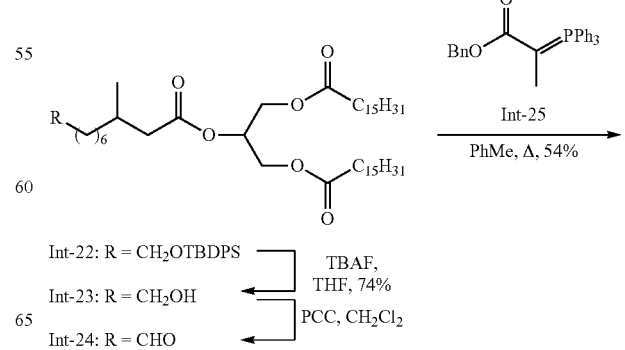

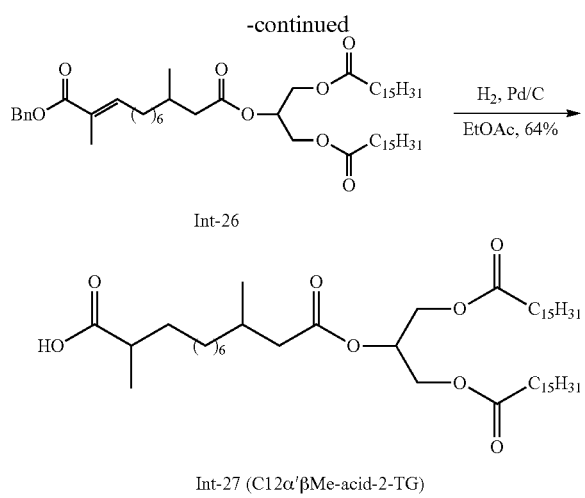

Int-26

Int-27 (C12α'βMe-acid-2-TG)

Int-13: prepared according to: Young, I. S.; Kerr, M. A. *J. Am. Chem. Soc.* 2007, 129, 1465-1469.

Int-14: prepared according to: Chowdhury, R; Ghosh, S. K. *Org. Lett.* 2009, 11, 3270-3273.

n-Butyllithium (n-BuLi, 1.6 M in hexanes, 765 μL, 1.23 mmol) was added slowly to a solution of TMS-acetylene (198 μL, 1.40 mmol) in THF (1.5 mL) at −78° C. and the mixture stirred at −78° C. for five minutes then warmed to rt and stirred for a further 15 minutes. The reaction was re-cooled to −50° C., a solution of bromide Int-14 (90.0 mg, 0.350 mmol) in THF (1 mL) was added dropwise and the mixture stirred at −50° C. for 15 minutes and then at room temperature for 17 hours. The reaction was diluted with brine (15 mL) and the aqueous phase extracted with ethyl acetate (3×15 mL). The combined organic extracts were washed with brine (30 mL), dried (MgSO$_4$) and concentrated under reduced pressure to give the crude product. Purification by silica gel chromatography (4% to 5% ethyl acetate/hexanes) gave TMS alkyne Int-15 (45.9 mg, 48%) as a colorless oil also containing desilylated alkyne Int-16 (9.7 mg, 14% by $^1$H NMR integration) and small amounts of PPh$_3$. NMR (400 MHz, CDCl$_3$) δ 7.37-7.26 (m, 5H), 4.50 (s, 2H), 3.48 (t, J=6.5 Hz, 2H), 2.23 (t, J=7.0 Hz, 2H), 1.68-1.60 (m, 2H), 1.58-1.42 (m, 4H), 0.14 (s, J=3.4 Hz, 7H).

Tetrabutylammonium fluoride (TBAF, 1.0 M in THF, 201 μL, 0.201 mmol) was added dropwise to a 7:2 mixture of silylalkyne Int-15 and alkyne Int-16 (55.6 mg combined, 0.215 mmol) in THF (1 mL) at 0° C. and the mixture stirred at room temperature for one hour. The reaction was diluted with water (5 mL) and sat. aq. NH$_4$Cl (3 mL) and the aqueous phase extracted with ethyl acetate (3×10 mL). The combined organic extracts were washed with brine (20 mL), dried (MgSO$_4$) and concentrated under reduced pressure to give the crude product. Purification by silica gel chromatography (4% ethyl acetate/hexanes) gave alkyne Int-16 (37.5 mg, 53% over two steps) as a colorless oil. $^1$H NMR (400 MHz, CDCl$_3$) δ 7.39-7.27 (m, 5H), 4.51 (s, 2H), 3.49 (t, J=6.5 Hz, 2H), 2.21 (td, J=6.9, 2.6 Hz, 2H), 1.95 (t, J=2.7 Hz, 1H), 1.70-1.61 (m, 2H), 1.60-1.48 (m, 4H); $^{13}$C NMR (101 MHz, CDCl$_3$) δ 138.7 (C), 128.5 (2C; CH), 127.7 (2C; CH), 127.6 (CH), 84.6 (C), 73.0 (CH$_2$), 70.3 (CH$_2$), 68.4 (CH), 29.4 (CH$_2$), 28.4 (CH$_2$), 25.5 (CH$_2$), 18.5 (CH$_2$).

Int-17: prepared according to: Kim, H.-O. et al. *Synlett* 1998, 1059-1060.

A suspension of PdCl$_2$(PPh$_3$)$_2$ (16.8 mg, 0.0240 mmol) in DMF (1.5 mL) was degassed using N$_2$ gas for five minutes, and then CuI (9.1 mg, 0.0480 mmol), Et$_3$N (66.8 μL, 0.480 mmol) and a degassed solution of alkyne Int-16 (48.5 mg, 0.240 mmol) and enol triflate Int-17 (94.3 mg, 0.360 mmol) in DMF (2 mL) were added. The mixture was degassed using a stream of N$_2$ for a further five minutes and then heated at 0° C. for one hour. The reaction was cooled to room temperature, diluted with ethyl acetate (30 mL), washed with 1 M HCl, sat. aq. NaHCO$_3$, water and brine (20 mL each), dried (MgSO$_4$) and concentrated under reduced pressure to give the crude product. Silica gel chromatography (4% to 5% ethyl acetate/hexanes) gave enyne Int-18 (46.6 mg, 62%) as a pale yellow oil. $^1$H NMR (400 MHz, CDCl$_3$) δ 7.37-7.24 (m, 5H), 5.92 (m, 1H), 4.50 (s, 2H), 4.17 (q, J=7.1 Hz, 2H), 3.48 (t, J=6.5 Hz, 2H), 2.45 (t, J=7.0 Hz, 2H), 2.01 (d, J=1.4 Hz, 3H), 1.69-1.59 (m, 4H), 1.56-1.49 (m, 2H), 1.27 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 102.9 (C), 80.0 (C), 73.0 (CH$_2$), 70.4 (CH$_2$), 60.0 (CH$_2$), 29.4 (CH$_2$), 28.4 (CH$_2$), 26.0 (CH$_3$), 25.7 (CH$_2$), 20.1 (CH$_2$), 14.4 (CH$_3$).

A solution of benzyl ether Int-18 (31.4 mg, 0.100 mmol) in ethyl acetate (8 mL) in a three-neck round-bottom flask was twice evacuated and flushed with N$_2$ gas, then palladium on carbon (10% w/w, 26.6 mg, 0.0250 mmol) was added and the resulting suspension re-evacuated and flushed with N$_2$ three times. The flask was fitted with a H$_2$ balloon, evacuated and flushed with H$_2$ three times and the reaction mixture stirred at RT under 1 atm of H$_2$ for one hour. The flask was then evacuated and flushed with N$_2$ and the reaction mixture filtered through a pad of Celite, washing with ethyl acetate (30 mL). The filtrate was concentrated under reduced pressure to give saturated alcohol Int-19 (23.0 mg, quant.) as a colorless oil that was used without purification. $^1$H NMR (400 MHz, CDCl$_3$) δ 4.12 (q, J=7.1 Hz, 2H), 3.63 (t, J=6.6 Hz, 2H), 2.28 (dd, J=14.6, 6.1 Hz, 1H), 2.09 (dd, J=14.6, 8.1 Hz, 1H), 1.94 (m, 1H), 1.60-1.50 (m, 2H), 1.25 (t, J=6.6 Hz, 3H), 1.40-1.13 (m, 10H), 0.92 (d, J=6.6 Hz, 3H); $^{13}$C NMR (101 MHz, CDCl$_3$) δ 173.6 (C), 63.2 (CH$_2$), 60.2 (CH$_2$), 42.1 (CH$_2$), 36.8 (CH$_2$), 32.9 (CH$_2$), 30.5 (CH), 29.8 (CH$_2$), 29.5 (CH$_2$), 26.9 (CH$_2$), 25.8 (CH$_2$), 19.9 (CH$_3$), 14.4 (CH$_3$).

Imidazole (9.6 mg, 0.141 mmol) and tert-butyl(chloro)diphenylsilane (TBDPSCl, 50.8 μL, 0.195 mmol) were added to a solution of alcohol Int-19 (18.0 mg, 0.0781 mmol) in DMF (3 mL) and the mixture stirred at RT for 16 hours. The reaction was diluted with ethyl acetate (20 mL), washed with brine (2×20 mL), dried (MgSO$_4$), and concentrated under reduced pressure to give the crude product. Purification by silica gel chromatography (4% ethyl acetate/hexanes with 0.5% Et$_3$N) gave TBDPS ether Int-20 (33.7 mg, 92%) as a colorless oil. $^1$H NMR (400 MHz, CDCl$_3$) δ 7.70-7.64 (m, 4H), 7.45-7.33 (m, 6H), 4.13 (q, J=7.1 Hz, 2H), 3.65 (t, J=6.5 Hz, 2H), 2.28 (dd, J=14.6, 6.0 Hz, 1H), 2.09 (dd, J=14.6, 8.2 Hz, 1H), 1.94 (m, 1H), 1.60-1.50 (m, 2H), 1.38-1.21 (m, 3H), 1.05 (s, J=2.9 Hz, 2H), 1.05 (s, 9H), 0.93 (d, J=6.6 Hz, 3H); $^{13}$C NMR (101 MHz, CDCl$_3$) δ 173.6 (C), 135.7 (4C; CH), 134.3 (2C; C), 129.6 (2C; CH), 127.7 (4C; CH), 64.1 (CH$_2$), 60.2 (CH$_2$), 42.1 (CH$_2$), 36.9 (CH$_2$), 32.7 (CH$_2$), 30.5 (CH), 29.9 (CH$_2$), 29.5 (CH$_2$), 27.01 (3C; CH$_3$), 26.99 (CH$_2$), 25.9 (CH$_2$), 19.9 (CH$_3$), 19.4 (C), 14.4 (CH$_3$).

A solution of potassium hydroxide (2.0 M, 427 μL, 0.853 mmol) was added to ester Int-20 (40.0 mg, 0.0853 mmol) in ethanol (2 mL) and the mixture heated at 80° C. for two hours. The reaction was cooled to RT, acidified to pH 1 by addition of 1 M HCl and the organic solvent removed under reduced pressure. The residue was diluted with water (5 mL) and the aqueous phase extracted with ethyl acetate (3×15 mL). The combined organic extracts were washed with brine (30 mL), dried (MgSO$_4$) and concentrated under reduced pressure to give crude acid Int-21 (37.6 mg, quant.) as a colorless oil that was used without purification. $^1$H NMR (400 MHz, CDCl$_3$) δ 7.74-7.63 (m, 4H), 7.45-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.61-1.50 (m, 2H), 1.38-1.18 (m, 10H), 1.04 (s, 9H), 0.96 (d, J=6.6 Hz, 3H); $^{13}$C NMR (101 MHz, CDCl$_3$) δ 179.5 (C), 135.7 (4C; CH), 134.3 (2C; C), 129.6 (2C; CH), 127.7 (4C; CH), 64.1 (CH$_2$), 41.7 (CH$_2$), 36.8 (CH$_2$), 32.7 (CH$_2$), 30.3 (CH), 29.8 (CH$_2$), 29.5 (CH$_2$), 27.01 (3C; CH$_3$), 26.97 (CH$_2$), 25.9 (CH$_2$), 19.8 (CH$_3$), 19.4 (C). Note: While two sets of signals were observed in both the $^1$H and $^{13}$C NMR spectra, only the major set of signals are reported above. It was unclear if the doubling was due to the presence of two closely-related compounds or the presence of both monomeric and dimeric species due to the high concentration of the NMR sample.

DMAP (10.1 mg, 0.0831 mmol), EDC-HCl (39.8 mg, 0.208 mmol) and Int-2 (1,3-DG) (70.9 mg, 0.125 mmol) were added to a solution of acid Int-21 (36.6 mg, 0.0831 mmol) in dichloromethane (2.5 mL) and the mixture stirred at room temperature for 21 hours. The reaction was diluted with dichloromethane (5 mL), silica gel was added and the mixture concentrated under reduced pressure. Purification by silica gel chromatography (4% to 5% ethyl acetate/hexanes) gave triglyceride Int-22 (39.9 mg, 48% over two steps) as a colorless solid. $^1$H NMR (400 MHz, CDCl$_3$) δ 7.69-7.64 (m, 4H), 7.44-7.34 (m, 6H), 5.28 (m, 1H), 4.289/4.287 (each dd, J=11.8, 4.2 Hz, 2H), 4.14 (dd, J=12.0, 5.9 Hz, 2H), 3.65 (t, J=6.5 Hz, 2H), 2.37-2.27 (m, 5H), 2.11 (dd, J=14.7, 8.4 Hz, 1H), 1.92 (m, 1H), 1.67-1.50 (m, 8H), 1.39-1.14 (m, 56H), 1.04 (s, 9H), 0.93 (d, J=6.6 Hz, 3H), 0.88 (t, J=6.9 Hz, 6H); $^{13}$C NMR (101 MHz, CDCl$_3$) δ 173.5 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 34.2 (2C; CH$_2$), 32.7 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.6 (2C; CH$_2$), 29.54 (CH$_2$), 29.51 (2C; CH$_2$), 29.4 (2C; CH$_2$), 29.3 (2C; CH$_2$), 27.02 (CH$_2$), 27.00 (3C; CH$_3$), 25.9 (CH$_2$), 25.0 (2C; CH$_2$), 22.8 (2C; CH$_2$), 19.7 (CH$_3$), 19.4 (C), 14.3 (2C; CH$_3$).

Tetrabutylammonium fluoride (TBAF, 1.0 M in THF, 98.3 µL, 98.3 µmol) was added to a solution of TBDPS ether Int-22 (39.0 mg, 39.3 µmol) in THF (2.5 mL) at 0° C. and the mixture stirred at room temperature for three hours. The reaction was diluted with water (10 mL), extracted with ethyl acetate (3×15 mL), and the organic extracts washed with brine (30 mL), dried (MgSO$_4$) and concentrated under reduced pressure to give the crude product. Purification by silica gel chromatography (10% to 20% ethyl acetate/hexanes) gave alcohol Int-23 (21.8 mg, 74%) as a colorless solid. $^1$H NMR (400 MHz, CDCl$_3$) δ 5.28 (m, 1H), 4.29 (dd, J=11.9, 4.3 Hz, 2H), 4.14 (dd, J=11.9, 5.9 Hz, 2H), 3.64 (t, J=6.6 Hz, 2H), 2.36-2.27 (m, 5H), 2.12 (dd, J=14.7, 8.2 Hz, 1H), 1.93 (m, 1H), 1.65-1.52 (m, 6H), 1.39-1.16 (m, 58H), 0.93 (d, J=6.6 Hz, 3H), 0.88 (t, J=6.9 Hz, 6H); $^{13}$C NMR (101 MHz, CDCl$_3$) δ 173.5 (2C; C), 172.5 (C), 68.9 (CH), 63.2 (CH$_2$), 62.3 (2C; CH$_2$), 41.8 (CH$_2$), 36.7 (CH$_2$), 34.2 (2C; CH$_2$), 32.9 (CH$_2$), 32.1 (2C; CH$_2$), 30.5 (CH), 29.84 (4C; CH$_2$), 29.83 (2C; CH$_2$), 29.80 (4C; CH$_2$), 29.77 (2C; CH$_2$), 29.6 (2C; CH$_2$), 29.5 (3C; CH$_2$), 29.4 (2C; CH$_2$), 29.3 (3C; CH$_2$), 26.9 (CH$_2$), 25.8 (CH$_2$), 25.0 (2C; CH$_2$), 22.8 (2C; CH$_2$), 19.7 (CH$_3$), 14.3 (2C; CH$_3$).

Pyridinium chlorochromate (PCC, 12.0 mg, 55.8 µmol) was added to a suspension of alcohol Int-23 (21.0 mg, 27.9 µmol) and celite (15 mg) in dichloromethane (1.5 mL) at 0° C. and the mixture stirred at room temperature for 1.75 hours. The reaction was filtered through a short pad of silica gel, eluting with ethyl acetate, and the filtrate concentrated under reduced pressure to give crude aldehyde Int-24 (20.9 mg, quant.) as a yellow oil that was used without purification. $^1$H NMR (400 MHz, CDCl$_3$) δ 9.76 (s, 1H), 5.28 (m, 1H), 4.29 (dd, J=11.6, 3.5 Hz, 2H), 4.14 (dd, J=11.6, 5.7 Hz, 2H), 2.42 (t, J=7.1 Hz, 2H), 2.36-2.25 (m, 5H), 2.12 (dd, J=14.5, 8.3 Hz, 1H), 1.93 (m, 1H), 1.72-1.53 (m, 6H), 1.42-1.05 (m, 56H), 0.93 (d, J=6.5 Hz, 3H), 0.88 (t, J=6.6 Hz, 6H).

Int-25: prepared according to: Gossauer, A.; Kuhne, G. Liebigs. Ann. Chem. 1977, 664-686.

A solution of ylide Int-25 (8.1 mg, 19.0 µmol) in toluene (0.4 mL) was added to aldehyde Int-24 (11.0 mg, 14.6 µmol) in toluene (0.6 mL) and the mixture heated at reflux for four hours. The reaction was cooled to rt and concentrated under reduced pressure to give the crude product. Purification by silica gel chromatography (5% to 10% ethyl acetate/hexanes) gave α,β-unsaturated benzyl ester Int-26 (7.1 mg, 54%) as a yellow oil. $^1$H NMR (401 MHz, CDCl$_3$) δ 7.41-7.27 (m, 5H), 6.81 (td, J=7.5, 1.4 Hz, 1H), 5.27 (m, 1H), 5.18 (s, 2H), 4.29 (dd, J=11.9, 4.3 Hz, 2H), 4.14 (dd, J=11.9, 6.0 Hz, 2H), 2.36-2.27 (m, 5H), 2.20-2.08 (m, 3H), 1.93 (m, 1H), 1.85 (d, j=1.2 Hz, 3H), 1.67-1.54 (m, 6H), 1.47-1.38 (m, 2H), 1.37-1.19 (m, 54H), 0.93 (d, J=6.6 Hz, 3H), 0.88 (t, J=6.9 Hz, 6H); $^{13}$C NMR (101 MHz, CDCl$_3$) δ 173.4 (2C; C), 172.4 (C), 168.2 (C), 143.2 (CH), 136.6 (C), 128.7 (2C; CH), 128.2 (CH), 128.1 (2C; CH), 127.6 (C), 69.0 (CH), 66.3 (CH$_2$), 62.3 (2C; CH$_2$), 41.8 (CH$_2$), 36.8 (CH$_2$), 34.2 (2C; CH$_2$), 32.1 (2C; CH$_2$), 30.5 (CH), 29.85 (6C; CH$_2$), 29.81 (4C; CH$_2$), 29.77 (2C; CH$_2$), 29.74 (CH$_2$), 29.63 (2C; CH$_2$), 29.56 (CH$_2$), 29.51 (2C; CH$_2$), 29.4 (2C; CH$_2$), 29.3 (2C; CH$_2$), 28.9 (CH$_2$), 28.7 (CH$_2$), 27.0 (CH$_2$), 25.0 (2C; CH$_2$), 22.8 (2C; CH$_2$), 19.7 (CH$_3$), 14.3 (2C; CH$_2$), 12.6 (CH$_2$).

A solution of benzyl ether Int-26 (48.5 mg, 54.0 µmol) in ethyl acetate (2.5 mL) in a two-neck flask was evacuated and flushed with N$_2$ gas (three times each), then palladium on carbon (10% w/w, 11.5 mg, 10.8 µmol) was added and the resulting suspension re-evacuated and flushed with N$_2$ (three times each). The flask was fitted with a H$_2$ balloon, evacuated and flushed with H$_2$ (three times each) and the reaction mixture stirred at room temperature under 1 atm of H$_2$ for three hours. The reaction was filtered through a pad of celite, washing with ethyl acetate, and concentrated under reduced pressure to give the crude product. Purification by silica gel chromatography (10% to 20% ethyl acetate/hexanes) gave saturated acid Int-27 (C12α'βMe-acid-2-TG) (28.1 mg, 64%) as a colorless oil. $^1$H NMR (401 MHz, CDCl$_3$) δ 5.27 (m, 1H), 4.29 (dd, J=11.9, 4.3 Hz, 2H), 4.14 (dd, j=11.9, 6.1 Hz, 2H), 2.46 (m, 1H), 2.37-2.26 (m, 5H), 2.12 (dd, J=14.7, 8.2 Hz, 1H), 1.94 (m, 1H), 1.73-1.55 (m, 5H), 1.41 (m, 1H), 1.37-1.20 (m, 60H), 1.18 (d, J=7.0 Hz, 3H), 0.93 (d, J=6.6 Hz, 3H), 0.88 (t, J=6.9 Hz, 6H); $^{13}$C NMR (101 MHz, CDCl$_3$) δ 182.3 (C), 173.5 (2C; C), 172.5 (C), 69.0 (CH), 62.3 (2C; CH$_2$), 41.8 (CH$_2$), 39.4 (CH), 36.8 (CH$_2$), 34.2 (2C; CH$_2$), 33.7 (CH$_2$), 32.1 (2C; CH$_2$), 30.5 (CH), 29.84 (6C; CH$_2$), 29.80 (4C; CH$_2$), 29.77 (2C; CH$_2$), 29.62 (2C; CH$_2$), 29.60 (CH$_2$), 29.57 (CH$_2$), 29.5 (2C; CH$_2$), 29.4 (2C; CH$_2$), 29.3 (2C; CH$_2$), 27.3 (CH$_2$), 27.0 (CH$_2$), 25.0 (2C; CH$_2$), 22.8 (2C; CH$_2$), 19.7 (CH$_3$), 17.0 (CH$_3$), 14.3 (2C; CH$_3$).

C4-acid-2-TG (Int-28):

Scheme 15. Synthesis of Int-28.

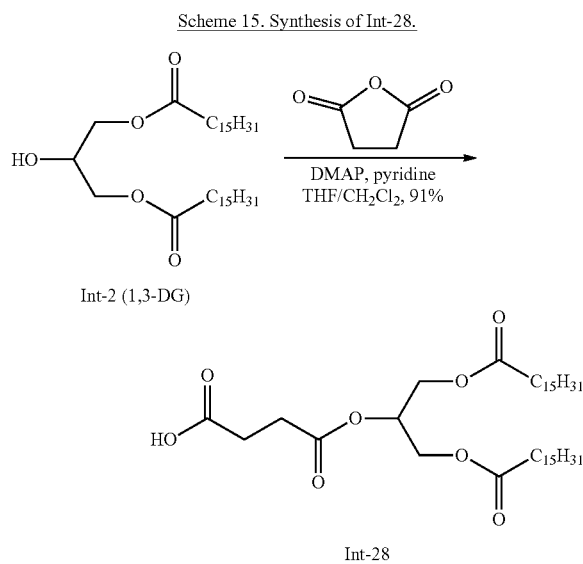

Int-2 (1,3-DG)

Int-28

4-(Dimethylamino)pyridine (DMAP, 15.5 mg, 0.127 mmol) was added to a solution of 1,3-diglyceride Int-2 (72.2 mg, 0.127 mmol) and succinic anhydride (25.4 mg, 0.254 mmol) in pyridine/THF/CH$_2$Cl$_2$ (0.5 mL each) and the mixture stirred at room temperature for 17 hours. An extra portion of succinic anhydride (25.4 mg, 0.254 mmol) and DMAP (15.5 mg, 0.127 mmol) was added and the solution heated at 40° C. for a further 22 hours. The reaction was diluted with ethyl acetate (25 mL), washed with 1 M HCl (20 mL) and brine (2×30 mL), dried (MgSO$_4$) and concentrated under reduced pressure to give the crude product. Silica gel chromatography (15% to 25% ethyl acetate/hexanes) gave acid-TG Int-28 (77.0 mg, 91%) as a colorless solid. $^1$H NMR (400 MHz, CDCl$_3$) δ 5.27 (m, 1H), 4.30 (dd, J=12.0, 4.3 Hz, 2H), 4.15 (dd, J=12.0, 5.8 Hz, 2H), 2.72-2.61 (m, 4H), 2.31 (t, J=7.6 Hz, 4H), 1.67-1.54 (m, 4H), 1.36-1.19 (m, 48H), 0.88 (t, J=6.9 Hz, 6H); $^{13}$C NMR (101 MHz, CDCl$_3$) δ 176.9 (C), 173.5 (2C; C), 171.4 (C), 69.8 (CH), 62.0 (2C; CH$_2$), 34.2 (2C; CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 29.0 (CH$_2$), 28.8 (CH$_2$), 25.0 (2C; CH$_2$), 22.8 (2C; CH$_2$), 14.3 (2C; CH$_3$).

C6-acid-2-TG (Int-29):

Scheme 16. Synthesis of Int-29.

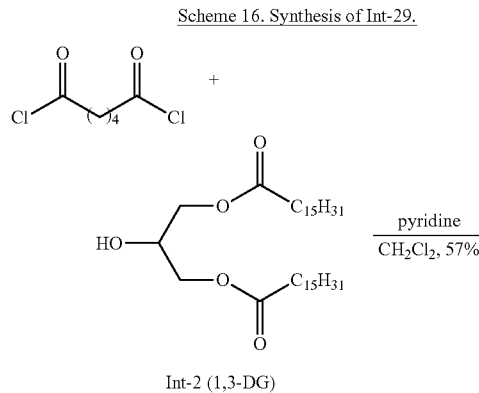

Int-2 (1,3-DG)

-continued

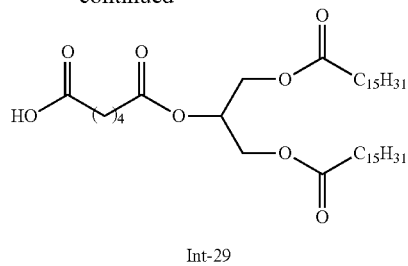

Int-29

A solution of 1,3-diglyceride Int-2 (75.0 mg, 0.132 mmol) and pyridine (107 µL, 1.32 mmol) in CH$_2$Cl$_2$ (2.5 mL) was added to diacid chloride 1 (96.1 mL, 0.659 mmol) in CH$_2$Cl$_2$ (2.5 mL) and the mixture heated at reflux for 3.5 hours. The reaction was cooled to room temperature, diluted with ethyl acetate (30 mL) and the organic extract washed with 1 M HCl (20 mL) and brine (2×20 mL), dried (MgSO$_4$) and concentrated under reduced pressure to give the crude product. Purification by silica gel chromatography (15% to 25% ethyl acetate/hexanes) gave acid-TG Int-29 (52.7 mg, 57%) as a colorless solid. $^1$H NMR (400 MHz, CDCl$_3$) δ 5.26 (m, 1H), 4.30 (dd, J=11.9, 4.3 Hz, 2H), 4.14 (dd, J=11.9, 5.9 Hz, 2H), 2.41-2.34 (m, 4H), 2.31 (t, J=7.6 Hz, 4H), 1.72-1.65 (m, 4H), 1.65-1.56 (m, 4H), 1.35-1.20 (m, 48H), 0.88 (t, J=6.8 Hz, 6H); $^{13}$C NMR (101 MHz, CDCl$_3$) δ 178.3 (C), 173.5 (2C; C), 172.4 (C), 69.3 (CH), 62.2 (2C; CH$_2$), 34.2 (2C; CH$_2$), 33.8 (CH$_2$), 33.5 (CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 24.3 (CH$_2$), 24.1 (CH$_2$), 22.8 (2C; CH$_2$), 14.3 (2C; CH$_2$).

C10βMe-acid-2-TG (Int-30):

Scheme 17. Synthesis of Int-30.

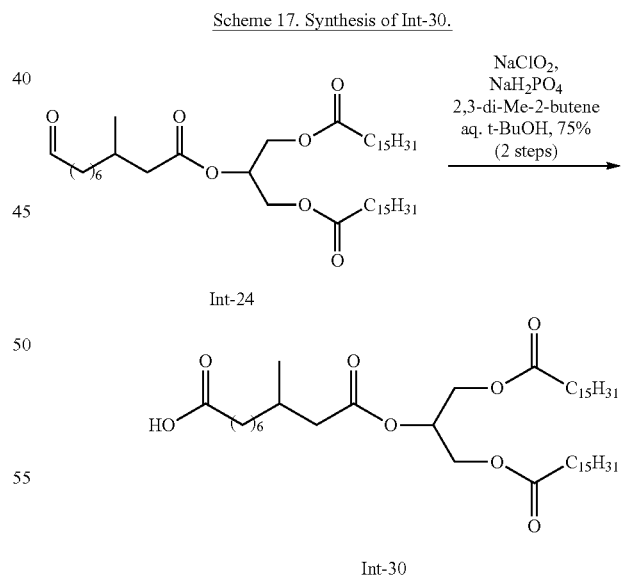

A solution of sodium chlorite (22.7 mg, 0.251 mmol) and sodium phosphate monobasic (NaH$_2$PO$_4$, 23.4 mg, 0.195 mmol) in water (1 mL) was added dropwise to aldehyde Int-24 (20.9 mg, 0.0279 mmol) in t-BuOH (1.5 mL) and 2,3-dimethyl-2-butene (0.3 mL) and the reaction stirred at room temperature for 2.25 hours. The reaction was diluted with water (10 mL) and the aqueous layer extracted with ethyl acetate (3×15 mL). The combined organic extracts were washed with brine (30 mL), dried (MgSO$_4$) and concentrated under reduced pressure to give the crude product. Purification by silica gel chromatography (10% to 20% ethyl acetate/hexanes with 0.5% acetic acid) gave acid Int-30 (16.1 mg, 75%) as a colorless solid. $^1$H NMR (400 MHz, CDCl$_3$) δ 5.27 (m, 1H), 4.29 (dd, J=11.9, 4.3 Hz, 2H), 4.14 (dd, J=12.0, 6.0 Hz, 2H), 2.37-2.27 (m, 7H), 2.12 (dd, J=14.7, 8.2 Hz, 1H), 1.93 (m, 1H), 1.67-1.55 (m, 6H), 1.40-1.14 (m, 56H), 0.93 (d, J=6.6 Hz, 3H), 0.88 (t, J=6.9 Hz, 6H); $^{13}$C NMR (101 MHz, CDCl$_3$) δ 179.7 (C), 173.5 (2C; C), 172.4 (C), 69.0 (CH), 62.3 (2C; CH$_2$), 41.8 (CH$_2$), 36.7 (CH$_2$), 34.2 (2C; CH$_2$), 34.1 (CH$_2$), 32.1 (2C; CH$_2$), 30.4 (CH), 29.82 (6C; CH$_2$), 29.79 (4C; CH$_2$), 29.75 (2C; CH$_2$), 29.6 (2C; CH$_2$), 29.5 (3C; CH$_2$), 29.4 (2C; CH$_2$), 29.24 (2C; CH$_2$), 29.16 (CH$_2$), 26.8 (CH$_2$), 25.0 (2C; CH$_2$), 24.8 (CH$_2$), 22.8 (2C; CH$_2$), 19.7 (CH$_3$), 14.2 (2C; CH$_3$).

C12βMe-OH-2-TG (Int-121):

Using similar methods to those described above for Int-24 synthesis, Int-121 was prepared:

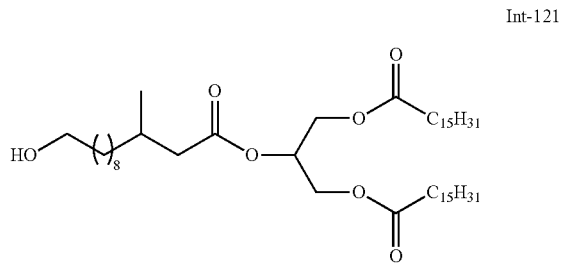
Int-121

$^1$H NMR (401 MHz, CDCl$_3$) δ 5.28 (m, 1H), 4.29 (dd, J=11.9, 4.3 Hz, 2H), 4.14 (dd, J=11.8, 6.0 Hz, 2H), 3.64 (t, J=6.6 Hz, 2H), 2.32 (dd, J=14.6, 5.8 Hz, 1H), 2.30 (t, J=7.5 Hz, 4H), 2.12 (dd, J=14.6, 8.2 Hz, 1H), 1.94 (m, 1H), 1.64-1.49 (m, 6H), 1.40-1.13 (m, 62H), 0.93 (d, J=6.6 Hz, 3H), 0.88 (t, j=6.9 Hz, 6H); $^{13}$C NMR (101 MHz, CDCl$_3$) δ 173.3 (2C; C), 172.4 (C), 68.9 (CH), 62.9 (CH$_2$), 62.2 (2C; CH$_2$), 41.7 (CH$_2$), 36.7 (CH$_2$), 34.1 (2C; CH$_2$), 32.9 (CH$_2$), 32.0 (2C; CH$_2$), 30.4 (CH), 29.80 (CH$_2$), 29.76 (6C; CH$_2$), 29.72 (4C; CH$_2$), 29.68 (2C; CH$_2$), 29.65 (CH$_2$), 29.62 (CH$_2$), 29.53 (2C; CH$_2$), 29.50 (CH$_2$), 29.4 (2C; CH$_2$), 29.3 (2C; CH$_2$), 29.2 (2C; CH$_2$), 27.0 (CH$_2$), 25.8 (CH$_2$), 24.9 (2C; CH$_2$), 22.7 (2C; CH$_2$), 19.6 (CH$_3$), 14.2 (2C; CH$_3$).

C12α'βMe-OH-2-TG (Int-143):

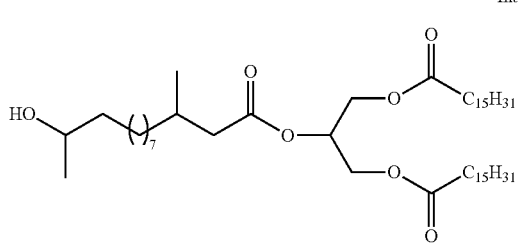
Int-143

Pyridinium chlorochromate (16.5 mg, 0.0765 mmol) and Celite (16.5 mg) were added to a solution of alcohol Int-121 (40.0 mg, 0.0512 mmol) in CH$_2$Cl$_2$ (2.5 mL) at 0° C. and the resulting suspension stirred at 0° C. for 15 minutes and then at room temperature for three hours. The reaction mixture was filtered through a plug of silica gel, eluting with ethyl acetate (50 mL) and the filtrate concentrated under reduced pressure to give the corresponding aldehyde as a pale yellow oil that was used without purification.

The crude aldehyde was re-dissolved in diethyl ether (2.5 mL) and cooled to −10° C. (ice/brine bath). Methylmagnesium bromide (3.0 M in diethyl ether, 18.8 μL, 0.0563 mmol) was added and the reaction vessel transferred into the freezer (−20° C.) and allowed to stand for 19 hours. The mixture was warmed to −10° C., slowly quenched by the addition of sat. aq. NH$_4$Cl solution (4 mL) and then warmed to room temperature. The aqueous layer was extracted with ethyl acetate (3×20 mL) and the combined organic extracts washed with water (25 mL) and brine (25 mL), dried (MgSO$_4$), and concentrated under reduced pressure to give the crude product. Silica gel chromatography (0% to 15% ethyl acetate/hexanes) gave alcohol Int-143 (21.6 mg, 53%) as a white solid. $^1$H NMR (401 MHz, CDCl$_3$) δ 5.27 (m, 1H), 4.29 (dd, J=11.9, 3.8 Hz, 2H), 4.14 (dd, j=11.9, 6.0 Hz, 2H), 3.78 (m, 1H), 2.32 (dd, J=14.6, 5.8 Hz, 1H), 2.30 (t, j=7.5 Hz, 4H), 2.12 (dd, J=14.7, 8.2 Hz, 1H), 1.93 (m, 1H), 1.66-1.56 (m, 6H), 1.52-1.21 (m, 62H), 1.18 (d, j=6.2 Hz, 3H), 0.93 (d, J=6.6 Hz, 3H), 0.88 (t, J=6.9 Hz, 6H). $^{13}$C NMR (101 MHz, CDCl$_3$) δ 173.5 (2C; C), 172.5 (C), 69.0 (CH), 68.3 (CH), 62.3 (2C; CH$_2$), 41.9 (CH$_2$), 39.5 (CH$_2$), 36.8 (CH$_2$), 34.2 (2C; CH$_2$), 32.1 (2C; CH$_2$), 30.5 (CH), 29.90 (CH$_2$), 29.85 (6C; CH$_2$), 29.81 (4C; CH$_2$), 29.78 (3C; CH$_2$), 29.75 (CH$_2$), 29.72 (CH$_2$), 29.6 (2C; CH$_2$), 29.5 (2C; CH$_2$), 29.4 (2C; CH$_2$), 29.3 (2C; CH$_2$), 27.1 (CH$_2$), 25.9 (CH$_2$), 25.0 (2C; CH$_2$), 23.7 (CH$_3$), 22.8 (2C; CH$_2$), 19.7 (CH$_3$), 14.3 (2C; CH$_3$).

C12β'βMe-OH-2-TG (Int-148h

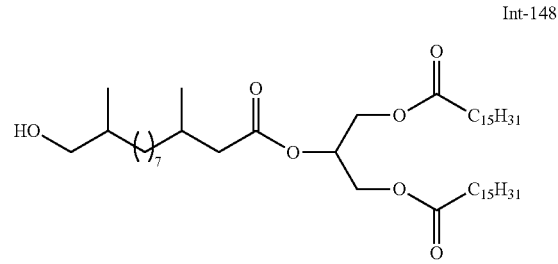
Int-148

Borane-dimethylsulfide complex (1.05 M in THF, 94.0 μL, 98.9 μmol), was added to a solution of carboxylic acid Int-27 (40.0 mg, 49.4 μmol) in THF (1.5 mL) at −5° C. and the mixture stirred at −5° C. for 40 minutes and then allowed to stand in refrigerator for 19 hours. The reaction was slowly diluted with cold water (20 mL) and the aqueous phase extracted with ethyl acetate (3×20 mL). The combined organic extracts were washed with brine (30 mL), dried (MgSO$_4$) and concentrated under reduced pressure to give the crude product. Purification by silica gel chromatography (5% to 15% ethyl acetate/hexanes) gave alcohol Int-148 (35.8 mg, 91%) as a colorless oil. $^1$H NMR (401 MHz, CDCl$_3$) δ 5.27 (m, 1H), 4.29 (dd, J=11.8, 4.2 Hz, 2H), 4.14 (dd, j=11.9, 5.9 Hz, 2H), 3.51 (dd, J=10.5, 5.8 Hz, 1H), 3.42 (dd, j=10.5, 6.5 Hz, 1H), 2.33 (dd, J=14.8, 6.0 Hz, 1H), 2.30 (t, j=7.6 Hz, 4H), 2.12 (dd, J=14.8, 8.2 Hz, 1H), 1.93 (m, 1H), 1.65-1.50 (m, 5H), 1.44-1.05 (m, 62H), 0.93 (d, J=6.7 Hz, 3H), 0.92 (d, J=6.7 Hz, 3H), 0.88 (t, J=6.9 Hz, 6H).

C12-acid-2-TG (Int-37):

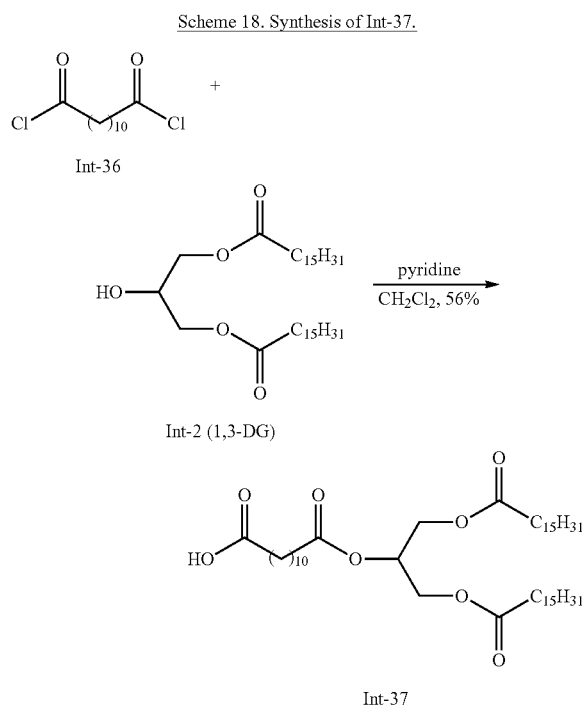

Scheme 18. Synthesis of Int-37.

A mixture of dodecanedioic acid (700 mg, 3.04 mmol) and DMF (two drops) in thionyl chloride (2.20 mL, 30.4 mmol) was heated at reflux for two hours. The reaction was cooled to room temperature, diluted with toluene (5 mL) and concentrated under reduced pressure to give diacid chloride Int-36 (812 mg, quant.) as a yellow oil that was used without purification. $^1$H NMR (400 MHz, CDCl$_3$): δ 2.88 (t, J=7.3 Hz, 4H), 1.76-1.65 (m, 4H), 1.42-1.23 (m, 12H).

A solution of 1,3-diglyceride Int-2 (40.0 mg, 0.0703 mmol) and pyridine (56.9 µL, 0.703 mmol) in CH$_2$Cl$_2$ (1.5 mL) was added to diacid chloride Int-36 (93.9 mg, 0.352 mmol) in CH$_2$Cl$_2$ (1.5 mL) and the mixture stirred at room temperature for 16 hours. The reaction was diluted with ethyl acetate (3 mL), water (10 mL) and 1 M HCl (2 mL) and the aqueous layer extracted with ethyl acetate (3×15 mL). The combined organic extracts were washed with 1 M HCl (30 mL) and brine (2×30 mL), dried (MgSO$_4$) and concentrated under reduced pressure to give the crude product. Purification by silica gel chromatography (20% to 45% ethyl acetate/hexanes) gave acid-TG Int-37 (30.7 mg, 56%) as a colorless solid. $^1$H NMR (400 MHz, CDCl$_3$): δ 5.26 (m, 1H), 4.29 (dd, J=11.9, 4.3 Hz, 2H), 4.14 (dd, J=11.9, 5.9 Hz, 2H), 2.38-2.26 (m, 8H), 1.69-1.54 (m, 8H), 1.38-1.19 (m, 60H), 0.87 (t, J=6.9 Hz, 6H).

C15βMe-acid-2-TG (Int-49):

Scheme 19. Synthesis of Int-49.

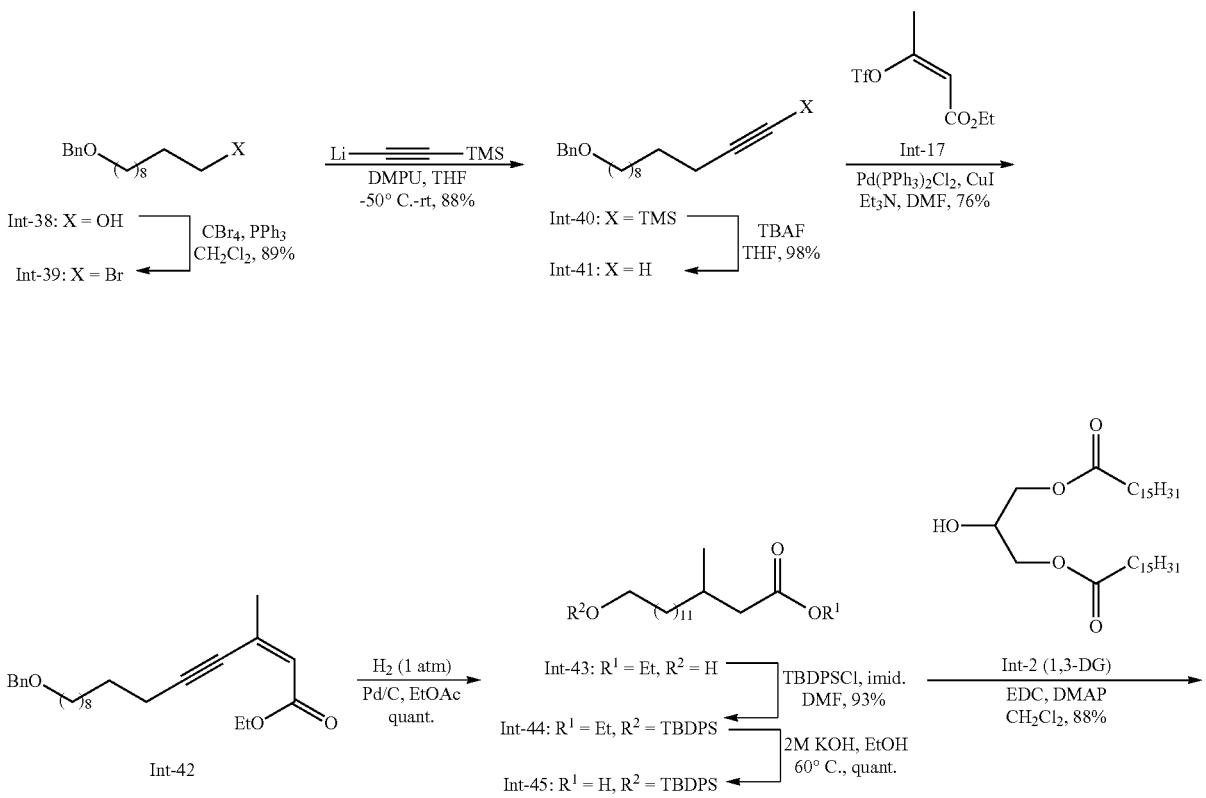

-continued

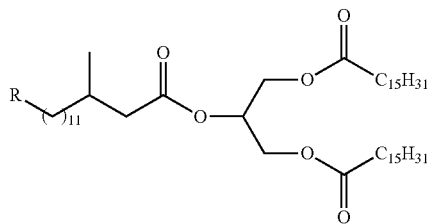

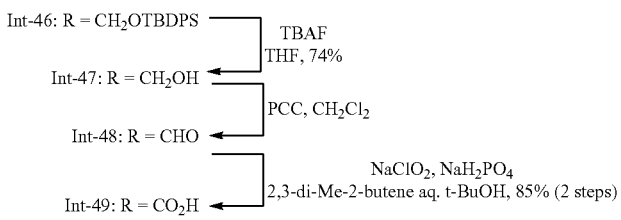

A solution of 1,10-decanediol (1.05 g, 6.00 mmol) in DMF (7 mL) was added dr op wise to a suspension of sodium hydride (60% w/w in mineral oil, washed twice with dry petrol, 240 mg, 6.00 mmol) in DMF (8 mL) at 0° C. and the mixture stirred at room temperature for one hour. Benzyl bromide (784 µL, 3.50 mmol) was added dropwise and the mixture stirred at room temperature for 1.5 hours. The reaction was diluted with ethyl acetate (30 mL), quenched with water (20 mL) and the aqueous phase extracted with ethyl acetate (3×30 mL). The combined organic extracts washed with water and brine (60 mL each), dried (MgSO$_4$) and concentrated under reduced pressure to give the crude product. Purification by silica gel chromatography (20% to 30% ethyl acetate/hexanes) gave benzyl ether Int-38 (657 mg, 41%) as a colorless oil. $^1$H NMR (400 MHz, CDCl$_3$) δ 7.39-7.24 (m, 5H), 4.50 (s, 2H), 3.64 (t, J=6.6 Hz, 2H), 3.46 (t, J=6.7 Hz, 2H), 1.65-1.52 (m, 4H), 1.40-1.25 (m, 12H).

Carbon tetrabromide (1.05 g, 3.17 mmol) and triphenylphosphine (1.07 g, 4.08 mmol) were added to a solution of alcohol Int-38 (600 mg, 1.11 mmol) in CH$_2$Cl$_2$ (20 mL) at 0° C. and the mixture stirred at room temperature for 2.5 hours. The reaction was diluted with CH$_2$Cl$_2$ (20 mL), silica gel was added and the solvent evaporated under reduced pressure. Purification by silica gel chromatography (3% to 4% ethyl acetate/hexanes) gave bromide Int-39 (658 mg, 89%) as a colorless oil. $^1$H NMR (400 MHz, CDCl$_3$) δ 7.41-7.26 (m, 5H), 4.50 (s, 2H), 3.46 (t, J=6.6 Hz, 2H), 3.40 (t, J=6.9 Hz, 2H), 1.91-1.79 (m, 2H), 1.68-1.56 (m, 2H), 1.47-1.23 (m, 12H).

n-Butyllithium (n-BuLi, 1.6 M in hexanes, 4.01 mL, 6.42 mmol) was added slowly to a solution of TMS-acetylene (1.02 mL, 7.22 mmol) in THF (9 mL) at −78° C. and the mixture stirred at −78° C. for five minutes then warmed to room temperature and stirred for a further 15 minutes. The reaction was re-cooled to −50° C., a solution of bromide Int-39 (525 mg, 1.60 mmol) and DMPU (1.06 mL, 8.82 mmol) in THF (6 mL) was added dropwise and the mixture stirred at −50° C. for 30 minutes and then at room temperature for 22 hours. The reaction was diluted with brine (15 mL) and the organic solvent evaporated under reduced pressure. The aqueous residue was extracted with ethyl acetate (3×25 mL) and the combined organic extracts washed with brine (50 mL), dried (MgSO$_4$) and concentrated under reduced pressure to give the crude product. Purification by silica gel chromatography (3.5% to 4.5% ethyl acetate/hexanes) gave TMS alkyne Int-40 (489 mg, 88%) as a colorless oil containing small amounts of desilylated alkyne Int-41 (<10%). $^1$H NMR (400 MHz, CDCl$_3$) δ 7.37-7.25 (m, 5H), 4.50 (s, 2H), 3.46 (t, J=6.7 Hz, 2H), 2.21 (t, J=7.2 Hz, 2H), 1.65-1.58 (m, 2H), 1.54-1.46 (m, 2H), 1.41-1.24 (m, 12H), 0.14 (s, 9H).

Tetrabutylammonium fluoride (TBAF, 1.0 Min THF, 1.61 mL, 1.61 mmol) was added dropwise to silylalkyne Int-40 (463 mg, 1.34 mmol) in THF (12 mL) at 0° C. and the mixture stirred at room temperature for 40 minutes. The reaction was diluted with water (10 mL) and the aqueous phase extracted with ethyl acetate (3×20 mL). The combined organic extracts were washed with brine (40 mL), dried (MgSO$_4$) and concentrated under reduced pressure to give the crude product. Purification by silica gel chromatography (4% to 5% ethyl acetate/hexanes) gave alkyne Int-41 (361 mg, 98%) as a colorless oil. NMR (400 MHz, CDCl$_3$) δ 7.38-7.25 (m, 5H), 4.50 (s, 2H), 3.46 (t, J=6.7 Hz, 2H), 2.18 (td, J=7.1, 2.6 Hz, 2H), 1.94 (t, J=2.7 Hz, 1H), 1.65-1.57 (m, 2H), 1.55-1.48 (m, 2H), 1.43-1.24 (m, 12H). $^{13}$C NMR (101 MHz, CDCl$_3$) δ 138.86 (C), 128.49 (2C; CH), 127.77 (2C; CH), 127.61 (CH), 84.97 (C), 73.00 (CH$_2$), 70.67 (CH$_2$), 68.18 (CH), 29.91 (CH$_2$), 29.67 (CH$_2$), 29.59 (CH$_2$), 29.57 (CH$_2$), 29.23 (CH$_2$), 28.89 (CH$_2$), 28.63 (CH$_2$), 26.33 (CH$_2$), 18.54 (CH$_2$).

A suspension of PdCl$_2$(PPh$_3$)$_2$ (32.2 mg, 0.0459 mmol) in DMF (4 mL) was degassed using a stream of N$_2$ gas for five minutes, and then CuI (35.0 mg, 0.184 mmol), Et$_3$N (256 µL, 1.84 mmol) and a degassed solution of alkyne Int-41 (250 mg, 0.918 mmol) and enol triflate Int-17 (313 mg, 1.19 mmol) in DMF (6 mL) were added. The mixture was degassed using a stream of N$_2$ for a further five minutes and then heated at 70° C. for one hour. The reaction was cooled to room temperature, diluted with ethyl acetate (40 mL), washed with 1 M HCl, sat. aq. NaHCO$_3$, water and brine (30 mL each), dried (MgSO$_4$) and concentrated under reduced pressure to give the crude product. Silica gel chromatography (4% to 5% ethyl acetate/hexanes) gave enyne Int-42 (269 mg, 76%) as a pale yellow oil. $^1$H NMR (400 MHz, CDCl$_3$) δ 7.38-7.24 (m, 5H), 5.92 (m, 1H), 4.50 (s, 2H), 4.18 (t, J=7.1 Hz, 2H), 3.46 (t, J=6.7 Hz, 2H), 2.43 (t, J=7.2 Hz, 2H), 2.01 (d, J=1.4 Hz, 3H), 1.65-1.55 (m, 4H), 1.46-1.24 (m, 12H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.3 (CH), 103.3 (C), 79.9 (C), 73.0 (CH$_2$), 70.6 (CH$_2$), 60.0 (CH$_2$), 29.9 (CH$_2$), 29.65 (CH$_2$), 29.59 (CH$_2$), 29.56 (CH$_2$), 29.2 (CH$_2$), 29.1 (CH$_2$), 28.6 (CH$_2$), 26.3 (CH$_2$), 26.0 (CH$_3$), 20.1 (CH$_2$), 14.4 (CH$_3$).

A solution of benzyl ether Int-42 (246 mg, 0.640 mmol) in ethyl acetate (25 mL) in a three-neck round-bottom flask was twice evacuated and flushed with N$_2$ gas, then palladium on carbon (10% w/w, 102 mg, 0.0960 mmol) was added and the resulting suspension re-evacuated and flushed with N$_2$ three times. The flask was fitted with a H$_2$ balloon, evacuated and flushed with H$_2$ three times and the reaction mixture stirred at room temperature under 1 atm of H$_2$ for one hour. The reaction mixture was then filtered through a pad of celite and the pad washed with ethyl acetate (40 mL). The filtrate was concentrated under reduced pressure to give saturated alcohol Int-43 (192 mg, quant.) as a colorless oil that was used without purification. $^1$H NMR (400 MHz, CDCl$_3$) δ 4.12 (q, J=7.1 Hz, 2H), 3.63 (t, J=6.6 Hz, 2H), 2.28 (dd, J=14.6, 6.0 Hz, 1H), 2.08 (dd, J=14.6, 8.1 Hz, 1H), 1.93 (m, 1H), 1.60-1.51 (m, 2H), 1.43-1.12 (m, 23H), 0.92 (d, J=6.6 Hz, 3H). $^{13}$C NMR (101 MHz, CDCl$_3$) δ 173.6 (C), 63.2 (CH$_2$), 60.2 (CH$_2$), 42.1 (CH$_2$), 36.9 (CH$_2$), 32.9 (CH$_2$), 30.5 (CH), 29.9 (CH$_2$), 29.74 (4C; CH$_2$), 29.70 (CH$_2$), 29.6 (CH$_2$), 27.0 (CH$_2$), 25.9 (CH$_2$), 19.9 (CH$_3$), 14.4 (CH$_3$).

Imidazole (32.0 mg, 0.0.469 mmol) and tert-butyl(chloro)diphenylsilane (TBDPSCl, 183 μL, 0.704 mmol) were added to a solution of alcohol Int-43 (70.5 mg, 0.235 mmol) in DMF (7 mL) and the mixture stirred at room temperature for 17 hours. The reaction was diluted with ethyl acetate (20 mL), washed with water (20 mL) and brine (2×20 mL), dried (MgSO$_4$) and concentrated under reduced pressure to give the crude product. Purification by silica gel chromatography (3% to 4% ethyl acetate/hexanes with 0.5% Et$_3$N) gave TBDPS ether Int-44 (117 mg, 93%) as a colorless oil. $^1$H NMR (400 MHz, CDCl$_3$) δ 7.70-7.63 (m, 4H), 7.44-7.34 (m, 6H), 4.12 (q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.60-1.50 (m, 2H), 1.38-1.14 (m, 23H), 1.04 (s, J=2.8 Hz, 9H), 0.92 (d, J=6.6 Hz, 3H); $^{13}$C NMR (101 MHz, CDCl$_3$) δ 173.5 (C), 135.7 (4C; CH), 134.3 (2C; C), 129.6 (2C; CH), 127.7 (4C; CH), 64.1 (CH$_2$), 60.2 (CH$_2$), 42.1 (CH$_2$), 36.9 (CH$_2$), 32.7 (CH$_2$), 30.5 (CH), 29.9 (CH$_2$), 29.79 (3C; CH$_2$), 29.77 (2C; CH$_2$), 29.5 (CH$_2$), 27.1 (CH$_2$), 27.0 (3C; CH$_3$), 25.9 (CH$_2$), 19.9 (CH$_3$), 19.4 (C), 14.4 (CH$_3$).

A solution of potassium hydroxide (2.0 M, 390 μL, 0.781 mmol) was added to ester Int-44 (42.1 mg. 0.0781 mmol) in ethanol (2 mL) and the mixture heated at 60° C. for 1.5 hours. The reaction was acidified to pH 1 by addition of 1 M HCl, diluted with water (10 mL) and the aqueous phase extracted with ethyl acetate (3×15 mL). The combined organic extracts were washed with brine (30 mL), dried (MgSO$_4$) and concentrated under reduced pressure to give crude acid Int-45 (39.9 mg, quant.) as a colorless oil that was used without purification. $^1$H NMR (400 MHz, CDCl$_3$) δ 7.75-7.66 (m, 4H), 7.46-7.35 (m, 6H), 3.67 (t, j=6.5 Hz, 2H), 2.36 (dd, j=15.0, 5.9 Hz, 1H), 2.15 (dd, J=14.9, 8.2 Hz, 1H), 1.97 (m, 1H), 1.61-1.52 (m, 2H), 1.41-1.17 (m, 20H), 1.06 (s, 9H), 0.98 (d, J=6.6 Hz, 3H); $^{13}$C NMR (101 MHz, CDCl$_3$) δ 179.7 (C), 135.7 (4C; CH), 134.3 (2C; C), 129.6 (2C; CH), 127.7 (4C; CH), 64.2 (CH$_2$), 41.7 (CH$_2$), 36.8 (CH$_2$), 32.7 (CH$_2$), 30.3 (CH), 29.9 (CH$_2$), 29.80 (2C; CH$_2$), 29.78 (2C; CH$_2$), 29.75 (CH$_2$), 29.5 (CH$_2$), 27.1 (CH$_2$), 27.0 (3C; CH$_3$), 25.9 (CH$_2$), 19.8 (CH$_3$), 19.4 (C).

4-(Dimethylamino)pyridine (DMAP, 9.5 mg, 0.0781 mmol), EDC.HCl (29.9 mg, 0.156 mmol) and 1,3-diglyceride Int-2 (53.3 mg, 0.0937 mmol) were added to a solution of acid Int-45 (39.9 mg, 0.0781 mmol) in CH$_2$Cl$_2$ (2.5 mL) and the mixture stirred at room temperature for 19 hours. The reaction was diluted with CH$_2$Cl$_2$ (5 mL), silica gel was added and the mixture concentrated under reduced pressure. Purification by silica gel chromatography (4% to 5% ethyl acetate/hexanes) gave triglyceride Int-46 (72.8 mg, 88% over two steps) as a colorless solid. $^1$H NMR (400 MHz, CDCl$_3$) δ 7.73-7.63 (m, 4H), 7.49-7.31 (m, 6H), 5.29 (m, 1H), 4.30 (dd, J=11.9, 4.2 Hz, 2H), 4.15 (dd, J=11.9, 6.1 Hz, 2H), 3.66 (t, J=6.5 Hz, 2H), 2.34 (dd, J=14.6, 6.0 Hz, 1H), 2.31 (t, j=7.5 Hz, 4H), 2.13 (dd, j=14.6, 8.3 Hz, 1H), 1.94 (m, 1H), 1.68-1.52 (m, 6H), 1.44-1.16 (m, 68H), 1.05 (s, 9H), 0.94 (d, j=6.6 Hz, 3H), 0.88 (t, J=6.8 Hz, 6H); $^{13}$C NMR (101 MHz, CDCl$_3$) δ 173.4 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 34.2 (2C; CH$_2$), 32.7 (CH$_2$), 32.1 (2C; CH$_2$), 30.5 (CH), 30.0 (CH$_2$), 29.84 (8C; CH$_2$), 29.80 (6C; CH$_2$), 29.76 (2C; CH$_2$), 29.61 (2C; CH$_2$), 29.54 (CH$_2$), 29.50 (3C; CH$_2$), 29.4 (2C; CH$_2$), 29.3 (2C; CH$_2$), 27.2 (CH$_2$), 27.0 (3C; CH$_3$), 25.9 (CH$_2$), 25.0 (2C; CH$_2$), 22.8 (2C; CH$_2$), 19.7 (CH$_3$), 19.3 (C), 14.3 (2C; CH$_3$).

Tetrabutylammonium fluoride (TBAF, 1.0 M in THF, 186 μL, 0.186 mmol) and acetic acid (10.6 μL, 0.186 mmol) were added dropwise to TBDPS ether Int-46 (65.7 mg, 0.0619 mmol) in THF (3 mL) at 0° C. and the mixture stirred at room temperature for 19 hours. The reaction was diluted with water (10 mL) and the aqueous phase extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (10% to 15% ethyl acetate/hexanes) gave alcohol Int-47 (34.2 mg, 67%) as a colorless oil. $^1$H NMR (400 MHz, CDCl$_3$) δ 5.27 (m, 1H), 4.28 (dd, J=11.9, 4.3 Hz, 2H), 4.14 (dd, J=11.8, 6.0 Hz, 2H), 3.63 (t, j=6.6 Hz, 2H), 2.32 (dd, j=14.6, 5.9 Hz, 1H), 2.30 (t, j=7.6 Hz, 4H), 2.11 (dd, j=14.6, 8.3 Hz, 1H), 1.92 (m, 1H), 1.66-1.52 (m, 6H), 1.40-1.13 (m, 68H), 0.92 (d, j=6.6 Hz, 3H), 0.87 (t, J=6.9 Hz, 6H); $^{13}$C NMR (101 MHz, CDCl$_3$) δ 173.5 (2C; C), 172.5 (C), 68.9 (CH), 63.2 (CH$_2$), 62.3 (2C; CH$_2$), 41.8 (CH$_2$), 36.8 (CH$_2$), 34.2 (2C; CH$_2$), 32.9 (CH$_2$), 32.1 (2C; CH$_2$), 30.5 (CH), 29.9 (CH$_2$), 29.84 (8C; CH$_2$), 29.80 (6C; CH$_2$), 29.76 (2C; CH$_2$), 29.73 (CH$_2$), 29.62 (2C; CH$_2$), 29.57 (CH$_2$), 29.5 (2C; CH$_2$), 29.4 (2C; CH$_2$), 29.3 (2C; CH$_2$), 27.1 (CH$_2$), 25.9 (CH$_2$), 25.0 (2C; CH$_2$), 22.8 (2C; CH$_2$), 19.7 (CH$_3$), 14.3 (2C; CH$_3$).

Pyridinium chlorochromate (PCC, 14.7 mg, 68.0 μmol) was added to a suspension of alcohol Int-47 (28.0 mg, 34.0 μmol) and celite (15 mg) in CH$_2$Cl$_2$ (1.5 mL) at 0° C. and the mixture stirred at room temperature for one hour. The reaction was filtered through a short pad of silica gel, eluting with ethyl acetate, and the filtrate concentrated under reduced pressure to give crude aldehyde Int-48 (27.9 mg, quant.) as a yellow oil that was used without purification. $^1$H NMR (400 MHz, CDCl$_3$) δ 9.76 (s, 1H), 5.28 (m, 1H), 4.29 (dd, J=11.6, 3.5 Hz, 2H), 4.14 (dd, J=11.9, 5.8 Hz, 2H), 2.42 (t, J=6.8 Hz, 2H), 2.36-2.25 (m, 5H), 2.12 (dd, J=14.4, 8.5

Hz, 1H), 1.94 (m, 1H), 1.69-1.51 (m, 6H), 1.42-1.09 (m, 66H), 0.93 (d, J=6.4 Hz, 3H), 0.88 (t, J=6.3 Hz, 6H).

A solution of sodium chlorite (27.6 mg, 0.306 mmol) and sodium phosphate monobasic (NaH$_2$PO$_4$, 28.8 mg, 0.238 mmol) in water (1.2 mL) was added dropwise to aldehyde Int-48 (27.9 mg, 0.0340 mmol) in t-BuOH (1.8 mL) and 2,3-dimethyl-2-butene (0.4 mL) and the reaction stirred at room temperature for 16 hours. The reaction was acidified to pH 2 using 1 MHCl, diluted with water (10 mL) and the aqueous layer extracted with ethyl acetate (3×15 mL). The combined organic extracts were washed with brine (30 mL), dried ((MgSO$_4$) and concentrated under reduced pressure to give the crude product. Purification by silica gel chromatography (10% to 15% ethyl acetate/hexanes with 0.5% acetic acid) gave acid Int-49 (24.3 mg, 85%) as a colorless solid. $^1$H NMR (400 MHz, CDCl$_3$) δ 5.29 (m, 1H), 4.29 (dd, J=11.9, 3.8 Hz, 2H), 4.14 (dd, J=11.9, 6.1 Hz, 2H), 2.37-2.27 (m, 7H), 2.11 (dd, J=14.7, 8.3 Hz, 1H), 1.92 (m, 1H), 1.68-1.54 (m, 6H), 1.40-1.13 (m, 66H), 0.93 (d, J=6.6 Hz, 3H), 0.87 (t, J=6.8 Hz, 6H); $^{13}$C NMR (101 MHz, CDCl$_3$) δ 179.5 (C), 173.5 (2C; C), 172.5 (C), 68.9 (CH), 62.3 (2C; CH$_2$), 41.9 (CH$_2$), 36.8 (CH$_2$), 34.2 (2C; CH$_2$), 34.1 (CH$_2$), 32.1 (2C; CH$_2$), 30.5 (CH), 29.93 (CH$_2$), 29.85 (8C; CH$_2$), 29.81 (4C; CH$_2$), 29.77 (2C; CH$_2$), 29.73 (CH$_2$), 29.62 (2C; CH$_2$), 29.58 (CH$_2$), 29.51 (2C; CH$_2$), 29.42 (2C; CH$_2$), 29.39 (CH$_2$), 29.26 (2C; CH$_2$), 29.2 (CH$_2$), 27.1 (CH$_2$), 25.0 (2C; CH$_2$), 24.8 (CH$_2$), 22.8 (2C; CH$_2$), 19.7 (CH$_2$), 14.3 (2C; CH$_2$).

Using similar methods, Int-118 was prepared from 1,8-octanediol:

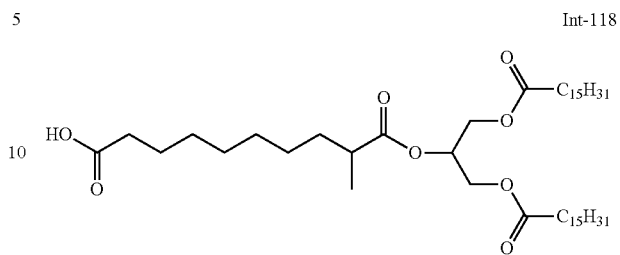

Int-118

$^1$H NMR (400 MHz, CDCl$_3$) δ 5.31 (s, 1H), 4.33 (dd, J=8.4, 4.4 Hz, 2H), 4.19 (dd, J=11.8, 5.9 Hz, 2H), 2.47 (m, 1H), 2.37 (dt, J=15.6, 7.4 Hz, 6H), 1.65 (s, 7H), 1.31 (d, J=13.3 Hz, 58H), 1.18 (d, J=6.9 Hz, 3H), 0.92 (t, J=6.6 Hz, 6H); $^{13}$C NMR (101 MHz, CDCl$_3$) δ 179.73 (1C), 175.87 (1C), 173.31 (2C), 68.70 (1C), 62.13 (1C), 39.50 (1C), 34.04 (3C), 33.57 (1C), 31.93 (4C), 29.71-29.01 (18C), 27.07 (1C), 24.85 (3C), 24.62 (1C), 22.70 (4C), 17.03 (1C), 14.14 (3C). MASS (ESI, −ve) m/z: 766.0 (M−1). (ESI, +ve) m/z: 785.0 (M+18).

C15α'βMe-acid-2-TG (Int-62):

Scheme 20. Synthesis of Int-62.

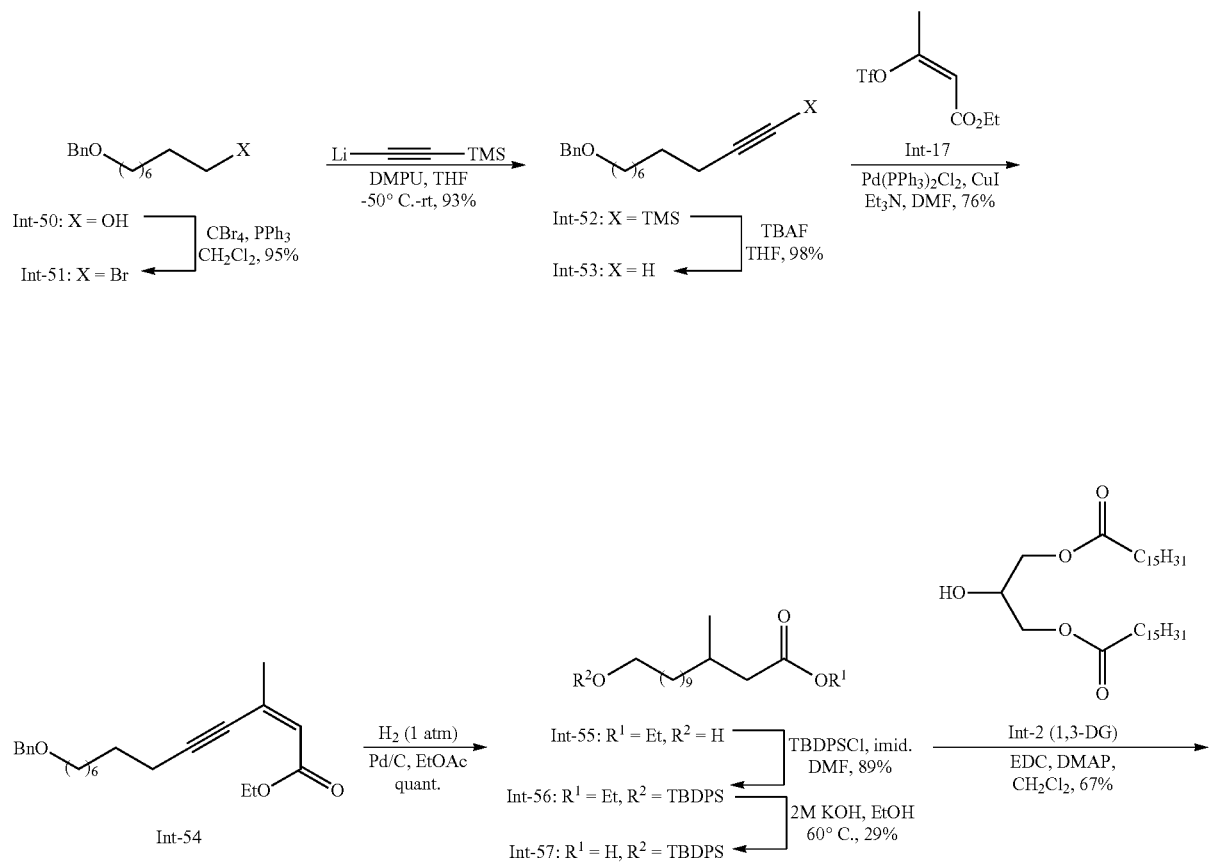

-continued

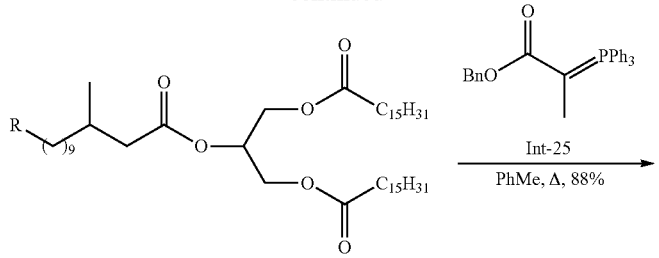

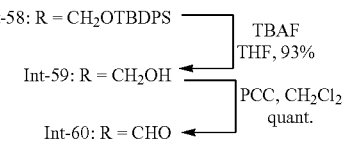

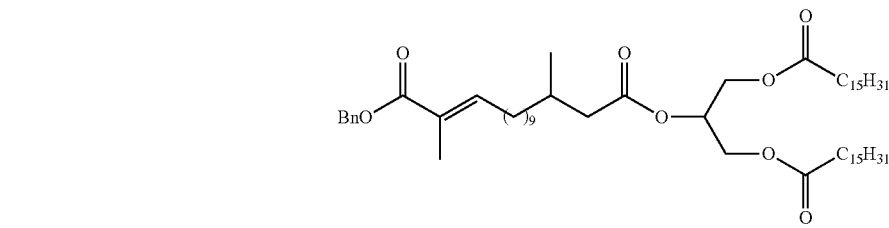

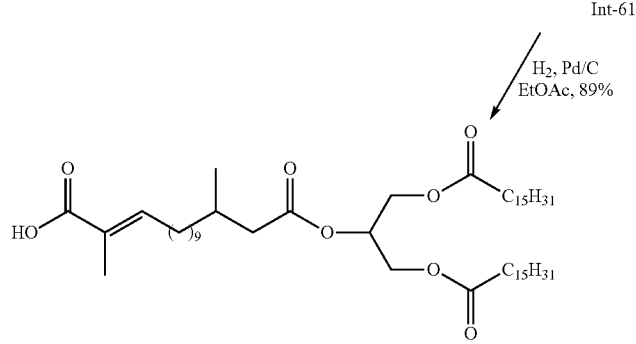

Int-50: prepared according to: Subba Reddy, B. V. et al. Helv. Chim. Acta. 2013, 96, 1983-1990.

Int-51: known compound that may be prepared as disclosed in Takagi, Y. et al. Tetrahedron: Asymm. 2004, 15, 2591-2594). NMR (401 MHz, CDCl$_3$) δ 7.39-7.23 (m, 5H), 4.50 (s, 2H), 3.47 (t, J=6.6 Hz, 2H), 3.40 (t, J=6.9 Hz, 2H), 1.90-1.80 (m, 2H), 1.66-1.57 (m, 2H), 1.48-1.26 (m, 8H).

n-Butyllithium (n-BuLi, 2.0 M in cyclohexane, 18.1 mL, 36.3 mmol) was added slowly to a solution of TMS-acetylene (5.7 mL, 41.5 mmol) in THF (45 mL) at −78° C. and the mixture stirred at −78° C. for five minutes then warmed to room temperature and stirred for a further 15 minutes. The reaction was re-cooled to −78° C., a solution of bromide Int-51 (3.10 g, 10.4 mmol) and DMPU (6.3 mL, 51.8 mmol) in THF (30 mL) was added slowly and the mixture stirred at -78° C. for 30 minutes and then at room temperature for 18 hours. The reaction was diluted with water (60 mL) and the majority of the organic solvent removed under reduced pressure. The residue was diluted with brine (120 mL) and the aqueous phase extracted with ethyl acetate (3×100 mL). The combined organic extracts were washed with brine (3×100 mL), dried (MgSO$_4$) and concentrated under reduced pressure to give the crude product. Purification by silica gel chromatography (Reveleris 80 g column, 60 mL/min, 4% to 40% ethyl acetate/hexanes) gave TMS alkyne Int-52 (3.05 g, 93%) as a colorless oil. $^1$H NMR (401 MHz, CDCl$_3$) δ 7.36-7.25 (m, 5H), 4.50 (s, 2H), 3.46 (t, J=6.6 Hz, 2H), 2.21 (t, J=12 Hz, 2H), 1.65-1.57 (m, 2H), 1.55-1.46 (m, 2H), 1.41-1.27 (m, 8H), 0.15 (s, 9H).

Tetrabutylammonium fluoride (TBAF, 1.0 M in THF, 9.7 mL, 9.70 mmol) was added dropwise to silylalkyne Int-52 (3.05 g, 9.62 mmol) in THF (40 mL) at 0° C. and the mixture stirred at room temperature for one hour. The reaction was diluted with water (25 mL) and the organic solvent removed under reduced pressure. The resulting solution was diluted with brine (100 mL) and the aqueous phase extracted with ethyl acetate (3×50 mL). The combined organic extracts were washed with brine (3×50 mL), dried (MgSO$_4$) and concentrated under reduced pressure to give the crude product. Purification by silica gel chromatography (Reveleris 80 g column, 60 mL/min, 3% to 10% ethyl acetate/hexanes) gave alkyne Int-53 (2.17 g, 92%). $^1$H NMR (401 MHz, CDCl$_3$) δ 7.38-7.25 (m, 5H), 4.50 (s, 2H), 3.46 (t, J=6.6 Hz, 2H), 2.18 (td, J=7.1, 2.6 Hz, 2H), 1.94 (t, J=2.7 Hz, 1H), 1.66-1.56 (m, 2H), 1.57-1.48 (m, 2H), 1.43-1.27

(m, 8H); $^{13}$C NMR (101 MHz, CDCl$_3$) δ 138.8 (C), 128.4 (2C; CH), 127.7 (2C; CH), 127.6 (CH), 84.8 (C), 73.0 (CH), 70.6 (CH$_2$), 68.2 (CH), 29.8 (CH$_2$), 29.4 (CH$_2$), 29.1 (CH$_2$), 28.8 (CH$_2$), 28.6 (CH$_2$), 26.2 (CH$_2$), 18.5 (CH$_2$).

Int-17 was prepared as described above.

A suspension of PdCl$_2$(PPh$_3$)$_2$ (605 mg, 0.862 mmol) in DMF (40 mL) was degassed using N$_2$ gas for five minutes, and then CuI (335 mg, 1.76 mmol), Et$_3$N (2.40 mL, 17.2 mmol) and a degassed solution of alkyne 4 (2.11 g, 8.62 mmol) and enol triflate Int-17 (3.40 g, 13.00 mmol) in DMF (50 mL) were added. The mixture was degassed using a stream of N$_2$ for a further five minutes and then heated at 70° C. for one hour. The reaction was cooled to room temperature and concentrated under reduced pressure to about one-quarter of its original volume. The resulting solution was diluted with ethyl acetate (80 mL), washed with 1 M HCl, sat. aq. NaHCO$_3$, water and brine (30 mL each), dried (MgSO$_4$) and concentrated under reduced pressure to give the crude product. Silica gel chromatography (Reveleris 80 g column, 60 mL/min, 5% to 20% ethyl acetate/hexanes) gave enyne Int-54 (2.35 g, 76%) as a pale yellow oil. $^1$H NMR (401 MHz, CDCl$_3$) δ 7.37-7.24 (m, 5H), 5.92 (d, J=1.4 Hz, 1H), 4.50 (s, 2H), 4.18 (q, J=7.1 Hz, 2H), 3.46 (t, J=6.6 Hz, 2H), 2.43 (t, J=7.2 Hz, 2H), 2.01 (d, J=1.4 Hz, 3H), 1.65-1.55 (m, 4H), 1.46-1.30 (m, 8H), 1.28 (t, J=7.1 Hz, 3H); $^{13}$C NMR (101 MHz, CDCl$_3$) δ 165.4 (C), 138.8 (C), 135.9 (C), 128.5 (2C; CH), 127.7 (2C; CH), 127.6 (CH), 123.4 (CH), 103.2 (C), 79.9 (C), 73.0 (CH$_2$), 70.6 (CH$_2$), 60.0 (CH$_2$), 29.9 (CH$_2$), 29.4 (CH$_2$), 29.2 (CH$_2$), 29.0 (CH$_2$), 28.6 (CH$_2$), 26.3 (CH$_2$), 26.0 (CH$_3$), 20.1 (CH$_2$), 14.4 (CH$_3$).

A solution of benzyl ether Int-54 (707 mg, 1.98 mmol) in ethyl acetate (80 mL) in a three-neck round-bottom flask was twice evacuated and flushed with N$_2$ gas, then palladium on carbon (10% w/w, 525 mg, 0.494 mmol) was added and the resulting suspension re-evacuated and flushed with N$_2$ three times. The flask was fitted with a H$_2$ balloon, evacuated and flushed with H$_2$ three times and the reaction mixture stirred at room temperature under 1 atm of H$_2$ for two hours. The flask was then evacuated and flushed with N$_2$ and the reaction mixture filtered through a pad of celite, washing with ethyl acetate (80 mL). The filtrate was concentrated under reduced pressure to give saturated alcohol Int-55 (540 mg, quant.) as a colorless oil that was used without purification. $^1$H NMR (401 MHz, CDCl$_3$) δ 4.13 (q, J=7.1 Hz, 2H), 3.64 (t, J=6.6 Hz, 2H), 2.28 (dd, J=14.6, 6.0 Hz, 1H), 2.09 (dd, J=14.6, 8.1 Hz, 1H), 1.94 (m, 1H), 1.62-1.51 (m, 2H), 1.39-1.21 (m, 16H), 1.25 (t, J=7.1 Hz, 3H), 0.93 (d, J=6.6 Hz, 3H).

Imidazole (670 mg, 9.85 mmol) and tert-butyl(chloro)diphenylsilane (TBDPSCl, 3.5 mL, 13.6 mmol) were added to a solution of alcohol Int-55 (1.48 g, 5.42 mmol) in CH$_2$Cl$_2$ (80 mL) at 0° C. and the mixture stirred at room temperature for 2.5 hours. The reaction was concentrated to half its volume under reduced pressure, washed with water (2×20 mL) and brine (30 mL), dried (MgSO$_4$) and concentrated under reduced pressure to give the crude product. Purification by silica gel chromatography (Reveleris 80 g column, 60 mL/min, 1% to 16% ethyl acetate/hexanes) gave TBDPS ether Int-56 (2.46 g, 89%) as a colorless oil. $^1$H NMR (401 MHz, CDCl$_3$) δ 7.75-7.64 (m, 4H), 7.46-7.35 (m, 6H), 4.13 (q, J=7.1 Hz, 2H), 3.65 (t, J=6.5 Hz, 2H), 2.29 (dd, J=14.6, 6.0 Hz, 1H), 2.09 (dd, J=14.6, 8.2 Hz, 1H), 1.95 (m, 1H), 1.61-1.50 (m, 2H), 1.38-1.20 (m, 19H), 1.05 (s, 9H), 0.93 (d, J=6.6 Hz, 3H).

A solution of potassium hydroxide (2.0 M, 11.3 mL, 22.6 mmol) was added to ester Int-56 (1.15 g, 2.26 mmol) in ethanol (40 mL) and the mixture stirred at room temperature for 19 hours. The reaction was adjusted to pH 2 by addition of 1 M HCl and the organic solvent removed under reduced pressure. The residue was diluted with water (15 mL) and the aqueous phase extracted with ethyl acetate (3×20 mL). The combined organic extracts were washed with brine (30 mL), dried (MgSO$_4$) and concentrated under reduced pressure to give the crude product. Silica gel chromatography (5% to 25% ethyl acetate/hexanes) gave a pure sample of acid Int-57 (321 mg, 29%) as a pale yellow oil that was used for analytical purposes. An additional >750 mg of 9 was obtained containing slight contamination by an unknown TBDPS species—this material was carried forward and purified at a later stage in the reaction sequence. $^1$H NMR (401 MHz, CDCl$_3$) δ 7.70-7.64 (m, 4H), 7.44-7.34 (m, 6H), 3.65 (t, J=6.5 Hz, 2H), 2.35 (dd, J=15.0, 5.9 Hz, 1H), 2.14 (dd, J=15.0, 8.2 Hz, 1H), 1.95 (m, 1H), 1.60-1.51 (m, 2H), 1.39-1.16 (m, 16H), 1.04 (s, 9H), 0.96 (d, J=6.6 Hz, 3H); $^{13}$C NMR (101 MHz, CDCl$_3$) δ 179.3 (C), 135.7 (4C; CH), 134.4 (2C; C), 129.6 (2C; CH), 127.7 (4C; CH), 64.2 (CH$_2$), 41.7 (CH$_2$), 36.8 (CH$_2$), 32.7 (CH$_2$), 30.3 (CH), 29.9 (CH$_2$), 29.76 (2C; CH$_2$), 29.72 (CH$_2$), 29.5 (CH$_2$), 27.1 (CH$_2$), 27.0 (3C; CH$_3$), 25.9 (CH$_2$), 19.8 (CH$_3$), 19.4 (C).

DMAP (80.8 mg, 0.661 mmol), EDC.HCl (230 mg, 1.20 mmol) and 1,3-diglyceride Int-2 (374 mg, 0.658 mmol) were added to a solution of acid Int-57 (288 mg, 0.597 mmol) in CH$_2$Cl$_2$ (20 mL) and the mixture stirred at room temperature for 20 hours. The reaction was diluted with CH$_2$Cl$_2$ (20 mL), silica gel was added and the mixture concentrated under reduced pressure. Purification by silica gel chromatography (5% to 8% ethyl acetate/hexanes) gave triglyceride Int-58 (416 mg, 67%) as a colorless solid. $^1$H NMR (401 MHz, CDCl$_3$) δ 7.69-7.64 (m, 4H), 7.44-7.34 (m, 6H), 5.28 (m, 1H), 4.289/4.288 (each dd, J=11.9, 4.3 Hz, 2H), 4.14 (dd, j=12.0, 6.0 Hz, 2H), 3.65 (t, J=6.5 Hz, 2H), 2.34 (dd, j=15.0, 5.9 Hz, 1H), 2.30 (t, J=7.5 Hz, 4H), 2.12 (dd, J=14.6, 8.3 Hz, 1H), 1.93 (m, 1H), 1.66-1.50 (m, 6H), 1.45-1.14 (m, 64H), 1.04 (s, 9H), 0.93 (d, J=6.6 Hz, 3H), 0.88 (t, J=6.6 Hz, 6H).

Tetrabutylammonium fluoride (TBAF, 1.0 M in THF, 574 μL, 0.574 mmol) and acetic acid (32.8 μL, 0.574 mmol) were added to a solution of TBDPS ether Int-58 (395 mg, 0.383 mmol) in THF (15 mL) at 0° C. and the mixture stirred at room temperature for 17 hours. The reaction was concentrated under reduced pressure and the residue diluted with ethyl acetate (30 mL), washed with water (2×20 mL) and brine (30 mL), dried (MgSO$_4$) and concentrated under reduced pressure to give the crude product. Purification by silica gel chromatography (5% to 25% ethyl acetate/hexanes) gave alcohol Int-59 (282 mg, 93%) as a colorless solid. $^1$H NMR (401 MHz, CDCl$_3$) δ 5.28 (m, 1H), 4.286/4.285 (each dd, J=11.8, 4.2 Hz, 2H), 4.14 (dd, J=11.9, 5.7 Hz, 2H), 3.63 (t, J=6.6 Hz, 2H), 2.33 (dd, J=15.0, 5.9 Hz, 1H), 2.30 (t, J=7.5 Hz, 4H), 2.12 (dd, J=14.7, 8.3 Hz, 1H), 1.93 (m, 1H), 1.68-1.52 (m, 6H), 1.49-1.15 (m, 64H), 0.93 (d, J=6.6 Hz, 3H), 0.88 (t, j=6.6 Hz, 6H); $^{13}$C NMR (101 MHz, CDCl$_3$) δ 173.5 (2C; C), 172.5 (C), 69.0 (CH), 63.2 (CH$_2$), 62.3 (2C; CH$_2$), 41.9 (CH$_2$), 36.8 (CH$_2$), 34.2 (2C; CH$_2$), 33.0 (CH$_2$), 32.1 (2C; CH$_2$), 30.5 (CH), 29.9 (CH$_2$), 29.84 (6C; CH$_2$), 29.81 (4C; CH$_2$), 29.77 (2C; CH$_2$), 29.74 (CH$_2$), 29.71 (CH$_2$), 29.62 (2C; CH$_2$), 29.57 (CH$_2$), 29.5 (2C; CH$_2$), 29.4 (2C; CH$_2$), 29.3 (3C; CH$_2$), 27.1 (CH$_2$), 25.9 (CH$_2$), 25.0 (2C; CH$_2$), 22.8 (2C; CH$_2$), 19.7 (CH$_3$), 14.3 (2C; CH$_3$).

Pyridinium chlorochromate (PCC, 143 mg, 0.664 mmol) was added to a suspension of alcohol Int-59 (263 mg, 0.331 mmol) and Celite (150 mg) in CH$_2$Cl2 (18 mL) at 0° C. and the mixture stirred at room temperature for four hours. The reaction was filtered through a short pad of silica gel, eluting with ethyl acetate, and the filtrate concentrated under reduced pressure to give crude aldehyde Int-60 (262 mg, quant.) as a yellow oil that was used without purification. $^1$H NMR (401 MHz, CDCl$_3$) δ 9.76 (t, j=1.8 Hz, 1H), 5.27 (m, 1H), 4.29 (dd, j=11.8, 4.1 Hz, 2H), 4.14 (dd, j=11.8, 6.0 Hz, 2H), 2.42 (td, j=7.4, 1.8 Hz, 2H), 2.33 (dd, j=15.0, 5.9 Hz, 1H), 2.30 (t, J=7.5 Hz, 4H), 2.12 (dd, j=14.7, 8.3 Hz, 1H), 1.93 (m, 1H), 1.69-1.53 (m, 6H), 1.45-1.16 (m, 62H), 0.93 (d, j=6.6 Hz, 3H), 0.88 (t, J=6.8 Hz, 6H).

Int-25 was prepared as described above.

A solution of ylide Int-25 (270 mg, 0.637 mmol) in toluene (10 mL) was added to aldehyde Int-60 (262 mg, 0.331 mmol) in toluene (8 mL) and the mixture heated at reflux for 20 hours. The reaction was cooled to room temperature and concentrated under reduced pressure to give the crude product. Purification by silica gel chromatography (5% to 15% ethyl acetate/hexanes) gave α,β-unsaturated benzyl ester Int-61 (273 mg, 88%) as a yellow oil. $^1$H NMR (401 MHz, CDCl$_3$) δ 7.40-7.27 (m, 5H), 6.82 (td, J=7.5, 1.4 Hz, 1H), 5.28 (m, 1H), 5.18 (s, 2H), 4.29 (dd, J=11.9, 4.3 Hz, 2H), 4.14 (dd, J=11.9, 6.0 Hz, 2H), 2.33 (dd, J=15.0, 5.9 Hz, 1H), 2.30 (t, J=7.5 Hz, 4H), 2.20-2.07 (m, 3H), 1.92 (m, 1H), 1.85 (d, J=1.2 Hz, 3H), 1.65-1.53 (m, 4H), 1.47-1.37 (m, 2H), 1.36-1.14 (m, 62H), 0.93 (d, J=6.6 Hz, 3H), 0.88 (t, J=6.9 Hz, 6H); $^{13}$C NMR (101 MHz, CDCl$_3$) δ 173.4 (2C; C), 172.5 (C), 168.2 (C), 143.3 (CH), 136.6 (C), 128.3 (CH), 128.13 (CH), 128.11 (2C; CH), 127.5 (C), 68.9 (CH), 66.3 (CH$_2$), 62.3 (2C; CH$_2$), 41.8 (CH$_2$), 36.8 (CH$_2$), 34.2 (2C; CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.70 (CH$_2$), 29.61 (3C; CH$_2$), 29.57 (CH$_2$), 29.5 (2C; CH$_2$), 29.4 (2C; CH$_2$), 29.3 (3C; CH$_2$), 28.9 (CH$_2$), 28.7 (CH$_2$), 27.1 (CH$_2$), 25.0 (2C; CH$_2$), 22.8 (2C; CH$_2$), 19.7 (CH$_3$), 14.3 (2C; CH$_3$), 12.5 (CH$_3$).

A solution of benzyl ester Int-61 (246 mg, 0.262 mmol) in ethyl acetate (10 mL) in a two-neck flask was evacuated and flushed with N$_2$ gas (three times each), then palladium on carbon (10% w/w, 55.7 mg, 0.0524 mmol) was added and the resulting suspension re-evacuated and flushed with N$_2$ (three times each). The flask was fitted with a H$_2$ balloon, evacuated and flushed with H$_2$ (three times each) and the reaction mixture stirred at room temperature under 1 atm of H$_2$ for 1.5 hours. The reaction was filtered through a pad of celite, washing with ethyl acetate, and concentrated under reduced pressure to give the crude product. Purification by silica gel chromatography (5% to 20% ethyl acetate/hexanes) gave saturated acid Int-62 (193 mg, 87%) as a colorless solid. $^1$H NMR (401 MHz, CDCl$_3$) δ 5.28 (m, 1H), 4.291/4.289 (each dd, j=11.8, 4.2 Hz, 2H), 4.147/4.144 (each dd, j=11.9, 6.0 Hz, 2H), 2.46 (m, 1H), 2.33 (dd, J=15.0, 5.9 Hz, 1H), 2.31 (t, j=7.5 Hz, 4H), 2.12 (dd, J=14.7, 8.2 Hz, 1H), 1.94 (m, 1H), 1.73-1.55 (m, 5H), 1.50-1.21 (m, 67H), 1.18 (d, j=7.0 Hz, 3H), 0.93 (d, J=6.6 Hz, 3H), 0.88 (t, J=6.9 Hz, 6H).

Ph-C3-phenol-2-TG (Int-67):

Scheme 21. Synthesis of Int-67.

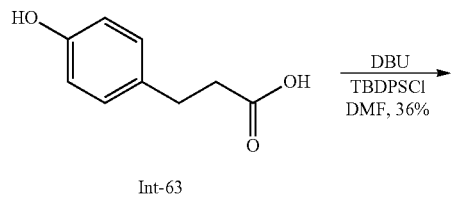

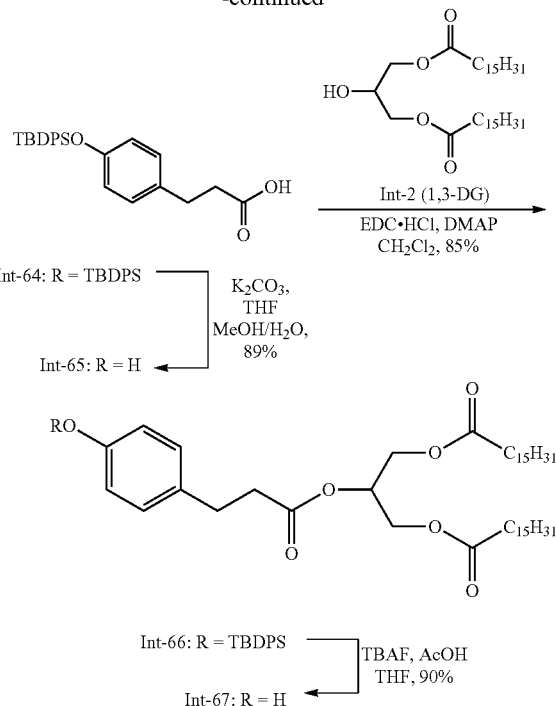

DBU (108 μL, 1.08 mmol) and t-butyldiphenylsilyl chloride (TBDPSCl, 338 μL, 1.30 mmol) were added to a solution of (4-hydroxyphenyl)propionic acid (Int-63; commercially available) (120 mg, 0.722 mmol) in DMF (4 mL) and the mixture stirred at room temperature for one hour. The reaction was diluted with ethyl acetate (15 mL) and organic phase washed with water and brine (15 mL each), dried (MgSO$_4$) and concentrated under reduced pressure to give the crude product. Silica gel chromatography (4.5% ethyl acetate/hexanes) gave silyl ester Int-64 (165 mg, 36%) as a colorless oil. $^1$H NMR (400 MHz, CDCl$_3$): δ 7.75-7.70 (m, 4H), 7.63-7.58 (m, 4H), 7.46-7.31 (m, 12H), 6.97-6.91 (m, 2H), 6.71-6.67 (m, 2H), 2.87 (t, J=7.6 Hz, 2H), 2.72 (t, J=7.6 Hz, 2H), 1.11 (s, 9H), 1.07 (s, 9H); $^{13}$C NMR (101 MHz, CDCl$_3$): δ 172.3 (C), 154.1 (C), 135.7 (4C; CH), 135.4 (4C; CH), 133.2 (2C; C), 133.0 (C), 132.0 (2C; C), 130.1 (2C; CH), 130.0 (2C; CH), 129.2 (2C; CH), 127.9 (4C; CH), 127.8 (4C; CH), 119.7 (2C; CH), 37.9 (CH$_2$), 30.4 (CH$_2$), 27.0 (3C; CH$_3$), 26.7 (3C; CH$_3$), 19.6 (C), 19.2 (C).

Potassium carbonate (157 mg, 1.14 mmol) was added to a solution of TBDPS ester Int-64 (147 mg, 0.228 mmol) in THF (3 mL), methanol (1.5 mL) and water (1.5 mmol) and the mixture stirred at room temperature for 2.5 hours. The reaction was acidified to pH 2 by the addition of 1 M HCl and the aqueous layer extracted with ethyl acetate (3×15 mL). The combined organic extracts were washed with water (30 mL), sat. aq. NaHCO$_3$ (30 mL) and brine (30 mL), dried (MgSO$_4$) and concentrated under reduced pressure to give the crude product. Purification by silica gel chromatography (20% to 35% to 50% ethyl acetate/hexanes) gave acid Int-65 (82.4 mg, 89%) as a colorless solid. $^1$H NMR (400 MHz, CDCl$_3$) δ 7.74-7.67 (m, 4H), 7.45-7.32 (m, 6H), 6.95-6.88 (m, 2H), 6.71-6.65 (m, 2H), 2.82 (t, J=7.8 Hz, 2H), 2.58 (t, J=7.8 Hz, 2H), 1.09 (s, 9H); $^{13}$C NMR (101 MHz, CDCl$_3$): δ 179.2 (C), 154.3 (C), 135.7 (4C; CH), 133.1 (2C; C), 132.7 (C), 130.0 (2C; CH), 129.1 (2C; CH), 127.9 (4C; CH), 119.8 (2C; CH), 35.9 (CH$_2$), 29.9 (CH$_2$), 26.7 (3C; CH$_3$), 19.6 (C).

DMAP (8.2 mg, 0.0667 mmol), EDC.HCl (25.6 mg, 0.133 mmol) and 1,3-diglyceride Int-2 (41.7 mg, 0.0734 mmol) were added to a solution of acid Int-65 (27.0 mg, 0.0666 mmol) in CH$_2$Cl$_2$ (2 mL) and the mixture stirred at room temperature for 19 hours. The reaction was diluted with CH$_2$Cl$_2$ (3 mL), silica gel was added and the mixture concentrated under reduced pressure. Purification by silica gel chromatography (5% to 7.5% ethyl acetate/hexanes) gave triglyceride Int-66 (54.4 mg, 85%) as a colorless solid. $^1$H NMR (400 MHz, CDCl$_3$) δ 7.74-7.66 (m, 4H), 7.45-7.33 (m, 6H), 6.94-6.87 (m, 2H), 6.71-6.64 (m, 2H), 5.24 (m, 1H), 4.25 (dd, J=11.9, 4.3 Hz, 2H), 4.11 (dd, J=11.9, 5.9 Hz, 2H), 2.81 (t, J=7.8 Hz, 2H), 2.60-2.51 (m, 2H), 2.28 (t, j=7.5 Hz, 4H), 1.64-1.56 (m, 4H), 1.35-1.20 (m, 48H), 1.09 (s, 9H), 0.88 (t, j=6.8 Hz, 6H); $^{13}$C NMR (101 MHz, CDCl$_3$) δ 173.4 (2C; C), 172.2 (C), 154.2 (C), 135.7 (4C; CH), 133.1 (2C; C), 132.7 (C), 130.0 (2C; CH), 129.1 (2C; CH), 127.9 (4C; CH), 119.8 (2C; CH), 69.2 (CH), 62.1 (2C; CH$_2$), 36.0 (CH$_2$), 34.2 (2C; CH$_2$), 32.1 (2C; CH$_2$), 30.1 (CH$_2$), 29.85 (2C; CH$_2$), 29.81 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.7 (3C; CH$_3$), 25.0 (2C; CH$_2$), 22.8 (2C; CH$_2$), 19.6 (C), 14.3 (2C; CH$_3$).

Acetic acid (6.5 μL, 0.114 mmol) and tetrabutylammonium fluoride (TBAF, 1.0 M in THF, 114 μL, 0.114 mmol) were added to a solution of TBDPS ether Int-66 (54.5 mg, 0.0570 mmol) in THF (1.2 mL) at 0° C. and the mixture stirred at room temperature for 30 minutes. The reaction was diluted with water (10 mL) and the aqueous layer extracted with ethyl acetate (3×10 mL). The combined organic extracts were washed with sat. aq. NaHCO$_3$ (20 mL) and brine (20 mL), dried (MgSO$_4$) and concentrated under reduced pressure to give the crude product. Purification by silica gel chromatography (10% to 15% ethyl acetate/hexanes) gave phenol Int-67 (37.0 mg, 90%) as a colorless solid. $^1$H NMR (400 MHz, CDCl$_3$) δ 7.09-7.03 (m, 2H), 6.78-6.72 (m, 2H), 5.25 (m, 1H), 4.62 (s, 1H), 4.25 (dd, j=11.9, 4.4 Hz, 2H), 4.11 (dd, j=11.9, 5.8 Hz, 2H), 2.88 (t, J=7.7 Hz, 2H), 2.61 (t, J=7.7 Hz, 2H), 2.29 (t, J=7.6 Hz, 4H), 1.64-1.56 (m, 4H), 1.34-1.18 (m, 48H), 0.88 (t, J=6.9 Hz, 6H); $^{13}$C NMR (101 MHz, CDCl$_3$) δ 173.6 (2C; C), 172.3 (C), 154.4 (C), 132.3 (C), 129.5 (2C; CH), 115.5 (2C; CH), 69.2 (CH), 62.2 (2C; CH$_2$), 36.2 (CH$_2$), 34.2 (2C; CH$_2$), 32.1 (2C; CH$_2$), 30.2 (CH$_2$), 29.83 (6C; CH$_2$), 29.79 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 25.0 (2C; CH$_2$), 22.8 (2C; CH$_2$), 14.3 (2C; CH$_3$).

C6-ET-alcohol-2-TG (Int-73):

Scheme 22. Synthesis of Int-73.

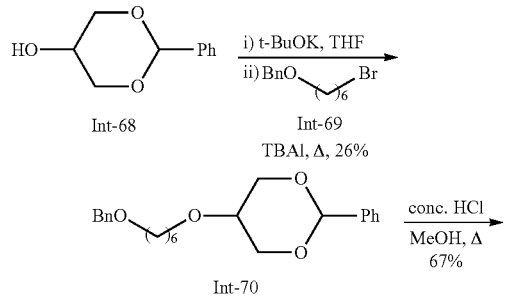

Int-69 is a known compound that may be prepared as described in, e.g., Sang-sup, J. et al. *Tetrahedron: Asymmetry* 1997, 8, 1187-1192).

Alcohol Int-68 (commercially available; 90.0 mg, 0.499 mmol) was added in a single portion to a suspension of t-BuOK (84.1 mg, 0.749 mmol) in THF (2 mL) and the mixture stirred at room temperature for one hour. A solution of bromide Int-69 (190 mg, 0.699 mmol) in THF (1 mL) and TBAI (36.9 mg, 0.100 mmol) were then added and the resulting mixture heated at reflux for 20 hours. The reaction was cooled to room temperature and diluted with ethyl acetate (10 mL), quenched with water (15 mL) and the aqueous phase extracted with ethyl acetate (3×20 mL). The combined organic extracts were washed with water and brine (50 mL each), dried (MgSO$_4$) and concentrated under reduced pressure to give the crude product. Silica gel chromatography (5 to 15% to 25% ethyl acetate/hexanes) gave a sample of semi-pure product, which was re-subjected to column chromatography (5% to 12.5% ethyl acetate/toluene) to give ether-linked glycerol Int-70 (48.0 mg, 26%) as a colorless oil. $^1$H NMR (400 MHz, CDCl$_3$): δ 7.54-7.49 (m, 2H), 7.39-7.26 (m, 8H), 5.55 (s, 1H), 4.50 (s, 2H), 4.33 (dd, J=12.5, 1.4 Hz, 2H), 4.07-4.01 (m, 2H), 3.55 (t, J=6.7 Hz, 2H), 3.47 (t, J=6.6 Hz, 2H), 3.25 (m, 1H), 1.71-1.59 (m, 4H), 1.45-1.39 (m, 4H).

A mixture of benzylidene acetal Int-70 (46.0 mg, 0.124 mmol), conc. HCl (2 drops) and MeOH (1.5 mL) was heated at reflux for two hours and then cooled to room temperature. The reaction was diluted with ethyl acetate (30 mL) and water (10 mL), and the organic phase washed sat. aq. NaHCO$_3$, water and brine (30 mL each), dried (MgSO$_4$) and concentrated under reduced pressure to give the crude product. Silica gel chromatography (40% to 80% ethyl acetate/hexanes) gave diol Int-71 (23.5 mg, 67%) as a colorless oil. $^1$H NMR (400 MHz, CDCl$_3$): δ 7.36-7.27 (m, 5H), 4.50 (s, 2H), 3.76 (dd, J=11.6, 4.4 Hz, 2H), 3.67 (dd, J=11.6, 5.1 Hz, 2H), 3.57 (t, J=6.6 Hz, 2H), 3.50-3.42 (m, 3H), 1.67-1.56 (m, 4H), 1.43-1.36 (m, 4H).

A solution of freshly-prepared palmitoyl chloride (91.6 mg, 0.333 mmol) in CH$_2$Cl$_2$ (1.5 mL) and pyridine (30.3 μL, 0.375 mmol) were added to the diol Int-71 (23.5 mg, 0.0833 mmol) and the reaction stirred at room temperature for 16 hours. The reaction mixture was diluted with CH$_2$Cl$_2$ (30 mL) and quenched with water (10 mL). The organic phase was washed with water, sat. aq. NaHCO$_3$ and brine (30 mL each), dried (MgSO$_4$) and concentrated under reduced pres-

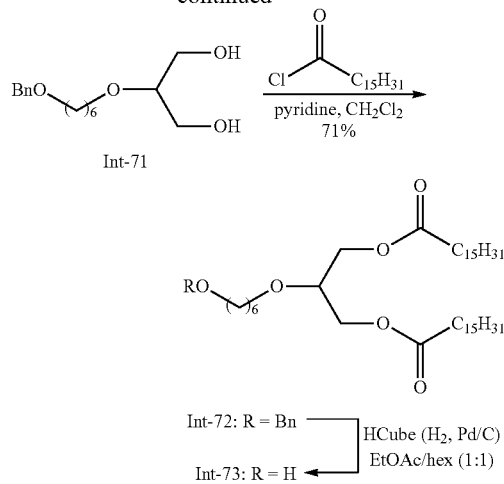

Int-72: R = Bn
Int-73: R = H
HCube (H$_2$, Pd/C)
EtOAc/hex (1:1)

sure to give the crude product. Silica gel chromatography (5% to 10% ethyl acetate/hexanes) gave glyceride Int-72 (44.8 mg, 71%) as a colorless solid. $^1$H NMR (400 MHz, CDCl$_3$): δ 7.36-7.26 (m, 5H), 4.50 (s, 2H), 4.18 (dd, J=11.6, 4.9 Hz, 2H), 4.11 (dd, J=11.6, 5.5 Hz, 2H), 3.68 (dd, J=10.4, 5.3 Hz, 1H), 3.55 (t, J=6.6 Hz, 2H), 3.46 (t, J=6.6 Hz, 2H), 2.32 (t, J=7.6 Hz, 4H), 1.67-1.54 (m, 8H), 1.34-1.21 (m, 52H), 0.88 (t, J=6.9 Hz, 6H); $^{13}$C NMR (100 MHz, CDCl$_3$): δ 173.7 (2C; C), 138.8 (C), 128.5 (2C; CH), 127.7 (2C; CH), 127.6 (CH), 75.3 (CH), 73.0 (CH$_2$), 70.7 (CH$_2$), 70.5 (CH$_2$), 63.2 (2C; CH$_2$), 34.3 (2C; CH$_2$), 32.1 (2C; CH$_2$), 30.0 (CH$_2$), 29.87 (CH$_2$), 29.84 (2C; CH$_2$), 29.80 (2C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.2 (CH$_2$), 26.0 (CH$_2$), 25.1 (2C; CH$_2$), 22.8 (2C; CH$_2$), 14.3 (2C; CH$_3$).

A solution of benzyl ether Int-72 (43.5 mg, 57.3 μmol) in ethyl acetate/hexanes (10 mL each) was subjected to hydrogenolysis using an HCube hydrogenation apparatus under recycling conditions (10% Pd/C cartridge, full H$_2$ mode at 6 bar, flow rate=1 mL/min), with the column temperature set at 25° C. for 1.5 hours then at 35° C. for a further hour. Concentration of the reaction mixture under reduced pressure gave alcohol Int-73 (38.2 mg, quant.) as a colorless solid that was used without purification. $^1$H NMR (400 MHz, CDCl$_3$): § 4.19 (dd, J=11.6, 4.9 Hz, 2H), 4.11 (dd, J=11.6, 5.5 Hz, 2H), 3.67 (m, 1H), 3.64 (t, J=6.5 Hz, 2H), 3.55 (t, J=6.5 Hz, 2H), 2.32 (t, J=7.6 Hz, 4H), 1.66-1.56 (m, 8H), 1.41-1.34 (m, 4H), 1.33-1.18 (m, 48H), 0.88 (t, J=6.8 Hz, 6H).

C4-ET-alcohol-2-TG (Int-78):

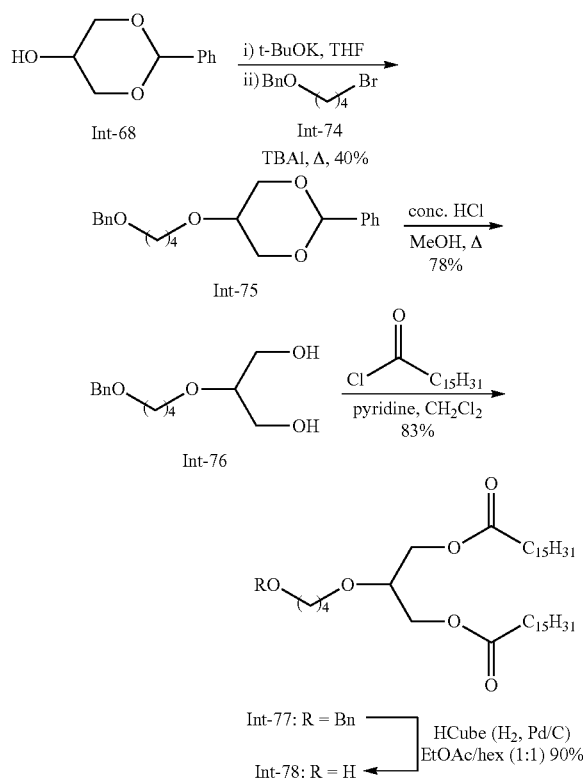

Scheme 23. Synthesis of Int-78.

Int-74 is a known compound that may be prepared as described in Charette, A. B. et al. *J. Am. Chem. Soc.* 2001, 123, 11829-11830.

Alcohol Int-68 (commercially available; 135 mg, 0.749 mmol) was added in a single portion to a suspension of t-BuOK (118 mg, 1.05 mmol) in THF (2.5 mL) and the mixture stirred at RT for one hour. A solution of bromide Int-74 (273 mg, 1.12 mmol) in THF (2 mL) was then added and the resulting mixture heated at reflux for 26 hours. The reaction was cooled to room temperature and diluted with ethyl acetate (10 mL), quenched with water (20 mL) and the aqueous phase extracted with ethyl acetate (3×25 mL). The combined organic extracts were washed with water and brine (60 mL each), dried (MgSO$_4$) and concentrated under reduced pressure to give the crude product. Silica gel chromatography (10% to 20% ethyl acetate/hexanes) gave ether-linked glycerol Int-75 (103 mg, 40%) as a colorless oil. $^1$H NMR (400 MHz, CDCl$_3$): δ 7.53-7.48 (m, 2H), 7.38-7.27 (m, 8H), 5.55 (s, 1H), 4.50 (s, 2H), 4.37-4.27 (m, 2H), 4.08-3.98 (m, 2H), 3.61-3.55 (m, 2H), 3.54-3.50 (m, 2H), 3.25 (m, 1H), 1.82-1.65 (m, 4H); $^{13}$C NMR (100 MHz, CDCl$_3$): δ 138.8 (C), 138.3 (C), 128.9 (CH), 128.4 (2C; CH), 128.3 (2C; CH), 127.7 (2C; CH), 127.6 (CH), 126.3 (2C; CH), 101.4 (C), 73.0 (CH$_2$), 70.7 (CH), 70.3 (CH$_2$), 69.1 (2C; CH$_2$), 68.7 (CH$_2$), 26.7 (CH$_2$), 26.6 (CH$_2$).

A mixture of benzylidene acetal Int-75 (102 mg, 0.298 mmol), conc. HCl (2 drops) and MeOH (4 mL) was heated at reflux for two hours and then cooled to RT. The reaction was diluted with ethyl acetate (40 mL) and water (15 mL), and the organic phase washed sat. aq. NaHCO$_3$, water and brine (40 mL each), dried (MgSO$_4$) and concentrated under reduced pressure to give the crude product. Silica gel chromatography (25% to 65% to 90% ethyl acetate/hexanes) gave diol Int-76 (58.8 mg, 78%) as a colorless oil. $^1$H NMR (400 MHz, CDCl$_3$): δ 7.38-7.24 (m, 5H), 4.50 (s, 2H), 3.71 (dd, J=11.6, 4.6 Hz, 2H), 3.64 (dd, J=11.6, 4.9 Hz, 2H), 3.60-3.55 (m, 2H), 3.52-3.46 (m, 2H), 3.41 (m, 1H), 2.59 (br s, 2H), 1.75-1.61 (m, 4H); $^{13}$C NMR (100 MHz, CDCl$_3$): δ 138.5 (C), 128.5 (2C; CH), 127.8 (2C; CH), 127.7 (CH), 78.8 (CH), 73.0 (CH$_2$), 70.2 (CH$_2$), 69.8 (CH$_2$), 62.2 (2C; CH$_2$), 27.1 (CH$_2$), 26.4 (CH$_2$).

A solution of palmitoyl chloride (131 mg, 0.475 mmol) in CH$_2$Cl$_2$ (2 mL) and pyridine (48.0 μL, 0.594 mmol) were added to the diol Int-76 (30.2 mg, 0.119 mmol) and the reaction stirred at room temperature for 19 hours. The reaction mixture was diluted with CH$_2$Cl$_2$ (40 mL) and quenched with water (20 mL). The organic phase was washed with water, sat. aq. NaHCO$_3$ and brine (40 mL each), dried (MgSO$_4$) and concentrated under reduced pressure to give the crude product. Silica gel chromatography (6% ethyl acetate/hexanes) gave triglyceride Int-77 (72.4 mg, 83%) as a colorless solid. $^1$H NMR (400 MHz, CDCl$_3$): δ 7.38-7.26 (m, 5H), 4.50 (s, 2H), 4.18 (dd, J=11.6, 4.9 Hz, 2H), 4.11 (dd, J=11.6, 5.5 Hz, 2H), 3.67 (m, 1H), 3.58 (t, J=6.1 Hz, 2H), 3.48 (t, J=6.1 Hz, 2H), 2.31 (t, J=7.6 Hz, 4H), 1.73-1.55 (m, 8H), 1.37-1.19 (m, 48H), 0.88 (t, J=6.9 Hz, 6H); $^{13}$C NMR (100 MHz, CDCl$_3$): δ 173.7 (2C; C), 138.7 (C), 128.5 (2C; CH), 127.7 (2C; CH), 127.6 (CH), 75.4 (CH), 73.0 (CH$_2$), 70.4 (CH$_2$), 70.2 (CH$_2$), 63.1 (2C; CH$_2$), 34.3 (2C; CH$_2$), 32.1 (2C; CH$_2$), 29.82 (6C; CH$_2$), 29.79 (4C; CH$_2$), 29.74 (2C; CH$_2$), 29.6 (2C; CH$_2$), 29.5 (2C; CH$_2$), 29.4 (2C; H2), 29.3 (2C; CH$_2$), 26.8 (CH$_2$), 26.5 (CH$_2$), 25.0 (2C; CH$_2$), 22.8 (2C; CH$_2$), 14.2 (2C; CH$_3$).

A solution of benzyl ether Int-77 (70.0 mg, 95.8 µmol) in ethyl acetate/hexanes (25 mL each) was subjected to hydrogenolysis using an HCube hydrogenation apparatus under recycling conditions (10% Pd/C cartridge, full $H_2$ mode at 6 bar, flow rate=1 mL/min), with the column temperature set at 50° C. for 2.5 hours. Concentration of the reaction mixture under reduced pressure gave the crude product, which was purified by silica gel chromatography (10% to 30% ethyl acetate/hexanes) to give alcohol Int-78 (55.0 mg, 90%) as a colorless solid. $^1$H NMR (400 MHz, $CDCl_3$): δ 4.20 (dd, J=11.7, 4.8 Hz, 2H), 4.11 (dd, J=11.7, 5.5 Hz, 2H), 3.69 (m, 1H), 3.64 (t, J=5.9 Hz, 2H), 3.60 (t, J=5.8 Hz, 2H), 2.32 (t, J=7.5 Hz, 4H), 1.70-1.55 (m, 8H), 1.33-1.19 (m, 48H), 0.87 (t, J=6.8 Hz, 6H); $^{13}$C NMR (100 MHz, $CDCl_3$): δ 173.7 (2C; C), 75.5 (CH), 70.5 ($CH_2$), 63.0 (2C; $CH_2$), 62.6 ($CH_2$), 34.3 (2C; $CH_2$), 32.0 (2C; $CH_2$), 29.9 ($CH_2$), 29.82 (2C; $CH_2$), 29.78 (2C; $CH_2$), 29.7 (2C; $CH_2$), 29.6 (2C; $CH_2$), 29.5 (2C; $CH_2$), 29.4 (2C; $CH_2$), 29.3 (2C; $CH_2$), 26.7 ($CH_2$), 25.0 (2C; $CH_2$), 22.8 (2C; $CH_2$), 14.2 (2C; $CH_3$).

C5ββDiMe-acid-2-TG (Int-79):

Scheme 24. Synthesis of Int-79.

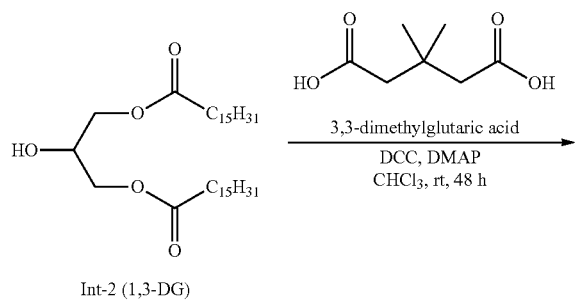

Int-2 (1,3-DG)

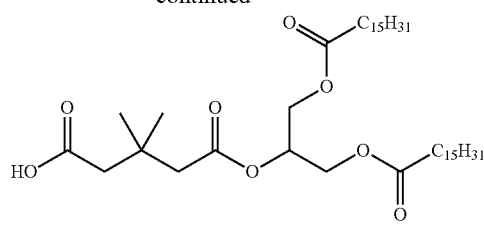

Int-79 (C5ββDiMe-acid-2-TG)

To a solution of compound Int-2 (5.0 g, 8.78 mmol) in chloroform (150 ml) was added DCC (3.62 g, 17.57 mmol) and DMAP (0.53 g, 4.39 mmol), followed by addition of 3,3-dimethylglutaric acid (2.81 g, 17.57 mmol) at room temperature and then stirring for 48h. The reaction was monitored by TLC. After completion of the reaction, the reaction mixture was filtered through a celite bed and washed with dichloromethane (100 ml) and the filtrate was evaporated to give the crude desired compound, which was purified by combi-flash purification. The compound was eluted using 6% ethyl acetate in hexane and concentrated to give Int-79 (C5ββDiMe-acid-2-TG) (2.0 g, 32%) as off-white solid. $^1$H NMR (400 MHz, $CDCl_3$) δ 5.33 (m, 1H), 4.33 (m, 2H), 4.18 (m, 2H), 2.51 (s, 4H), 2.35 (t, 4H), 1.64 (t, 4H), 1.29 (m, 49H), 1.19 (s, 6H), 0.92 (t, 6H); $^{13}$C NMR (101 MHz, $CDCl_3$) δ 176.4 (1C), 173.3 (2C), 171.0 (1C), 69.1 (1C), 62.1 (2C), 45.0 (1C) 44.7 (1C), 34.0 (3C), 32.6 (1C), 31.9 (3H), 29.7-29.1 (14C), 27.7 (3C), 24.8 (3C), 22.7 (3C), 14.1 (3C); HPLC (ELSD): 10.07 mm, 97.74% purity; MASS (ESI, -ve) m/z: 710 (M-1).

C12a'aMe-acid-2-TG (Int-81):

Scheme 25. Synthesis of Int-81.

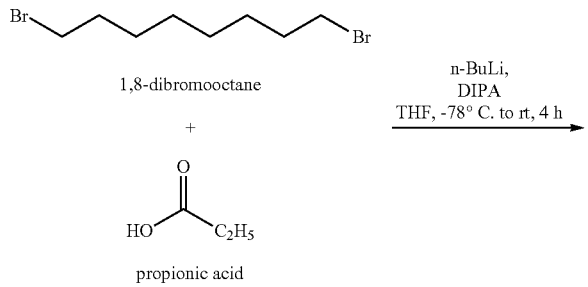

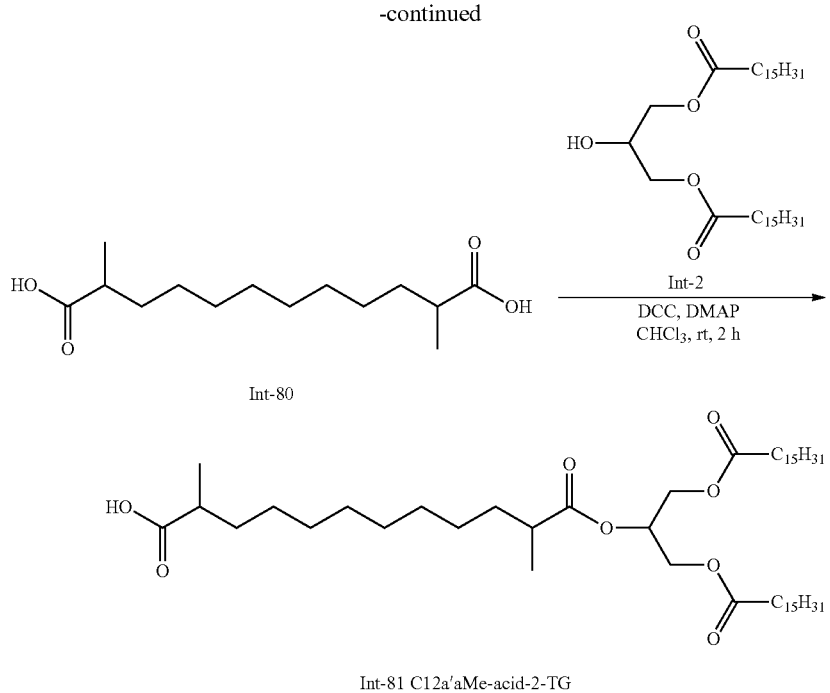

Int-80

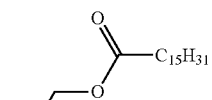

Int-81 C12a'aMe-acid-2-TG

To a solution of diisopropylamine (DIPA) (3.18 g, 81.08 mmol) in dry THF (45 mL) was added n-BuLi (2.5 M in hexane) (32 mL, 81.08 mmol) at −78° C. The reaction mixture was stirred at −78° C. for 30 min, then propionic acid (1.5 g, 20.27 mmol) was added and the reaction mixture was stirred at −78° C. for further 30 min. 1,8-dibromooctane (2.75 g, 10.13 mmol) was added and the reaction mixture was stirred and allowed to warm from −78° C. to room temperature over 3h. The reaction was monitored by TLC for completeness. An additional identical batch starting with 1.5 g propionic acid was prepared and the two batches combined before workup. The combined reaction mixture was diluted with water (100 mL) and acidified with 1N HCl (25 ml) and extracted with ethyl acetate (3×100 ml), and the combined organic layer was dried over $Na_2SO_4$ and evaporated to give crude compound. The title compound was purified by combi flash purification, eluting with 10% ethyl acetate/hexane as the mobile phase. After evaporation, Int-80 (0.99 g, 9.5%) was obtained as an off-white solid. $^1$H NMR (400 MHz, $CDCl_3$) δ 2.57-2.39 (m, 2H), 1.71 (m, 2H), 1.50-1.43 (m, 2H), 1.40-1.25 (m, 14H), 1.22 (d, J=12 Hz 6H).

To a solution of compound Int-2 (2.7 g, 4.74 mmol) in chloroform (50 ml) was added DCC (1.95 g, 9.49 mmol) and DMAP (0.28 g, 2.30 mmol), then the reaction was stirred at room temperature for 30 min. Int-80 (2.44 g, 9.49 mmol) was added at room temperature and stirred for 2h. The reaction was monitored by TLC until completion, after which the reaction mixture was filtered through celite and washed with DCM (45 ml), then evaporated to give the crude product, which was purified by combi flash purification, eluting with 7% ethyl acetate/hexane. After evaporation, Int-81 (C12a'aMe-acid-2-TG) (1.7 g, 44.3%) was obtained as an off-white solid. $^1$H NMR (400 MHz, $CDCl_3$) δ 5.32 (m, 1H), 4.33 (m, 2H), 4.19 (m, 2H), 2.49 (m, 2H), 2.34 (m, 4H), 1.72-1.62 (m, 4H), 1.49-1.40 (m, 4H), 1.38-1.29 (m, 59H), 1.24-1.17 (m, 8H), 0.92 (m, 6H); $^{13}$C NMR (101 MHz, $CDCl_3$) δ 181.7 (1C), 176.0 (1C), 173.4 (2C), 68.7 (2C), 62.2 (3C), 39.6 (2C), 39.2 (1C), 34.1 (3C), 33.7 (1C), 32.0 (3C), 29.7-29.2 (17C), 27.2 (1C), 24.9 (3C), 22.7 (3C), 17.1 (2C), 16.9 (1C), 14.2 (3C).

Scheme 26. Synthesis of Int-91.

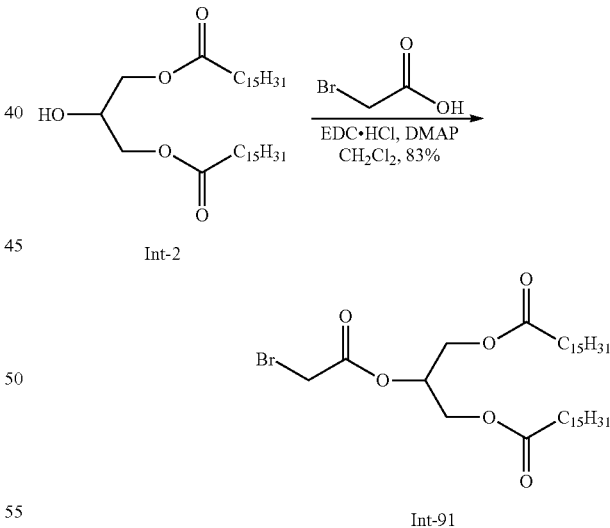

Int-91

Bromotriglyceride Int-91:

DMAP (10.7 mg, 0.0979 mmol) and EDC.HCl (41.8 mg, 0.220 mmol) were added to a solution of bromoacetic acid (24.4 mg, 0.176 mmol) and Int-2 (50.0 mg, 0.0879 mmol) in $CH_2Cl_2$ (2 mL) and the mixture stirred at RT for 22 hours. The reaction was diluted with $CH_2Cl_2$ (5 mL), silica gel was added, and the solvent removed under reduced pressure. Silica gel chromatography (4% ethyl acetate/hexanes) gave bromotriglyceride Int-91 (50.3 mg, 83%) as a colorless solid. $^1$H NMR (400 MHz, $CDCl_3$) δ 5.31 (m, 1H), 4.34 (dd, J=12.1, 4.0 Hz, 2H), 4.17 (dd, J=12.1, 6.1 Hz, 2H), 3.84 (s, 2H), 2.32 (t, J=7.6 Hz, 4H), 1.66-1.56 (m, 4H), 1.35-1.20 (m, 48H), 0.88 (t, J=6.9 Hz, 6H); $^{13}$C NMR (101 MHz, CDCl$_3$) δ 173.4 (2C; C), 166.7 (C), 71.3 (CH), 61.9 (2C; CH$_2$), 34.1 (2C; CH$_2$), 32.1 (2C; CH$_2$), 29.84 (2C; CH$_2$), 29.80 (2C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 25.5 (CH$_2$), 25.0 (2C; CH$_2$), 22.8 (2C; CH$_2$), 14.3 (2C; CH$_2$).

Iodotriglyceride Int-95:

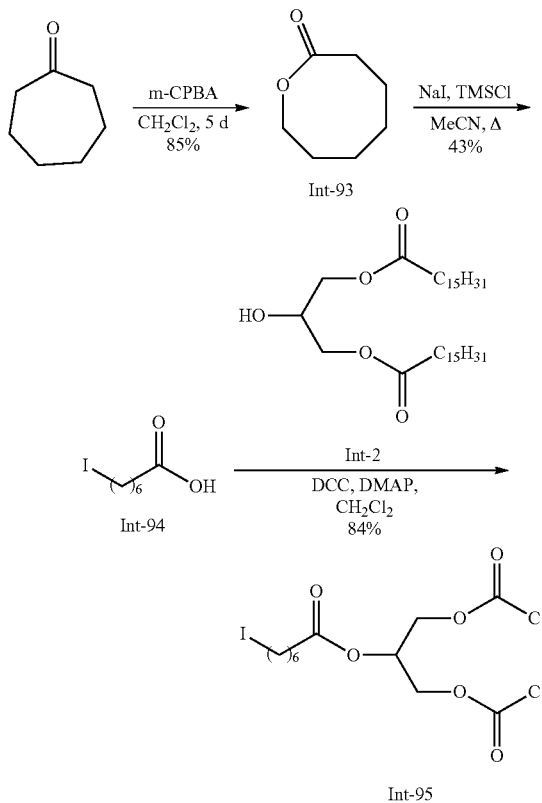

Int-93 is a known compound prepared from cycloheptanone as shown above (see Kai, K. et al. *Tetrahedron* 2008, 64, 6760-6769). To prepare Int-94, chlorotrimethylsilane (TMSCl, 208 μL, 1.64 mmol) was added to a suspension of lactone Int-93 (70.0 mg, 0.546 mmol) and sodium iodide (246 mg, 1.64 mmol) in acetonitrile (1.5 mL) and the mixture heated at reflux for 16 hours. The reaction was cooled to RT, diluted with ethyl acetate and water (10 mL each), and extracted with ethyl acetate (3×15 ml). The combined organic extracts were washed with 1 M Na$_2$S$_2$O$_3$ and brine (40 mL each), dried (MgSO$_4$) and concentrated under reduced pressure to give the crude product. Silica gel chromatography (100% CH$_2$Cl$_2$ to 50% ethyl acetate/hexanes) gave semi-pure acid Int-94 (59.8 mg, 43%) as a yellow oil. However, an accurate yield and clean NMR spectra could not be obtained due to the presence of the m-CPBA impurities, which were carried forward to the next step. $^1$H NMR (400 MHz, CDCl$_3$) δ 3.19 (t, J=7.0 Hz, 2H), 2.37 (t, J=7.4 Hz, 2H), 1.88-1.80 (m, 2H), 1.71-1.61 (m, 2H), 1.46-1.33 (m, 4H).

DMAP (15.2 mg, 0.124 mmol) and DCC (51.3 mg, 0.248 mmol) were added sequentially to a solution of acid Int-94 (35.0 mg, 0.137 mmol) and 1,3-diglyceride Int-2 (70.7 mg, 0.124 mmol) in CH$_2$Cl$_2$ (4 mL) and the mixture stirred at RT for 17 hours. The resulting suspension was diluted with CH$_2$Cl$_2$, cooled to 0° C. and filtered through Celite, washing with further CH$_2$Cl$_2$. The organic phase was washed with 1 M HCl, sat. aq. NaHCO$_3$ and brine, dried (MgSO$_4$) and concentrated under reduced pressure to give the crude product. Silica gel chromatography (3.5% to 4.5% ethyl acetate/hexanes) gave semi-pure iodotriglyceride Int-95 (83.6 mg, 84%) as a colorless solid. However, an accurate yield and clean NMR spectra could not be obtained due to the presence of the m-CPBA impurities, which were carried forward to the next step. $^1$H NMR (400 MHz, CDCl$_3$) δ 5.26 (m, 1H), 4.30 (dd, J=11.9, 4.4 Hz, 2H), 4.14 (dd, J=11.9, 5.9 Hz, 2H), 3.18 (t, J=7.0 Hz, 2H), 2.36-2.27 (m, 6H), 1.86-1.77 (m, 2H), 1.68-1.52 (m, 6H), 1.45-1.18 (m, 52H), 0.88 (t, J=6.9 Hz, 6H).

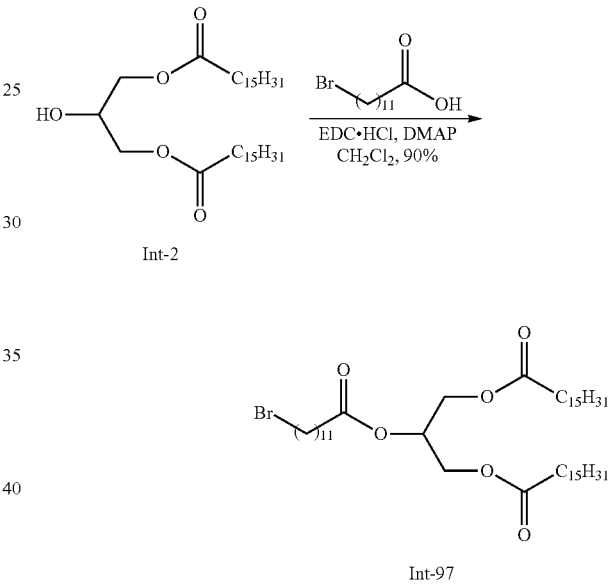

DMAP (17.2 mg, 0.141 mmol) and EDC.HCl (67.4 mg, 0.352 mmol) were added to a solution of 1,3-diglyceride Int-2 (80.0 mg, 0.141 mmol) and 12-bromododecanoic acid (51.0 mg, 0.183 mmol) in CH$_2$Cl$_2$ (2.5 mL) and the mixture stirred at RT for 18 hours. The reaction was diluted with CH$_2$Cl$_2$ (10 mL), silica gel was added, and the mixture concentrated under reduced pressure. Purification by silica gel chromatography (5% to 10% ethyl acetate/hexanes) gave bromotriglyceride Int-97 (105 mg, 90%) as a colorless solid. $^1$H NMR (401 MHz, CDCl$_3$) δ 5.25 (m, 1H), 4.28 (dd, J=11.9, 4.3 Hz, 2H), 4.13 (dd, J=11.9, 5.9 Hz, 2H), 3.38 (t, J=6.9 Hz, 2H), 2.30 (t, J=7.5 Hz, 2H), 2.29 (t, J=7.5 Hz, 4H), 1.88-1.79 (m, 2H), 1.65-1.55 (m, 6H), 1.45-1.36 (m, 2H), 1.34-1.18 (m, 60H), 0.86 (t, J=6.8 Hz, 6H); $^{13}$C NMR (101 MHz, CDCl$_3$) δ 173.4 (2C; C), 172.9 (C), 69.0 (CH), 62.2 (2C; CH$_2$), 34.3 (CH$_2$), 34.2 (2C; CH$_2$), 34.0 (CH$_2$), 33.0 (CH$_2$), 32.1 (2C; CH$_2$), 29.82 (6C; CH$_2$), 29.78 (4C; CH$_2$), 29.74 (2C; CH$_2$), 29.60 (3C; CH$_2$), 29.54 (2C; CH$_2$), 29.48 (2C; CH$_2$), 29.39 (2C; CH$_2$), 29.38 (CH$_2$), 29.23 (2C; CH$_2$), 29.17 (CH$_2$), 28.9 (CH$_2$), 28.3 (CH$_2$), 25.0 (2C; CH$_2$), 22.8 (2C; CH$_2$), 14.2 (2C; CH$_3$).

Int-105:

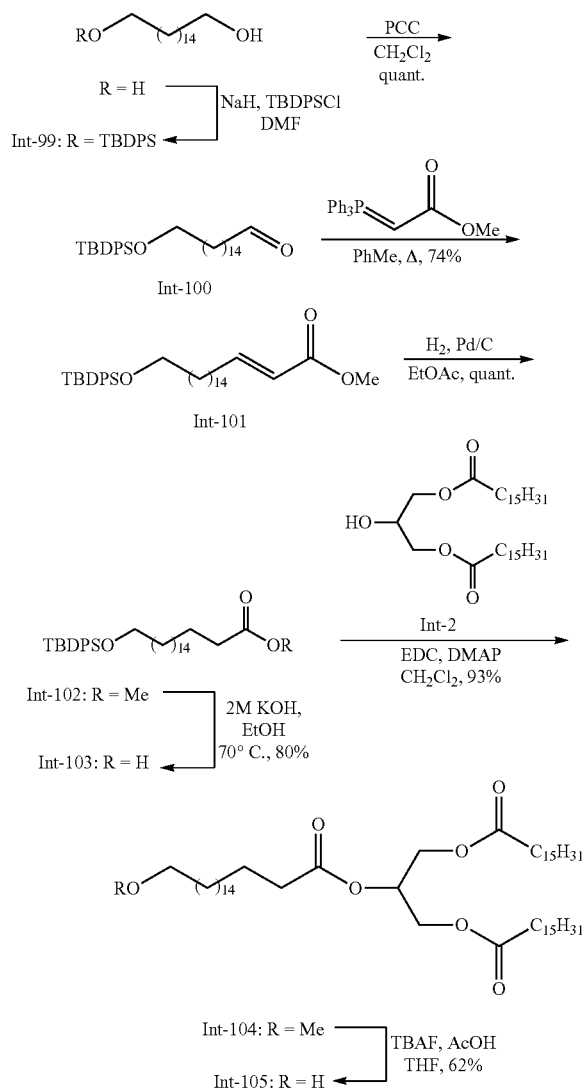

Scheme 29. Synthesis of Int-105.

Int-99:
A suspension of 1,16-hexanediol (200 mg, 0.774 mmol) in DMF (2 mL) was added a suspension of NaH (34.1 mg, 60% w/w dispersion in mineral oil, washed twice with dry petrol, 8.51 mmol) in DMF (1 mL) at 0° C. and the mixture stirred at 0° C. for 10 minutes and then at rt for 30 minutes. TBDPSCl (221 µL, 0.851 mmol) was added and the mixture stirred at rt for 17 hours. The reaction was diluted with ethyl acetate (50 mL), washed with water and brine (2×40 mL each), dried (MgSO$_4$) and concentrated under reduced pressure to give the crude product. Silica gel chromatography (15% ethyl acetate/hexanes) gave TBDPS ether Int-99 (124 mg, 32%) as a colorless solid. $^1$H NMR (401 MHz, CDCl$_3$) δ 7.70-7.63 (m, 4H), 7.45-7.34 (m, 6H), 3.64 (td, J=6.5, 3.6 Hz, 4H), 1.61-1.46 (m, 4H), 1.39-1.19 (m, 24H), 1.04 (s, 9H).

Int-100:
Pyridinium chlorochromate (PCC, 106 mg, 0.491 mmol) and Celite (100 mg) were added to alcohol Int-99 (122 mg, 0.246 mmol) in CH$_2$Cl$_2$ (6 mL) at 0° C. and the mixture stirred at 0° C. for 10 minutes and then at rt for 1.5 hours. The reaction was filtered through a short pad of silica gel, eluting with 50% ethyl acetate/hexanes (80 mL), and the filtrate concentrated under reduced pressure to give crude aldehyde Int-100 (121 mg, quant.) as a yellow oil that was immediately used without purification.

Int-101:
Ylide methyl 2-(triphenyl-λ$^5$-phosphaneylidene)acetate (205 mg, 0.614 mmol) was added to crude aldehyde Int-100 (121 mg, 0.246 mmol) in toluene (6 mL) and the mixture heated at reflux for one hour. The reaction was cooled to rt and concentrated under reduced pressure to give the crude product. Purification by silica gel chromatography (4% ethyl acetate/hexanes) gave alpha,beta-unsaturated methyl ester Int-101 (100 mg, 74%, 6:1 mixture of F/Z isomers) as a yellow oil. NMR data is provided for the major isomer. $^1$H NMR (401 MHz, CDCl$_3$) δ 7.74-7.66 (m, 4H), 7.48-7.36 (m, 6H), 7.01 (dt, J=15.6, 7.0 Hz, 1H), 5.85 (dt, J=15.6, 1.5 Hz, 1H), 3.74 (s, 3H), 3.69 (t, J=6.5 Hz, 2H), 2.22 (qd, J=7.3, 1.5 Hz, 2H), 1.64-1.55 (m, 2H), 1.47 (dd, J=13.9, 6.9 Hz, 2H), 1.42-1.25 (m, 22H), 1.09 (s, 9H); $^{13}$C NMR (101 MHz, CDCl$_3$) δ 167.3 (C), 149.9 (CH), 135.7 (4C; CH), 134.3 (2C; C), 129.6 (2C; CH), 127.7 (4C; CH), 120.9 (CH), 64.1 (CH$_2$), 51.4 (CH$_3$), 32.7 (CH$_2$), 32.3 (CH$_2$), 29.79 (2C; CH$_2$), 29.75 (2C; CH$_2$), 29.74 (CH$_2$), 29.66 (CH$_2$), 29.52 (CH$_2$), 29.50 (CH$_2$), 29.3 (CH$_2$), 28.1 (CH$_2$), 27.0 (3C; CH$_2$), 25.9 (CH$_2$), 19.3 (C).

Int-102:
A solution of alkene Int-101 (99.0 mg, 0.180 mmol) in ethyl acetate (5 mL) in a two-neck flask was evacuated and flushed with N$_2$ gas three times each, then palladium on carbon (10% w/w, 28.7 mg, 0.0270 mmol) was added and the resulting suspension re-evacuated and flushed with N$_2$ three times. The flask was fitted with a H$_2$ balloon, evacuated and flushed with H$_2$ three times and the reaction mixture stirred at rt under 1 atm of H$_2$ for one hour. The reaction was filtered through a pad of Celite, washing with ethyl acetate (80 mL), and concentrated under reduced pressure to give saturated methyl ester Int-102 (99.4 mg, quant.) as a colorless oil that was used without purification. $^1$H NMR (401 MHz, CDCl$_3$) δ 7.75-7.67 (m, 4H), 7.47-7.36 (m, 6H), 3.69 (t, j=6.5 Hz, 2H), 3.68 (s, 3H), 2.33 (t, j=7.5 Hz, 2H), 1.70-1.54 (m, 4H), 1.43-1.23 (m, 26H), 1.09 (s, 9H); $^{13}$C NMR (101 MHz, CDCl$_3$) δ 174.4 (C), 135.7 (4C; CH), 134.3 (2C; C), 129.6 (2C; CH), 127.7 (4C; CH), 64.1 (CH$_2$), 51.5 (CH$_3$), 34.2 (CH$_2$), 32.7 (CH$_2$), 29.82 (2C; CH$_2$), 29.81 (2C; CH$_2$), 29.78 (CH$_2$), 29.76 (CH$_2$), 29.75 (CH$_2$), 29.73 (CH$_2$), 29.6 (CH$_2$), 29.5 (CH$_2$), 29.4 (CH$_2$), 29.3 (CH$_2$), 27.0 (3C; CH$_3$), 25.9 (CH$_2$), 25.1 (CH$_2$), 19.3 (C).

Int-103:
A solution of potassium hydroxide (2.0 M, 530 µL, 1.06 mmol) was added to ester Int-102 (26.0 mg. 0.0854 mmol) in ethanol (3 mL) and the mixture heated at 70° C. for 50 minutes. The reaction was acidified to pH 3 by addition of 1 M HCl and diluted with ethyl acetate (40 mL). The organic phase was washed with water (2×30 mL) and brine (30 mL), dried (MgSO$_4$) and concentrated under reduced pressure to give the crude product. Purification by silica gel chromatography (15% ethyl acetate/hexanes) gave acid Int-103 (76.8 mg, 80%) as a colorless oil. $^1$H NMR (401 MHz, CDCl$_3$) δ 7.73-7.67 (m, 4H), 7.44-7.37 (m, 6H), 3.68 (t, J=6.5 Hz, 2H), 2.37 (t, J=7.5 Hz, 2H), 1.70-1.53 (m, 4H), 1.41-1.23 (m, 26H), 1.07 (s, 9H); $^{13}$C NMR (101 MHz, CDCl$_3$) δ 180.4 (C), 135.7 (4C; CH), 134.3 (2C; C), 129.6 (2C; CH), 127.7 (4C; CH), 64.2 (CH$_2$), 34.2 (CH$_2$), 32.7 (CH$_2$), 29.83 (4C; CH$_2$), 29.81 (CH$_2$), 29.78 (2C; CH$_2$), 29.76 (CH$_2$), 29.6 (CH$_2$), 29.5 (CH$_2$), 29.4 (CH$_2$), 29.2 (CH$_2$), 27.0 (3C; CH$_3$), 25.9 (CH$_2$), 24.8 (CH$_2$), 19.4 (C).

Int-104:

DMAP (10.2 mg, 0.0839 mmol), EDC·HCl (40.2 mg, 0.210 mmol) and 1,3-diglyceride Int-2 (52.5 mg, 0.0923 mmol) were added to a solution of acid Int-103 (45.2 mg, 0.0839 mmol) in $CH_2Cl_2$ (4 mL) and the mixture stirred at RT for 22 hours. The reaction was diluted with $CH_2Cl_2$ (10 mL), silica gel was added and the mixture concentrated under reduced pressure. Purification by silica gel chromatography (4% to 6% ethyl acetate/hexanes) gave triglyceride Int-104 (84.9 mg, 93%) as a colorless solid. $^1$H NMR (401 MHz, $CDCl_3$) δ 7.71-7.65 (m, 4H), 7.45-7.34 (m, 6H), 5.28 (m, 1H), 4.31 (dd, J=11.9, 4.3 Hz, 2H), 4.16 (dd, J=11.9, 6.0 Hz, 2H), 3.66 (t, J=6.5 Hz, 2H), 2.325 (t, J=7.5 Hz, 2H), 2.319 (t, J=7.5 Hz, 4H), 1.69-1.52 (m, 8H), 1.42-1.20 (m, 74H), 1.06 (s, 9H), 0.89 (t, J=6.8 Hz, 6H); $^{13}$C NMR (101 MHz, $CDCl_3$) δ 173.4 (2C; C), 173.0 (C), 135.7 (4C; CH), 134.3 (2C; C), 129.6 (2C; CH), 127.7 (4C; CH), 69.0 (CH), 64.1 ($CH_2$), 62.2 (2C; $CH_2$), 34.3 ($CH_2$), 34.2 (2C; $CH_2$), 32.7 ($CH_2$), 32.1 (2C; $CH_2$), 29.86 (2C; $CH_2$), 29.84 (9C; $CH_2$), 29.80 (5C; $CH_2$), 29.77 (2C; $CH_2$), 29.76 (2C; $CH_2$), 29.65 ($CH_2$), 29.61 (2C; $CH_2$), 29.53 ($CH_2$), 29.50 (2C; $CH_2$), 29.44 ($CH_2$), 29.41 (2C; $CH_2$), 29.25 (2C; $CH_2$), 29.22 ($CH_2$), 27.0 (3C; $CH_3$), 25.9 ($CH_2$), 25.04 ($CH_2$), 24.99 (2C; $CH_2$), 22.8 (2C; $CH_2$), 19.3 (C), 14.2 (2C; $CH_3$).

Int-105:

Tetrabutylammonium fluoride (TBAF, 1.0 M in THF, 154 μL, 0.154 mmol) and acetic acid (8.8 μL, 0.154 mmol) were added to a solution of TBDPS ether Int-104 (84.0 mg, 0.0771 mmol) in THF (3 mL) at 0° C. and the mixture stirred at 0° C. for 15 minutes and then at rt for seven hours. The reaction was diluted with ethyl acetate (40 mL), washed with water (30 mL) and brine (2×30 mL), dried ($MgSO_4$) and concentrated under reduced pressure to give the crude product. Purification by silica gel chromatography (7.5% to 20% ethyl acetate/hexanes) gave alcohol Int-105 (40.5 mg, 62%) as a colorless solid. $^1$H NMR (401 MHz, $CDCl_3$) δ 5.26 (m, 1H), 4.29 (dd, J=11.9, 4.3 Hz, 2H), 4.14 (dd, j=11.9, 6.0 Hz, 2H), 3.64 (t, j=6.6 Hz, 2H), 2.31 (t, J=7.5 Hz, 2H), 2.30 (t, J=7.5 Hz, 4H), 1.67-1.51 (m, 8H), 1.44-1.17 (m, 74H), 0.88 (t, J=6.8 Hz, 6H); $^{13}$C NMR (101 MHz, $CDCl_3$) δ 173.5 (2C; C), 173.1 (C), 69.0 (CH), 63.3 ($CH_2$), 62.3 (2C; $CH_2$), 34.4 ($CH_2$), 34.2 (2C; $CH_2$), 33.0 ($CH_2$), 32.1 (2C; $CH_2$), 29.82 (10C; $CH_2$), 29.80 (6C; $CH_2$), 29.76 (3C; $CH_2$), 29.75 ($CH_2$), 29.65 ($CH_2$), 29.63 (2C; $CH_2$), 29.59 ($CH_2$), 29.51 (2C; $CH_2$), 29.45 ($CH_2$), 29.42 (2C; $CH_2$), 29.27 (2C; $CH_2$), 29.23 ($CH_2$), 25.9 ($CH_2$), 25.1 ($CH_2$), 25.0 (2C; $CH_2$), 22.8 (2C; $CH_2$), 14.3 (2C; $CH_3$).

Int-110 (TML($CO_2$H)-C4-2TG):

Scheme 30. Synthesis of Int-110.

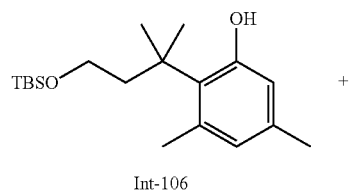

Int-106

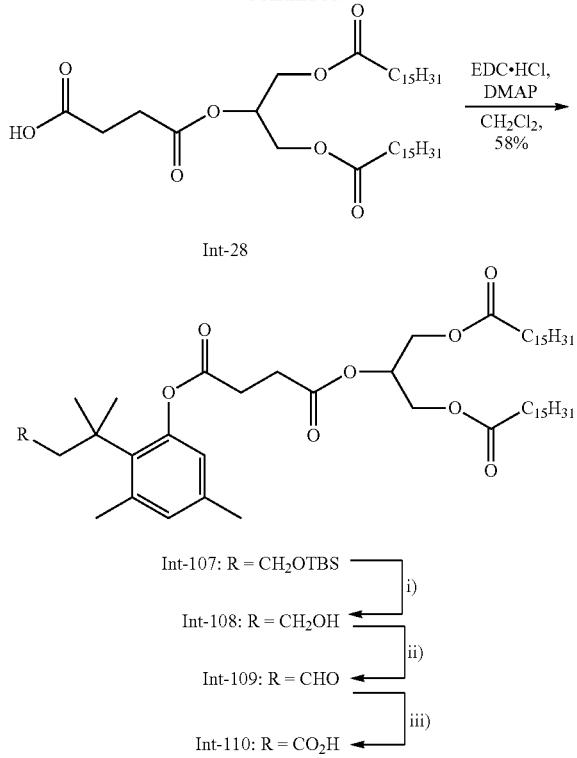

i) 10-CSA, $CH_2Cl_2$/MeOH, 81%;
ii) PCC, $CH_2Cl_2$;
iii) $KMnO_4$, acetone/$H_2O$, 50% (2 steps)

Int-106: prepared according to: Amsberry, K. L. et al. Pharm Res. 1991, 8, 455-461.

DMAP (18.3 mg, 0.149 mmol) and EDC.HCl (71.6 mg, 0.374 mmol) were added to a solution of Int-28 (100 mg, 0.149 mmol) and phenol Int-106 (53.0 mg, 0.164 mmol) in $CH_2Cl_2$ (4 mL) and the mixture stirred at room temperature for 19 hours. The reaction was diluted with $CH_2Cl_2$ (5 mL), silica gel was added, and the mixture concentrated under reduced pressure. Purification by silica gel chromatography (3% to 7.5% ethyl acetate/hexanes) gave TML-TG Int-107 (84.6 mg, 58%) as a colourless oil. $^1$H NMR (400 MHz, $CDCl_3$) δ 6.80 (d, J=2.0 Hz, 1H), 6.55 (d, J=1.9 Hz, 1H), 5.29 (m, 1H), 4.31 (dd, J=11.9, 4.4 Hz, 2H), 4.16 (dd, J=12.0, 5.8 Hz, 2H), 3.51-3.44 (m, 2H), 2.85 (t, J=6.9 Hz, 2H), 2.75 (t, J=6.9 Hz, 2H), 2.51 (s, 3H), 2.30 (t, J=7.6 Hz, 4H), 2.22 (s, 3H), 2.06-1.99 (m, 2H), 1.65-1.56 (m, 4H), 1.46 (s, 6H), 1.37-1.20 (m, 48H), 0.88 (t, J=6.9 Hz, 6H), 0.84 (s, 9H), -0.03 (s, 6H); $^{13}$C NMR (101 MHz, $CDCl_3$) δ 173.4 (2C; C), 171.5 (C), 171.3 (C), 149.7 (C), 138.5 (C), 136.1 (C), 134.1 (C), 132.5 (CH), 123.1 (CH), 69.8 (CH), 62.0 (2C; $CH_2$), 60.9 ($CH_2$), 46.1 ($CH_2$), 39.2 (C), 34.1 (2C; $CH_2$), 32.1 (2C; $CH_2$), 31.9 (2C; $CH_3$), 29.9 ($CH_2$), 29.83 (6C; $CH_2$), 29.79 (4C; $CH_2$), 29.75 (2C; $CH_2$), 29.6 (2C; $CH_2$), 29.5 (2C; $CH_2$), 29.4 (2C; $CH_2$), 29.2 (2C; $CH_2$), 29.0 ($CH_2$), 26.1 (3C; $CH_3$), 25.4 ($CH_3$), 25.0 (2C; $CH_2$), 22.8 (2C; $CH_2$), 20.3 ($CH_3$), 18.3 (C), 14.3 (2C; $CH_3$), -5.21 (2C; $CH_3$). ESI-HRMS: calcd. for $C_{55}H_{105}O_9Si$ [M+H$^+$] 973.7522; found 973.7515.

10-Camphorsulfonic acid (3.0 mg, 12.9 μmol) was added to TBS ether Int-107 (83.7 mg, 86.0 μmol) in $CH_2Cl_2$ (1 mL) and MeOH (1 mL) and the mixture stirred at room temperature for one hour. The reaction was diluted with $CH_2Cl_2$ (20 mL) and the organic phase washed with sat. aq. $NaHCO_3$ and brine (20 mL each), dried (MgSO$_4$) and concentrated under reduced pressure to give the crude product. Purification by silica gel chromatography (15% to 25% ethyl acetate/hexanes) gave alcohol Int-108 (59.9 mg, 81%) as a colourless oil. $^1$H NMR (400 MHz, CDCl$_3$) δ 6.81 (d, J=2.0 Hz, 1H), 6.56 (d, J=1.4 Hz, 1H), 5.28 (m, 1H), 4.30 (dd, J=12.0, 4.4 Hz, 2H), 4.17 (dd, J=12.0, 5.8 Hz, 2H), 3.51 (t, J=6.8 Hz, 2H), 2.88 (t, J=6.6 Hz, 2H), 2.75 (t, J=6.6 Hz, 2H), 2.52 (s, 3H), 2.29 (t, J=7.6 Hz, 4H), 2.22 (s, 3H), 2.05 (t, J=7.4 Hz, 2H), 1.65-1.57 (m, 4H), 1.50 (s, 6H), 1.37-1.20 (m, 48H), 0.88 (t, J=6.9 Hz, 6H); $^{13}$C NMR (101 MHz, CDCl$_3$) δ 173.5 (2C; C), 171.71 (C), 171.70 (C), 149.8 (C), 138.5 (C), 136.3 (C), 133.9 (C), 132.6 (CH), 123.2 (CH), 69.8 (CH), 62.0 (2C; CH$_2$), 60.5 (CH$_2$), 45.9 (CH$_2$), 39.2 (C), 34.1 (2C; CH$_2$), 32.1 (2C; CH$_3$), 32.0 (2C; CH$_2$), 29.84 (CH$_2$), 29.80 (6C; CH$_2$), 29.77 (4C; CH$_2$), 29.72 (2C; CH$_2$), 29.6 (2C; CH$_2$), 29.5 (2C; CH$_2$), 29.4 (2C; CH$_2$), 29.2 (2C; CH$_2$), 28.9 (CH$_2$), 25.5 (CH$_3$), 24.9 (2C; CH$_2$), 22.8 (2C; CH$_2$), 20.3 (CH$_3$), 14.2 (2C; CH$_3$). ESI-HRMS: calcd. for C$_{52}$H$_{90}$NaO$_9$ [M+Na$^+$] 881.6477; found 881.6489.

Pyridinium chlorochromate (PCC, 30.1 mg, 0.139 mmol) was added to a suspension of alcohol Int-108 (59.9 mg, 0.0697 mmol) and Celite (30 mg) in CH$_2$Cl$_2$ (3 mL) at 0° C. and the mixture stirred at room temperature for two hours. The reaction was filtered through a short pad of silica gel, eluting with 50% ethyl acetate/hexanes (50 mL), and the filtrate concentrated under reduced pressure to give crude aldehyde Int-109 (59.8 mg, quant.) as a yellow oil that was used without purification. $^1$H NMR (400 MHz, CDCl$_3$) δ 9.54 (t, J=2.6 Hz, 1H), 6.84 (d, J=2.0 Hz, 1H), 6.60 (d, J=1.4 Hz, 1H), 5.28 (m, 1H), 4.30 (dd, J=12.0, 4.3 Hz, 2H), 4.16 (dd, J=12.0, 5.8 Hz, 2H), 2.86 (t, J=6.7 Hz, 2H), 2.83 (d, J=2.6 Hz, 2H), 2.75 (t, J=6.3 Hz, 2H), 2.53 (s, 3H), 2.30 (t, J=7.6 Hz, 4H), 2.23 (s, 3H), 1.64-1.58 (m, 4H), 1.56 (s, 3H), 1.55 (s, 3H), 1.32-1.22 (m, 48H), 0.88 (t, j=6.9 Hz, 6H).

Potassium permanganate (12.2 mg, 76.7 µmol) in 1:1 acetone/water (1.6 mL total) was added to aldehyde Int-109 (59.8 mg, 69.7 µmol) in acetone (1.6 mL) and the mixture stirred at room temperature for 17 hours. The reaction was diluted with water (10 mL), acidified to pH 2 using 1 MHCl, and the aqueous layer extracted with CH$_2$Cl$_2$ (3×15 mL). The combined organic extracts were washed with brine (40 mL), dried (MgSO$_4$) and concentrated under reduced pressure to give the crude product. Purification by silica gel chromatography (10% to 25% ethyl acetate/hexanes) gave acid Int-110 (30.4 mg, 50%) as a colorless solid. $^1$H NMR (400 MHz, CDCl$_3$) δ 6.81 (d, J=1.6 Hz, 1H), 6.58 (d, J=1.4 Hz, 1H), 5.28 (m, 1H), 4.30 (dd, J=11.9, 4.4 Hz, 2H), 4.16 (dd, J=12.0, 5.8 Hz, 2H), 2.88 (t, J=6.6 Hz, 2H), 2.84 (s, 2H), 2.75 (t, J=6.6 Hz, 2H), 2.53 (s, 3H), 2.29 (t, J=7.6 Hz, 4H), 2.22 (s, 3H), 1.64-1.58 (m, J=9.3 Hz, 4H), 1.57 (s, 6H), 1.34-1.20 (m, 48H), 0.88 (t, J=6.8 Hz, 6H); $^{13}$C NMR (101 MHz, CDCl$_3$) δ 176.1 (C), 173.6 (2C; C), 171.6 (C), 171.4 (C), 149.5 (C), 138.2 (C), 136.5 (C), 133.4 (C), 132.7 (CH), 123.0 (CH), 69.8 (CH), 62.0 (2C; CH$_2$), 47.6 (CH$_2$), 38.8 (C), 34.1 (2C; CH$_2$), 32.1 (2C; CH$_2$), 31.5 (2C; CH$_3$), 29.9 (CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 29.0 (CH$_2$), 25.4 (CH$_3$), 25.0 (2C; CH$_2$), 22.8 (2C; CH$_2$), 20.4 (CH$_3$), 14.3 (2C; CH$_3$). ESI-HRMS: calcd. for C$_{52}$H$_{88}$NaO$_{10}$ [M+Na$^+$] 895.6270; found 895.6266.

Using similar methods, Int-119 was prepared by EDC coupling with Int-37 in 84% yield:

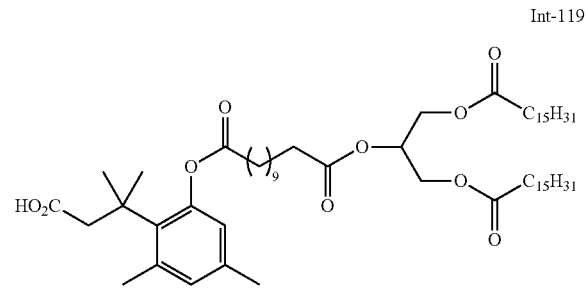

Int-119

$^1$H NMR (401 MHz, CDCl$_3$) δ 6.80 (d, J=1.9 Hz, 1H), 6.55 (d, J=1.7 Hz, 1H), 5.26 (m, 1H), 4.29 (dd, J=11.9, 4.4 Hz, 2H), 4.14 (dd, J=11.9, 5.9 Hz, 2H), 2.83 (s, 2H), 2.55 (t, J=7.5 Hz, 2H), 2.53 (s, 3H), 2.32 (t, J=7.5 Hz, 2H), 2.31 (t, J=7.5 Hz, 4H), 2.22 (s, 3H), 1.78-1.69 (m, 2H), 1.67-1.54 (m, 6H), 1.57 (s, 6H), 1.45-1.20 (m, 60H), 0.88 (t, J=6.8 Hz, 6H); $^{13}$C NMR (101 MHz, CDCl$_3$) δ 176.3 (C), 173.5 (2C; C), 173.1 (C), 173.0 (C), 149.7 (C), 138.2 (C), 136.4 (C), 133.5 (C), 132.5 (CH), 123.2 (CH), 69.0 (CH), 62.2 (2C; CH$_2$), 47.4 (CH$_2$), 38.9 (C), 35.2 (CH$_2$), 34.3 (CH$_2$), 34.2 (2C; CH$_2$), 32.1 (2C; CH$_2$), 31.4 (2C; CH$_3$), 29.84 (6C; CH$_2$), 29.80 (4C; CH$_2$), 29.76 (2C; CH$_2$), 29.62 (2C; CH$_2$), 29.53 (2C; CH$_2$), 29.50 (2C; CH$_2$), 29.41 (2C; CH$_2$), 29.38 (2C; CH$_2$), 29.30 (CH$_2$), 29.26 (2C; CH$_2$), 29.19 (CH$_2$), 25.4 (CH$_3$), 25.0 (3C; CH$_2$), 24.8 (CH$_2$), 22.8 (2C; CH$_2$), 20.4 (CH$_3$), 14.3 (2C; CH$_3$).

Int-122 was also prepared using similar methods:

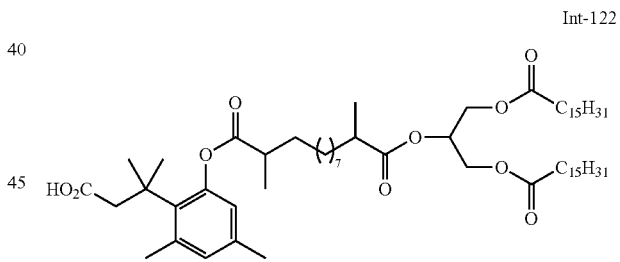

Int-122

$^1$H NMR (401 MHz, CDCl$_3$) δ 6.79 (d, J=1.9 Hz, 1H), 6.51 (d, J=1.8 Hz, 1H), 5.26 (m, 1H), 4.292/4.284 (each dd, J=11.8, 4.2 Hz, 2H), 4.14 (dd, J=11.9, 6.1 Hz, 2H), 2.84 (s, 2H), 2.67 (m, 1H), 2.53 (s, 3H), 2.44 (m, 1H), 2.30 (t, J=7.6 Hz, 4H), 2.22 (s, 3H), 1.84 (m, 1H), 1.69-1.45 (m, 7H), 1.573 (s, 3H), 1.567 (s, 3H), 1.45-1.19 (m, 63H), 1.14 (d, J=7.0 Hz, 3H), 0.88 (t, J=6.9 Hz, 6H); $^{13}$C NMR (101 MHz, CDCl$_3$) δ 176.1 (2C; C), 175.9 (C), 173.5 (2C; C), 150.1 (C), 138.2 (C), 136.4 (C), 133.6 (C), 132.5 (CH), 123.0 (CH), 68.9 (CH), 62.30/62.27 (2C; CH$_2$), 47.3 (CH$_2$), 40.2 (CH), 39.7 (CH), 39.0 (C), 34.2 (2C; CH$_2$), 33.8 (CH$_2$), 33.6 (CH$_2$), 32.1 (2C; CH$_2$), 31.5 (CH$_3$), 29.84 (2C; CH$_2$), 29.80 (2C; CH$_2$), 29.76 (2C; CH$_2$), 29.65 (2C; CH$_2$), 29.61 (2C; CH$_2$), 29.59 (2C; CH$_2$), 29.5 (2C; CH$_2$), 29.4 (2C; CH$_2$), 29.28/29.27 (2C; CH$_2$), 27.34 (CH$_2$), 27.28 (CH$_2$), 25.5 (CH$_3$), 25.0 (2C; CH$_2$), 22.8 (2C; CH$_2$), 20.4 (CH$_3$), 17.2 (CH$_3$), 16.9 (CH$_3$), 14.3 (2C; CH$_3$).

Int-154 was also prepared using similar methods:

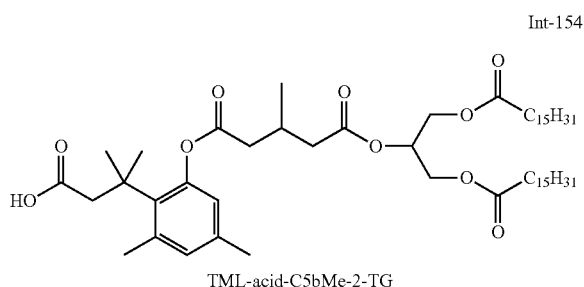

TML-acid-C5bMe-2-TG $^1$H NMR (400 MHz, CDCl$_3$) δ 6.84 (s, 1H), 6.58 (s, 1H), 5.30 (m, 1H), 4.34 (dd, J=11.9, 3.4 Hz, 2H), 4.18 (dd, J=11.9, 6.0 Hz, 2H), 2.84 (s, 2H), 2.75-2.47 (m, 5H), 2.44-2.31 (m, 4H), 2.25 (s, 3H), 1.59 (d, J=14.7 Hz, 4H), 1.27 (m, 58H), 1.15 (d, J=6.2 Hz, 3H), 0.90 (t, J=6.6 Hz, 6H); $^{13}$C NMR (101 MHz, CDCl$_3$) δ 176.09 (1C), 173.42 (2C), 171.36 (1C), 171.23 (1C), 149.25 (1C), 138.10 (1C), 136.27 (1C), 133.31 (1C), 132.49 (1C), 122.95 (2C), 69.20 (1C), 62.06 (2C), 47.38 (1C), 41.11 (1C), 40.52 (1C), 38.63 (1C), 34.02 (2C), 31.94 (3C), 31.34 (1C), 31.30 (1C), 29.71-29.13 (16C), 27.20 (1C), 25.31 (1C), 24.84 (2C), 22.71 (3C), 20.28 (1C), 19.81 (1C), 14.15 (3C). HPLC (ELSD): 9.17 mm, 99.22% purity; MASS (ESI, +ve) m/z: 919.31 (M+18). LCMS (m/z): 919.0 (M+18), 08.14 mm, 100% purity.

Int-112 1,3-di-oleoyl glycerol (1,3-DG-oleate):

To a solution of 2,5-bis(hydroxymethyl)-1,4-dioxane-2,5-diol (5 g, 27.7 mol) in chloroform (20 vol) was added pyridine (5.5 mL, 69.4 mol) followed by oleoyl chloride (11 mL, 54.9 mol) and the mixture was stirred at room temperature for 1 h. The solvent was evaporated and the reaction mixture dissolved in ethyl acetate (30 vol) and washed with 1N HCl (10 vol). The organic layer was dried and solvent evaporated under vacuum. The crude material was recrystallized with cold methanol (20 vol). The solid obtained was further washed with cold methanol, and dried to give ketone Int-111 (11 g, 62%) as a white solid. $^1$H NMR (400 MHz, CDCl$_3$) δ 5.36 (t, J=11.6 Hz, 4H), 4.78 (s, 4H), 2.47 (m, 4H), 2.38 (m, 8H), 1.71 (m, 2H), 1.34-1.30 (m, 42H), 0.93 (m, 6H).

Sodium borohydride (NaBH$_4$, 307 mg, 8.09 mmol), was added to a solution of Int-111 (5 g, 8.09 mmol) in THE (20 vol) at 0° C. and then the reaction mixture was stirred at room temperature for 15 mins. The reaction was monitored by TEC and after completion, the reaction mixture was filtered through a celite bed to remove excess of sodium borohydride and the celite bed was washed with ethyl acetate (30 vol), the organic layer was washed with 1N solution of acetic acid (10 vol). The solvent was dried over Na$_2$SO$_4$ and solvent removed under vacuum. The crude material was column purified. The product was eluted at 5%-10% ethyl acetate/hexane to afford 1,3-DG-oleate (Int-112) (2 g, 39%) as viscous liquid. $^1$H NMR (400 MHz, CDCl$_3$) δ 5.39 (m, 4H), 4.20 (m, 5H), 2.44 (d, 1H), 2.36 (m, 4H), 2.01 (m, 8H), 2.47-2.25 (m, 12H), 2.17 (m, 1H), 2.02 (ddd, J=13.4, 4.9, 3.3 Hz, 1H), 1.85 (m, 1H), 1.77 (m, 1H), 1.64 (m, 2H), 1.57-1.26 (m, 42H), 0.9 (/, 6H); $^{13}$C NMR

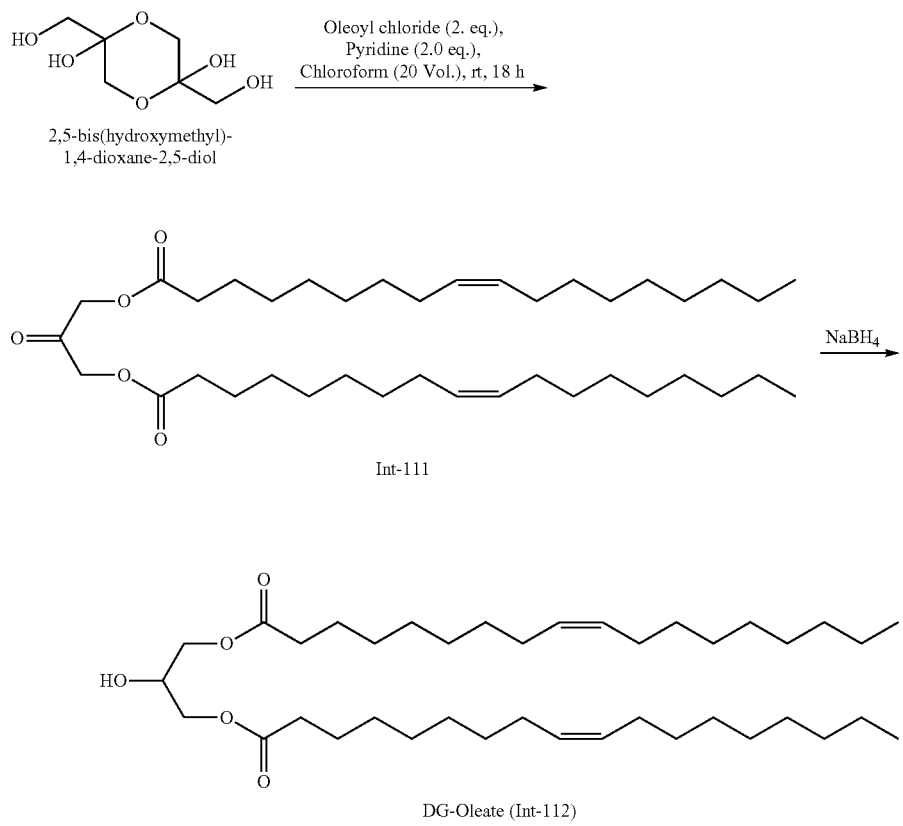

Scheme 31. Synthesis of Int-112.

(101 MHz, CDCl$_3$) δ 173.9 (2C, C=O), 130.1 (2C), 129.7 (2C), 68.4 (C, CH), 65.1 (2C), 34.1 (2C), 31.9 (2C), 29.8-29.1 (18C), 27.3 (2C), 24.9 (2C), 22.7 (2C), 14.1 (2C). HPLC (ELSD): 9.62 mm, 99.27% purity. MS (ESI, +ve) m/z: 639.2 (MH$^+$+H$_2$O).

Int-113 (C10-acid-TG-oleate):

C=O, 173.3 (2C, C=O), 172.8 (1C, C=O), 130.1 (2C), 129.8 (2C), 68.9 (C, CH), 62.1 (2C), 60.5 (2C), 34.2 (4C), 31.9 (2C), 29.8-29.0 (18C), 27.3 (4C), 24.9 (4C), 22.7 (2C), 14.2 (2C). HPLC (ELSD): 10.90 mm, 99% purity. MS (ESI, +ve) m/z: 823.8 (MH$^+$+H$_2$O).

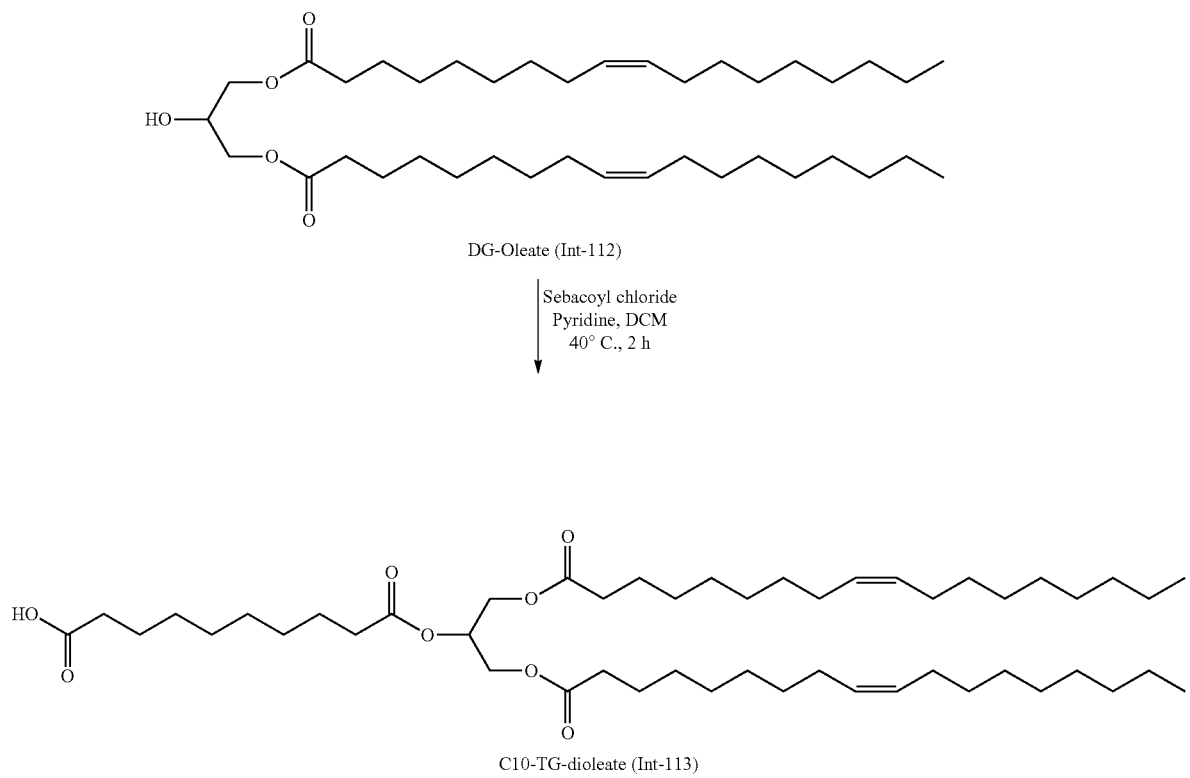

Pyridine (0.19 mL, 2.41 mmol) was added to a suspension of DG-oleate Int-112 (150 mg, 0.241 mmol) in DCM (20 Vol). After 5 min, sebacoyl chloride (289 mg, 1.2 mmol) was added dropwise with stirring at room temperature. Reaction mixture allowed to stir at 40° C. for 2 h. The reaction was monitored by TEC and after completion, diluted with DCM (20 vol), washed with water (20 vol), aqueous sodium bicarbonate (10 vol) and brine (10 vol). The obtained organic layer was dried over Na$_2$SO$_4$, filtered and solvent was removed under reduced pressure. The crude material was column purified. The product was eluted at 5-10% ethyl acetate/hexane to afford C10-acid-TG-oleate Int-113 (60 mg, 30%) as viscous liquid. $^1$H NMR (400 MHz, CDCl$_3$) δ 5.43 (m, 4H), 5.29 (m, 1H), 4.35 (d, 2H), 4.20 (m, 2H), 2.40 (m, 8H), 2.05 (m, 8H), 1.65 (m, 10H), 1.33-1.18 (m 46H), 0.93 (t, 6H); $^{13}$C NMR (101 MHz, CDCl$_3$) δ 1.78 (1C, Int-115 (1,3-DG-butyrate):

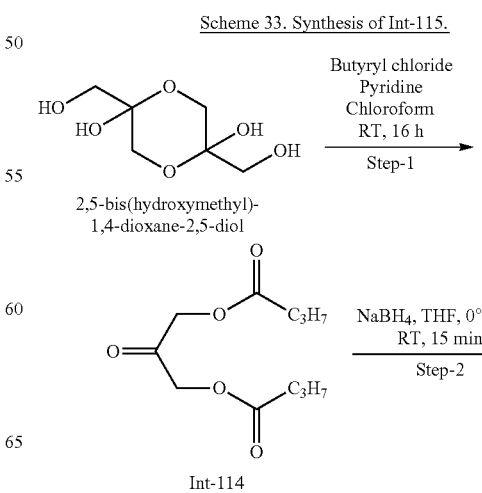

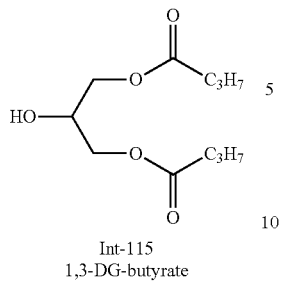

Int-115
1,3-DG-butyrate

To a solution of 2,5-bis-(hydroxymethyl)-1,4-dioxane-2,5-diol (2.0 g, 1.11 mmol) in chloroform (40 ml) was added pyridine (2.2 mL, 2.77 mmol) followed by butyryl chloride (2.3 mL, 2.22 mol) before stirring at room temperature for 16 h. After completion, the solvent was evaporated and re-dissolved in ethyl acetate (60 ml) and washed with 1N HCl (20 ml). The combined organic layer was dried and evaporated under vacuum. The crude material was purified by column. The product was eluted at 5-10% ethyl acetate/hexane to afford Int-114 (1.4 g, 54%) as viscous liquid. $^1$H NMR (400 MHz, CDCl$_3$) δ 4.8 (s, 4H), 2.45 (t, 4H), 1.79-1.69 (m, 4H), 1.04-0.98 (t, 6H); $^{13}$C NMR (101 MHz, CDCl$_3$) δ 198.2 (1C=O), 172.2 (2C=O), 66.1 (2C), 35.9 (2C), 18.3 (2C), 14.1 (2C). HPLC (ELSD): 1.73 mm, 99.8% purity.

Sodium borohydride (NaBH$_4$, 230 mg, 6.10 mmol), was added to a solution of Int-114 (1.3 g, 6.1 mmol) in THF (26 ml) at 0° C. and then the reaction mixture was stirred at room temperature for 15 mins. The reaction was monitored by TEC and after completion, the reaction mixture was filtered through a celite bed to remove excess sodium borohydride, the celite bed was washed with ethyl acetate (40 ml), and the combined organic layer was washed with a 1N solution of acetic acid (13 ml). The organic layer was dried over Na$_2$SO$_4$ and solvent removed under vacuum. The crude material was purified by column. The product was eluted at 5-10% ethyl acetate/hexane to afford Int-115 (1.0 g, 70.6%) as a viscous liquid. $^1$H NMR (400 MHz, CDCl$_3$) δ 4.25-4.13 (m, 5H), 2.4 (s, 1H), 2.38 (t, 4H), 1.75-1.66 (m, 4H), 1.01-0.98 (t, 6H); $^{13}$C NMR (101 MHz, CDCl$_3$) δ 173.8 (2C=O), 68.3 (1C), 65.0 (2C), 35.9 (2C), 18.4 (2C), 13.6 (2C). HPLC (ELSD): 1.8 mm, 100% purity. MS (ESI, +ve) m/z: 255.37 (M$^+$+23).

Int-125:

Scheme 34-A. Synthesis of Int-125.

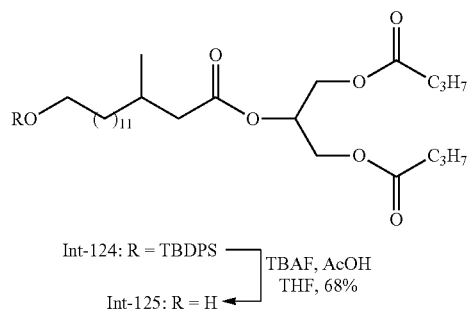

Int-45 was prepared as described above and coupled with Int-115 using EDC and DMAP similarly to methods described above to provide Int-124. Int-124: $^1$H NMR (401 MHz, CDCl$_3$) δ 7.70-7.64 (m, 4H), 7.42-7.35 (m, 6H), 5.29 (m, 1H), 4.307/4.305 (each dd, J=11.9, 4.2 Hz, 2H), 4.159/4.157 (each dd, J=11.9, 6.0 Hz, 2H), 3.66 (t, j=6.5 Hz, 2H), 2.34 (dd, j=14.7, 5.9 Hz, 1H), 2.30 (t, j=7.4 Hz, 4H), 2.13 (dd, j=14.7, 8.3 Hz, 1H), 1.95 (m, 1H), 1.70-1.50 (m, 6H), 1.37-1.17 (m, 20H), 1.05 (s, 9H), 0.95 (t, J=7.5 Hz, 6H). 0.94 (d, J=6.4 Hz, 3H); $^{13}$C NMR (101 MHz, CDCl$_3$) δ 173.2 (2C; C), 172.5 (C), 135.7 (4C; CH), 134.3 (2C; C), 129.6 (2C; CH), 127.7 (4C; CH), 68.9 (CH), 64.1 (CH$_2$), 62.3 (2C; CH$_2$), 41.8 (CH$_2$), 36.8 (CH$_2$), 36.0 (2C; CH$_2$), 32.7 (CH$_2$), 30.5 (CH), 29.9 (CH$_2$), 29.80 (3C; CH$_2$), 29.76 (CH$_2$), 29.75 (CH$_2$), 29.5 (CH$_2$), 27.1 (CH$_2$), 27.0 (3C; CH$_3$), 25.9 (CH$_2$), 19.7 (CH$_3$), 19.3 (C) 18.5 (2C; CH$_2$), 13.7 (2C; CH$_3$).

Int-125:

Tetrabutylammonium fluoride (TBAF, 1.0 M in THF, 243 μL, 0.243 mmol) and AcOH (13.9 L, 0.243 mmol) were added dropwise to TBDPS ether 3 (58.7 mg, 0.0809 mmol) in THF (4 mL) at 0° C. and the mixture stirred at rt for 19 hours. The reaction was diluted with water (10 mL) and the aqueous phase extracted with ethyl acetate (3×15 mL). The combined organic extracts were washed with sat. aq. NaHCO$_3$ and brine (30 mL each), dried (MgSO$_4$) and concentrated under reduced pressure to give the crude product. Purification by silica gel chromatography (6% to 20% ethyl acetate/hexanes) gave alcohol Int-125 (26.7 mg, 68%) as a colorless oil. $^1$H NMR (401 MHz, CDCl$_3$) δ 5.28 (m, 1H), 4.298/4.295 (each dd, J=11.9, 4.3 Hz, 2H), 4.153/4.151 (each dd, J=11.9, 6.0 Hz, 2H), 3.64 (t, J=6.6 Hz, 2H), 2.33 (dd, J=14.7, 5.9 Hz, 1H), 2.30 (t, J=8.4, 6.5 Hz, 4H), 2.12 (dd, j=14.7, 8.3 Hz, 1H), 1.93 (m, 1H), 1.70-1.46 (m, 8H), 1.38-1.16 (m, 18H), 0.95 (t, J=7.4 Hz, 6H), 0.93 (d, j=6.7 Hz, 3H); $^{13}$C NMR (101 MHz, CDCl$_3$) δ 173.3 (2C; C), 172.5 (C), 69.0 (CH), 63.2 (CH$_2$), 62.3 (2C; CH$_2$), 41.9 (CH$_2$), 36.8 (CH$_2$), 36.1 (2C; CH$_2$), 33.0 (CH$_2$), 30.5 (CH), 29.9 (CH$_2$), 29.78 (CH$_2$), 29.76 (2C; CH$_2$), 29.74 (CH$_2$), 29.71 (CH$_2$), 29.6 (CH$_2$), 27.1 (CH$_2$), 25.9 (CH$_2$), 19.7 (CH$_3$), 18.5 (2C; CH$_2$), 13.8 (2C; CH$_3$).

Int-126:

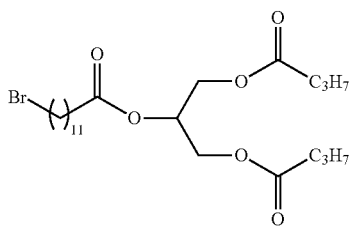

Int-126

Prepared using similar methods as those shown above. $^1$H NMR (401 MHz, CDCl$_3$) δ 5.23 (m, 1H), 4.26 (dd, j=11.9, 4.3 Hz, 2H), 4.11 (dd, j=11.9, 6.0 Hz, 2H), 3.36 (t, j=6.9 Hz, 2H), 2.28 (t, j=7.4 Hz, 2H), 2.26 (t, j=7.4 Hz, 4H), 1.84-1.75 (m, 2H), 1.66-1.52 (m, 6H), 1.42-1.33 (m, 2H), 1.31-1.19 (m, 12H), 0.90 (t, J=7.4 Hz, 6H); $^{13}$C NMR (101 MHz, CDCl$_3$) δ 173.1 (2C; C), 172.9 (C), 68.9 (CH), 62.1 (2C; CH$_2$), 35.9 (2C; CH$_2$), 34.2 (CH$_2$), 34.0 (CH$_2$), 32.9 (CH$_2$), 29.5 (CH$_2$), 29.43 (CH$_2$), 29.42 (CH$_2$), 29.3 (CH$_2$), 29.1 (CH$_2$), 28.8 (CH$_2$), 28.2 (CH$_2$), 24.9 (CH$_2$), 18.4 (2C; CH$_2$), 13.7 (2C; CH$_3$); ESI-HRMS: calcd. for C$_{23}$H$_{41}$$^{79}$BrNaO$_6$ [M+Na$^+$]515.1979; found 515.1995.

Int-117 1,3-bis-decanoyl glycerol (1,3-DG-decanoate):

Scheme 34-B. Synthesis of Int-117.

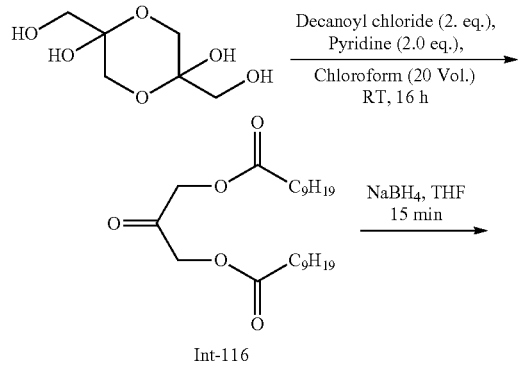

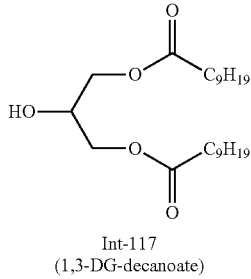

Int-117
(1,3-DG-decanoate)

To a solution of 2, 5-bis-(hydroxymethyl)-1,4-dioxane-2,5-diol (0.2 g, 1.11 mmol) in chloroform (4.0 ml) was added pyridine (0.22 mL, 2.77 mmol) followed by decanoyl chloride (0.45 mL, 2.22 mmol) and stirred at room temperature for 16 h. The solvent was evaporated and re-dissolved in ethyl acetate (6 ml) and washed with 1N HCl (2 ml). The organic layer was dried and solvent evaporated under vacuum. The crude material was purified by column. The product was eluted at 5-10% ethyl acetate/hexane to afford Int-116 (0.09 g, 20.36%) as viscous liquid. $^1$H NMR (400 MHz, CDCl$_3$) δ 4.8 (m, 4H), 2.46 (m, 4H), 1.73-1.66 (m, 4H), 1.30 (m, 24H), 0.91 (t, 6H); $^{13}$C NMR (101 MHz, CDCl$_3$) δ 198.2 (1C=O), 172.0 (2C=O), 66.1 (2C), 33.7 (2C), 31.8 (2C), 29.3 (2C), 29.2 (2C), 29.0 (2C), 24.8 (2C), 22.6 (2C), 14.12 (2C). HPLC (ELSD): 2.88 mm, 100% purity.

Sodium borohydride (NaBH$_4$) (7 mg, 0.2 mmol), was added to a solution of Int-116 (80 mg, 0.2 mmol) in THF (2 ml) at 0° C. and then the reaction mixture was stirred at room temperature for 15 mins. The reaction was monitored by TLC and after completion, the reaction mixture was filtered through a celite bed to remove excess sodium borohydride and the celite bed was washed with ethyl acetate (3 ml). The organic layer was washed with 1 M acetic acid (1 ml). The solvent was dried over Na$_2$SO$_4$ and solvent removed under vacuum. The crude material was purified by column. The product was eluted at 5-10% ethyl acetate/hexane to afford Int-117 (70 mg, 100%) as viscous liquid. $^1$H NMR (400 MHz, CDCl$_3$) δ 4.2-4.1 (m, 5H), 2.51 (s, 1H), 2.38 (t, 4H), 1.68-1.64 (m, 4H), 1.32-1.29 (m, 22H), 0.91 (t, 6H); $^{13}$C NMR (101 MHz, CDCl$_3$) δ 173.0 (2C=O), 68.3 (1C), 65.0 (2C), 34.1 (2C), 31.8 (2C), 29.7 (2C), 29.4 (2C), 29.3 (2C), 29.1 (2C), 24.9 (2C), 22.7 (2C), 14.1 (2C). HPLC (ELSD): 10.70 mm, 97.6% purity.

Int-123:

Scheme 34-C. Synthesis of Int-123.

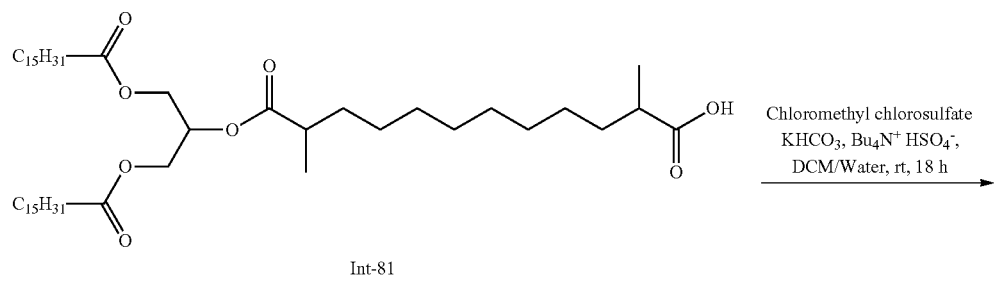

Int-81

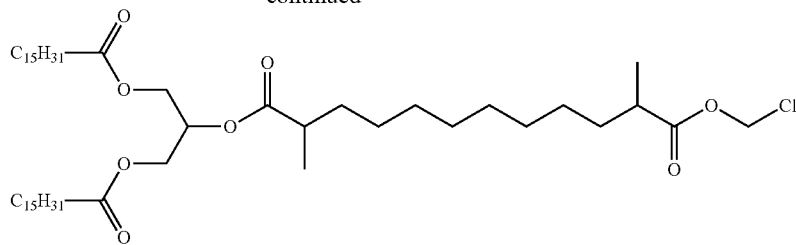

Int-123

Tetra-n-butyl ammonium hydrogen sulfate (0.034 g, 0.098 mmol) and potassium bicarbonate (0.198 g, 1.977 mmol) in distilled water (10 ml) was added to a stirred solution of Int-81 (0.4 g, 0.494 mmol) and tetra-n-butyl ammonium hydrogen sulfate (0.034 g, 0.098 mmol) in dichloromethane (10 ml) at rt and stirred for 0.5 h. Then chloromethyl chlorosulfate (0.062 ml, 0.618 mmol) was added dropwise at rt and stirred vigorously at rt for 18 h. The reaction was monitored by TLC, and after completion of reaction, the reaction mixture was diluted with DCM (25 ml). The organic phase was separated and the aqueous phase extracted with DCM (2×50 ml). Combined organic layers were washed with water (50 ml), brine (50 mL), dried over sodium sulphate, filtered and concentrated at reduced pressure to get crude material. Crude material was purified by column chromatography over silica 100-200 mesh; compound eluted at 20% ethyl acetate/hexane as a mobile phase; visualization was with KMnO$_4$ solution. Int-123 (0.250 g, 59%) was obtained as a viscous liquid. $^1$H NMR (400 MHz, CDCl$_3$) δ 5.75 (m, 2H), 5.32-5.30 (m, 1H), 4.33 (dd, J=11.9, 4.3 Hz, 2H), 4.18 (dd, J=11.9, 6.0 Hz, 2H), 2.56-2.45 (m, 2H), 2.36-2.32 (t, J=7.2 Hz, 4H), 1.66-1.62 (m, 4H), 1.48-1.40 (m, 8H), 1.29 (m, 56H), 1.19 (dd, J=11.2, 7.0 Hz, 6H), 0.92 (t, J=6.7 Hz, 6H).

Using similar methods. Int-155 was prepared:

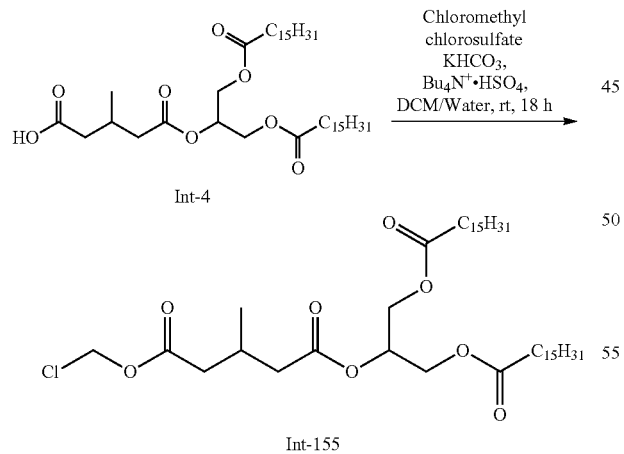

Tetra-n-butyl ammonium hydrogen sulfate (24 mg, 0.072 mmol) and potassium bicarbonate (286 mg, 2.86 mmol) in distilled water (10 ml) was added to a stirred solution of acid linker Int-4 (0.5 g, 0.72 mmol) and tetra-n-butyl ammonium hydrogen sulfate (24 mg, 0.072 mmol) in dichloromethane (10 ml) at rt and stir for 0.5 h. Then chloromethyl chlorosulfate (0.092 ml, 0.89 mmol) was dropwise added at room temperature and stirred vigorously at rt for 18h. The reaction was monitored by TLC, after completion of reaction; reaction mixture was diluted with DCM (5 ml). The organic phase was separated and the aqueous phase was extracted with DCM (2×5 ml). The combined organic layers were washed with water (10 ml), brine (10 mL), dried over sodium sulfate, filtered and concentrated at reduced pressure to get crude material. Crude material was purified by column chromatography over silica, compound eluted at 15% ethyl acetate/hexane as a mobile phase. Pure fractions were concentrated in the rotavap to give Int-155 C5bMe-chloromethyl ester: (0.250 g, 47%) as white solid. $^1$H NMR (400 MHz, CDCl$_3$) δ 5.76 (s, 2H), 5.33 (m, 1H), 4.34 (dd, 2H), 4.18 (dd, 2H), 2.5-2.3 (m, 8H), 1.66-1.64 (m, 2H), 1.60 (s, 3H), 1.29 (m, 48H), 1.09 (d, 3H), 0.91 (t, 6H). MS (ESI, +ve) m/z: 763 (MH$^+$+18).

C15-acid-2-TG (Int-129):

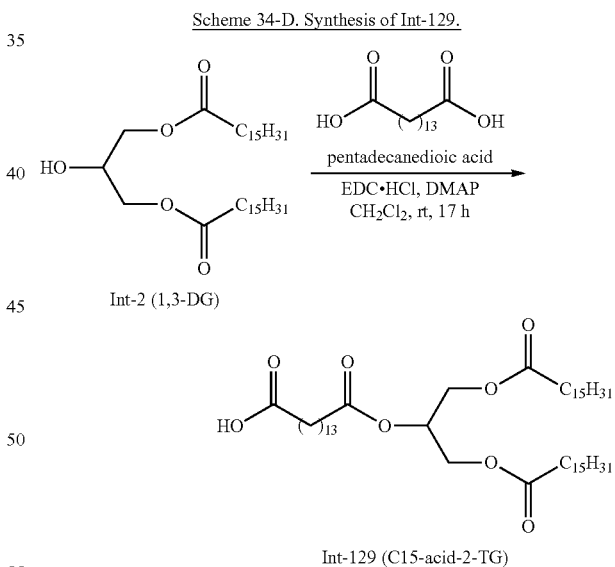

4-(Dimethylamino)pyridine (22.5 mg, 0.184 mmol) and N-(3-dimethylaminopropyl)-N'-ethyl-carbodiimide (EDOHCl, 88.3 mg, 0.461 mmol) were added to a solution of pentadecanedioic acid (100 mg, 0.369 mmol) and compound Int-2 (105 mg, 0.184 mmol) in CH$_2$Cl$_2$ (5 mL) and the mixture stirred at room temperature for 17 hours. The reaction was diluted with CH$_2$Cl$_2$ (10 mL), silica gel was added and the mixture concentrated under reduced pressure. Purification by silica gel chromatography (15% to 25% ethyl acetate/hexanes) gave Int-129 (05-acid-2-TG) (113 mg, 75%) as a colourless solid. $^1$H NMR (401 MHz, CDCl$_3$) δ

5.26 (m, 1H), 4.29 (dd, J=11.9, 4.3 Hz, 2H), 4.14 (dd, J=11.9, 6.0 Hz, 2H), 2.34 (t, j=7.5 Hz, 2H), 2.31 (t, j=7.5 Hz, 2H), 2.30 (t, j=7.5 Hz, 4H), 1.67-1.56 (m, 8H), 1.38-1.17 (m, 66H), 0.87 (t, J=6.8 Hz, 6H); $^{13}$C NMR (101 MHz, CDCl$_3$) δ 179.6 (C), 173.5 (2C; C), 173.0 (C), 69.0 (CH), 62.2 (2C; CH$_2$), 34.4 (CH$_2$), 34.2 (2C; CH$_2$), 34.1 (CH$_2$), 32.1 (2C; CH$_2$), 29.84 (6C; CH$_2$), 29.80 (4C; CH$_2$), 29.76 (2C; CH$_2$), 29.75 (2C; CH$_2$), 29.72 (CH$_2$), 29.62 (2C; CH$_2$), 29.58 (CH$_2$), 29.50 (2C; CH$_2$), 29.43 (CH$_2$), 29.41 (2C; CH$_2$), 29.38 (CH$_2$), 29.25 (2C; CH$_2$), 29.21 (2C; CH$_2$), 25.03 (CH$_2$), 25.00 (2C; CH$_2$), 24.8 (CH$_2$), 22.8 (2C; CH$_2$), 14.3 (2C; CH$_3$).

Int-136:

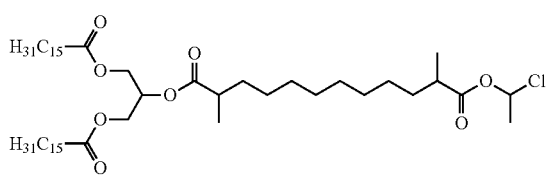

Int-136

A solution of Int-81 (0.5 g, 0.618 mmol) in DCM (5 ml), DMF (two drops) and oxalyl chloride (1.1 ml, 12.36 mmol) was added at 0° C. then reaction mixture was stirred at RT for 2 h. The reaction mixture was concentrated under reduced pressure, and then co-evaporated three times with DCM (5 mL each) and dried under reduced pressure. The resulting acid chloride was dissolved in DCM (20 ml), then ZrCl$_4$ (0.33 g, 1.45 mmol) in DCM (10 mL) was added dropwise to the reaction mixture at 0° C. and stirred at 0° C. for 10 minutes. Then paraldehyde (0.383 g, 2.90 mmol) was added and the reaction mixture was stirred at 0° C. for 0.5 h and RT for 1 h. The reaction mixture was diluted with DCM (50 mL) and water (50 mL). The organic layer was washed with water (25 mL) and brine (25 mL), dried over Na$_2$SO$_4$, and concentrated under reduced pressure to give the crude product. Purification by column chromatography over silica gel eluting with 5% to 15% ethyl acetate/hexanes gave Int-136 (0.135 g, 21%) as a viscous oil. $^1$H NMR (400 MHz, CDCl$_3$) δ 6.61-6.57 (q, 1H), 5.32 (m, 1H), 4.33 (dd, J=11.6, 3.7 Hz, 2H), 4.19 (dd, J=11.9, 6.1 Hz, 2H), 2.49 (m, 2H), 2.34 (t, J=7.6 Hz, 4H), 1.83 (d, J=5.6 Hz, 2H), 1.72-1.62 (m, 4H), 1.49-1.40 (m, 5H). 1.38-1.29 (m, 60H), 1.24-1.17 (m, 6H), 0.92 (t, 6H).

Int-142:

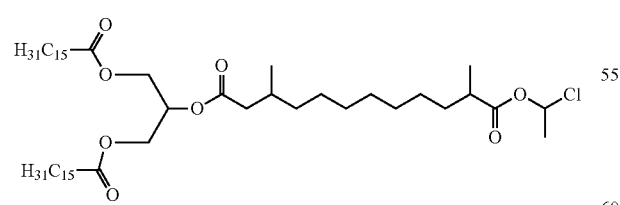

Int-142

A solution of Int-27 (0.5 g, 0.618 mmol) in DCM (5 ml), DMF (two drops) and oxalyl chloride (1.1 ml, 12.36 mmol) was added at 0° C., then the reaction mixture was stirred at RT for 2 h. The reaction mixture was concentrated under reduced pressure, and then co-evaporated three times with DCM (5 mL each) and dried under reduced pressure. The resulting acid chloride was dissolved in DCM (20 ml), then ZrCl$_4$ (0.33 g, 1.45 mmol) in DCM (10 mL) was added dropwise to the reaction mixture at 0° C. and stirred at 0° C. for 10 minutes. Then paraldehyde (0.383 g, 2.90 mmol) was added and the reaction mixture was stirred at 0° C. for 0.5 h and RT for 1 h. The reaction mixture was diluted with DCM (50 mL) and water (50 mL). The organic layer was washed with water (25 mL) and brine (25 mL), dried over Na$_2$SO$_4$, and concentrated under reduced pressure to give the crude product. Purification by column chromatography over silica gel eluting with 5% to 15% ethyl acetate/hexanes gave Int-142 (0.170 g, 32%) as a viscous oil. $^1$H NMR (400 MHz, CDCl$_3$) δ 6.61-6.57 (q, J=5.6 Hz, 1H), 5.32 (m, 1H), 4.33 (dd, J=11.6, 3.7 Hz, 2H), 4.19 (dd, J=11.9, 6.1 Hz, 2H), 2.49 (m, 2H), 2.39-2.32 (t, J=7.6 Hz, 6H), 2.18-2.12 (m, 2H), 2.08-1.97 (m, 2H), 1.83 (d, 1=5.6 Hz, 3H), 1.64-1.56 (m, 8H), 1.38-1.29 (m, 54H), 1.21-1.19 (m, 6H), 0.92 (t, J=6.0 Hz, 6H).

C10α'αMe-acid-2-TG (Int-150):

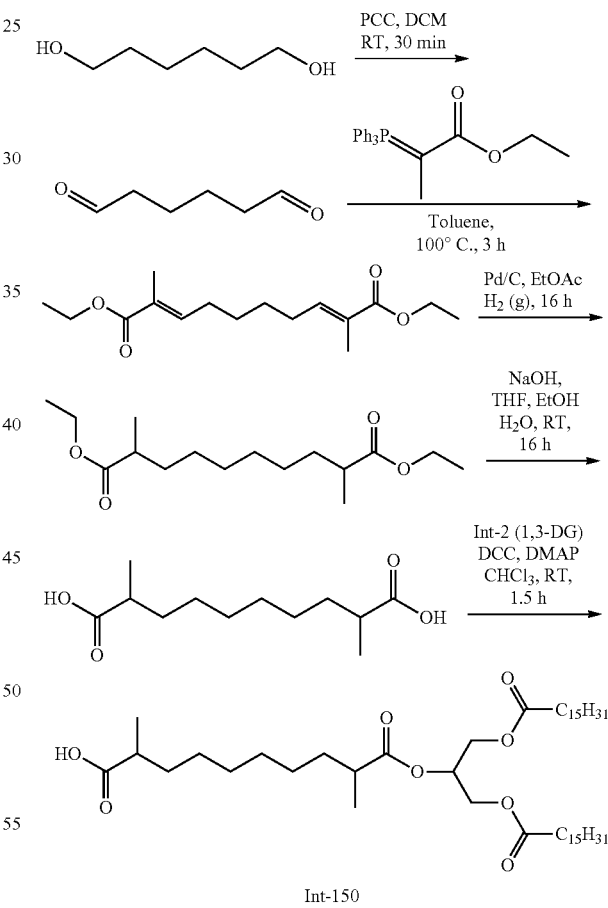

Scheme 34-E. Synthesis of Int-150.

Intermediate C10α'αMe-acid-2-TG (Int-150) was prepared from hexane-1,6-diol as shown in Scheme 34-E, using methods described above. $^1$H NMR (400 MHz, CDCl$_3$) δ 5.35-5.24 (m, 1H), 4.31 (dd, J=11.8, 4.0 Hz, 2H), 4.17 (dd, J=11.9, 6.0 Hz, 2H), 2.47 (p, 1=7.2 Hz, 2H), 2.33 (t, J=7.7 Hz, 6H), 1.69-1.60 (m, 6H), 1.44-1.39 (m, 4H), 1.27 (s, 52H), 1.18 (dd, J=14.8, 7.0 Hz, 6H), 0.89 (t, J=6.4 Hz, 6H);

<sup>13</sup>C NMR (101 MHz, CDCl<sub>3</sub>) δ 182.44 (1C), 175.90 (1C), 173.36 (2C), 68.72 (1C), 62.16 (2C), 39.54 (1C), 39.27 (1C), 34.08 (2C), 33.61 (1C), 33.51 (1C), 31.97 (3C), 29.74-28.98 (22C), 27.12 (1C), 24.89 (2C), 22.73 (2C), 17.07 (1C), 16.89 (1C), 14.17 (2C); MS (ESI, +ve) m/z: 798.6 (M+18).
C10ααMe-acid-2-TG (Int-151):
Scheme 34-F. Synthesis of Int-151.
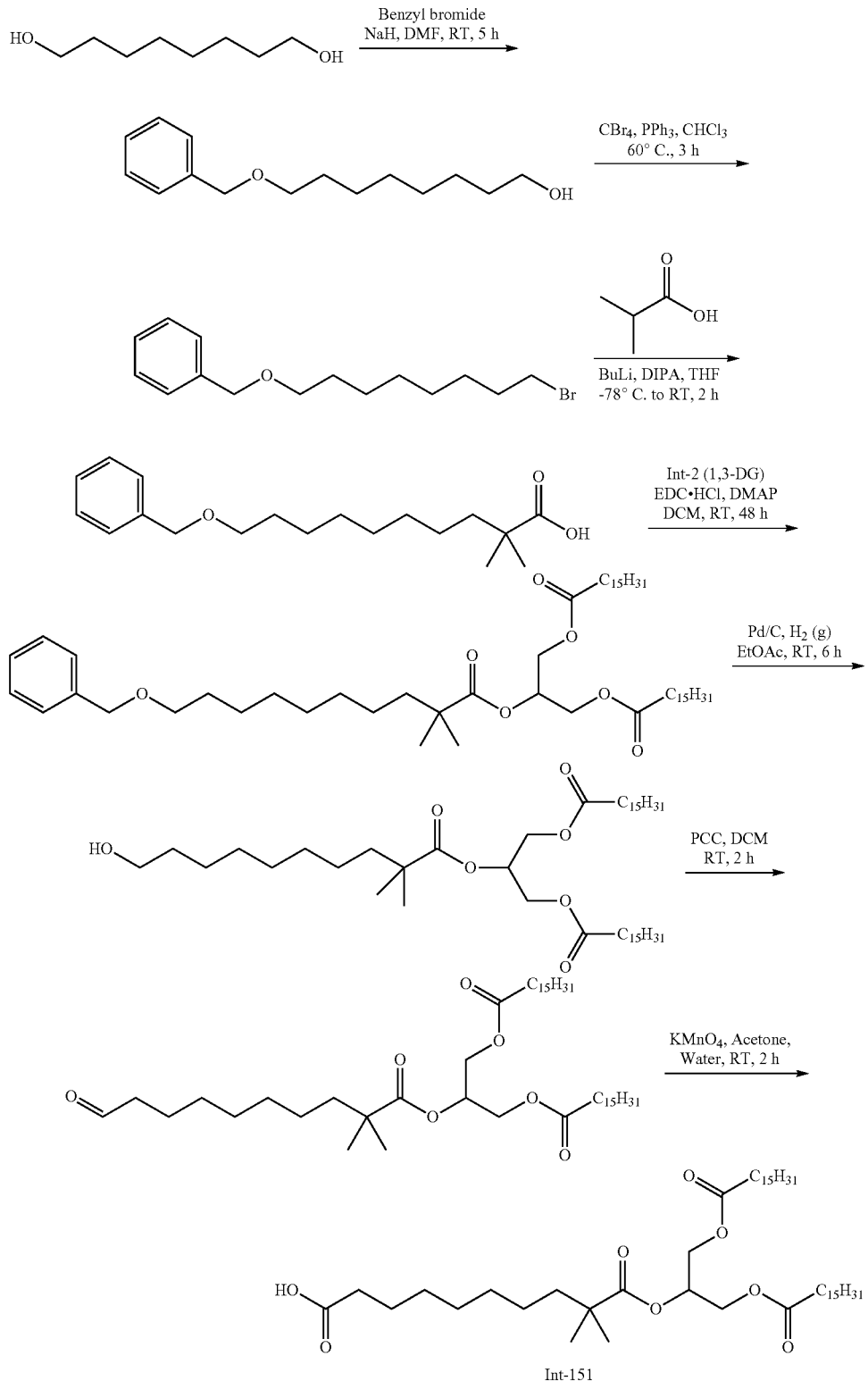

Intermediate C10ααMe-acid-2-TG (Int-151) was prepared from octane-1,8-diol as shown in Scheme 34-F, using methods described above. $^1$H NMR (400 MHz, CDCl$_3$) δ 5.28 (m, 1H), 4.34 (dd, J=11.8, 4.2 Hz, 2H), 4.18 (dd, J=11.8, 6.1 Hz, 2H), 2.36 (dt, J=17.1, 7.5 Hz, 4H), 1.65-1.51 (m, 8H), 1.29 (s, 58H), 1.19 (s, 6H), 0.91 (t, J=6.5 Hz, 6H); $^{13}$C NMR (101 MHz, CDCl$_3$) δ 179.57 (1C), 177.49 (1C), 173.33 (2C), 68.94 (1C), 62.16 (1C), 42.40 (1C), 40.63 (1C), 34.24 (2C), 31.96 (2C), 30.06-29.15 (26C), 25.07 (1C), 24.89 (2C), 24.81 (1C), 24.65 (1C), 22.73 (2C), 14.16 (2C); MS (ESI, −ve) m/z: 780.08 (M−1); MS (ESI, +ve) m/z: 799.16 (M+18).
C11αMe-acid-2-TG (Int-152):
Scheme 34-G. Synthesis of Int-152.
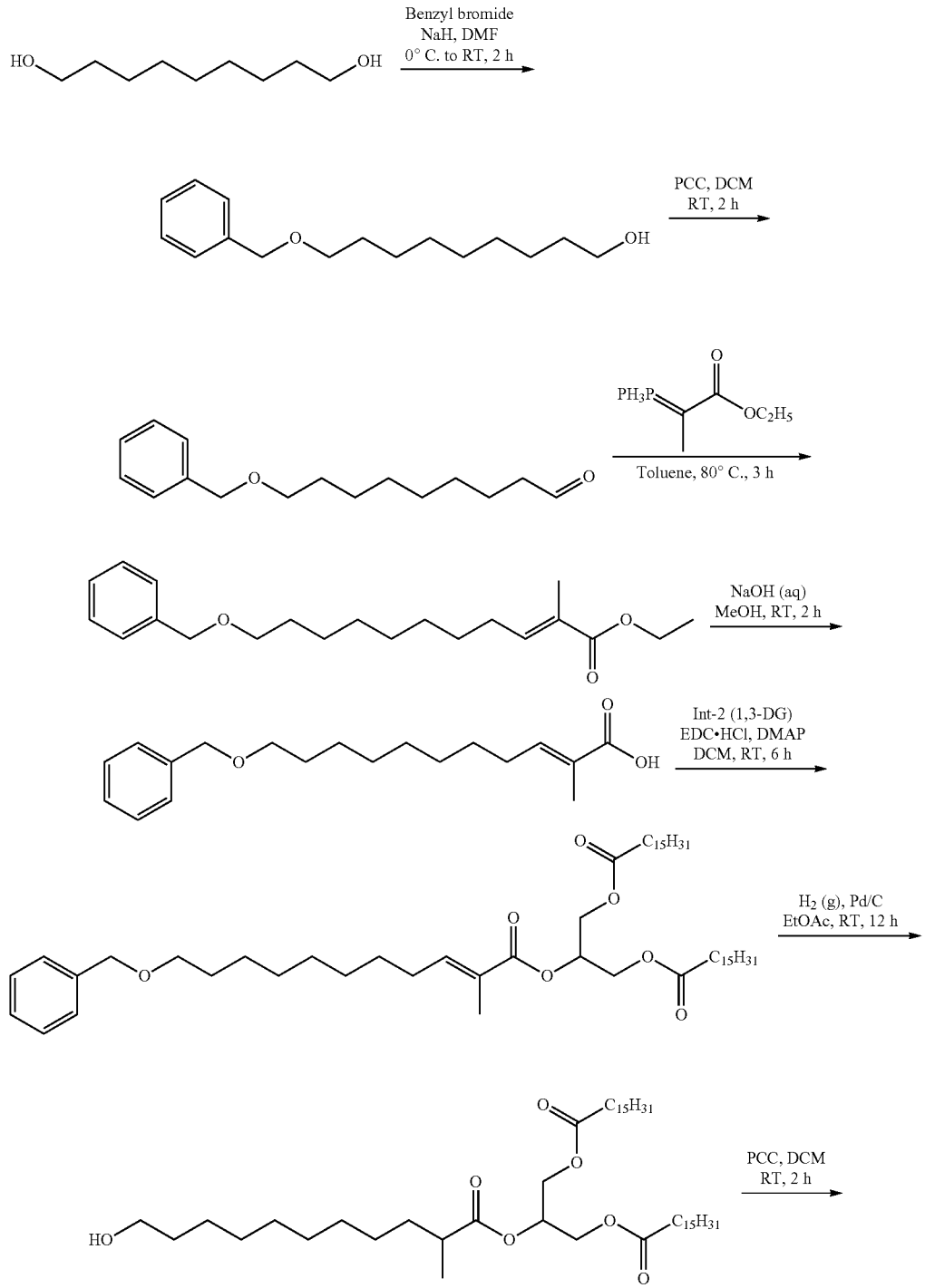

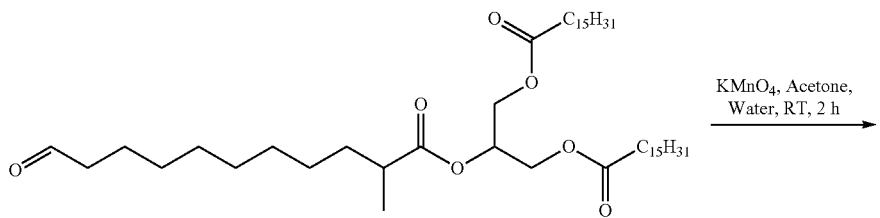

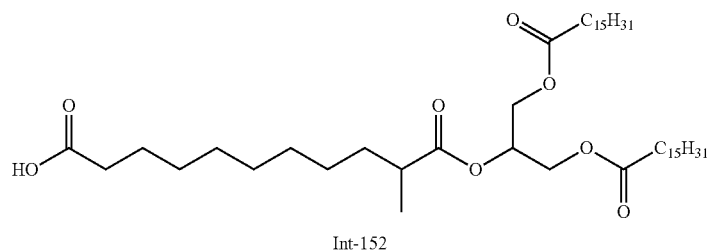

Int-152

Intermediate C11αMe-acid-2-TG (Int-152) was prepared from nonane-1,9-diol as shown in Scheme 34-G, using methods described above. $^1$H NMR (400 MHz, CDCl$_3$) δ 5.32 (m, 1H), 4.33 (dd, J=11.8, 3.7 Hz, 2H), 4.19 (dd, 1=11.9, 6.0 Hz, 2H), 2.48 (h, J=6.9 Hz, 1H), 2.37 (dt, J=15.5, 7.5 Hz, 6H), 1.71-1.58 (m, 8H), 1.29 (m, 58H), 1.18 (d, J=6.9 Hz, 3H), 0.91 (t, J=6.5 Hz, 6H); $^{13}$C NMR (101 MHz, CDCl$_3$) δ 179.64 (1C), 175.92 (1C), 173.34 (2C), 68.73 (1C), 62.18 (2C), 39.54 (1C), 34.08 (2C), 34.01 (1C), 33.63 (1C), 31.96 (2C), 29.73-29.07 (23C), 27.14 (1C), 24.88 (2C), 24.68 (1C), 22.73 (3C), 17.05 (1C), 14.16 (2C); MS (ESI, –ve) m/z: 779.0 (M–1); MS (ESI, +ve) m/z: 798.0 (M+18).

C12αMe-acid-TG (Int-156):

Using similar methods to those used for Int-152, Int-156 was prepared.

Int-156

C12aMe-acid-TG $^1$H NMR (400 MHz, CDCl$_3$) δ 5.34-5.29 (m, 1H), 4.34 (dd, J=11.8, 3.8 Hz, 2H), 4.19 (dd, J=11.8, 6.0 Hz, 2H), 2.50-2.45 (m, 1H), 2.40-2.32 (m, 6H), 1.69-1.64 (m, 8H), 1.29 (s, 60H), 1.18 (d, J=6.9 Hz, 3H), 0.92 (t, J=6.7 Hz, 6H); $^{13}$C NMR (101 MHz, CDCl$_3$) δ 179.38 (1C), 175.93 (1C), 173.33 (2C), 68.69 (1C), 62.17 (2C), 39.53 (1C), 34.06 (2C), 33.94 (1C), 33.63 (1C), 31.94 (2C), 29.71-29.05 (23C), 27.15 (1C), 24.86 (2C), 24.67 (1C), 22.71 (3C), 17.03 (1C), 14.14 (3C). HPLC (ELSD): 10.78 mm, 100% purity. MASS (ESI, −ve) m/z: 794.0 (M−1).
Example 2: Synthesis of (E)-6-(4-(((4-((1,3-bis(palmitoyloxy)propan-2-yl)oxy)-4-oxobutanoyl)oxy)methoxy)-6-methoxy-7-methyl-3-oxo-1,3-dihydroisobenzofuran-5-yl)-4-methylhex-4-enoic acid (I-6)
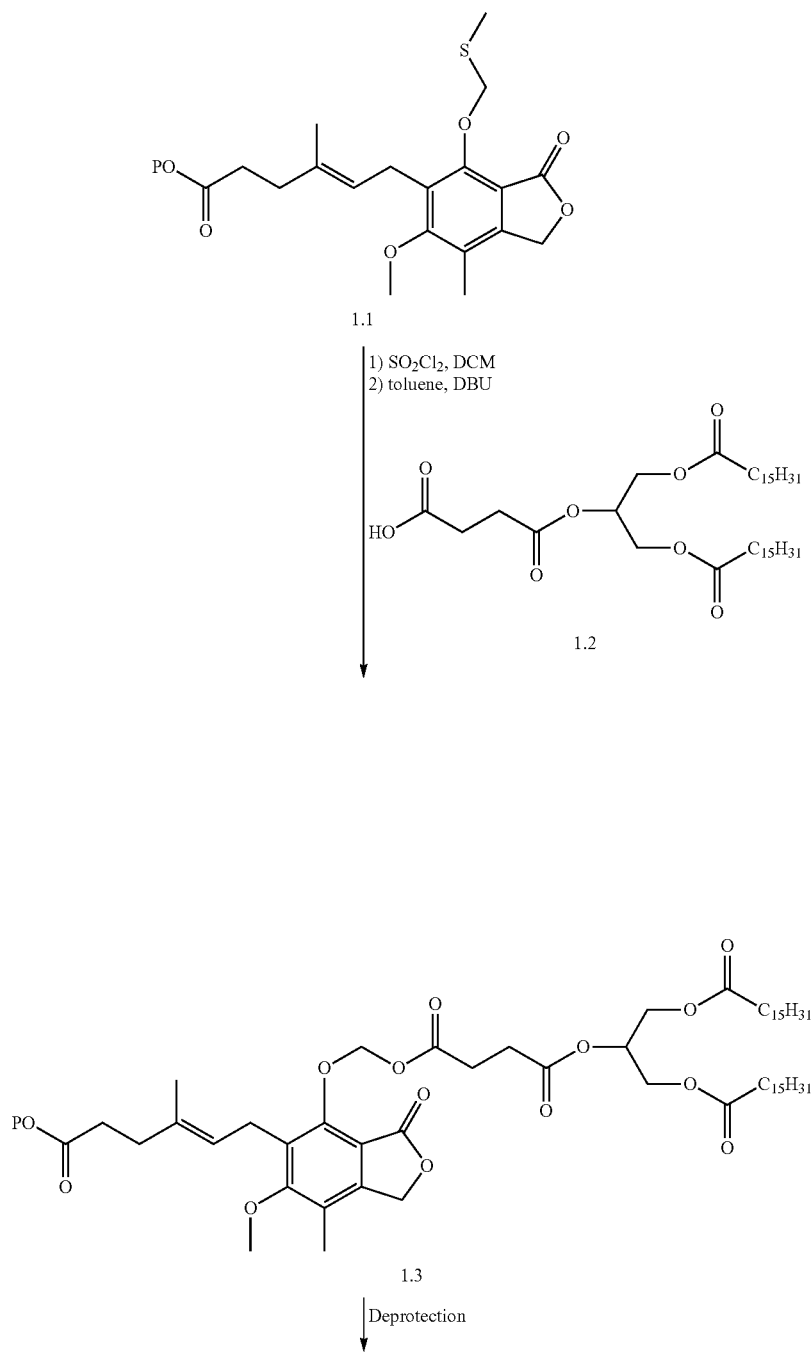

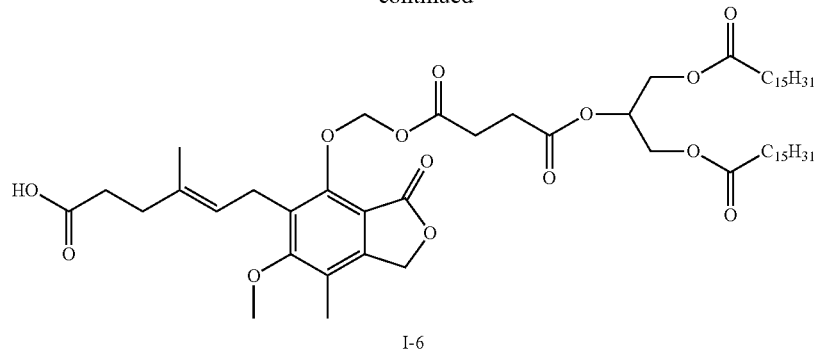

I-6

Synthesis of I-6

I-6 is prepared according to the following procedure. 1.1 is prepared by treating a suitably protected mycophenolic acid (i.e., wherein P is a suitable carboxyl protecting group) with chloromethyl methyl thioether as described in WO 2009/143295, which is hereby incorporated by reference in its entirety. A solution of sulfuryl chloride (2.2 equiv.) in $CH_2Cl_2$ (0.16 M) is added to a solution of 1.1 (1.8 equiv.) in $CH_2Cl_2$ (0.07 M) at 0° C. and the mixture stirred at 0° C. for 30 minutes and then at rt for a further hour. The reaction is concentrated under a stream of $N_2$, co-evaporated from toluene (twice) and dried under reduced pressure. The crude residue is re-dissolved in toluene (0.1 M based on 1.1), added to a solution of acid 1.2 (1 equiv.), as prepared in WO 2017/041139, and DBU (1.5 equiv.) in toluene (0.05 M) that had been pre-stirred for one hour, and the mixture is stirred at rt for two hours. The reaction is diluted with $CH_2Cl_2$ (20 mL) and the organic phase washed with sat. aq. $NaHCO_3$ (20 mL) and brine (20 mL), dried ($MgSO_4$) and concentrated under reduced pressure to give the crude product. Deprotection and purification by silica gel chromatography with a suitable solvent mixture affords 1-6.

Example 3: Synthesis of (E)-6-(6-methoxy-7-methyl-3-oxo-4-((5,8,13-trioxo-10-((palmitoyloxy)methyl)-2,4,9,12-tetraoxaoctacosanoyl)oxy)-1,3-dihydroisobenzofuran-5-yl)-4-methylhex-4-enoic acid, I-7

Scheme 36. Synthesis of I-7.

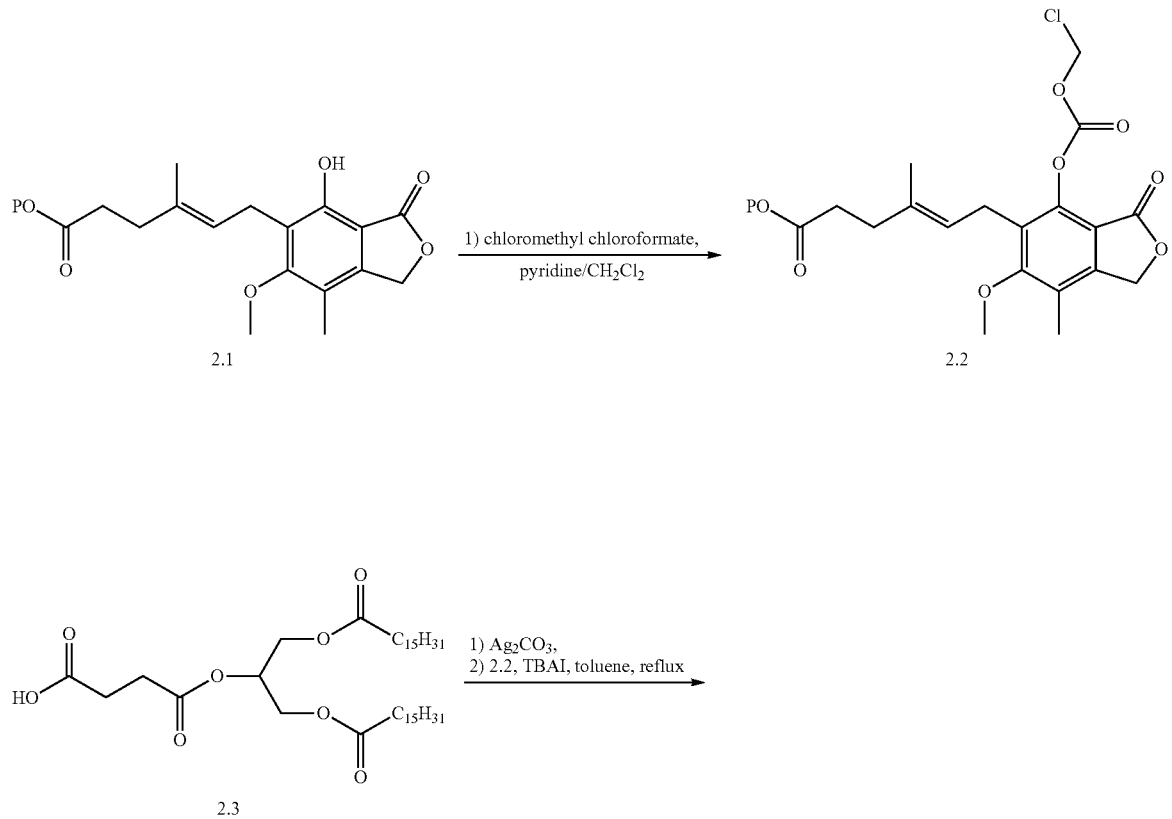

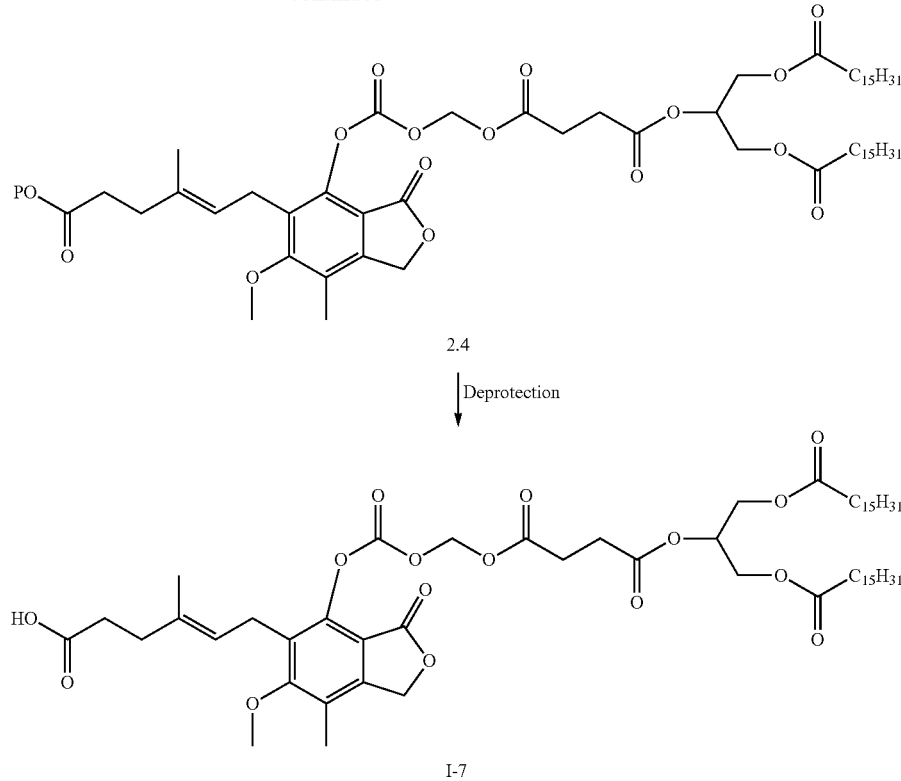

2.4

↓ Deprotection

I-7

Synthesis of 2.2.

2.2 is prepared according to the following procedure. Chloromethyl chloroformate (1.6 equiv.) and pyridine (3.0 equiv.) are added to a suitably protected mycophenolic acid (ie where P is a suitable carboxyl protecting group) 2.1 (1.0 equiv.) in $CH_2Cl_2$ (0.03 M) at 0° C. and the mixture is stirred at 0° C. for 15 minutes and then at rt for one hour. The reaction is diluted with $CH_2Cl_2$ and the organic phase washed with sat. aq. $NaHCO_3$ and brine, dried ($MgSO_4$) and concentrated under reduced pressure to give 2.2 which is used without purification.

Synthesis of I-7.

2.4 is prepared according to the following procedure. Silver carbonate (0.7 equiv.) is added to acid 2.3 (1.2 equiv.) as prepared in WO 2017/041139, in DMF (0.03 M) and the mixture stirred at rt for one hour. The reaction is concentrated under reduced pressure to give a grey residue, to which is added chloromethyl carbonate 2.2 (1.0 equiv.) in toluene (0.03 M) and TBAI (0.3 equiv.) and the mixture heated at reflux for 1.5 hours. The reaction is cooled to rt, then diluted with ethyl acetate. The organic phase is washed with water and brine, dried ($MgSO_4$) and concentrated under reduced pressure to give the crude product 2.4. Deprotection and purification by silica gel chromatography with a suitable solvent mixture affords I-7.

Example 4: Synthesis of (E)-6-(4-((3-(2-((4-((1,3-bis(palmitoyloxy)propan-2-yl)oxy)-4-oxobutanoyl)oxy)-4,6-dimethylphenyl)-3-methylbutanoyl)oxy)-6-methoxy-7-methyl-3-oxo-1,3-dihydroisobenzofuran-5-yl)-4-methylhex-4-enoic acid, I-8

Scheme 37. Synthesis of I-8.

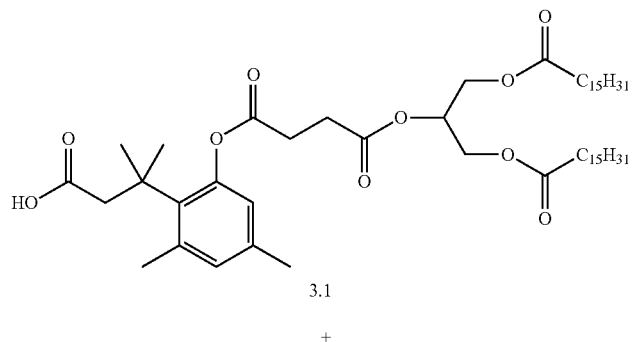

3.1

+

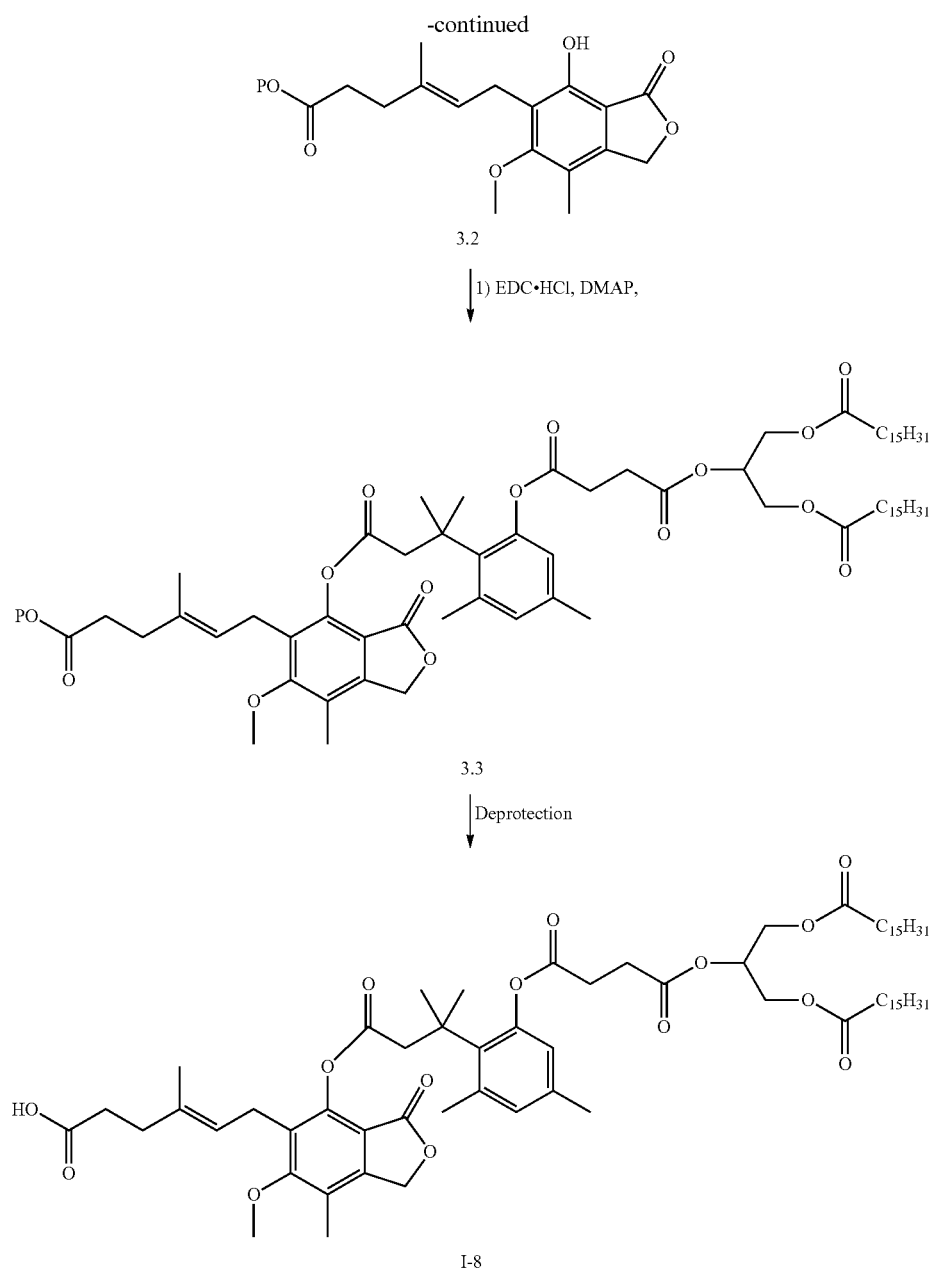

Synthesis of I-8.

I-8 is prepared according to the following procedure. DMAP (1.3 equiv.) and EDC.HCl (2.1 equiv.) is added to a solution of acid 3.1 (1.0 equiv.) as prepared in WO 2017/041139, and a suitably protected mycophenolic acid (i.e. where P is a suitable carboxyl protecting group such as an alkyl or phenyl ester) 3.2 (1.3 equiv.) in $CH_2Cl_2$ (0.02 M) and the mixture stirred at RT for 19 hours. The reaction is diluted with $CH_2Cl_2$ (10 mL), silica gel is added, and the mixture concentrated under reduced pressure and purified by silica gel chromatography. Deprotection of the ester and purification, e.g. by silica gel chromatography with a suitable solvent mixture, affords I-8.

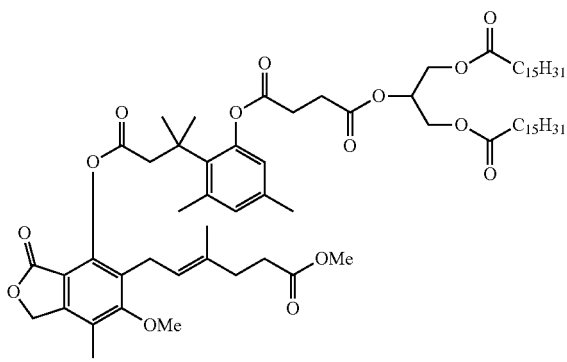

I-8'

Compound I-8' was prepared as follows. DMAP (2.4 mg, 19.8 µmol) and EDC.HCl (9.5 mg, 49.4 µmol) were added to a solution of TML acid-TG 3.1 (19.0 mg, 21.8 µmol) and methyl ester 3.2 (6.6 mg, 19.8 µmol, P=Me) in CH$_2$Cl$_2$ (1 mL) and the mixture stirred at RT for 3.5 hours. The reaction was diluted with CH$_2$Cl$_2$ (10 mL), silica gel was added and the mixture concentrated under reduced pressure. Purification by silica gel chromatography (20% to 25% ethyl acetate/hexanes) gave prodrug MPA-(O-TML-C4-2-TG)-OMe (I-8') (22.0 mg, 94%) as a colorless solid. $^1$H NMR (401 MHz, CDCl$_3$) δ 6.78 (d, J=1.9 Hz, 1H), 6.58 (d, j=1.8 Hz, 1H), 5.28 (m, 1H), 5.10 (s, 2H), 4.99 (m, 1H), 4.29 (dd, j=11.9, 4.4 Hz, 2H), 4.16 (dd, j=11.9, 5.8 Hz, 2H), 3.72 (s, 3H), 3.61 (s, 3H), 3.32 (s, 2H), 3.11 (d, J=5.1 Hz, 2H), 2.92 (t, J=6.7 Hz, 2H), 2.76 (t, j=6.7 Hz, 2H), 2.57 (s, 3H), 2.36-2.22 (m, 8H), 2.19 (s, 3H), 2.17 (s, 3H), 1.73 (s, 3H), 1.65 (s, 6H), 1.64-1.54 (m, 4H), 1.35-1.19 (m, 48H), 0.87 (t, j=6.8 Hz, 6H); $^{13}$C NMR (101 MHz, CDCl$_3$) δ 173.8 (C), 173.5 (2C; C), 171.5 (C), 171.4 (C), 170.0 (C), 168.4 (C), 162.8 (C), 149.6 (C), 146.3 (C), 146.0 (C), 138.2 (C), 136.3 (C), 134.2 (C), 133.5 (C), 132.6 (CH), 129.6 (C), 123.1 (CH), 122.79 (C), 122.77 (CH), 113.6 (C), 69.7 (CH), 68.4 (CH$_2$), 62.0 (2C; CH$_2$), 61.2 (CH$_3$), 51.6 (CH$_3$), 47.0 (CH$_2$), 38.9 (C), 34.5 (CH$_2$), 34.1 (2C; CH$_2$), 32.8 (CH$_2$), 32.1 (2C; CH$_2$), 31.4 (2C; CH$_3$), 29.9 (CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.2 (2C; CH$_2$), 29.0 (CH$_2$), 25.5 (CH$_3$), 25.0 (2C; CH$_2$), 23.5 (CH$_2$), 22.8 (2C; CH$_2$), 20.4 (CH$_3$), 16.4 (CH$_3$), 14.3 (2C; CH$_3$), 11.9 (CH$_3$); ESI-HRMS: calcd. for C$_{70}$H$_{108}$NaO$_{15}$ [M+Na$^+$] 1211.7580; found 1211.7563.

Example 5: Synthesis of (E)-6-(4-(2-((4-((4-((1,3-bis(palmitoyloxy)propan-2-yl)oxy)-4-oxobutanoyl)oxy)benzyl)oxy)-2-oxoethoxy)-6-methoxy-7-methyl-3-oxo-1,3-dihydroisobenzofuran-5-yl)-4-methylhex-4-enoic acid, I-9

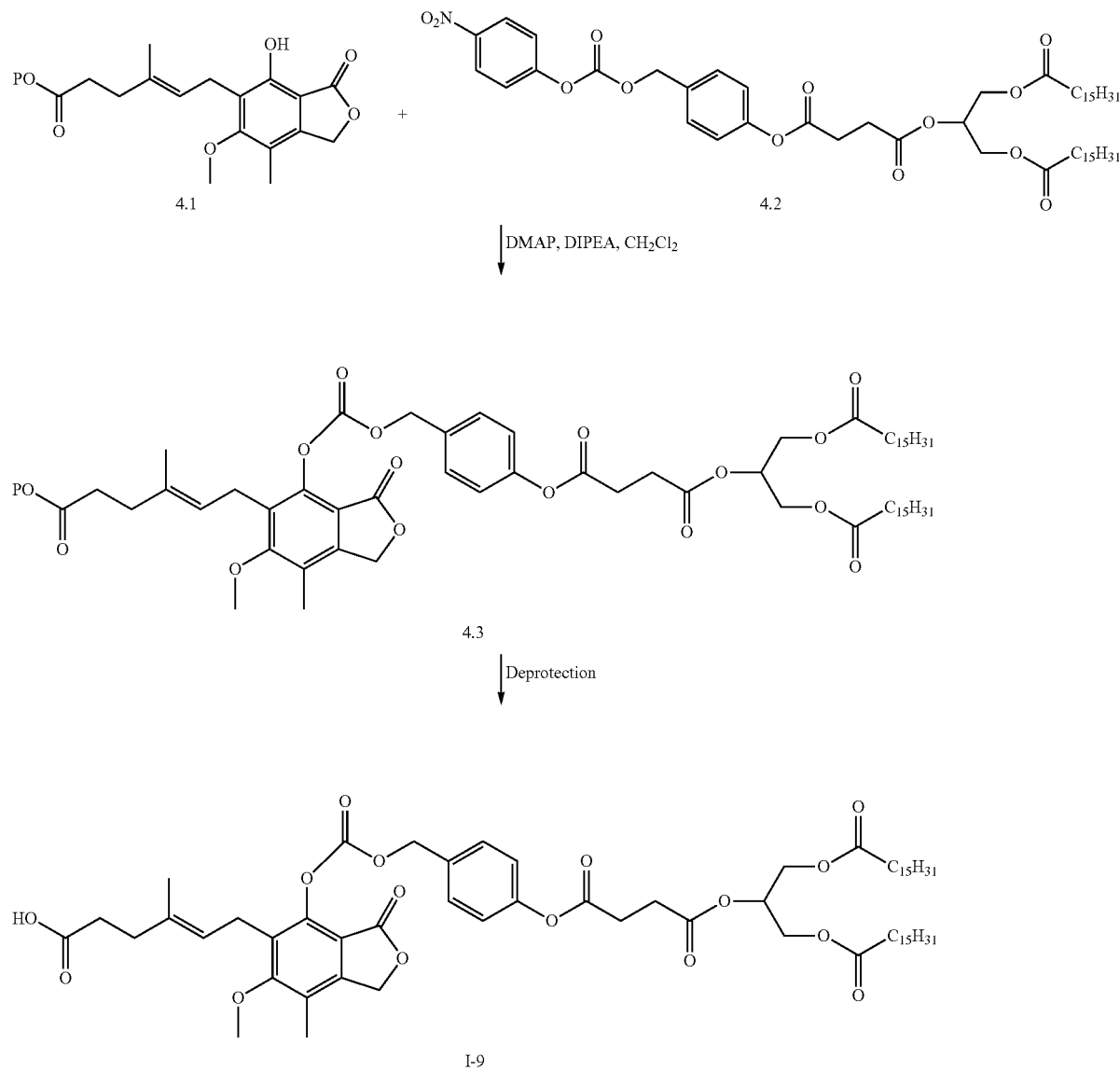

Synthesis of I-9.

I-9 is prepared according to the following procedure. DMAP (1.3 equiv.) and DIPEA (0.3 equiv.) are added to a solution of a suitably protected mycophenolic acid (i.e. where P is a suitable carboxyl protecting group), 4.1 (1.2 equiv.) and PNP carbonate 4.2 (1.0 equiv.) as prepared in WO 2017/041139, in CH$_2$Cl$_2$ (0.01 M) and the mixture stirred at rt for about five days. The reaction is diluted with CH$_2$Cl$_2$, washed with 1 M HCl, water and brine, dried (MgSO$_4$) and concentrated under reduced pressure to give the crude product. Deprotection and purification by silica gel chromatography with a suitable solvent mixture affords 1-9.

Example 6: Synthesis of (E)-6-(4-((4-((4-((1,3-bis (palmitoyloxy)propan-2-yl)oxy)-4-oxobutanoyl)oxy) butanoyl)oxy)-6-methoxy-7-methyl-3-oxo-1,3-dihydroisobenzofuran-5-yl)-4-methylhex-4-enoic acid, I-10

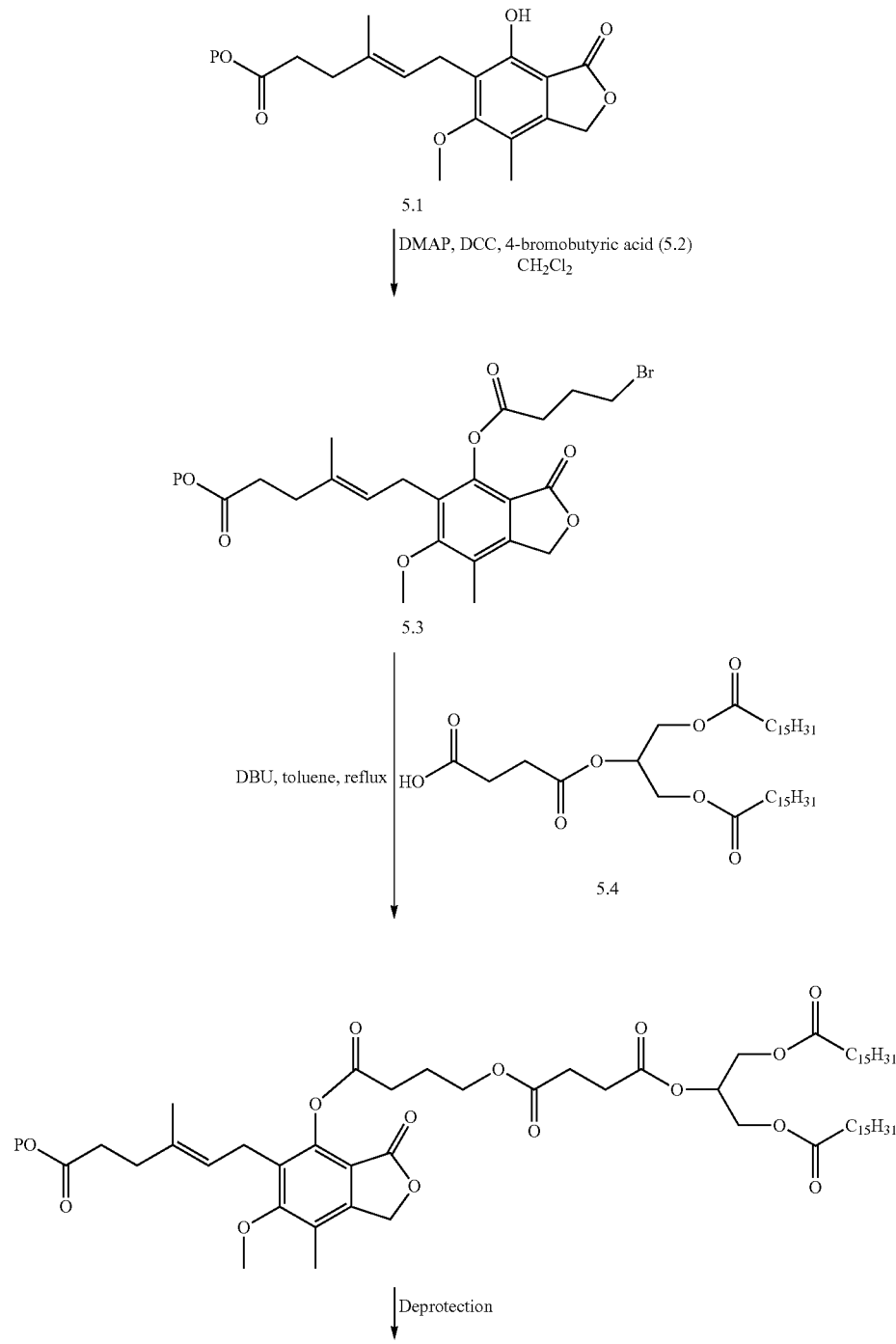

Scheme 39. Synthesis of I-10.

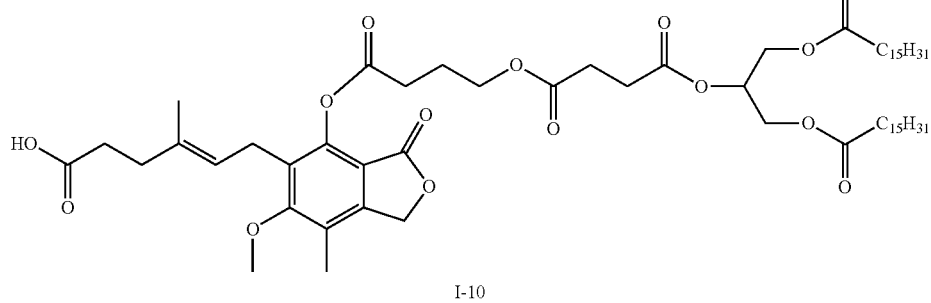

I-10

Synthesis of 5.3.

DMAP (1.3 equiv.) and DCC (2.1 equiv.) are added to a solution of a suitably protected mycophenolic acid (i.e., where P is a suitable carboxyl protecting group) (1.0 equiv.) and 4-bromobutyric acid 5.2 (1.3 equiv.) in $CH_2Cl_2$ (0.03 M) and the mixture is stirred at rt for 24 hours. Another 0.6 eq. of acid, 1 eq. of DCC, 0.6 eq. of DMAP are added and the mixture is stirred at rt for a further two days. The reaction is diluted with $CH_2Cl_2$, silica gel is added, and the mixture is concentrated under reduced pressure. Purification by silica gel chromatography gives bromide 5.3.

Synthesis of I-10.

DBU (1.6 equiv.) is added to a suspension of acid 5.4 (1.1 equiv.) as prepared in WO 2017/041139, and bromide 5.3 (1.0 equiv.) in toluene (0.03 M) and the mixture is heated at reflux for 21 hours. The reaction is cooled to rt, then diluted with ethyl acetate. The organic phase is washed with water and brine, dried ($MgSO_4$) and concentrated under reduced pressure to give the crude product. Deprotection and purification by silica gel chromatography with a suitable solvent mixture affords I-10.

Compounds I-1, I-2, I-3, I-4, I-5, I-11, I-12, I-13, I-14, and I-15 may be prepared by methods substantially similar to those described in Examples 1 through 5, the General Synthetic Schemes provided herein, and methods known to one of ordinary skill in the art.

Example 7: Synthesis of MPA-Phenol Prodrugs

Scheme 40: Synthesis of MPA-phenol prodrugs (directly-linked).

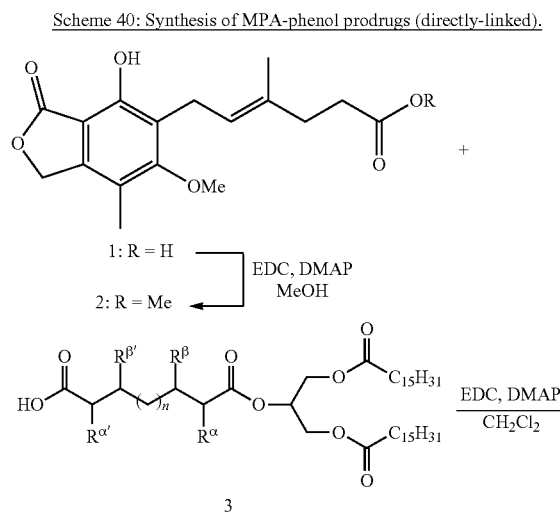

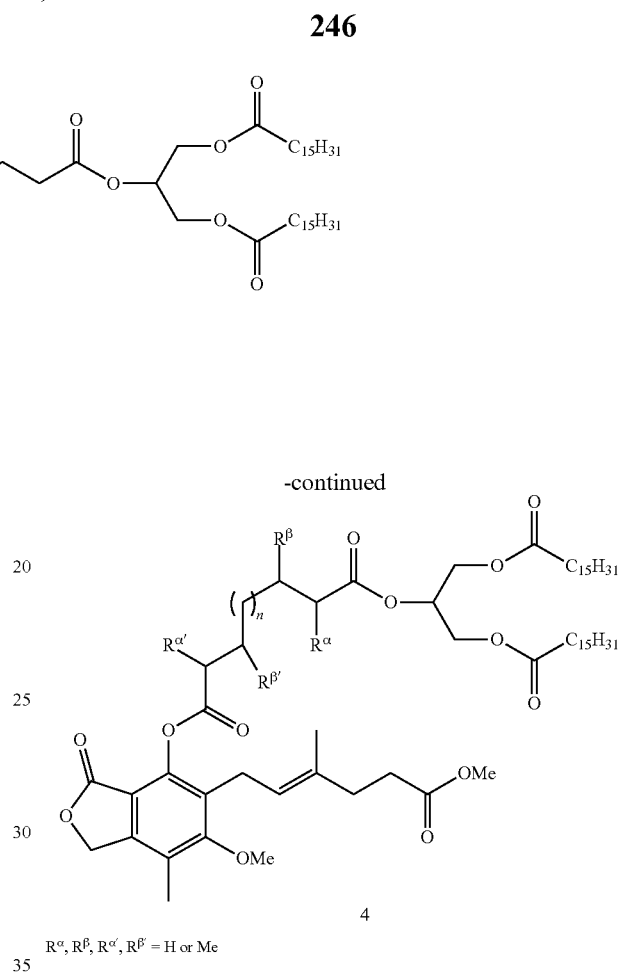

$R^\alpha, R^\beta, R^{\alpha'}, R^{\beta'}$ = H or Me

MPA Methyl Ester (Methyl (E)-6-(4-hydroxy-6-methoxy-7-methyl-3-oxo-1,3-dihydroisobenzofuran-5-yl)-4-methylhex-4-enoate) (2)

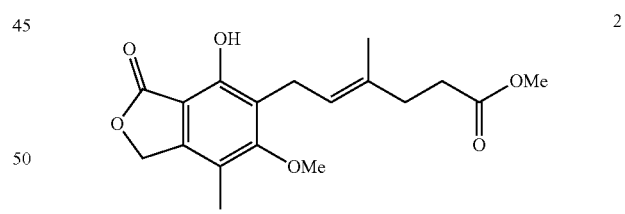

DMAP (95.3 mg, 0.280 mmol) and EDC.HCl (300 mg, 1.56 mmol) were added to a solution of mycophenolic acid (1) (250 mg, 0.780 mmol) in $CH_2Cl_2$ (5 mL) and MeOH (3 mL) and the mixture stirred at rt for 17 hours. The reaction was diluted with $CH_2Cl_2$ (20 mL), silica gel was added and the solvent removed under reduced pressure. Purification by silica gel chromatography (25% to 30% ethyl acetate/hexanes) gave methyl ester 2 (125 mg, 48%) as a colorless solid. $^1$H NMR (401 MHz, CDCl$_3$) δ 7.66 (s, 1H), 5.23 (m, 1H), 5.19 (s, 2H), 3.75 (s, 3H), 3.61 (s, 3H), 3.37 (d, J=6.8 Hz, 2H), 2.42-2.36 (m, 2H), 2.33-2.26 (m, 2H), 2.14 (s, 3H), 1.79 (s, 3H). $^{13}$C NMR (101 MHz, CDCl$_3$) δ 173.9 (C), 173.1 (C), 163.8 (C), 153.8 (C), 144.1 (C), 134.3 (C), 122.9

(CH), 122.3 (C), 116.8 (C), 106.5 (C), 70.2 (CH$_2$), 61.1 (CH$_3$), 51.6 (CH$_3$), 34.7 (CH$_2$), 33.0 (CH$_2$), 22.7 (CH$_2$), 16.2 (CH$_3$), 11.7 (CH$_3$).

(E)-1-(1,3-Bis(palmitoyloxy)propan-2-yl) 10-(6-methoxy-5-(6-methoxy-3-methyl-6-oxohex-2-en-1-yl)-7-methyl-3-oxo-1,3-dihydroisobenzofuran-4-yl) 3-methyldecanedioate (4d; n=4, R$^\beta$=Me) (I-16)

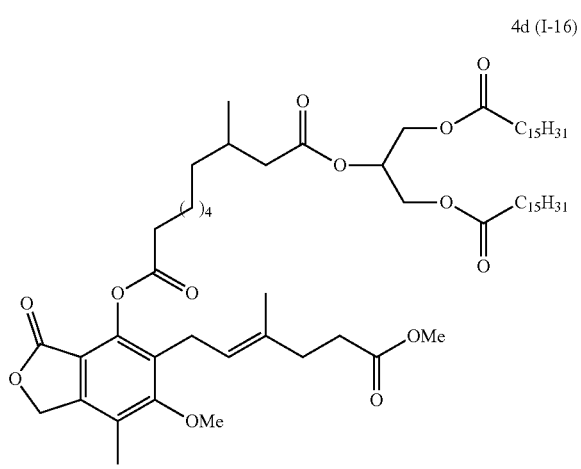

4d (I-16)

DMAP (2.4 mg, 19.6 µmol) and EDC.HCl (9.4 mg, 48.9 µmol) were added to a solution of methyl ester 2 (6.5 mg, 19.6 µmol) and acid-TG Int-30 (15.0 mg, 19.6 µmol) in CH$_2$Cl$_2$ (1.2 mL) and the mixture stirred at RT for 18 hours. The reaction was diluted with CH$_2$Cl$_2$ (5 mL), silica gel was added and the mixture concentrated under reduced pressure. Purification by silica gel chromatography (25% ethyl acetate/hexanes) gave MPA prodrug MPA-(O-C10bMe-2-TG)-OMe (4d) (I-16) (19.3 mg, 91%) as a colorless ml. $^1$H NMR (401 MHz, CDCl$_3$) δ 5.27 (m, 1H), 5.13 (s, 2H), 5.10 (m, 1H), 4.28 (dd, J=12.0, 3.9 Hz, 2H), 4.14 (dd, J=11.9, 5.9 Hz, 2H), 3.78 (s, 3H), 3.62 (s, 3H), 3.33 (d, J=6.5 Hz, 2H), 2.67 (t, J=7.5 Hz, 2H), 2.41-2.25 (m, 9H), 2.21 (s, 3H), 2.11 (dd, J=14.7, 8.6 Hz, 1H), 1.94 (m, 1H), 1.83-1.73 (m, 2H), 1.76 (s, 3H), 1.65-1.55 (m, 4H), 1.49-1.16 (m, 56H), 0.93 (d, J=6.6 Hz, 3H), 0.87 (t, J=6.8 Hz, 6H); $^{13}$C NMR (101 MHz, CDCl$_3$) δ 173.8 (C), 173.4 (2C; C), 172.5 (C), 171.8 (C), 168.4 (C), 162.8 (C), 146.3 (C), 146.2 (C), 134.6 (C), 129.4 (C), 122.9 (C), 122.5 (CH), 113.7 (C), 68.9 (CH), 68.4 (CH$_2$), 62.3 (2C; CH$_2$), 61.3 (CH$_3$), 51.6 (CH$_3$), 41.8 (CH$_2$), 36.8 (CH$_2$), 34.6 (CH$_2$), 34.2 (2C; CH$_2$), 34.0 (CH$_2$), 32.9 (CH$_2$), 32.1 (2C; CH$_2$), 30.5 (CH), 29.84 (6C; CH$_2$), 29.80 (4C; CH$_2$), 29.76 (2C; CH$_2$), 29.62 (3C; CH$_2$), 29.50 (2C; CH$_2$), 29.41 (2C; CH$_2$), 29.30 (CH$_2$), 29.26 (2C; CH$_2$), 26.9 (CH$_2$), 25.0 (2C; CH$_2$), 24.7 (CH$_2$), 23.7 (CH$_2$), 22.8 (2C; CH$_2$), 19.6 (CH$_3$), 16.4 (CH$_3$), 14.3 (2C; CH$_3$), 11.9 (CH$_3$).

Further compounds were prepared in a similar manner as described below.

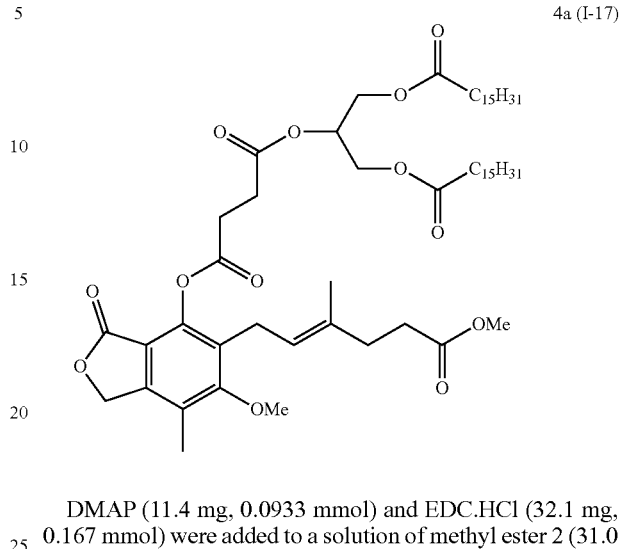

4a (I-17)

DMAP (11.4 mg, 0.0933 mmol) and EDC.HCl (32.1 mg, 0.167 mmol) were added to a solution of methyl ester 2 (31.0 mg, 0.0930 mmol) and acid-TG Int-28 (62.2 mg, 0.0930 µmol) in CH$_2$Cl$_2$ (4 mL) and the mixture stirred at RT for 18 hours. The reaction was diluted with CH$_2$Cl$_2$ (20 mL), washed with water (20 mL), dried (MgSO$_4$) and concentrated under reduced pressure to give the crude product. Purification by silica gel chromatography (15% ethyl acetate/hexanes) gave MPA prodrug MPA-(O-C4-2-TG)-OMe (I-17) (38.5 mg, 42%) as a colorless ml. $^1$H NMR (400 MHz, CDCl$_3$) δ 5.28 (m, 1H), 5.14 (s, 2H), 5.12 (m, 1H), 4.29 (dd, J=11.9, 4.4 Hz, 2H), 4.16 (dd, J=11.9, 5.7 Hz, 2H), 3.78 (s, 3H), 3.61 (s, 3H), 3.35 (d, J=6.8 Hz, 2H), 3.03 (t, J=7.1 Hz, 2H), 2.83 (t, J=7.0 Hz, 2H), 2.41-2.35 (m, 2H), 2.33-2.27 (m, 6H), 2.22 (s, 3H), 1.79 (s, 3H), 1.64-1.55 (m, 4H), 1.37-1.17 (m, 48H), 0.87 (t, J=6.9 Hz, 6H).

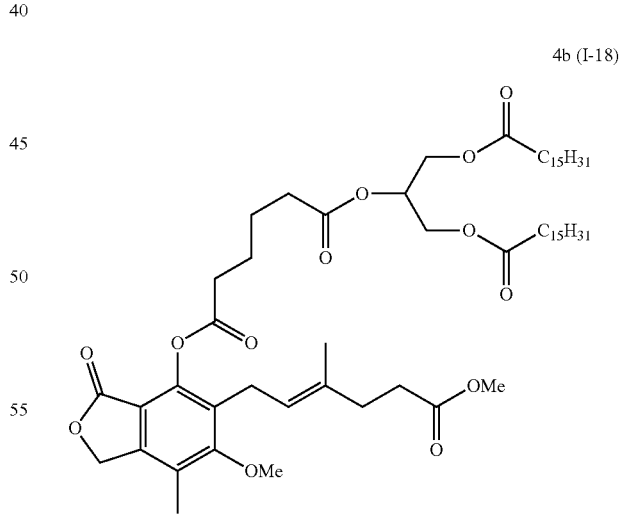

4b (I-18)

DMAP, 6.0 mg, 49.1 µmol) and DCC (19.0 mg, 92.1 µmol) were added to a solution of methyl ester 2 (17.0 mg, 50.8 µmol) and acid-TG Int-29 (35.0 mg, 50.2 µmol) in CH$_2$Cl$_2$ (2 mL) and the mixture stirred at RT for 18 hours. The reaction was diluted with CH$_2$Cl$_2$ (5 mL), silica gel was added and the mixture concentrated under reduced pressure. Purification by silica gel chromatography (20% ethyl acetate/hexanes) gave MPA prodrug MPA-(O-C6-2-TG)-OMe (4b) (I-18) (25.0 mg, 49%) as a colorless oil. $^1$H NMR (400 MHz, CDCl$_3$) δ 5.26 (m, 1H), 5.14 (s, 2H), 5.10 (td, J=6.7, 1.1 Hz, 1H), 4.30 (dd, J=11.9, 4.4 Hz, 2H), 4.15 (dd, J=11.9, 5.8 Hz, 2H), 3.78 (s, 3H), 3.62 (s, 3H), 3.33 (d, J=6.5 Hz, 2H), 2.70 (t, J=6.8 Hz, 2H), 2.44-2.25 (m, 10H), 2.22 (s, 3H), 1.89-1.73 (m, 4H), 1.77 (s, 3H), 1.65-1.55 (m, 4H), 1.33-1.20 (m, 48H), 0.88 (t, J=6.9 Hz, 6H).

4c (I-19)

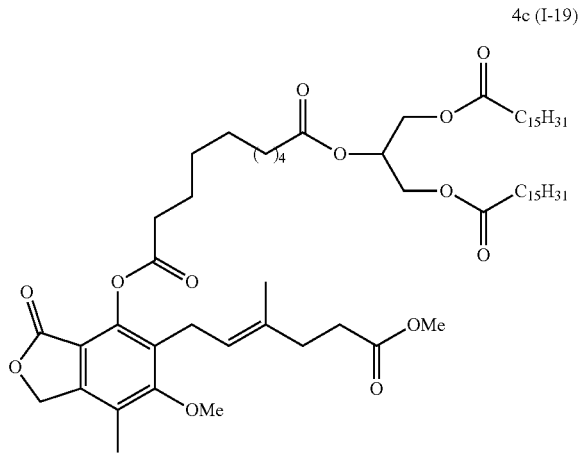

DMAP (5.2 mg, 42.5 μmol) and EDC.HCl (14.1 mg, 73.5 μmol) were added to a solution of methyl ester 2 (12.0 mg, 35.8 μmol) and acid-TG Int-9 (28.0 mg, 19.6 μmol) in CH$_2$Cl$_2$ (0.8 mL) and the mixture stirred at RT for 20 hours. The reaction was diluted with CH$_2$Cl$_2$ (5 mL), silica gel was added and the mixture concentrated under reduced pressure. Purification by silica gel chromatography (10% to 25% ethyl acetate/hexanes) gave MPA prodrug MPA-(O-C10-2-TG)-OMe (4c) (I-19) (30.5 mg, 80%) as a colorless oil. $^1$H NMR (401 MHz, CDCl$_3$) δ 5.26 (m, 1H), 5.13 (s, 2H), 5.10 (td, J=6.7, 1.1 Hz, 1H), 4.29 (dd, J=11.9, 4.4 Hz, 2H), 4.14 (dd, J=11.9, 5.9 Hz, 2H), 3.77 (s, 3H), 3.62 (s, 3H), 3.33 (d, J=6.6 Hz, 2H), 2.67 (t, J=7.6 Hz, 2H), 2.41-2.25 (m, 10H), 2.21 (s, 3H), 1.82-1.73 (m, 2H), 1.76 (s, 3H), 1.68-1.55 (m, 6H), 1.47-1.19 (m, 66H), 0.87 (t, J=6.8 Hz, 6H).

4e (I-20)

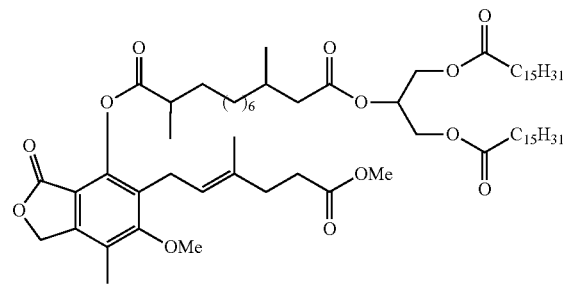

DMAP (2.2 mg, 17.9 μmol) and EDC.HCl (7.1 mg, 37.1 μmol) were added to a solution of methyl ester 2 (6.0 mg, 17.9 μmol) and acid-TG Int-27 (14.5 mg, 17.9 μmol) in CH$_2$Cl$_2$ (1 mL) and the mixture stirred at RT for 18 hours. The reaction was diluted with CH$_2$Cl$_2$ (5 mL), silica gel was added and the mixture concentrated under reduced pressure. Purification by silica gel chromatography (20% ethyl acetate/hexanes) gave MPA prodrug MPA-(O-C12a'bMe-2-TG)-OMe (4e) (I-20) (18.8 mg, 93%) as a colorless oil. $^1$H NMR (401 MHz, CDCl$_3$) δ 5.27 (m, 1H), 5.13 (s, 2H), 5.10 (td, J=6.5, 1.1 Hz, 1H), 4.284/4.282 (each dd, J=11.8, 4.3 Hz, 2H), 4.14 (dd, J=11.8, 6.0 Hz, 2H), 3.77 (s, 3H), 3.61 (s, 3H), 3.32 (hr s, 2H), 2.79 (m, 1H), 2.40-2.34 (m, 2H), 2.33-2.26 (m, 7H), 2.21 (s, 3H), 2.11 (dd, J=14.7, 8.5 Hz, 1H), 1.98-1.85 (m, 2H), 1.76 (s, 3H), 1.65-1.54 (m, 4H), 1.36 (d, J=7.0 Hz, 3H), 1.47-1.16 (m, 61H), 0.93 (d, J=6.6 Hz, 3H), 0.87 (t, J=6.9 Hz, 6H); $^{13}$C NMR (101 MHz, CDCl$_3$) δ 174.6 (C), 173.7 (C), 173.4 (2C; C), 172.5 (C), 168.3 (C), 162.8 (C), 146.3 (C), 146.2 (C), 134.6 (C), 129.4 (C), 122.9 (C), 122.6 (CH), 113.8 (C), 68.9 (CH), 68.3 (CH$_2$), 62.3 (2C; CH$_2$), 61.2 (CH$_3$), 51.6 (CH$_3$), 41.8 (CH$_2$), 39.5 (CH), 36.9 (CH$_2$), 34.5 (CH$_2$), 34.2 (2C; CH$_2$), 33.4 (CH$_2$), 32.9 (CH$_2$), 32.1 (2C; CH$_2$), 30.5 (CH), 29.9 (CH$_2$), 29.82 (6C; CH$_2$), 29.78 (4C; CH$_2$), 29.74 (3C; CH$_2$), 29.68 (CH$_2$), 29.6 (2C; CH$_2$), 29.5 (2C; CH$_2$), 29.4 (2C; CH$_2$), 29.2 (2C; CH$_2$), 27.3 (CH$_2$), 27.1 (CH$_2$), 25.0 (2C; CH$_2$), 23.6 (CH$_2$), 22.8 (2C; CH$_2$), 19.6 (CH$_3$), 16.8 (CH$_3$), 16.5 (CH$_3$), 14.2 (2C; CH$_3$), 11.9 (CH$_3$).

(E)-15-(1,3-bis(palmitoyloxy)propan-2-yl) 1-(6-methoxy-5-(6-methoxy-3-methyl-6-oxohex-2-en-1-yl)-7-methyl-3-oxo-1,3-dihydroisobenzofuran-4-yl) 2,13-dimethylpentadecanedioate (I-29)

4f (I-29)

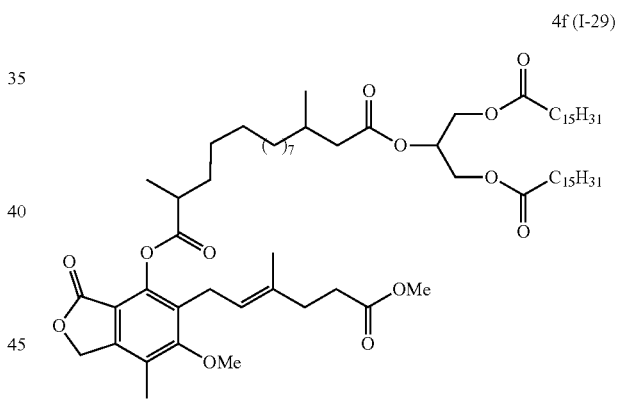

DMAP (4.3 mg, 35.1 μmol) and EDC.HCl (11.8 mg, 61.5 μmol) were added to a solution of methyl ester 2 (10.0 mg, 29.9 μmol) and acid-TG Int-62 (27.5 mg, 32.3 μmol) in CH$_2$Cl$_2$ (0.8 mL) and the mixture stirred at RT for 18 hours. The reaction was diluted with CH$_2$Cl$_2$ (5 mL), silica gel was added, and the mixture was concentrated under reduced pressure. Purification by silica gel chromatography (25% ethyl acetate/hexanes) gave prodrug MPA-(O-C15a'bMe-2-TG)-OMe 4f (I-29) (34.3 mg, 98%) as a colorless oil. $^1$H NMR (401 MHz, CDCl$_3$) δ 5.27 (m, 1H), 5.14 (s, 2H), 5.10 (td, J=6.6, 1.2 Hz, 1H), 4.29 (dd, J=11.9, 4.3 Hz, 2H), 4.14 (td, J=11.9, 6.0 Hz, 2H), 3.77 (s, 3H), 3.62 (s, 3H), 3.32 (hr s, 2H), 2.80 (dd, J=13.9, 7.0 Hz, 1H), 2.41-2.26 (m, 9H), 2.22 (s, 3H), 2.11 (dd, J=14.7, 8.4 Hz, 1H), 1.97-1.86 (s, 2H), 1.76 (s, 3H), 1.65-1.53 (m, 6H), 1.36 (d, J=7.0 Hz, 3H), 1.47-1.15 (m, 69H), 0.92 (d, J=6.6 Hz, 3H), 0.87 (t, J=6.9 Hz, 6H).

251

(E)-1-(1,3-bis(palmitoyloxy)propan-2-yl) 12-(6-methoxy-5-(6-methoxy-3-methyl-6-oxohex-2-en-1-yl)-7-methyl-3-oxo-1,3-dihydroisobenzofuran-4-yl) dodecanedioate (I-30)

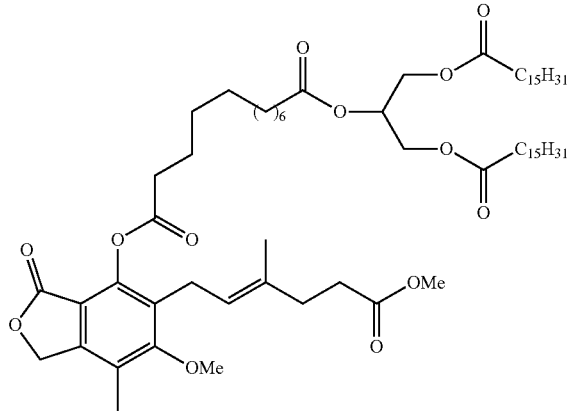

4g (I-30)

DMAP (2.9 mg, 23.9 μmol) and EDC.HCl (11.5 mg, 59.8 μmol) were added to a solution of methyl ester 2 (8.0 mg, 23.9 μmol) and acid-TG Int-37 (22.4 mg, 28.7 μmol) in CH$_2$Cl$_2$ (0.8 mL) and the mixture stirred at RT for 17 hours. The reaction was diluted with CH$_2$Cl$_2$ (5 mL), silica gel was added and the mixture concentrated under reduced pressure. Purification by silica gel chromatography (4% to 8% ethyl acetate/toluene) gave prodrug MPA(O-C12-2-TG)-OMe 4 g (I-30) (9.1 mg, 35%) as a colorless ml. $^1$H NMR (400 MHz, CDCl$_3$) δ 5.26 (m, 1H), 5.14 (s, 2H), 5.10 (td, J=6.7, 1.2 Hz, 1H), 4.29 (dd, J=11.9, 4.4 Hz, 2H), 4.14 (dd, J=11.9, 5.9 Hz, 2H), 3.78 (s, 3H), 3.62 (s, 3H), 3.33 (d, J=6.6 Hz, 2H), 2.67 (t, J=7.6 Hz, 2H), 2.41-2.35 (m, 2H), 2.34-2.27 (m, 8H), 2.22 (s, 3H), 1.83-1.73 (m, 2H), 1.76 (s, 3H), 1.66-1.55 (m, 6H), 1.48-1.20 (m, 60H), 0.88 (t, J=6.9 Hz, 6H); $^{13}$C NMR (101 MHz, CDCl$_3$) δ 173.8 (C), 173.5 (2C; C), 173.0 (C), 171.8 (C), 168.4 (C), 162.8 (C), 146.3 (C), 146.2 (C), 134.6 (C), 129.4 (C), 122.9 (C), 122.5 (CH), 113.8 (C), 69.0 (CH), 68.4 (CH$_2$), 62.2 (2C; CH$_2$), 61.3 (CH$_3$), 51.6 (CH$_3$), 34.6 (CH$_2$), 34.4 (CH$_2$), 34.2 (2C; CH$_2$), 34.0 (CH$_2$), 32.9 (CH$_2$), 32.1 (2C; CH$_2$), 29.85 (6C; CH$_2$), 29.81 (4C; CH$_2$), 29.77 (2C; CH$_2$), 29.62 (4C; CH$_2$), 29.51 (2C; CH$_2$), 29.47 (CH$_2$), 29.44 (CH$_2$), 29.42 (2C; CH$_2$), 29.34 (CH$_2$), 29.27 (3C; CH$_2$), 25.1 (CH$_2$), 25.0 (2C; CH$_2$), 24.8 (CH$_2$), 23.7 (CH$_2$), 22.8 (2C; CH$_2$), 16.4 (CH$_3$), 14.3 (2C; CH$_3$), 11.9 (CH$_3$).

252

(E)-1-(1,3-bis(palmitoyloxy)propan-2-yl) 15-(6-methoxy-5-(6-methoxy-3-methyl-6-oxohex-2-en-1-yl)-7-methyl-3-oxo-1,3-dihydroisobenzofuran-4-yl) 3-methylpentadecanedioate (I-31)

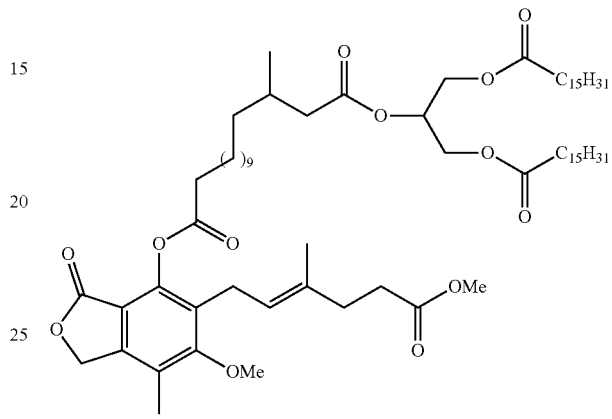

4h (I-31)

DMAP (1.5 mg, 11.9 μmol) and EDC.HCl (5.7 mg, 29.9 μmol) were added to a solution of methyl ester 2 (4.0 mg, 11.9 μmol) and acid-TG Int-49 (12.0 mg, 14.3 μmol) in CH$_2$Cl$_2$ (0.8 mL) and the mixture stirred at RT for five hours. The reaction was diluted with CH$_2$Cl$_2$ (5 mL), silica gel was added, and the mixture concentrated under reduced pressure. Purification by silica gel chromatography (5% to 8% ethyl acetate/toluene) gave prodrug MPA(O-C15bMe-2-TG)-OMe 4h (I-31) (10.8 mg, 78%) as a colorless oil. $^1$H NMR (400 MHz, CDCl$_3$) δ 5.27 (m, 1H), 5.14 (s, 2H), 5.10 (td, J=6.7, 1.2 Hz, 1H), 4.286/4.285 (each dd, J=11.9, 4.2 Hz, 2H), 4.141-4.139 (dd, J=11.9, 6.0 Hz, 2H), 3.78 (s, 3H), 3.62 (s, 3H), 3.33 (d, J=6.5 Hz, 2H), 2.67 (t, J=7.6 Hz, 2H), 2.41-2.25 (m, 5H), 2.30 (t, J=7.6 Hz, 4H), 2.22 (s, 3H), 2.11 (dd, J=14.7, 8.4 Hz, 1H), 1.93 (m, 1H), 1.83-1.73 (m, 2H), 1.76 (s, 3H), 1.65-1.55 (m, 4H), 1.47-1.14 (m, 66H), 0.93 (d, J=6.6 Hz, 3H), 0.87 (t, J=6.8 Hz, 6H); $^{13}$C NMR (101 MHz, CDCl$_3$) δ 173.8 (C), 173.5 (2C; C), 172.5 (C), 171.8 (C), 168.4 (C), 162.8 (C), 146.3 (C), 146.2 (C), 134.6 (C), 129.4 (C), 122.9 (C), 122.5 (CH), 113.8 (C), 68.9 (CH), 68.4 (CH$_2$), 62.3 (2C; CH$_2$), 61.3 (CH$_3$), 51.7 (CH$_3$), 41.9 (CH$_2$), 36.9 (CH$_2$), 34.6 (CH$_2$), 34.2 (2C; CH$_2$), 34.0 (CH$_2$), 32.9 (CH$_2$), 32.1 (2C; CH$_2$), 30.5 (CH), 30.0 (CH$_2$), 29.85 (7C; CH$_2$), 29.81 (4C; CH$_2$), 29.77 (2C; CH$_2$), 29.67 (CH$_2$), 29.62 (2C; CH$_2$), 29.51 (4C; CH$_2$), 29.42 (2C; CH$_2$), 29.36 (CH$_2$), 29.27 (3C; CH$_2$), 27.1 (CH$_2$), 25.0 (2C; CH$_2$), 24.8 (CH$_2$), 23.7 (CH$_2$), 22.8 (2C; CH$_2$), 19.7 (CH$_3$), 16.4 (CH$_3$), 14.3 (2C; CH$_3$), 11.9 (CH$_3$).

(E)-12-(1,3-bis(palmitoyloxy)propan-2-yl) 1-(6-methoxy-7-methyl-5-(3-methyl-6-(2-morpholinoethoxy)-6-oxohex-2-en-1-yl)-3-oxo-1,3-dihydroisobenzofuran-4-yl) 2,10-dimethyldodecanedioate (I-32)

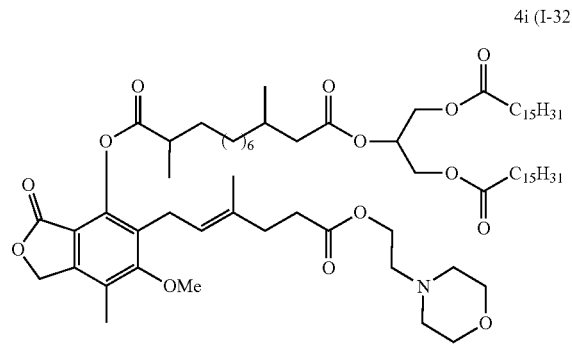

4i (I-32)

DMAP (1.7 mg, 13.6 μmol) and EDC.HCl (6.5 mg, 34.0 μmol) were added to a solution of mofetil (prepared by esterification of MPA with 2-(morpholino)ethanol; see, e.g., US 2010/0298560, hereby incorporated by reference in its entirety) (5.9 mg, 13.6 μmol) and acid-TG Int-27 (11.0 mg, 13.6 μmol) in $CH_2Cl_2$ (0.8 mL) and the mixture stirred at RT for 18 hours. The reaction was diluted with $CH_2Cl_2$ (5 mL), silica gel was added, and the mixture concentrated under reduced pressure. Purification by silica gel chromatography (50% to 75% ethyl acetate/hexanes) gave prodrug MPA-(O-C12a'bMe-2-TG)-OMF 4i (I-32) (11.7 mg, 70%) as a colorless oil. $^1$H NMR (400 MHz, $CD_3OD$) δ 5.31-5.24 (m, 3H), 5.07 (td, J=6.3, 1.0 Hz, 1H), 4.357/4.355 (each dd, J=11.9, 3.8 Hz, 2H), 4.21 (t, J=5.4 Hz, 2H), 4.159/4.155 (each dd, J=12.0, 6.3 Hz, 2H), 3.81 (s, 3H), 3.77-3.68 (m, 4H), 3.37 (d, J=5.0 Hz, 2H), 2.94-2.64 (m, 7H), 2.49-2.41 (m, 2H), 2.36-2.24 (m, 7H), 2.27 (s, 3H), 2.15 (dd, J=14.7, 7.7 Hz, 1H), 1.98-1.84 (m, 2H), 1.80 (s, 3H), 1.66-1.54 (m, 4H), 1.34 (d, J=7.0 Hz, 3H), 1.52-1.19 (m, 62H), 0.96 (d, J=6.7 Hz, 3H), 0.90 (t, J=6.8 Hz, 6H); $^{13}$C NMR (101 MHz, $CD_3OD$) δ 174.8 (2C; C), 170.3 (C), 164.2 (C), 148.5 (C), 147.1 (C), 135.8 (C), 130.4 (C), 124.7 (C), 123.8 (CH), 114.5 (C), 70.6 (CH), 69.9 ($CH_2$), 66.9 (2C; $CH_2$), 63.4 (2C; $CH_2$), 61.9 ($CH_3$), 61.3 ($CH_2$), 57.8 ($CH_2$), 54.5 (2C; $CH_2$), 42.6 ($CH_2$), 40.6 (CH), 37.7 ($CH_2$), 35.3 ($CH_2$), 34.9 ($CH_2$), 34.7 ($CH_2$), 33.5 ($CH_2$), 33.1 ($CH_2$), 31.6 (CH), 30.9 ($CH_2$), 30.82 (6C; $CH_2$), 30.81 (5C; $CH_2$), 30.75 (3C; $CH_2$), 30.6 (2C; $CH_2$), 30.5 (2C; $CH_2$), 30.4 (2C; $CH_2$), 30.2 (2C; $CH_2$), 28.3 ($CH_2$), 28.1 ($CH_2$), 26.0 (2C; $CH_2$), 24.4 ($CH_2$), 23.7 (2C; $CH_2$), 20.2 ($CH_3$), 17.4 ($CH_3$), 16.7 ($CH_3$), 14.5 (2C; $CH_3$), 11.8 ($CH_3$). Note: A number of C=O signals were not observed, while a number of other signals were significantly broadened in both the $^1$H and $^{13}$C NMR spectra. A larger amount of sample will be required to re-acquire the $^{13}$C NMR spectrum to observe all signals; ESI-HRMS: calcd. for $C_{72}H_{122}NO_{14}$ [M+H$^+$]1224.8860; found 1224.8866.

(E)-1-(1,3-bis(palmitoyloxy)propan-2-yl) 12-(6-methoxy-5-(6-methoxy-3-methyl-6-oxohex-2-en-1-yl)-7-methyl-3-oxo-1,3-dihydroisobenzofuran-4-yl) 2,11-dimethyldodecanedioate (I-42)

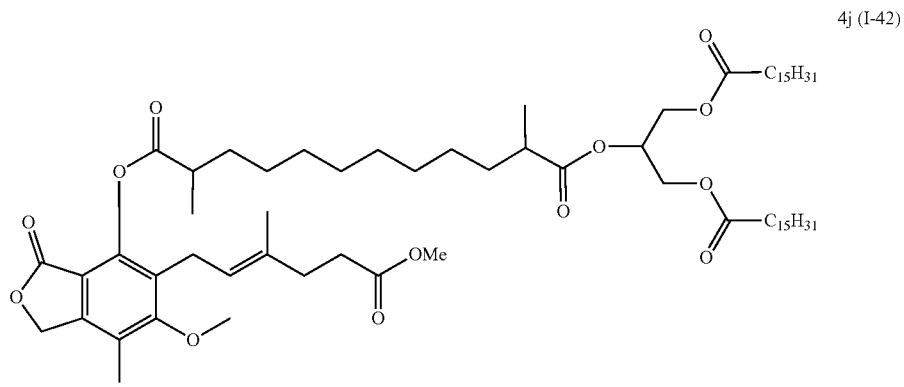

4j (I-42)

To a solution of methyl ester 2 (0.2 g, 0.247 mmol) in chloroform (10 ml) were added DCC (0.101 g, 0.494 mmol) and DMAP (0.060 g, 0.494 mmol), then the reaction mixture was stirred at rt for 30 min, then Int-81 (0.165 g, 0.494 mmol) was added and stirred at rt for 18 h. The reaction was monitored by TLC. After completion of the reaction, the reaction mixture was filtered through a celite bed and washed with DCM (50 mL), then the filtrate was evaporated to obtain crude product, which was purified by combi flash purification to obtain MPA-(O-C12a'αMe-2-TG)-OMe (I-42) (0.080 g, 28.7%) as a viscous liquid. $^1$H NMR (400 MHz, $CDCl_3$) δ 5.30 (t, J=5.3 Hz, 1H), 5.16 (s, 2H,), 5.13 (d, J=16.8 Hz, 1H), 4.31 (dd, J=11.7, 3.7 Hz, 2H), 4.17 (dd, J=11.9, 6.1 Hz, 2H), 3.79 (s, 3H), 3.64 (s, 3H), 3.34 (bs, 2H), 2.82 (q, J=6.9 Hz, 1H), 2.48-2.30 (m, 10H), 2.24 (s, 3H), 1.92 (s, 2H), 1.78 (s, 3H), 1.64-1.52 (m, 10H), 1.39-1.37 (m, 1 OH), 1.28 (m, 48H), 1.16 (d, J=6.8 Hz, 3H), 0.89 (t, J=6.8 Hz, 6H); $^{13}$C NMR (101 MHz, $CDCl_3$) δ 175.96 (1C), 174.55 (1C), 173.65 (1C), 173.32 (2C), 168.19 (1C), 162.63 (1C), 146.22 (1C), 146.01 (1C), 134.53 (1C), 129.32 (1C), 122.80 (1C), 122.47 (2C), 113.72 (1C), 68.69 (1C), 68.26 (1C), 62.16 (1C), 61.15 (1C), 51.55 (1C), 39.55 (1C), 39.39

(1C), 34.38 (1C), 34.07 (2C), 33.65 (1C), 33.33 (1C), 32.74 (1C), 31.96 (3C), 29.73-29.16 (23C), 27.22 (1C), 24.88 (2C), 23.53 (1C), 22.73 (2C), 17.04 (1C), 16.74 (1C), 16.39 (1C), 14.17 (3C), 11.79 (1C). HPLC (ELSD): 9.90 min, 100% purity; HPLC (uv-215 nm): 9.86 min, 99.03% purity; LCMS: 9.22 min 100% purity. MASS (ESI, +ve) m/z: 1143.05 (MH+1). ELSD Method: -PDS_HPLC_GEMINI_C4_JUPITER_GRA-1. Mobile Phase: 100% MeOH; System: Agilent Technologies 1260 Infinity with PDA Detector & ELSD Detector; Column: Phenomenex JUPITER C4, 100*4.6 mm, 5p; Column Flow: 1.0 ml/min; Column Temp: Ambient; ELSD: SPRAY CHAMBER -50° C.

Compound MPA-(O-C10aMe-2-TG)-OMe (I-45) was prepared using similar methods as those described above.

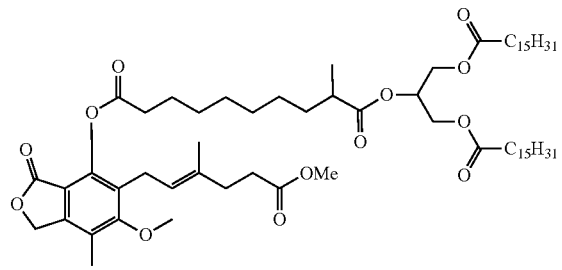

4k (I-45)

$^1$H NMR (400 MHz, CDCl$_3$) δ 5.31 (t, J=4.8 Hz, 1H), 5.18 (s, 2H), 5.14 (m, 1H), 4.31 (dd, J=11.9, 3.9 Hz, 2H), 4.17 (dd, J=11.9, 6.1 Hz, 2H), 3.82 (s, 3H), 3.67 (s, 3H), 3.38 (d, J=6.0 Hz, 2H), 2.71 (t, J=6.8 Hz, 2H), 2.51-2.49 (m, 1H), 2.47 (m, 2H), 2.38 (dt, J=28.8, 7.3 Hz, 6H), 2.26 (s, 3H), 1.81 (s, 4H), 1.69-1.58 (m, 4H), 1.45 (s, 4H), 1.29 (s, 54H), 1.19 (d, J=7.0 Hz, 4H), 0.92 (t, J=6.7 Hz, 6H); $^{13}$C NMR (101 MHz, CDCl$_3$) δ 175.93 (1C), 173.66 (1C), 173.33 (2C), 171.65 (1C), 168.29 (1C), 162.65 (1C), 146.18 (1C), 146.02 (1C), 134.48 (1C), 129.23 (1C), 122.84 (1C), 122.37 (2C), 113.60 (1C), 68.71 (1C), 68.34 (1C), 62.16 (2C), 61.19 (2C), 51.55 (2C), 39.53 (1C), 34.43 (1C), 34.08 (2C), 33.84 (1C), 33.58 (1C), 32.74 (1C), 31.96 (2C), 29.74-28.95 (20C), 27.16 (1C), 24.89 (2C), 24.60 (1C), 23.57 (1C), 22.73 (2C), 17.04 (1C), 16.30 (1C), 14.17 (2C), 11.82 (1C). HPLC (ELSD): 9.42 mm, 100% purity; HPLC (uv-215 nm): 8.95 mm, 96.05% purity; LCMS: 9.08 mm 100% purity; MS (ESI, +ve) m/z: 1101.10 (MH$^+$18). ELSD Method: PDS_HPLC_GEMINI_C4_JUPITER_GRA-1; Mobile Phase: 100% MeOH; System: Agilent Technologies 1260 Infinity with PDA Detector & ELSD Detector; Column: Phenomenex JUPITER C4, 100*4.6 mm, 5p; Column Flow: 1.0 ml/min; Column Temp: Ambient; ELSD: SPRAY CHAMBER -50° C.

MPA-phenol lipid prodrugs such as MPA(O-TML-C12-2-TG)-OMe (I-47), which includes a trimethyl lock SI group, were synthesized in a similar manner, i.e., by coupling of the appropriate carboxylic acid-containing prodrug group with DMAP and EDC.

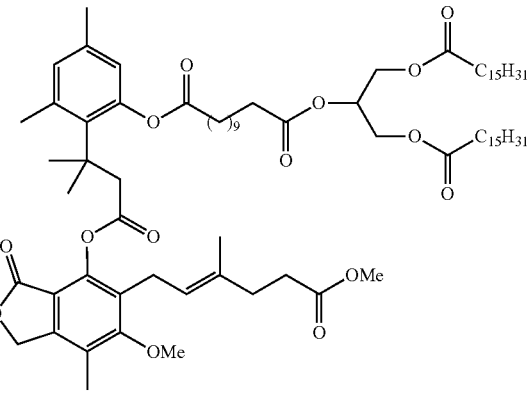

4l (I-47)

I-47 was prepared by coupling methyl ester 2 to the appropriate prodrug intermediate in 80% yield using DMAP and EDC. $^1$H NMR (401 MHz, CDCl$_3$) δ 6.77 (d, J=2.0 Hz, 1H), 6.55 (d, J=1.9 Hz, 1H), 5.26 (m, 1H), 5.10 (s, 2H), 4.98 (m, 1H), 4.29 (dd, J=11.9, 4.4 Hz, 2H), 4.14 (dd, J=11.9, 5.9 Hz, 2H), 3.72 (s, 3H), 3.61 (s, 3H), 3.32 (hr s, 2H), 3.10 (hr d, J=4.9 Hz, 2H), 2.58 (t, J=7.6 Hz, 2H), 2.57 (s, 3H), 2.36-2.20 (m, 10H), 2.19 (s, 3H), 2.17 (s, 3H), 1.79-1.71 (m, 2H), 1.73 (s, 3H), 1.65 (hr s, 6H), 1.67-1.56 (m, 6H), 1.43-1.20 (m, 60H), 0.88 (t, J=6.9 Hz, 6H); $^{13}$C NMR (101 MHz, CDCl$_3$) δ 173.8 (C), 173.4 (2C; C), 173.0 (C), 172.9 (C), 170.1 (C), 168.4 (C), 162.8 (C), 149.8 (C), 146.2 (C), 146.0 (C), 138.2 (C), 136.2 (C), 134.1 (C), 133.5 (C), 132.5 (CH), 129.6 (C), 123.2 (CH), 122.82 (CH), 122.77 (C), 113.6 (C), 69.0 (CH), 68.4 (CH$_2$), 62.2 (2C; CH$_2$), 61.2 (CH$_3$), 51.6 (CH$_3$), 47.1 (CH$_2$), 39.0 (C), 35.2 (CH$_2$), 34.5 (CH$_2$), 34.3 (CH$_2$), 34.2 (2C; CH$_2$), 32.8 (CH$_2$), 32.1 (2C; CH$_2$), 31.5 (2C; CH$_3$), 29.84 (6C; CH$_2$), 29.80 (4C; CH$_2$), 29.77 (2C; CH$_2$), 29.62 (4C; CH$_2$), 29.50 (2C; CH$_2$), 29.48 (CH$_2$), 29.44 (CH$_2$), 29.41 (2C; CH$_2$), 29.38 (CH$_2$), 29.26 (3C; CH$_2$), 25.5 (CH$_3$), 25.03 (CH$_2$), 25.00 (2C; CH$_2$), 24.9 (CH$_2$), 23.5 (CH$_2$), 22.8 (2C; CH$_2$), 20.4 (CH$_3$), 16.4 (CH$_3$), 14.3 (2C; CH$_3$), 11.9 (CH$_3$); ESI-HRMS: calcd. for C$_{78}$H$_{124}$NaO$_{15}$ [M+Na$^+$] 1323.8832; found 1323.8844.

Compound MPA(O-TML-C12a'αMe-2-TG)-OMe (I-52) was prepared using similar methods as those described above and employing Int-122.

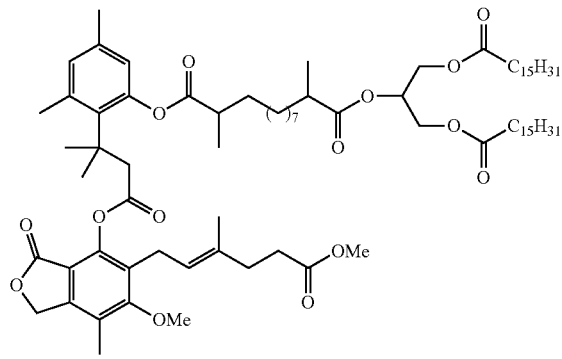

I-52

Note: The ¹H NMR spectrum of this compound suggested the presence of ca. 10% of a related MPA species that could not be removed even after a second attempt at chromatography. ¹H NMR (401 MHz, CDCl$_3$) δ 6.76 (d, J=1.8 Hz, 1H), 6.50 (d, J=1.6 Hz, 1H), 5.26 (m, 1H), 5.10 (s, 2H), 4.97 (m, 1H), 4.291/4.283 (each dd, J=11.8, 4.2 Hz, 2H), 4.14 (dd, J=11.9, 6.1 Hz, 2H), 3.72 (s, 3H), 3.61 (s, 3H), 3.33 (hr s, 2H), 3.12 (hr s, 2H), 2.69 (m, 1H), 2.57 (s, 3H), 2.43 (m, 1H), 2.36-2.27 (m, 6H), 2.25-2.14 (m, 2H), 2.19 (s, 3H), 2.17 (s, 3H), 1.84 (m, 1H), 1.72 (s, 3H), 1.70-1.51 (m, 13H), 1.46-1.19 (m, 63H), 1.13 (d, J=7.0 Hz, 3H), 0.88 (t, J=6.8 Hz, 6H).

Compound MPA(O-C11-2-TG)-OMe (I-48) was prepared using similar methods as those described above.

Compound MPA(O-C12bMe-2-TG)-OMe (I-53) was prepared using similar methods as those described above.

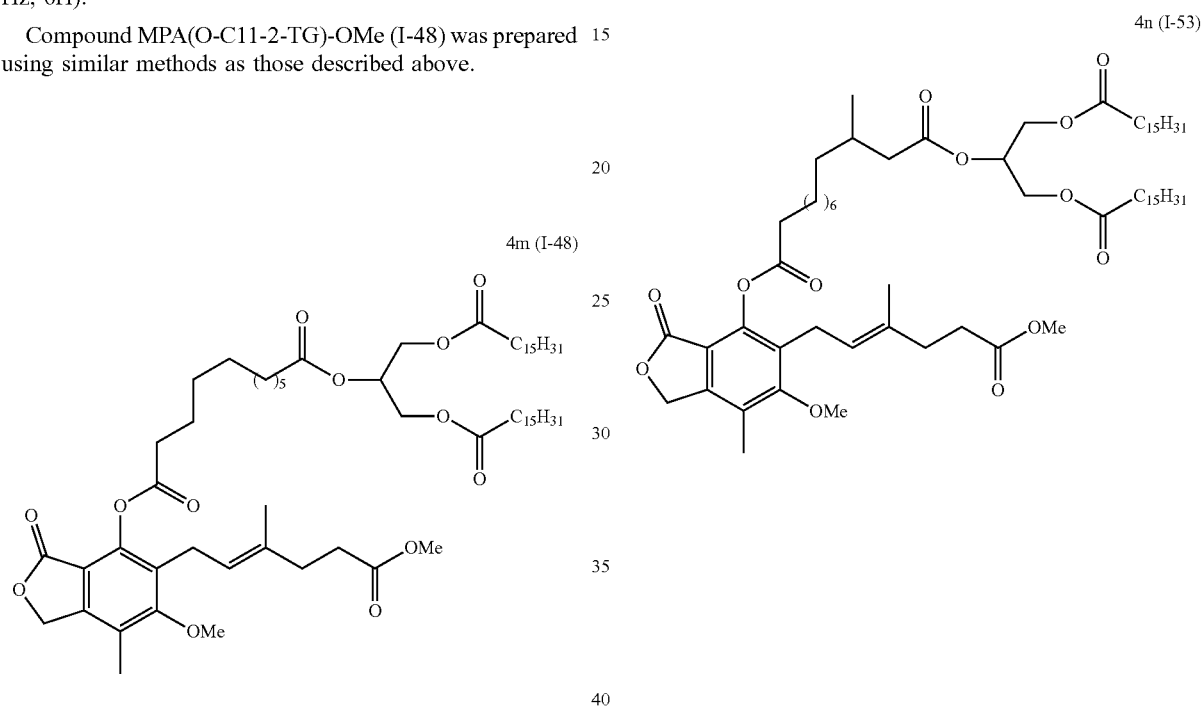

4m (I-48)

4n (I-53)

¹H NMR (401 MHz, CDCl$_3$) δ 5.25 (m, 1H), 5.13 (s, 2H), 5.10 (m, 1H), 4.28 (dd, J=11.9, 4.4 Hz, 2H), 4.14 (dd, J=11.9, 5.9 Hz, 2H), 3.77 (s, 3H), 3.61 (s, 3H), 3.32 (d, J=6.5 Hz, 2H), 2.66 (t, J=7.6 Hz, 2H), 2.40-2.24 (m, 10H), 2.21 (s, 3H), 1.81-1.72 (m, 2H), 1.76 (d, J=0.8 Hz, 3H), 1.66-1.55 (m, 6H), 1.46-1.18 (m, 58H), 0.87 (t, J=6.8 Hz, 6H); ¹³C NMR (101 MHz, CDCl$_3$) δ 173.8 (C), 173.4 (2C; C), 173.0 (C), 171.8 (C), 168.4 (C), 162.8 (C), 146.3 (C), 146.2 (C), 134.6 (C), 129.3 (C), 122.9 (C), 122.5 (CH), 113.7 (C), 69.0 (CH), 68.4 (CH$_2$), 62.2 (2C; CH$_2$), 61.3 (CH$_3$), 51.6 (CH$_3$), 34.5 (CH$_2$), 34.3 (CH$_2$), 34.2 (2C; CH$_2$), 34.0 (CH$_2$), 32.8 (CH$_2$), 32.1 (2C; CH$_2$), 29.83 (6C; CH$_2$), 29.79 (4C; CH$_2$), 29.75 (2C; CH$_2$), 29.60 (2C; CH$_2$), 29.49 (2C; CH$_2$), 29.45 (CH$_2$), 29.42 (CH$_2$), 29.40 (2C; CH$_2$), 29.28 (CH$_2$), 29.24 (2C; CH$_2$), 29.21 (CH$_2$), 25.01 (CH$_2$), 24.99 (2C; CH$_2$), 24.7 (CH$_2$), 23.7 (CH$_2$), 22.8 (2C; CH$_2$), 16.4 (CH$_3$), 14.3 (2C; CH$_3$), 11.9 (CH$_3$); ESI-HRMS: calcd. for C$_{64}$H$_{107}$O$_{13}$ [M+H]$^+$ 1083.7706; found 1083.7710.

¹H NMR (401 MHz, CDCl$_3$) δ 5.27 (m, 1H), 5.13 (s, 2H), 5.10 (m, 1H), 4.284/4.282 (each dd, J=11.8, 4.3 Hz, 2H), 4.139/4.138 (each dd, J=11.9, 6.0 Hz, 2H), 3.77 (s, 3H), 3.62 (s, 3H), 3.33 (d, J=6.5 Hz, 2H), 2.67 (t, J=7.6 Hz, 2H), 2.41-2.25 (m, 9H), 2.21 (s, 3H), 2.11 (dd, J=15.4, 9.2 Hz, 1H), 1.93 (m, 1H), 1.82-1.73 (m, 2H), 1.76 (d, j=0.8 Hz, 3H), 1.65-1.55 (m, 4H), 1.47-1.15 (m, 60H), 0.93 (d, j=6.6 Hz, 3H), 0.87 (t, j=6.9 Hz, 6H); ¹³C NMR (101 MHz, CDCl$_3$) δ 173.8 (C), 173.4 (2C; C), 172.5 (C), 171.8 (C), 168.4 (C), 162.8 (C), 146.3 (C), 146.2 (C), 134.6 (C), 129.4 (C), 122.9 (C), 122.5 (C), 113.7 (C), 68.9 (CH), 68.4 (CH$_2$), 62.3 (2C; CH$_2$), 61.3 (CH$_3$), 51.6 (CH$_3$), 41.8 (CH$_2$), 36.9 (CH$_2$), 34.5 (CH$_2$), 34.2 (2C; CH$_2$), 34.0 (CH$_2$), 32.9 (CH$_2$), 32.1 (2C; CH$_2$), 30.5 (CH), 29.9 (CH$_2$), 29.83 (6C; CH$_2$), 29.79 (4C; CH$_2$), 29.76 (2C; CH$_2$), 29.63 (CH$_2$), 29.61 (2C; CH$_2$), 29.50 (2C; CH$_2$), 29.47 (CH$_2$), 29.40 (2C; CH$_2$), 29.33 (CH$_2$), 29.25 (2C; CH$_2$), 27.1 (CH$_2$), 25.0 (2C; CH$_2$), 24.8 (CH$_2$), 23.7 (CH$_2$), 22.8 (2C; CH$_2$), 19.7 (CH$_3$), 16.4 (CH$_3$), 14.3 (2C; CH$_3$), 11.9 (CH$_3$).

(E)-1-(1,3-bis(palmitoyloxy)propan-2-yl) 15-(6-methoxy-5-(6-methoxy-3-methyl-6-oxohex-2-en-1-yl)-7-methyl-3-oxo-1,3-dihydroisobenzofuran-4-yl) pentadecanedioate (I-57)

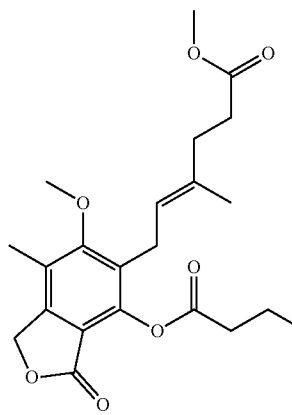
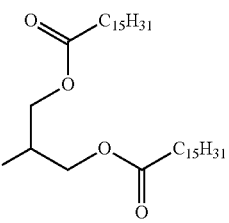

4o (I-57)

DMAP (2.4 mg, 19.4 μmol) and EDC.HCl (9.3 mg, 48.6 μmol) were added to a solution of methyl ester 2 (6.5 mg, 19.4 μmol) and acid-TG Int-129 (19.2 mg, 23.3 μmol) in $CH_2Cl_2$ (1.2 mL) and the mixture stirred at RT for sixteen hours. The reaction was diluted with $CH_2Cl_2$ (5 mL), silica gel was added, and the mixture concentrated under reduced pressure. Purification by silica gel chromatography (20% ethyl acetate/hexanes) gave prodrug MPA(O-C15-2-TG)-OMe 4o (I-57) (21.5 mg, 97%) as a colorless oil. $^1$H NMR (401 MHz, $CDCl_3$) δ 5.26 (m, 1H), 5.14 (s, 2H), 5.10 (m, 1H), 4.29 (dd, J=11.9, 4.3 Hz, 2H), 4.14 (dd, J=11.9, 5.9 Hz, 2H), 3.78 (s, 3H), 3.62 (s, 3H), 3.33 (d, J=6.5 Hz, 2H), 2.67 (t, J=7.6 Hz, 2H), 2.40-2.24 (m, 10H), 2.22 (s, 3H), 1.83-1.73 (m, 2H), 1.76 (s, 3H), 1.67-1.52 (m, 8H), 1.47-1.16 (m, 64H), 0.87 (t, J=6.9 Hz, 6H); $^{13}$C NMR (101 MHz, $CDCl_3$) δ 173.8 (C), 173.4 (2C; C), 173.0 (C), 171.8 (C), 168.4 (C), 162.8 (C), 146.3 (C), 146.2 (C), 134.6 (C), 129.4 (C), 122.9 (C), 122.5 (CH), 113.7 (C), 69.0 (CH), 68.4 ($CH_2$), 62.2 (2C; $CH_2$), 61.3 ($CH_3$), 51.6 ($CH_3$), 34.5 ($CH_2$), 34.4 ($CH_2$), 34.2 (2C; $CH_2$), 34.0 ($CH_2$), 32.9 ($CH_2$), 32.1 (2C; $CH_2$), 29.84 (6C; $CH_2$), 29.80 (7C; $CH_2$), 29.76 (2C; $CH_2$), 29.67 ($CH_2$), 29.66 ($CH_2$), 29.62 (2C; $CH_2$), 29.50 (3C; $CH_2$), 29.46 ($CH_2$), 29.41 (2C; $CH_2$), 29.35 ($CH_2$), 29.25 (3C; $CH_2$), 25.1 ($CH_2$), 25.0 (2C; $CH_2$), 24.8 ($CH_2$), 23.7 ($CH_2$), 22.8 (2C; $CH_2$), 16.4 ($CH_3$), 14.3 (2C; $CH_3$), 11.9 ($CH_3$).

Compound MPA(O-C12αMe-2-TG)-OMe (I-60) was prepared from Int-156 using similar methods to those described above.

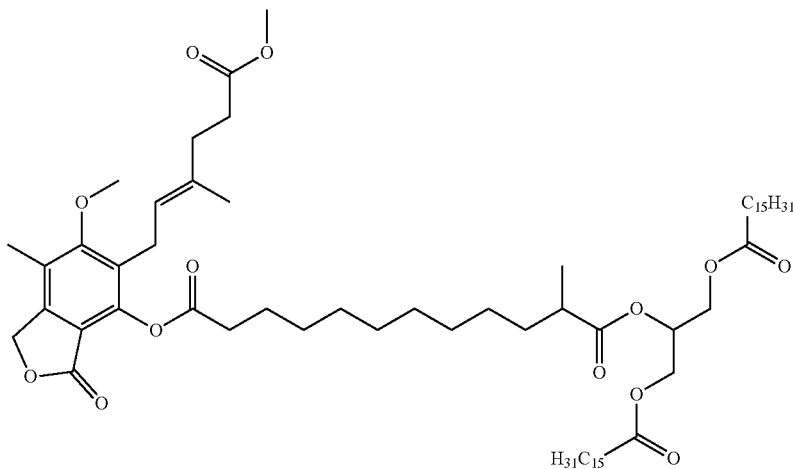

4p (I-60)

$^1$H NMR (400 MHz, $CDCl_3$) δ 5.32 (dq, J=10.3, 5.0 Hz, 1H), 5.18 (s, 2H), 5.16-5.13 (m, 1H), 4.33 (dd, J=11.6, 3.7 Hz, 2H), 4.19 (dd, J=11.9, 6.1 Hz, 2H), 3.82 (s, 3H), 3.67 (s, 3H), 3.37 (d, J=6.7 Hz, 2H), 2.71 (t, J=7.6 Hz, 2H), 2.49 (q, J=6.9 Hz, 1H), 2.47-2.45 (m, 2H), 2.36-20.30 (m, 6H), 2.26 (s, 3H), 1.81 (s, 4H), 1.71-1.59 (m, 4H), 1.46 (t, J=7.5 Hz, 4H), 1.31 (s, 60H), 1.19 (d, J=7.0 Hz, 3H), 0.92 (t, J=6.6 Hz, 6H); $^{13}$C NMR (101 MHz, $CDCl_3$) δ 175.92 (1C), 173.64 (1C), 173.30 (1C), 171.67 (1C), 168.27 (1C), 162.62 (1C), 146.15 (1C), 146.00 (1C), 134.44 (1C), 129.20 (1C), 122.80 (1C), 122.34 (2C), 113.57 (1C), 68.67 (1C), 68.31 (1C), 62.14 (1C), 61.16 (1C), 51.52 (1C), 39.52 (1C), 34.40 (1C), 34.05 (2C), 33.85 (1C), 33.63 (1C), 32.71 (1C), 31.94 (2C), 29.71-29.13 (25C), 27.18 (1C), 24.86 (2C), 24.62 (1C), 23.55 (1C), 22.71 (2C), 17.02 (1C), 16.28 (1C), 14.14 (3C), 11.79 (1C). HPLC (ELSD): 9.67 mm, 100% purity; HPLC (uv-215 nm): 9.64 min, 97.41% purity; LCMS: 9.13 min 100% purity; MS (ESI, +ve) m/z: 1128.80 (MH⁺18).

Compound MPA(O-C10a'αMe-2-TG)-OMe (I-61) was prepared from Int-150 using similar methods as those described above.

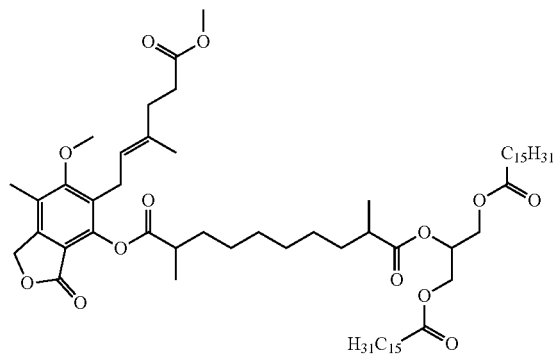

4q (I-61)

¹H NMR (400 MHz, CDCl₃) δ 5.32 (dq, J=10.3, 5.0 Hz, 1H), 5.18 (s, 2H), 5.16-5.13 (m, 1H), 4.31 (dd, J=11.9, 4.4, 2.4 Hz, 2H), 4.17 (dd, J=11.9, 6.0 Hz, 2H), 3.79 (s, 3H), 3.64 (s, 3H), 3.34 (s, 2H), 2.82 (h, J=7.0 Hz, 1H), 2.48-2.38 (m, 3H), 2.30-2.37 (m, 6H), 2.24 (s, 3H), 1.79 (s, 2H), 1.66-1.53 (m, 4H), 1.45 (s, 6H), 1.27 (s, 58H), 1.16 (d, J=6.9 Hz, 3H), 0.90 (t, J=6.7 Hz, 6H); ¹³C NMR (101 MHz, CDCl₃) δ 175.89 (1C), 174.46 (1C), 173.61 (1C), 173.30 (2C), 168.15 (1C), 162.61 (1C), 146.20 (1C), 145.97 (1C) 134.52 (1C), 129.29 (1C), 122.78 (1C), 122.43 (2C), 113.70 (1C), 68.68 (1C), 68.23 (1C), 62.12 (1C), 61.12 (1C), 51.52 (1C), 39.50 (1C), 39.35 (1C), 34.36 (2C), 34.04 (1C), 33.56 (1C), 33.26 (1C), 32.71 (1C), 31.93 (3C), 29.70-29.13 (21C), 27.17 (1C), 24.85 (2C), 23.50 (1C), 22.70 (3C), 17.01 (1C), 16.75 (1C), 16.36 (1C), 14.14 (2C), 11.76 (1C). HPLC (ELSD): 9.52 mm, 100% purity; HPLC (uv-215 nm): 9.48 mm, 100% purity; LCMS: 8.54 min 100% purity; MS (ESI, +ve) m/z: 1114.7 (MH⁺18).

Compound MPA(O-C10ααMe-2-TG)-OMe (I-40) was prepared from Int-151 using similar methods as those described above.

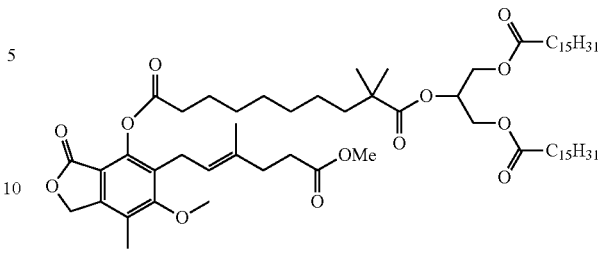

4r (I-40)

¹H NMR (400 MHz, CDCl₃) δ 5.28 (m, 1H), 5.18 (s, 2H) 5.14 (m, 1H), 4.33 (dd, J=11.9, 4.3 Hz, 2H), 4.19 (dd, J=11.9, 5.9 Hz, 2H), 3.82 (s, 3H), 3.66 (s, 3H), 3.34 (d, J=6.0 Hz, 2H), 2.72 (t, J=7.2 Hz 2H), 2.48-2.36 (m, 3H), 2.35 (t, J=7.5 Hz, 6H), 2.26 (s, 3H), 1.81 (m, 6H), 1.57-1.44 (m, 8H), 1.30-1.25 (m, 52H), 1.19 (s, 6H), 0.91 (t, J=6.4 Hz, 6H); ¹³C NMR (101 MHz, CDCl₃) δ 177.06 (1C), 173.66 (1C), 173.29 (2C), 171.64 (1C), 168.27 (1C), 162.63 (1C), 146.15 (2C), 134.45 (1C), 129.20 (1C), 122.81 (1C), 122.34 (1C), 113.58 (1C), 68.76 (1C), 68.32 (1C), 62.12 (1C), 61.17 (1C), 51.54 (1C), 42.38 (1C), 40.45 (2C), 34.41 (1C), 34.06 (2C), 33.83 (1C), 32.71 (1C), 31.95 (2C), 29.72-29.15 (26C), 25.04 (1C), 24.87 (1C), 24.60 (1C), 23.55 (1C), 22.72 (2C), 16.29 (1C), 14.16 (2C), 11.80 (1C); MS (ESI, +ve) m/z: 1115.13 (MH⁺18).

Compound MPA(O-C11αMe-2-TG)-OMe (I-73) was prepared from Int-152 using similar methods as those described above.

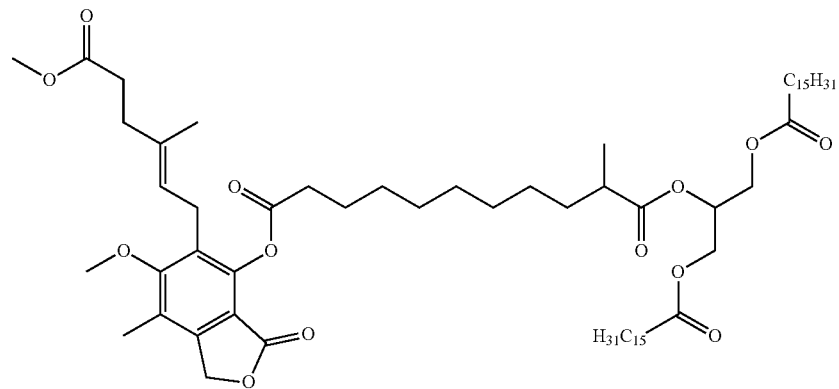

4s (I-73)

¹H NMR (400 MHz, CDCl₃) δ 5.32 (t, J=4.4 Hz, 1H), 5.19 (s, 2H), 5.15 (m, 1H), 4.34 (dd, J=11.9, 4.4 Hz, 2H), 4.19 (dd, J=11.9, 6.1 Hz, 2H), 3.82 (s, 3H), 3.67 (s, 3H), 3.37 (d, J=6.6 Hz, 2H), 2.71 (t, J=7.7 Hz, 2H), 2.54-2.28 (m, 8H), 2.26 (s, 3H), 1.81 (m, 4H), 1.50-1.40 (m, 10H), 1.30 (m, 56H), 1.19 (d, J=6.9 Hz, 3H), 0.92 (t, J=6.6 Hz, 6H); ¹³C NMR (101 MHz, CDCl₃) δ 175.92 (1C), 173.65 (1C), 173.31 (2C), 171.66 (1C), 168.28 (1C), 162.62 (1C), 146.15 (2C), 134.45 (1C), 129.21 (1C), 122.81 (1C), 122.34 (2C), 113.58 (1C), 68.67 (1C), 68.32 (1C), 62.14 (1C), 61.17 (1C), 51.53 (1C), 39.52 (1C), 34.41 (1C), 34.05 (2C), 33.84 (1C), 33.60 (1C), 32.71 (1C), 31.94 (2C), 29.71-29.14 (23C), 27.16 (1C), 25.62 (1C), 24.86 (2C), 24.62 (1C), 23.55 (1C), 22.71 (2C), 17.02 (1C), 16.28 (1C), 14.15 (2C), 11.80 (1C); MS (ESI, +ve) m/z: 1115.14 (MH⁺18).

1-(1,3-bis(oleoyloxy)propan-2-yl) 10-(6-methoxy-5-((E)-6-methoxy-3-methyl-6-oxohex-2-en-1-yl)-7-methyl-3-oxo-1,3-dihydroisobenzofuran-4-yl)decanedioate (I-78)

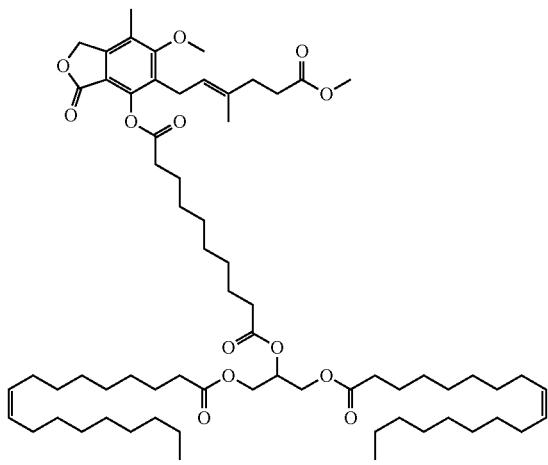

4t (I-78)

DMAP (4.0 mg, 32.9 µmol) and EDC·HCl (15.8 mg, 82.2 µmol) were added to a solution of methyl ester 2 (11.0 mg, 32.9 µmol) and acid-TG Int-113 (27.8 mg, 34.5 µmol) in CH$_2$Cl$_2$ (1.5 mL) and the mixture stirred at RT for 24 hours. The reaction was diluted with CH$_2$Cl$_2$ (5 mL), silica gel was added, and the mixture concentrated under reduced pressure. Purification by silica gel chromatography (20% ethyl acetate/hexanes) gave prodrug MPA(O-C10-2-TG-oleate)-OMe 4t (I-78) as a colorless oil (34.1 mg, 92%). $^1$H NMR (401 MHz, CDCl$_3$) δ 5.38-5.28 (m, 4H), 5.25 (m, 1H), 5.13 (s, 2H), 5.10 (m, 1H), 4.29 (dd, J=11.9, 4.4 Hz, 2H), 4.14 (dd, J=11.9, 5.9 Hz, 2H), 3.78 (s, 3H), 3.62 (s, 3H), 3.33 (d, J=6.6 Hz, 2H), 2.67 (t, J=7.5 Hz, 2H), 2.40-2.26 (m, 10H), 2.21 (s, 3H), 2.04-1.97 (m, 8H), 1.82-1.74 (m, 2H), 1.76 (s, 3H), 1.64-1.55 (m, 6H), 1.48-1.19 (m, 48H), 0.87 (t, J=6.9 Hz, 6H); $^{13}$C NMR (101 MHz, CDCl$_3$) δ 173.8 (C), 173.4 (2C; C), 173.0 (C), 171.8 (C), 168.4 (C), 162.8 (C), 146.3 (C), 146.2 (C), 134.6 (C), 130.1 (2C; CH), 129.9 (2C; CH), 129.4 (C), 122.9 (C), 122.5 (CH), 113.7 (C), 69.0 (CH), 68.4 (CH$_2$), 62.2 (2C; CH$_2$), 61.3 (CH$_3$), 51.6 (CH$_3$), 34.5 (CH$_2$), 34.3 (CH$_2$), 34.2 (2C; CH$_2$), 33.9 (CH$_2$), 32.9 (CH$_2$), 32.0 (2C; CH$_2$), 29.91 (2C; CH$_2$), 29.85 (2C; CH$_2$), 29.7 (2C; CH$_2$), 29.5 (4C; CH$_2$), 29.32 (3C; CH$_2$), 29.25 (4C; CH$_2$), 29.23 (2C; CH$_2$), 29.19 (CH$_2$), 27.4 (2C; CH$_2$), 27.3 (2C; CH$_2$), 25.0 (3C; CH$_2$), 24.7 (CH$_2$), 23.7 (CH$_2$), 22.8 (2C; CH$_2$), 16.4 (CH$_3$), 14.3 (2C; CH$_3$), 11.9 (CH$_3$).

Example 8: Synthesis of MPA-Phenol Prodrugs with CASI/CMSI Group

Scheme 41. Synthesis of MPA-phenol prodrugs with CASI/CMSI group.

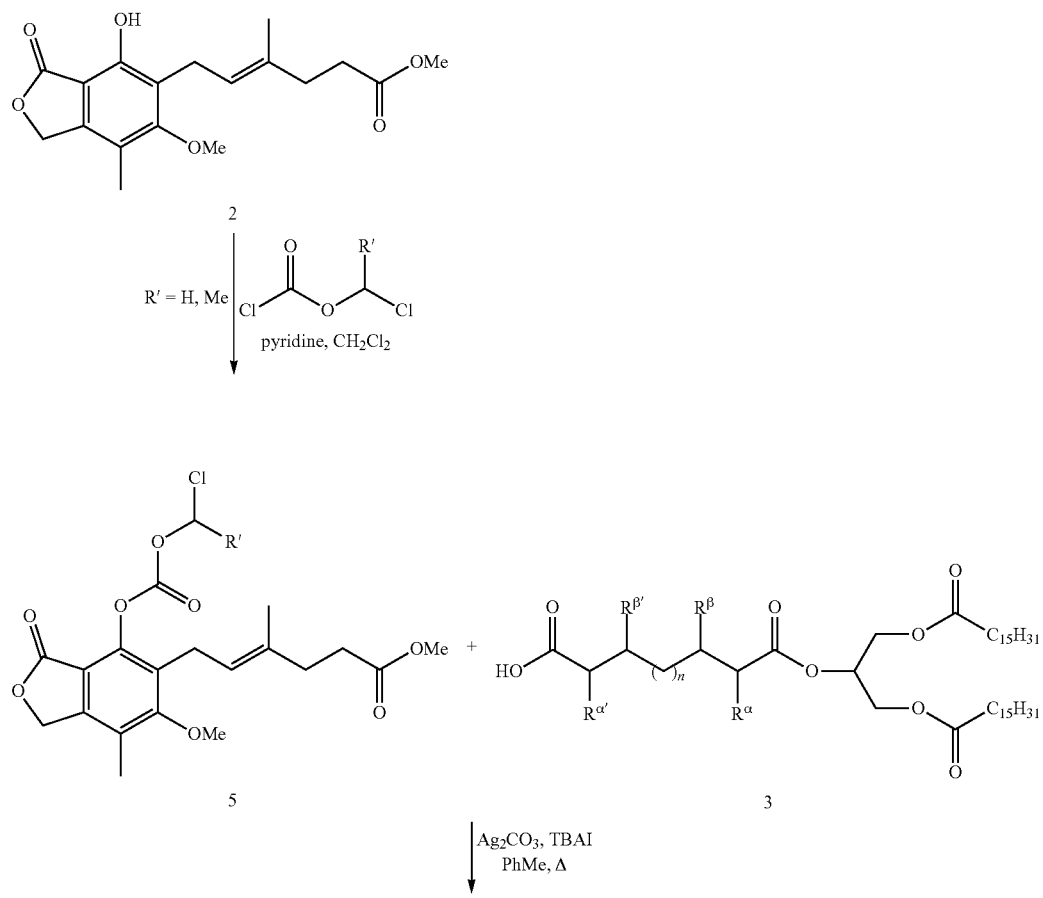

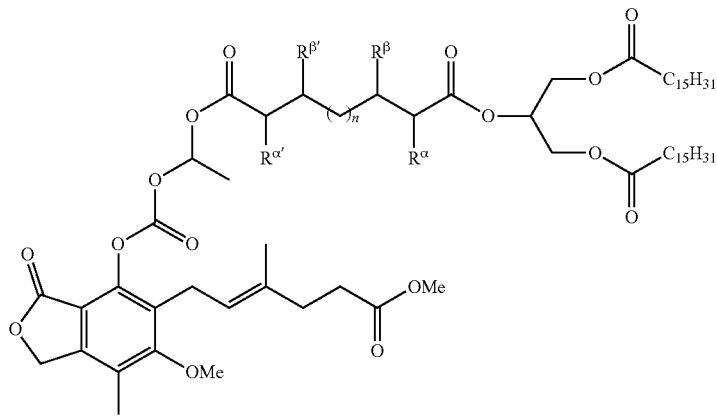

6

Methyl (E)-6-(4-(((chloromethoxy)carbonyl)oxy)-6-methoxy-7-methyl-3-oxo-1,3-dihydroisobenzofuran-5-yl)-4-methylhex-4-enoate (5a; R=H)

Methyl (E)-6-(4-(((1-chloroethoxy)carbonyl)oxy)-6-methoxy-7-methyl-3-oxo-1,3-dihydro-isobenzofuran-5-yl)-4-methylhex-4-enoate (5b; R=Me)

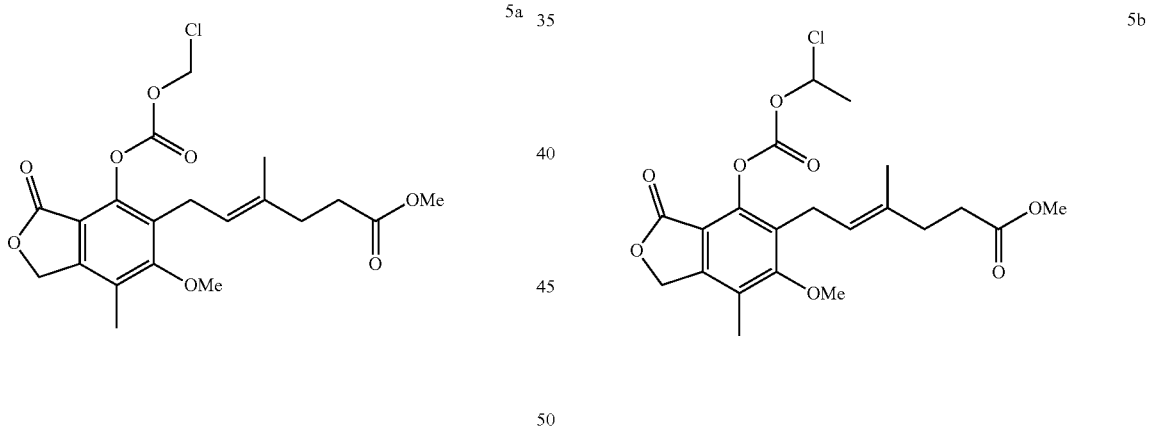

Chloromethyl chloroformate (7.3 µL, 82.2 µmol) and pyridine (12.5 µL, 154 µmol) were added to methyl ester 2 (17.2 mg, 51.4 µmol) in $CH_2Cl_2$ (1.5 mL) at 0° C. and the mixture stirred at 0° C. for 20 minutes and then at RT for one hour. The reaction was diluted with $CH_2Cl_2$ (20 mL) and the organic phase washed with sat. aq. $NaHCO_3$ (3×20 mL) and brine (2×20 mL each), dried ($MgSO_4$) and concentrated under reduced pressure to give chloromethyl carbonate 5a (21.9 mg, quant.) as a colorless oil that was used without purification; NMR (401 MHz, $CDCl_3$) δ 5.85 (s, 2H), 5.18 (s, 2H), 5.10 (m, 1H), 3.81 (s, 3H), 3.62 (s, 3H), 3.41 (d, J=6.8 Hz, 2H), 2.41-2.36 (m, 2H), 2.32-2.26 (m, 2H), 2.25 (s, 3H), 1.78 (d, J=0.8 Hz, 3H).

1-Chloroethyl chloroformate (5.8 µL, 53.8 µmol) and pyridine (6.5 µL, 80.7 µmol) were added to methyl ester 2 (15.0 mg, 44.9 µmol) in $CH_2Cl_2$ (1 mL) at 0° C. and the mixture stirred at 0° C. for five minutes and then at rt for 40 minutes. The reaction was diluted with $CH_2Cl_2$ (30 mL) and the organic phase washed with water and brine (30 mL each), dried ($MgSO_4$) and concentrated under reduced pressure to give chloroethyl carbonate 5b (19.8 mg, quant.) as a colorless oil that was used without purification. $^1$H NMR (401 MHz, $CDCl_3$) δ 6.52 (q, J=5.8 Hz, 1H), 5.18 (s, 2H), 5.11 (td, j=6.9, 1.2 Hz, 1H), 3.80 (s, 3H), 3.62 (s, 3H), 3.46-3.34 (m, 2H), 2.41-2.35 (m, 2H), 2.32-2.25 (m, 2H), 2.24 (s, 3H), 1.94 (d, j=5.8 Hz, 3H), 1.78 (d, j=0.6 Hz, 3H).

267

(E)-12-(1,3-Bis(palmitoyloxy)propan-2-yl) 1-(((((6-methoxy-5-(6-methoxy-3-methyl-6-oxohex-2-en-1-yl)-7-methyl-3-oxo-1,3-dihydroisobenzofuran-4-yl)oxy)carbonyl)oxy)methyl) 2,10-dimethyldodecanedioate (6a) (I-21)

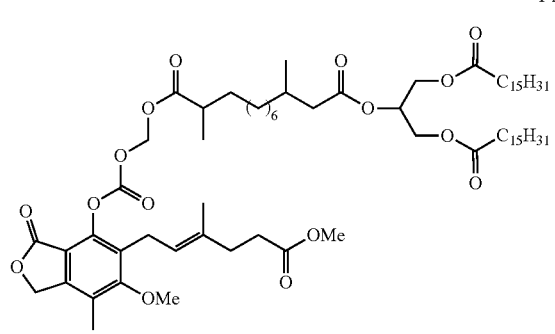

268

Potassium carbonate (13.8 mg, 99.8 μmol) and tetra-n-butylammonium iodide (TBAI, 10.2 mg, 27.6 μmol) were added to a solution of acid-TG Int-27 (50.0 mg, 61.7 μmol) and chloride 5a (24.0 mg, 56.2 μmol) in DMF (2 mL) and the mixture heated at 80° C. for two hours. The reaction was cooled to RT, diluted with water (20 mL) and the aqueous phase extracted with ethyl acetate (3×20 mL). The combined organic extracts were washed with water (2×20 mL), dried (MgSO$_4$) and concentrated under reduced pressure to give the crude product. Silica gel chromatography (5% to 20% ethyl acetate/hexanes) gave MPA-CASI prodrug MPA(O-CASI-C12a$^t$bMe-2-TG)-OMe (6a) (I-21) (8.6 mg, 13%) as a colorless oil. $^1$H NMR (401 MHz, CDCl$_3$) δ 5.91 (d, J=5.6 Hz, 1H), 5.86 (d, J=5.6 Hz, 1H), 5.37 (m, 1H), 5.16 (s, 2H), 5.11 (m, 1H), 4.28 (dd, J=11.8, 4.2 Hz, 2H), 4.14 (dd, J=12.3, 5.1 Hz, 2H), 3.79 (s, 3H), 3.62 (s, 3H), 3.38 (d, J=7.1 Hz, 2H), 2.55 (m, 1H), 2.41-2.26 (m, 9H), 2.23 (s, 3H), 2.10 (dd, J=14.7, 8.5 Hz, 1H), 1.92 (m, 1H), 1.76 (s, 3H), 1.66-1.50 (m, 6H), 1.38-1.23 (m, 60H), 1.21 (d, J=7.0 Hz, 3H), 0.92 (d, J=6.6 Hz, 3H), 0.88 (t, J=6.9 Hz, 6H).

Example 9: Synthesis of MPA-Phenol Prodrugs with FSI5 Group

Scheme 42. Synthesis of MPA-phenol prodrugs with FSI5 group.

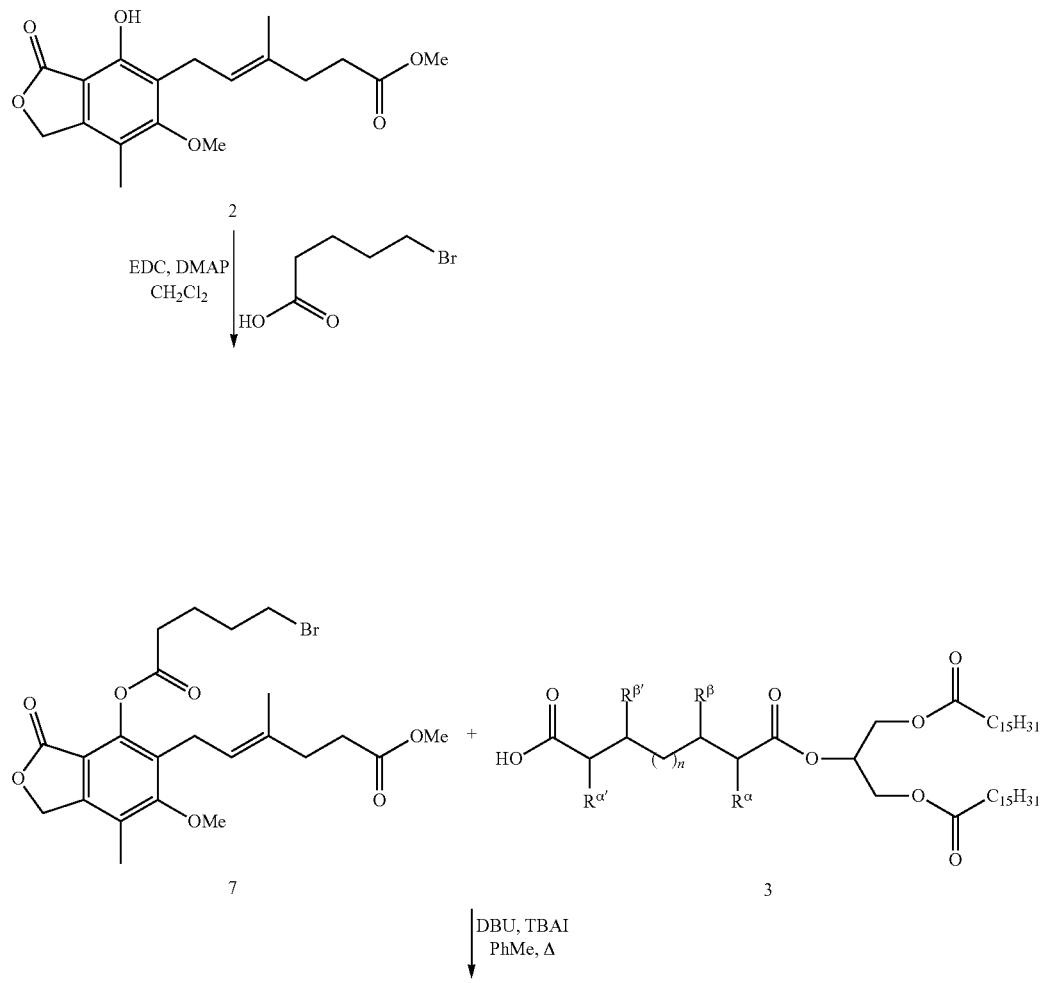

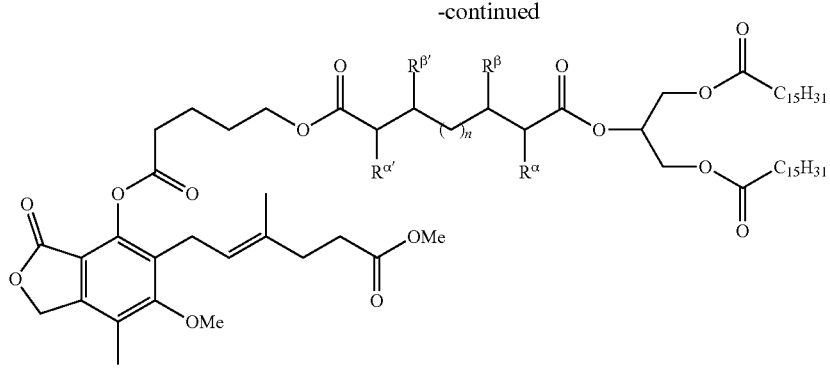

8

Methyl (E)-6-(4-((5-bromopentanoyl)oxy)-6-methoxy-7-methyl-3-oxo-1,3-dihydroisobenzofuran-5-yl)-4-methylhex-4-enoate (7)

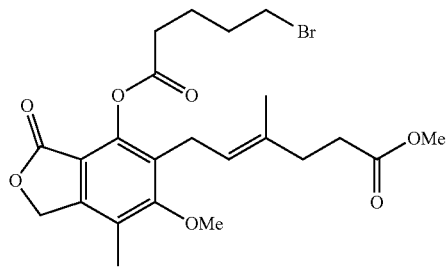

7

DMAP (10.9 mg, 0.0897 mmol) and EDC.HCl (43.0 mg, 0.224 mmol) were added to a solution of 5-bromovaleric acid (24.4 mg, 0.135 mmol) and methyl ester 2 (30.0 mg, 0.0897 mmol) in CH$_2$Cl$_2$ (2 mL) and the mixture stirred at RT for 30 minutes. The reaction was diluted with CH$_2$Cl$_2$ (5 mL), silica gel was added, and the mixture concentrated under reduced pressure. Purification by silica gel chromatography (35% ethyl acetate/hexanes) gave 5-bromovalerate ester 7 (38.1 mg, 85%) as a colorless solid; $^1$H NMR (401 MHz, CDCl$_3$) δ 5.13 (s, 2H), 5.08 (m, 1H), 3.77 (s, 3H), 3.61 (s, 3H), 3.47 (t, J=6.4 Hz, 2H), 3.33 (d, J=6.6 Hz, 2H), 2.71 (t, J=7.0 Hz, 2H), 2.40-2.33 (m, 2H), 2.32-2.25 (m, 2H), 2.21 (s, 3H), 2.07-1.88 (m, 4H), 1.76 (d, J=0.7 Hz, 3H). $^{13}$C NMR (101 MHz, CDCl$_3$) δ 173.7 (C), 171.2 (C), 168.4 (C), 162.8 (C), 146.3 (C), 146.0 (C), 134.7 (C), 129.3 (C), 123.1 (C), 122.4 (CH), 113.6 (C), 68.5 (CH$_2$), 61.3 (CH$_3$), 51.6 (CH$_3$), 34.5 (CH$_2$), 33.4 (CH$_2$), 32.82 (CH$_2$), 32.81 (CH$_2$), 31.9 (CH$_2$), 23.7 (CH$_2$), 23.2 (CH$_2$), 16.4 (CH$_3$), 11.9 (CH$_3$).

(E)-12-(1,3-Bis(palmitoyloxy)propan-2-yl) 1-(5-((6-methoxy-5-(6-methoxy-3-methyl-6-oxohex-2-en-1-yl)-7-methyl-3-oxo-1,3-dihydroisobenzofuran-4-yl)oxy)-5-oxopentyl) 2,10-dimethyldodecanedioate (8a) (I-22)

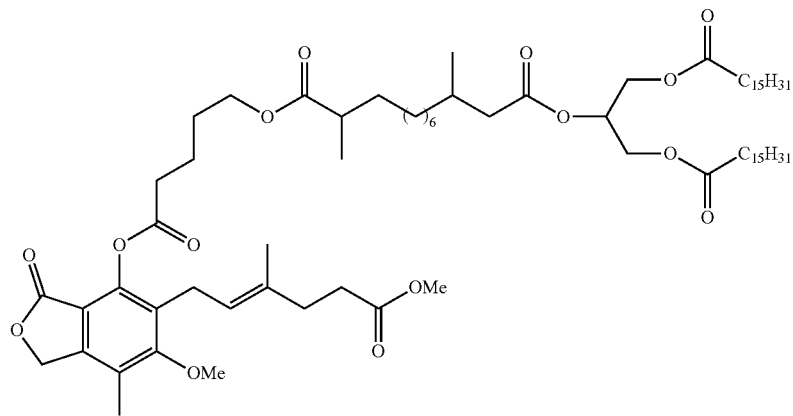

I-22

Silver carbonate (4.3 mg, 15.4 µmol) and tetra-n-butylammonium iodide (TBAI, 3.5 mg, 9.7 µmol) were added to a solution of acid-TG Int-27 (17.2 mg, 21.2 µmol) and bromide 7 (9.6 mg, 19.3 μmol) in toluene (1 mL) and the mixture heated at 90° C. for two hours. The reaction was cooled to RT, diluted with ethyl acetate (40 mL) and the organic phase washed with water and brine (30 mL each), dried (MgSO$_4$) and concentrated under reduced pressure to give the crude product. Silica gel chromatography (20% to 25% ethyl acetate/hexanes) gave MPA-(O-FSI5-C12a'bMe-2-TG)-OMe prodrug 8a (I-22) (17.6 mg, 74%) as a colorless ml; $^1$H NMR (401 MHz, CDCl$_3$) δ 5.27 (m, 1H), 5.14 (s, 2H), 5.10 (td, J=6.6, 1.1 Hz, 1H), 4.28 (dd, J=11.9, 3.6 Hz, 2H), 4.17-4.08 (m, 4H), 3.78 (s, 3H), 3.62 (s, 3H), 3.33 (d, J=6.7 Hz, 2H), 2.73 (t, J=6.5 Hz, 1H), 2.46-2.25 (m, 6H), 2.30 (t, J=7.6 Hz, 4H), 2.22 (s, 2H), 2.10 (dd, J=14.7, 8.4 Hz, 1H), 1.97-1.74 (m, 5H), 1.77 (d, J=0.8 Hz, 3H), 1.70-1.52 (m, 6H), 1.45-1.20 (m, 60H), 1.14 (d, J=7.0 Hz, 3H), 0.92 (d, J=6.6 Hz, 3H), 0.88 (t, J=6.9 Hz, 6H); $^{13}$C NMR (101 MHz, CDCl$_3$) δ 177.1 (C), 173.7 (C), 173.4 (2C; C), 172.5 (C), 171.3 (C), 168.4 (C), 162.8 (C), 146.3 (C), 146.1 (C), 134.7 (C), 129.3 (C), 123.0 (C), 122.5 (CH), 113.7 (C), 68.9 (CH), 68.5 (CH$_2$), 63.9 (CH$_2$), 62.3 (2C; CH$_2$), 61.3 (CH$_3$), 51.7 (CH$_3$), 41.8 (CH$_2$), 39.7 (CH), 36.9 (CH$_2$), 34.5 (CH$_2$), 34.2 (2C; CH$_2$), 33.9 (CH$_2$), 33.4 (CH$_2$), 32.9 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.72 (CH$_2$), 29.68 (CH$_2$), 29.6 (2C; CH$_2$), 29.5 (2C; CH$_2$), 29.4 (2C; CH$_2$), 29.3 (2C; CH$_2$), 28.2 (CH$_2$), 27.4 (CH$_2$), 27.1 (CH$_2$), 25.0 (2C; CH$_2$), 23.7 (CH$_2$), 22.8 (2C; CH$_2$), 21.3 (CH$_2$), 19.7 (CH$_3$), 17.2 (CH$_3$), 16.4 (CH$_3$), 14.3 (2C; CH$_3$), 11.9 (CH$_3$).

(E)-1-(1,3-bis(palmitoyloxy)propan-2-yl) 10-(5-((6-methoxy-5-(6-methoxy-3-methyl-6-oxohex-2-en-1-yl)-7-methyl-3-oxo-1,3-dihydroisobenzofuran-4-yl)oxy)-4-methyl-5-oxopentyl) 3-methyldecanedioate (I-33)

Scheme 43. Synthesis of Additional MPA-phenol prodrugs with FSI5 group.

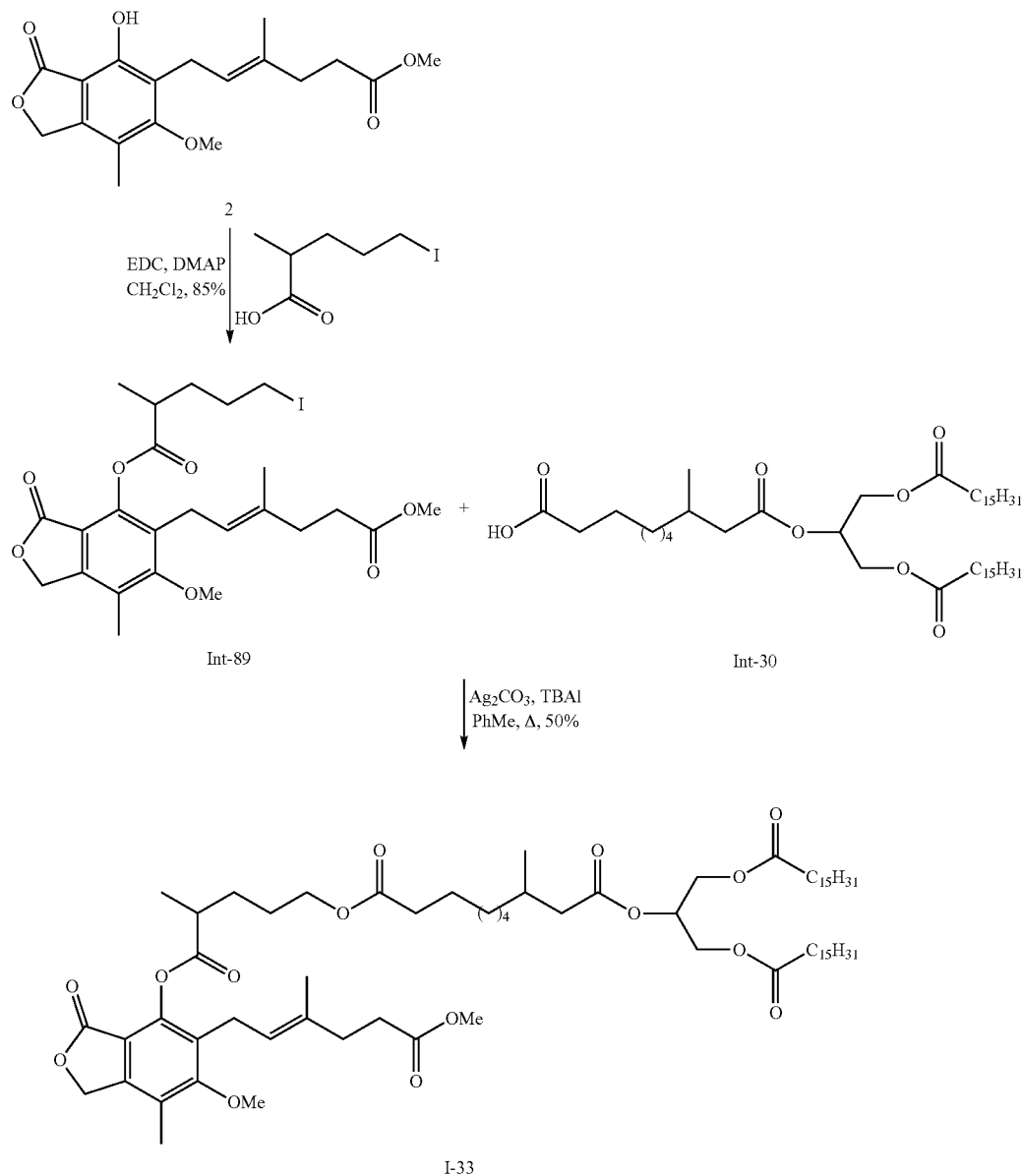

Methyl (E)-6-(4-((5-iodo-2-methylpentanoyl)oxy)-6-methoxy-7-methyl-3-oxo-1,3-dihydroisobenzofuran-5-yl)-4-methylhex-4-enoate (Int-89)

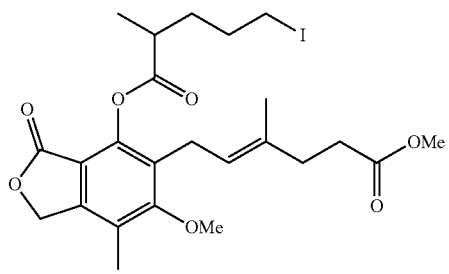

DMAP (3.4 mg, 27.5 μmol) and EDC.HCl (13.2 mg, 68.8 mmol) were added to a solution of 5-iodo-2-valeric acid (9.9 mg, 41.3 mmol) and MPA methyl ester 2 (9.2 mg, 27.5 mmol) in $CH_2Cl_2$ (0.8 mL) and the mixture stirred at RT for 17 hours. The reaction was diluted with $CH_2Cl_2$ (5 mL), silica gel was added, and the mixture concentrated under reduced pressure. Purification by silica gel chromatography (40% ethyl acetate/hexanes) gave semi-pure ester Int-89 (13.0 mg, 85%) as a colorless solid. Note: The quoted yield is not accurate due to significant amounts of inseparable impurities in the sample, presumably carried forward from 5-iodo-2-valeric acid. As a result, the NMR spectra contained a number of additional signals—the major peaks are reported. NMR (401 MHz, $CDCl_3$) δ 5.14 (s, 2H), 5.09 (m, 1H), 3.77 (s, 3H), 3.62 (s, 3H), 3.35-3.22 (m, 4H), 2.83 (m, 1H), 2.40-2.33 (m, 2H), 2.32-2.25 (m, 2H), 2.22 (s, 3H), 2.03-1.93 (m, 2H), 1.77 (s, 3H), 1.67-1.58 (m, 2H), 1.39 (d, J=7.0 Hz, 3H); $^{13}C$ NMR (101 MHz, $CDCl_3$) δ 174.0 (C), 173.7 (C), 168.4 (C), 162.8 (C), 146.4 (C), 146.0 (C), 134.9 (C), 129.5 (C), 123.1 (C), 122.5 (CH), 113.8 (C), 68.4 ($CH_2$), 61.3 ($CH_3$), 51.7 ($CH_3$), 38.6 (CH), 34.5 ($CH_2$), 34.3 ($CH_2$), 32.9 ($CH_2$), 31.0 ($CH_2$), 23.6 ($CH_2$), 17.2 ($CH_3$), 16.6 ($CH_3$), 11.9 ($CH_3$), 6.8 ($CH_2$).

Silver carbonate (2.6 mg, 9.3 μmol) and tetra-n-butylammonium iodide (TBAI, 1.7 mg, 4.7 μmol) were added to a solution of acid-TG Int-30 (9.8 mg, 12.8 μmol) and iodide Int-89 (6.5 mg, 11.6 μmol) in toluene (0.8 mL) and the mixture heated at reflux for two hours. The reaction was cooled to RT, diluted with ethyl acetate (40 mL) and the organic phase washed with water and brine (30 mL each), dried ($MgSO_4$) and concentrated under reduced pressure to give the crude product. Silica gel chromatography (20% to 25% ethyl acetate/hexanes) gave prodrug MPA-(O-FSI5α-C10βMe-2-TG)-OMe (I-33) (6.9 mg, 50%) as a colorless oil. $^1H$ NMR (401 MHz, $CDCl_3$) δ 5.26 (m, 1H), 5.14 (s, 2H), 5.09 (td, J=6.4, 1.0 Hz, 1H), 4.28 (dd, J=12.0, 4.1 Hz, 2H), 4.18-4.06 (m, 4H), 3.77 (s, 3H), 3.62 (s, 3H), 3.32 (br s, 2H), 2.84 (m, 1H), 2.40-2.25 (m, 11H), 2.22 (s, 3H), 2.10 (dd, J=14.7, 8.5 Hz, 1H), 2.01-1.87 (m, 2H), 1.85-1.77 (m, 2H), 1.76 (s, 3H), 1.69-1.52 (m, 7H), 1.39 (d, J=7.0 Hz, 3H), 1.35-1.14 (m, 56H), 0.92 (d, J=6.6 Hz, 3H), 0.88 (t, J=6.8 Hz, 6H); $^{13}C$ NMR (101 MHz, $CDCl_3$) δ 174.2 (C), 174.0 (C), 173.5 (2C; C), 172.5 (C), 168.3 (C), 162.8 (C), 146.4 (C), 146.0 (C), 134.8 (C), 129.4 (C), 123.0 (C), 122.5 (CH), 113.8 (C), 69.0 (CH), 68.4 ($CH_2$), 64.3 ($CH_2$), 62.3 (2C; $CH_2$), 61.3 ($CH_3$), 51.7 ($CH_3$), 41.8 ($CH_2$), 39.2 (CH), 36.8 ($CH_2$), 34.5 ($CH_2$), 34.4 ($CH_2$), 34.2 (2C; $CH_2$), 32.9 ($CH_2$), 32.1 (2C; $CH_2$), 30.5 (CH), 29.85 (6C; $CH_2$), 29.81 (4C; $CH_2$), 29.77 (2C; $CH_2$), 29.6 (3C; $CH_2$), 29.5 (2C; $CH_2$), 29.4 (2C; $CH_2$), 29.34 ($CH_2$), 29.27 (2C; $CH_2$), 26.9 ($CH_2$), 26.4 ($CH_2$), 25.1 ($CH_2$), 25.0 (2C; $CH_2$), 23.6 ($CH_2$), 22.8 (2C; $CH_2$), 19.6 ($CH_3$), 17.1 ($CH_3$), 16.5 ($CH_3$), 14.3 (2C; $CH_3$), 11.9 ($CH_3$). Note: Two signals were not observed in the $^{13}C$ NMR spectrum, possibly due to broadening of signals in proximity to the phenol ester functionality.

(E)-12-(1,3-bis(palmitoyloxy)propan-2-yl) 1-(4-((6-methoxy-5-(6-methoxy-3-methyl-6-oxohex-2-en-1-yl)-7-methyl-3-oxo-1,3-dihydroisobenzofuran-4-yl)oxy)-4-oxobutyl) 2,10-dimethyldodecanedioate (I-62)

Using similar methods, (E)-12-(1,3-bis(palmitoyloxy)propan-2-yl) 1-(4-((6-methoxy-5-(6-methoxy-3-methyl-6-

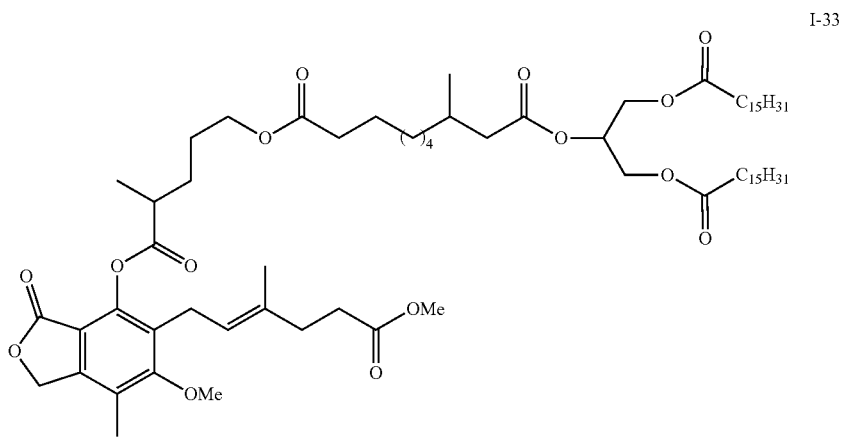

oxohex-2-en-1-yl)-7-methyl-3-oxo-1,3-dihydroisobenzo-furan-4-yl)oxy)-4-oxobutyl) 2,10-dimethyldodecanedioate (I-62) was prepared from methyl ester 2:

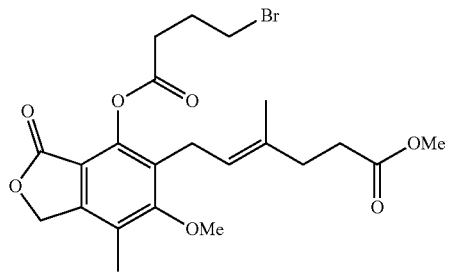

4-(Dimethylamino)pyridine (12.8 mg, 0.105 mmol) and N-(3-dimethylaminopropyl)-N'-ethyl-carbodiimide hydrochloride (EDC.HCl, 60.2 mg, 0.314 mmol) were added to a solution of 4-bromobutyric acid (42.0 mg, 0.251 mmol) and methyl ester 2 (35.0 mg, 0.105 mmol) in $CH_2Cl_2$ (3 mL) and the mixture stirred at RT for 2.5 hours. The reaction was diluted with $CH_2Cl_2$ (5 mL), silica gel was added and the mixture was concentrated under reduced pressure. Purification by silica gel chromatography (40% ethyl acetate/hexanes) gave 4-bromobutyrate ester Int-137 (42.5 mg, 84%) as a colorless oil. $^1$H NMR (401 MHz, $CDCl_3$) δ 5.15 (s, 2H), 5.09 (m, 1H), 3.78 (s, 3H), 3.63 (s, 3H), 3.58 (t, J=6.4 Hz, 2H), 3.34 (d, J=6.6 Hz, 2H), 2.88 (t, J=7.1 Hz, 2H), 2.41-2.24 (m, 6H), 2.22 (s, 3H), 1.78 (d, J=0.8 Hz, 3H).

Synthesis of I-62:

Silver carbonate (8.0 mg, 29.0 μmol) and tetra-n-butylammonium iodide (TBAI, 5.3 mg, 14.5 μmol) were added to a solution of acid-TG Int-27 (24.6 mg, 30.4 μmol) and 4-bromobutyrate ester Int-137 (14.0 mg, 29.0 μmol) in toluene (2 mL) and the mixture heated at reflux for three hours. The reaction was cooled to RT, diluted with ethyl acetate (40 mL) and the organic phase washed with water and brine (40 mL each), dried ($MgSO_4$), and concentrated under reduced pressure to give the crude product. Silica gel chromatography (20% to 25% ethyl acetate/hexanes) gave MPA-(O-FSI4-C12α'βMe-2-TG)-OMe prodrug 1-62 (23.3 mg, 66%) as a colorless oil. $^1$H NMR (401 MHz, $CDCl_3$) δ 5.27 (m, 1H), 5.15 (s, 2H), 5.10 (m, 1H), 4.284/4.282 (each dd, J=11.8, 4.3 Hz, 2H), 4.200/4.196 (each t, J=6.5 Hz, 2H), 4.14 (dd, J=11.9, 6.0 Hz, 2H), 3.78 (s, 3H), 3.62 (s, 3H), 3.34 (d, J=6.6 Hz, 2H), 2.77 (t, J=7.3 Hz, 2H), 2.45 (m, 1H), 2.40-2.25 (m, 9H), 2.22 (s, 3H), 2.18-2.08 (m, 3H), 1.93 (m, 1H), 1.77 (s, 3H), 1.71-1.54 (m, 6H), 1.46-1.19 (m, 60H), 1.16 (d, J=7.0 Hz, 3H), 0.92 (d, J=6.6 Hz, 3H), 0.88 (t, J=6.9 Hz, 6H); $^{13}$C NMR (101 MHz, $CDCl_3$) δ 176.9 (C), 173.4 (2C; C), 172.5 (C), 171.0 (C), 162.8 (C), 146.3 (C), 146.0 (C), 134.7 (C), 129.3 (C), 123.1 (C), 122.4 (CH), 113.6 (C), 68.9 (CH), 68.5 ($CH_2$), 63.2 ($CH_2$), 62.3 (2C; $CH_2$), 61.3 ($CH_3$), 51.6 ($CH_3$), 41.8 ($CH_2$), 39.7 (CH), 36.9 ($CH_2$), 34.5 ($CH_2$), 34.2 (2C; $CH_2$), 33.9 ($CH_2$), 32.8 ($CH_2$), 32.1 (2C; $CH_2$), 30.6 ($CH_2$), 30.5 (CH), 29.93 ($CH_2$), 29.83 (6C; $CH_2$), 29.79 (4C; $CH_2$), 29.76 (2C; $CH_2$), 29.72 ($CH_2$), 29.68 ($CH_2$), 29.6 (2C; $CH_2$), 29.5 (2C; $CH_2$), 29.4 (2C; $CH_2$), 29.3 (2C; $CH_2$), 27.4 ($CH_2$), 27.1 ($CH_2$), 25.0 (2C; $CH_2$), 24.1 ($CH_2$), 23.7 ($CH_2$), 22.8 (2C; $CH_2$), 19.7 ($CH_3$), 17.2 ($CH_3$), 16.4 ($CH_3$), 14.3 (2C; $CH_3$), 11.9 ($CH_3$).

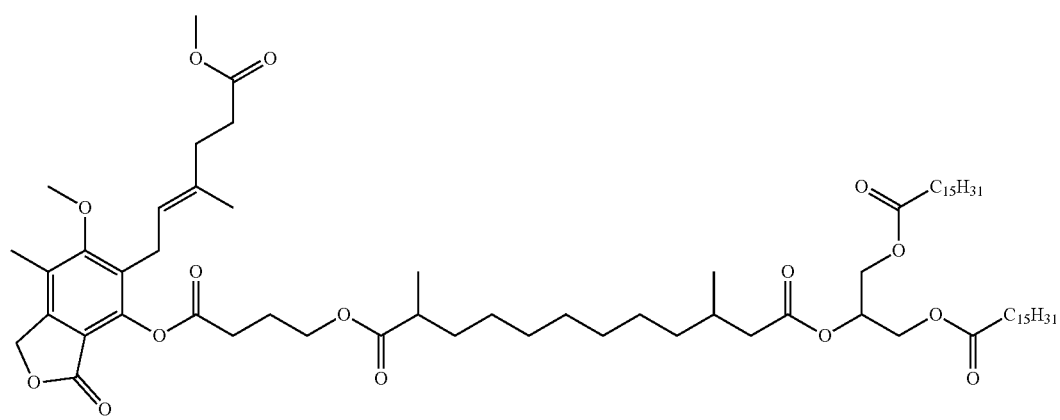

Example 10: Synthesis of MPA-Phenol Prodrugs with ASI Group

Scheme 44. Synthesis of I-41 and other MPA-phenol prodrugs.

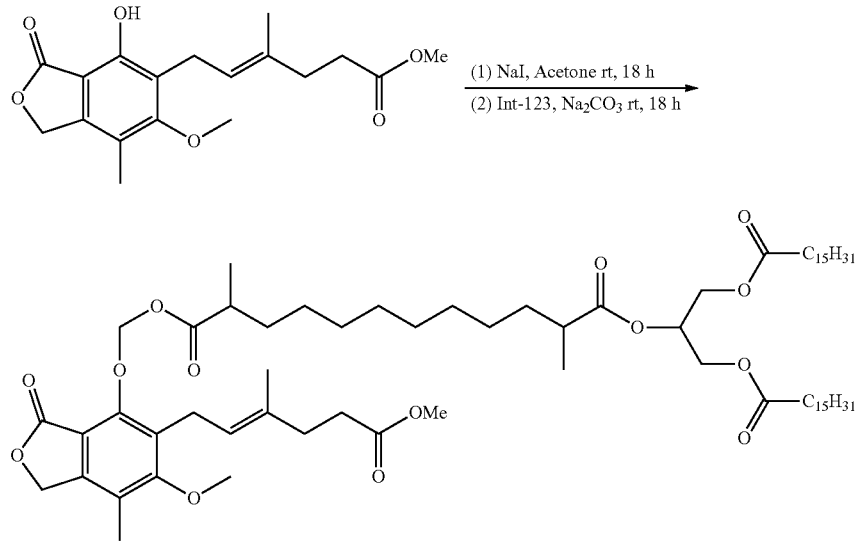

To a solution of compound Int-123 (0.190 g, 0.250 mmol) in acetone (10 ml) was added NaI (0.093 g, 0.626 mmol) at room temperature and the mixture stirred at rt for 18 h. Then mycophenolic acid methyl ester 2 (0.084 g, 0.250 mmol) and sodium carbonate (0.066 g, 0.626 mmol) were added at rt and stirred for 18 h. Progress of the reaction was monitored by TLC/Mass analysis; TLC analysis showed one non-polar spot along with some amount of unreacted 2. Then the reaction mixture was diluted with DCM (25 mL) and filtered through celite and washed with DCM (10 ml). Then the organic layer was directly distilled out at reduced pressure; the resulting crude material was purified by combi flash purification, pure product eluted with 10% ethyl acetate/hexane to obtain pure compound MPA-(O-ASI-C12ααDiMe-2-TG)-OMe (I-41) (50 mg, 17%) as a viscous liquid. $^1$H NMR (400 MHz, CDCl$_3$) δ 6.01 (d, J=6.4 Hz, 1H), 5.96 (d, J=6.4 Hz, 1H), 5.31 (d, J=6.3 Hz, 1H), 5.20 (s, 3H), 4.33 (dd, J=11.9, 4.3 Hz, 2H), 4.18 (dd, J=11.9, 6.0 Hz, 2H), 3.80 (s, 3H), 3.66 (s, 3H), 3.39 (d, J=6.9 Hz, 2H), 2.51-2.34 (m, 12H), 2.23 (s, 3H), 1.81 (s, 2H), 1.61 (s, 15H), 1.35-1.29 (m, 52H), 1.17 (dd, J=11.2, 7.0 Hz, 6H), 0.92 (t, J=6.7 Hz, 6H); $^{13}$C NMR (101 MHz, CDCl$_3$) δ 175.91 (2C), 175.86 (1C), 173.78 (1C), 173.31 (2C), 169.09 (1C), 162.79 (1C), 153.07 (1C), 146.68 (1C), 13.95 (1C), 129.03 (1C), 123.05 (2C), 120.93 (1C), 111.91 (1C), 90.06 (2C), 68.67 (1C), 68.43 (1C), 62.13 (1C), 60.95 (1C), 51.50 (1C), 39.52 (1C), 39.40 (1C), 34.58 (1C), 34.05 (3C), 33.61 (1C), 33.43 (1C), 32.83 (1C), 31.94 (3C), 29.72-29-14 (17C), 27.17 (1C), 24.86 (3C), 23.77 (1C), 22.71 (3C), 17.04 (1C), 16.83 (1C), 16.16 (1C), 14.15 (4C), 11.68 (1C). HPLC (ELSD): 9.73 mm, 100% purity; HPLC (uv-215 nm): 9.69 mm, 97.28% purity; LCMS: 7.91 mm 100% purity. MASS (ESI, +ve) m/z: 1173.10 (MH$^+$18). ELSD Method: PDS_HPLC_GEMINI_C4_JUPITER_GRA-1; Mobile Phase: 100% Methanol; Column: Phenomenex JUPITER C4 (100*4.6) mm, 5p; Column Flow: 1.0 mL/min; Column Temperature: Ambient; ELSD: SPRAY CHAMBER-50° C.

Compound MPA(O-ASI-C12α'bMe-2-TG)-OMe (I-44) was prepared using similar methods.

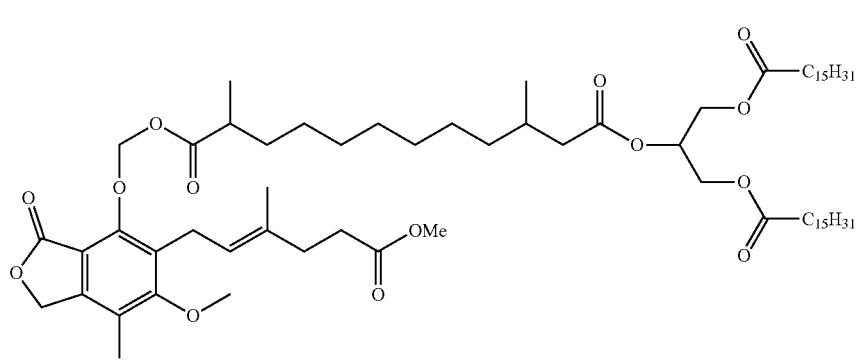

I-44

$^1$H NMR (400 MHz, CDCl$_3$) δ 6.01-5.99 (dd, J=6.4 Hz, 2H), 5.34-5.30 (m, 1H), 5.19 (s, 3H), 4.34-4.30 (dd, J=11.9, 4.3 Hz, 2H), 4.20-4.16 (dd, J=11.9, 6.0 Hz, 2H), 3.80 (s, 3H), 3.65 (s, 3H), 3.40-3.38 (d, J=6.9 Hz, 2H), 2.48-2.40 (m, 4H), 2.38-2.29 (m, 7H), 2.22 (s, 3H), 1.96 (m, 1H), 1.81 (s, 3H), 1.65-1.62 (m, 4H), 1.38-1.24 (m, 4H), 1.29 (m, 57H), 1.15 (d, J=7.0 Hz, 4H), 0.97-0.93 (d, J=7.0 Hz, 3H), 0.91-0.90 (t, J=6.7 Hz, 6H); $^{13}$C NMR (101 MHz, CDCl$_3$) 175.87 (1C), 173.78 (1C), 173.32 (1C), 172.35 (1C), 169.09 (1C), 162.82 (1C), 153.10 (1C), 146.70 (1C), 133.97 (1C), 129.07 (1C), 123.10 (1C), 120.94 (1C), 111.94 (1C), 90.09 (1C), 68.82 (1C), 68.43 (1C), 62.16 (1C), 60.96 (1C), 51.50 (1C), 41.71 (1C), 39.43 (1C), 36.73 (1C), 34.61 (1C), 34.07 (1C), 33.45 (1C), 32.86 (1C), 31.96 (1C), 30.38 (1C), 29.80-29.15 (30C), 27.17 (1C), 26.96 (1C), 24.88 (1C), 23.80 (1C), 22.73 (1C), 19.55 (1C), 16.84 (1C), 16.18 (1C), 14.16 (1C), 11.68 (1C). HPLC (ELSD): 9.77 mm, 98.71% purity; HPLC (uv-215 nm): 9.74 mm, 95.42% purity; LCMS: 8.80 mm 100% purity; MS (ESI, +ve) m/z: 1173.10 (MH$^+$18). ELSD Method: -PDS_HPLC_GEMINI_C4_JUPITER_GRA-1; Mobile Phase: 100% MEOH; System: Agilent Technologies 1260 Infinity with PDA Detector & ELSD Detector. Column: Phenomenex JUPITER C4, 100*4.6 mm, 5p; Column Flow: 1.0 ml/min; Column Temp: Ambient; ELSD: SPRAY CHAMBER -50° C.

Using similar methods to those described above, compound MPA-(O-ET-C2-2-TG)-OMe (I-23) was prepared.

mixture heated at 100° C. for 30 minutes. The reaction was cooled to rt, diluted with ethyl acetate (20 mL) and the organic phase washed with water and brine (20 mL each), dried (MgSO$_4$) and concentrated under reduced pressure to give the crude product. Silica gel chromatography (15% to 20% ethyl acetate/hexanes) gave MPA prodrug 1-23 (10.1 mg, 45%) as a colorless solid. NMR (401 MHz, CDCl$_3$) δ 5.32 (m, 1H), 5.20 (m, 1H), 5.13 (s, 2H), 5.08 (s, 2H), 4.30 (dd, J=12.0, 4.4 Hz, 2H), 4.15 (dd, J=12.0, 5.9 Hz, 2H), 3.77 (s, 3H), 3.60 (s, 3H), 3.56 (d, J=6.8 Hz, 2H), 2.41-2.34 (m, 2H), 2.32-2.26 (m, 6H), 2.17 (s, 3H), 1.78 (s, 3H), 1.68-1.54 (m, 4H), 1.35-1.19 (m, 48H), 0.88 (t, J=6.8 Hz, 6H); $^{13}$C NMR (101 MHz, CDCl$_3$) δ 173.9 (C), 173.4 (2C; C), 169.2 (C), 168.7 (C), 163.1 (C), 154.6 (C), 146.7 (C), 134.0 (C), 129.1 (C), 123.6 (CH), 120.4 (C), 111.4 (C), 71.0 (CH$_2$), 70.0 (CH), 68.7 (CH$_2$), 62.0 (2C; CH$_2$), 61.1 (CH$_3$), 51.6 (CH$_3$), 34.7 (CH$_2$), 34.1 (2C; CH$_2$), 33.0 (CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 24.9 (2C; CH$_2$), 23.9 (CH$_2$), 22.8 (2C; CH$_2$), 16.3 (CH$_3$), 14.3 (2C; CH$_3$), 11.7 (CH$_3$); ESI-HRMS: Calcd. for C$_{55}$H$_{91}$O$_{12}$ [M+H$^+$]943.6505; found 943.6508.

Using similar methods to those described above, compound MPA-(O-ET-C5-2-TG)-OMe (I-24) was prepared.

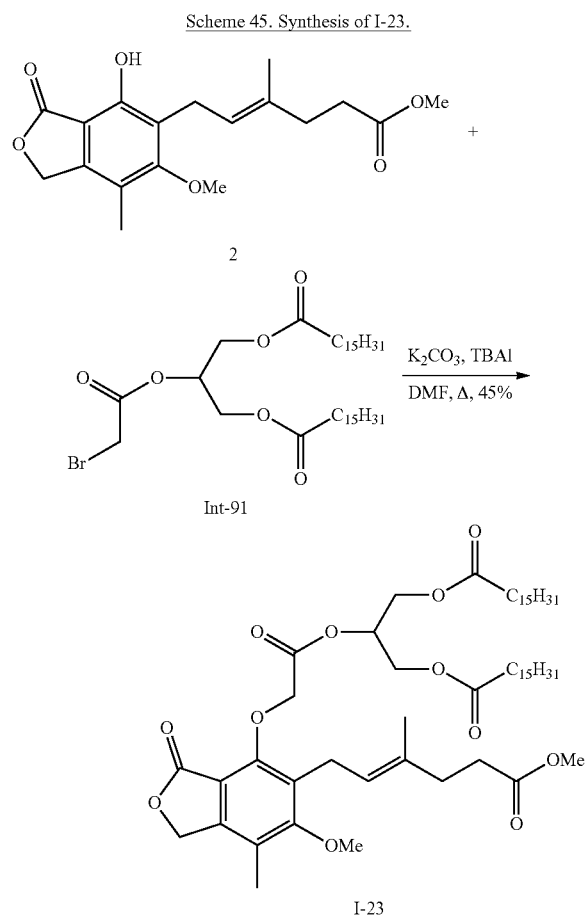

Scheme 45. Synthesis of I-23.

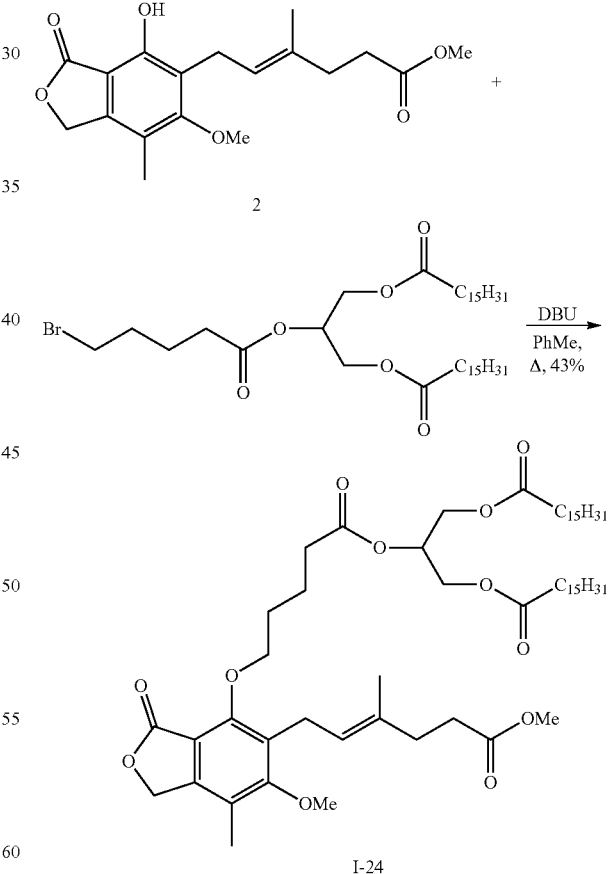

Scheme 46. Synthesis of I-24.

Potassium carbonate (6.6 mg, 47.9 µmol) and tetra-n-butylammonium iodide (4.4 mg, 12.0 µmol) were added to a solution of methyl ester 2 (8.0 mg, 23.9 µmol) and bromide Int-91 (20.1 mg, 31.1 µmol) in DMF (1.5 mL) and the DBU (4.4 µL, 29.6 µmol) was added to a suspension of methyl ester 2 (5.5 mg, 16.4 µmol) and the bromide intermediate above (13.2 mg, 18.1 µmol) in toluene (0.8 mL) and the mixture heated at reflux for two hours. The reaction was cooled to rt, then diluted with ethyl acetate (40 mL). The organic phase was washed with water and brine (30 mL each), dried (MgSO₄) and concentrated under reduced pressure to give the crude product. Silica gel chromatography (15% to 20% ethyl acetate/hexanes) gave MPA prodrug I-24 (7.0 mg, 43%) as a colorless solid. $^1$H NMR (401 MHz, CDCl₃) δ 5.26 (m, 1H), 5.15 (m, 1H), 5.11 (s, 2H), 4.29 (dd, J=11.9, 4.4 Hz, 2H), 4.21 (t, J=6.0 Hz, 2H), 4.14 (dd, J=11.9, 5.9 Hz, 2H), 3.76 (s, 3H), 3.61 (s, 3H), 3.40 (d, J=6.6 Hz, 2H), 2.44 (t, j=7.1 Hz, 2H), 2.41-2.26 (m, 4H), 2.31 (t, J=7.5 Hz, 4H), 2.17 (s, 3H), 1.92-1.81 (m, 4H), 1.79 (s, 3H), 1.67-1.55 (m, 4H), 1.36-1.19 (m, 48H), 0.88 (t, j=6.9 Hz, 6H); $^{13}$C NMR (101 MHz, CDCl₃) δ 173.48 (3C; C), 172.70 (C), 169.07 (C), 163.00 (C), 155.82 (C), 146.85 (C), 133.91 (C), 129.13 (C), 123.89 (CH), 120.00 (C), 112.75 (C), 74.99 (CH₂), 69.11 (CH), 68.37 (CH₂), 65.19 (CH₂), 62.20 (2C; CH₂), 61.07 (CH₃), 51.62 (CH₃), 34.68 (CH₂), 34.26 (CH₂), 34.17 (2C; CH₂), 33.92 (CH₂), 32.97 (CH₂), 32.08 (2C; CH₂), 29.85 (2C; CH₂), 29.81 (2C; CH₂), 29.77 (2C; CH₂), 29.64 (2C; CH₂), 29.51 (3C; CH₂), 29.43 (2C; CH₂), 29.27 (2C; CH₂), 25.00 (2C; CH₂), 23.65 (CH₂), 22.84 (2C; CH₂), 21.41 (CH₂), 16.39 (CH₃), 14.27 (2C; CH₃), 11.68 (CH₃); ESI-HRMS: Calcd. for $C_{58}H_{97}O_{12}$ [M+H⁺] 985.6975; found 985.6971.

Example 11: Synthesis of (E)-2-(4-((6-(4-hydroxy-6-methoxy-7-methyl-3-oxo-1,3-dihydroisobenzo-furan-5-yl)-4-methylhex-4-enoyl)oxy)butoxy)propane-1,3-diyl dipalmitate (I-25) and (E)-2-((6-((6-(4-hydroxy-6-methoxy-7-methyl-3-oxo-1,3-dihydroisobenzofuran-5-yl)-4-methylhex-4-enoyl)oxy)hexyl)oxy)propane-1,3-diyl dipalmitate (I-25 and I-26)

Synthesis of Int-82:

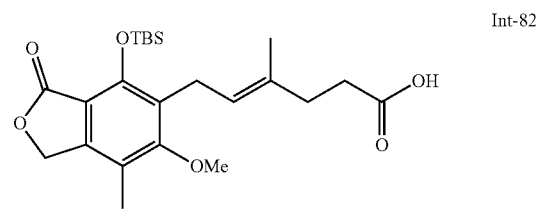 [SMILES: COc1c(C)c2c(c(O[Si](C)(C)C(C)(C)C)c1C/C=C(\C)CCC(=O)O)C(=O)OC2]

Imidazole (128 mg, 1.87 mmol) and tert-butyl(chloro)dimethylsilane (TBSCl, 141 mg, 0.937 mmol) were added to a solution of mycophenolic acid (MPA, 200 mg, 0.624 mmol) in DMF (7 mL) and the mixture stirred at rt for 22 hours. Extra portions of imidazole (65.0 mg, 0.954 mmol) and TBSCl (80.0 mg, 0.531 mmol) were added and the mixture stirred at rt for an additional two days and 18 hours. The reaction was diluted with ethyl acetate (20 mL) and water (30 mL) and the aqueous phase extracted with ethyl acetate (3×30 mL). The combined organic extracts were washed with water and brine (80 mL each), dried (MgSO₄) and concentrated under reduced pressure to give the crude product. Purification by silica gel chromatography (10% to 35% ethyl acetate/hexanes) gave MPA(OTBS) Int-82 (164 mg, 60%) as a colorless solid. $^1$H NMR (400 MHz, CDCl₃) δ 5.19 (m, 1H), 5.06 (s, 2H), 3.73 (s, 3H), 3.38 (d, J=6.3 Hz, 2H), 2.46-2.36 (m, 2H), 2.33-2.24 (m, 2H), 2.14 (s, 3H), 1.75 (s, 3H), 1.02 (s, 9H), 0.23 (s, 6H); $^{13}$C NMR (101 MHz, CDCl₃) δ 179.4 (C), 169.4 (C), 163.3 (C), 151.9 (C), 146.2 (C), 133.5 (C), 127.7 (C), 124.0 (CH), 118.1 (C), 111.8 (C), Scheme 47. Synthesis of I-25.

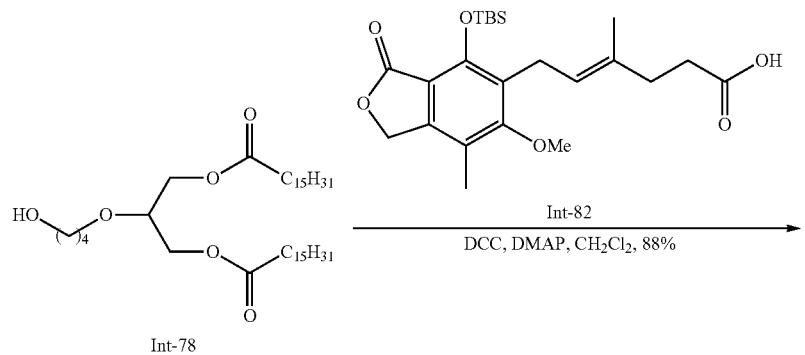

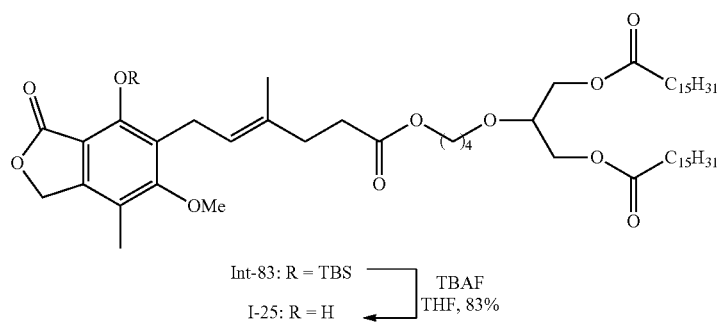

67.8 (CH$_2$), 60.8 (CH$_3$), 34.2 (CH$_2$), 32.9 (CH$_2$), 26.2 (3C; CH$_3$), 23.8 (CH$_2$), 18.9 (C), 16.4 (CH$_3$), 11.5 (CH$_3$), −3.4 (2C; CH$_3$).

Synthesis of Int-83:

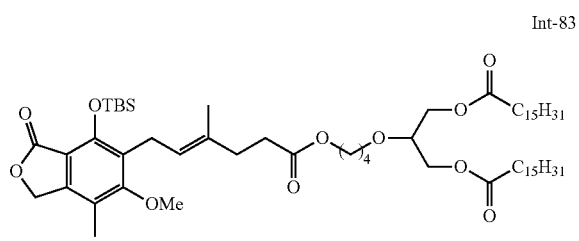

DMAP (5.0 mg, 40.6 µmol) and DCC (11.7 mg, 56.9 µmol) were added to a solution of acid Int-82 (17.8 mg, 40.6 µmol) and alcohol Int-78 (26.0 mg, 40.6 µmol) in CH$_2$Cl$_2$ (1.5 mL) and the mixture stirred at rt for 16 hours. To ensure complete reaction, extra portions of DMAP (4 mg) and DCC (8 mg) were added and stirring continued at rt for a further five hours. The resulting suspension was diluted with CH$_2$Cl$_2$ (15 mL), cooled to 0° C. and filtered through Celite, washing with further CH$_2$Cl$_2$ (50 mL). The organic phase was washed with 1 M HCl, water, sat. aq. NaHCO$_3$ and brine (60 mL each), dried (MgSO$_4$) and concentrated under reduced pressure to give the crude product. Silica gel chromatography (12.5% to 17.5% ethyl acetate/hexanes) gave protected MPA triglyceride Int-83 (37.8 mg, 88%) as a colorless oil. $^1$H NMR (400 MHz, CDCl$_3$): δ 5.17 (dt, J=6.5, 3.2 Hz, 1H), 5.06 (s, 2H), 4.18 (dd, J=11.6, 4.9 Hz, 2H), 4.10 (dd, J=11.6, 5.5 Hz, 2H), 4.03 (t, J=6.4 Hz, 2H), 3.73 (s, 3H), 3.67 (m, 1H), 3.56 (t, J=6.1 Hz, 2H), 3.37 (d, J=6.3 Hz, 2H), 2.41-2.22 (m, 8H), 2.15 (s, 3H), 1.75 (s, 3H), 1.70-1.53 (m, 8H), 1.36-1.16 (m, 48H), 1.03 (s, 9H), 0.88 (t, j=6.9 Hz, 6H), 0.24 (s, 6H); $^{13}$C NMR (100 MHz, CDCl$_3$): δ 173.7 (2C; C), 173.5 (C), 169.3 (C), 163.4 (C), 151.9 (C), 146.2 (C), 133.9 (C), 127.8 (C), 123.7 (CH), 118.0 (C), 111.8 (C), 75.5 (CH), 70.0 (CH$_2$), 67.8 (CH$_2$), 64.2 (CH$_2$), 63.1 (2C; CH$_2$), 60.9 (CH$_3$), 34.6 (CH$_2$), 34.3 (2C; CH$_2$), 33.2 (CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.5 (CH$_2$), 26.2 (CH$_2$), 25.5 (CH$_2$), 25.1 (2C; CH$_2$), 23.8 (CH$_2$), 22.8 (2C; CH$_2$), 18.9 (C), 16.5 (CH$_3$), 14.3 (2C; CH$_3$), 11.6 (CH$_3$), −3.4 (CH$_3$).

Synthesis of I-25:

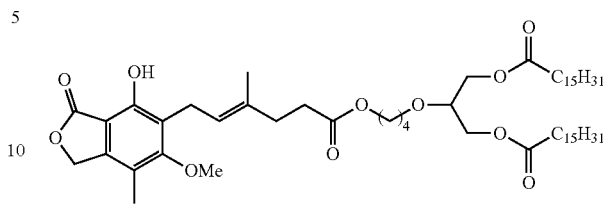

Tetrabutylammonium fluoride (TBAF, 1 M in THF, 38.1 µL, 38.1 µmol) was added to a solution of TBS ether Int-83 (26.9 mg, 38.1 µmol) in THF (1.5 mL) at 0° C. and the mixture was stirred at 0° C. for 50 minutes. The reaction was diluted with ethyl acetate, quenched with water and the aqueous phase extracted with ethyl acetate. The combined organic extracts were washed with water and brine, dried (MgSO$_4$) and concentrated under reduced pressure to give the crude product. Silica gel chromatography (20% ethyl acetate/hexanes) gave prodrug MPA-C4-ET-2-TG (I-25) (20.0 mg, 83%) as a colorless solid. $^1$H NMR (400 MHz, CDCl$_3$): δ 7.68 (s, 1H), 5.23 (dd, J=7.5, 6.4 Hz, 1H), 5.19 (s, 2H), 4.18 (dd, J=11.6, 4.9 Hz, 2H), 4.10 (dd, J=11.6, 5.5 Hz, 2H), 4.03 (t, J=6.3 Hz, 2H), 3.76 (s, 3H), 3.67 (m, 1H), 3.56 (t, j=6.0 Hz, 2H), 3.38 (d, J=6.9 Hz, 2H), 2.41-2.35 (m, 2H), 2.34-2.26 (m, 6H), 2.14 (s, 3H), 1.79 (s, 3H), 1.69-1.56 (m, 8H), 1.35-1.20 (m, 48H), 0.88 (t, j=6.8 Hz, 6H); $^{13}$C NMR (100 MHz, CDCl$_3$): δ 173.7 (2C; C), 173.5 (C), 173.1 (C), 163.8 (C), 153.8 (C), 144.2 (C), 134.3 (C), 122.8 (CH), 122.3 (C), 116.8 (C), 106.5 (C), 75.5 (CH), 70.2 (CH$_2$), 70.0 (CH$_2$), 64.2 (CH$_2$), 63.1 (2C; CH$_2$), 61.1 (CH$_3$), 34.8 (CH$_2$), 34.3 (2C; CH$_2$), 33.3 (CH$_2$), 32.1 (2C; CH$_2$), 29.84 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 26.5 (CH$_2$), 25.5 (CH$_2$), 25.1 (2C; CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{56}$H$_{94}$NaO$_{11}$ [M+Na$^+$] 965.6688; found 965.6697.

Using similar procedures employing Int-73 instead of Int-78, compound (E)-2-((6-((6-(4-hydroxy-6-methoxy-7-methyl-3-oxo-1,3-dihydroisobenzofuran-5-yl)-4-methyl-hex-4-enoyl)oxy)hexyl)oxy)propane-1,3-diyl dipalmitate (I-26) was prepared, Scheme 48. Synthesis of I-26.

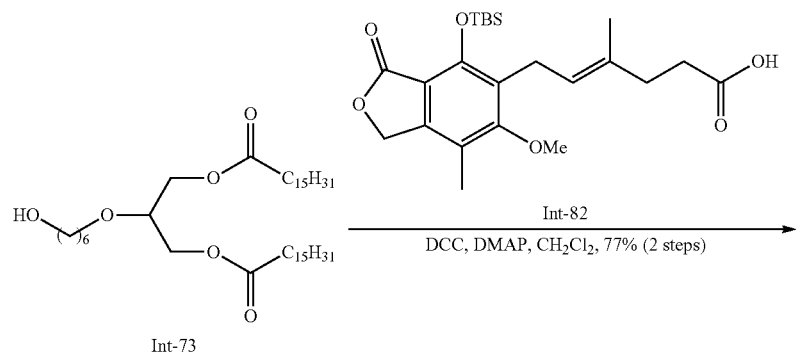

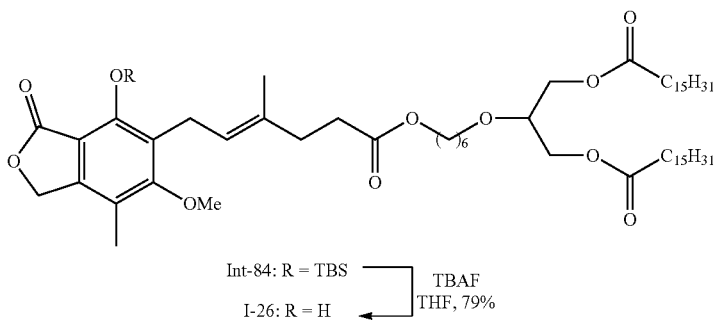

Int-84: R = TBS
I-26: R = H

TBAF
THF, 79%

Synthesis of Int-84:

Int-84

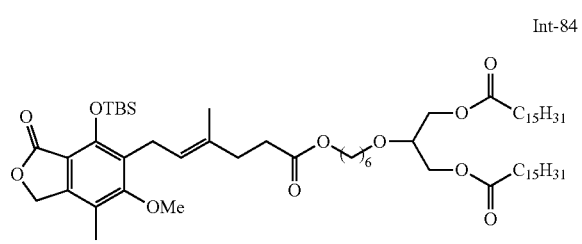

Synthesis of I-26:

I-26

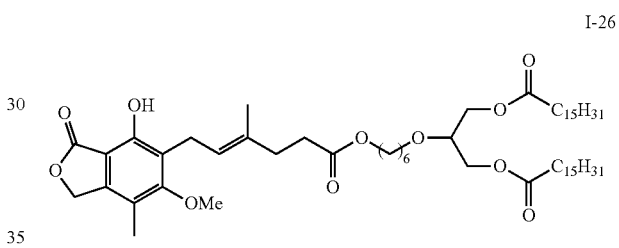

DMAP (6.4 mg, 52.1 μmol) and DCC (15.1 mg, 72.9 μmol) were added to a solution of acid Int-82 (22.7 mg, 52.1 μmol) and alcohol Int-73 (38.2 mg, 57.3 μmol) in $CH_2Cl_2$ (1.5 mL) and the mixture stirred at rt for 16 hours. The resulting suspension was diluted with $CH_2Cl_2$ (10 mL), cooled to 0° C. and filtered through Celite, washing with further $CH_2Cl_2$ (40 mL). The organic phase was washed with 1 M HCl, water, sat. aq. $NaHCO_3$ and brine (40 mL each), dried ($MgSO_4$) and concentrated under reduced pressure to give the crude product. Silica gel chromatography (10% to 15% ethyl acetate/hexanes) gave MPA triglyceride Int-84 (43.6 mg, 77% over two steps) as a colorless oil; $^1H$ NMR (400 MHz, $CDCl_3$): δ 5.18 (dd, J=6.5, 5.3 Hz, 1H), 5.06 (s, 2H), 4.18 (dd, J=11.6, 5.0 Hz, 2H), 4.11 (dd, J=11.6, 5.5 Hz, 2H), 4.00 (t, J=6.7 Hz, 2H), 3.74 (s, 3H), 3.66 (m, 1H), 3.54 (t, J=6.5 Hz, 2H), 3.38 (d, J=6.3 Hz, 2H), 2.40-2.24 (m, 8H), 2.15 (s, 3H), 1.75 (s, 3H), 1.66-1.51 (m, 8H), 1.39-1.18 (m, 52H), 1.03 (s, 9H), 0.88 (t, J=6.9 Hz, 6H), 0.23 (s, 6H); $^{13}C$ NMR (101 MHz, $CDCl_3$) δ 173.7 (2C; C), 173.6 (C), 169.3 (C), 163.3 (C), 151.9 (C), 146.2 (C), 133.9 (C), 127.8 (C), 123.7 (CH), 118.1 (C), 111.8 (C), 75.4 (CH), 70.6 ($CH_2$), 67.8 ($CH_2$), 64.5 ($CH_2$), 63.1 (2C; $CH_2$), 60.9 ($CH_3$), 34.6 ($CH_2$), 34.3 (2C; $CH_2$), 33.2 ($CH_2$), 32.1 (2C; $CH_2$), 30.0 ($CH_2$), 29.85 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.3 (2C; $CH_2$), 28.7 ($CH_2$), 26.2 (3C; $CH_3$), 25.9 ($CH_2$), 25.8 ($CH_2$), 25.1 (2C; $CH_2$), 23.8 ($CH_2$), 22.8 (2C; $CH_2$), 18.9 (C), 16.5 ($CH_3$), 14.3 (2C; $CH_3$), 11.6 ($CH_3$), −3.4 (2C; $CH_3$).

Tetrabutylammonium fluoride (TBAF, 1 M in THF, 60.2 μL, 60.2 μmol) was added to a solution of TBS ether Int-84 (43.6 mg, 40.2 μmol) in THF (2.5 mL) at 0° C. and the mixture was stirred at 0° C. for one hour. The reaction was diluted with ethyl acetate (10 mL) and water (20 mL) and the aqueous phase extracted with ethyl acetate (3×20 mL). The combined organic extracts were washed with water and brine (50 mL each), dried ($MgSO_4$) and concentrated under reduced pressure to give the crude product. Silica gel chromatography (20% ethyl acetate/hexanes) gave MPA prodrug MPA-C6-ET-2-TG (I-26) (30.8 mg, 79%) as a colorless solid. $^1H$ NMR (400 MHz, $CDCl_3$): δ 7.67 (s, 1H), 5.24 (td, J=6.9, 1.1 Hz, 1H), 5.19 (s, 2H), 4.18 (dd, J=11.6, 5.0 Hz, 2H), 4.11 (dd, J=11.6, 5.5 Hz, 2H), 4.00 (t, J=6.7 Hz, 2H), 3.76 (s, 3H), 3.67 (m, 1H), 3.54 (t, J=6.5 Hz, 2H), 3.38 (d, J=6.9 Hz, 2H), 2.42-2.35 (m, 2H), 2.35-2.26 (m, 6H), 2.14 (s, 3H), 1.80 (s, 3H), 1.66-1.51 (m, 8H), 1.39-1.19 (m, 52H), 0.88 (t, J=6.8 Hz, 6H); $^{13}C$ NMR (100 MHz, $CDCl_3$): δ 173.7 (C), 173.6 (2C; C), 173.1 (C), 163.8 (C), 153.8 (C), 144.1 (C), 134.2 (C), 122.8 (CH), 122.3 (C), 116.8 (C), 106.5 (C), 75.4 (CH), 70.6 ($CH_2$), 70.2 ($CH_2$), 64.5 ($CH_2$), 63.1 (2C; $CH_2$), 61.1 ($CH_3$), 34.8 ($CH_2$), 34.3 ($CH_2$), 33.3 ($CH_2$), 32.1 ($CH_2$), 30.0 ($CH_2$), 29.84 (6C; $CH_2$), 29.80 (4C; $CH_2$), 29.76 (2C; $CH_2$), 29.6 (2C; $CH_2$), 29.5 (2C; $CH_2$), 29.4 (2C; $CH_2$), 29.3 (2C; $CH_2$), 28.7 ($CH_2$), 25.9 ($CH_2$), 25.8 ($CH_2$), 25.1 (2C; $CH_2$), 22.8 (2C; $CH_2$), 22.7 ($CH_2$), 16.3 ($CH_3$), 14.3 (2C; $CH_3$), 11.7 ($CH_3$); ESI-HRMS: calcd. for $C_{58}H_{98}NaO_{11}$ [M+Na]$^+$ 993.7001; found 993.7012.

Example 12: Synthesis of (E)-2-(((3-((6-(4-hydroxy-6-methoxy-7-methyl-3-oxo-1,3-dihydroisobenzofuran-5-yl)-4-methylhex-4-enoyl)oxy)propoxy)carbonyl)oxy)propane-1,3-diyl dipalmitate (I-27)

C. and the mixture stirred at RT for 18 hours. The reaction was diluted with $CH_2Cl_2$ (30 mL) and the organic phase washed with water, sat. aq. $NaHCO_3$ and brine (25 mL each), dried ($MgSO_4$) and concentrated under reduced pressure to give the crude product. Silica gel chromatography (4% to 5.5% ethyl acetate/hexanes) gave an inseparable mixture of chloropropyl carbonates Int-85 and a regioisomer (ca. 1:1

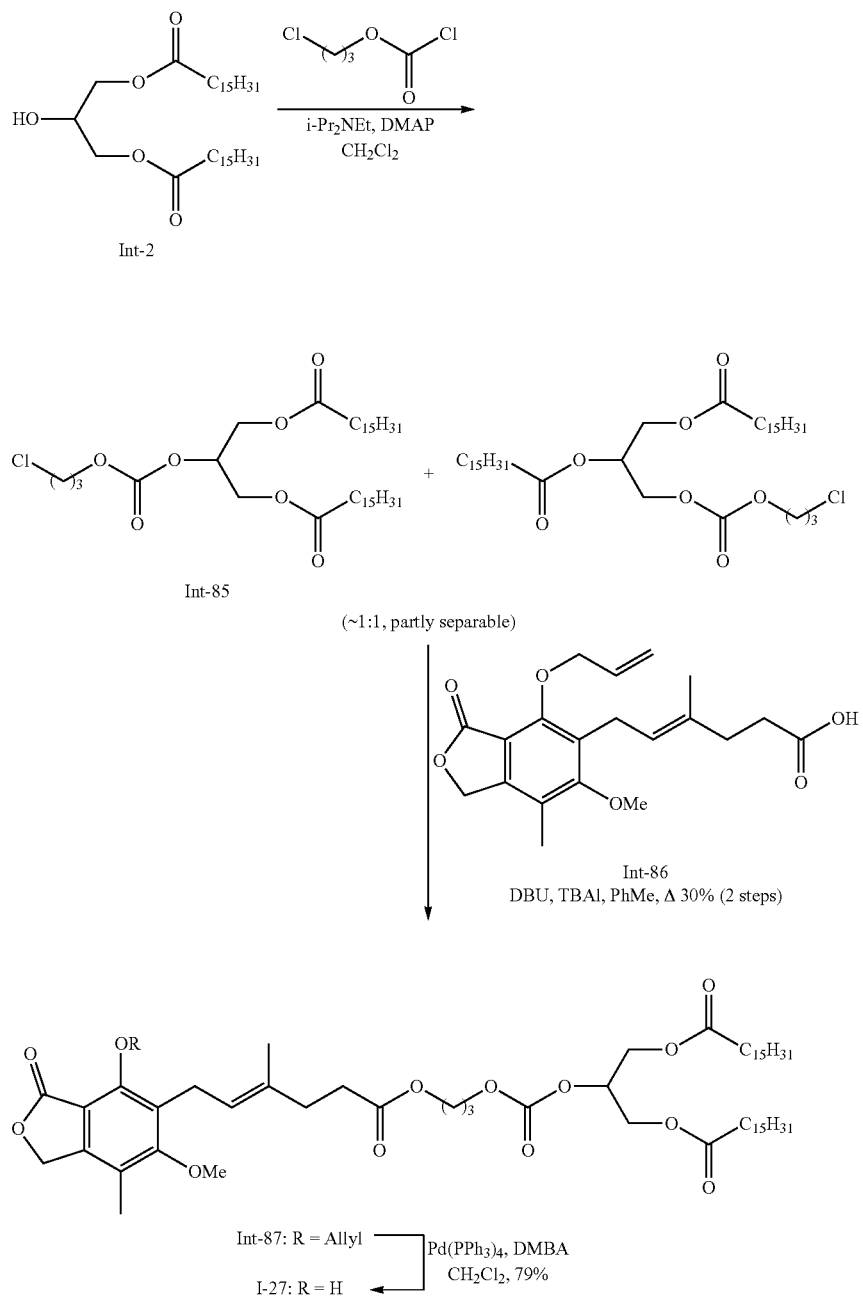

3-Chloropropyl chloroformate (20.3 µL, 0.169 mmol) and N,N-diethyl isopropyl amine (DIPEA, 54.2 µL, 0.316 mmol) were added to 1,3-diglyceride Int-2 (60.0 mg, 0.105 mmol) and DMAP (2.6 mg, 0.0211 mmol) in $CH_2Cl_2$ (3 mL) at 0° ratio, 49.8 mg, 69%) as a colorless solid. This mixture was used in the next step without further purification. $^1$H NMR (400 MHz, $CDCl_3$) δ 5.28 (m, 1H), 4.38-4.13 (m, 6H), 3.63 (t, J=6.3 Hz, 2H), 2.35-2.29 (m, 4H), 2.18-2.10 (m, 2H), 1.66-1.56 (m, 4H), 1.36-1.19 (m, 48H), 0.88 (t, J=6.9 Hz, 6H). Note: The $^1$H NMR spectrum was acquired using a sample enriched in target carbonate Int-85.

Compound Int-86 is a known compound that may be prepared as described in WO 2016/023082, hereby incorporated by reference in its entirety.

DBU (15.1 µL, 0.101 mmol) was added to a suspension of acid Int-86 (31.2 mg, 0.0867 mmol) and chloride Int-85 and its regioisomer (49.8 mg combined, 0.0722 mmol) and the mixture heated at reflux for 30 minutes. TLC analysis at this time showed very little reaction progress, so tetra-n-butylammonium iodide (TBAI, 5.0 mg, 0.0135 mmol) was added and the mixture heated at reflux for a further 3.5 hours. The reaction was cooled to rt, then diluted with ethyl acetate and water (10 mL each). The aqueous layer was separated and acidified to pH 2 with 1 M HCl, and then extracted with ethyl acetate (3×15 mL). The combined organic extracts were washed with water, sat. aq. NaHCO$_3$ and brine (40 mL each), dried (MgSO$_4$) and concentrated under reduced pressure to give the crude product. Silica gel chromatography (10% to 20% ethyl acetate/hexanes) gave unreacted chlorides Int-85 and its regioisomer (ca. 3:1 ratio, 30 mg) along with protected MPA prodrug Int-87 (14.5 mg) as a colorless oil. Re-subjection of the unreacted starting materials under the same reaction conditions (acid Int-86, DBU, TBAI, reflux for four hours) gave an additional batch of product Int-87 (31.9 mg total, 30% over two steps from 1,3-diglyceride Int-2). $^1$H NMR (400 MHz, CDCl$_3$): δ 6.09 (ddt, J=16.3, 10.4, 5.9 Hz, 1H), 5.37 (ddd, J=17.2, 3.0, 1.5 Hz, 1H), 5.23 (dd, J=10.4, 1.5 Hz, 1H), 5.13 (s, 2H), 5.06 (m, 1H), 4.78 (dt, J=5.9, 1.2 Hz, 2H), 4.33 (dd, J=12.1, 4.2 Hz, 2H), 4.20 (t, J=6.7 Hz, 2H), 4.18 (dd, J=12.3, 5.9 Hz, 2H), 4.12 (t, J=6.3 Hz, 2H), 3.76 (s, 3H), 3.41 (d, J=6.7 Hz, 2H), 2.42-2.36 (m, 2H), 2.34-2.26 (m, 6H), 2.18 (s, 3H), 2.02-1.93 (m, 2H), 1.78 (s, 3H), 1.64-1.56 (m, 4H), 1.39-1.16 (m, 48H), 0.87 (t, J=6.8 Hz, 3H); $^{13}$C NMR (100 MHz, CDCl$_3$): δ 173.4 (2C; C), 173.3 (C), 169.2 (C), 162.9 (C), 155.4 (C), 154.4 (C), 146.8 (C), 134.0 (CH), 133.8 (C), 129.3 (C), 123.8 (CH), 120.1 (C), 118.3 (CH$_2$), 112.8 (C), 76.2 (CH$_2$), 73.3 (CH), 68.4 (CH$_2$), 65.2 (CH$_2$), 62.0 (2C; CH$_2$), 61.1 (CH$_3$), 60.8 (CH$_2$), 34.6 (CH$_2$), 34.1 (2C; CH$_2$), 33.0 (CH$_2$), 32.1 (2C; CH$_2$), 29.84 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 28.1 (CH$_2$), 24.9 (2C; CH$_2$), 23.8 (CH$_2$), 22.8 (2C; CH$_2$), 16.4 (CH$_3$), 14.3 (2C; CH$_3$), 11.7 (CH$_3$).

Synthesis of I-27:

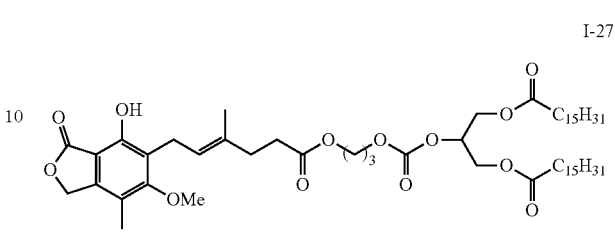

I-27

1,3-Dimethylbarbituric acid (DMBA; 9.1 mg, 58.2 µmol) and Pd(PPh$_3$)$_4$ (1.7 mg, 1.5 µmol) were added to allyl ether Int-87 (29.5 mg, 29.1 µmol) in CH$_2$Cl$_2$ (1.5 mL) and the mixture stirred at rt for one hour. The reaction mixture was directly applied to a short pad of silica gel and eluted with ethyl acetate (50 mL). The eluent was concentrated under reduced pressure to give the crude product. Silica gel chromatography (20% ethyl acetate/hexanes) gave prodrug MPA-C5-CN-2-TG (I-27) (22.3 mg, 79%) as a colorless solid. $^1$H NMR (400 MHz, CDCl$_3$): δ 7.68 (s, 1H), 5.23 (td, J=6.9, 1.2 Hz, 1H), 5.19 (s, 2H), 5.07 (tt, J=5.8, 4.3 Hz, 1H), 5.29-5.21 (m, 2H), 4.33 (dd, J=12.1, 4.2 Hz, 2H), 4.20 (t, j=6.5 Hz, 2H), 4.18 (dd, J=12.1, 5.8 Hz, 2H), 4.12 (t, J=6.3 Hz, 2H), 3.76 (s, 3H), 3.38 (d, j=6.9 Hz, 2H), 2.43-2.35 (m, 2H), 2.35-2.26 (m, 6H), 2.14 (s, 3H), 2.01-1.94 (m, 2H), 1.79 (s, 3H), 1.63-1.56 (m, 4H), 1.34-1.19 (m, 48H), 0.87 (t, j=6.9 Hz, 6H); $^{13}$C NMR (100 MHz, CDCl$_3$): δ 173.4 (2C; C), 173.3 (C), 173.0 (C), 163.8 (C), 154.5 (C), 153.8 (C), 144.2 (C), 134.2 (C), 122.9 (CH), 122.2 (C), 116.9 (C), 106.5 (C), 73.3 (CH), 70.2 (CH$_2$), 65.2 (CH$_2$), 62.0 (2C; CH$_2$), 61.1 (CH$_3$), 60.7 (CH$_2$), 34.7 (CH$_2$), 34.1 (2C; CH$_2$), 33.1 (CH$_2$), 32.1 (2C; CH$_2$), 29.83 (6C; CH$_2$), 29.80 (4C; CH$_2$), 29.75 (2C; CH$_2$), 29.6 (2C; CH$_2$), 29.5 (2C; CH$_2$), 29.4 (2C; CH$_2$), 29.2 (2C; CH$_2$), 28.1 (CH$_2$), 24.9 (2C; CH$_2$), 22.8 (2C; CH$_2$), 22.7 (CH$_2$), 16.3 (CH$_3$), 14.3 (2C; CH$_3$), 11.7 (CH$_3$).

Using similar methods, (E)-2-((3-(4-((6-(4-hydroxy-6-methoxy-7-methyl-3-oxo-1,3-dihydroisobenzofuran-5-yl)-4-methylhex-4-enoyl)oxy)phenyl)propanoyl)oxy)propane-1,3-diyl dipalmitate (I-28) was prepared.

Scheme 50. Synthesis of I-28.

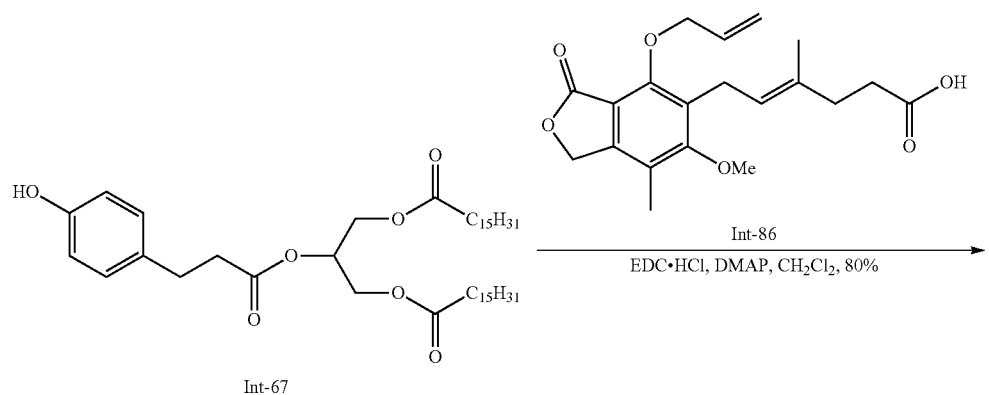

Int-67

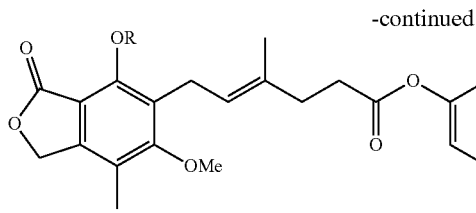
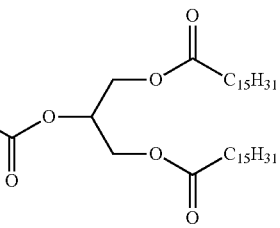

The allyl ether Int-88 was prepared as follows. DMAP (5.5 mg, 44.6 µmol), EDC.HCl (17.1 mg, 89.3 µmol) and MPA allyl ether Int-86 (16.1 mg, 44.6 µmol) were added to a solution of phenol intermediate Int-67 (32.0 mg, 44.6 µmol) in CH$_2$Cl$_2$ (3 mL) and the mixture stirred at RT for 18 hours. The reaction was diluted with CH$_2$Cl$_2$ (5 mL), silica gel was added and the mixture concentrated under reduced pressure. Purification by silica gel chromatography (15% to 20% ethyl acetate/hexanes) gave the allyl ether Int-88 (37.8 mg, 80%) as a colorless solid. $^1$H NMR (400 MHz, CDCl$_3$) δ 7.18-7.12 (m, 2H), 6.93-6.88 (m, 2H), 6.10 (ddt, J=16.3, 10.4, 5.9 Hz, 1H), 5.37 (ddd, J=17.2, 3.1, 1.5 Hz, 1H), 5.30-5.20 (m, 3H), 5.14 (s, 2H), 4.79 (dt, J=5.9, 1.3 Hz, 2H), 4.28 (dd, J=11.9, 4.4 Hz, 2H), 4.13 (dd, J=11.9, 5.9 Hz, 2H), 3.76 (s, 3H), 3.45 (d, J=6.6 Hz, 2H), 2.92 (t, J=7.8 Hz, 2H), 2.66-2.58 (m, 4H), 2.41 (t, J=7.7 Hz, 2H), 2.29 (t, j=7.6 Hz, 4H), 2.18 (s, 3H), 1.84 (s, 3H), 1.66-1.54 (m, 4H), 1.34-1.17 (m, 48H), 0.88 (t, J=6.9 Hz, 6H); $^{13}$C NMR (101 MHz, CDCl$_3$) δ 173.4 (2C; C), 171.9 (2C; C), 169.1 (C), 162.9 (C), 155.4 (C), 149.3 (C), 146.8 (C), 137.8 (C), 133.9 (CH), 133.6 (C), 129.3 (2C; CH), 129.2 (C), 124.1 (CH), 121.7 (2C; CH), 120.1 (C), 118.3 (CH$_2$), 112.8 (C), 76.2 (CH$_2$), 69.4 (CH), 68.4 (CH$_2$), 62.1 (2C; CH$_2$), 61.1 (CH$_3$), 35.7 (CH$_2$), 34.7 (CH$_2$), 34.1 (2C; CH$_2$), 33.1 (CH$_2$), 32.0 (2C; CH$_2$), 30.3 (CH$_2$), 29.81 (6C; CH$_2$), 29.77 (4C; CH$_2$), 29.73 (2C; CH$_2$), 29.6 (2C; CH$_2$), 29.5. (2C; CH$_2$), 29.4 (2C; CH$_2$), 29.2 (2C; CH$_2$), 25.0 (2C; CH$_2$), 23.8 (CH$_2$), 22.8 (2C; CH$_2$), 16.5 (CH$_3$), 14.2 (2C; CH$_3$), 11.7 (CH$_3$).

DMBA (11.1 mg, 71.4 µmol) and Pd(PPh$_3$)$_4$ (8.2 mg, 7.1 µmol) were added to allyl ether Int-88 (37.8 mg, 35.7 µmol) in CH$_2$Cl$_2$ (2 mL) and the mixture stirred at RT for 18 hours. The reaction mixture was directly applied to a short pad of silica gel and eluted with ethyl acetate. The eluent was concentrated under reduced pressure to give the crude product. Silica gel chromatography (15% to 20% ethyl acetate/hexanes) gave prodrug MPA-Ph-C3-2-TG 1-28 (28.0 mg, 77%) as a colorless solid. $^1$H NMR (400 MHz, CDCl$_3$) δ 7.69 (s, 1H), 7.17-7.12 (m, 2H), 6.94-6.87 (m, 2H), 5.33 (td, J=6.9, 1.2 Hz, 1H), 5.25 (m, 1H), 5.20 (s, 2H), 4.28 (dd, J=11.9, 4.3 Hz, 2H), 4.13 (dd, J=11.9, 5.8 Hz, 2H), 3.76 (s, 3H), 3.42 (d, J=6.9 Hz, 2H), 2.92 (t, J=7.8 Hz, 2H), 2.68-2.59 (m, 4H), 2.42 (t, J=7.6 Hz, 2H), 2.29 (t, J=7.6 Hz, 4H), 2.15 (s, 3H), 1.85 (s, 3H), 1.66-1.54 (m, 4H), 1.36-1.18 (m, 48H), 0.87 (t, J=6.9 Hz, 6H); $^{13}$C NMR (101 MHz, CDCl$_3$) δ 173.5 (2C; C), 173.0 (C), 171.99 (C), 171.96 (C), 163.8 (C), 153.8 (C), 149.3 (C), 144.2 (C), 137.8 (C), 134.0 (C), 129.3 (2C; CH), 123.2 (CH), 122.2 (C), 121.7 (2C; CH), 116.9 (C), 106.5 (C), 70.2 (CH$_2$), 69.4 (CH), 62.1 (2C; CH$_2$), 61.1 (CH$_3$), 35.8 (CH$_2$), 34.8 (CH$_2$), 34.2 (2C; CH$_2$), 33.2 (CH$_2$), 32.1 (2C; CH$_2$), 30.3 (CH$_2$), 29.83 (6C; CH$_2$), 29.80 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 22.83 (2C; CH$_2$), 22.76 (CH$_2$), 16.3 (CH$_3$), 14.3 (2C; CH$_3$), 11.7 (CH$_3$).

Using similar methods, (E)-2-((6-(4-hydroxy-6-methoxy-7-methyl-3-oxo-1,3-dihydroisobenzofuran-5-yl)-4-methylhex-4-enoyl)oxy)propane-1,3-diyl dipalmitate (I-34) was prepared from allyl-protected MPA Int-86 and Int-2 as follows.

I-34

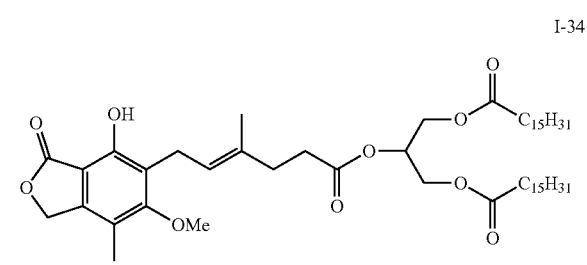

Synthesis of (E)-2-((6-(4-(allyloxy)-6-methoxy-7-methyl-3-oxo-1,3-dihydroisobenzofuran-5-yl)-4-methylhex-4-enoyl)oxy)propane-1,3-diyl dipalmitate (Int-90)

Int-90

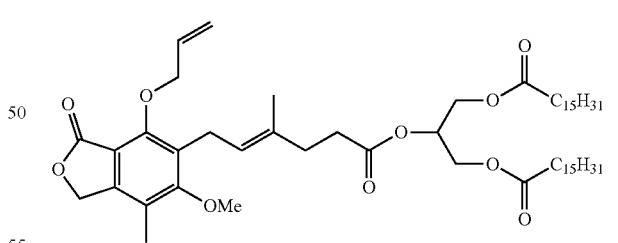

DMAP (55.0 mg, 0.450 mmol) and EDC.HCl (173 mg, 0.900 mmol) were added to a solution of Int-86 (162 mg, 0.450 mmol) and Int-2 (282 mg, 0.495 mmol) in CH$_2$Cl$_2$ (10 mL) and the mixture stirred at RT for 18 hours. The reaction was diluted with CH$_2$Cl$_2$ (20 mL), silica gel was added, and the solvent removed under reduced pressure. Silica gel chromatography (10% to 20% ethyl acetate/hexanes) gave the desired allyl-protected product (E)-2-((6-(4-(allyloxy)-6-methoxy-7-methyl-3-oxo-1,3-dihydroisobenzofuran-5-yl)-4-methylhex-4-enoyl)oxy)propane-1,3-diyl dipalmitate Int-90 (356 mg, 87%) as a colorless solid. $^1$H NMR (400

MHz, CDCl$_3$) δ 6.10 (ddt, J=16.3, 10.4, 5.9 Hz, 1H), 5.37 (dq, j=17.2, 1.5 Hz, 1H), 5.25-5.15 (m, 3H), 5.13 (s, 2H), 4.79 (dt, j=5.9, 1.3 Hz, 2H), 4.24 (dd, j=11.9, 4.5 Hz, 2H), 4.11 (dd, j=11.9, 5.8 Hz, 2H), 3.77 (s, 3H), 3.42 (d, J=6.7 Hz, 2H), 2.43-2.37 (m, 2H), 2.33-2.25 (m, 6H), 2.18 (s, 3H), 1.79 (s, 3H), 1.63-1.51 (m, 8H), 1.35-1.21 (s, 48H), 0.88 (t, j=6.9 Hz, 6H); $^{13}$C NMR (101 MHz, CDCl$_3$) δ 173.1 (2C; C), 172.2 (C), 168.9 (C), 162.8 (C), 155.2 (C), 146.7 (C), 133.9 (CH), 133.5 (C), 129.0 (C), 123.8 (CH), 119.9 (C), 118.0 (CH$_2$), 112.6 (C), 76.0 (CH$_2$), 69.0 (CH), 68.2 (CH$_2$), 61.9 (2C; CH$_2$), 60.9 (CH$_3$), 34.4 (CH$_2$), 34.0 (2C; CH$_2$), 32.9 (CH$_2$), 31.9 (2C; CH$_2$), 29.68 (6C; CH$_2$), 29.64 (4C; CH$_2$), 29.60 (2C; CH$_2$), 29.5 (2C; CH$_2$), 29.4 (2C; CH$_2$), 29.2 (2C; CH$_2$), 29.1 (2C; CH$_2$), 24.8 (2C; CH$_2$), 23.6 (CH$_2$), 22.7 (2C; CH$_2$), 16.2 (CH$_3$), 14.1 (2C; CH$_3$), 11.5 (CH$_3$).

DMBA (122 mg, 0.781 mmol) and Pd(PPh$_3$)$_4$ (67.7 mg, 0.0586 mmol) were added to allyl-protected prodrug Int-90 from the previous step (356 mg, 0.391 mmol) in CH$_2$Cl$_2$ (15 mL) and the mixture stirred at RT for 2.5 hours. The reaction mixture was directly applied to a short pad of silica gel, eluted with ethyl acetate (100 mL) and the filtrate concentrated under reduced pressure to give the crude product. Silica gel chromatography (15% ethyl acetate/hexanes) gave a slightly impure white solid, which was recrystallized from hexanes to give prodrug MPA-2-TG (I-34) (226 mg, 66%) as a colorless solid. $^1$H NMR (400 MHz, CDCl$_3$) δ 7.68 (s, 1H), 5.26-5.20 (m, 2H), 5.20 (s, 2H), 4.24 (dd, J=11.9, 4.5 Hz, 2H), 4.12 (dd, J=11.9, 5.8 Hz, 2H), 3.76 (s, 3H), 3.38 (d, J=6.9 Hz, 2H), 2.45-2.38 (m, 2H), 2.35-2.26 (m, 6H), 2.15 (s, 3H), 1.80 (s, 3H), 1.64-1.52 (m, 8H), 1.35-1.18 (m, 48H), 0.88 (t, J=6.9 Hz, 6H); $^{13}$C NMR (101 MHz, CDCl$_3$) δ 173.4 (2C; C), 173.0 (C), 172.5 (C), 163.8 (C), 153.8 (C), 144.1 (C), 134.1 (C), 123.0 (CH), 122.2 (C), 116.9 (C), 106.6 (C), 70.2 (CH$_2$), 69.1 (CH), 62.1 (2C; CH$_2$), 61.1 (CH$_3$), 34.6 (CH$_2$), 34.2 (2C; CH$_2$), 33.1 (CH$_2$), 32.1 (2C; CH$_2$), 29.85 (6C; CH$_2$), 29.81 (4C; CH$_2$), 29.77 (2C; CH$_2$), 29.6 (2C; CH$_2$), 29.5 (2C; CH$_2$), 29.4 (2C; CH$_2$), 29.3 (2C; CH$_2$), 25.0 (2C; CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{52}$H$_{87}$O$_{10}$ [M+H$^+$] 871.6294; found 871.6328.

Using similar methods, (E)-2-(2-((6-(4-hydroxy-6-methoxy-7-methyl-3-oxo-1,3-dihydroisobenzofuran-5-yl)-4-methylhex-4-enoyl)oxy)acetoxy)propane-1,3-diyl dipalmitate (I-35) was prepared from allyl-protected MPA Int-86 and Int-91 as follows.

I-35

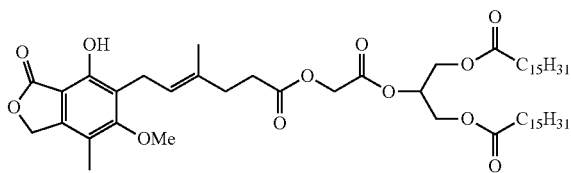

Synthesis of (E)-2-(2-((6-(4-(allyloxy)-6-methoxy-7-methyl-3-oxo-1,3-dihydroisobenzofuran-5-yl)-4-methylhex-4-enoyl)oxy)acetoxy)propane-1,3-diyl dipalmitate (Int-92)

Int-92

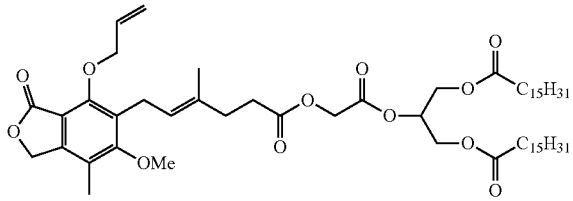

DBU (15.6 µL, 104 µmol) was added to a suspension of acid Int-86 (25.9 mg, 71.7 µmol) and bromide Int-91 (prepared as described above) (45.0 mg, 65.2 µmol) in toluene (3 mL) and the mixture heated at reflux for three hours. The reaction was cooled to RT and diluted with water (10 mL). The aqueous phase was extracted with ethyl acetate (3×15 mL) and the combined organic extracts washed with sat. aq. NaHCO$_3$ and brine (30 mL each), dried (MgSO$_4$) and concentrated under reduced pressure to give the crude product. Silica gel chromatography (12% to 15% ethyl acetate/hexanes) gave the allyl-protected MPA triglyceride Int-92 (45.6 mg, 72%) as a colorless oil. $^1$H NMR (400 MHz, CDCl$_3$) δ 6.09 (ddt, J=16.3, 10.4, 5.9 Hz, 1H), 5.37 (ddd, J=17.2, 3.1, 1.5 Hz, 1H), 5.30 (m, 1H), 5.25-5.17 (m, 2H), 5.13 (s, 2H), 4.78 (dt, J=5.9, 1.3 Hz, 2H), 4.57 (s, 2H), 4.28 (dd, J=12.1, 4.2 Hz, 2H), 4.15 (dd, J=12.0, 5.9 Hz, 2H), 3.76 (s, 3H), 3.42 (d, J=6.7 Hz, 2H), 2.52-2.45 (m, 2H), 2.37-2.27 (m, 6H), 2.17 (s, 3H), 1.79 (s, 3H), 1.63-1.55 (m, 4H), 1.37-1.17 (m, 48H), 0.87 (t, J=6.8 Hz, 6H); $^{13}$C NMR (101 MHz, CDCl$_3$) δ 173.4 (2C; C), 172.6 (C), 169.2 (C), 167.2 (C), 163.0 (C), 155.4 (C), 146.8 (C), 134.0 (CH), 133.7 (C), 129.2 (C), 123.9 (CH), 120.1 (C), 118.2 (CH$_2$), 112.8 (C), 76.2 (CH$_2$), 70.4 (CH), 68.4 (CH$_2$), 61.9 (CH$_2$), 61.1 (CH$_3$), 60.4 (CH$_2$), 34.4 (CH$_2$), 34.1 (2C; CH$_2$), 32.6 (CH$_2$), 32.1 (2C; CH$_2$), 29.82 (6C; CH$_2$), 29.78 (4C; CH$_2$), 29.74 (2C; CH$_2$), 29.6 (2C; CH$_2$), 29.5 (2C; CH$_2$), 29.4 (2C; CH$_2$), 29.2 (2C; CH$_2$), 24.9 (2C; CH$_2$), 23.8 (CH$_2$), 22.8 (2C; CH$_2$), 16.4 (CH$_3$), 14.2 (2C; CH$_3$), 11.7 (CH$_3$).

DMBA (13.4 mg, 85.6 µmol) and Pd(PPh$_3$)$_4$ (2.5 mg, 2.14 µmol) were added to allyl ether Int-92 (41.5 mg, 42.8 µmol) in CH$_2$Cl$_2$ (2.5 mL) and the mixture stirred at rt for 2.5 hours. The reaction mixture was directly applied to a short pad of silica gel, eluted with ethyl acetate (40 mL) and the filtrate concentrated under reduced pressure to give the crude product. Silica gel chromatography (15% ethyl acetate/hexanes) gave prodrug MPA-C2-2-TG (I-35) (30.9 mg, 78%) as a colorless solid. $^1$H NMR (400 MHz, CDCl$_3$) δ 7.67 (s, 1H), 5.31 (m, 1H), 5.25 (m, 1H), 5.20 (s, 2H), 4.57 (s, 2H), 4.29 (dd, J=12.1, 4.2 Hz, 2H), 4.16 (dd, J=12.1, 6.0 Hz, 2H), 3.76 (s, 3H), 3.38 (d, J=6.9 Hz, 2H), 2.54-2.47 (m, 2H), 2.35-2.29 (m, 6H), 2.14 (s, 3H), 1.80 (s, 3H), 1.64-1.55 (m, 4H), 1.34-1.19 (m, 48H), 0.87 (t, J=6.8 Hz, 6H); $^{13}$C NMR (101 MHz, CDCl$_3$) δ 173.42 (2C; C), 173.04 (C), 172.61 (C), 167.26 (C), 163.79 (C), 153.77 (C), 144.16 (C), 134.01 (C), 123.02 (CH), 122.20 (C), 116.84 (C), 106.51 (C), 70.41 (CH), 70.17 (CH$_2$), 61.86 (2C; CH$_2$), 61.12 (CH$_3$), 60.44 (CH$_2$), 34.46 (CH$_2$), 34.08 (2C; CH$_2$), 32.64 (CH$_2$), 32.06 (2C; CH$_2$), 29.83 (6C; CH$_2$), 29.79 (4C; CH$_2$), 29.75 (2C; CH$_2$), 29.60 (2C; CH$_2$), 29.50 (2C; CH$_2$), 29.39

(2C; CH$_2$), 29.24 (2C; CH$_2$), 24.93 (2C; CH$_2$), 22.82 (2C; CH$_2$), 22.72 (CH$_2$), 16.27 (CH$_3$), 14.26 (2C; CH$_3$), 11.69 (CH$_3$).

Using similar methods, (E)-2-((7-((6-(4-hydroxy-6-methoxy-7-methyl-3-oxo-1,3-dihydroisobenzofuran-5-yl)-4-methylhex-4-enoyl)oxy)heptanoyl)oxy)propane-1,3-diyl dipalmitate (I-36) was prepared from allyl-protected MPA Int-86 and Int-95 as follows.

I-36

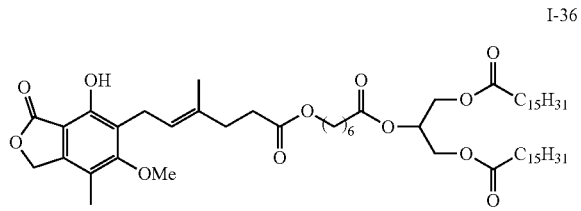

Synthesis of (E)-2-((7-((6-(4-(allyloxy)-6-methoxy-7-methyl-3-oxo-1,3-dihydroisobenzofuran-5-yl)-4-methylhex-4-enoyl)oxy)heptanoyl)oxy)propane-1,3-diyl dipalmitate (Int-96)

Int-96

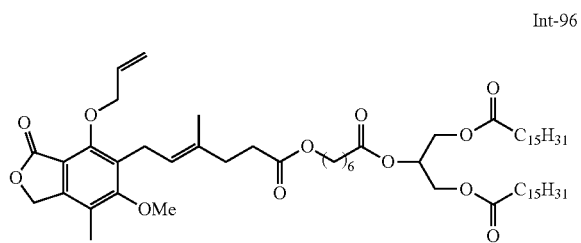

DBU (13.6 µL, 90.7 µmol) was added to a suspension of acid Int-86 (26.2 mg, 72.6 µmol) and iodide Int-95 (48.8 mg, 60.5 µmol) and the mixture heated at reflux for 3.5 hours. The reaction was cooled to RT, then diluted with ethyl acetate and water and the aqueous layer extracted with ethyl acetate. The combined organic extracts were washed with water and brine, dried (MgSO$_4$) and concentrated under reduced pressure to give the crude product. Silica gel chromatography (7.5% to 15% to 20% ethyl acetate/hexanes) gave protected MPA prodrug Int-96 (47.5 mg, 76%) as a colorless oil. $^1$H NMR (400 MHz, CDCl$_3$) δ 6.09 (ddt, J=17.1, 10.4, 5.9 Hz, 1H), 5.37 (dq, J=17.2, 1.5 Hz, 1H), 5.28-5.21 (m, 2H), 5.17 (m, 1H), 5.12 (s, 2H), 4.78 (dt, J=5.9, 1.3 Hz, 2H), 4.29 (dd, J=11.9, 4.4 Hz, 2H), 4.13 (dd, J=11.9, 5.9 Hz, 2H), 4.00 (t, J=6.7 Hz, 2H), 3.76 (s, 3H), 3.41 (d, J=6.7 Hz, 2H), 2.40-2.34 (m, 2H), 2.33-2.25 (m, 8H), 2.17 (s, 3H), 1.78 (s, 3H), 1.66-1.54 (m, 8H), 1.36-1.18 (m, 52H), 0.87 (t, J=6.9 Hz, 6H); $^{13}$C NMR (100 MHz, CDCl$_3$) δ 173.5 (C), 173.4 (2C; C), 172.8 (C), 169.2 (C), 163.0 (C), 155.4 (C), 146.8 (C), 133.99 (CH), 133.97 (C), 129.3 (C), 123.7 (CH), 120.1 (C), 118.2 (CH), 112.8 (C), 76.2 (CH$_2$), 69.1 (CH), 68.4 (CH$_2$), 64.4 (CH$_2$), 62.2 (2C; CH$_2$), 61.1 (CH$_3$), 34.7 (CH$_2$), 34.17 (2C; CH$_2$), 34.16 (CH$_2$), 33.2 (CH$_2$), 32.1 (2C; CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 28.8 (CH$_2$), 28.6 (CH$_2$), 25.8 (CH$_2$), 25.0 (2C; CH$_2$), 24.8 (CH$_2$), 23.8 (CH$_2$), 22.8 (2C; CH$_2$), 16.4 (CH$_3$), 14.3 (2C; CH$_3$), 11.7 (CH$_3$).

DMBA (10.8 mg, 69.3 µmol) and Pd(PPh$_3$)$_4$ (2.0 mg, 1.7 µmol) were added to allyl ether Int-96 (36.0 mg, 34.6 µmol) in CH$_2$Cl$_2$ (2 mL) and the mixture stirred at RT for one hour. The reaction mixture was directly applied to a short pad of silica gel and eluted with ethyl acetate (50 mL). The eluent was concentrated under reduced pressure to give the crude product. Silica gel chromatography (5% ethyl acetate/toluene) gave MPA prodrug MPA-C7-2-TG 1-36 (30.6 mg, 88%) as a colorless solid. $^1$H NMR (400 MHz, CDCl$_3$) δ 7.67 (s, 1H), 5.28-5.22 (m, 2H), 5.19 (s, 2H), 4.29 (dd, J=11.9, 4.3 Hz, 2H), 4.14 (dd, J=11.9, 5.9 Hz, 2H), 4.00 (t, J=6.7 Hz, 2H), 3.75 (s, 3H), 3.38 (d, J=6.9 Hz, 2H), 2.40-2.35 (m, 2H), 2.34-2.25 (m, 8H), 2.14 (s, 3H), 1.80 (s, 3H), 1.66-1.52 (m, 8H), 1.37-1.19 (m, 52H), 0.87 (t, J=6.8 Hz, 6H); $^{13}$C NMR (100 MHz, CDCl$_3$) δ 173.6 (C), 173.4 (2C; C), 173.1 (C), 172.8 (C), 163.8 (C), 153.8 (C), 144.1 (C), 134.3 (C), 122.8 (CH), 122.3 (C), 116.8 (C), 106.5 (C), 70.2 (CH$_2$), 69.1 (CH), 64.4 (CH$_2$), 62.2 (2C; CH$_2$), 61.1 (CH$_3$), 34.8 (CH$_2$), 34.2 (3C; CH$_2$), 33.2 (CH$_2$), 32.1 (2C; CH$_2$), 29.83 (6C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.2 (2C; CH$_2$), 28.8 (CH$_2$), 28.6 (CH$_2$), 25.8 (CH$_2$), 25.0 (2C; CH$_2$), 24.8 (CH$_2$), 22.8 (2C; CH$_2$), 22.7 (CH$_2$), 16.3 (CH$_3$), 14.3 (2C; CH$_3$), 11.7 (CH$_3$); ESI-HRMS: calcd. for C$_{59}$H$_{98}$NaO$_{12}$ [M+Na$^+$] 1021.6951; found 1021.6946.

Using similar methods, (E)-2-((12-((6-(4-hydroxy-6-methoxy-7-methyl-3-oxo-1,3-dihydroisobenzofuran-5-yl)-4-methylhex-4-enoyl)oxy)dodecanoyl)oxy)propane-1,3-diyl dipalmitate (I-37) was prepared from allyl-protected MPA Int-86 and Int-97 as follows.

I-37

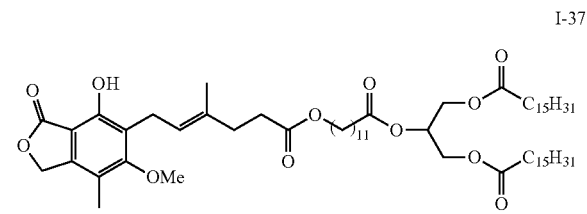

Synthesis of (E)-2-((12-((6-(4-(allyloxy)-6-methoxy-7-methyl-3-oxo-1,3-dihydroisobenzofuran-5-yl)-4-methylhex-4-enoyl)oxy)dodecanoyl)oxy)propane-1,3-diyl dipalmitate (Int-98)

Int-98

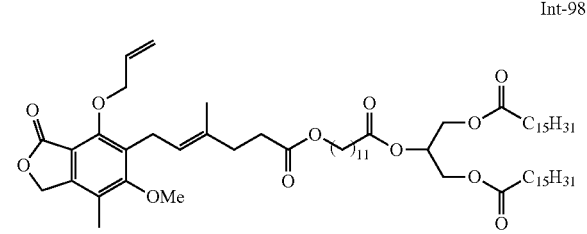

DBU (27.4 µL, 0.183 mmol) was added to a suspension of Int-86 (43.3 mg, 0.120 mmol) and bromide Int-97 (95.0 mg, 0.114 mmol) in toluene (4 mL) and the mixture heated at reflux for two hours. The reaction was cooled to rt, then diluted with ethyl acetate (40 mL). The organic phase was washed with water and brine (30 mL each), dried (MgSO$_4$) and concentrated under reduced pressure to give the crude product. Silica gel chromatography (10% to 20% ethyl acetate/hexanes) gave Int-98 (88.2 mg, 69%) as a colorless solid. $^1$H NMR (401 MHz, CDCl$_3$) δ 6.07 (ddt, J=16.3, 10.4, 5.9 Hz, 1H), 5.35 (dq, j=17.2, 1.5 Hz, 1H), 5.28-5.13 (m, 3H), 5.10 (s, 2H), 4.76 (dt, j=5.9, 1.2 Hz, 2H), 4.27 (dd, j=11.9, 4.3 Hz, 2H), 4.12 (dd, j=11.9, 5.9 Hz, 2H), 3.98 (t, j=6.8 Hz, 2H), 3.74 (s, 3H), 3.39 (d, J=6.7 Hz, 2H), 2.39-2.23 (m, 10H), 2.16 (s, 3H), 1.76 (s, 3H), 1.63-1.51 (m, 8H), 1.35-1.13 (m, 62H), 0.85 (t, j=6.8 Hz, 6H); $^{13}$C NMR (101 MHz, CDCl$_3$) δ 173.5 (C), 173.4 (2C; C), 172.9 (C), 169.1 (C), 162.9 (C), 155.4 (C), 146.7 (C), 133.94 (CH), 133.92 (C), 129.3 (C), 123.6 (CH), 120.0 (C), 118.1 (CH$_2$), 112.7 (C), 76.1 (CH$_2$), 69.0 (CH), 68.4 (CH$_2$), 64.6 (CH$_2$), 62.2 (2C; CH$_2$), 61.0 (CH$_3$), 34.7 (CH$_2$), 34.3 (CH$_2$), 34.1 (2C; CH$_2$), 33.1 (CH$_2$), 32.0 (2C; CH$_2$), 29.78 (6C; CH$_2$), 29.74 (4C; CH$_2$), 29.70 (2C; CH$_2$), 29.63 (CH$_2$), 29.60 (CH$_2$), 29.55 (3C; CH$_2$), 29.44 (2C; CH$_2$), 29.35 (4C; CH$_2$), 29.19 (2C; CH$_2$), 29.15 (CH$_2$), 28.7 (CH$_2$), 26.0 (CH$_2$), 24.9 (2C; CH$_2$), 23.7 (CH$_2$), 22.8 (2C; CH$_2$), 16.4 (CH$_3$), 14.2 (2C; CH$_3$), 11.6 (CH$_3$).

DMBA (24.2 mg, 0.155 mmol) and Pd(PPh$_3$)$_4$ (13.4 mg, 0.0116 mmol) were added to allyl ether Int-98 (86.0 mg, 0.0775 mmol) in CH$_2$Cl$_2$ (3 mL) and the mixture stirred at rt for 4.5 hours. The reaction mixture was directly applied to a short pad of silica gel and eluted with ethyl acetate. The eluent was concentrated under reduced pressure to give the crude product. Silica gel chromatography (15% to 20% ethyl acetate/hexanes) gave prodrug I-37 (80.0 mg, 96%) as a colorless solid. $^1$H NMR (401 MHz, CDCl$_3$) δ 7.66 (s, 1H), 5.27-5.19 (m, 2H), 5.17 (s, 2H), 4.28 (dd, j=11.9, 4.3 Hz, 2H), 4.13 (dd, j=11.8, 5.9 Hz, 2H), 3.98 (t, j=6.8 Hz, 2H), 3.74 (s, 3H), 3.36 (d, j=6.9 Hz, 2H), 2.40-2.33 (m, 2H), 2.32-2.24 (m, 8H), 2.13 (s, 3H), 1.78 (s, 3H), 1.64-1.50 (m, 8H), 1.37-1.18 (m, 62H), 0.86 (t, J=6.8 Hz, 6H); $^{13}$C NMR (101 MHz, CDCl$_3$) δ 173.5 (C), 173.4 (2C; C), 173.0 (C), 172.9 (C), 163.8 (C), 153.7 (C), 144.1 (C), 134.3 (C), 122.7 (CH), 122.2 (C), 116.8 (C), 106.4 (C), 70.1 (CH$_2$), 69.0 (CH), 64.5 (CH$_2$), 62.2 (2C; CH$_2$), 61.1 (CH$_3$), 34.7 (CH$_2$), 34.3 (CH$_2$), 34.1 (2C; CH$_2$), 33.2 (CH$_2$), 32.0 (2C; CH$_2$), 29.79 (6C; CH$_2$), 29.75 (4C; CH$_2$), 29.71 (2C; CH$_2$), 29.63 (CH$_2$), 29.61 (CH$_2$), 29.56 (2C; CH$_2$), 29.45 (2C; CH$_2$), 29.36 (4C; CH$_2$), 29.20 (2C; CH$_2$), 29.16 (CH$_2$), 28.7 (CH$_2$), 26.0 (CH$_2$), 24.97 (CH$_2$), 24.95 (2C; CH$_2$), 22.8 (2C; CH$_2$), 22.7 (CH$_2$), 16.2 (CH$_3$), 14.2 (2C; CH$_3$), 11.6 (CH$_3$).

Using similar methods, (E)-2-((18-((6-(4-hydroxy-6-methoxy-7-methyl-3-oxo-1,3-dihydroisobenzofuran-5-yl)-4-methylhex-4-enoyl)oxy)octadecanoyl)oxy)propane-1,3-diyl dipalmitate (I-38) was prepared from allyl-protected MPA Int-86 and Int-105 as follows.

Synthesis of (E)-2-((18-((6-(4-(allyloxy)-6-methoxy-7-methyl-3-oxo-1,3-dihydroisobenzofuran-5-yl)-4-methylhex-4-enoyl)oxy)octadecanoyl)oxy)propane-1,3-diyl dipalmitate (Int-128)

Int-128

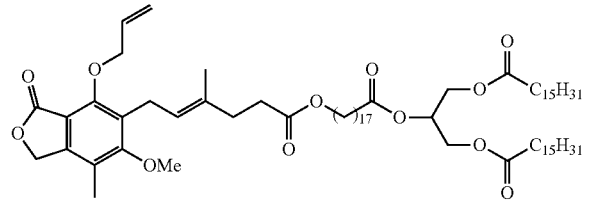

DMAP (4.6 mg, 37.4 μmol), EDC-HCl (17.9 mg, 93.4 μmol) and Int-86 (18.8 mg, 52.3 μmol) were added to a solution of alcohol Int-105 (31.8 mg, 37.4 μmol) in CH$_2$Cl$_2$ (1 mL) and the mixture stirred at RT for 19 hours. The reaction was diluted with CH$_2$Cl$_2$ (5 mL), silica gel was added and the mixture concentrated under reduced pressure. Purification by silica gel chromatography (12.5% to 17.5% ethyl acetate/hexanes) gave allyl-protected prodrug Int-128 (40.6 mg, 91%) as a colorless solid. $^1$H NMR (401 MHz, CDCl$_3$) δ 6.10 (ddt, J=17.1, 10.4, 5.9 Hz, 1H), 5.37 (ddd, J=17.2, 3.1, 1.5 Hz, 1H), 5.30-5.21 (m, 2H), 5.17 (td, J=6.7, 1.1 Hz, 1H), 5.13 (s, 2H), 4.78 (dt, J=5.9, 1.3 Hz, 2H), 4.29 (dd, J=11.9, 4.3 Hz, 2H), 4.14 (dd, J=11.9, 6.0 Hz, 2H), 4.00 (t, J=6.8 Hz, 2H), 3.76 (s, 3H), 3.41 (d, J=6.7 Hz, 2H), 2.39-2.25 (m, 10H), 2.18 (s, 3H), 1.78 (s, 3H), 1.66-1.52 (m, 8H), 1.37-1.18 (m, 74H), 0.88 (t, J=6.9 Hz, 6H); $^{13}$C NMR (101 MHz, CDCl$_3$) δ 173.6 (C), 173.4 (2C; C), 173.0 (C), 169.1 (C), 163.0 (C), 155.4 (C), 146.8 (C), 134.00 (C), 133.97 (CH), 129.3 (C), 123.7 (CH), 120.1 (C), 118.2 (CH$_2$), 112.8 (C), 76.2 (CH$_2$), 69.0 (CH), 68.4 (CH$_2$), 64.6 (CH$_2$), 62.2 (2C; CH$_2$), 61.1 (CH$_3$), 34.7 (CH$_2$), 34.3 (CH$_2$), 34.2 (2C; CH$_2$), 33.2 (CH$_2$), 32.1 (2C; CH$_2$), 29.83 (10C; CH$_2$), 29.79 (6C; CH$_2$), 29.75 (3C; CH$_2$), 29.68 (CH$_2$), 29.65 (CH$_2$), 29.60 (2C; CH$_2$), 29.49 (2C; CH$_2$), 29.44 (CH$_2$), 29.40 (3C; CH$_2$), 29.24 (2C; CH$_2$), 29.22 (CH$_2$), 28.7 (CH$_2$), 26.0 (CH$_2$), 25.03 (CH$_2$), 24.99 (2C; CH$_2$), 23.8 (CH$_2$), 22.8 (2C; CH$_2$), 16.4 (CH$_3$), 14.2 (2C; CH$_3$), 11.7 (CH$_3$).

DMBA (10.6 mg, 68.0 μmol) and Pd(PPh$_3$)$_4$ (7.8 mg, 6.8 μmol) were added to allyl ether Int-128 (40.6 mg, 34.0 μmol) in CH$_2$Cl$_2$ (1.5 mL) and the mixture stirred at RT for 4 h. The reaction was diluted with (10 mL), silica gel was added, and the mixture concentrated under reduced pressure. Silica gel chromatography (15% to 20% ethyl acetate/hexanes) gave MPA prodrug I-38 (38.3 mg, 98%) as a colorless solid. $^1$H NMR (401 MHz, CDCl$_3$) δ 7.67 (s, 1H), 5.29-5.21 (m, 2H), 5.20 (s, 2H), 4.29 (dd, J=11.9, 4.3 Hz, 2H), 4.14 (dd, J=11.9, 5.9 Hz, 2H), 4.00 (t, j=6.7 Hz, 2H), 3.76 (s, 3H), 3.38 (d, J=6.7 Hz, 2H), 2.42-2.35 (m, 2H), 2.35-2.26 (m, 8H), 2.14 (s, 3H), 1.80 (s, 3H), 1.67-1.51 (m, 8H), 1.45-1.15 (m, 74H), 0.88 (t, j=6.7 Hz, 6H); $^{13}$C NMR (101 MHz, CDCl$_3$) δ 173.6 (C), 173.4 (2C; C), 173.0 (2C; C), 163.8 (C), 153.8 (C), 144.1 (C), 134.4 (C), 122.8 (CH), 122.3 (C), 116.8 (C), 106.5 (C), 70.2 (CH$_2$), 69.0 (CH), 64.6 (CH$_2$), 62.2 (2C; CH$_2$), 61.1 (CH$_3$), 34.8 (CH$_2$), 34.4 (CH$_2$), 34.2 (2C; CH$_2$), 33.3 (CH$_2$), 32.1 (2C; CH$_2$), 29.83 (10C; CH$_2$), 29.79 (6C; CH$_2$), 29.75 (3C; CH$_2$), 29.68 (CH$_2$), 29.65 (CH$_2$), 29.61 (2C; CH$_2$), 29.49 (2C; CH$_2$), 29.44 (CH$_2$), 29.40 (3C; CH$_2$), 29.25 (2C; CH$_2$), 29.22 (CH$_2$), 28.7 (CH$_2$), 26.1 (CH$_2$), 25.04 (CH$_2$), 24.99 (2C; CH$_2$), 22.8 (2C; CH$_2$), 22.7 (CH$_2$), 16.3 (CH$_3$), 14.2 (2C; CH$_3$), 11.7 (CH$_3$).

Using similar methods, (E)-2-((4-((6-(4-hydroxy-6-methoxy-7-methyl-3-oxo-1,3-dihydroisobenzofuran-5-yl)-4-methylhex-4-enoyl)oxy)-3-methylbutanoyl)oxy)propane-1,3-diyl dibutyrate (I-43) was prepared from Int-86 and Int-125 via the allyl-protected intermediate Int-127:

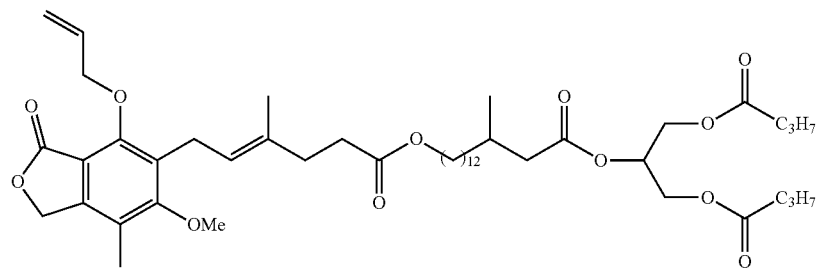

Int-127

Int-127: ¹H NMR (401 MHz, CDCl₃) δ 6.09 (ddt, j=17.1, 10.4, 5.9 Hz, 1H), 5.37 (dq, J=17.2, 1.5 Hz, 1H), 5.28 (m, 1H), 5.23 (m, 1H), 5.18 (m, 1H), 5.13 (s, 2H), 4.78 (dt, J=5.9, 1.3 Hz, 2H), 4.296/4.293 (each dd, J=11.9, 4.3 Hz, 2H), 4.150/4.148 (each dd, J=11.9, 6.0 Hz, 2H), 4.00 (t, J=6.8 Hz, 2H), 3.76 (s, 3H), 3.41 (d, J=6.7 Hz, 2H), 2.39-2.25 (m, 9H), 2.17 (s, 3H), 2.12 (dd, J=14.7, 8.3 Hz, 1H), 1.93 (m, 1H), 1.78 (d, J=0.7 Hz, 3H), 1.68-1.52 (m, 8H), 1.35-1.17 (m, 18H), 0.94 (t, J=7.4 Hz, 6H), 0.93 (d, J=6.7 Hz, 3H).

I-43:

122.3 (C), 116.8 (C), 106.5 (C), 70.2 (CH₂), 68.9 (CH), 64.6 (CH₂), 62.3 (2C; CH₂), 61.1 (CH₃), 41.9 (CH₂), 36.8 (CH₂), 36.1 (2C; CH₂), 34.8 (CH₂), 33.3 (CH₂), 30.5 (CH), 29.9 (CH₂), 29.81 (CH₂), 29.79 (2C; CH₂), 29.74 (CH₂), 29.68 (CH₂), 29.4 (CH₂), 28.8 (CH₂), 27.1 (CH₂), 26.1 (CH₂), 22.7 (CH₂), 19.7 (CH₃), 18.5 (2C; CH₂), 16.3 (CH₃), 13.8 (2C; CH₃), 11.7 (CH₃).

Using similar methods, MPA-C10-2-TG (I-46) was prepared.

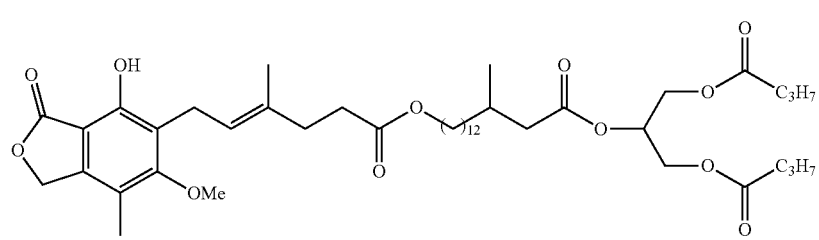

I-43

I-43 was prepared from the corresponding allyl-protected compound in 58% yield after Pd-mediated deprotection. ¹H NMR (401 MHz, CDCl₃) δ 7.67 (s, 1H), 5.31-5.21 (m, 2H), 5.19 (s, 2H), 4.295/4.292 (each dd, J=11.9, 4.2 Hz, 2H), 4.149/4.197 (each dd, J=11.9, 6.0 Hz, 2H), 4.00 (t, J=6.8 Hz, 2H), 3.76 (s, 3H), 3.38 (d, J=6.9 Hz, 2H), 2.41-2.26 (m, 9H), 2.14 (s, 3H), 2.12 (dd, J=14.7, 8.3 Hz, 1H), 1.93 (m, 1H), 1.79 (s, 3H), 1.69-1.52 (m, 8H), 1.36-1.15 (m, 18H), 0.94 (t, J=7.4, 2.8 Hz, 6H), 0.92 (d, J=6.7 Hz, 3H); ¹³C NMR (101 MHz, CDCl₃) δ 173.6 (C), 173.3 (2C; C), 173.1 (C), 172.5 (C), 163.8 (C), 153.8 (C), 144.1 (C), 134.4 (C), 122.8 (CH),

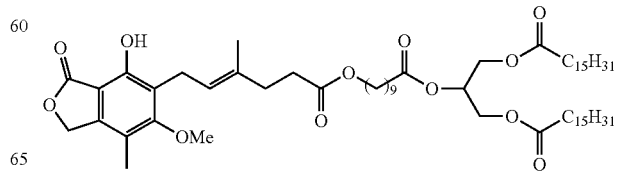

I-46

¹H NMR (401 MHz, CDCl₃) δ 7.67 (s, 1H), 5.29-5.21 (m, 2H), 5.19 (s, 2H), 4.29 (dd, J=11.9, 4.4 Hz, 2H), 4.14 (dd, J=11.9, 5.9 Hz, 2H), 4.00 (t, J=6.8 Hz, 2H), 3.76 (s, 3H), 3.38 (d, J=6.9 Hz, 2H), 2.41-2.35 (m, 2H), 2.33-2.24 (m, 8H), 2.14 (s, 3H), 1.80 (s, 3H), 1.66-1.52 (m, 8H), 1.37-1.17 (m, 58H), 0.87 (t, J=6.8 Hz, 6H); ¹³C NMR (101 MHz, CDCl₃) δ 173.6 (C), 173.4 (2C; C), 173.1 (C), 173.0 (C), 163.8 (C), 153.8 (C), 144.1 (C), 134.4 (C), 122.8 (CH), 122.3 (C), 116.8 (C), 106.5 (C), 70.2 (CH₂), 69.0 (CH), 64.6 (CH₂), 62.2 (2C; CH₂), 61.1 (CH₃), 34.8 (CH₂), 34.3 (CH₂), 34.2 (2C; CH₂), 33.3 (CH₂), 32.1 (2C; CH₂), 29.84 (6C; CH₂), 29.80 (4C; CH₂), 29.76 (2C; CH₂), 29.62 (2C; CH₂), 29.50 (3C; CH₂), 29.41 (2C; CH₂), 29.36 (2C; CH₂), 29.26 (2C; CH₂), 29.19 (CH₂), 28.8 (CH₂), 26.1 (CH₂), 25.0 (3C; CH₂), 22.8 (2C; CH₂), 22.7 (CH₂), 16.3 (CH₃), 14.3 (2C; CH₃), 11.7 (CH₃).

Using similar methods to those described above, MPA-C12-2-TG-butyrate (I-49) was prepared using Int-126.

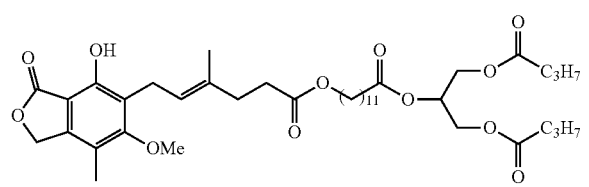

I-49

¹H NMR (401 MHz, CDCl₃) δ 7.66 (s, 1H), 5.29-5.19 (m, 2H), 5.18 (s, 2H), 4.29 (dd, J=11.9, 4.3 Hz, 2H), 4.14 (dd, J=11.9, 6.0 Hz, 2H), 3.99 (t, J=6.8 Hz, 2H), 3.75 (s, 3H), 3.37 (d, J=7.0 Hz, 2H), 2.41-2.34 (m, 2H), 2.33-2.24 (m, 8H), 2.13 (s, 3H), 1.78 (s, 3H), 1.69-1.51 (m, 8H), 1.35-1.19 (m, 14H), 0.93 (t, J=7.4 Hz, 6H); ¹³C NMR (101 MHz, CDCl₃) δ 173.6 (C), 173.2 (2C; C), 173.0 (2C; C), 163.8 (C), 153.8 (C), 144.1 (C), 134.3 (C), 122.8 (CH), 122.3 (C), 116.8 (C), 106.5 (C), 70.2 (CH₂), 69.0 (CH), 64.6 (CH₂), 62.2 (2C; CH₂), 61.1 (CH₃), 36.0 (2C; CH₂), 34.8 (CH₂), 34.3 (CH₂), 33.2 (CH₂), 29.63 (CH₂), 29.61 (CH₂), 29.5 (CH₂), 29.4 (2C; CH₂), 29.2 (CH₂), 28.7 (CH₂), 26.0 (CH₂), 25.0 (CH₂), 22.7 (CH₂), 18.5 (2C; CH₂), 16.3 (CH₃), 13.7 (2C; CH₃), 11.7 (CH₃).

(E)-2-((10-((6-(4-hydroxy-6-methoxy-7-methyl-3-oxo-1,3-dihydroisobenzofuran-5-yl)-4-methylhex-4-enoyl)oxy)-3-methyldecanoyl)oxy)propane-1,3-diyl dipalmitate (I-50)

Using similar methods to those described above, MPA-C1 ObMe-2-TG (I-50) was prepared using Int-23:

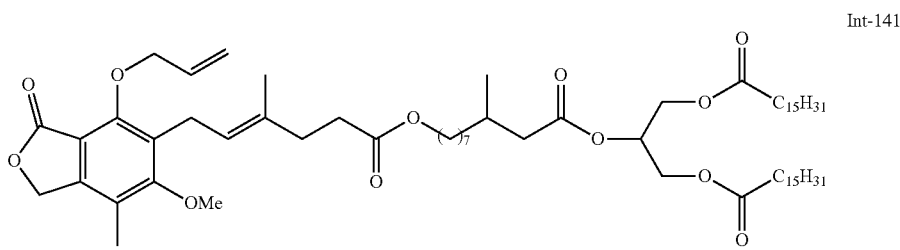

Int-141

4-(Dimethylamino)pyridine (3.2 mg, 26.6 μmol) and N-(3-dimethylaminopropyl)-N'-ethyl-carbodiimide (EDC.HCl, 12.7 mg, 66.4 μmol) were added to a solution of acid Int-86 (14.4 mg, 39.8 μmol) and alcohol Int-23 (20.0 mg, 26.6 μmol) in CH₂Cl₂ (1.5 mL) and the mixture stirred at RT for 22 hours. The reaction was diluted with CH₂Cl₂ (5 mL), silica gel was added, and the mixture was concentrated under reduced pressure. Purification by silica gel chromatography (20% ethyl acetate/hexanes) gave ester Int-141 (28.5 mg, 98%) as a colorless oil. ¹H NMR (401 MHz, CDCl₃) δ 6.09 (ddt, J=17.1, 10.4, 5.9 Hz, 1H), 5.37 (dq, j=17.2, 1.5 Hz, 1H), 5.30-5.14 (m, 3H), 5.12 (s, 2H), 4.77 (dt, J=5.9, 1.3 Hz, 2H), 4.282/4.280 (each dd, j=11.9, 4.3 Hz, 2H), 4.13 (dd, j=11.9, 6.0 Hz, 2H), 3.99 (t, j=6.8 Hz, 2H), 3.76 (s, 3H), 3.41 (d, J=6.7 Hz, 2H), 2.39-2.25 (m, 9H), 2.17 (s, 3H), 2.11 (dd, j=14.7, 8.4 Hz, 1H), 1.92 (m, 1H), 1.78 (d, J=0.7 Hz, 3H), 1.67-1.51 (m, 5H), 1.36-1.14 (m, 58H), 0.92 (d, j=6.6 Hz, 3H), 0.87 (t, J=6.9 Hz, 6H); ¹³C NMR (101 MHz, CDCl₃) δ 173.6 (C), 173.4 (2C; C), 172.4 (C), 169.1 (C), 163.0 (C), 155.4 (C), 146.8 (C), 134.00 (C), 133.97 (CH), 129.3 (C), 123.7 (CH), 120.1 (C), 118.2 (CH₂), 112.8 (C), 76.2 (CH₂), 68.9 (CH), 68.4 (CH₂), 64.6 (CH₂), 62.3 (2C; CH₂), 61.1 (CH₃), 41.8 (CH₂), 36.8 (CH₂), 34.7 (CH₂), 34.2 (2C; CH₂), 33.2 (CH₂), 32.1 (2C; CH₂), 30.5 (CH), 29.83 (7C; CH₂), 29.79 (4C; CH₂), 29.75 (2C; CH₂), 29.6 (2C; CH₂), 29.5 (2C; CH₂), 29.4 (3C; CH₂), 29.3 (2C; CH₂), 28.7 (CH₂), 27.0 (CH₂), 26.0 (CH₂), 25.0 (2C; CH₂), 23.8 (CH₂), 22.8 (2C; CH₂), 19.7 (CH₃), 16.4 (CH₃), 14.3 (2C; CH₃), 11.7 (CH₃); ESI-HRMS: Calcd. for C₆₆H₁₁₀NaO₁₂ [M+Na⁺]1117.7890. Found 1117.7907.

Synthesis of I-50:

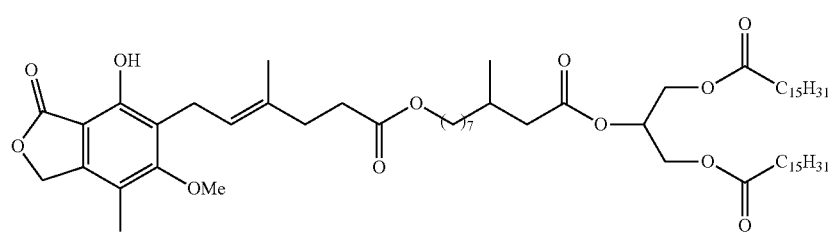

1,3-Dimethylbarbituric acid (8.3 mg, 52.9 μmol) and Pd(PPh$_3$)$_4$ (6.1 mg, 5.3 μmol) were added to allyl ether Int-141 (28.0 mg, 25.6 μmol) in CH$_2$Cl$_2$ (1 mL) and the mixture stirred at RT for one hour. The reaction was diluted with CH$_2$Cl$_2$ (5 mL), silica gel was added, and the mixture was concentrated under reduced pressure. Silica gel chromatography (15% to 20% ethyl acetate/hexanes) gave MPA-C1 ObMe-2-TG prodrug 1-50 (24.1 mg, 89%) as a pale yellow oil.

$^1$H NMR (401 MHz, CDCl$_3$) δ 7.67 (s, 1H), 5.30-5.20 (m, 2H), 5.19 (s, 2H), 4.28 (dd, J=11.9, 4.3 Hz, 2H), 4.13 (dd, J=13.1, 4.8 Hz, 2H), 4.00 (t, J=6.8 Hz, 2H), 3.75 (s, 3H), 3.38 (d, J=6.9 Hz, 2H), 2.41-2.35 (m, 2H), 2.34-2.26 (m, 7H), 2.14 (s, J=6.2 Hz, 3H), 2.11 (dd, J=14.7, 8.4 Hz, 1H), 1.90 (m, 1H), 1.79 (s, 3H), 1.67-1.52 (m, 6H), 1.36-1.14 (m, 58H), 0.92 (d, j=6.6 Hz, 3H), 0.87 (t, j=6.9 Hz, 6H); $^{13}$C NMR (101 MHz, CDCl$_3$) δ 173.6 (C), 173.4 (2C; C), 173.1 (C), 172.4 (C), 163.8 (C), 153.8 (C), 144.1 (C), 134.4 (C), 122.8 (CH), 122.3 (C), 116.8 (C), 106.5 (C), 70.2 (CH$_2$), 69.0 (CH), 64.6 (CH$_2$), 62.3 (2C; CH$_2$), 61.1 (CH$_3$), 41.8 (CH$_2$), 36.8 (CH$_2$), 34.8 (CH$_2$), 34.2 (2C; CH$_2$), 33.3 (CH$_2$), 32.1 (2C; CH$_2$), 30.5 (CH), 29.83 (7C; CH$_2$), 29.79 (4C; CH$_2$), 29.76 (2C; CH$_2$), 29.6 (2C; CH$_2$), 29.5 (2C; CH$_2$), 29.4 (3C; CH$_2$), 29.3 (2C; CH$_2$), 28.7 (CH$_2$), 27.0 (CH$_2$), 26.1 (CH$_2$), 25.0 (2C; CH$_2$), 22.8 (2C; CH$_2$), 22.7 (CH$_2$), 19.7 (CH$_3$), 16.3 (CH$_3$), 14.3 (2C; CH$_3$), 11.7 (CH$_3$); ESI-HRMS: calcd. for C$_{63}$H$_{106}$NaO$_{12}$ [M+Na$^+$] 1077.7576; found 1077.7576.

(E)-2-((12-(((6-(4-hydroxy-6-methoxy-7-methyl-3-oxo-1,3-dihydroisobenzofuran-5-yl)-4-methylhex-4-enoyl)oxy)-3-methyldodecanoyl)oxy)propane-1,3-diyl dipalmitate (I-51)

Using similar methods to those described above, MPA-C12bMe-2-TG (I-51) was prepared using Lit-121.

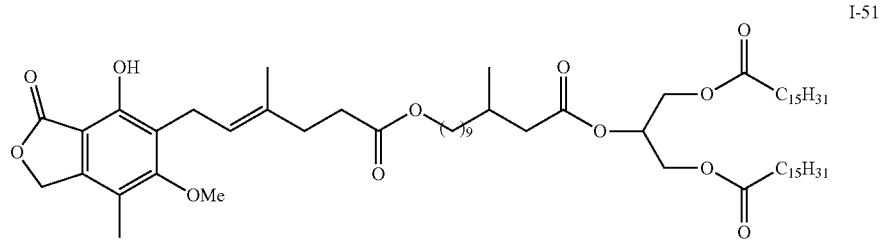

$^1$H NMR (401 MHz, CDCl$_3$) δ 7.67 (s, 1H), 5.30-5.21 (m, 2H), 5.19 (s, 2H), 4.285/4.283 (each dd, j=11.8, 4.3 Hz, 2H), 4.14 (dd, j=11.9, 5.9 Hz, 2H), 4.00 (t, j=6.8 Hz, 2H), 3.75 (s, 3H), 3.38 (d, J=6.9 Hz, 2H), 2.41-2.26 (m, 9H), 2.14 (s, 3H), 2.09 (dd, j=14.8, 8.3 Hz, 1H), 1.93 (m, 1H), 1.79 (d, j=0.7 Hz, 3H), 1.64-1.52 (m, 6H), 1.41-1.15 (m, 62H), 0.92 (d, j=6.6 Hz, 3H), 0.87 (t, j=6.9 Hz, 6H); $^{13}$C NMR (101 MHz, CDCl$_3$) δ 173.6 (C), 173.4 (2C; C), 173.1 (C), 172.5 (C), 163.8 (C), 153.8 (C), 144.1 (C), 134.4 (C), 122.8 (CH), 122.3 (C), 116.8 (C), 106.5 (C), 70.2 (CH$_2$), 68.9 (CH), 64.6 (CH$_2$), 62.3 (2C; CH$_2$), 61.1 (CH$_3$), 41.8 (CH$_2$), 36.8 (CH$_2$), 34.8 (CH$_2$), 34.2 (2C; CH$_2$), 33.3 (CH$_2$), 32.1 (2C; CH$_2$), 30.5 (CH), 29.9 (CH$_2$), 29.84 (6C; CH$_2$), 29.80 (4C; CH$_2$), 29.76 (2C; CH$_2$), 29.74 (CH$_2$), 29.68 (CH$_2$), 29.62 (2C; CH$_2$), 29.5 (2C; CH$_2$), 29.4 (3C; CH$_2$), 29.3 (2C; CH$_2$), 28.8 (CH$_2$), 27.1 (CH$_2$), 26.1 (CH$_2$), 25.0 (2C; CH$_2$), 22.8 (2C; CH$_2$), 22.7 (CH$_2$), 19.7 (CH$_3$), 16.3 (CH$_3$), 14.3 (2C; CH$_3$), 11.7 (CH$_3$).

(E)-2-((12-((6-(4-hydroxy-6-methoxy-7-methyl-3-oxo-1,3-dihydroisobenzofuran-5-yl)-4-methylhex-4-enoyl)oxy)-3-methyltridecanoyl)oxy)propane-1,3-diyl dipalmitate (I-56)

Using similar methods to those described above, MPA-C12a'bMeOH-2-TG (I-56) was prepared using Int-143:

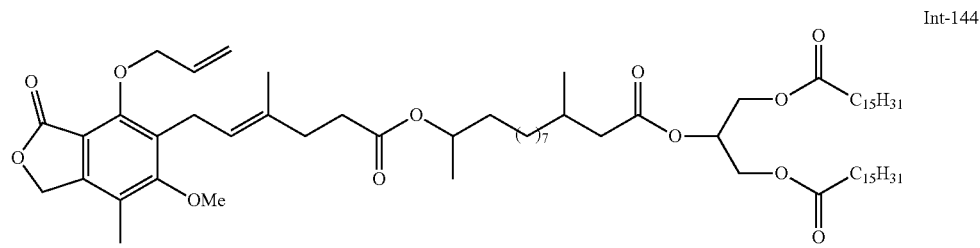
Int-144

4-(Dimethylamino)pyridine (DMAP, 7.0 mg, 57.5 μmol) and *N*-(3-dimethylaminopropyl)-N'-ethyl-carbodiimide (EDC.HCl, 14.7 mg, 76.7 μmol) were added to a solution of acid Int-86 (13.8 mg, 38.4 μmol) and alcohol Int-143 (30.5 mg, 38.4 μmol) in $CH_2Cl_2$ (2 mL) and the mixture stirred at at room temperature for 19 hours. TLC analysis at this time indicated the presence of significant unreacted alcohol Int-143, so additional DMAP (3.5 mg, 28.6 μmol), EDC.HCl (6.2 mg, 32.3 μmol) and acid Int-86 (5.0 mg, 13.9 μmol) were added and the mixture stirred at room temperature for a further 24 hours, then allowed to stand in a refrigerator for four days. The reaction was diluted with $CH_2Cl_2$ (5 mL), silica gel was added and the mixture concentrated under reduced pressure. Silica gel chromatography (0% to 4% ethyl acetate/toluene) gave some fractions of high purity Int-144, along with other fractions containing a more polar contaminant. Preparative thin-layer chromatography of the mixed fractions (15% ethyl acetate/toluene) gave a further batch of clean product. Combination of the pure fractions from both chromatographic purifications and concentration gave Int-144 (25.0 mg, 57%) as a pale yellow oil. $^1$H NMR (401 MHz, $CDCl_3$) δ 6.10 (ddt, J=16.3, 10.4, 5.9 Hz, 1H), 5.37 (m, 1H), 5.28 (m, 1H), 5.23 (m, 1H), 5.18 (m, 1H), 5.13 (s, 2H), 4.84 (m, 1H), 4.78 (dt, J=5.9, 1.2 Hz, 2H), 4.29 (dd, J=11.9, 4.3 Hz, 2H), 4.14 (dd, J=11.9, 5.9 Hz, 2H), 3.76 (s, 3H), 3.42 (d, J=6.7 Hz, 2H), 2.38-2.24 (m, 9H), 2.18 (s, 3H), 2.11 (dd, J=14.7, 8.4 Hz, 1H), 1.93 (m, 1H), 1.79 (s, 3H), 1.68-1.49 (m, 6H), 1.46-1.18 (m, 62H), 1.14 (d, J=6.2 Hz, 3H), 0.92 (d, J=6.6 Hz, 3H), 0.88 (t, J=6.8 Hz, 6H).

Synthesis of I-56:

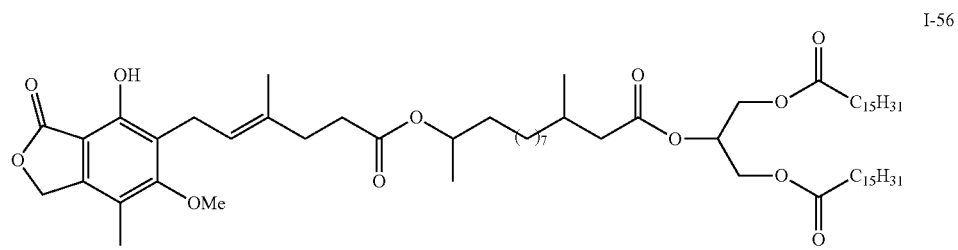
I-56

1,3-Dimethylbarbituric acid (7.3 mg, 46.8 µmol) and Pd(PPh$_3$)$_4$ (5.3 mg, 4.6 µmol) were added to allyl ether Int-144 (23.9 mg, 21.0 µmol) in CH$_2$Cl$_2$ (2 mL) and the mixture stirred at room temperature for 20 hours. The reaction was diluted with CH$_2$Cl$_2$ (5 mL), silica gel was added and the mixture concentrated under reduced pressure. Silica gel chromatography (12.5% to 15% ethyl acetate/hexanes) gave MPA-C12α'bMeOH-2-TG 1-56 (16.3 mg, 71%) as a colorless oil. $^1$H NMR (401 MHz, CDCl$_3$) δ 7.67 (s, 1H), 5.30-5.20 (m, 2H), 5.19 (s, 2H), 4.84 (m, 1H), 4.28 (dd, J=11.9, 4.1 Hz, 2H), 4.14 (dd, j=11.8, 6.0 Hz, 2H), 3.76 (s, 3H), 3.38 (d, j=6.9 Hz, 2H), 2.39-2.25 (m, 9H), 2.14 (s, 3H), 2.11 (dd, j=14.4, 8.0 Hz, 1H), 1.93 (s, 1H), 1.80 (s, 3H), 1.66-1.49 (m, 6H), 1.46-1.17 (m, 62H), 1.14 (d, j=6.2 Hz, 3H), 0.92 (d, j=6.6 Hz, 3H), 0.87 (t, j=6.8 Hz, 6H); $^{13}$C NMR (101 MHz, CDCl$_3$) δ 173.4 (2C; C), 173.14 (C), 173.06 (C), 172.5 (C), 163.8 (C), 153.8 (C), 144.1 (C), 134.4 (C), 122.7 (CH), 122.3 (C), 116.8 (C), 106.5 (C), 71.0 (CH), 70.2 (CH$_2$), 69.0 (CH), 62.3 (2C; CH$_2$), 61.1 (CH$_3$), 41.8 (CH$_2$), 36.9 (CH$_2$), 36.1 (CH$_2$), 34.8 (CH$_2$), 34.2 (2C; CH$_2$), 33.6 (CH$_2$), 32.1 (2C; CH$_2$), 30.5 (CH), 29.93 (CH$_2$), 29.84 (7C; CH$_2$), 29.80 (2C; CH$_2$), 29.76 (3C; CH$_2$), 29.70 (CH$_2$), 29.6 (3C; CH$_2$), 29.5 (2C; CH$_2$), 29.4 (2C; CH$_2$), 29.3 (2C; CH$_2$), 27.1 (CH$_2$), 25.6 (CH$_2$), 25.0 (2C; CH$_2$), 22.8 (2C; CH$_2$), 22.7 (CH$_2$), 20.0 (CH$_3$), 19.7 (CH$_3$), 16.3 (CH$_3$), 14.3 (2C; CH$_3$), 11.7 (CH$_3$); ESI-HRMS: calcd. for C$_{66}$H$_{112}$NaO$_{12}$ [M+Na$^+$] 1119.8046; found 1119.8055.

(E)-2-((12-((6-(4-hydroxy-6-methoxy-7-methyl-3-oxo-1,3-dihydroisobenzofuran-5-yl)-4-methylhex-4-enoyl)oxy)-3,11-dimethyldodecanoyl)oxy)propane-1,3-diyl dipalmitate (I-70)

Using similar methods to those described above, MPA-C12b'bMeOH-2-TG (I-70) was prepared using Int-148:

4-(Dimethylamino)pyridine (DMAP, 7.1 mg, 58.1 µmol) and N-(3-dimethylaminopropyl)-N'-ethyl-carbodiimide (EDC.HCl, 13.9 mg, 72.5 µmol) were added to a solution of acid Int-86 (12.5 mg, 34.7 µmol) and alcohol Int-148 (28.0 mg, 35.2 µmol) in CH$_2$Cl$_2$ (2 mL) and the mixture stirred at room temperature for 24 hours, then allowed to stand in a refrigerator for five days. The reaction was diluted with CH$_2$Cl$_2$ (5 mL), silica gel was added and the mixture concentrated under reduced pressure. Silica gel chromatography (0% to 5% ethyl acetate/toluene) gave Int-149 (37.2 mg, 94%) as a colourless oil; $^1$H NMR (401 MHz, CDCl$_3$) δ 6.09 (ddt, J=16.3, 10.4, 5.9 Hz, 1H), 5.36 (m, 1H), 5.27 (m, 1H), 5.23 (m, 1H), 5.17 (m, 1H), 5.12 (s, 2H), 4.78 (dt, J=5.9, 1.2 Hz, 2H), 4.28 (dd, J=11.9, 4.2 Hz, 2H), 4.14 (dd, J=11.9, 6.0 Hz, 2H), 3.90 (dd, J=10.7, 5.7 Hz, 1H), 3.78 (dd, j=10.7, 7.0 Hz, 1H), 3.76 (s, 3H), 3.41 (d, j=6.7 Hz, 2H), 2.41-2.25 (m, 9H), 2.17 (s, 3H), 2.11 (dd, j=14.7, 8.4 Hz, 1H), 1.92 (m, 1H), 1.78 (s, 3H), 1.75-1.55 (m, 5H), 1.37-1.06 (m, 62H), 0.92 (d, J=6.6 Hz, 3H), 0.870 (d, J=6.7 Hz, 3H), 0.869 (t, j=6.8 Hz, 6H); $^{13}$C NMR (101 MHz, CDCl$_3$) δ 173.6 (C), 173.4 (2C; C), 172.5 (C), 169.1 (C), 163.0 (C), 155.4 (C), 146.8 (C), 134.00 (C), 133.98 (CH), 129.3 (C), 123.7 (CH), 120.1 (C), 118.2 (CH$_2$), 112.8 (C), 76.2 (CH$_2$), 69.5 (CH$_2$), 68.9 (CH), 68.4 (CH$_2$), 62.3 (2C; CH$_2$), 61.1 (CH$_3$), 41.8 (CH$_2$), 36.8 (CH$_2$), 34.7 (CH$_2$), 34.2 (2C; CH$_2$), 33.5 (CH$_2$), 33.2 (CH$_2$), 32.7 (CH), 32.1 (2C; CH$_2$), 30.5 (CH), 30.0 (CH$_2$), 29.9 (CH$_2$), 29.82 (7C; CH$_2$), 29.79 (4C; CH$_2$), 29.75 (2C; CH$_2$), 29.6 (2C; CH$_2$), 29.5 (2C; CH$_2$), 29.4 (2C; CH$_2$), 29.3 (2C; CH$_2$), 27.1 (CH$_2$), 27.0 (CH$_2$), 25.0 (2C; CH$_2$), 23.8 (CH$_2$), 22.8 (2C; CH$_2$), 19.7 (CH$_3$), 17.0 (CH$_3$), 16.4 (CH$_3$), 14.2 (2C; CH$_3$), 11.7 (CH$_3$).

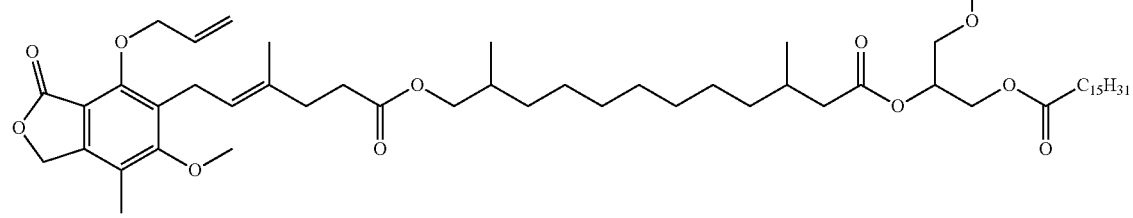

Int-149

Synthesis of I-70:

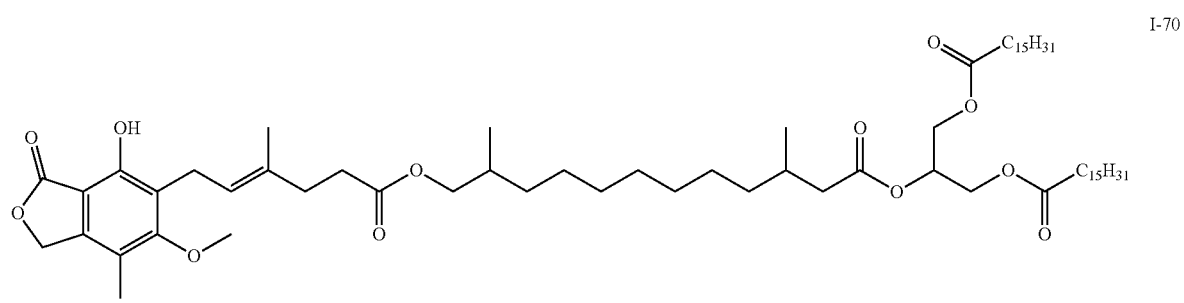

1,3-Dimethylbarbituric acid (9.3 mg, 59.6 µmol) and Pd(PPh$_3$)$_4$ (7.3 mg, 6.3 µmol) were added to allyl ether Int-149 (34.0 mg, 29.9 µmol) in CH$_2$Cl$_2$ (2.5 mL) and the mixture stirred at room temperature for 20 hours. The reaction was diluted with CH$_2$Cl$_2$ (5 mL), silica gel was added and the mixture was concentrated under reduced pressure. Silica gel chromatography (5% to 15% ethyl acetate/hexanes) gave MPA-C123'3MeOH-2-TG prodrug 1-70 (21.0 mg, 64%) as a colorless oil. $^1$H NMR (401 MHz, CDCl$_3$) δ 7.67 (hr s, 1H), 5.30-5.21 (m, 2H), 5.19 (s, 2H), 4.28 (dd, J=11.9, 4.0 Hz, 2H), 4.14 (dd, J=11.9, 6.0 Hz, 2H), 3.91 (dd, J=10.7, 5.7 Hz, 1H), 3.79 (dd, J=11.7, 4.7 Hz, 1H), 3.75 (s, 3H), 3.38 (d, J=6.9 Hz, 2H), 2.43-2.27 (m, 9H), 2.14 (s, 3H), 2.11 (dd, J=14.7, 8.4 Hz, 1H), 1.93 (m, 1H), 1.80 (s, 3H), 1.71 (m, 1H), 1.63-1.56 (m, 4H), 1.37-1.06 (m, 62H), 0.92 (d, J=6.6 Hz, 3H), 0.90-0.83 (m, 9H); $^{13}$C NMR (101 MHz, CDCl$_3$) δ 173.6 (C), 173.4 (2C; C), 173.1 (C), 172.5 (C), 163.8 (C), 153.8 (C), 144.1 (C), 134.4 (C), 122.8 (CH), 122.3 (C), 116.8 (C), 106.5 (C), 70.2 (CH$_2$), 69.5 (CH$_2$), 68.9 (CH), 62.3 (2C; CH$_2$), 61.1 (CH$_3$), 41.8 (CH$_2$), 36.8 (CH$_2$), 34.8 (CH$_2$), 34.2 (2C; CH$_2$), 33.5 (CH$_2$), 33.3 (CH$_2$), 32.7 (CH), 32.1 (2C; CH$_2$), 30.5 (CH), 30.0 (CH$_2$), 29.9 (CH$_2$), 29.83 (7C; CH$_2$), 29.79 (4C; CH$_2$), 29.76 (2C; CH$_2$), 29.6 (2C; CH$_2$), 29.5 (2C; CH$_2$), 29.4 (2C; CH$_2$), 29.3 (2C; CH$_2$), 27.1 (CH$_2$), 27.0 (CH$_2$), 25.0 (2C; CH$_2$), 22.8 (2C; CH$_2$), 22.7 (CH$_2$), 19.7 (CH$_3$), 17.0 (CH$_3$), 16.3 (CH$_3$), 14.3 (2C; CH$_3$), 11.7 (CH$_3$); ESI-HRMS: calcd. for C$_{66}$H$_{113}$NaO$_{12}$ [M+Na$^+$] 1097.8227; found 1097.8219.

Example 13: Synthesis of (E)-12-(1,3-bis(palmitoyloxy)propan-2-yl) 1-(4-(((6-methoxy-5-(6-methoxy-3-methyl-6-oxohex-2-en-1-yl)-7-methyl-3-oxo-1,3-dihydroisobenzofuran-4-yl)oxy)methyl)-2,6-dimethylphenyl) 2,10-dimethyldodecanedioate (I-55)

Scheme 51. Synthesis of I-55.

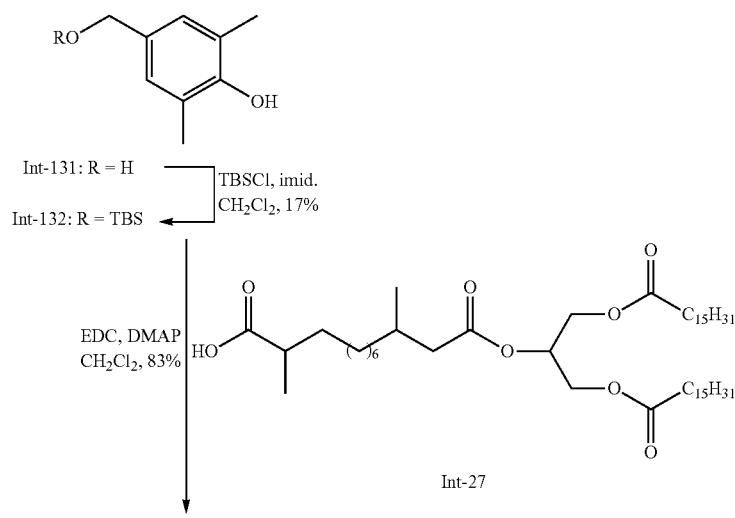

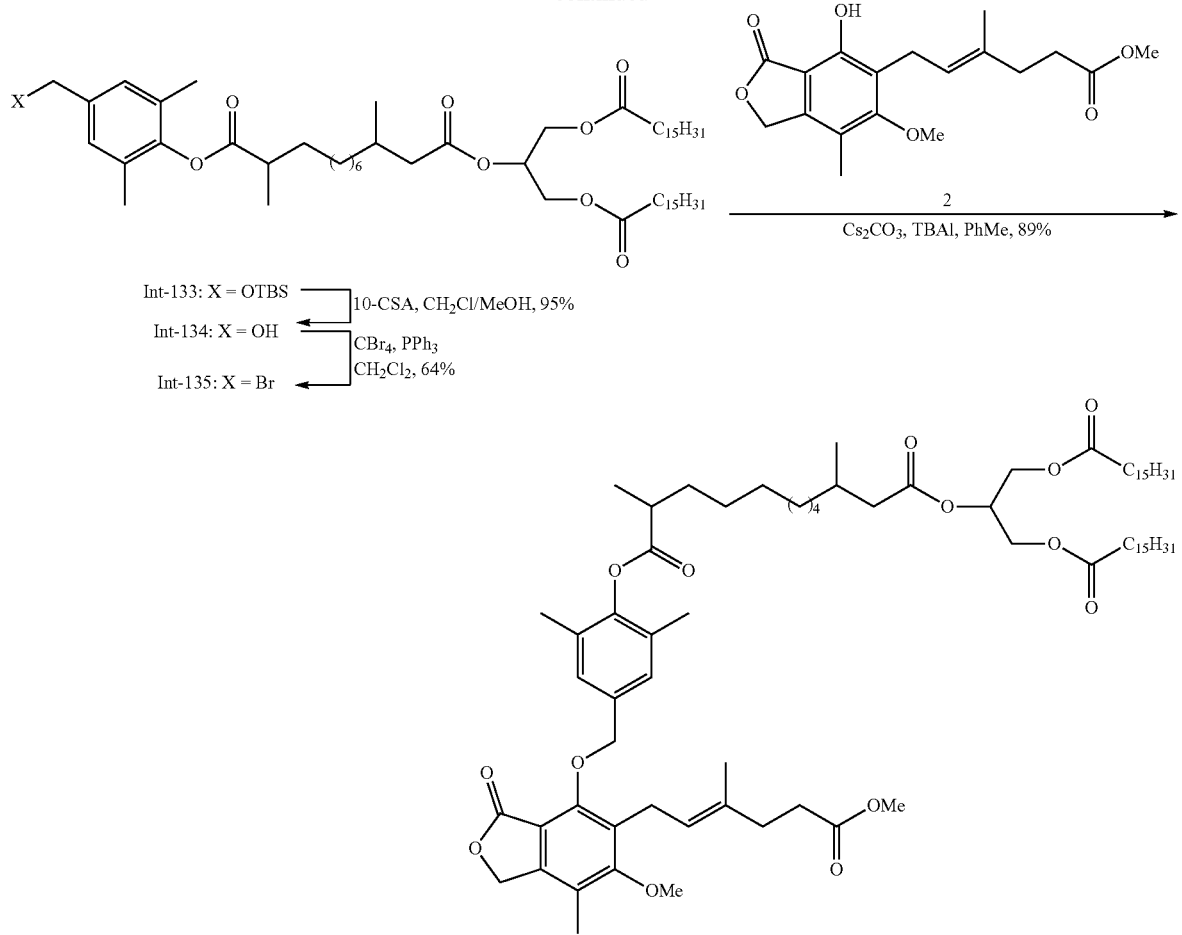

Sodium borohydride (378 mg, 9.99 mmol) was added in 4-5 portions to a solution of 4-hydroxy-3,5-dimethylbenzaldehyde (500 mg, 3.33 mmol) in methanol (8 mL) at 0° C. and the resulting mixture stirred at 0° C. for 45 minutes. The reaction mixture was acidified to pH 2 by the addition of 1 M HCl (10-15 mL) and the organic solvent removed under reduced pressure. The aqueous residue was extracted with $CH_2Cl_2$ (2×20 mL) and the combined organic extracts dried ($MgSO_4$) and concentrated under reduced pressure to give crude diol Int-131 (600 mg), which was used in the next step without further purification.

Imidazole (161 mg, 2.37 mmol) and tert-butyl(chloro)dimethylsilane (TBSCl, 297 mg, 1.97 mmol) were added to a solution of Int-131 (300 mg of crude material described above) in $CH_2Cl_2$ (8 mL) at 0° C. and the mixture stirred at RT for 45 minutes. The reaction was diluted with $CH_2Cl_2$ (40 mL), washed with water and brine (40 mL each), dried ($MgSO_4$) and concentrated under reduced pressure to give the crude product. Purification by silica gel chromatography (12.5% to 17.5% ethyl acetate/hexanes) gave TBS ether Int-132 (90.5 mg, 17%) as a colorless oil. $^1H$ NMR (401 MHz, $CDCl_3$) δ 6.93 (s, 2H), 4.60 (s, 2H), 2.24 (s, 6H), 0.93 (s, 9H), 0.09 (s, 6H).

4-(Dimethylamino)pyridine (DMAP, 11.5 mg, 0.0938 mmol) and EDC.HCl (36.0 mg, 0.188 mmol) were added to a solution of Int-27 (79.7 mg, 0.0985 mmol) and phenol Int-132 (25.0 mg, 0.0938 mmol) in $CH_2Cl_2$ (4 mL) and the mixture stirred at RT for about three days. The reaction was diluted with $CH_2Cl_2$ (10 mL), silica gel was added and the mixture concentrated under reduced pressure. Purification by silica gel chromatography (8% to 10% ethyl acetate/hexanes) gave Int-133 (82.8 mg, 83%) as a colorless oil. $^1H$ NMR (401 MHz, $CDCl_3$) δ 7.00 (s, 2H), 5.28 (m, 1H), 4.65 (s, 2H), 4.29 (dd, J=11.9, 3.9 Hz, 2H), 4.14 (dd, J=11.8, 5.9 Hz, 2H), 2.72 (m, 1H), 2.33 (dd, J=14.6, 6.0 Hz, 1H), 2.30 (t, J=7.5 Hz, 4H), 2.13 (s, 6H), 2.12 (dd, J=14.6, 8.4 Hz, 1H), 1.97-1.81 (m, 2H), 1.66-1.48 (m, 5H), 1.34 (d, J=7.0 Hz, 3H), 1.46-1.13 (m, 60H), 0.94 (s, 9H), 0.93 (d, J=6.9 Hz, 3H), 0.88 (t, J=6.9 Hz, 6H), 0.09 (s, 6H); $^{13}C$ NMR (101 MHz, $CDCl_3$) δ 174.6 (C), 173.4 (2C; C), 172.4 (C), 147.1 (C), 138.7 (C), 129.9 (2C; C), 126.4 (2C; CH), 68.9 (CH), 64.7 ($CH_2$), 62.3 (2C; $CH_2$), 41.8 ($CH_2$), 39.9 (CH), 36.8 ($CH_2$), 34.2 (2C; $CH_2$), 33.8 ($CH_2$), 32.1 (2C; $CH_2$), 30.5 (CH), 29.87 ($CH_2$), 29.82 (6C; $CH_2$), 29.79 (4C; $CH_2$), 29.75 (2C; $CH_2$), 29.67 ($CH_2$), 29.65 ($CH_2$), 29.60 (2C; $CH_2$), 29.5 (2C; $CH_2$), 29.4 (2C; $CH_2$), 29.2 (2C; $CH_2$), 27.5 ($CH_2$), 27.0 ($CH_2$), 26.1 (3C; $CH_3$), 25.0 (2C; $CH_2$), 22.8 (2C; $CH_2$), 19.7 ($CH_3$), 17.6 ($CH_3$), 16.6 (2C; $CH_3$), 14.2 (2C; $CH_3$), −5.1 (2C; $CH_3$).

10-Camphorsulfonic acid (3.6 mg, 15.1 μmol) was added to Int-133 (80.0 mg, 75.6 μmol) in $CH_2Cl_2$ (1 mL) and MeOH (1 mL) and the mixture stirred at RT for one hour. The reaction was diluted with $CH_2Cl_2$ (30 mL), washed with sat. aq. $NaHCO_3$ and brine (25 mL each), dried ($MgSO_4$) and concentrated under reduced pressure to give the crude product. Purification by silica gel chromatography (20% ethyl acetate/hexanes) gave alcohol Int-134 (67.7 mg, 95%) as a colorless oil. $^1$H NMR (401 MHz, CDCl$_3$) δ 7.05 (s, 2H), 5.27 (m, 1H), 4.58 (s, 2H), 4.28 (dd, J=11.9, 4.3 Hz, 2H), 4.13 (dd, J=11.9, 6.0 Hz, 2H), 2.73 (m, 1H), 2.32 (dd, J=14.6, 6.0 Hz, 1H), 2.30 (t, J=7.5 Hz, 4H), 2.13 (s, 6H), 2.11 (dd, j=14.7, 8.2 Hz, 1H), 1.98-1.80 (m, 2H), 1.64-1.49 (m, 5H), 1.34 (d, j=7.0 Hz, 3H), 1.46-1.17 (m, 60H), 0.93 (d, j=6.6 Hz, 3H), 0.87 (t, J=6.8 Hz, 6H); $^{13}$C NMR (101 MHz, CDCl$_3$) δ 174.6 (C), 173.4 (2C; C), 172.4 (C), 147.7 (C), 138.4 (C), 130.4 (2C; C), 127.4 (2C; CH), 68.9 (CH), 65.0 (CH$_2$), 62.3 (2C; CH$_2$), 41.8 (CH$_2$), 39.9 (CH), 36.8 (CH$_2$), 34.2 (2C; CH$_2$), 33.8 (CH$_2$), 32.0 (2C; CH$_2$), 30.5 (CH), 29.83 (CH$_2$), 29.81 (6C; CH$_2$), 29.77 (4C; CH$_2$), 29.74 (2C; CH$_2$), 29.63 (CH$_2$), 29.62 (CH$_2$), 29.59 (2C; CH$_2$), 29.5 (2C; CH$_2$), 29.4 (2C; CH$_2$), 29.2 (2C; CH$_2$), 27.5 (CH$_2$), 27.0 (CH$_2$), 25.0 (2C; CH$_2$), 22.8 (2C; CH$_2$), 19.7 (CH$_3$), 17.5 (CH$_3$), 16.6 (2C; CH$_3$), 14.2 (2C; CH$_3$).

Carbon tetrabromide (CBr$_4$, 28.6 mg, 86.4 μmol) and triphenylphosphine (PPh$_3$, 27.2 mg, 104 μmol) were added to alcohol Int-134 (32.6 mg, 34.6 μmol) in CH$_2$Cl$_2$ (2 mL) at 0° C. and the reaction stirred at RT for 1.5 hours. The reaction was diluted with CH$_2$Cl$_2$ (5 mL), silica gel was added, and the solvent removed under reduced pressure. Purification by silica gel chromatography (5% to 6% ethyl acetate/hexanes) gave bromide Int-135 (22.2 mg, 64%) as a colorless ml. $^1$H NMR (401 MHz, CDCl$_3$) δ 7.09 (s, 2H), 5.27 (m, 1H), 4.42 (s, 2H), 4.29 (dd, J=11.9, 3.8 Hz, 2H), 4.14 (dd, J=11.9, 6.0 Hz, 2H), 2.73 (m, 1H), 2.33 (dd, J=14.8, 5.8 Hz, 1H), 2.30 (t, J=7.5 Hz, 4H), 2.123 (s, 6H), 2.118 (dd, j=14.6, 8.4 Hz, 1H), 1.97-1.80 (m, 2H), 1.65-1.48 (m, 5H), 1.34 (d, j=7.0 Hz, 3H), 1.46-1.14 (m, 60H), 0.93 (d, j=6.6 Hz, 3H), 0.88 (t, J=6.9 Hz, 6H); $^{13}$C NMR (101 MHz, CDCl$_3$) δ 174.4 (C), 173.4 (2C; C), 172.5 (C), 148.4 (C), 135.1 (C), 130.9 (2C; C), 129.5 (2C; CH), 69.0 (CH), 62.3 (2C; CH$_2$), 41.8 (CH$_2$), 39.9 (CH), 36.8 (CH$_2$), 34.2 (2C; CH$_2$), 33.8 (CH$_2$), 33.3 (CH$_2$), 32.1 (2C; CH$_2$), 30.5 (CH), 29.88 (CH$_2$), 29.84 (6C; CH$_2$), 29.80 (4C; CH$_2$), 29.77 (2C; CH$_2$), 29.67 (CH$_2$), 29.66 (CH$_2$), 29.62 (2C; CH$_2$), 29.5 (2C; CH$_2$), 29.4 (2C; CH$_2$), 29.3 (2C; CH$_2$), 27.5 (CH$_2$), 27.1 (CH$_2$), 25.0 (2C; CH$_2$), 22.8 (2C; CH$_2$), 19.7 (CH$_3$), 17.6 (CH$_3$), 16.6 (2C; CH$_3$), 14.3 (2C; CH$_3$).

Synthesis of I-55:

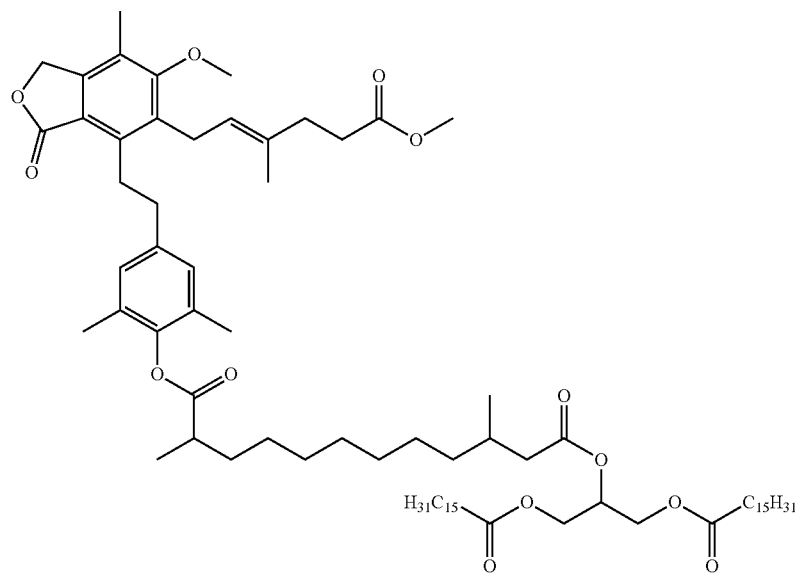

I-55

Cesium carbonate (6.5 mg, 19.9 μmol) and tetra-n-butylammonium iodide (TBAI, 3.7 mg, 9.9 μmol) were added to a solution of methyl ester 2 (8.0 mg, 23.9 μmol) and bromide Int-135 (20.0 mg, 19.9 μmol) in toluene (1.5 mL) and the mixture heated at 80° C. for two hours and then at 40° C. for a further 17 hours. The reaction was cooled to RT, diluted with ethyl acetate (40 mL) and the organic phase washed with water and brine (40 mL each), dried (MgSO$_4$) and concentrated under reduced pressure to give the crude product. Silica gel chromatography (20% ethyl acetate/hexanes) gave MPA(O-DMPHB-C12α'βMe-2-TG)-OMe prodrug 1-55 (22.3 mg, 89%) as a colorless oil. $^1$H NMR (401 MHz, CDCl$_3$) δ 7.21 (s, 2H), 5.28 (m, 1H), 5.16 (s, 4H), 5.13 (m, 1H), 4.29 (dd, J=11.9, 4.2 Hz, 2H), 4.14 (dd, j=11.8, 5.9 Hz, 2H), 3.75 (s, 3H), 3.58 (s, 3H), 3.36 (d, J=6.5 Hz, 2H), 2.73 (m, 1H), 2.39-2.23 (m, 9H), 2.19 (s, 3H), 2.14 (s, 6H), 2.12 (dd, j=14.7, 8.4 Hz, 1H), 1.98-1.82 (m, 2H), 1.70 (s, 3H), 1.64-1.49 (m, 5H), 1.34 (d, J=7.0 Hz, 3H), 1.45-1.20 (m, 60H), 0.93 (d, j=6.6 Hz, 3H), 0.87 (t, J=6.8 Hz, 6H); $^{13}$C NMR (101 MHz, CDCl$_3$) δ 174.5 (C), 173.9 (C), 173.4 (2C; C), 172.5 (C), 169.2 (C), 163.1 (C), 155.4 (C), 148.2 (C), 146.9 (C), 134.5 (C), 134.0 (C), 130.3 (2C; C), 129.6 (C), 129.0 (2C; CH), 123.8 (CH), 120.3 (C), 113.0 (C), 76.8 (CH$_2$), 69.0 (CH), 68.5 (CH$_2$), 62.3 (2C; CH$_2$), 61.1 (CH$_3$), 51.6 (CH$_3$), 41.8 (CH$_2$), 39.9 (CH), 36.9 (CH$_2$), 34.6 (CH$_2$), 34.2 (2C; CH$_2$), 33.8 (CH$_2$), 33.0 (CH$_2$), 32.1 (2C; CH$_2$), 30.5 (CH), 29.92 (CH$_2$), 29.83 (6C; CH$_2$), 29.80 (4C; CH$_2$), 29.76 (2C; CH$_2$), 29.71 (CH$_2$), 29.69 (CH$_2$), 29.6 (2C; CH$_2$), 29.5 (2C; CH$_2$), 29.4 (2C; CH$_2$), 29.3 (2C; CH$_2$), 27.6 (CH$_2$), 27.1 (CH$_2$), 25.0 (2C; CH$_2$), 23.7 (CH$_2$), 22.8 (2C; CH$_2$), 19.7 (CH$_3$), 17.6 (CH$_3$), 16.6 (2C; CH$_3$), 16.4 (CH$_3$), 14.3 (2C; CH$_3$), 11.7 (CH$_3$).

(E)-12-(1,3-bis(palmitoyloxy)propan-2-yl) 1-(4-(((6-methoxy-5-(6-methoxy-3-methyl-6-oxohex-2-en-1-yl)-7-methyl-3-oxo-1,3-dihydroisobenzofuran-4-yl)oxy)methyl)phenyl) 2,10-dimethyldodecanedioate (I-54)

Using similar methods, (E)-12-(1,3-bis(palmitoyloxy)propan-2-yl) 1-(4-(((6-methoxy-5-(6-methoxy-3-methyl-6-oxohex-2-en-1-yl)-7-methyl-3-oxo-1,3-dihydroisobenzofuran-4-yl)oxy)methyl)phenyl) 2,10-dimethyldodecanedioate (I-54) was prepared from 4-(((tert-butyldimethylsilyl)oxy)methyl)phenol (a known compound that may be prepared as described in, e.g., Smith, J. H. et al. *Angew. Chem. Int. Fd.* 2011, 50, 5075-5080):

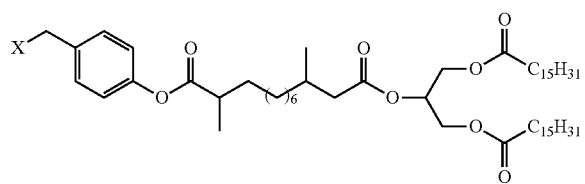

Int-138: X = OTBS
Int-139: X = OH
Int-140: X = Br 4-(Dimethylamino)pyridine (DMAP, 7.7 mg, 0.0629 mmol) and EDC.HCl (24.1 mg, 0.126 mmol) were added to a solution of Int-27 (56.0 mg, 0.0692 mmol) and 4-(((tert-butyldimethylsilyl)oxy)methyl)phenol (15.0 mg, 0.0629 mmol) in CH$_2$Cl$_2$ (1.5 mL) and the mixture stirred at RT for 19 hours. The reaction was diluted with CH$_2$Cl$_2$ (5 mL), silica gel was added, and the mixture was concentrated under reduced pressure. Purification by silica gel chromatography (7.5% to 10% ethyl acetate/hexanes) gave Int-138 (31.0 mg, 48%) as a colorless oil. $^1$H NMR (401 MHz, CDCl$_3$) δ 7.34-7.29 (m, 2H), 7.04-6.99 (m, 2H), 5.28 (m, 1H), 4.72 (s, 2H), 4.29 (dd, J=11.9, 3.9 Hz, 2H), 4.14 (dd, J=11.9, 5.8 Hz, 2H), 2.66 (m, 1H), 2.33 (dd, J=14.7, 8.3 Hz, 1H), 2.30 (t, j=7.5 Hz, 4H), 2.12 (dd, J=14.7, 8.3 Hz, 1H), 1.94 (m, 1H), 1.80 (m, 1H), 1.66-1.48 (m, 6H), 1.45-1.15 (m, 59H), 1.28 (d, J=6.9 Hz, 3H), 0.94 (s, 9H), 0.88 (d, j=6.6 Hz, 3H), 0.88 (t, j=6.8 Hz, 6H), 0.09 (s, 6H); $^{13}$C NMR (101 MHz, CDCl$_3$) δ 175.5 (C), 173.4 (2C; C), 172.5 (C), 149.8 (C), 139.0 (C), 127.1 (2C; CH), 121.4 (2C; CH), 69.0 (CH), 64.6 (CH$_2$), 62.3 (2C; CH$_2$), 41.8 (CH$_2$), 39.8 (CH), 36.8 (CH$_2$), 34.2 (2C; CH$_2$), 33.9 (CH$_2$), 32.1 (2C; CH$_2$), 30.5 (CH), 29.89 (CH$_2$), 29.84 (6C; CH$_2$), 29.80 (4C; CH$_2$), 29.77 (2C; CH$_2$), 29.69 (CH$_2$), 29.67 (CH$_2$), 29.62 (2C; CH$_2$), 29.5 (2C; CH$_2$), 29.4 (2C; CH$_2$), 29.3 (2C; CH$_2$), 27.4 (CH$_2$), 27.1 (CH$_2$), 26.1 (3C; CH$_3$), 25.0 (2C; CH$_2$), 22.8 (2C; CH$_2$), 19.7 (CH$_3$), 17.2 (CH$_3$), 14.3 (2C; CH$_3$), −5.1 (2C; CH$_3$); ESI-HRMS: Calcd. for C$_{62}$H$_{112}$NaO$_9$Si [M+Na$^+$] 1051.7968. Found 1051.7962.

10-Camphorsulfonic acid (1.4 mg, 6.0 µmol) was added to TBS ether Int-138 (31.0 mg, 30.1 µmol) in CH$_2$Cl$_2$ (0.6 mL) and MeOH (0.6 mL) and the mixture stirred at RT for one hour. The reaction was diluted with CH$_2$Cl$_2$ (20 mL), washed with sat. aq. NaHCO$_3$ and brine (20 mL each), dried (MgSO$_4$), and concentrated under reduced pressure to give the crude product. Purification by silica gel chromatography (15% to 25% ethyl acetate/hexanes) gave alcohol Int-139 (22.0 mg, 80%) as a colorless oil. $^1$H NMR (401 MHz, CDCl$_3$) δ 7.41-7.34 (m, 2H), 7.08-7.03 (m, 2H), 5.27 (m, 1H), 4.68 (s, 2H), 4.283/4.281 (each dd, J=11.8, 4.3 Hz, 2H), 4.14 (dd, J=11.8, 6.0 Hz, 2H), 2.67 (m, 1H), 2.32 (dd, j=14.7, 5.8 Hz, 1H), 2.30 (t, J=7.6 Hz, 1H), 2.11 (dd, j=14.7, 8.3 Hz, 1H), 1.93 (m, 1H), 1.80 (m, 1H), 1.70 (hr s, 1H), 1.65-1.49 (m, 5H), 1.45-1.16 (m, 63H), 0.93 (d, J=6.6 Hz, 3H), 0.88 (t, J=6.9 Hz, 6H); $^{13}$C NMR (101 MHz, CDCl$_3$) δ 175.5 (C), 173.5 (2C; C), 172.5 (C), 150.4 (C), 138.5 (C), 128.2 (2C; CH), 121.8 (2C; CH), 69.0 (CH), 64.9 (CH$_2$), 62.3 (2C; CH$_2$), 41.8 (CH$_2$), 39.8 (CH), 36.8 (CH$_2$), 34.2 (2C; CH$_2$), 33.9 (CH$_2$), 32.1 (2C; CH$_2$), 30.5 (CH), 29.84 (7C; CH$_2$), 29.80 (4C; CH$_2$), 29.77 (2C; CH$_2$), 29.6 (4C; CH$_2$), 29.5 (2C; CH$_2$), 29.4 (2C; CH$_2$), 29.3 (2C; CH$_2$), 27.4 (CH$_2$), 27.0 (CH$_2$), 25.0 (2C; CH$_2$), 22.8 (2C; CH$_2$), 19.7 (CH$_3$), 17.2 (CH$_3$), 14.3 (2C; CH$_3$); ESI-HRMS: Calcd. for C$_{56}$H$_{98}$NaO$_9$ [M+Na$^+$] 937.7103. Found 937.7136.

Carbon tetrabromide (CBr$_4$, 15.0 mg, 58.7 µmol) and triphenylphosphine (PPh$_3$, 18.5 mg, 70.5 µmol) were added to alcohol Int-139 (21.5 mg, 23.5 µmol) in CH$_2$Cl$_2$ (1.5 mL) at 0° C. and the reaction stirred at rt for one hour. The reaction was diluted with CH$_2$Cl$_2$ (5 mL), silica gel was added and the solvent removed under reduced pressure. Purification by silica gel chromatography (2% to 6% ethyl acetate/hexanes) gave bromide Int-140 (20.1 mg, 87%) as a colorless oil. $^1$H NMR (401 MHz, CDCl$_3$) δ 7.42-7.37 (m, 2H), 7.06-7.02 (m, 2H), 5.27 (m, 1H), 4.49 (s, 2H), 4.288/4.287 (each dd, j=11.8, 4.2 Hz, 2H), 4.14 (dd, J=11.9, 6.0 Hz, 2H), 2.67 (m, 1H), 2.33 (dd, j=14.7, 5.8 Hz, 1H), 2.30 (t, j=7.5 Hz, 4H), 2.12 (dd, j=14.7, 8.3 Hz, 1H), 1.93 (m, 1H), 1.79 (m, 1H), 1.66-1.50 (m, 5H), 1.45-1.14 (m, 63H), 0.93 (d, j=6.6 Hz, 3H), 0.88 (t, J=6.9 Hz, 6H); $^{13}$C NMR (101 MHz, CDCl$_3$) δ 175.3 (C), 173.4 (2C; C), 172.5 (C), 150.9 (C), 135.3 (C), 130.3 (2C; CH), 122.1 (2C; CH), 69.0 (CH), 62.3 (2C; CH$_2$), 41.8 (CH$_2$), 39.8 (CH), 36.8 (CH$_2$), 34.2 (2C; CH$_2$), 33.9 (CH$_2$), 32.9 (CH$_2$), 32.1 (2C; CH$_2$), 30.5 (CH), 29.87 (CH$_2$), 29.84 (6C; CH$_2$), 29.81 (4C; CH$_2$), 29.77 (2C; CH$_2$), 29.66 (CH$_2$), 29.65 (CH$_2$), 29.62 (2C; CH$_2$), 29.5 (2C; CH$_2$), 29.4 (2C; CH$_2$), 29.3 (2C; CH$_2$), 27.4 (CH$_2$), 27.1 (CH$_2$), 25.0 (2C; CH$_2$), 22.8 (2C; CH$_2$), 19.7 (CH$_3$), 17.1 (CH$_3$), 14.3 (2C; CH$_3$).

Synthesis of I-54:

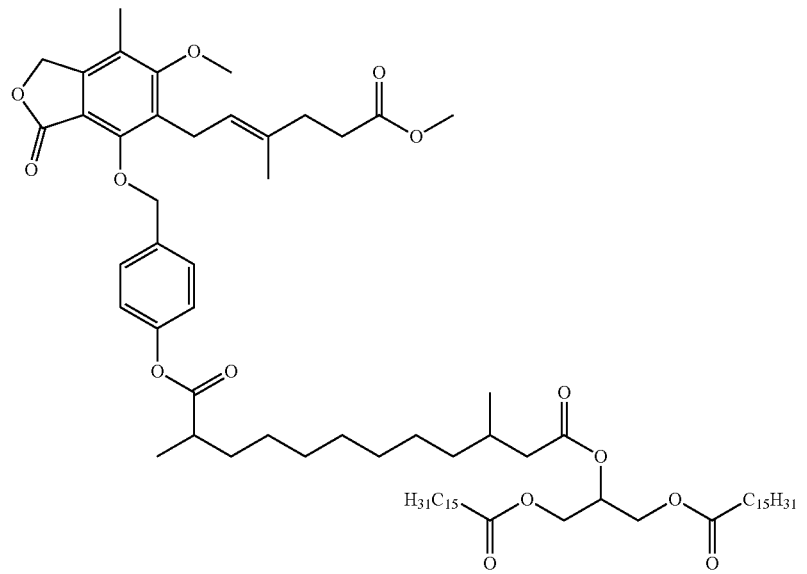

I-54

Cesium carbonate (6.5 mg, 19.9 µmol) and tetra-n-butylammonium iodide (TBAI, 2.2 mg, 6.0 µmol) were added to a solution of methyl ester 2 (8.0 mg, 23.9 µmol) and bromide Int-140 (19.5 mg, 19.9 µmol) in toluene (1.5 mL) and the mixture heated at 80° C. for three hours and then at 40° C. for a further 16 hours. The reaction was cooled to RT, diluted with ethyl acetate (30 mL) and the organic phase washed with brine (30 mL), dried ($MgSO_4$) and concentrated under reduced pressure to give the crude product. Silica gel chromatography (25% ethyl acetate/hexanes) gave MPA(O-PHB-C12α'βMe-2-TG)-OMe prodrug 1-54 (17.8 mg, 72%) as a colorless oil. $^1$H NMR (401 MHz, $CDCl_3$) δ 7.53-7.49 (m, 2H), 7.09-7.03 (m, 2H), 5.27 (m, 1H), 5.25 (s, 2H), 5.16 (s, 2H), 5.12 (m, 1H), 4.29 (dd, J=11.9, 3.8 Hz, 2H), 4.14 (dd, J=11.9, 5.6 Hz, 2H), 3.75 (s, 3H), 3.58 (s, 3H), 3.34 (d, J=6.6 Hz, 2H), 2.67 (m, 1H), 2.40-2.22 (m, 9H), 2.19 (s, 3H), 2.12 (dd, J=14.6, 8.3 Hz, 1H), 1.94 (m, 1H), 1.79 (m, 1H), 1.69 (d, J=0.8 Hz, 3H), 1.64-1.49 (m, 5H), 1.44-1.17 (m, 63H), 0.93 (d, J=6.6 Hz, 3H), 0.87 (t, J=6.9 Hz, 6H); $^{13}$C NMR (101 MHz, $CDCl_3$) δ 175.4 (C), 173.9 (C), 173.4 (2C; C), 172.5 (C), 169.3 (C), 163.1 (C), 155.3 (C), 150.9 (C), 146.9 (C), 134.7 (C), 134.0 (C), 129.8 (2C; CH), 129.5 (C), 123.7 (CH), 121.7 (2C; CH), 120.4 (C), 112.9 (C), 76.5 ($CH_2$), 68.9 (CH), 68.5 ($CH_2$), 62.3 (2C; $CH_2$), 61.1 ($CH_3$), 51.6 ($CH_3$), 41.8 ($CH_2$), 39.8 (CH), 36.9 ($CH_2$), 34.6 ($CH_2$), 34.2 (2C; $CH_2$), 33.9 ($CH_2$), 32.9 ($CH_2$), 32.1 (2C; $CH_2$), 30.5 (CH), 29.92 ($CH_2$), 29.84 (6C; $CH_2$), 29.80 (4C; $CH_2$), 29.76 (2C; $CH_2$), 29.71 ($CH_2$), 29.69 ($CH_2$), 29.6 (2C; $CH_2$), 29.5 (2C; $CH_2$), 29.4 (2C; $CH_2$), 29.3 (2C; $CH_2$), 27.4 ($CH_2$), 27.1 ($CH_2$), 25.0 (2C; $CH_2$), 23.8 ($CH_2$), 22.8 (2C; $CH_2$), 19.7 ($CH_3$), 17.1 ($CH_3$), 16.4 ($CH_3$), 14.3 (2C; $CH_3$), 11.7 ($CH_3$); ESI-HRMS: Calcd. for $C_{74}H_{118}NaO_{14}$ [M+Na$^+$] 1253.8414. Found 1253.8405.

(E)-1-(1,3-bis(palmitoyloxy)propan-2-yl) 10-(4-(((6-methoxy-5-(6-methoxy-3-methyl-6-oxohex-2-en-1-yl)-7-methyl-3-oxo-1,3-dihydroisobenzofuran-4-yl)oxy)methyl)-2,6-dimethylphenyl) 3-methyldecanedioate (I-63)

Using similar methods as described for the synthesis of I-55, compound I-63 was prepared from Int-132 and Int-30:

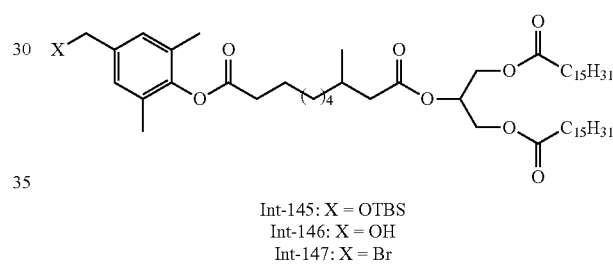

Int-145: X = OTBS
Int-146: X = OH
Int-147: X = Br 4-(Dimethylamino)pyridine (DMAP, 6.9 mg, 0.0563 mmol) and EDC.HCl (21.6 mg, 0.113 mmol) were added to a solution of acid-TG Int-30 (45.3 mg, 0.0591 mmol) and phenol Int-132 (15.0 mg, 0.0563 mmol) in $CH_2Cl_2$ (3 mL) and the mixture stirred at room temperature for three days. The reaction was diluted with $CH_2Cl_2$ (10 mL), silica gel was added, and the mixture concentrated under reduced pressure. Purification by silica gel chromatography (8% to 10% ethyl acetate/hexanes) gave ester Int-145 (46.6 mg, 81%) as a colorless oil. $^1$H NMR (401 MHz, $CDCl_3$) δ 7.00 (s, 2H), 5.28 (m, 1H), 4.65 (s, 2H), 4.29 (dd, J=11.8, 4.1 Hz, 2H), 4.14 (dd, J=11.9, 6.0 Hz, 2H), 2.58 (t, J=7.6 Hz, 2H), 2.33 (dd, J=14.6, 6.0 Hz, 1H), 2.31 (t, J=7.5 Hz, 4H), 2.13 (s, 6H), 2.12 (dd, J=14.7, 8.2 Hz, 1H), 1.96 (m, 1H), 1.83-1.74 (m, 2H), 1.69-1.54 (m, 4H), 1.47-1.19 (m, 56H), 0.94 (s, 9H), 0.88 (d, J=6.2 Hz, 3H), 0.88 (t, J=6.8 Hz, 6H), 0.09 (s, 6H); $^{13}$C NMR (101 MHz, $CDCl_3$) δ 173.4 (2C; C), 172.4 (C), 171.7 (C), 147.1 (C), 138.8 (C), 129.9 (2C; C), 126.4 (2C; CH), 69.0 (CH), 64.7 ($CH_2$), 62.3 (2C; $CH_2$), 41.8 ($CH_2$), 36.8 ($CH_2$), 34.2 (3C; $CH_2$), 32.1 (2C; $CH_2$), 30.5 (CH), 29.84 (6C; $CH_2$), 29.80 (4C; $CH_2$), 29.76 (2C; $CH_2$), 29.61 (2C; $CH_2$), 29.55 ($CH_2$), 29.50 (2C; $CH_2$), 29.41 (2C; $CH_2$), 29.26 (2C; $CH_2$), 26.9 ($CH_2$), 26.1 (3C; $CH_3$), 25.3 ($CH_2$), 25.0 (2C; $CH_2$), 22.8 (2C; $CH_2$), 19.7

(CH₃), 16.6 (2C; CH₃), 14.3 (2C; CH₃), -5.1 (2C; CH₃); ESI-HRMS: calcd. for C₆₁H₁₁₀NaO₉Si [M+Na⁺] 1037.7811; found 1037.7815.

10-Camphorsulfonic acid (2.1 mg, 8.9 µmol) was added to TBS ether Int-145 (45.0 mg, 44.3 µmol) in CH₂Cl₂ (1 mL) and MeOH (1 mL) and the mixture stirred at room temperature for one hour. The reaction was diluted with CH₂Cl₂ (30 mL), washed with sat. aq. NaHCO₃ and brine (25 mL each), dried (MgSO₄) and concentrated under reduced pressure to give the crude product. Purification by silica gel chromatography (20% ethyl acetate/hexanes) gave alcohol Int-146 (30.4 mg, 76%) as a colorless oil. ¹H NMR (401 MHz, CDCl₃) δ 7.06 (s, 2H), 5.27 (m, 1H), 4.60 (s, 2H), 4.287/ 4.285 (each dd, J=11.8, 4.2 Hz, 2H), 4.14 (dd, J=11.9, 6.0 Hz, 2H), 2.59 (t, J=7.6 Hz, 2H), 2.33 (dd, J=14.6, 6.0 Hz, 1H), 2.30 (t, J=7.5 Hz, 4H), 2.14 (s, 6H), 2.12 (dd, J=14.7, 8.3 Hz, 1H), 1.95 (m, 1H), 1.84-1.73 (m, 2H), 1.69 (hr s, 1H), 1.65-1.54 (m, 4H), 1.46-1.18 (m, 56H), 0.94 (d, J=6.6 Hz, 3H), 0.87 (t, J=6.8 Hz, 6H); ¹³C NMR (101 MHz, CDCl₃) δ 173.4 (2C; C), 172.4 (C), 171.6 (C), 147.7 (C), 138.4 (C), 130.4 (2C; C), 127.4 (2C; CH), 69.0 (CH), 65.1 (CH₂), 62.3 (2C; CH₂), 41.8 (CH₂), 36.7 (CH₂), 34.2 (2C; CH₂), 34.1 (CH₂), 32.1 (2C; CH₂), 30.4 (CH), 29.83 (6C; CH₂), 29.79 (4C; CH₂), 29.76 (2C; CH₂), 29.61 (2C; CH₂), 29.53 (CH₂), 29.50 (2C; CH₂), 29.40 (2C; CH₂), 29.39 (CH₂), 29.25 (2C; CH₂), 26.9 (CH₂), 25.2 (CH₂), 25.0 (2C; CH₂), 22.8 (2C; CH₂), 19.7 (CH₃), 16.5 (2C; CH₃), 14.3 (2C; CH₃); ESI-HRMS: calcd. for C₅₅H₉₆NaO₉ [M+Na⁺] 923.6947; found 923.6973.

Carbon tetrabromide (CBr₄, 26.7 mg, 80.4 µmol) and triphenylphosphine (PPh₃, 25.3 mg, 96.5 µmol) were added to alcohol Int-146 (29.0 mg, 32.2 µmol) in CH₂Cl₂ (1.5 mL) at 0° C. and the reaction stirred at room temperature for 50 minutes. The reaction was diluted with CH₂Cl₂ (5 mL), silica gel was added and the solvent was removed under reduced pressure. Purification by silica gel chromatography (6% to 10% ethyl acetate/hexanes) gave bromide Int-147 (23.6 mg, 76%) as a colorless ml; ¹H NMR (401 MHz, CDCl₃) δ 7.09 (s, 2H), 5.28 (m, 1H), 4.42 (s, 2H), 4.29 (dd, j=11.9, 4.3 Hz, 2H), 4.14 (dd, J=11.9, 6.0 Hz, 2H), 2.59 (t, j=7.6 Hz, 2H), 2.33 (dd, j=14.6, 6.0 Hz, 1H), 2.30 (t, j=7.5 Hz, 4H), 2.13 (dd, j=14.7, 8.3 Hz, 1H), 2.12 (s, 6H), 1.94 (m, 1H), 1.83-1.72 (m, 2H), 1.66-1.55 (m, 4H), 1.47-1.17 (m, 56H), 0.94 (d, J=6.6 Hz, 3H), 0.88 (t, j=6.9 Hz, 6H); ¹³C NMR (101 MHz, CDCl₃) δ 173.4 (2C; C), 172.4 (C), 171.4 (C), 148.4 (C), 135.2 (C), 130.8 (2C; C), 129.5 (2C; CH), 69.0 (CH), 62.3 (2C; CH₂), 41.8 (CH₂), 36.7 (CH₂), 34.2 (2C; CH₂), 34.1 (CH₂), 33.3 (CH₂), 32.1 (2C; CH₂), 30.4 (CH), 29.84 (6C; CH₂), 29.80 (4C; CH₂), 29.77 (2C; CH₂), 29.62 (2C; CH₂), 29.54 (CH₂), 29.51 (2C; CH₂), 29.41 (2C; CH₂), 29.39 (CH₂), 29.27 (2C; CH₂), 26.9 (CH₂), 25.2 (CH₂), 25.0 (2C; CH₂), 22.8 (2C; CH₂), 19.7 (CH₃), 16.5 (2C; CH₃), 14.3 (2C; CH₃).

Synthesis of I-63:

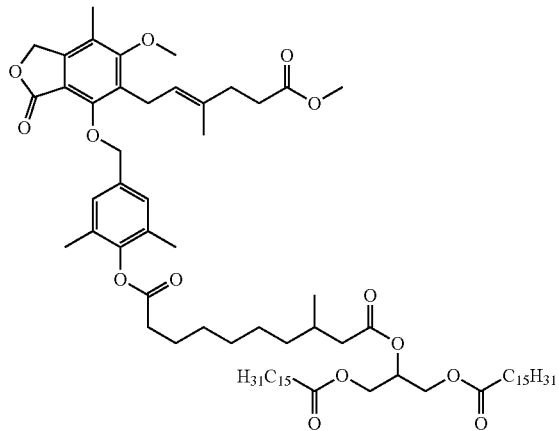

I-63

Cesium carbonate (3.9 mg, 11.9 µmol) and tetra-n-butylammonium iodide (TBAI, 2.2 mg, 6.0 µmol) were added to a solution of methyl ester 2 (4.8 mg, 14.3 µmol) and bromide Int-147 (11.5 mg, 11.9 µmol) in toluene (1.5 mL) and the mixture heated at 70° C. for 1.5 hours, and then at 40° C. for a further 18 hours. The reaction was cooled to room temperature, diluted with ethyl acetate (40 mL) and the organic phase washed with water and brine (40 mL each), dried (MgSO₄) and concentrated under reduced pressure to give the crude product. Silica gel chromatography (5% to 10% ethyl acetate/toluene) gave MPA(O-DMPHB-C10βMe-2-TG)-OMe prodrug 1-63 (11.0 mg, 76%) as a colorless ml. ¹H NMR (401 MHz, CDCl₃) δ 7.21 (s, 2H), 5.27 (m, 1H), 5.16 (s, 4H), 5.13 (m, 1H), 4.29 (dd, J=12.0, 4.3 Hz, 2H), 4.14 (dd, j=11.9, 5.9 Hz, 2H), 3.75 (s, 3H), 3.58 (s, 3H), 3.36 (d, J=6.7 Hz, 2H), 2.59 (t, J=7.6 Hz, 2H), 2.41-2.23 (m, 9H), 2.19 (s, 3H), 2.15 (s, 6H), 2.13 (dd, j=14.7, 8.4 Hz, 1H), 1.95 (m, 1H), 1.83-1.75 (m, 2H), 1.70 (d, j=0.8 Hz, 3H), 1.64-1.55 (m, 4H), 1.46-1.18 (m, 56H), 0.94 (d, j=6.6 Hz, 3H), 0.87 (t, J=6.9 Hz, 6H); ¹³C NMR (101 MHz, CDCl₃) δ 173.9 (C), 173.4 (2C; C), 172.4 (C), 171.5 (C), 169.2 (C), 163.1 (C), 155.4 (C), 148.2 (C), 146.9 (C), 134.6 (C), 134.0 (C), 130.3 (2C; C), 129.6 (C), 129.0 (2C; CH), 123.9 (CH), 120.4 (C), 113.0 (C), 76.8 (CH₂), 69.0 (CH), 68.5 (CH₂), 62.3 (2C; CH₂), 61.1 (CH₃), 51.6 (CH₃), 41.8 (CH₂), 36.8 (CH₂), 34.6 (CH₂), 34.2 (3C; CH₂), 33.0 (CH₂), 32.1 (2C; CH₂), 30.5 (CH), 29.84 (6C; CH₂), 29.81 (4C; CH₂), 29.77 (2C; CH₂), 29.62 (2C; CH₂), 29.59 (CH₂), 29.51 (2C; CH₂), 29.44 (CH₂), 29.42 (2C; CH₂), 29.27 (2C; CH₂), 26.9 (CH₂), 25.3 (CH₂), 25.0 (2C; CH₂), 23.7 (CH₂), 22.8 (2C; CH₂), 19.7 (CH₃), 16.5 (2C; CH₃), 16.4 (CH₃), 14.3 (2C; CH₃), 11.7 (CH₃).

Example 14: Synthesis of (E)-12-(1,3-bis(palmitoyloxy)propan-2-yl) 1-(1-(((6-methoxy-5-(6-methoxy-3-methyl-6-oxohex-2-en-1-yl)-7-methyl-3-oxo-1,3-dihydroisobenzofuran-4-yl)oxy)ethyl) 2,10-dimethyldodecanedioate (I-58)
Scheme 52. Synthesis of I-58.
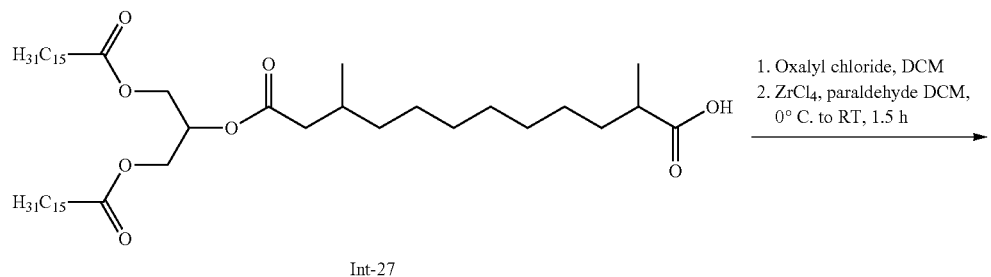
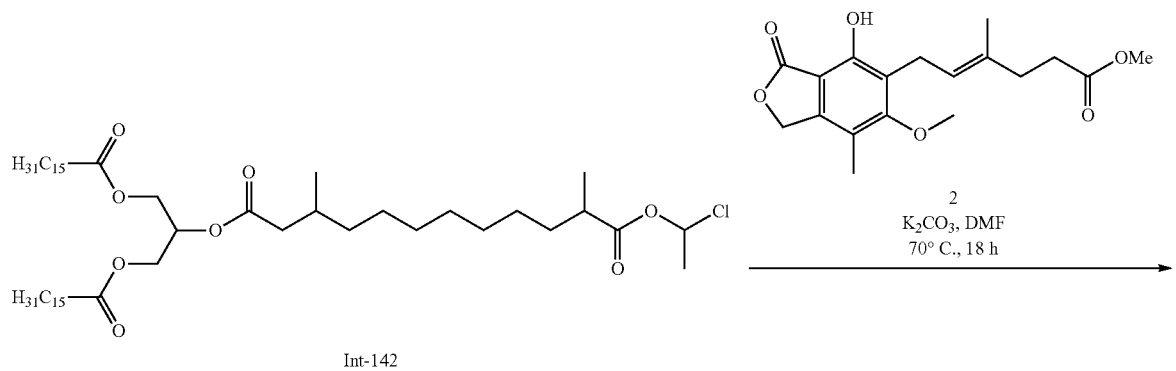
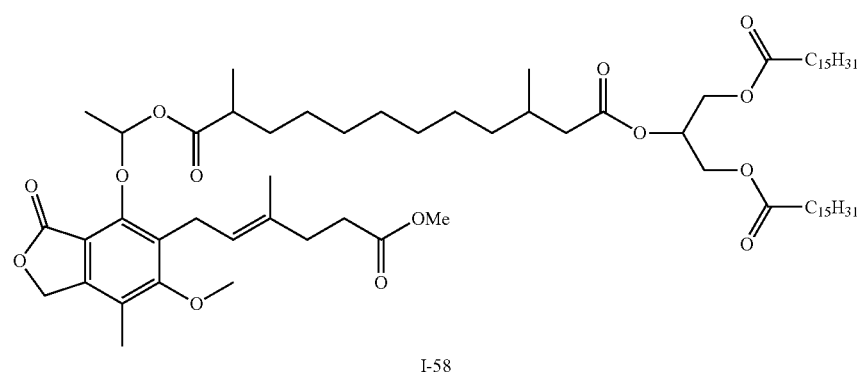

Synthesis of I-58:

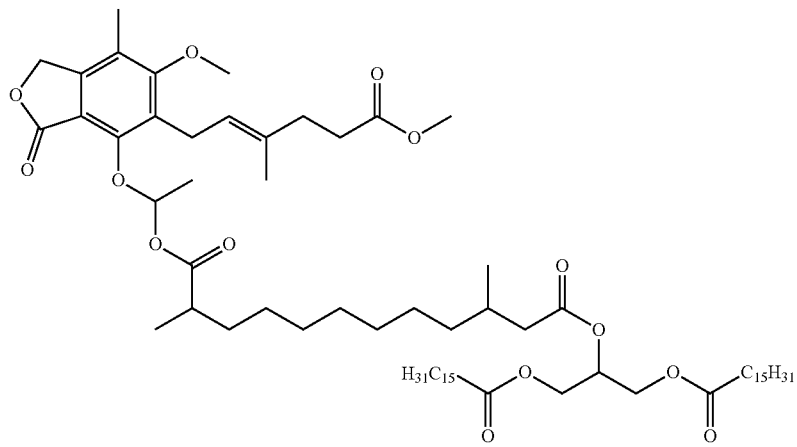

I-58

To a solution of compound Int-142 (0.115 g, 0.195 mmol) and methyl ester 2 (0.039 g, 0.117 mmol) in DMF (3 mL) was added $K_2CO_3$ (0.135 g, 0.975 mmol) and the reaction mixture was stirred at 70° C. for 18 h. The reaction mixture was diluted with water (50 mL) and extracted with ethyl acetate (3×50 mL). The combined organic layers were dried over $Na_2SO_4$, then concentrated under reduced pressure to afford the crude product. Silica gel chromatography (10% ethyl acetate/hexanes) provided slightly impure compound, which was further purified using prep HPLC to afford pure MPA-(O-MASI-C12α'βMe-2-TG)-OMe prodrug 1-58 (0.045 g, 19.08%) as a viscous oil. $^1$H NMR (400 MHz, $CDCl_3$) δ 6.77 (q, J=5.2 Hz, 1H), 5.32 (m, 1H), 5.23 (s, 2H) 5.15 (m, 1H), 4.33 (dd, J=11.9, 4.3 Hz, 2H), 4.19 (dd, J=11.9, 5.9 Hz, 2H), 3.77 (s, 3H), 3.66 (s, 3H), 3.59 (m, 1H), 3.36 (dd, J=14.0, 7.0 Hz, 1H), 2.48-2.36 (m, 3H), 2.35 (t, J=7.5 Hz, 8H), 2.21 (s, 3H), 2.18-2.12 (m, 2H), 1.97 (s, 2H), 1.85 (s, 3H), 1.80-1.78 (m, 3H), 1.66-1.60 (m, 6H), 1.38-1.29 (m, 57H), 1.08 (d, J=6.8 Hz, 3H), 1.02 (d, J=7.2 Hz, 3H), 0.92 (t, J=6.4 Hz, 6H); $^{13}$C NMR (101 MHz, $CDCl_3$) δ 175.74 (1C), 175.52 (1C), 173.79 (1C), 173.32 (2C), 172.35 (1C), 169.11 (1C) 162.57 (1C), 152.79 (1C), 146.71 (1C), 133.72 (1C), 129.20 (1C), 123.22 (1C), 123.20 (1C), 120.96 (1C), 112.74 (1C), 98.43 (1C), 98.36 (1C), 68.82 (1C), 68.43 (1C), 62.14 (1C), 60.89 (1C), 51.51 (1C), 41.70 (1C), 39.70 (1C), 39.39 (1C), 36.72 (1C), 34.64 (1C), 34.06 (2C), 33.61 (1C), 33.35 (1C), 32.88 (1C), 31.95 (2C), 30.37 (1C), 29.81-29.14 (18C), 27.10 (1C), 26.97 (1C), 26.95 (1C), 24.87 (2C), 23.93 (1C), 22.72 (2C), 20.72 (1C), 19.55 (1C), 16.95 (1C), 16.21 (1C), 14.16 (2C), 11.67 (1C). HPLC (ELSD): 16.27 mm, 100% purity; HPLC (uv-215 nm): 16.27 mm, 100% purity; LCMS: 15.25 mm, 100% purity. MS (ESI, +ve) m/z: 1187.4 (MH$^+$18).

(E)-1-(1,3-bis(palmitoyloxy)propan-2-yl) 12-(1-((6-methoxy-5-(6-methoxy-3-methyl-6-oxohex-2-en-1-yl)-7-methyl-3-oxo-1,3-dihydroisobenzofuran-4-yl)oxy)ethyl) 2,11-dimethyldodecanedioate (I-59)

Using similar methods, (E)-1-(1,3-bis(palmitoyloxy)propan-2-yl) 12-(1-(((6-methoxy-5-(6-methoxy-3-methyl-6-oxohex-2-en-1-yl)-7-methyl-3-oxo-1,3-dihydroisobenzofuran-4-yl)oxy)ethyl) 2,11-dimethyldodecanedioate (I-59) was prepared from Int-81 and Int-136.

Synthesis of I-59:

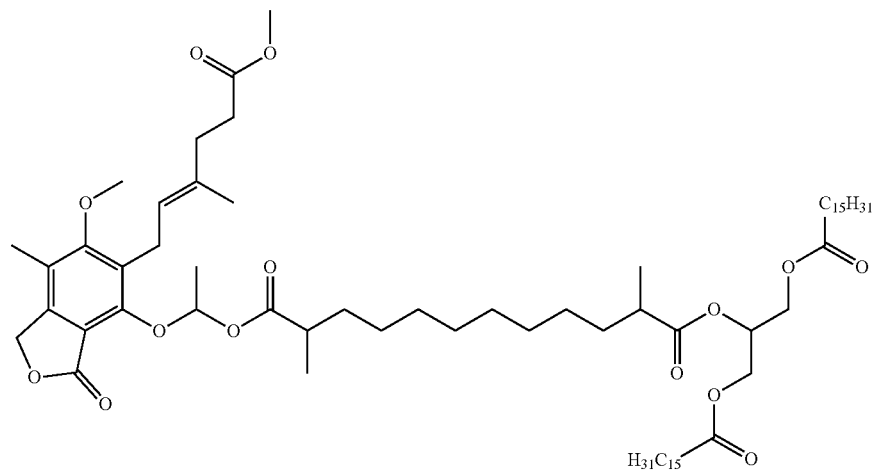

I-59

To a solution of compound Int-136 (0.130 g, 0.149 mmol) and methyl ester 2 (0.030 g, 0.089 mmol) in DMF (3 mL) was added $K_2CO_3$ (0.102 g, 0.746 mmol) and the reaction mixture was stirred at 70° C. for 18 h. The reaction mixture was diluted with water (50 mL) and extracted with ethyl acetate (3×50 mL). The combined organic layers were dried over $Na_2SO_4$, then concentrated under reduced pressure to afford the crude product. Silica gel chromatography (10% ethyl acetate/hexanes) provided slightly impure compound, which was further purified using prep HPLC to afford pure MPA-(O-MASI-C12α'αMe-2-TG)-OMe prodrug 1-59 (0.039 g, 22%) as a Viscous Oil. $^1H$ NMR (400 MHz, $CDCl_3$) δ 6.76 (q, J=5.4 Hz, 1H), 5.37-5.27 (m, 1H), 5.25-5.13 (m, 3H), 4.33 (dd, J=11.6, 3.7 Hz, 2H), 4.19 (dd, J=11.9, 6.0 Hz, 2H), 3.77 (s, 3H), 3.66 (s, 3H), 3.56 (dd, J=14.1, 7.1 Hz, 1H), 3.36 (dd, J=14.0, 7.1 Hz, 1H), 2.45-2.41 (dq, J=24.3, 9.4, 8.1 Hz, 3H), 2.34 (t, J=7.5 Hz, 7H), 2.21 (s, 3H), 1.86 (s, 3H), 1.79 (d, J=5.2 Hz, 3H), 1.71-1.60 (m, 6H), 1.29 (s, 58H), 1.26-1.12 (m, 6H), 1.05 (dd, J=22.0, 6.9 Hz, 4H), 0.92 (t, J=6.5 Hz, 6H); $^{13}C$ NMR (101 MHz, $CDCl_3$) δ 175.89 (1C), 175.73 (1C), 175.50 (1C), 173.78 (1C), 173.29 (1C), 169.09 (1C), 162.54 (1C), 152.78 (1C), 146.68 (1C), 133.72 (1C), 129.16 (1C), 123.19 (1C), 120.9 (1C) 112.72 (1C), 98.42 (1C), 98.34 (1C), 68.68 (1C), 68.42 (1C), 62.12 (1C), 60.88 (1C), 51.51 (1C), 39.69 (1C), 39.52 (1C), 39.37 (1C), 34.62 (1C), 34.05 (2C), 33.61 (1C), 33.33 (1C), 32.86 (1C), 31.94 (2C), 29.71-29.14 (19C), 27.17 (1C), 27.13 (1C) 24.86 (2C), 23.99 (1C), 23.91 (1C), 22.71 (2C), 20.70 (1C), 20.65 (1C), 17.03 (1C), 16.93 (1C), 16.84 (1C), 16.20 (1C), 14.15 (3C), 11.66 (1C). HPLC (ELSD): 9.93 mm, 100% purity; HPLC (uv-215 nm): 9.91 min, 100% purity; LCMS: 8.89 min, 100% purity. MS (ESI, +ve) m/z: 1186.8 ($MH^+18$).

Example 15: Lymphatic Transport Assay in Rats

In order to assess the lymphatic transport of disclosed lipid prodrugs in rats, the mesenteric lymph ducts of the rats used in this study were cannulated to allow continual collection of mesenteric lymph. Lipid formulations containing the compound of interest were then administered to the animals, lymph was collected, and drug concentrations in the lymph samples were quantified.

Lipid-based formulations of the compounds of the invention or control compounds were prepared as previously described (Trevaskis, N. L. et al., *Pharmaceutical Research*, 2005, 22(11), 1863-1870, WO 2016/023082, and WO 2017/041139, hereby incorporated by reference.

In brief, either 1 or 2 mg of test prodrug, 40 mg oleic acid and 25 mg Tween 80 were mixed in a glass vial and incubated at 37° C. for 12-18 h to equilibrate. An aqueous phase consisting of 5.6 ml phosphate buffered saline (PBS, pH 7.4) was subsequently added to the lipid phase (MPA was dissolved in PBS for the preparation of MPA containing formulations) and the formulation emulsified by ultrasonication with a Misonix XL 2020 ultrasonic processor (Misonix, Farmingdale, N.Y., USA) equipped with a 3.2-mm microprobe tip running at 30% of the maximal amplitude of 240 μm and a frequency of 20 kHz for 2 min at room temperature. Doses for administering to more than one animal can be prepared in one batch by suitably increasing the quantities given above. Drug/prodrug concentrations in all formulations were verified using HPLC-MS.

Male Sprague-Dawley (SD) rats were selected for the lymphatic transport studies. Rats (typically 240-320 g) were maintained on a standard diet and fasted overnight with free access to water prior to experiments.

Anesthetized rats were placed on a heated pad at 37° C. and cannulas inserted into the duodenum (for formulation administration and rehydration), mesenteric lymph duct (for lymph collection), and carotid artery (in cases where blood collection was conducted). Post-surgery, rats were re-hydrated for 0.5 h via intraduodenal infusion of normal saline at 2.8 mL/h. The lipid formulations were infused into the duodenum at 2.8 mL/h for 2 h after which, normal saline was infused at 2.8 mL/h for the remainder of the experiment. Lymph was continuously collected for up to 8 h into pre-weighed Eppendorf tubes containing 10 μL of 1,000 IU/mL heparin. The collection tubes were changed hourly and lymph flow was measured gravimetrically. Aliquots of hourly lymph samples were stored at −20° C. prior to assay.

Drug concentration in lymph is expressed as total drug and includes free drug and drug associated with different glycerides. Lymph samples are first treated with a lipase or other appropriate conditions to liberate free active agent prior to measurement of active agent levels in the lymph. Treatment with a lipase or other hydrolysis conditions liberates free active agent from any corresponding re-esterified glycerides. Porcine pancreatic lipase is appropriate for this purpose. Alternatively, hydrolysis with 0.5 M NaOH may be used. For MPA "phenol" prodrugs (i.e. prodrugs linked to the triglyceride at the aromatic —OH group of MPA), hydrolysis was performed with 0.5 M NaOH except for the lymph samples collected from 3 rats in the group of compound I-20 (MPA-O-C12α'βMe-TG), which were hydrolyzed by porcine pancreatic lipase.

Transport of compounds into lymph during each hourly collection period was calculated from the product of the volume of lymph collected and the measured concentrations in lymph. For fluorescently-labelled compounds such as a BDP-conjugate, the concentrations of total compound may be measured by fluorescence spectroscopy without hydrolysis.

The results of the lymphatic transport assays are summarized in Table 2, below, and FIGS. 1-19. Table 2 summarizes lymphatic transport of total MPA related compound (% of administered dose) following intraduodenal infusion to anaesthetised, mesenteric lymph-duct cannulated rats. Data are presented as mean±SD when n≥3 or mean±range when n=2. Compounds with a lymphatic transport assay result of greater than 10% (>10%) are designated as "A." Compounds with a lymphatic transport assay result between 1% and 10% (1%-10%) are designated as "B." Compounds with a lymphatic transport assay result of less than 1% and greater than 0.24% (<1% and >0.24%) are designated as "C."

Importantly, the cumulative lymphatic transport percentages of MPA and MMF measured in this assay are very low (0.17±0.12% for MPA and even less for MMF; see FIG. 8). Accordingly, a lymphatic transport assay result of "A" means that the lipid prodrug increases cumulative lymphatic transport relative to MPA or MMF by a factor of >59. A result of "B" indicates an increase by a factor of between 5.9 and 59. A result of "C" indicates an increase by a factor of between about 1.4 and <5.9.

TABLE 2

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA (n = 5) | — | 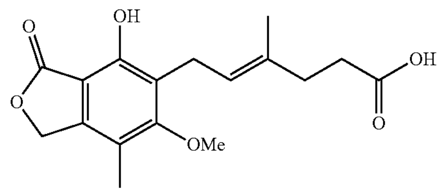 [SMILES: COc1c(C)c2c(c(O)c1C/C=C(\C)CCC(=O)O)C(=O)OC2] | 0.17 ± 0.12 |
| MMF (n = 3) | — | 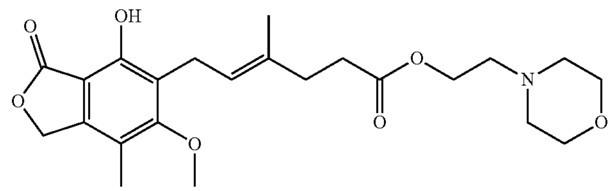 [SMILES: COc1c(C)c2c(c(O)c1C/C=C(\C)CCC(=O)OCCN1CCOCC1)C(=O)OC2] | 0.14 ± 0.08 |
| MPA-TG (n = 5) | I-34 | 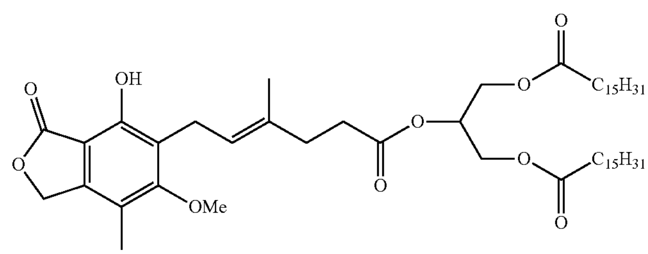 | A |
| MPA-Ph-C3-TG | I-28 | 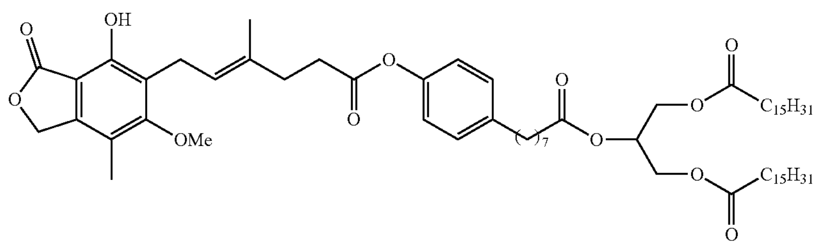 | B |
| MPA-C4(ether)-TG (n = 3) | I-25 | 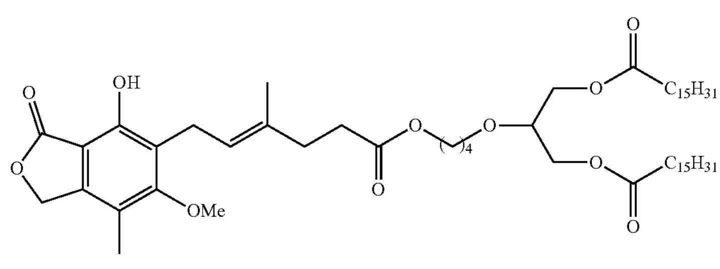 | C |
| MPA-C5-Carbonate-TG (n = 4) | I-27 | 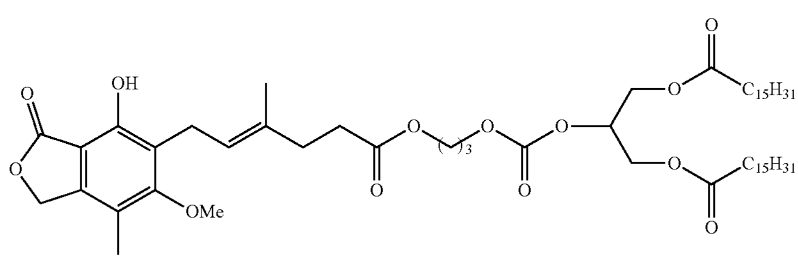 | B |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-C6(ether)-TG (n = 4) | I-26 | 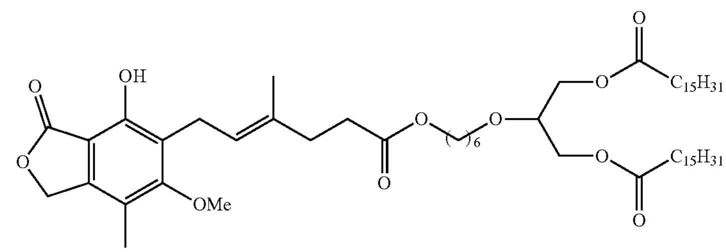 | C |
| MPA-C7-TG (n = 2) | I-36 | 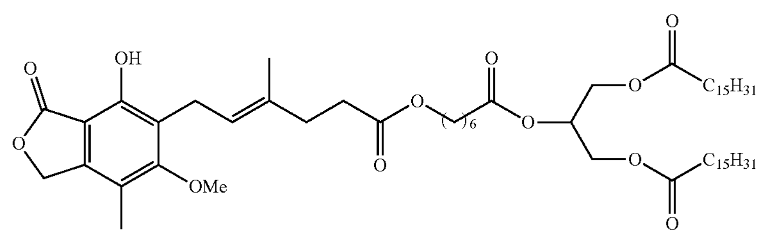 | B |
| MPA-C12-TG (n = 2) (dose 1 mg/rat) | I-37 | 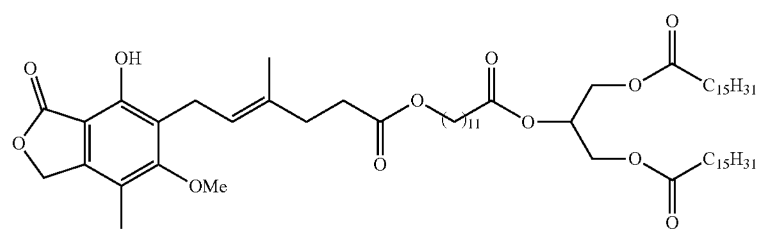 | A |
| MPA-C18-TG (n = 3) (dose 1 mg/rat) | I-38 | 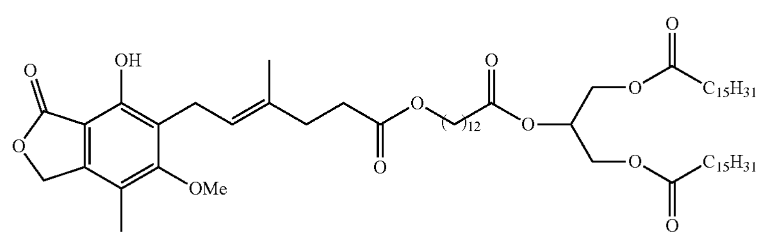 | B |
| MPA-O-C4-TG(OMe) (n = 2) | I-17 | 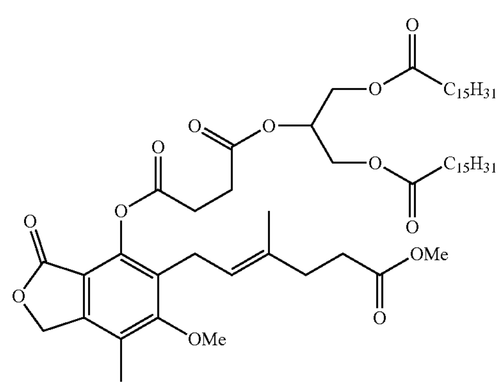 | C |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-C6-TG(OMe) (n = 2) | I-18 | 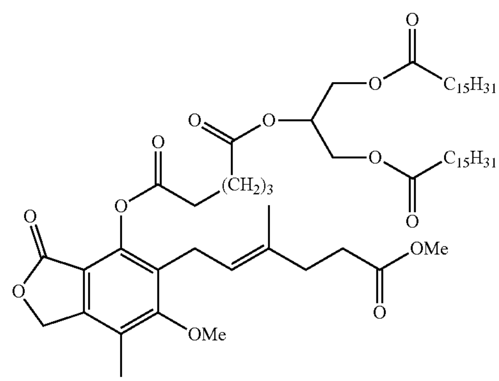 | B |
| MPA-O-C10-TG(OMe) (n = 3) | I-19 | 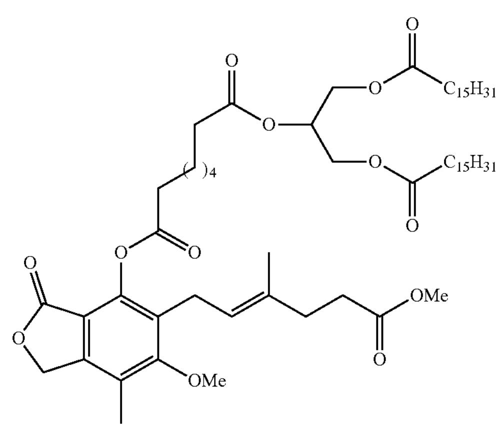 | A |
| MPA-O-C12-TG(OMe) (n = 3) | I-30 | 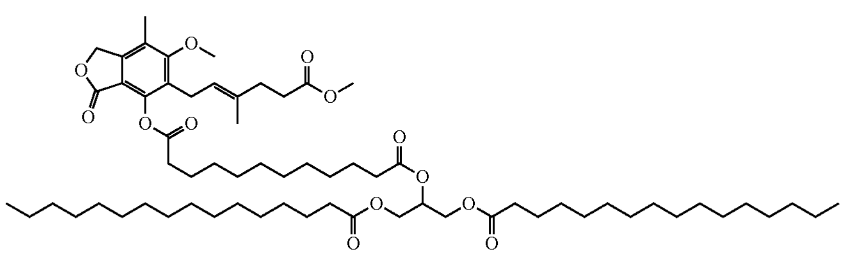 [SMILES: CCCCCCCCCCCCCCCC(=O)OCC(COC(=O)CCCCCCCCCCCCCCC)OC(=O)CCCCCCCCCCC(=O)Oc1c(C/C=C(\C)CCC(=O)OC)c(OC)c(C)c2c1C(=O)OC2] | A |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-C12α'MeβMe-TG(OMe) (n = 5) | I-20 | 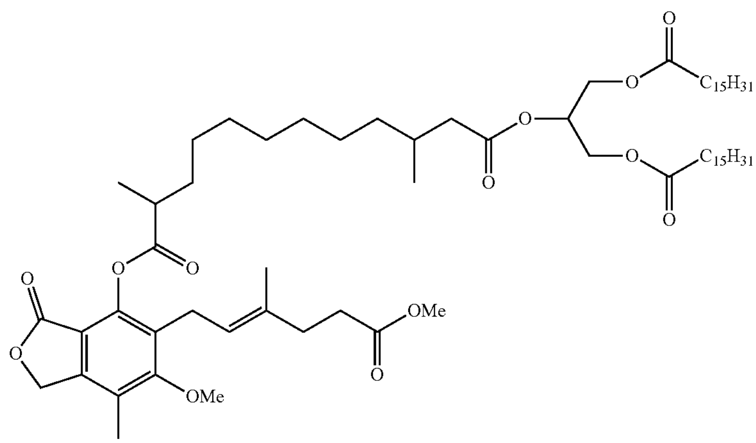 | A |
| MPA-O-CASI-C12α'MeβMe-TG(OMe) (n = 3) | I-21 | 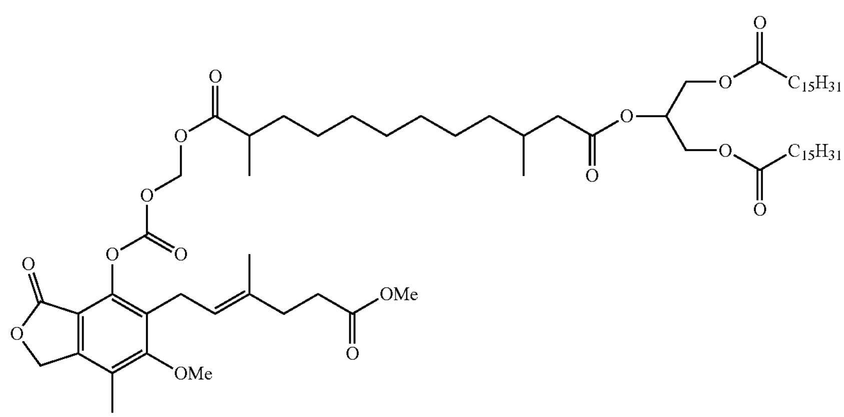 | B |
| MPA-O-C12α'βMe-TG(OMF) (n = 3) | I-32 | 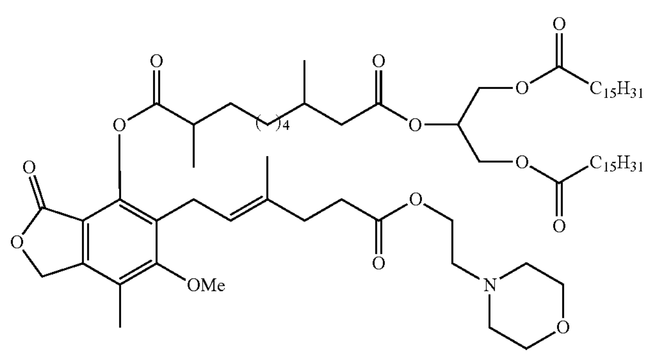 | A |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-FSI(5)-C12α'MeβMe-TG (OMe) (n = 5) | I-22 | 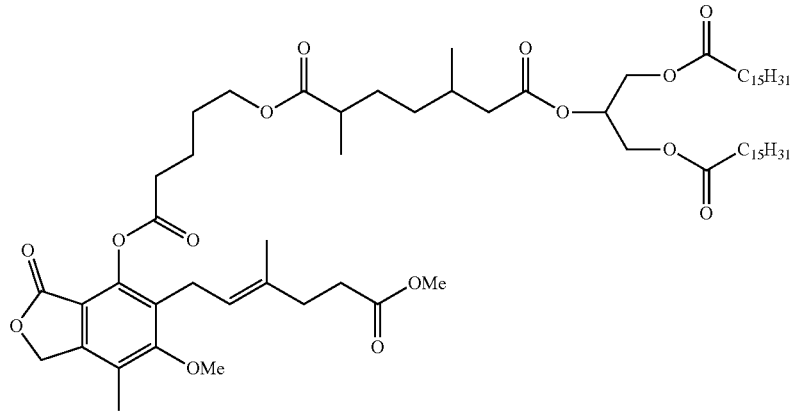 | A |
| MPA-2-PL (n = 4) | I-39 | 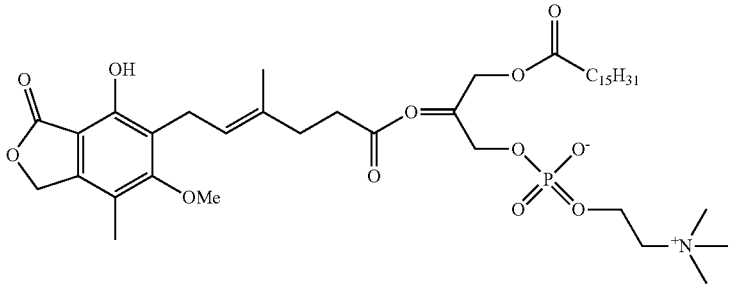 | C |
| MPA-O-TML-C12-TG (n = 3) | I-47 | 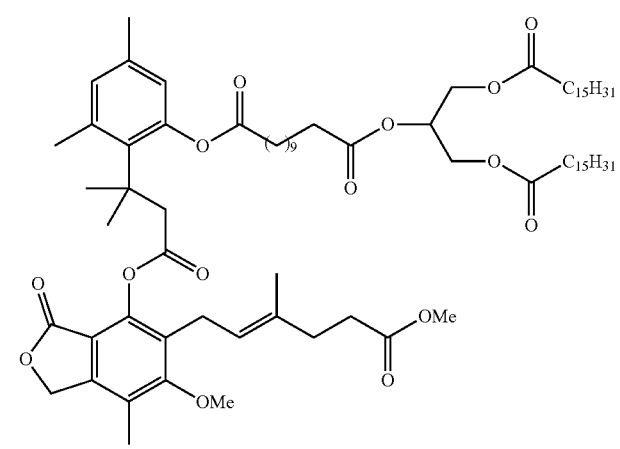 | B |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-O-ASI-C12α′βMe-TG (n = 3) | I-44 | | A |
| MPA-O-C15β-TG (n = 2) | I-31 | 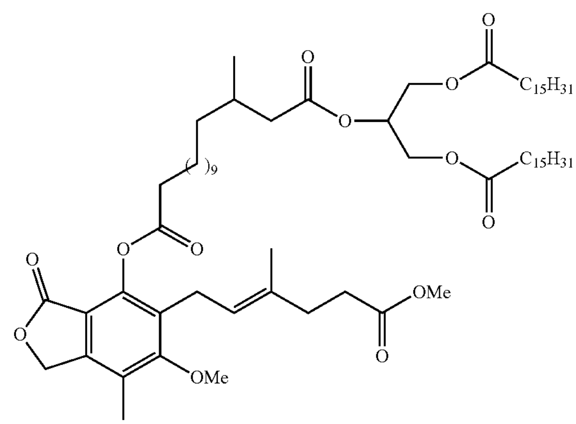 | A |
| MPA-C10-TG (n = 3) | I-46 | 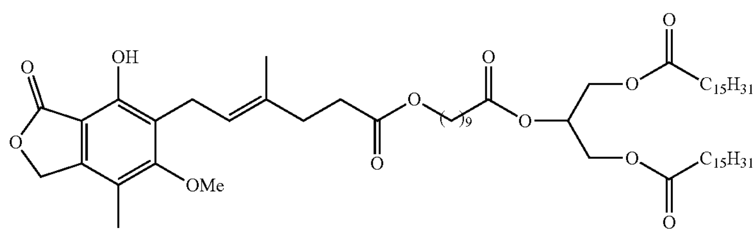 | A |
| MPA(O-C11-2-TG)-OMe (n = 3) | I-48 | 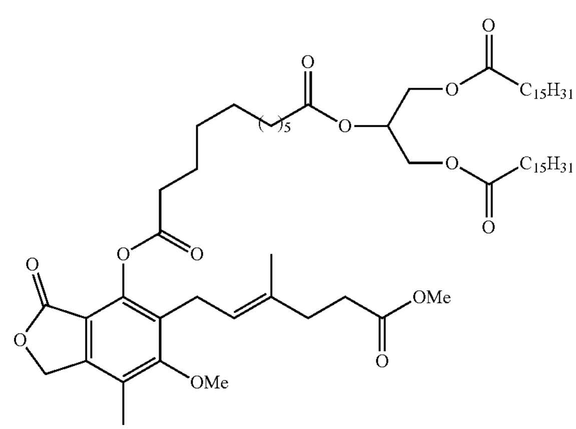 | A |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-C10β-TG (n = 3) | I-50 | 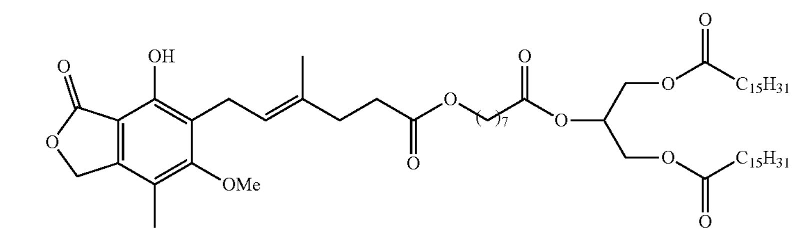 | A |
| MPA-C15β-TG-butyrate (n = 2) | I-43 | 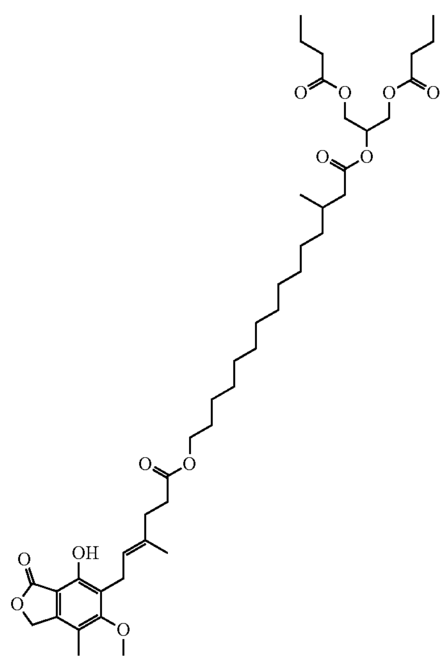 [SMILES: CCCC(=O)OCC(COC(=O)CCC)OC(=O)CC(C)CCCCCCCCCCCCOC(=O)CC/C(C)=C/Cc1c(O)c2c(c(C)c1OC)COC2=O] | A |
| MPA-(O-ASI-C12α'αMe-2-TG)-OMe (n = 1) | I-41 | 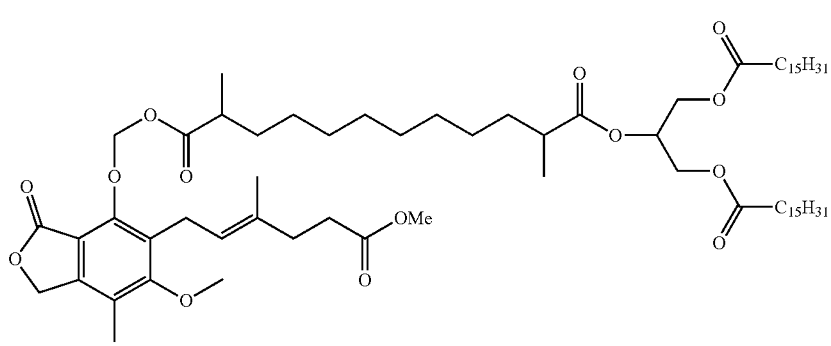 | A |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-(O-C10αMe-2-TG)-OMe (n = 2) | I-45 | 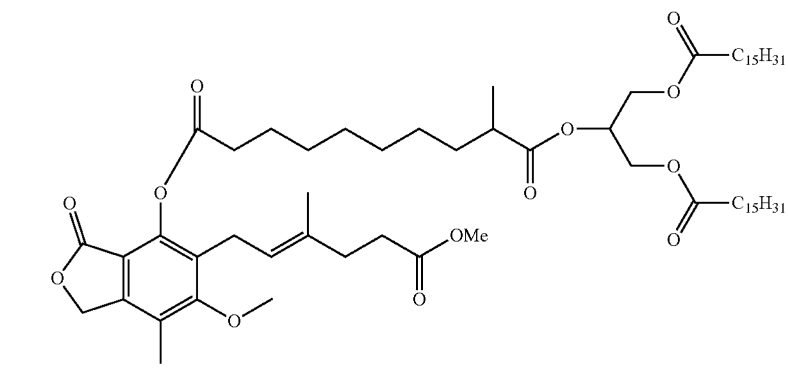 | A |
| MPA-C12βMe-2-TG (n = 3) | I-51 | 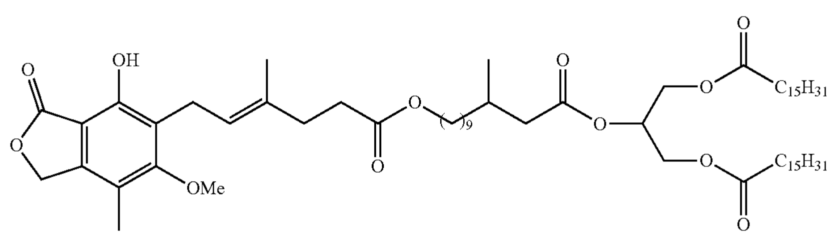 | A |
| MPA(O-TML-C12α'αMe-2-TG)-OMe (n = 3) | I-52 | 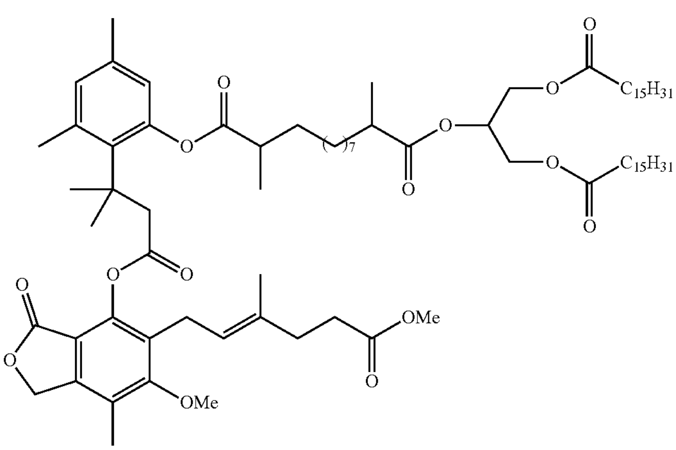 | B |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA(O-C12βMe-2-TG)-OMe (n = 3) | I-53 | 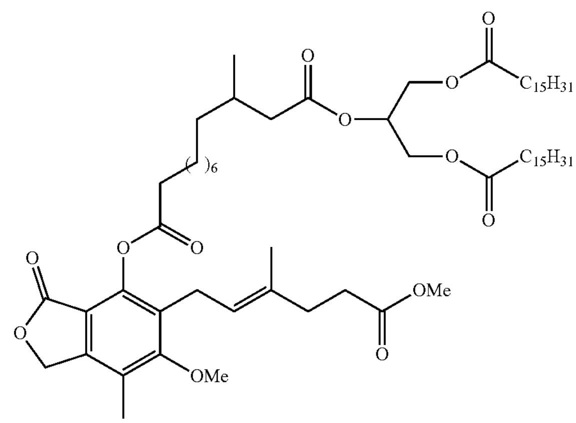 | A |
| MPA(O-PHB-C12α'βMe-2-TG)-OMe (n = 3) | I-54 | 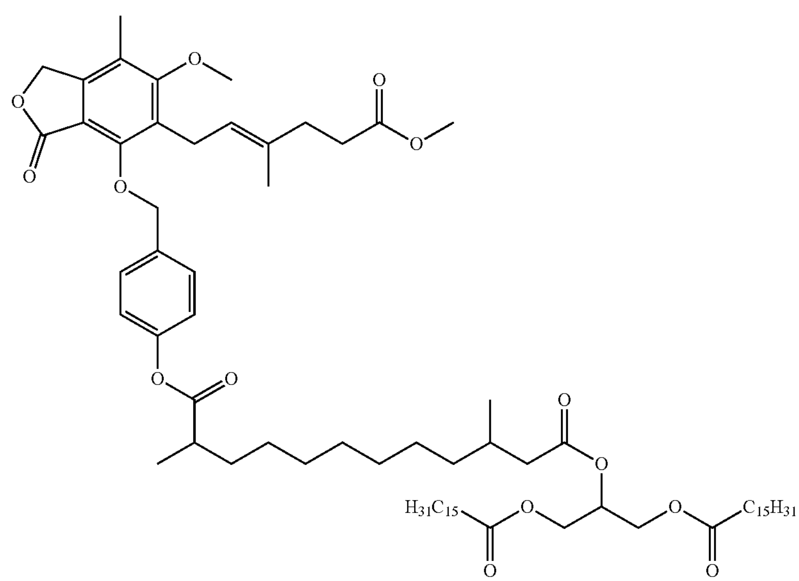 | B |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA-(O-C12αMe-2-TG)-OMe (n = 2) | I-60 | 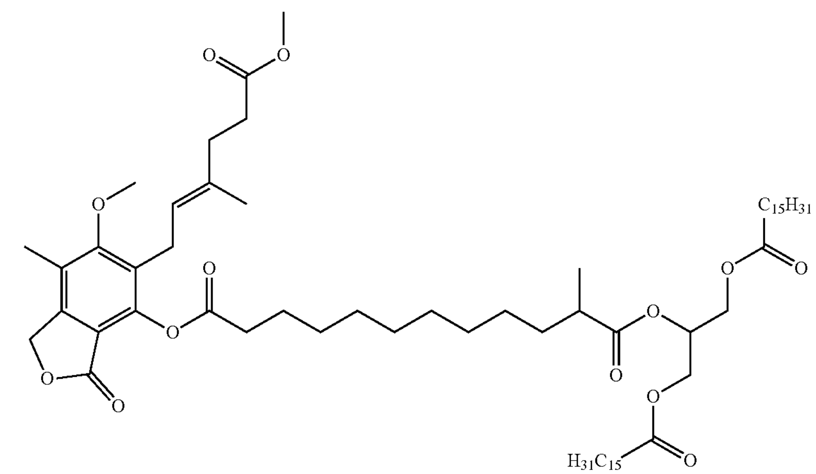 | A |
| MPA-(O-C10α'αMe-2-TG)-OMe (n = 3) | I-61 | 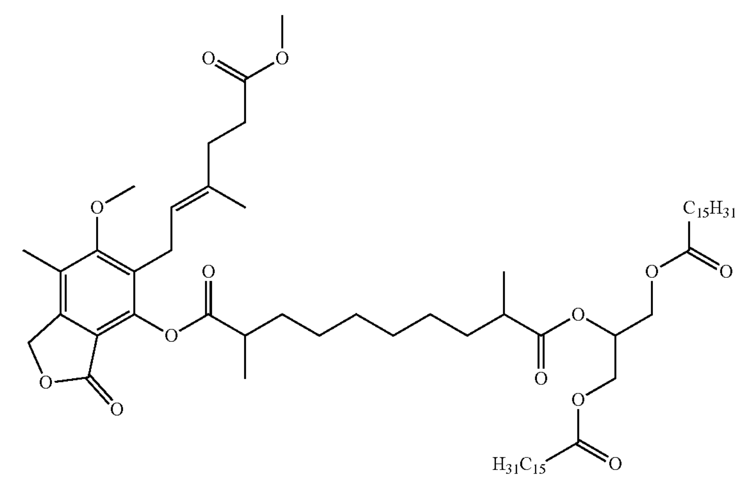 | A |
| MPA(O-FSI(4)-C12α'βMe-2-TG)-OMe (n = 2) | I-62 | 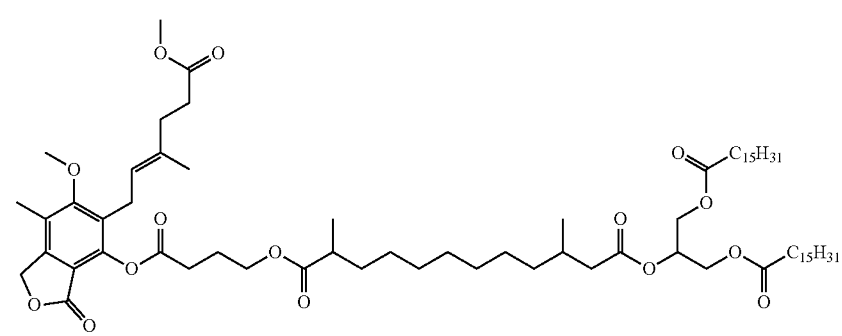 | A |

TABLE 2-continued

Lymphatic transport of total MPA related compound (% of administered dose) following intraduodenal infusion to anesthetised, mesenteric lymph-duct cannulated rats (data are presented as mean ± SD when n ≥ 3 or as mean ± range when n = 2).

| Compound Name | # | Structure | Cumulative lymphatic transport % dose (Mean ± SD, or Range if n = 2) |
|---|---|---|---|
| MPA(O-C10βMe-2-TG)-OMe (n = 3) | I-16 | 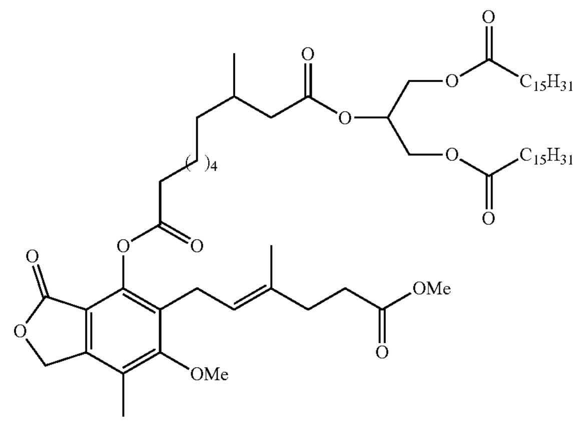 | A |
| MPA(O-C15-2-TG)-OMe (n = 2) | I-57 | 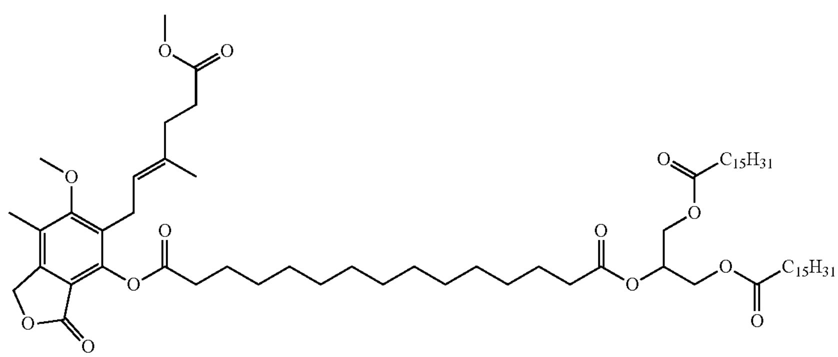 | A |
| MPA(O-MASI-C12α'βMe-2-TG)-OMe (n = 4) | I-58 | 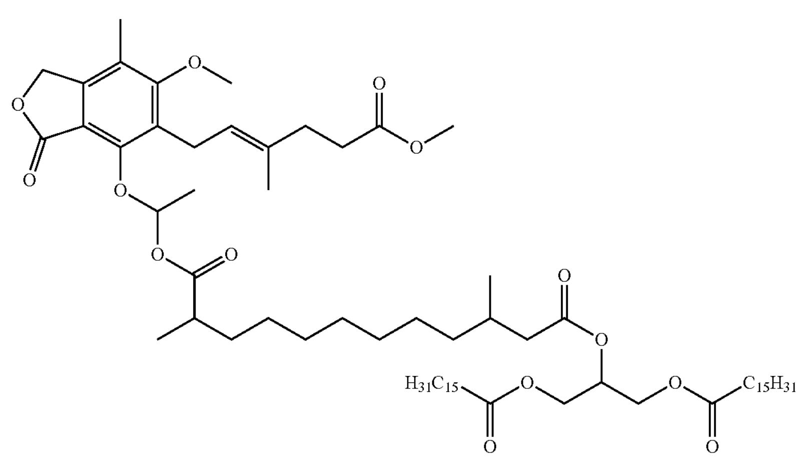 | A |

The half-life of monoglyceride (MG) intermediates in rat bile and pancreatic fluid was determined for selected compounds. The data are presented in Table 3 below. The designation "A" indicates that the half-life of the MG intermediate was between 15 and 90 minutes. "B" indicates a half-life between >90 minutes and 300 minutes. "C" indicates a half-life between >300 minutes and 600 minutes. "D" indicates a half-life between >600 and 1200 minutes.

The percentage of MPA released at 60 minutes in LPL-supplemented rat plasma was also determined for selected compounds. As shown in Table 3 below, the designation "*" indicates a release % of 1 to 25%. The designation "" indicates a release % of >25% to 50%. The designation "*" indicates a release % of >50% to 75%. The designation "****" indicates a release % of >75%.

TABLE 3

Stability of the Monoglyceride (MG) Intermediates of Lipid Prodrugs in Rat Plasma, Bile, and Pancreatic Fluid.

| Compound Name | # | Half-life of MG intermediates in rat bile and pancreatic fluid (min) (n = 3 unless specified otherwise) | Percentage MPA release at 60 min in LPL supplemented rat plasma (n = 3 unless specified otherwise) |
| --- | --- | --- | --- |
| MPA-TG (n = 5) | I-34 | C | *** |
| MPA-C4(ether)-TG (n = 3) | I-25 | C | |
| MPA-C5-Carbonate-TG (n = 4) | I-27 | A | |
| MPA-C6(ether)-TG (n = 4) | I-26 | B | |
| MPA-C7-TG (n = 2) | I-36 | A | |
| MPA-O-C10-TG(OMe) (n = 3) | I-19 | | **** |
| MPA-O-C12α'Meβ Me-TG(OMe) (n = 3) | I-20 | | *** |
| MPA-O-FSI(5)-C12α'Meβ Me-TG(OMe) (n = 2) | I-22 | | *** |
| MPA-2-PL (n = 4) | I-39 | D | |

DESCRIPTION OF THE DRAWINGS

FIG. 1: Lymphatic transport of mycophenolic acid prodrug I-17 in rats following the procedure described above. Rat 1 (●); rat 2 (■).

Figure 2:
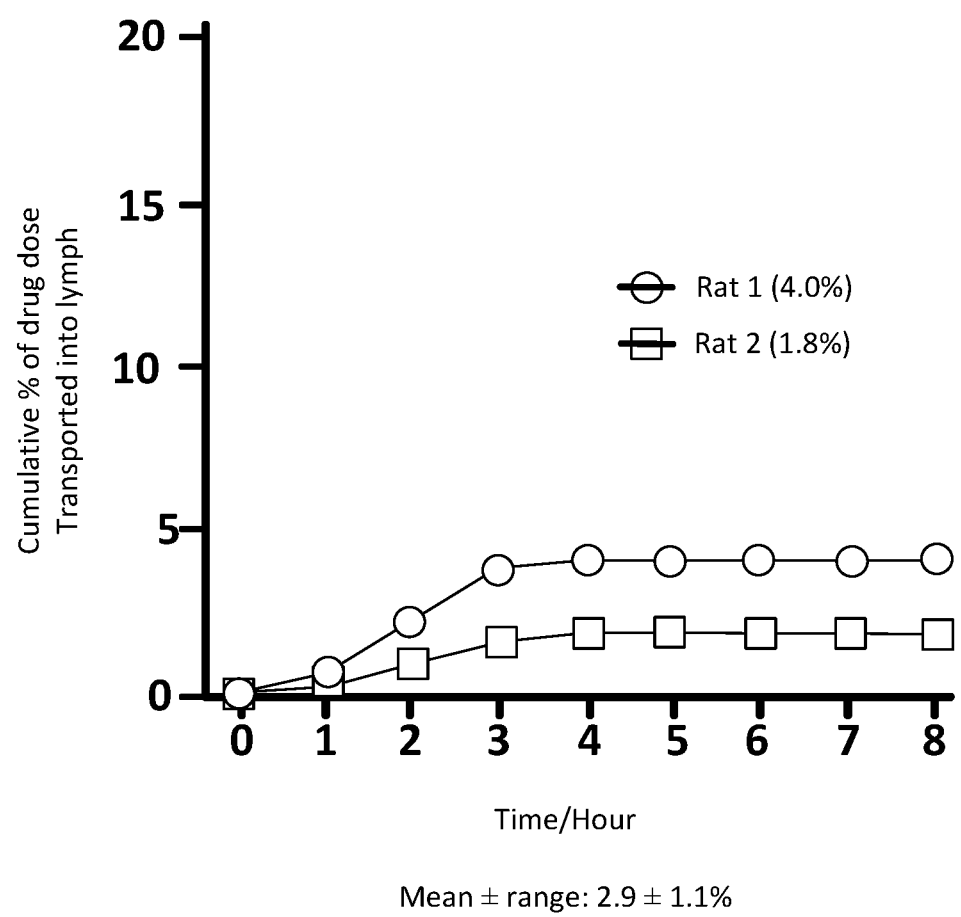
FIG. 2 shows lymphatic transport data for mycophenolic acid prodrug I-18 in rats.

FIG. 2: Lymphatic transport of mycophenolic acid prodrug I-18 in rats following the procedure described above. Rat 1 (●); rat 2 (■).

Figure 3:
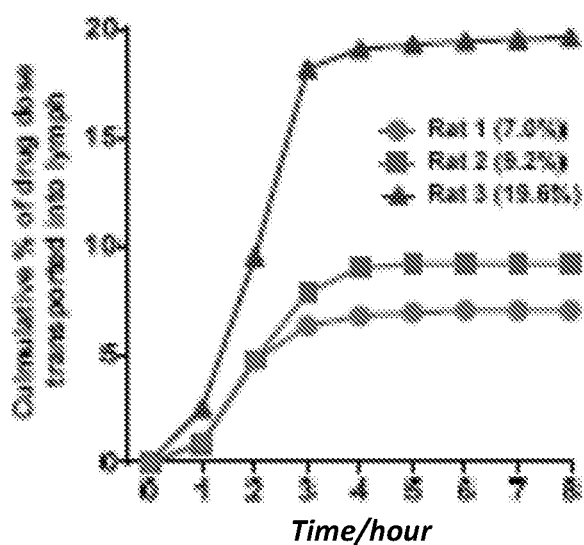
FIG. 3 shows lymphatic transport data for mycophenolic acid prodrug I-19 in rats.

FIG. 3: Lymphatic transport of mycophenolic acid prodrug I-19 in rats following the procedure described above. Rat 1 (●); rat 2 (■); rat 3 (▲).

Figure 4:
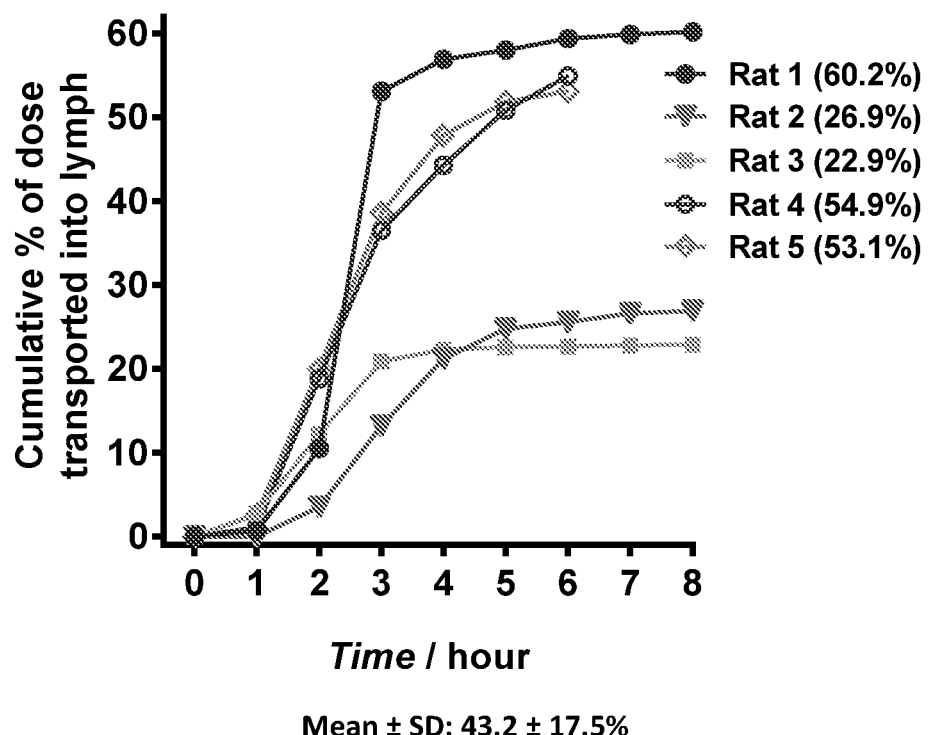
FIG. 4 shows lymphatic transport data for mycophenolic acid prodrug I-20 in rats.

FIG. 4: Lymphatic transport of mycophenolic acid prodrug I-20 in rats following the procedure described above. Rat 1 (●); rat 2 (▼); rat 3 (■); rat 4 (○); rat 5 (◊).

Figure 5:
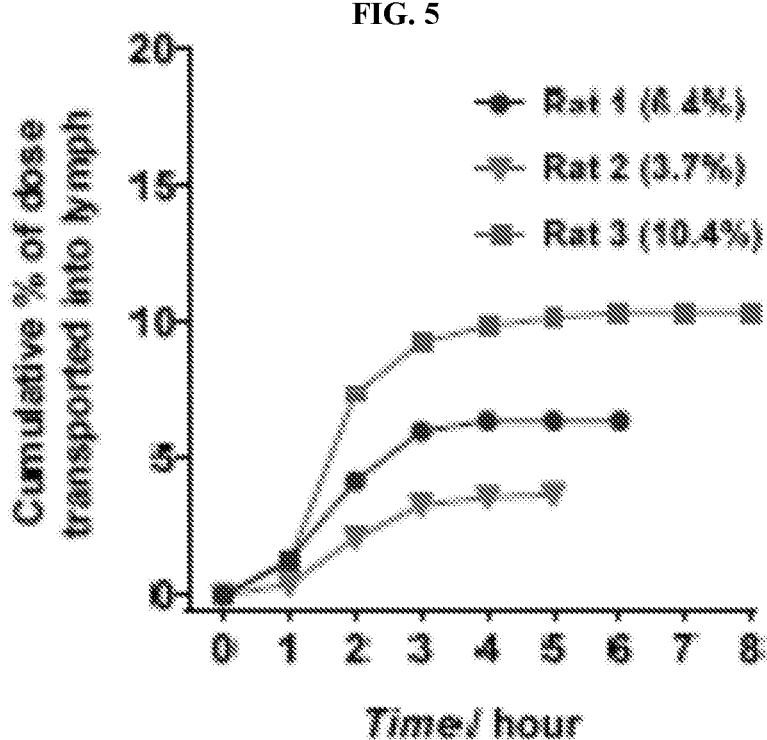
FIG. 5 shows lymphatic transport data for mycophenolic acid prodrug I-21 in rats.

FIG. 5: Lymphatic transport of mycophenolic acid prodrug I-21 in rats following the procedure described above. Rat 1 (●); rat 2 (▼); rat 3 (■).

Figure 6:
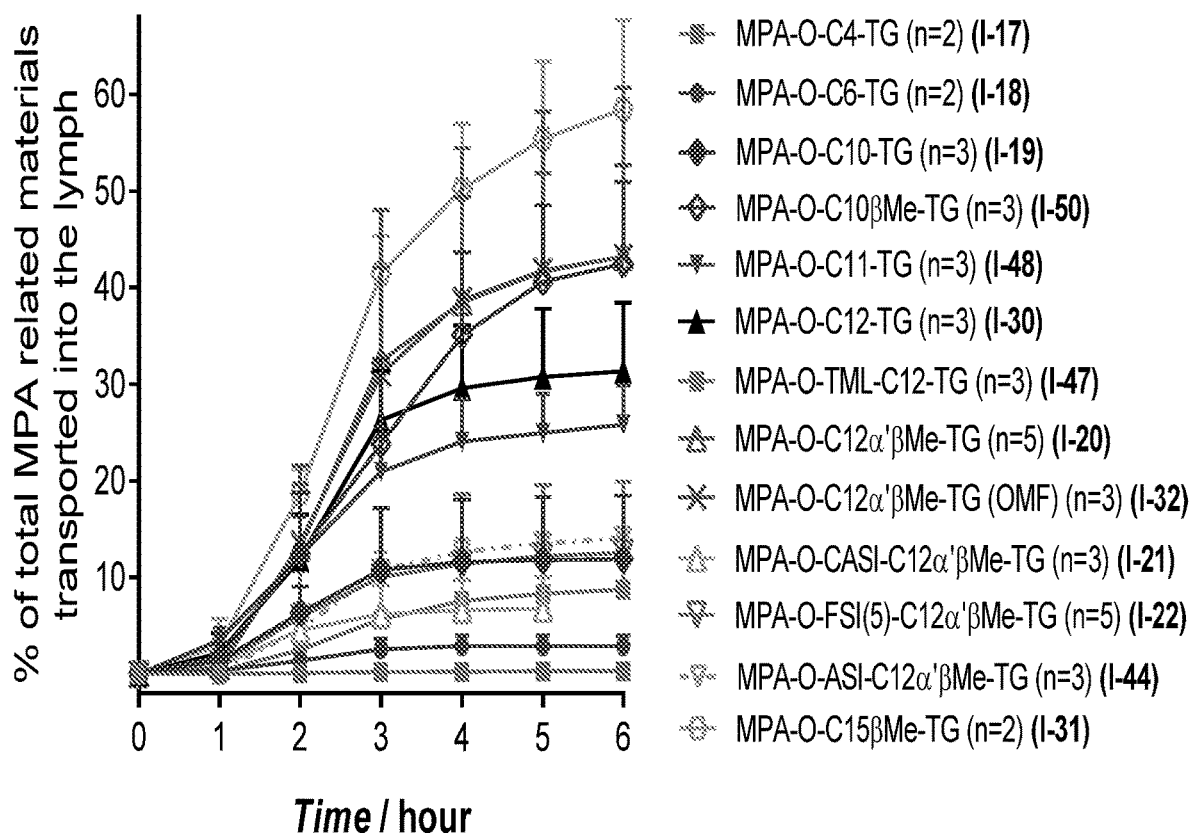
FIG. 6 shows lymphatic transport of phenol-conjugated mycophenolic acid prodrugs (mean±SD when n≥3 or as mean±range when n=2).

FIG. 6: lymphatic transport of phenol-conjugated MPA prodrugs (mean±SD when n≥3 or as mean±range when n=2).

Figure 7:
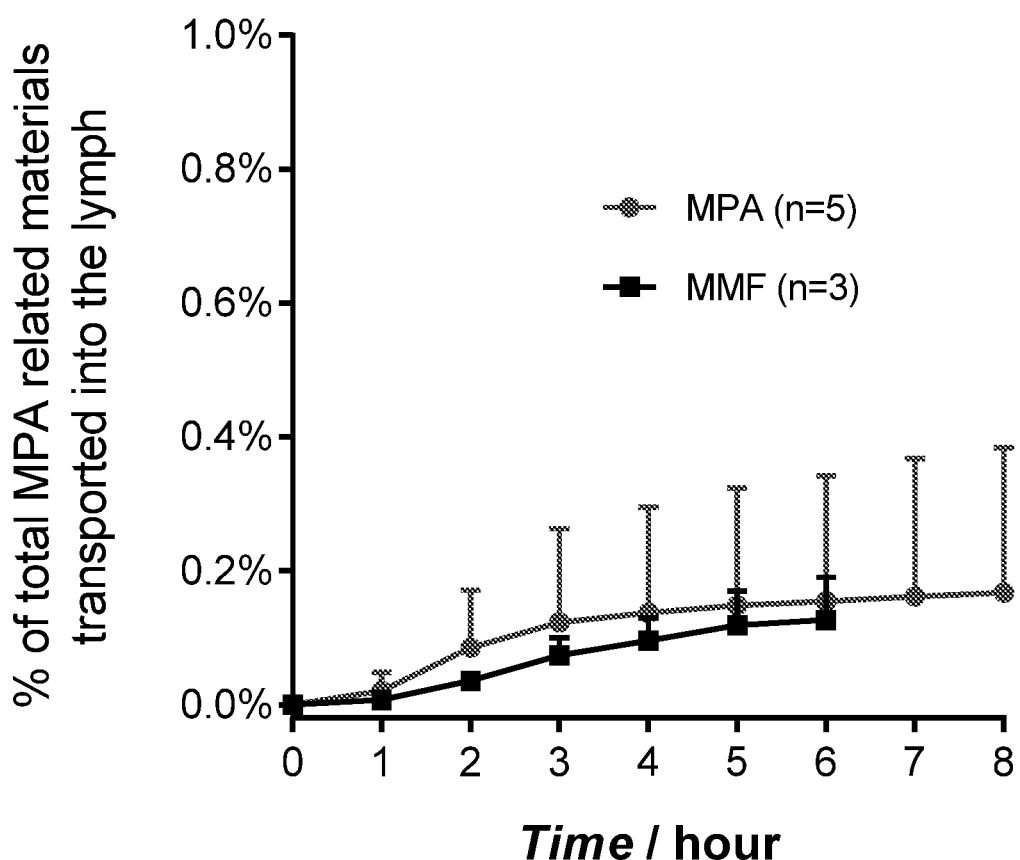
FIG. 7 shows lymphatic transport of mycophenolic acid (MPA) and mycophenolate mofetil (MMF) (mean±SD). MPA (0.13%) and MMF (0.17%) had similar, very low lymphatic transport values in rats. Both compounds were administered as an intraduodenal infusion of 2 mg compound in 5.6 mL of a lipid formulation.

FIG. 7: lymphatic transport of mycophenolic acid (MPA) and mycophenolate mofetil (MMF) (mean±SD).

Example 16: Prodrug Lymph Node Studies in Mice

This experiment included a single and multiple dose study. In the multiple dose study, dosing of either free MPA or MPA-2-TG (I-34, structure below) 2 times daily was performed for 2 days followed by collecting samples from mesenteric or peripheral lymph nodes on the $3^{rd}$ day after dosing.

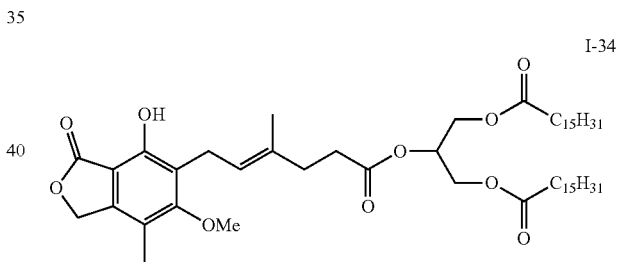

I-34

The concentrations of free MPA were measured for both groups of mice.

Figure 8A:
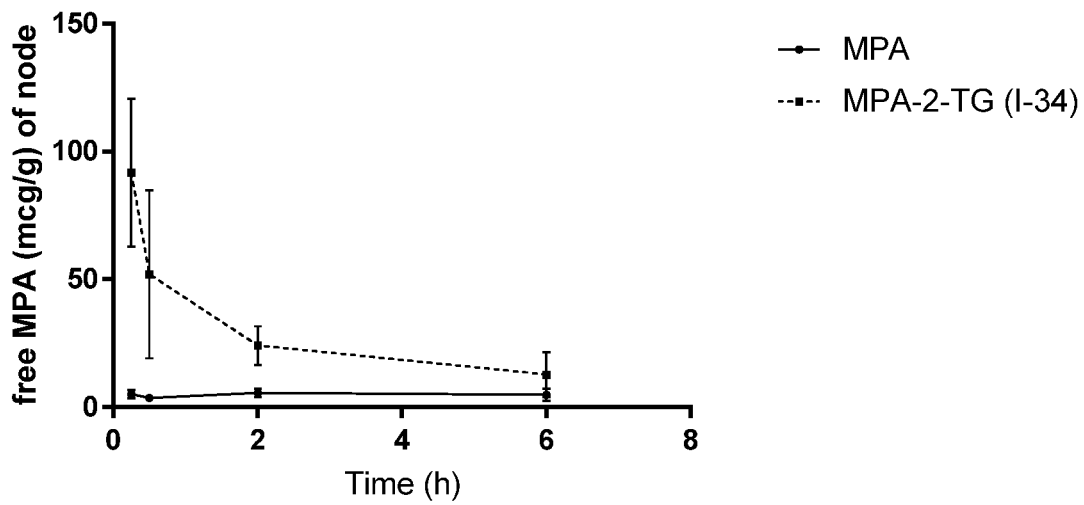
FIG. 8A and FIG. 8B show measured concentrations of free mycophenolic acid (MPA) in mouse mesenteric and peripheral lymph nodes after oral administration of I-34 or MPA.
Figure 8B:
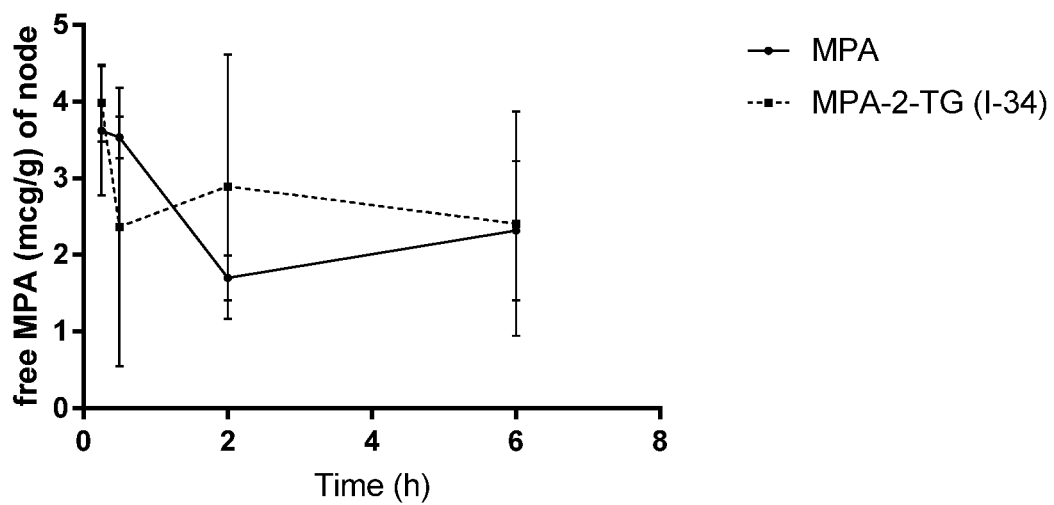

Much higher concentrations in mesenteric lymph nodes after MPA-TG administration were observed compared with MPA. In contrast, the peripheral lymph nodes showed similar concentrations following administration of MPA-TG and MPA. The results of the multi-dose study are shown in FIGS. 8A and 8B.

Figure 9:
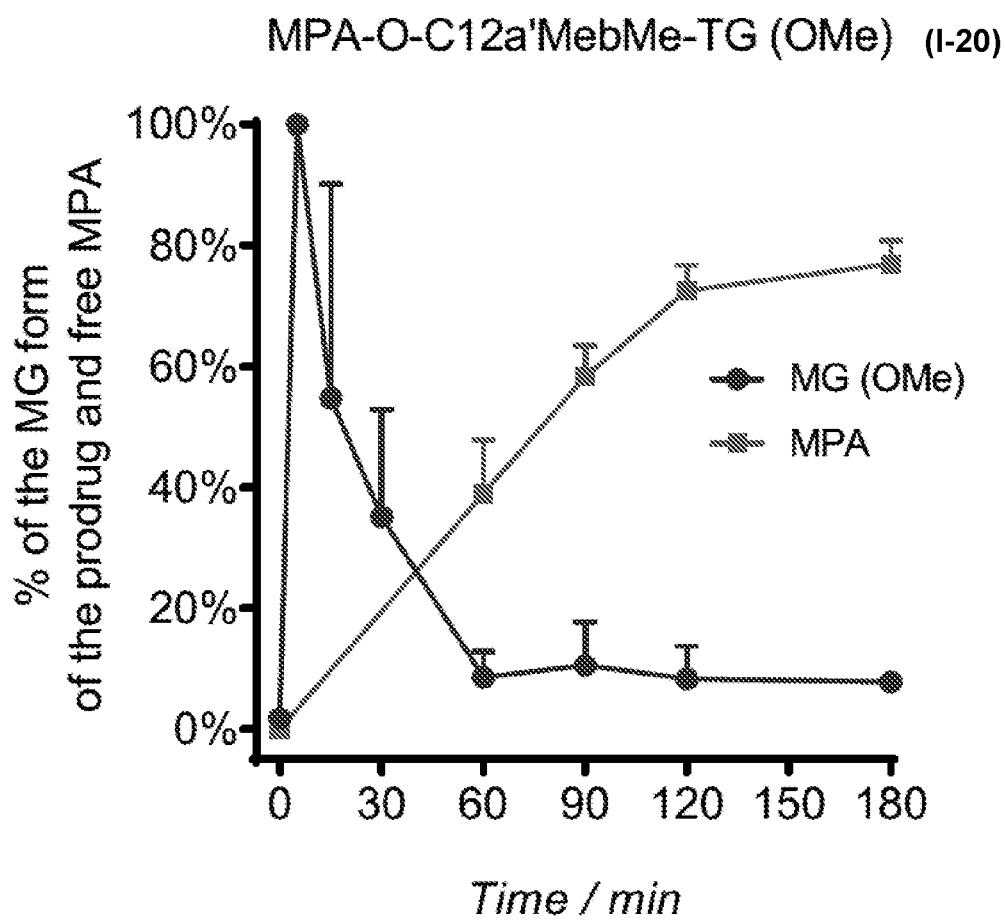
FIG. 9 shows measured concentrations of the monoglyceride form of I-20 (in which both palmitic acid groups are cleaved) and free MPA released from the monoglyceride over time in rat plasma supplemented with LPL.
Figure 10:
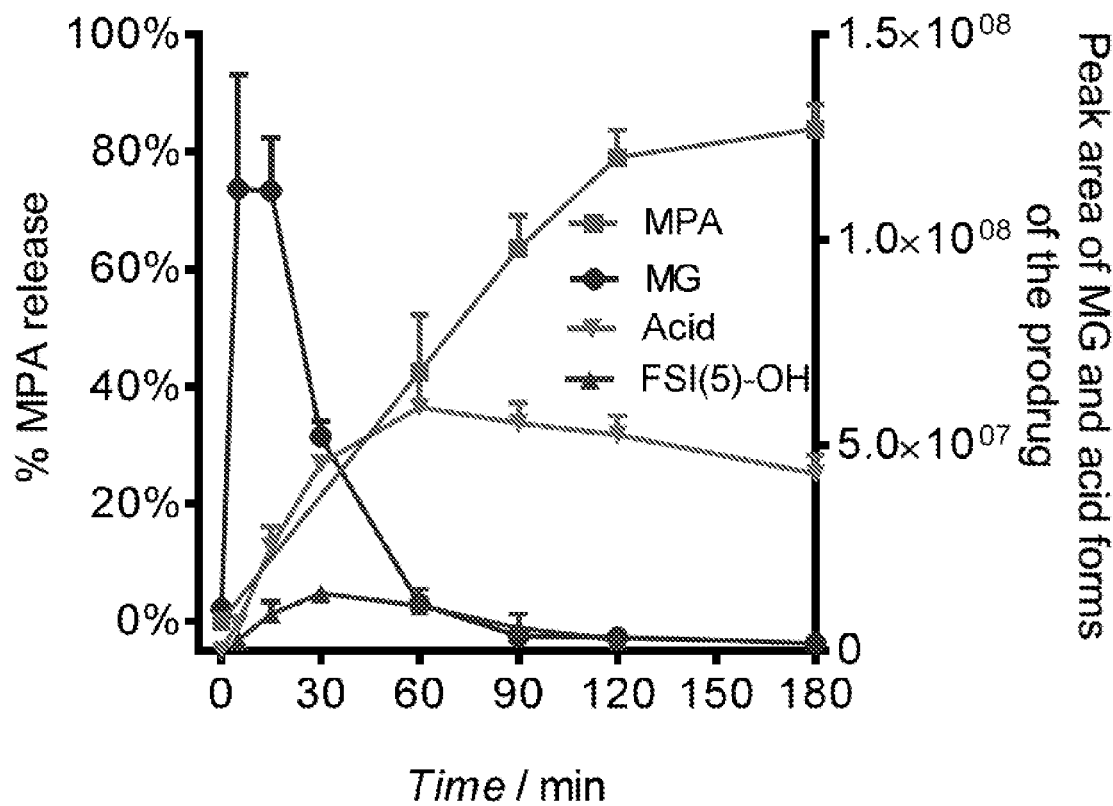
FIG. 10 shows conversion of I-22 into its monoglyceride form (in which both palmitic acid groups are cleaved) and release of MPA from the monoglyceride followed over time in rat plasma supplemented with LPL.
Figure 11:
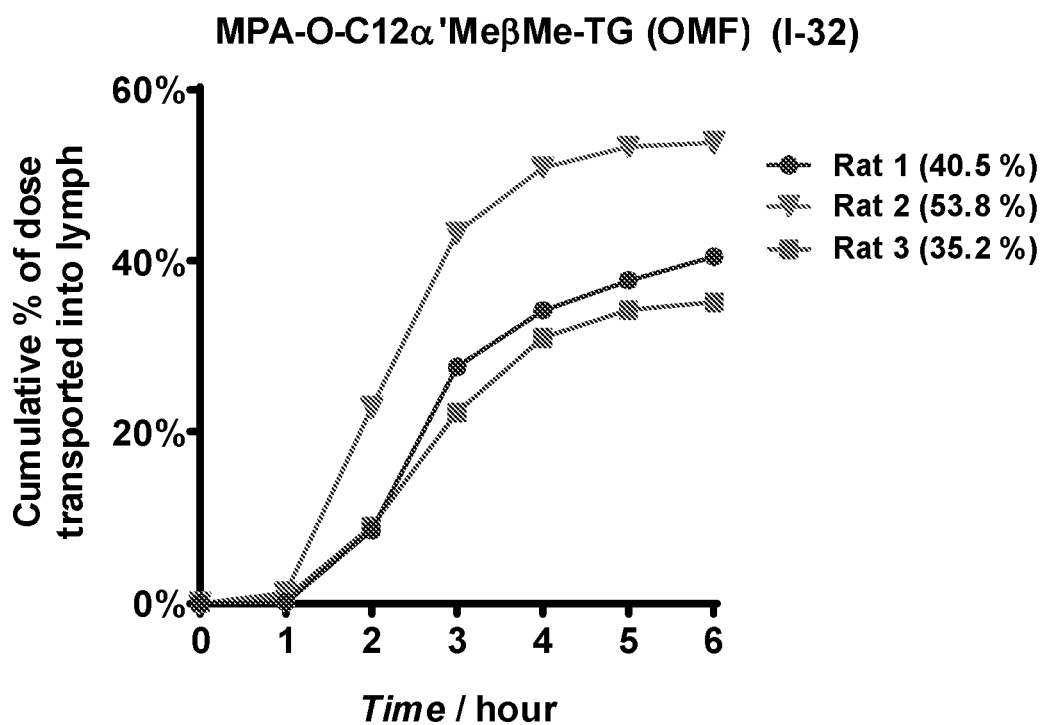
FIG. 11 shows lymphatic transport data for MMF prodrug compound I-32. The compound was administered as an intraduodenal infusion of 2 mg compound in 5.6 mL of a lipid formulation. Lymphatic transport of approximately 40% was observed.
Figure 12:
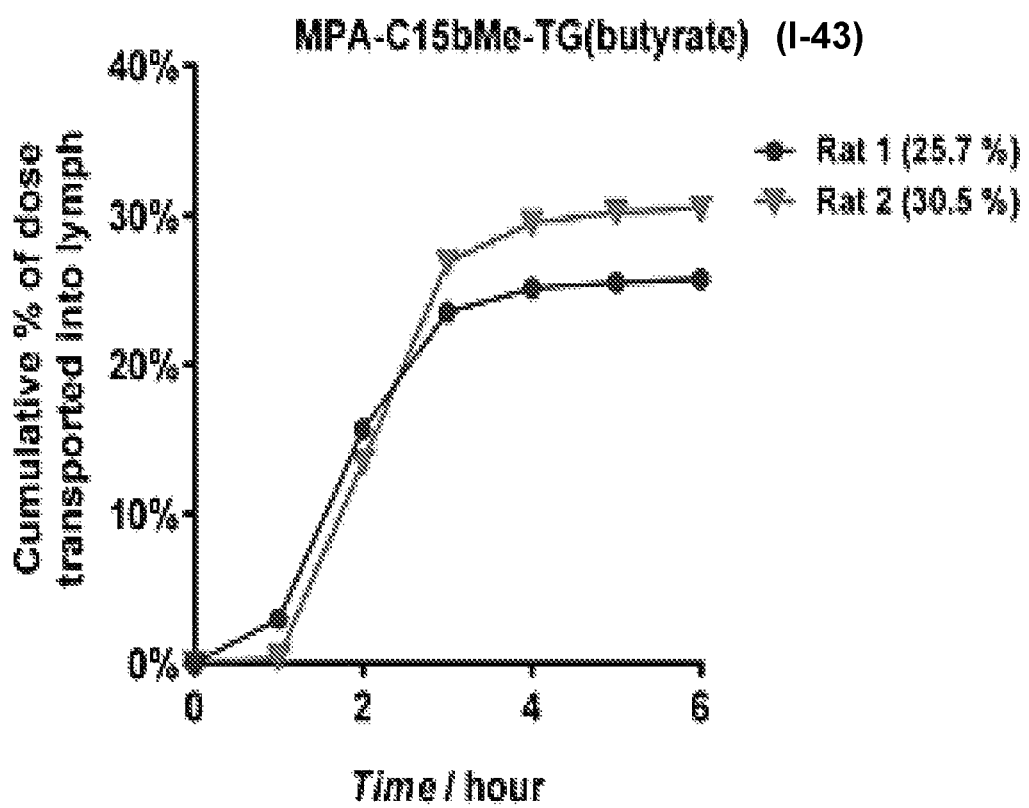
FIG. 12 shows lymphatic transport data for mycophenolic acid prodrug I-43 in rats (plot of cumulative dose into lymph vs. time for each rat).
Figure 13:
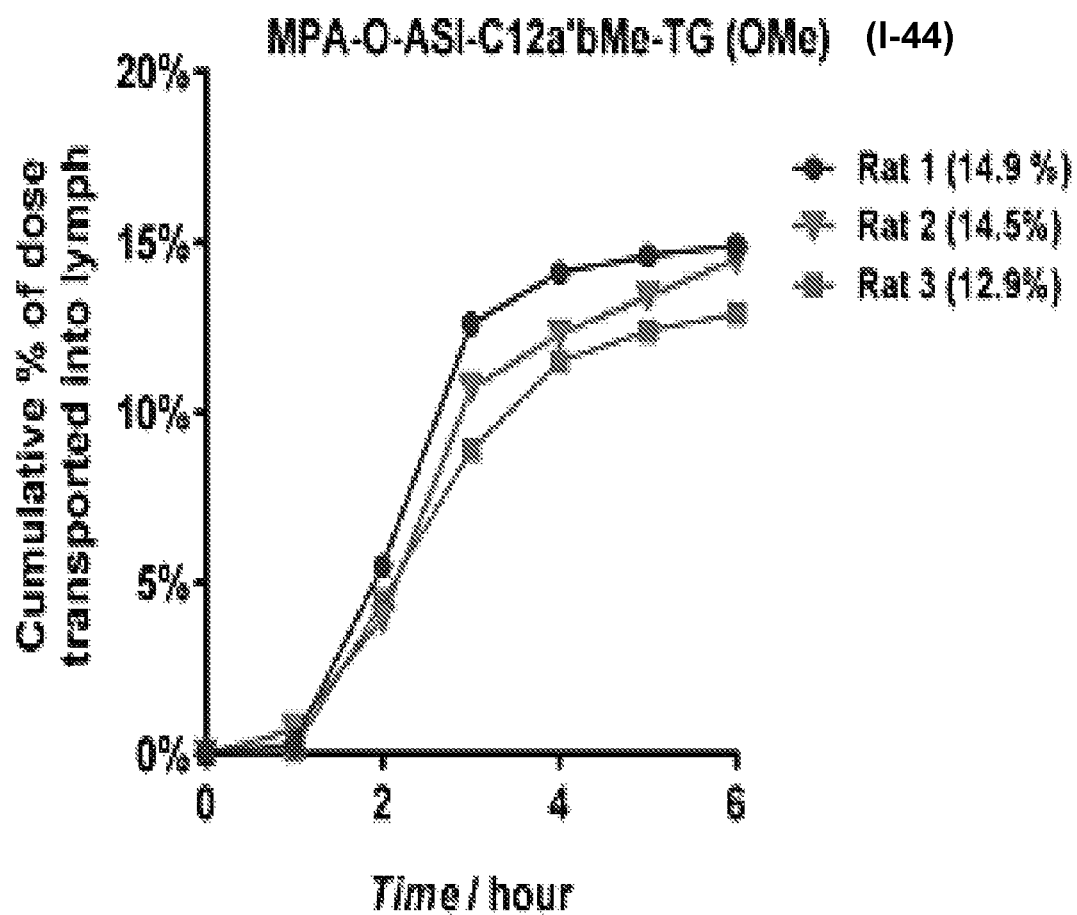
FIG. 13 shows lymphatic transport data for mycophenolic acid prodrug I-44 in rats.
Figure 14:
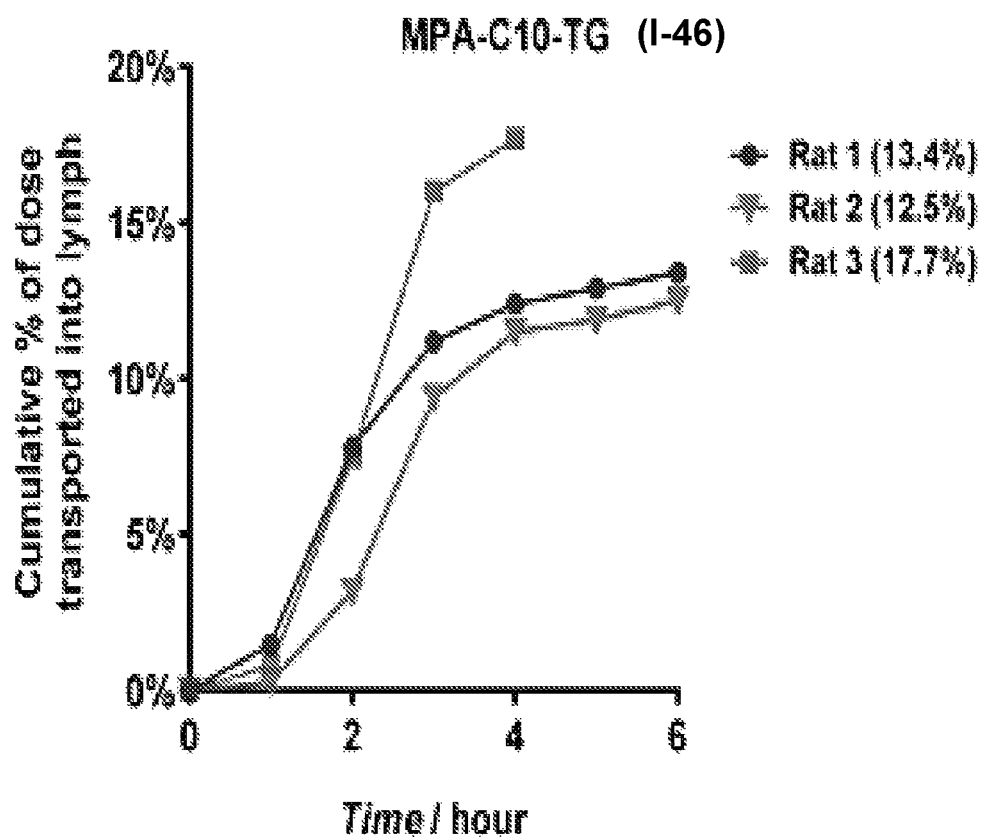
FIG. 14 shows lymphatic transport data for mycophenolic acid prodrug I-46 in rats.
Figure 15:
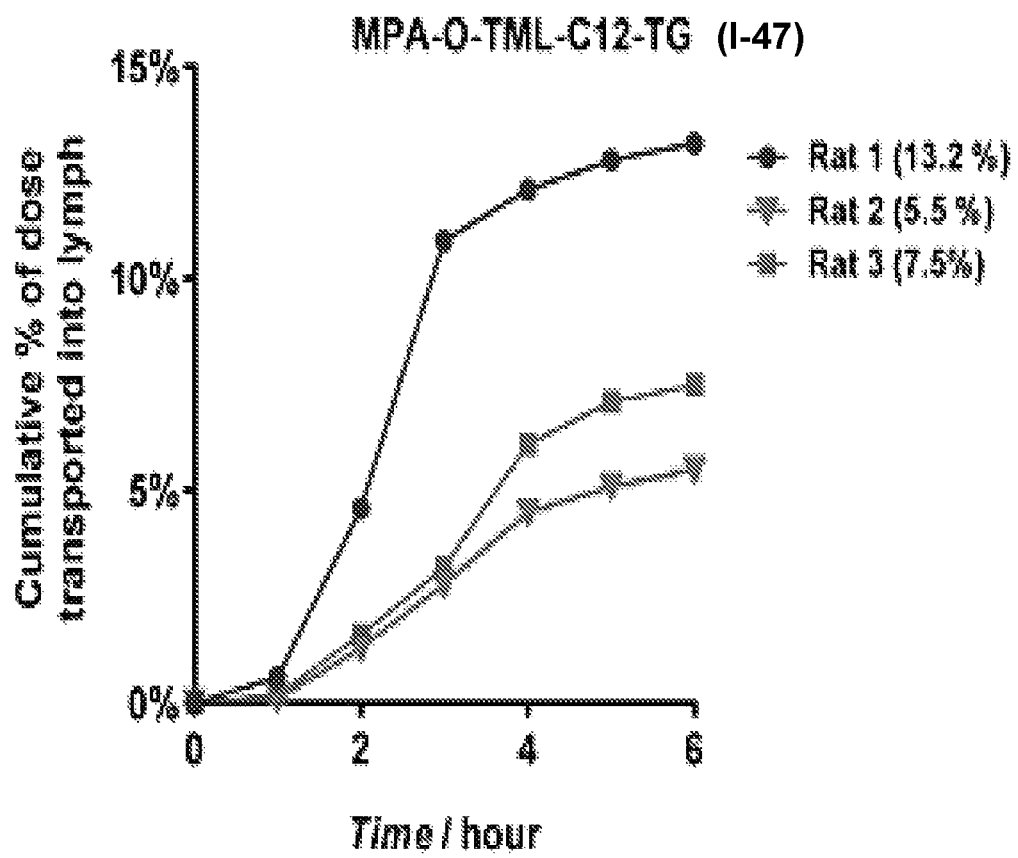
FIG. 15 shows lymphatic transport data for mycophenolic acid prodrug I-47 in rats.
Figure 16:
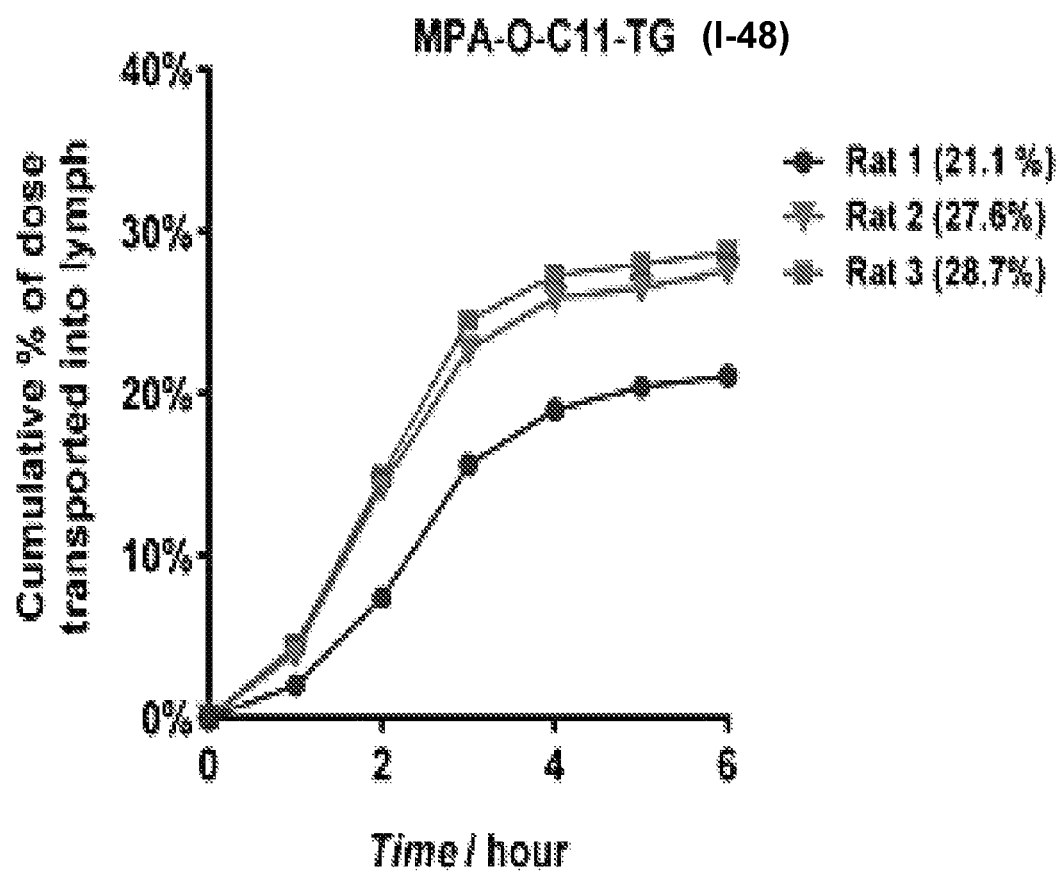
FIG. 16 shows lymphatic transport data for mycophenolic acid prodrug I-48 in rats.
Figure 17:
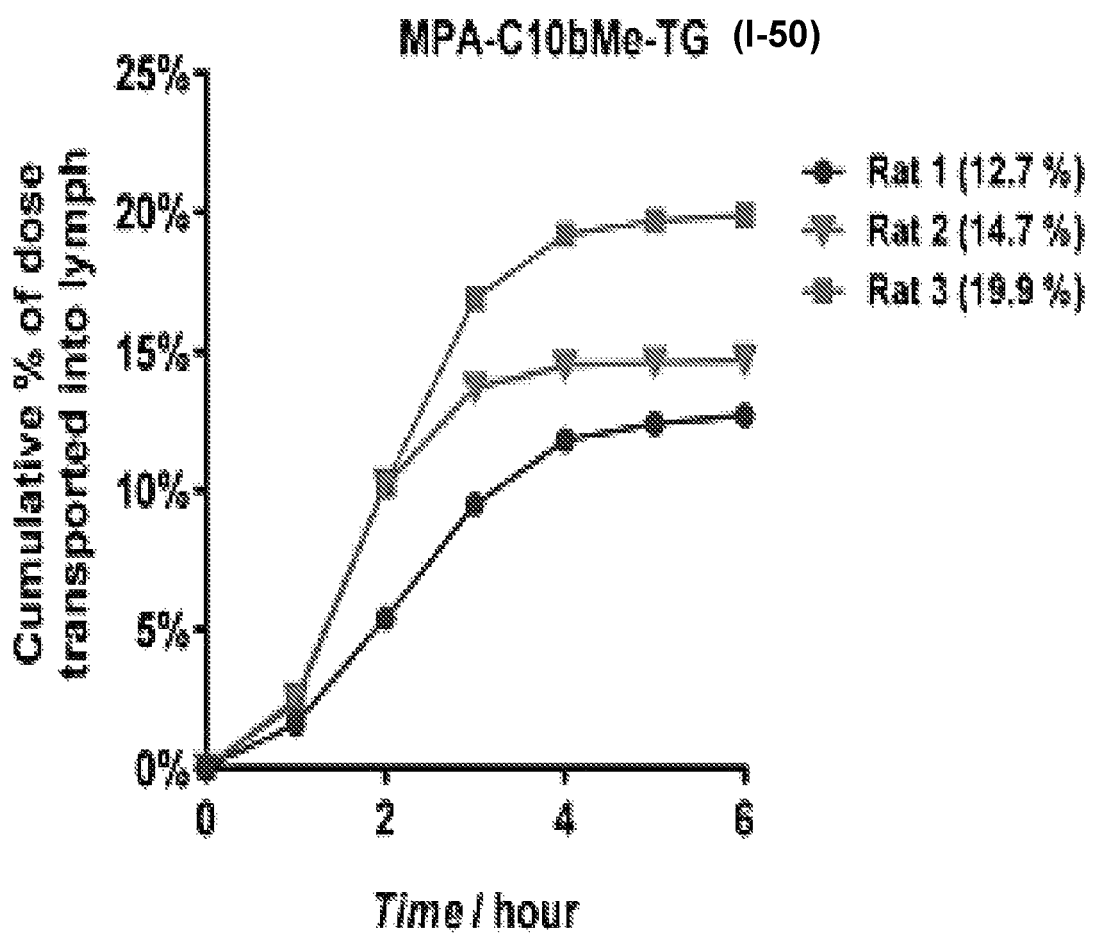
FIG. 17 shows lymphatic transport data for mycophenolic acid prodrug I-50 in rats.
Figure 18:
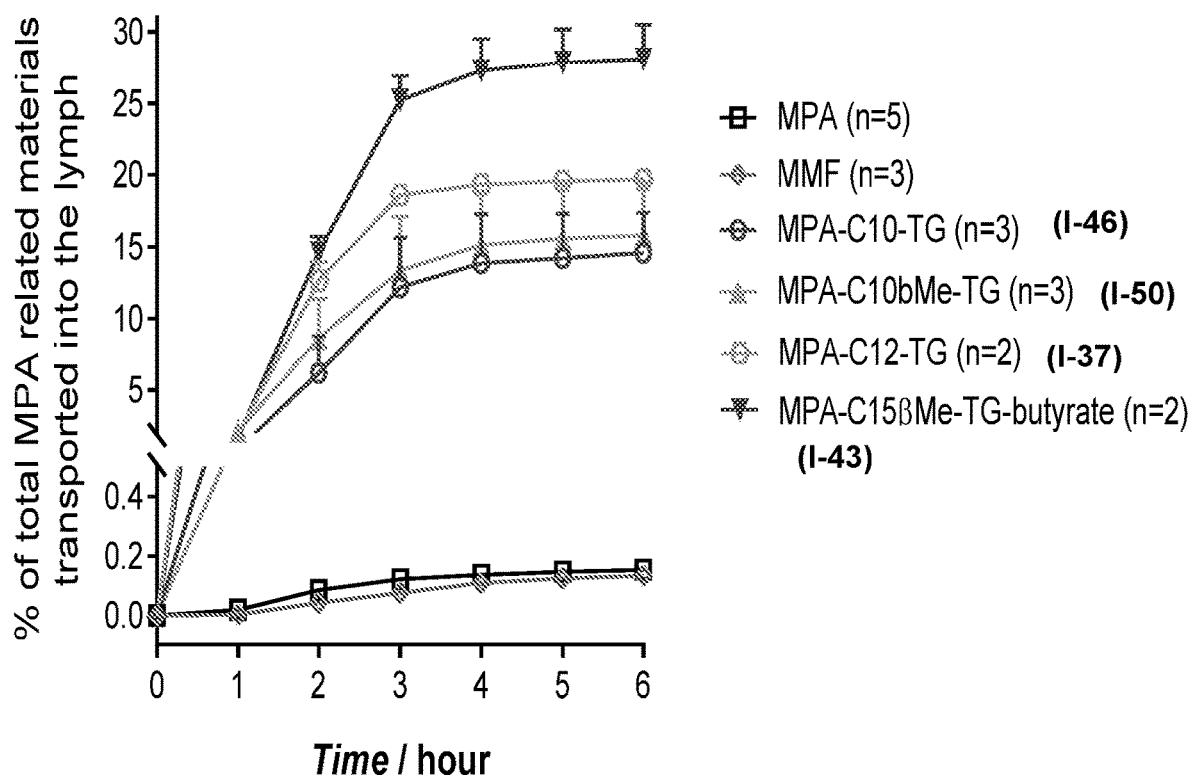
FIG. 18 shows lymphatic transport data for several mycophenolic acid prodrugs (mycophenolic acid (MPA) and mycophenolate mofetil (MMF) shown for comparison).

As shown in FIG. 9, conversion of I-20 into its monoglyceride form (in which both palmitic acid groups are cleaved) and release of MPA from the monoglyceride could be followed over time in rat plasma supplemented with LPL. FIG. 10 shows conversion over time after administration of I-22. For both I-20 and I-22, about 80% of the MPA was released after 180 min and the monoglyceride (MG) peak had almost completely disappeared.

In FIG. 10, the "Acid" intermediate is believed to have the following structure:

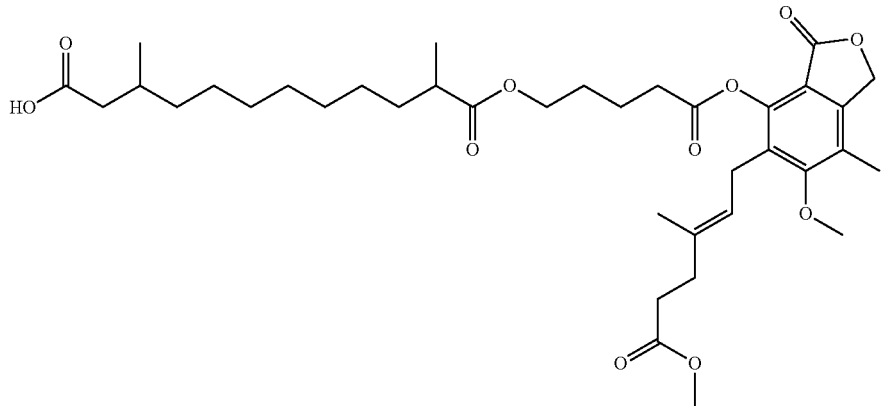 [SMILES: COC(=O)CC/C(C)=C/Cc1c(OC)c(C)c2c(c1OC(=O)CCCCOC(=O)C(C)CCCCCCCC(C)CC(=O)O)C(=O)OC2]

"FSI(5)-OH" refers to the following intermediate structure:

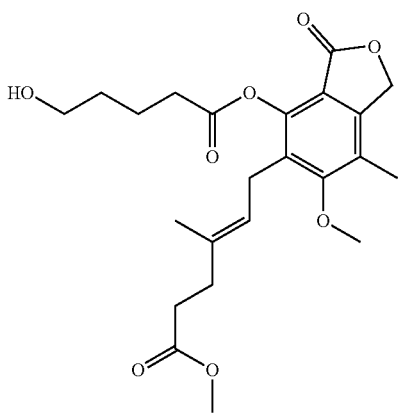 [SMILES: COC(=O)CC/C(C)=C/Cc1c(OC)c(C)c2c(c1OC(=O)CCCCO)C(=O)OC2]

Example 17: Pharmacokinetic (PK) Studies in Rats and Dogs

In order to assess the oral bioavailability of test compounds, pharmacokinetic studies were conducted using the following procedure. The day before drug administration, male Sprague-Dawley rats (240-320 g) were anesthetised and the carotid artery cannulated. The rats were then allowed to regain consciousness and fasted overnight prior to the commencement of experiments with free access to water. The next morning, formulations containing parent compounds or prodrugs were administered via oral gavage and blood samples collected from the carotid artery cannula from −5 min up to 24 h post dosing and centrifuged at 5000 rpm for 5 min to separate plasma. During the blood sample collection period, the rats had free access to water but remained fasted for a further 8 h following drug administration. Plasma samples were stored at −80° C. prior to assay by HPLC-MS-MS. Samples were assayed for free drug (i.e. non-glyceride associated drug) to determine hydrolysis (if any) prior to assay.

For the dog studies, male beagle dogs will be held in a large-animal research facility prior to the commencement of studies. The dogs will be fasted for 12 h up to 30 min prior to drug administration. For the fed state studies, dogs will receive 20 g of high fat dog food (containing ~34% fat), administered by hand, followed by 10 mL water to aid in swallowing, followed by 100 g standard canned dog food (~2.5% fat) 30 min prior to drug administration. Water will be available ad libitum throughout the study for all dogs. Test compounds may be prepared in a suitable formulation such as a long-chain lipid based self-emulsifying drug delivery system (SEDDS) consisting of 30.5% w/w soybean oil, 30.5% w/w Maisine-CC, 31.6% w/w Cremophor EL and 7.4% w/w ethanol. Formulations may be filled into hard gelatin capsules. Compound dissolved in the formulation may be administrated to the fed dog by placing the capsules as far posterior to the pharynx as possible, closing the mouth and rubbing the throat to stimulate swallowing. Subsequently 50 mL of water will be administered orally via a syringe. After oral administration, blood samples (approx. 1.5 mL each) will be taken via venepuncture of the cephalic vein 5 min prior to administration up to 120 hours post-dosing. Plasma will be separated by centrifugation and aliquots of each plasma sample transferred into eppendorf tubes and stored at -80° C. prior to analysis.

For comparison purposes and to allow calculation of bioavailability, the parent drug may be administered intravenously by either infusion (over 5 min) or bolus injection of a suitable dose of drug dissolved in appropriate aqueous formulation (dependent on the nature of the parent drug; for example, for MPA, 95:5 PBS/ethanol may be used, while for other drugs such as MMF or prodrugs of MPA, a 20% hydroxypropyl- β-cyclodextrin solution may be used if deemed preferable). The dose also depends on the nature of the parent drug. For MPA, about 2-3 mg per beagle is used, while for MMF or other analogs differing doses will be calculated based on typical doses for the drug in clinical use or other factors. After IV administration, blood samples (approx. 1.5 mL each) will be taken via venepuncture of the cephalic vein 5 min prior to administration up to 120 hours post-dosing. Plasma will be separated by centrifugation and aliquots of each plasma sample transferred into eppendorf tubes and stored at −80° C. prior to analysis.

Example 18: In Vitro Hydrolysis of Compounds by Rat Digestive Fluid or Porcine Pancreatic Lipase In vitro hydrolysis of test compounds may be performed via incubation with rat digestive fluid. Rat digestive fluid will be collected from anesthetized rats via cannulation of the common bile-pancreatic duct immediately prior to the entry of the duct into the duodenum (i.e. below the point of entry of pancreatic secretions). This allows simultaneous collection of bile and pancreatic fluid. The digestive fluid will be collected continuously for 2 h, during which time a blank lipid formulation (prepared as described in the rat lymphatic transport studies but without the addition of drug) will be infused into the duodenum at a rate of 2.8 mL/h to mimic conditions following drug administration. Bile and pancreatic fluid will be maintained at 37° C. and used within 0.5 h of collection for in vitro prodrug hydrolysis experiments. The hydrolysis experiments will be conducted via incubation (at 37° C.) of ~0.375 mL of rat digestive fluid with ~0.625 ml of the drug-loaded lipid formulations (as described in the rat lymphatic transport studies). The volume ratio of digestive fluid to formulation will mimic the flow rate of bile and pancreatic fluid (~1.5 mL/h) and the infusion rate of the intraduodenal formulations (2.8 mL/h) during the in vivo lymphatic transport studies. Aliquots of 10 µL (samples taken at 0, 2, 5, 10, 15, 30, 60, 90, 120, 180 min) will be added to 990 µL of acetonitrile/water (4:1, v/v) to stop lipolysis, vortexed for 1 min and centrifuged at 4500 g for 5 min to precipitate proteins prior to analysis. The supernatant will be analyzed by HPLC-MS for residual compound concentrations, and the potential products of compound hydrolysis analyzed.

To provide for higher throughput of experiments, unless otherwise stated, in vitro hydrolysis of test compounds will generally be performed via incubation with porcine pancreatic lipase. This provides a more reproducible source of pancreatic enzymes, facilitates enhanced experimental throughput, and is also a greater challenge than collected rat enzymes (since enzyme activity in rat intestinal fluid is low). Briefly, pancreatic lipase solution will be prepared prior to the hydrolysis experiment by dispersion of 1 g porcine pancreatin in 5 ml of lipolysis buffer and 16.9 µL of 0.5 M NaOH. The suspension will be mixed well and centrifuged at 3500 rpm for 15 minutes at 5° C. to provide a supernatant. An amount of 1000 mL of lipolysis buffer will be prepared with 0.474 g of tris-maleate (2 mM), 0.206 g of $CaCl_2.H_2O$ (1.4 mM) and 8.775 g of NaCl (150 mM) adjusted with NaOH to pH 6.5. To assess the potential for prodrug hydrolysis in the intestine, 20 µL of prodrug solution (1 mg/mL dissolved in acetonitrile), 900 µL of simulated intestinal micellar solution [prepared with 0.783 g of NaTDC (3 mM) and 0.291 g of phosphatidyl choline (0.75 mM) in 500 mL lipolysis buffer] and 100 µL of enzyme solution will be incubated at 37° C. 20 µL samples of the incubation solution will be taken at 0, 5, 10, 15, 30, 60, 90, 120 and 180 minutes post incubation and added to 180 µL of MeCN to stop lipolysis. The mixture will be vortexed and centrifuged at 5000 rpm for 5 minutes to precipitate proteins prior to analysis. The supernatant will be analyzed by HPLC-MS for residual compound concentrations, and the potential products of compound hydrolysis analyzed.

On incubation with digestive enzymes, the monoglyceride forms of the prodrugs are formed very rapidly. The stability in simulated intestinal conditions is therefore better assessed by the stability of the monoglyceride form that is generated by the initial digestion process. The monoglyceride form must remain intact to be absorbed and re-esterified in the enterocyte prior to entry into the lymphatics. A comparison of the stability profiles of the monoglyceride forms of test compounds during in vitro incubation with freshly collected rat bile and pancreatic fluid (BPF) or porcine pancreatic lipase will be used to evaluate the influence of linker structure on the stability of the monoglyceride intermediates.

Example 19: In Vitro Release of Therapeutic Agent from Prodrugs in Lymph Supplemented with Lipoprotein Lipase In order to probe the release of free therapeutic agent from lipid prodrugs in the lymphatics, prodrugs will be incubated with rat lymph supplemented with lipoprotein lipase (LPL, 200 unit/mL). LPL is a key enzyme required for the hydrolysis of lipoprotein associated TG in normal physiological conditions and is therefore expected to be a key contributor to lipolysis of the re-esterified drug-TG construct in plasma, largely via liberation of fatty acids in the sn-1 and the sn-3 position of the TG-mimetic, prior to drug release from the 2' position via esterase hydrolysis. LPL is tethered to lymphocytes or lymphatic/vascular endothelial cells under physiological conditions. In these in vitro studies, rat lymph will therefore be supplemented with LPL to better reflect the in vivo situation. To start hydrolysis, 10 µL of LPL solution (10,000 unit/ml) will be added to a mixture of 10 µL of prodrug solution (1 mg/mL dissolved in acetonitrile) and 500 µL of blank Sprague Dawley rat lymph. The solution will be incubated at 37° C. Samples (20 µL) of the incubation solution will be taken at 0, 5, 10, 15, 30, 60, 90, 120 and 180 minutes post incubation and added to 980 µL of 9:1 (v/v) MeCN/water to stop lipolysis. The mixture will be vortexed and centrifuged at 4500 g for 5 minutes to precipitate proteins prior to analysis. The supernatant will be analyzed by HPLC-MS/MS for concentrations of the released therapeutic agent.

Example 20: Lymphocyte Proliferation Assay

Immune cells from rats (MLN and spleen cells) and PBMCs from human participants will be cultured in flat clear-bottom 96-well microplates (Thermo Scientific Nunc®) at a concentration of $8.4 \times 10^4$ and $5.2 \times 10^4$ cells/well, respectively. Working stock solutions of test and control compounds in RMPI-1640 culture medium-DMSO (99:1, v/v) will be prepared at concentrations of 10, 25, 50, 75, 100, 150, and 200 µg/mL. Working stock solutions of test and control compounds will be incubated with cells at final concentrations of 1, 2.5, 5, 7.5, 10, 15, and 20 µg/mL in a humidified atmosphere of 5% $CO_2$ at 37° C. for 30 min. Cells will then be stimulated by the T cell-selective mitogen Phytohaemagglutinin (PHA, 10 µg/mL, Sigma Aldrich; see Janossy, G. et al., Clin. Exp. Immunol. 9, 483-& (1971)) or other stimulant such as Concanavalin A (ConA), and incubated in a humidified atmosphere of 5% $CO_2$ at 37° C. for 2 days. Cell proliferation will be assessed by enzyme-linked immunosorbent assay (ELISA) based on bromo-2'-deoxyuridine (BrdU) incorporation into newly synthesized DNA according to the manufacturer protocol (Roche Applied Science, Roche Diagnostics Ltd, UK). Finally, the absorbance of these wells will be observed at 370 nm, with reference wavelength at 492 nm using plate reader (EnVision® Multilabel Plate Reader, PerkinElmer Inc., USA). Absorbance values will be normalized to the absorbance of culture medium-treated cells.

Reference: Zgair, A. et al., Scientific Reports 2017, 7: 14542, 1-12.

Example 21: Flow Cytometry Analysis

Freshly isolated immune cells of MEN and splenocytes from rats and thawed PBMCs from human participants will be incubated with control or test compound (I-20 µg/mL) for 30 min in FACS tubes. Cells will then be stimulated with phorbol myristate acetate and ionomycin (PMA & I) in the presence of brefeldin A and incubated in a humidified atmosphere of 5% $CO_2$ at 37° C. for 5 hours. After stimulation, cells will be washed with PBS and centrifuged to pellet (290 g, 5 min, 20° C.). Cell pellet will be resuspended and labelled with Zombie UV™ Fixable Viability kit according to the manufacturer's protocol (Biolegend) for the purpose of excluding dead cells during the analysis of data (effect of relevant control compounds on the variability of immune cells isolated from healthy volunteers can be evaluated by methods known in the art). Fixation and permeabilization will be performed using BD Cytofix/Cytoperm™ kit according to the manufacturer's protocol (BD Bioscience). Rat immune cells will be labelled with APC anti-rat CD3, PE anti-mouse/rat TNF-α, and FITC anti-rat IFN-γ antibodies (Biolegend). Human PBMCs will be labelled with BV421 anti-human TNF-α and PerCP/Cy5.5 anti-human IL-2 antibodies (Biolegend), ECD anti-human CD3, FITC anti-human IFN-γ antibodies (Beckman Coulter), and PE anti-human IL-17A, and APC anti-human GM-CSF antibodies (eBioscience). Isotype and fluorescence minus one (FMO) controls will be prepared for all antibodies in each flow cytometry run. Data will be collected on MoFlo® Astrios™ EQ flow cytometer and analyzed using Kaluza analysis software v 1.5 (Beckman Coulter). An appropriate gating strategy may be selected using methods known in the art and the reference below.

Reference: Zgair, A. et al., Scientific Reports 2017, 7: 14542, 1-12.

Example 22: Preparation of Single-Cell Suspension from Mesenteric Lymph Node (MEN) and Spleen of Rats Following 5 days of acclimatization, animals will be euthanized and the ventral abdominal wall incised to expose the intestine. MLN and spleen will be aseptically collected. MLN will be gently dissected from surrounding tissue and spleen will be scored with a clean scalpel before being mashed on cell strainer (70 µm Nylon, Corning Falcon™). Red blood cells in the cell suspension of the splenocytes will be lysed by lysing buffer (BD Bioscience). Immune cells from MLN and splenocytes will then be washed twice with PBS. Cell suspension will be centrifuged (400 g, 5 min at room temperature) and resuspended in complete RMPI-1640 culture medium (RMPI-1640 culture medium with L-glutamine supplemented with 10% fetal bovine serum (FBS) and 1% penicillin-streptomycin, all purchased, e.g., from Sigma-Aldrich) at concentration of $1.2 \times 10^6$ cells/mL to be used for proliferation and flow cytometry experiments.

Reference: Zgair, A. et al., Scientific Reports 2017, 7: 14542, 1-12 and Han, S. et al., Journal of Controlled Release 2014, 177, 1-10.

Example 23: In Vitro Release of Therapeutic Agent from Prodrugs in Plasma Supplemented with Lipoprotein Lipase In order to probe the release of free drug from TG prodrugs in the systemic circulation, prodrugs were incubated with plasma (rat, mouse, dog, pig or human) supplemented with lipoprotein lipase (LPL, 200 IU/ml). LPL is a key enzyme required for the hydrolysis of lipoprotein associated TG in the systemic circulation and is therefore expected to be a key contributor to lipolysis of the re-esterified drug-TG construct in plasma, largely via liberation of fatty acids in the sn-1 and the sn-3 position of the TG-mimetic, prior to drug release from the 2' position via esterase hydrolysis. LPL is active in plasma but is tethered to the luminal surface of vascular endothelial cells under physiological conditions. In the current in vitro studies, plasma was therefore supplemented with LPL to better reflect the in vivo situation. To start hydrolysis, 10 µl of LPL solution (10,000 IU/ml) was added to a mixture of 10 µl of prodrug solution (1 mg/ml dissolved in acetonitrile) and 500 µl of blank plasma. The mixture was incubated at 37° C. Samples (20 µl) of the incubation solution were taken at 0, 5, 15, 30, 60, 90, 120 and 180 minutes post-incubation and added to 180 µl of MeCN to stop lipolysis. The mixture was vortexed and centrifuged at 4500×g for 5 minutes to precipitate proteins prior to analysis. The supernatant was analyzed by HPLC-MS/MS for the potential products (MG form, acid form, and free drug) of prodrug hydrolysis.

Example 24: Oral Ovalbumin Challenge Model

Purification and Labelling of Ovalbumin Specific T Cells

OVA specific $CD4^+$ and $CD8^+$ T cells were purified from the lymph nodes of OT2 and OT1 mice, respectively, and employed in independent experiments to simplify the studies. Lymph nodes collected from OT mice (including MLN, inguinal, brachial, axillary, cervical, iliac) were pressed through a 40 µm sieve using the back of 1 ml syringe plunger, to form a single cell suspension in RPMI 1640 with 2% Fetal Bovine Serum. T cells were then purified using negative selection separation and employing a magnet assisted cell sorting (MACS®) protocol from Miltenyi Biotec. The protocol provided in the kit supplied by Miltenyi Biotec was followed. Briefly, cell suspensions obtained from the lymph node of the OT mice were resuspended in MACS buffer (PBS with 2 mMEDTA and 0.2% Bovine Serum Albumin (BSA)) and labelled with antibodies against all other surface markers, except for the marker for the cells of interest (i.e. CD4+ T cells are isolated by depletion of non CD4+ T cells using a cocktail of biotin-conjugated antibodies against CD8a, CD11b, CD11c, CD 19, CD45R (B220), CD49b (DX5), CD105, Anti-MHC-class II, Ter-119 and TCR γ/δ as primary labelling reagent). The cells were then incubated with Anti-biotin labelled magnetic microbeads and passed through the MACS LS column along with MACS buffer within the magnetic field of the Vario MACS separator. The labelled cells are retained within the column while the unlabelled cells flow through the column. The quantity of reagents used was as described in the kit. The purity of the isolated cells was confirmed by flow cytometry of a small sample. These cells were stained with antibodies to CD4 (OT2) or CD8 (OT1) and for Ly 5.1 (surface protein present in lymphocytes of OT mice). The purified CD4 or CD8 T cells were subsequently labelled with CellTrace violet (CTV) dye to allow downstream quantification of cell proliferation. CTV labelling was performed in two steps. First the CTV dye was diluted 100 fold (from 5 mM to 50 µM) with 0.1% BSA in PBS in an eppendorf tube. This solution was then further diluted 10 fold (to 5 µm) at the same time as adding to the cell suspension ($\leq 50 \times 10^6$ cells/ml) in a 10 mL Falcon tube. The tube was sealed and vortexed immediately to allow even distribution of the dye to the cells. The number of OT cells purified and thus labelled were counted using a haemocytometer under the microscope. The cells were then pelleted and resuspended in PBS, pH 7.4 ($10^7$ cells/ml), for administration to the recipient mice.

Oral Ovalbumin Challenge Model (Late Dosing Protocol)

Recipient female C57Bl/6 mice (20-22 g) were administered 50 mg ovalbumin in 0.2 mL of PBS as a single dose, by oral gavage on Day 1. A negative control group received only PBS (the saline "treatment" group). Each mouse was then administered 0.2 ml of the appropriate cell suspension containing $2 \times 10^6$ donor cells, by the tail vein (from above; purified and labelled CD4 or CD8 T cells, obtained from donor OT mice), within 0.5-3 hours of ovalbumin administration. The ovalbumin dosed mice were then divided into four treatment groups and administered different treatments via oral gavage. One group received no additional treatment (OVA treated group), a second received 50 mg/kg parent drug (MPA) as a suspension in 0.2 ml of 0.5% CMC (MPA treatment group), a third received the MPA-2-TG prodrug at a dose equivalent to 50 mg/kg of MPA formulated in a lipid emulsion (MPA-2-TG treatment group) and the fourth received the blank lipid emulsion (blank lipid treatment group) in which the prodrug was administered. The treatments were administered on days 2, 3 and 4, twice a day in the morning and evening. The mice were killed on day 5 and mesenteric lymph nodes (MEN) and peripheral lymph nodes (PEN, including inguinal, brachial, axillary, cervical, iliac) were collected and analyzed by flow cytometry (as below) to assess the proliferation of ovalbumin specific T cells.

Flow Cytometry Analysis

For flow cytometry analysis, cells were isolated from the MEN and PEN and formed into a single cell suspension as described above in PBS buffer containing 2% Foetal Bovine Serum. The cells were then incubated for 20 mins at 4° C. with FITC anti-mouse CD45.1 antibody or FITC anti-mouse TCR Vα2 antibody to label lymphocytes derived from the OT mice (for transgenic mice obtained from WEHI, TCR Vα2 antibody was used, for mice from Bio21 CD45.1 antibody was employed). APC anti-mouse CD8a antibody was used to label CD8 cells and PE anti-mouse CD4 antibody to label CD4 cells. Cells were then washed with buffer. All antibodies were used as per the dilution suggested by the commercial (Biolegend) labelling procedure. Propidium iodide, 10 ng/ml, was added to the cells just prior to flow cytometry analysis to stain for dead cells. Cells that were double positive for CD4/CD8 and CD45.1 (i.e. CD4 or CD8 lymphocytes derived from OT mice) were selected to detect the CTV fluorescence, using the Pacific blue filter (450/50). One million total events were acquired by the flow cytometer (BD Biosciences FACS Canto II analyser, Becton, Dickinson and Company, NJ, USA) and data were analysed using FlowJo software, by Tree Star Inc., Ashland, Oreg., USA.

Example 25: Lymph Transport Study in Beagle Dogs

A modified version of protocols described in Han, S. et al., "Lymphatic Transport and Lymphocyte Targeting of a Triglyceride Mimetic Prodrug Is Enhanced in a Large Animal Model: Studies in Greyhound Dogs," *Mol. Pharm.* 2016, 13 (10), 3351-3361, may be used to perform lymph transport assays of test compounds in beagle dogs. The assay will be performed as follows.

The thoracic lymph duct will be cannulated under surgical anesthesia as previously described (Edwards, et al. *Adv. Drug Delivery Rev.* 2001, 50 (I-2), 45-60.). Following surgery, dogs will be allowed to recover unrestrained in a closed run overnight (12-16 h) and returned to normal ambulatory movement before commencement of the study. In the initial recovery period fluids will be administered IV to ensure adequate hydration and to prevent hypoproteinemia. Water will be also available ad libitum throughout the experiment period. Prior to drug administration, a 20 G intravenous catheter will be inserted into the cephalic vein to enable serial blood sampling and the catheter kept patent by periodic flushing with heparinized saline (1 IU/mL). To limit possible dehydration due to the continuous collection of thoracic lymph, 25 mL of normal saline will be also administered hourly by IV bolus during the sampling period. The dogs will be fasted for 12 h up to 30 min prior to drug administration. For fed state studies, dogs will receive 20 g of high fat dog food (containing ~34% fat), administered by hand, followed by 10 mL water to aid in swallowing, followed by 100 g standard canned dog food (~2.5% fat) 30 min prior to drug administration. Water will be available ad libitum throughout the study for all dogs. Test compounds may be prepared in a suitable formulation such as a long-chain lipid based self-emulsifying drug delivery system (SEDDS) consisting of 30.5% w/w soybean oil, 30.5% w/w Maisine-CC, 31.6% w/w Cremophor EL and 7.4% w/w ethanol. Formulations may be filled into hard gelatin capsules. Compound dissolved in the formulation may be administrated to the fed dog by placing the capsules as far posterior to the pharynx as possible, closing the mouth and rubbing the throat to stimulate swallowing. Subsequently 50 mL of water will be administered orally via a syringe. Lymph will be collected continuously into preweighed 50 mL collection tubes containing 75 mg of disodium EDTA for the duration of the 10 h postdosing period. Individual lymph samples for each half hourly or hourly collection period will be combined, and the mass of lymph collected will be determined gravimetrically. Several 20 and 200 μL aliquots of each lymph sample will be transferred into individual 1.5 mL Eppendorf tubes and stored at −80° C. until analysis of drug concentrations. The remaining lymph from each collection period (half hourly or hourly) will be transferred into 10 mL tubes, which will be centrifuged at 2000 g for 10 min to obtain lymphocyte pellets, which will be stored at −80° C. until analysis of drug concentrations. Systemic blood samples (3 mL) will be taken via the indwelling cephalic vein catheter and placed in individual heparinized tubes (13×75 mm BD Vacutainer, 68 IU). Blood samples will be collected at predose (−5 min) and at 0.5, 1, 1.5, 2, 2.5, 3, 3.5, 4, 5, 6, 8, and 10 h following drug administration. Plasma will be separated by centrifugation and stored at −80° C. prior to analysis.

Example 26: Organ Rejection Drug in Prodrug and Active Drug Formulations

Mycophenolic acid (MPA) is a routine component of immunosuppression regimens following kidney transplantation. Accordingly, the efficacy of lipid prodrugs of mycophenolic acid are assessed in a peripheral antigen challenge model.

Mice are treated with an organ-rejection medication (either MPA or mycophenolate mofetil (MMF)) and the prodrug formulations of the disclosure. The efficacy of these prodrug formulations is compared to MPA or MMF, as appropriate. The prodrugs comprise MPA or MMF conjugated to one of various TG (triglyceride) groups. To determine the immune response, the animals are administered incomplete Freud's adjuvant (IFA). Modification of immune response by IF A caused by MPA or MMF drug is determined by tissue analysis. This experiment is conducted in both mice and rats.

MPA or MMF is administered in active or prodrug formulations orally via oral gavage once daily for 6 days in formulation containing PBS, 0.2% ethanol, 4% oleic acid, and 2.5% Tween 80 (Group 1—MPA 6 mg/animal; Group 2—MPA 2 mg/animal; Group 3—MPA 0.66 mg/animal; Group 4—MPA-TG 6 mg/animal; Group 5—MPA-c10-bMe (or other test prodrug) 6 mg/animal; for all groups n=4). On the same day of the first drug oral gavage, mice or rats are immunized subcutaneously near one or both hocks with up to 25 ug proteins/peptides emulsified in incomplete Freund's adjuvant plus 15 ng monophosphoryl lipid A (25 ul total volume per hock). Mice or rats are placed in a restraining device for less than 5 minutes for hock injection. The monophosphoryl lipid A is localized at the injection site because it is formulated within an emulsion, which mediates the maturation of dendritic cells, which in turn induces the development of effector CD4 T helper 1 and B cells without causing systemic effects. Monophosphoryl A is a de-toxified version of LPS, thus monophosphoryl lipid A will not cause adverse effects.

Animals are observed three times per week after administration of drug and are weighed twice a week. After 6 days, animals are sacrificed and blood, lymph nodes, spleen, and other major organs harvested for flow cytometry, Elispots, Elisas, and snap freezing. In flow cytometry, we will quantify B cells (by CD 19 and B220 co-staining for mice or CD45RA for rats) and T cells (by CD4, CD3, CD25, CD69, CD62L, and/or tetramer co-staining). In Elispots, we will quantify antigen-specific T cells by IFN-g and IE-2 production. In Elisas, antigen-specific antibodies will be quantified. Rats are used when large amounts of tissues are required for analysis.

Example 27: Assessment of Immune System Distribution of Lipid Prodrugs Using BoDiPy -Labeling To determine absorption of the lipid prodrug, oral formulations of a fluorescent agent conjugated to a lipid prodrug are administered with the purpose of visualizing which tissues and immune cells have absorbed the lipid prodrug. Exemplary fluorescent lipid prodrugs are described in PCT/US2018/048624, filed Aug. 29, 2018, which is hereby incorporated by reference in its entirety. Fluorescent lipid prodrugs (BoDiPy) are introduced into mice or rat via oral gavage (Group 1—BoDiPy 0.033 mg/animal; Group 2—BoDiPy-2-TG 0.1 mg/animal; Group 3—naïve; n=2 for all groups). Animals are observed 3×/wk after administration of drug and are weighed twice a week. BoDiPy-2-TG has the following structure:

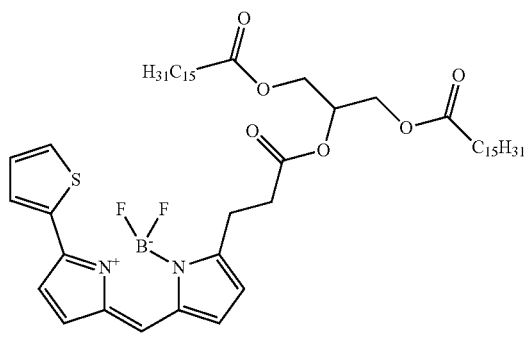

At 9 different timepoints between 5 mins-30 days (5 minutes, 15 minutes, 1 hour, 3 hours, 6 hours, 18 hours, 24 hours, 7 days, 30 days), animals are sacrificed and their major organs/tissues (duodenum, jejunum, ileum, colon, liver, spleen, lung, kidney, bone marrow, heart, and brain), lymph nodes (cervical, inguinal, mesenteric), and blood collected to identify tissues and immune cells (F4/80+ macrophages, Ly6Chi monocytes, CD4+ and CD8+ T cells, CD 19+ B cells, CD45 negative non-hematopoietic, Nkp46+ natural killer cells, CD11c+ dendritic cells, Ly6G+ neutrophils) which have taken up the fluorescent dye over time via flow cytometry. Rats are used to determine whether the distribution is significantly different than mice.

Example 28: Lymph and Blood Absorption of Lipid Prodrugs in Cannulated Animals

To determine the timing of absorption of oral prodrugs into the lymph fluid, terminal surgery is conducted on mice and rats which involves cannulation of the intestine using angiocatheter placement (to emulate oral dosing) and the mesenteric lymph duct. MPA will be used as a control, but MMF may be substituted. Testing of compounds I-16 and I-34 is described, but the procedure is applicable to other lipid prodrugs as well.

Each animal (mouse or rat) receives a mesenteric lymph duct cannula and a duodenal cannula in the same terminal procedure. Animals (Group 1—MPA; Group 2—MPA-TG (lipid prodrug); all groups n=5) are anesthetized and maintained under deep anesthesia throughout the duration of the 6-hour collections period. The doses used for this experiment are matched with the doses used from the two previous examples to compare results between the lymph transport experiments and the experiments mentioned above. Up to 6 mg MPA or lipid prodrug formulated in PBS, 0.2% ethanol, 4% oleic acid, and 2.5% Tween 80 is infused into each animal.

An incision is made on the right side of the animal from the midline to the right flank approximately 2 cm below the ribcage. The superior mesenteric lymph duct is located perpendicular to the right kidney and parallel to the mesenteric artery. Next, a 24-g catheter is inserted into the lymph duct, and the needle removed.

Once the flow of lymph is observed, a drop of tissue glue is applied to secure the catheter in place. The flow of lymph is observed for several minutes to ensure the successful cannulation of the lymph duct. Tubing that has been pre-rinsed with anti-coagulant (heparin) is connected to the catheter via the luer-lock ends. The collection end of the tubing is placed in a collection tube containing anti-coagulant, which is placed on ice throughout the collection period. The collection tube is changed every hour, for a total of 6 samples from each animal.

Following successful cannulation of the mesenteric lymph duct, the duodenum is cannulated to directly infuse MPA or the MPA lipid prodrugs. The duodenum is identified as the bright pink section of the small intestine. A small hole will be made in the duodenum approximately 2 cm below the junction with the stomach using a sterile needle. The cannula will be inserted and secured with tissue glue. Prior to drug infusion, the animals are hydrated with normal saline at a rate of 2.8 mL/hour. Following the recovery/hydration period of 30 minutes (collected lymph during this time could be used as blank lymph for analytical purposes—see below), formulated MPA prodrug or MPA standard is infused into the duodenum via the cannula at a rate of 2.8 mL/hr. Pre-weighed tubes containing anti-coagulant (10 uL of 1000

IU/mL sodium heparin) are used to collect lymph from the cannula. After 1 hour of lymph collection, the weight of the tube is recorded. The collected lymph is then aliquoted into tubes suitable for bioanalysis (20 uL aliquots) and frozen at −80° C. until bioanalysis is performed (see Experimental Procedures below for details regarding lymph processing). Lymph is collected for 6 hours after the infusion of the lipid prodrugs or MPA into the duodenum (6 samples per animal). After the collection period has ended, the animals are sacrificed while still under anesthesia, via thoracotomy. Animals are continuously monitored the entire time that they are under anesthesia (from start to sacrifice).

The main objective of this study is to evaluate the transport of lipid prodrugs into the lymph by cannulating the mesenteric lymph duct, following drug dosing into the duodenum. The amount of free drugs is quantified in the lymph fluid after the MPA prodrugs are delivered via duodenum cannulation. Measurements may also be performed of "total" MPA species (free and various prodrug/hydrolysis forms combined) by a hydrolysis assay, such as that described above in Example 23. Without wishing to be bound by theory, it is believed that the prodrug forms of tacrolimus can transport better/preferentially in the lymph compared to unmodified tacrolimus. See Examples 15 and 16 above for additional procedures to evaluate lymphatic transport of test compounds.

Example 29: Effects of MPA Lipid Prodrugs Administered in an Indomethacin-Induced Crohn's Disease Model in Rats The objective of this study is to determine the efficacy of lipid prodrugs of MPA in a model of Crohn's disease (indomethacin induced intestinal injury) in rats. One injection of indomethacin causes transient gastric injury resulting in inflammation of the small bowel, including sloughing of the epithelium and ulcerations (e.g., as described in Stadnyk et al., "Neutrophil migration into indomethacin induced rat small intestinal injury is CD11a/CD18 and CD11b/CD18 co-dependent," *Gut* 2002; 50:629-635; Okayama et al., "Mast cells are involved in the pathogenesis of indomethacin-induced rat enteritis," *J Gastroenterol* 2009; 44 [Suppl XIX]: 35-39). MPA will be used as a control, but MMF may be substituted. Testing of compounds I-16 and I-34 is described, but the procedure is applicable to other lipid prodrugs as well.

On study day −3, rats are weighed and randomized into treatment groups based on body weight as shown in Table 4 and on study day 0, treatments are initiated and continue as indicated in Table 4. Also, on study day 0, rats are briefly anesthetized, shoulders shaved and rats receive a subcutaneous injection of indomethacin (9 mg/kg, 1 ml/kg) in 5% sodium bicarbonate (sterile water). On study day 1, rats receive a second subcutaneous injection of indomethacin (8 mg/kg, 1 ml/kg) in 5% sodium bicarbonate (sterile water). Bodyweight is monitored daily throughout the study.

TABLE 4

Study Group Designations

| Group | N | Disease | Treatment | Dose Level (mg/kg) | Dose Route | Regimen[1] | Dosing Days | Dose Vol (ml/kg)[2] | Dose Conc (mg/ml) |
|---|---|---|---|---|---|---|---|---|---|
| 1 | 5 | N | Normal | N/A | PO | QD | D0-3 | 5 | N/A |
| 2 | 10 | Y | Vehicle | N/A | PO | QD | D0-3 | 5 | N/A |
| 3 | 10 | Y | Dexamethasone | 0.1 | PO | QD | D0-3 | 5 | 0.02 |
| 4 | 10 | Y | MPA | 1 | PO | QD | D0-3 | 5 | 0.2 |
| 5 | 10 | Y | MPA | 0.33 | PO | QD | D0-3 | 5 | 0.066 |
| 6 | 10 | Y | MPA | 0.11 | PO | QD | D0-3 | 5 | 0.022 |
| 7 | 10 | Y | MPA-2-TG (I-34) | 0.66 | PO | QD | D0-3 | 5 | 0.132 |
| 8 | 10 | Y | MPA—(O—C10bMe-2-TG)—OMe (I-16) | 0.99 | PO | QD | D0-3 | 5 | 0.198 |
| 9 | 10 | Y | MPA-2-TG (I-34) | 0.66 | PO | BID | D0-3 | 5 | 0.132 |
| 10 | 10 | Y | MPA—(O—C10bMe-2-TG)—OMe (I-16) | 0.99 | PO | BID | D0-3 | 5 | 0.198 |

[1]QD dosing to occur at approximately 24 hr intervals.
BID dosing to occur at approximately 10-12 hr intervals.
[2]The doses of test item to be administered is calculated daily in mg/kg based on the latest body weight of the animal On study day 4, animals are anesthetized with isoflurane and bled to exsanguination followed by bilateral pneumothorax. A section of the small intestine is removed and weighed. At necropsy, the small intestine is evaluated visually and given a gross score according to the following criteria 0=Normal; 0.5=Very Minimal thickening, multifocal in area at risk; 1=Minimal thickening, fairly diffuse in area at risk; 2=Mild to moderate small intestinal/mesenteric thickening throughout area at risk; 3=Moderate thickening with 1 or more definite adhesions that would be easy to separate; 4=Marked thickening with numerous hard to separate adhesions; 5=Severe intestinal lesion resulting in death.

Samples of the small intestine are prepared for histology (IHC). Plasma is collected (anticoagulant $K_2EDTA$) and stored at −80° C. Tissue samples (Mesenteric lymph nodes (collected each in order, individually into separate cryovials), spleen, brain, liver, kidney, lung, colon from cecum to anus, cecum, inguinal lymph nodes, cervical lymph nodes, and axillary lymph nodes) are collected and snap frozen into separately labeled cryovials for the quantification of drugs by bioanalysis methods. Overall efficacy of MPA and MPA lipid prodrugs is based on body weight, small intestine weight (10 cm), small intestine gross score, and optionally histopathology.

Example 30: Study to Assess the Efficacy of Lipid Prodrugs in a Model of Adoptive Transfer Colitis The objective of this study is to test multiple lipid prodrugs of MPA (at multiple doses) in the modification of colitis induced by adoptive cell transfer of naïve T cells (CD44−/CD62L+) from C57Bl/6 donors into RAG2−/− recipients. MPA will be used as a control, but MMF may be substituted. Testing of compounds I-16 and I-34 is described, but the procedure is applicable to other lipid prodrugs as well.

Colitis is induced on Day 0 in male RAG2−/− mice by IP injection of CD44−/CD62L+ T cells isolated and purified from C57Bl/6 recipients. Group 1 animals do not receive a cell transfer and remain as the naïve control group. Group 2 animals receive $0.5 \times 10^6$ memory cells (the CD44+ labeled cell fraction from the magnetic separation) and serve as an additional negative control group. All other Groups (3-11) receive $0.5 \times 10^6$ naïve TH cells.

Donor cells are processed as follows. Spleens are harvested from C57Bl/6 mice and processed/sorted using Miltenyi MACS columns. All recipient mice are weighed daily and assessed visually for the presence of diarrhea and/or bloody stool. Cages are changed every two weeks, with care taken to capture V4 of dirty cage material for transfer to the new cage.

On Day 13, blood is collected via RO eye bleed in cohorts of animals from Groups 3-10 at 1, 2, and 4 hours post MPA/MPA lipid prodrug dose. The PK bleeds occur in Groups 3-10 as follows. In each group, animals 1-4 are bled 1 hour after the MPA/MPA lipid prodrug dose, animals 5-8 are bled 2 hours after the MPA/MPA lipid prodrug dose, and animals 9-13 are bled 4 hours after the lipid prodrug dose. For group 10, the PK time points occur following the first dose of MPA/MPA lipid prodrug. The whole blood is centrifuged, and plasma is frozen at −80° C. for potential downstream analysis. The pelleted cells are used to determine the presence of T cells by FACS analysis of CD45+/CD4+ events (engraftment check). All animals from Groups 1 and 2 are also bled for an engraftment check on Day 13.

Treatment with lipid prodrugs begins for all groups except Group 6 on Day 0 and continues through Day 42 as is outlined in Table 5. In Group 6, MPA/MPA lipid prodrug dosing begins on Day 13 and continues through Day 42. The animals in Groups 1 and 2 are not treated. Test MPA/MPA lipid prodrug are administered once per day (QD) via oral gavage (PO), or twice per day (BID) as in Group 10. There are at least 6 hours in between MPA/MPA lipid prodrug doses for Group 10. The animals in Group 3 receive an appropriate vehicle QD at an equivalent volume as the other treatment groups. MPA is administered to groups 4-5 and 7 at 6, 2, 0.66 mg per dose, respectively. Group 6 receives MPA at a dose of 2 mg daily. Groups 8 and 10 receive MPA-2-TG (compound I-34) at 4.02 mg per dose, with Group 10 receiving two doses per day. Lastly, Group 9 receives MPA-(O-C10bMe-2-TG)-OMe (compound I-16) at a dose of 5 mg daily.

TABLE 5

Study Dosing Outline

| Group | No. Animals | T Cell Transfer | Treatment | Dose and Route | Dose Schedule |
|---|---|---|---|---|---|
| 1 | 6 | — | — | — | — |
| 2 | 8 | $0.5 \times 10^6$ memory $T_H$ cells | — | — | — |
| 3 | 13 | $0.5 \times 10^6$ naïve $T_H$ | Vehicle | — PO | QD Days 0-42 |
| 4 | 13 | cells | MPA | 1 mg/kg PO | QD Days 0-42 |
| 5 | 13 | | MPA | 0.33 mg/kg PO | QD Days 0-42 |
| 6 | 13 | | MPA | 0.33 mg/kg PO | QD Days 13-42 |
| 7 | 13 | | MPA | 0.11 mg/kg PO | QD Days 0-42 |
| 8 | 13 | | MPA-2-TG (I-34) | 0.66 mg/kg PO | QD Days 0-42 |
| 9 | 13 | | MPA-(O-C10bMe-2-TG)-OMe (I-16) | 0.99 mg/kg PO | QD Days 0-42 |
| 10 | 13 | | MPA-2-TG (I-34) | 0.66 mg/kg PO | BID Days 0-42 |
| 11 | 13 | | MPA-(O-C10bMe-2-TG)-OMe (I-16) | 0.99 mg/kg PO | BID Days 0-42 |

Mice undergo HD video endoscopy on Days 14, 28, and 40 to assess colitis severity. Each mouse undergoes video endoscopy on Days 14, 28, and 40 using a small animal endoscope (Karl Storz Endoskope, Germany), under isoflurane anesthesia. During each endoscopic procedure, still images as well as video are recorded to evaluate the extent of colitis and the response to treatment. Additionally, an image from each animal at the most severe region of disease identified during endoscopy is captured. Colitis severity is scored using a 0-4 scale (0=normal; 1=loss of vascularity; 2=loss of vascularity and friability; 3=friability and erosions; 4=ulcerations and bleeding). Additionally, stool consistency will be scored during endoscopy using the following parameters: 0=normal, well-formed pellet; 1=loose stool, soft, staying in shape; 2=loose stool, abnormal form with excess moisture; 3=watery or diarrhea; 4=bloody diarrhea.

Animals are observed daily (weight, morbidity, survival, presence of diarrhea and/or bloody stool) in order to assess possible differences among treatment groups and/or possible toxicity resulting from the treatments.

On day 35, three (3) animals from group 2-10 are sacrificed via $CO_2$ inhalation for tissue collection. Whole blood is collected into $K^{2+}$EDTA tubes and centrifuged to collect plasma. The cell pellet is washed and stored in a media (DMEM+5% FBS+1% anti-anti) on ice. The cell pellet is used for FACS analysis. The following fresh tissues are collected into media and placed on ice: colon (entire colon from cecum to anus), mesenteric lymph nodes, Peyer's patches, and spleen. The fresh tissues are also used for FACS analysis. For FACs analyses of blood and tissues, the frequency of IFN-gamma, IL-17A, IL-17F, CD25, CD69, CD62L CD4 T cells will be quantified. In addition, the following tissues are collected, weighed, and snap frozen: brain, liver, kidney (both), lungs, small intestine (whole), heart, and cervical+submandibular lymph nodes (axillary and brachial can be taken if cervical and submandibular cannot be located).

On Day 42, the remaining animals are sacrificed as described above. Terminal blood is collected via cardiac puncture, processed for plasma, and stored at −80° C. for potential downstream analysis or shipment to study sponsor. The cell pellet from the blood is handled as stated above.

The colon is excised, rinsed, measured, weighed, and then placed in 10% neutral buffered formalin for 24 hours. Tissues are then moved to 70% ethanol for storage until histopathology is performed (H&E, whole colon swiss roll). The spleen and mesenteric lymph nodes from all remaining animals are collected fresh and stored in media on ice and are used for FACS analysis. For FACs analyses, the frequency of IFN-gamma, IL-17A, IL-17F, CD25, CD69, CD62L CD4 T cells will be quantified. In addition, the following tissues are collected, weighed, and snap frozen: brain, liver, kidney (both), lungs, small intestine (whole), heart, and cervical+submandibular lymph nodes (axillary or brachial can be taken if cervical and submandibular cannot be located). All plasma and snap frozen tissue are stored at −80° C.

Groups 4-10 are tested for efficacy of the treatment arms using a one-way ANOVA comparing all groups to the vehicle-treated group 2 animals. Non-parametric tests are used for endoscopy and stool scores, and the appropriate post hoc tests are applied.

Example 31: Heart Transplantation Study to Assess Ability to Prevent Organ Rejection Rat heterotopic heart transplants are the basis of organ transplant and immunology studies. The ability of MPA lipid prodrugs to prevent organ rejection as compared to unmodified MPA is assessed in a rat heterotopic heart transplants.

Rat strains are selected to create an animal model where the recipient rat predictably rejects the heart after about 2 weeks without any therapeutic immunosuppressant drugs (e.g., Brown Norway=Donor; Lewis rat=Recipient). For the study, 4 recipient rats and 4 donor rats per group are required (Group 1: saline; Group 2: cyclosporine; Group 3: MPA; Group 4: 1-34 (MPA-2-TG); Group 5:1-16 (MPA-(O-C10bMe-2-TG)-OMe)).

To remove the hearts from the donor rat, the chest cavity and pericardial sac is opened with scissors to expose the heart. The inferior vena cava (IVC) is dissected and a loose silk suture is placed around the IVC adjacent to its insertion into the right atrium. Injections (5×2 mL) of 4° C. heparinized saline or lactated ringers (100-200 u/cc) are injected into the IVC and equal amounts of blood allowed to drain. The IVC is then ligated by tying off the silk suture. The right superior vena cava (rSVC) is isolated in a similar fashion and ligated with silk suture. This is repeated to isolate and ligate the left superior vena cava (lSVC) and expose the left pulmonary artery. The heart is secured with wet gauze. The aortic arch and pulmonary artery trunk is bluntly dissected from surrounding tissues. This section of the aortic arch forms the arterial cuff for the implant process.

To implant the heart into the recipient, a silk suture is placed around the base of the heart and tied. The heart is then cut free at the base and placed in 4° C. saline. A 7 cm midline vertical abdominal incision is made through skin, abdominal muscle, and peritoneum to enter the abdominal cavity. The intestines are retracted to the left outside the abdominal cavity and preserved with saline soaked gauze. The abdominal aorta and inferior vena cava (IVC) are isolated below the renal vessels and 4-0 cotton ties are placed around the aorta and IVC superior. The large vessels (abdominal aorta to the left of midline and IVC to the right of midline) are dissected from the surrounding tissue using a cotton tip or fine pick-up forceps. The veins, usually 1 or 2 iliolumbar veins, are exposed and cauterized or tied with 5-0 to 7-0 silk sutures. Vascular micro-clamps are placed distally, then proximally, on the abdominal aorta and IVC, isolating a 1-1.5 cm segment of the vessels between the clamps. The aorta is punctured close to the distal clamps using a 25-gauge needle to release the blood. Extra-fine scissors are used to perform an arteriotomy about 4 mm long. The lumen is washed with heparinized lactated Ringer solution (100-200u/ml). The donor heart is placed on the field for end-to-side anastomosis. The organ is positioned with the apex toward the tail and the aorta above the pulmonary artery. The aortic anastomosis is performed by placing an anchor stitch in the proximal end of the arteriotomy (out-in) on the abdominal aorta, then an in-out stitch on the graft aorta, and is secured using a triple knot. A second (out-in) anchor suture is placed on the opposite side of the first stitch in-out to the distal end of the arteriotomy. After placing the second anchor suture, a continuous suture (5-6 stitches) is run on the anterior wall from the proximal end toward the distal end of the arteriotomy. The heart graft is repositioned by flipping it over to expose the posterior wall. The anastomosis is completed using a continuous running suture. The graft is flipped again to expose the anterior wall of the graft where the pulmonary artery is collapsed above the aorta. An opening 5 to 7 mm long is made in the recipient IVC using scissors, and the lumen is flushed with heparinized LRS to remove any thrombus. The IVC opening is larger (5-6 mm long) than the aortic opening to fit the pulmonary artery. An out-in stitch is placed on the distal end of the pulmonary artery and in-out on the distal margin of the IVC opening. A continuous suture is run along the posterior wall of the pulmonary artery-IVC first, then along the anterior wall. Before releasing the microvascular clamps, the suture line is carefully checked for a loose stitch. The distal clamp is released first, and 30 seconds later, the proximal clamp. Spontaneous heart contractions occur seconds after reperfusion of the graft. Total ischemia time for a successful operation will range from 45 minutes to 2 hours. The intestines are reinserted into the abdomen, averting torsion. The incision is closed in 2 layers with absorbable suture in a continuous pattern. Skin is closed with absorbable suture in a subcuticular pattern or with non-absorbable suture in an interrupted or continuous pattern.

Once heart transplants are completed, the beating heart is palpated through the abdomen of the recipient rat. Additionally, ultrasound imaging is used to examine the donor heartbeat.

Recipient rats are injected with the established anti-organ rejection medication (MPA) or administered a test lipid prodrug compound. Mice are weighed and separated into groups as follows: Group 1: Saline (control vehicle; 0.9% saline or lactated ringer's solution (LRS)); Group 2: Cyclosporine Injectable; Group 3: tacrolimus injectable; Group 4: Prodrug 1 oral; Group 5 Prodrug 2 oral. The dose of tacrolimus will be between 0.1 mg/kg and 1 mg/kg since that has been published to be potent (See Jeong, J.-H. et al., "Dose optimization of tacrolimus for improving survival time of PEGylated islets in a rat-to-mouse xenograft model," December 2016, Volume 24, Issue 12, pp 1047-1054). Animals are checked 3 times a day for 3 days post-operatively. Weights are taken prior to surgery and again once a week or more often if signs of decline. Donor heartbeats are palpated in recipients daily. The donor heart stops beating once it is rejected. Rejections/cessation of palpable beating of donor heart are used as an experimental endpoint. Endpoints occur around 2 weeks without treatment/control and up to 12 weeks with treatment. Additional tissue analyses and histology is performed on donor and recipient organs post-mortem to evaluate for extent of inflammation.

Example 32: Effects of Lipid Prodrugs of MPA Administered in an MOG-Induced EAE Model The objective of this study is to determine the efficacy of lipid prodrugs of MPA in a model of multiple sclerosis in mice. Experimental autoimmune encephalomyelitis (EAE) in mice is a model commonly used to model of CNS inflammatory autoimmune disease. To determine the potential utility of the prodrugs described herein in the treatment of multiple sclerosis, the efficacy of the compounds was assessed in a mouse model of MOG-induced experimental autoimmune encephalomyelitis (EAE) was assessed. MPA will be used as a control, but MMF may be substituted. Testing of compounds I-16 and I-34 is described, but the procedure is applicable to other lipid prodrugs as well.

Experimental autoimmune encephalomyelitis (EAE) can be induced in C57BL/6 mice by immunization with the peptide corresponding to the immunodominant epitope of MOG (MOG35-55) (as described in Miller et al., Experimental Autoimmune Encephalomyelitis in the Mouse; Curr Protoc Immunol. 2007 May; CHAPTER: Unit-15.1, the contents of which is herein incorporated by reference in its entirety). The model further requires the administration of pertussis toxin.

Briefly, for active induction of EAE in C57BL/, 0.1 ml emulsion or MOG35-55 (200 µg) and complete Freund's Adjuvant are injected subcutaneously in the shaved backs of the mice, distributed over three sites (midline of the back between the shoulders, and either side of the midline on the lower back). On day 0 and day 2, 200 ng pertussis toxin is injected i.p. Mice are separated into groups as described in Table 6, and monitored every other day for the development of clinical symptoms. EAE scoring is conducted on days 4-35 as follows: 0—normal mouse; no overt signs of disease; 1—limp tail or hind limb weakness but not both; 2—limp tail and hind limb weakness; 3—partial hind limb paralysis; 4—complete hind limb paralysis; 5—Moribund state; death by EAE: sacrifice for humane reasons.

On Day 13, plasma for pharmacokinetics studies is collected. For mouse 1-3 of each group, plasma is collected 1 hour after dose, for mouse 4-6, plasma is collected 2 hours after dose, and for mouse 7-10, plasma is collected 6 hours after dose. On Day 31, whole blood, spleen, mesenteric lymph nodes, and CNS draining lymph nodes are harvested for FACS. For FACs analyses, the frequency of IFN-gamma, IL-17A, IL-17F, CD25, CD69, and CD62L CD4 T cells will be quantified. Day 31, tissue is collected for IHC Spinal Cord, and mice are scored for EAE and survival. Body weight is monitored daily.

Example 33: Effects of Lipid Prodrug Administered in an Asthma Model

The innate immune system plays a key role in asthma development. The efficacy of lipid prodrugs are compared to unmodified MPA in an asthma model in mice.

Mice do not develop asthma spontaneously, ergo, in animal models asthma is induced in the airways, for example by ovalbumin (OVA) and other aeroallergens.

A mouse model of ovalbumin sensitization and challenges is used (as described in Pie et al., Natural Killer Cells Accumulate in Lung-Draining Lymph Nodes and Regulate Airway Eosinophilia in a Murine Model of Asthma; Blackwell Publishing Ltd. Scandinavian Journal of Immunology 72, 118-127) to assess the potential of MPA prodrugs described herein in the treatment of asthma. MPA will be used as a control, but MMF may be substituted. Testing of compounds I-16 and I-34 is described, but the procedure is applicable to other lipid prodrugs as well.

Seven-week-old female BALB/cByJ mice are separated into groups as described in Table 7, maintained on OVA-free diet, and then are sensitized by i.p injection of 20 ug OVA (Grade V; Sigma-Aldrich, St. Louis, Mo., USA) emulsified in 100 µL of aluminum hydroxide (adjuvant) on days 0 and 10 and challenged with OVA (in 2% in Phosphate Buffered Saline (PBS)) by aerosol on days 20, 21 and 22 (as described in Barrier et al., Natural Killer Cells Accumulate in Lung-Draining Lymph Nodes and Regulate Airway Eosinophilia in a Murine Model of Asthma; Scandinavian Journal of

TABLE 6

Study Dosing Regimen

| Group | No. Animals | MOG SC Day 0 | PTX IP Days 0 and 2 | EAE Scoring | Treatment | Dose | Schedule (QD or BID) |
|---|---|---|---|---|---|---|---|
| 1 | 5 | — | — | Days 4-35 | — | — | — |
| 2 | 15 | 400 µg | 200 ng | | vehicle | — | Days 0-31 |
| 3 | 10 | | | | MPA | 1 mg/kg | Days 0-31 QD |
| 4 | 10 | | | | | 0.33 mg/kg | Days 14-31 QD |
| 5 | 10 | | | | | | Days 0-31 QD |
| 6 | 10 | | | | | 0.11 mg/kg | Days 0-31 QD |
| 7 | 10 | | | | MPA-2-TG (I-34) | 0.66 mg/animal | Days 0-31 QD |
| 8 | 10 | | | | MPA—O—C10bMe-2-TG—OMe (I-16) (I-16) | 0.99 mg/animal | Days 0-31 QD |
| 9 | 10 | | | | FTY720* | 3 mg/kg | Days 0-31 QD |

*Fingolimod, a positive control that shows efficacy in multiple sclerosis.

Immunology 72, 118-127). The aerosol administrations are performed for 20 min using an ultrasonic nebulizer. I.p. injection of PBS emulsified in 100 µL of aluminum hydroxide and subsequent challenge by PBS aerosols is used as a control for the induction of asthma.

TABLE 7

Study Dosing Outline

| Group | No. Animals | Injection | Aerosol | Treatment | Dose and Route | Dose Schedule |
|---|---|---|---|---|---|---|
| 1 | 8 | Day 0 PBS in in 100 µL of aluminum hydroxide | PBS on days 20, 21 and 22 | — | — | — |
| 2 | 16 | Day 0 20 ug OVA in 100 ul of aluminum hydroxide | OVA [2% in Phosphate Buffer Saline (PBS)] on days 20, 21 and 22 | Vehicle | — PO | QD Days 19-24 |
| 3 | 16 | | | MPA | 1 mg/kg PO | QD Days 1-24 |
| 4 | 16 | | | MPA | 0.33 mg/kg PO | QD Days 1-24 |
| 5 | 16 | | | | 0.33 mg/kg | BID Days 1-24 |
| 6 | 16 | | | MPA | 0.11 mg/kg | QD Days 1-24 |
| 7 | 16 | | | MPA-2-TG (I-34) | 2 mg/kg PO | QD Days 1-24 |
| 8 | 16 | | | MPA-2-TG (I-34) | 0.66 mg/kg PO | QD Days 1-24 |
| 9 | 16 | | | MPA-2-TG (I-34) | 0.22 mg/kg PO | QD Days 1-24 |
| 10 | 16 | | | MPA—(O—C10bMe-2-TG)—OMe (I-16) | 2 mg/kg PO | QD Days 1-24 |
| 11 | 16 | | | MPA—(O—C10bMe-2-TG)—OMe (I-16) | 0.66 mg/kg PO | QD Days 1-24 |
| 12 | 16 | | | MPA—(O—C10bMe-2-TG)—OMe (I-16) | 0.22 mg/kg PO | QD Days 1-24 |

Before Day 0 and at various times post OVA challenge (24, 48, 72 h or 7 days), lungs, lung-draining mediastinal lymph nodes (MLN), blood, bone marrow and spleen are harvested and cells are isolated described in Pie et al. using 4 mice per group at each time point. Flow cytometry and/or Elispots is performed on cells isolated from lung and lung-draining mediastinal lymph nodes to assess immune cell infiltration and composition and inflammatory status. For Elispot, IL-4 producing Ova-specific CD4 T cells will be quantified. For Facs, we will quantify CD25, CD69, CD44, CD62L CD4 T cells. Forty-eight hours after the last OVA challenge on day 24, lung resistance is measured as described in Pie et al, and immediately thereafter, lungs are washed via the tracheal cannula with 1 mL of PBS and immune cells within the wash are counted and analyzed using hematological procedures. Levels of OVA-specific serum IgG1 and IgG2a is measured by ELISA as described by Pie et al. at the various harvest time points throughout the study.

Example 34: Effects of Lipid Prodrugs Administered in a Celiac Disease Model

The objective of this study is to determine the efficacy of the lipid prodrugs of the disclosure in a model of celiac disease in mice. When gliadin sensitized CD4+CD25− T cell fractions are adoptively transferred into lymphopenic Rag −/− mice, Rag1−/− recipients challenged with gluten suffer from duodenitis, show deterioration of mucosal histological features characteristic of celiac disease, and have increased Th1/Th17 cell polarization in the duodenum and the periphery (as described in Freitag et al., Gliadin-primed CD4+CD45RBlowCD25− T cells drive gluten dependent small intestinal damage after adoptive transfer into lymphopenic mice; Gut. 2009 December; 58(12): 1597-1605). These symptoms can be reversed when the mice are put on a gluten free diet. MPA will be used as a control, but MMF may be substituted. Testing of compounds I-16 and I-34 is described, but the procedure is applicable to other lipid prodrugs as well.

To assess the effect of MPA lipid prodrugs as compared to MPA in this model, male C57BL/6 donor mice are maintained on a gluten-free standardized diet from birth (AIN-76A, Research Diets). Mice are immunized at the tail base on day −28 (100 µg antigen in CFA) and day −14 (50 µg antigen in IF A) with gliadin or ovalbumin (all Sigma) and sacrificed on day 1. Rag1−/− (Jackson Laboratory) are kept in autoclaved cages and changed to irradiated AIN-76A on day −7. On day 1, groups of weight-matched male Rag1−/− (7-9 weeks of age) recipient mice are injected intraperitoneally with $0.45 \times 10^6$ fractionated donor splenic donor TH cells. Detailed study design is shown in Table 8.

TABLE 8

Study Design

| Group | No. RAG-/- | T Cell Transfer | Treatment | Dose and Route | Dose Schedule |
|---|---|---|---|---|---|
| 1 | 5 | None | — | — PO | QD Days 1-56 |
| 2 | 10 | $0.45 \times 10^6$ donor $T_H$ cells | Gluten-free diet | 1 mg/kg PO | QD Days 1-56 |
| 3 | 10 | | Vehicle | 0.33 mg/kg PO | QD Days 1-56 |
| 4 | 10 | | MPA | 0.33 mg/kg PO | QD Days 30-56 |
| 5 | 10 | | MPA | 0.11 mg/kg PO | QD Days 1-56 |
| 6 | 10 | | MPA | 0.66 mg/kg PO | QD Days 1-56 |
| 7 | 10 | | MPA | 0.66 mg/kg PO | BID Days 1-56 |
| 8 | 10 | | MPA-2-TG (I-34) | 0.99 mg/kg PO | QD days 1-56 |
| 9 | 10 | | MPA-2-TG (I-34) | — PO | QD Days 1-56 |
| 10 | 10 | | MPA-(O-C10bMe-2-TG)-OMe (I-16) | 1 mg/kg PO | QD Days 1-56 |

On Day 15 and Day 30 of the study, plasma is collected from groups 3-7 according to the following scheme: animals 1-3: plasma is collected 1 hr post drug dosing; animals 4-6: plasma is collected 2 hrs post TA dose; animals 7-10: plasma is collected 4 hrs post TA dose for FACS analysis.

On Day 56 of the study, survival and body weight is assessed; from the collected tissue, duodenitis is scored and histology analyzed. The following tissues are collected: mesenteric lymph nodes (collected each in order, individually placed into separate cryovials), spleen, brain, liver, kidneys, lungs, heart, colon from cecum to anus, cecum, inguinal lymph nodes, cervical lymph nodes, and axillary lymph nodes. FACS analysis is performed (from 3 mice per group) with spleen and mesenteric lymph node tissue to assess Th1/Th17 polarization. ELISAs are performed on plasma from the cardiac puncture to assess levels of inflammatory markers, e.g., IFN-g, IL-4, IL-10, and IL-17.

Example 35: Effects of Lipid Prodrugs Administered on a Model of Rheumatoid Arthritis The objective of this study is to determine the efficacy of the lipid prodrugs of the disclosure in a model of rheumatoid arthritis in mice. The collagen-induced arthritis (CIA) mouse model a common autoimmune model of rheumatoid arthritis. MPA will be used as a control, but MMF may be substituted. Testing of compounds I-16 and I-34 is described, but the procedure is applicable to other lipid prodrugs as well.

Collagen induced arthritis is induced as described in Brand et al., Collagen-induced arthritis; Nature Protocols, Vol. 2; No. 5, 2007). On day 1, a 50 ml volume of emulsion with complete Freund's adjuvant and CII collagen 1:1 is injected intradermally (i.d.) into the tail 1.5 cm distal from the base of the tail of groups of weight-matched DBA/1 mice, grouped according to Table 9. A secondary immunization is performed 14 days after the primary immunization to ensure induction of a high incidence of CIA. The same concentration of CII is used as for the primary immunization; however, CII is emulsified in incomplete Freund's adjuvant for this immunization. Arthritis incidence is monitored for 5-8 weeks; Animals are evaluated two to three times per week for arthritis incidence. Each paw is evaluated and scored individually on a scale of 0-4 as follows three times weekly: 0—No evidence of erythema and swelling; 1—Erythema and mild swelling confined to the tarsals or ankle Joint; 2—Erythema and mild swelling extending from the ankle to the tarsals; 3—Erythema and moderate swelling extending from the ankle to metatarsal joints; 4—Erythema and severe swelling encompass the ankle, foot and digits, or ankylosis of the limb. In addition to the severity and incidence of arthritis, the autoimmune response to CII is also evaluated by measuring CH-specific T-cell proliferative responses in vitro or by measuring the quantity of the CH-specific antibody in the sera of the mice at multiple time points, e.g., at 3, 5 and 8 weeks. Detailed study design is shown in Table 9.

TABLE 9

Study Design

| Group | No. DBA/1 | Immunization and booster | Treatment | Dose and Route | Dose Schedule |
|---|---|---|---|---|---|
| 1 | 5 | CFA day 0 and IFA day 14 | — | — | — |
| 2 | 10 | CFA plus CII day 0 and IFA plus CII day 14 | — | — | — |
| 3 | 10 | CFA plus CII day 0 and IFA plus CII day 14 | Vehicle | — PO | QD Days 1-56 |
| 4 | 10 | CFA plus CII day 0 and IFA plus CII day 14 | MPA | 1 mg/kg PO | QD Days 1-56 |
| 5 | 10 | CFA plus CII day 0 and IFA plus CII day 14 | MPA | 0.33 mg/kg PO | QD Days 1-56 |
| 6 | 10 | CFA plus CII day 0 and IFA plus CII day 14 | MPA | 0.11 mg/kg PO | QD Days 1-56 |
| 7 | 10 | CFA plus CII day 0 and IFA plus CII day 14 | MPA | 0.33 mg/kg PO | QD Days 30-56 |
| 8 | 10 | CFA plus CII day 0 and IFA plus CII day 14 | MPA-2-TG (I-34) | 0.66 mg per dose PO | QD Days 1-56 |
| 9 | 10 | CFA plus CII day 0 and IFA plus CII day 14 | MPA-2-TG (I-34) | 0.66 mg per dose PO | BID Days 1-56 |
| 10 | 10 | CFA day 0 and IFA day 14 | MPA-(O-C10bMe-2-TG)-OMe (I-16) | 0.99 mg per dose PO | QD days 1-56 |

Example 36: Effects of Lipid Prodrugs Administered in Acute and Chronic Models of TNBS- and DSS-Induced Colitis Oral administration of the sulfated polysaccharide DSS to mice via drinking water induces severe colitis characterized by weight loss, bloody diarrhea, ulcer formation, loss of epithelial cells and infiltrations with neutrophils, resembling some features of flares in human ulcerative colitis (UC). The efficacy and potential benefits of lipid prodrugs over unlipidated MPA are assessed in acute and chronic models of colitis. MPA will be used as a control, but MMF may be substituted. Testing of compounds I-16 and I-34 is described, but the procedure is applicable to other lipid prodrugs as well.

Acute colitis: Acute colitis is induced essentially as described in Wirtz et al., "Chemically induced mouse models of acute and chronic intestinal inflammation," *Nature Protocols*, Vol. 12 No. 7, 2017, p. 1295-1309. In brief, on day 0, mice are weighed and separated into groups (n=8) as described in Table 10. To induce colitis, on day 0, Balb/c mice are desensitized to TNBS by 150 μl of 1% (wt/vol) TNBS presensitization solution (or no TNBS solution as control) to the shaved skin area. On day 8, mice are weighed, anesthetized and colitis is induced in each mouse by rectal perfusion with 100 ul 2.5% (wt/vol) TNBS solution. A heating lamp is positioned ~20 cm distant from the cage to keep the animal warm. At the time points of choice (i.e., day 1, 2 or 3 post intrarectal TNBS administration), in vivo imaging of inflammatory activity or mini-endoscopy is performed for noninvasive imaging to determine levels of inflammation. Plasma for pharmacokinetics studies is collected. For mouse 1-3 of each group, plasma is collected 1 hour after dose, for mouse 4-6, plasma is collected 2 hours after dose, and for mouse 7-10, plasma is collected 6 hours after dose. On day 12, spleen, brain, liver, kidney, lung, colon from cecum to anus, cecum, inguinal lymph nodes, cervical lymph nodes, and axillary lymph nodes) are collected and snap frozen into separately labeled cryovials for drug quantification by bioanalysis. At the endpoint on day 12, enzyme-linked immunosorbent assay (ELISA) is used to determine the serum levels of TNF-α, IL-10, IL-1β, IFN-γ, IL-12 and IL-6 in mice according to the manufacturer's instructions (Biolegend). FACS analysis is performed to analyze immune cells and for the presence of inflammatory markers. Colons are fixed, sectioned, and stained with hematoxylin/eosin; inflammation is graded from 0 to 4 as described elsewhere.

TABLE 10

Study Design

| Group | BALB/c | Presensitization | Colitis induction | Treatment | Dose and Route | Dose Schedule |
|---|---|---|---|---|---|---|
| 1 | 3 | 150 μl of 1% (wt/vol) TNBS presensitization solution without TNBS | None | — | — | — |
| 2 | 10 | 150 μl of 1% (wt/vol) TNBS presensitization solution | 100 ul 2.5% (wt/vol) TNBS | Vehicle | — | — |
| 3 | 10 | 150 μl of 1% (wt/vol) TNBS presensitization solution | 100 ul 2.5% (wt/vol) TNBS | MPA | 1 mg per kg PO | QD Days 1-12 |
| 4 | 10 | 150 μl of 1% (wt/vol) TNBS presensitization solution | 100 ul 2.5% (wt/vol) TNBS | MPA | 0.33 mg per kg PO | QD Days 1-12 |
| 5 | 10 | 150 μl of 1% (wt/vol) TNBS presensitization solution | 100 ul 2.5% (wt/vol) TNBS | MPA | 0.11 mg per kg PO | QD Days 1-12 |
| 6 | | 150 μl of 1% (wt/vol) TNBS presensitization solution | 100 ul 2.5% (wt/vol) TNBS | MPA-2-TG (I-34) | 2 mg per kg PO | QD Days 1-12 |
| 7 | | 150 μl of 1% (wt/vol) TNBS presensitization solution | 100 ul 2.5% (wt/vol) TNBS | MPA-2-TG (I-34) | 0.66 mg per kg PO | QD Days 1-12 |
| 8 | 10 | 150 μl of 1% (wt/vol) TNBS presensitization solution | 100 ul 2.5% (wt/vol) TNBS | MPA-2-TG (I-34) | 0.22 mg per kg PO | QD Days 1-12 |
| 9 | 10 | 150 μl of 1% (wt/vol) TNBS presensitization solution | 100 ul 2.5% (wt/vol) TNBS | MPA-2-TG (I-34) | 0.66 mg per kg PO | BIG Days 1-12 |
| 10 | 10 | 150 μl of 1% (wt/vol) TNBS presensitization solution | 100 ul 2.5% (wt/vol) TNBS | MPA—(O—C10bMe-2-TG)—OMe (I-16) | 3 mg per kg PO | QD Days 1-12 |
| 11 | 10 | 150 μl of 1% (wt/vol) TNBS presensitization solution | 100 ul 2.5% (wt/vol) TNBS | MPA—(O—C10bMe-2-TG)—OMe (I-16) | 0.99 mg per kg PO | QD Days 1-12 |
| 12 | 10 | 150 μl of 1% (wt/vol) TNBS presensitization solution | 100 ul 2.5% (wt/vol) TNBS | MPA—(O—C10bMe-2-TG)—OMe (I-16) | 0.33 mg per kg PO | QD Days 1-12 |

TABLE 10-continued

Study Design

| Group | BALB/c | Presensitization | Colitis induction | Treatment | Dose and Route | Dose Schedule |
|---|---|---|---|---|---|---|
| 13 | 10 | 150 μl of 1% (wt/vol) TNBS presensitization solution | 100 ul 2.5% (wt/vol) TNBS | MPA—(O—C10bMe-2-TG)—OMe (I-16) | 0.99 mg per kg PO | BID Days 1-12 |

Chronic TNBS Colitis:

For chronic colitis, mice separated into groups as shown in Table 11 are desensitized as described above and colitis is induced in each mouse on day 8 by rectal perfusion with 100 ul 2.5% (wt/vol) TNBS solution into the lumen of the colon, as described in Wirtz et al. A heating lamp is positioned 20 cm distant from the cage during recovery. Animals are monitored for distress levels and daily determination of weight is performed. On day 15, determine the weight of the mouse. On day 22, 29, 36, and 43, animals are weighed, and rectal perfusion with 100 ul 2.5% (wt/vol) TNBS solution is repeated. Analysis is conducted as described above.

TABLE 11

Study Design

| Group | BALB/c | Presensitization | Colitis induction | Treatment | Dose and Route | Dose Schedule |
|---|---|---|---|---|---|---|
| 1 | 6 | 150 μl of 1% (wt/vol) TNBS solution without TNBS | None | — | — | — |
| 2 | 6 | 150 μl of 1% (wt/vol) TNBS presensitization solution | 100 ul 2.5% (wt/vol) TNBS on day 8, 22, 29, 36, and 43 | Vehicle | — | — |
| 3 | 6 | 150 μl of 1% (wt/vol) TNBS presensitization solution | 100 ul 2.5% (wt/vol) TNBS on day 8, 22, 29, 36, and 43 | MPA | 6 mg per dose PO | QD Days 8-12 |
| 4 | 6 | 150 μl of 1% (wt/vol) TNBS presensitization solution | 100 ul 2.5% (wt/vol) TNBS on day 8, 22, 29, 36, and 43 | MPA | 2 mg per dose PO | QD Days 8-12 |
| 5 | 6 | 150 μl of 1% (wt/vol) TNBS presensitization solution | 100 ul 2.5% (wt/vol) TNBS on day 8, 22, 29, 36, and 43 | MPA | 1 mg per dose PO | QD Days 8-12 |
| 6 | 6 | 150 μl of 1% (wt/vol) TNBS presensitization solution | 100 ul 2.5% (wt/vol) TNBS on day 8, 22, 29, 36, and 43 | MPA | 0.66 mg per dose PO | QD Days 8-12 |
| 7 | 6 | 150 μl of 1% (wt/vol) TNBS presensitization solution | 100 ul 2.5% (wt/vol) TNBS on day 8, 22, 29, 36, and 43 | MPA-2-TG (I-34) | 6 mg per dose PO | QD Days 8-12 |
| 8 | 6 | 150 μl of 1% (wt/vol) TNBS presensitization solution | 100 ul 2.5% (wt/vol) TNBS on day 8, 22, 29, 36, and 43 | MPA-2-TG (I-34) | 2 mg per dose PO | QD Days 8-12 |
| 9 | 6 | 150 μl of 1% (wt/vol) TNBS presensitization solution | 100 ul 2.5% (wt/vol) TNBS on day 8, 22, 29, 36, and 43 | MPA-2-TG (I-34) | 1 mg per dose PO | QD Days 8-12 |
| 10 | 6 | 150 μl of 1% (wt/vol) TNBS presensitization solution | 100 ul 2.5% (wt/vol) TNBS on day 8, 22, 29, 36, and 43 | MPA-2-TG (I-34) | 0.66 mg per dose PO | QD Days 8-12 |
| 11 | 6 | 150 μl of 1% (wt/vol) TNBS presensitization solution | 100 ul 2.5% (wt/vol) TNBS on day 8, 22, 29, 36, and 43 | MPA—(O—C10bMe-2-TG)—OMe (I-16) | 6 mg per dose PO | QD Days 8-12 |
| 12 | 6 | 150 μl of 1% (wt/vol) TNBS presensitization solution | 100 ul 2.5% (wt/vol) TNBS on day 8, 22, 29, 36, and 43 | MPA—(O—C10bMe-2-TG)—OMe (I-16) | 2 mg per dose PO | QD Days 8-12 |
| 13 | 6 | 150 μl of 1% (wt/vol) TNBS presensitization solution | 100 ul 2.5% (wt/vol) TNBS on day 8, 22, 29, 36, and 43 | MPA—(O—C10bMe-2-TG)—OMe (I-16) | 1 mg per dose PO | QD Days 8-12 |

TABLE 11-continued

| | | | | | | |
|---|---|---|---|---|---|---|
| | | | Study Design | | | |
| Group | BALB/c | Colitis Presensitization | Colitis induction | Treatment | Dose and Route | Dose Schedule |
| 14 | 6 | 150 μl of 1% (wt/vol) TNBS presensitization solution | 100 ul 2.5% (wt/vol) TNBS on day 8, 22, 29, 36, and 43 | MPA—(O—C10bMe-2-TG)—OMe (I-16) | 0.66 mg per dose PO | QD Days 8-12 |

Table 12 shows the scoring system employed in the TNBS studies for calculating a disease activity index based on weight loss, stool consistency and the degree of intestinal bleeding (as described in Wirtz et al. and references therein).

TABLE 12

| | | | |
|---|---|---|---|
| | | Colitis Scoring | |
| Score | Weight loss | Stool consistency | Blood |
| 0 | None | Normal | Negative hemocult |
| 1 | 1-5% | Soft but still formed | Negative hemocult |
| 2 | 6-10% | Soft | Positive hemocult |
| 3 | 11-18% | Very soft; wet | Blood traces in stool visible |
| 4 | >18% | Watery diarrhea | Gross rectal bleeding |

Alternatively or in combination, acute and chronic DSS models are used, e.g., as described in Wirtz et al.

Example 37: Effects of Lipid Prodrug Administered in Acute and Chronic Models of Systemic Lupus Erythematosus Systemic lupus erythematosus (SLE) is a chronic multi-system autoimmune disorder that can affect almost all organ systems including the kidneys, skin, joints, and central nervous system. The efficacy and potential benefits of lipid prodrugs over MPA are assessed in animal models of SLE. The three most commonly studied spontaneous models are MRL/lpr, BXSB, and NZBWF1 (FI hybrid of New Zealand Black [NZB] and New Zealand White [NZW] strains). All three develop autoantibodies and immune complex-mediated glomerulonephritis, one of the hallmark characteristics of SLE (Taylor and Ryan, "Understanding mechanisms of hypertension in systemic lupus erythematosus," Ther Adv Cardiovasc Dis 2017, Vol. 11(1) 20-32). MPA will be used as a control, but MMF may be substituted. Testing of compounds I-16 and I-34 is described, but the procedure is applicable to other lipid prodrugs as well.

MPA and lipid prodrugs thereof are assessed in MRL/lpr mice. MRL/lpr mice spontaneously develop an autoimmune disease that resembles human SLE and is characterized by immune-complex mediated glomerulonephritis, splenomegaly, lymphadenopathy and autoantibody formation. The study is essentially carried out as described in Lui et al., "Effect of mycophenolate mofetil on severity of nephritis and nitric oxide production in lupus-prone MRL=lpr mice," Lupus (2002) 11, 411-418 and van Bruggen et al., "Attenuation of Murine Lupus Nephritis by Mycolate Mofetil," J. Am. Soc. Nephrol. 9: 1407-1415, 1998).

In brief, eight-week-old female MRL/lpr mice are weighed and separated into groups as shown in Table 13. Mice are treated with MMF as indicated or the lipidated prodrugs thereof in carboxymethyl-cellulose vehicle by oral gavage. Control mice receive equal volume of vehicle alone on the same schedule. The total duration of treatment is 12 weeks. In this model, the mice do not display signs of glomerulonephritis at the start of the treatment (Lui et al.). Twenty-four-hour urinary collection is performed at weeks 4, 8 and 12 after the commencement of treatment to determine the amount of proteinuria and urinary nitrite nitrate excretion. The mice are sacrificed after 12 weeks of treatment. The left and right kidneys are harvested for histological, immunohistochemical analysis, and FACS analysis. Kidnes are histologically assessed for mesangial cell proliferation, hyaline deposition, leukocyte in glomeruli, interstitial infiltration, and Crescent. In addition, whole blood and spleen, brain, liver, lung, colon from cecum to anus, cecum, inguinal lymph nodes, cervical lymph nodes, and axillary lymph nodes are collected for analysis.

TABLE 13

| | | | | |
|---|---|---|---|---|
| | | Study Design | | |
| Group | No. MRL/Ipc | Treatment | Dose and Route | Dose Schedule |
| 1 | 6 | — | — | — |
| 2 | 6 | Vehicle | — | — |
| 3 | 6 | MPA | 1 mg per kg PO | QD Days 1-84 |
| 4 | 6 | MPA | 0.33 mg per kg PO | QD Days 1-84 |
| 5 | 6 | MPA | 0.11 mg per kg PO | QD Days 1-84 |
| 6 | 6 | MPA | 2 mg per kg PO | QD Days 1-84 |
| 7 | 6 | MPA-2-TG (I-34) | 0.66 mg per kg PO | QD Days 1-84 |
| 8 | 6 | MPA-2-TG (I-34) | 0.22 mg per kg PO | QD Days 1-84 |
| 9 | 6 | MPA-2-TG (I-34) | 0.66 mg per kg PO | BID Days 1-84 |
| 10 | 6 | MPA-2-TG (I-34) | 3 mg per kg PO | QD Days 1-84 |
| 11 | 6 | MPA-(O-C10bMe-2-TG)-OMe (I-16) | 0.99 mg per kg PO | QD Days 1-84 |
| 12 | 6 | MPA-(O-C10bMe-2-TG)-OMe (I-16) | 0.33 mg per kg PO | QD Days 1-84 |
| 13 | 6 | MPA-(O-C10bMe-2-TG)-OMe (I-16) | 0.99 mg per kg PO | BID Days 1-84 |

We claim:
1. A compound of Formula VI:

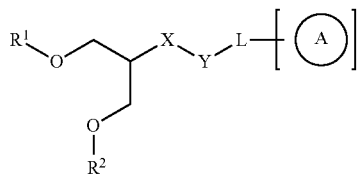

or a pharmaceutically acceptable salt thereof, wherein:
$R^1$ and $R^2$ are each independently hydrogen, an acid-labile group, a lipid, or —C(O)$R^3$;
each $R^3$ is independently a saturated or unsaturated, straight or branched, optionally substituted $C_{1-37}$ hydrocarbon chain;
X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
Y is absent or is —C(O)—, —C(NR)—, or —C(S)—;
L is a covalent bond or a saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or
L is

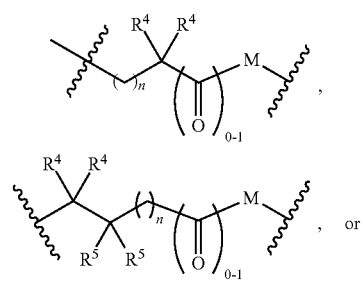

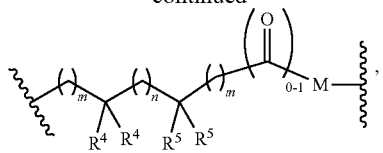

wherein either the right-hand side or left-hand side of L is attached to A;
each -Cy- is independently an optionally substituted 3-6 membered bivalent saturated, partially unsaturated, or aromatic ring having 0-4 heteroatoms independently selected from nitrogen, oxygen, or sulfur;
each $R^4$ and $R^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or
two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;
M- is a self-immolative group;
n is 0-18;
each m is independently 0-6; and
A is a therapeutic agent selected from mycophenolic acid or a derivative, analogue, or prodrug thereof, provided that when A is

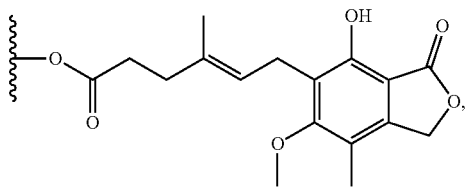 [SMILES: *OC(=O)CC/C(C)=C/Cc1c(O)c2c(c(C)c1OC)COC2=O]

X is —O—, and Y is —C(O)—, L is

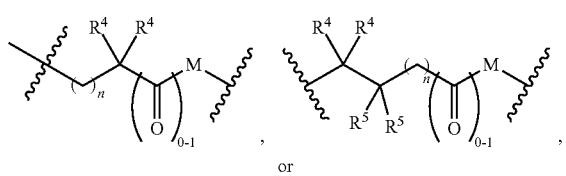
or

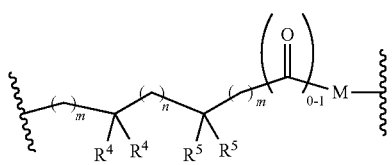

and -M- is not

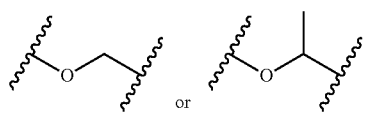

2. The compound according to claim 1, wherein $R^1$ and $R^2$ are —C(O)$R^3$ and each $R^3$ is independently a saturated or unsaturated, unbranched $C_{2-37}$ hydrocarbon chain.

3. The compound according to claim 1, wherein X is —O— and Y is —C(O)—.

4. The compound according to claim 1, wherein L is a saturated or unsaturated, straight or branched, optionally substituted bivalent $C_{5-25}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-.

5. The compound according to claim 1, wherein L is a covalent bond or a saturated or unsaturated, straight or branched, optionally substituted bivalent $C_{6-20}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid selected from

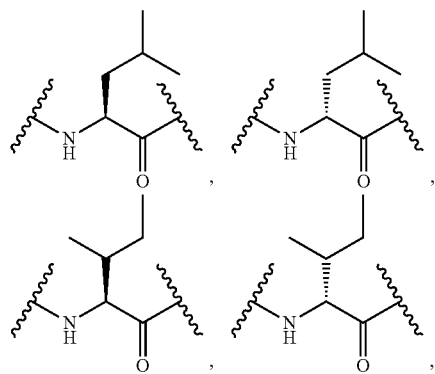

-continued

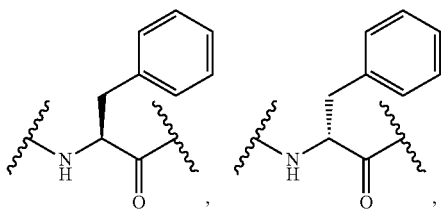

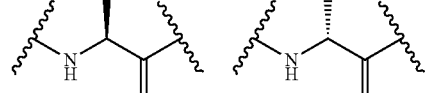

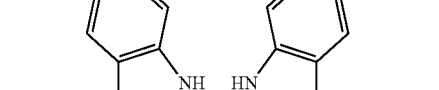

, or ;

and wherein 1 methylene unit of L is optionally replaced with -M-; or

L is

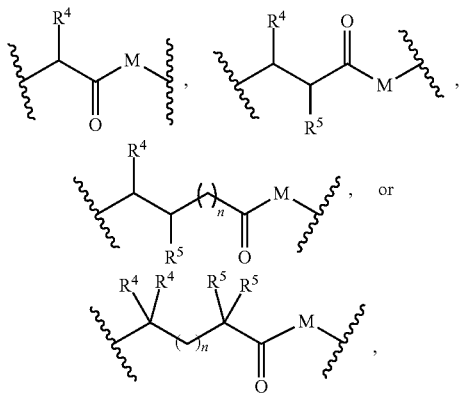

wherein either the right-hand side or left-hand side of L is attached to A.

6. The compound according to claim 1, wherein L is a saturated bivalent $C_{3-25}$ hydrocarbon chain optionally substituted with 1, 2, 3, or 4 groups selected from deuterium, halogen, —CN, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

7. The compound according to claim 1, wherein -M- is:

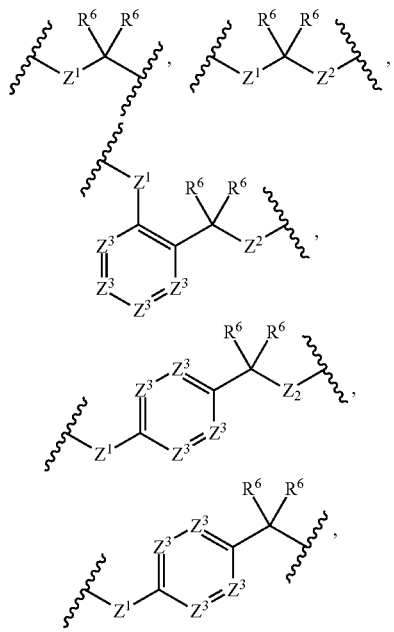

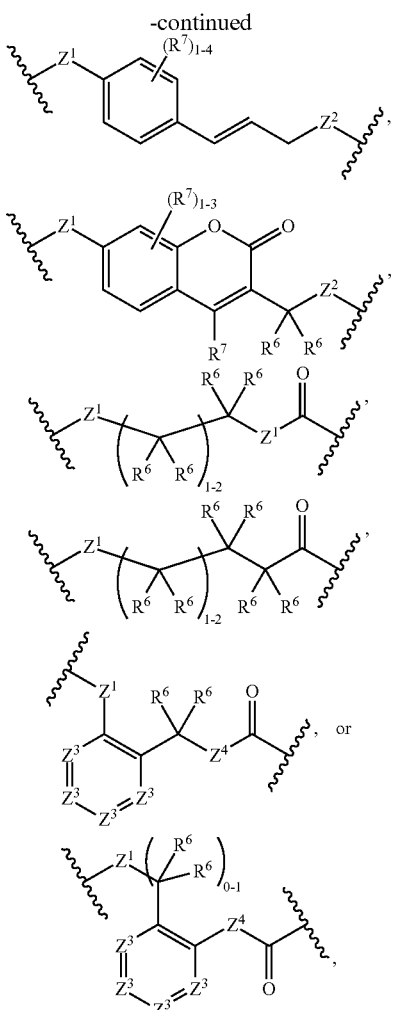

wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —NR$_2$, —NO$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C($R^7$)—; and each $Z^4$ is independently selected from —O—, —NR—, —S—, —C($R^6$)$_2$—, or a covalent bond.

8. The compound according to claim 7, wherein -M- is selected from

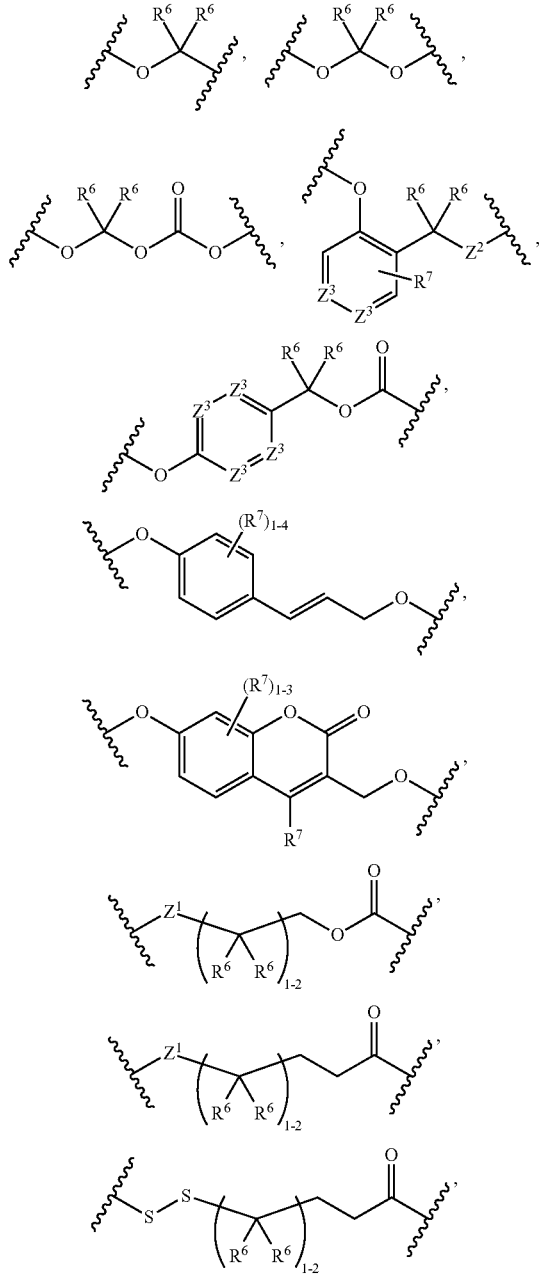

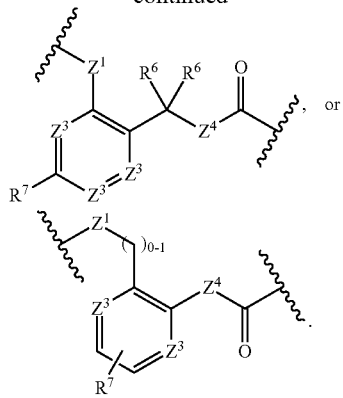

9. The compound according to claim 7, wherein -M- is selected from

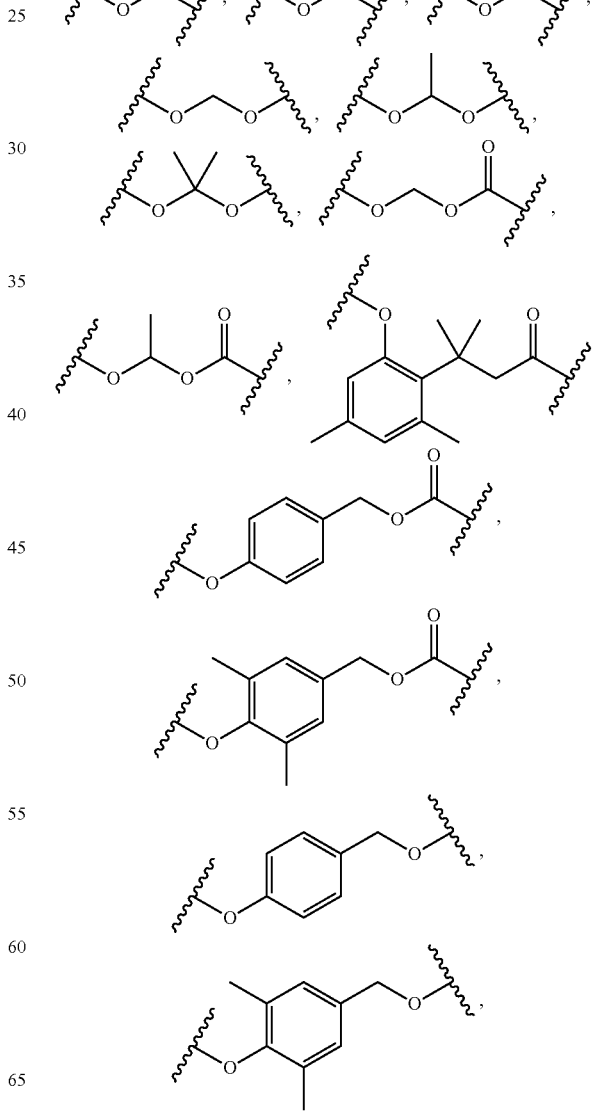

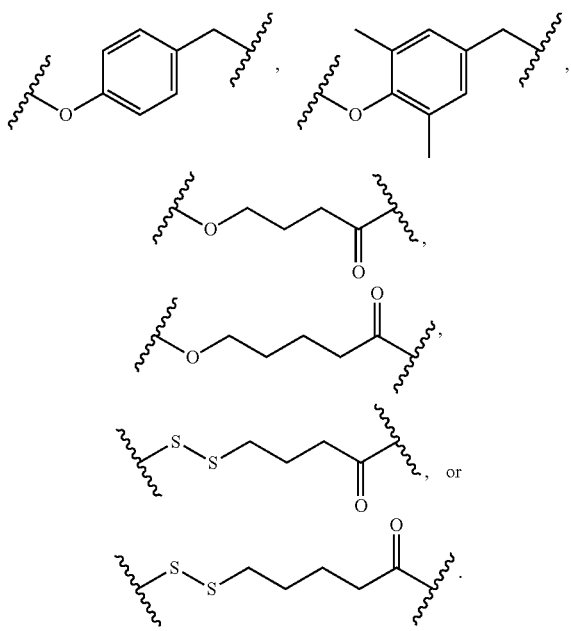

10. The compound according to claim 1, wherein each $R^4$ is independently hydrogen, deuterium, halogen, —CN, or $C_{1-4}$ aliphatic optionally substituted with 1, 2, 3, 4, 5, or 6 deuterium or halogen atoms; or two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

11. The compound according to claim 10, wherein each $R^5$ is independently hydrogen, deuterium, halogen, —CN, or $C_{1-4}$ aliphatic optionally substituted with 1, 2, 3, 4, 5, or 6 deuterium or halogen atoms; or two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

12. The compound according to claim 1, wherein each $R^4$ and $R^5$ is independently hydrogen or $C_{1-4}$ alkyl optionally substituted with 1, 2, 3, 4, 5, or 6 deuterium or halogen atoms.

13. The compound according to claim 1, wherein the compound is of Formula VI-a or VI-b:

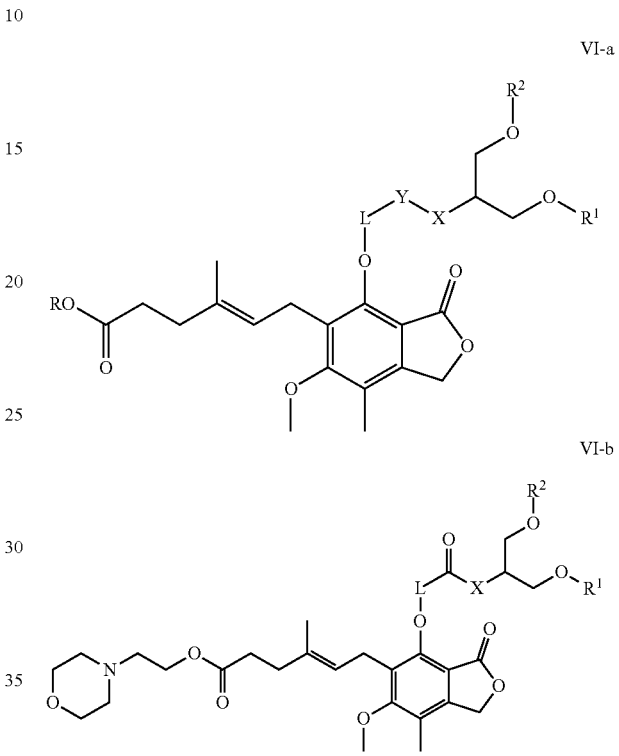

or a pharmaceutically acceptable salt thereof.

14. The compound according to claim 1, wherein said compound is of Formula VIII-a or VIII-b:

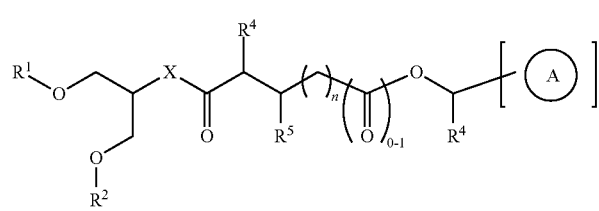

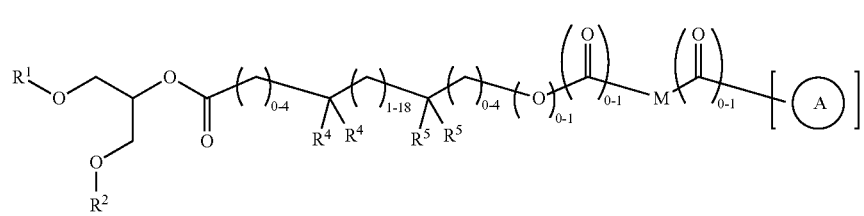

or a pharmaceutically acceptable salt thereof; wherein A is
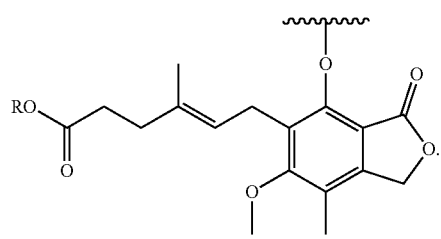
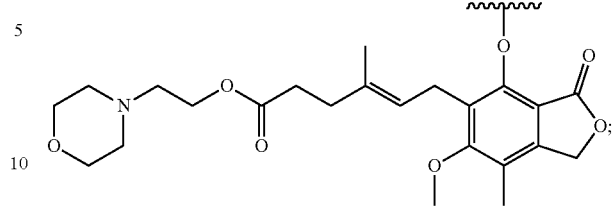
15. The compound according to claim 14, wherein A is
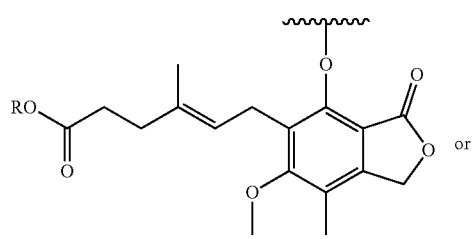
or
and R is $C_{1-6}$ aliphatic or phenyl.
16. A compound selected from:
I-1
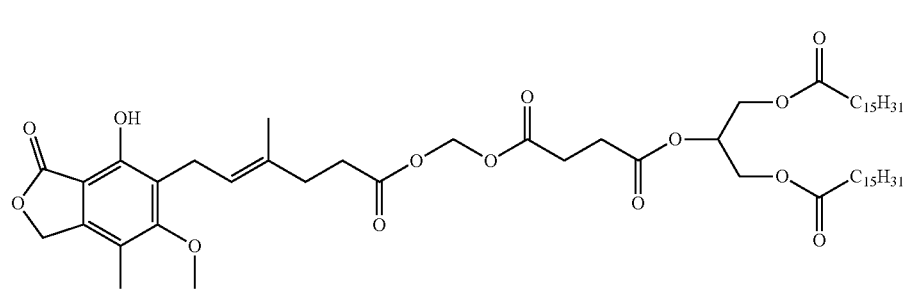
I-2
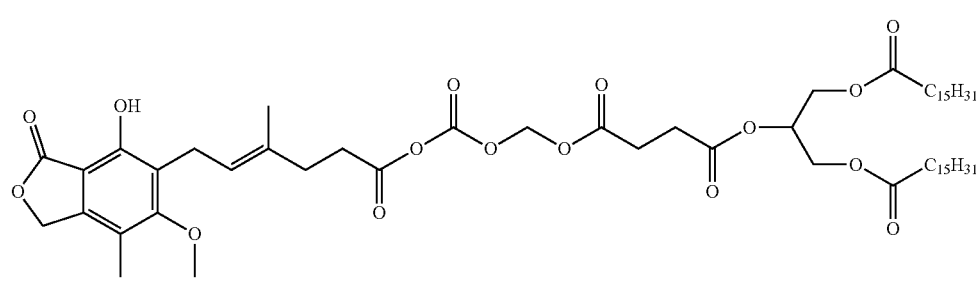
I-3
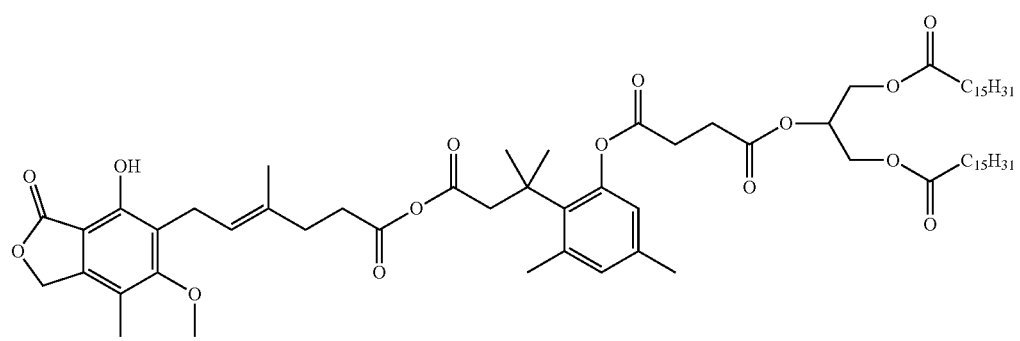

-continued
I-4
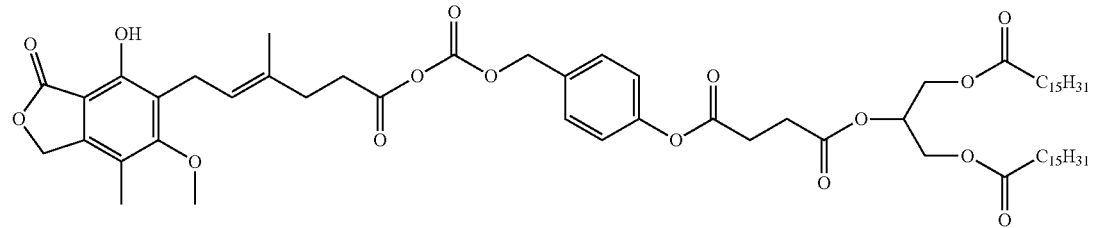
I-5
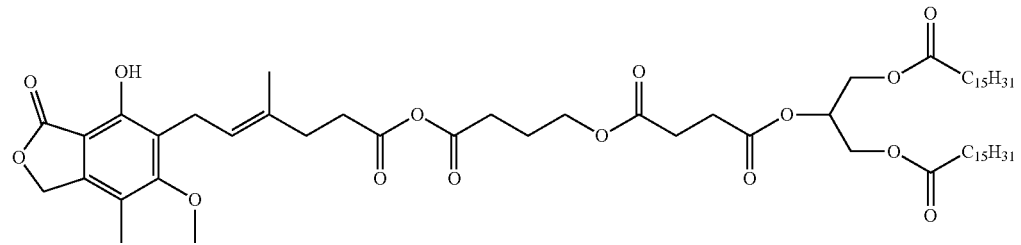
I-6
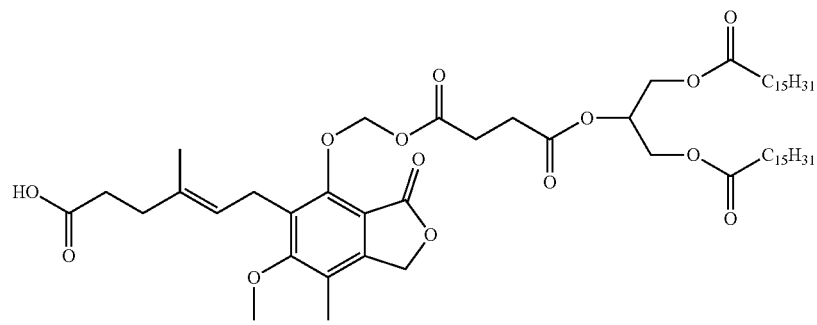
I-7
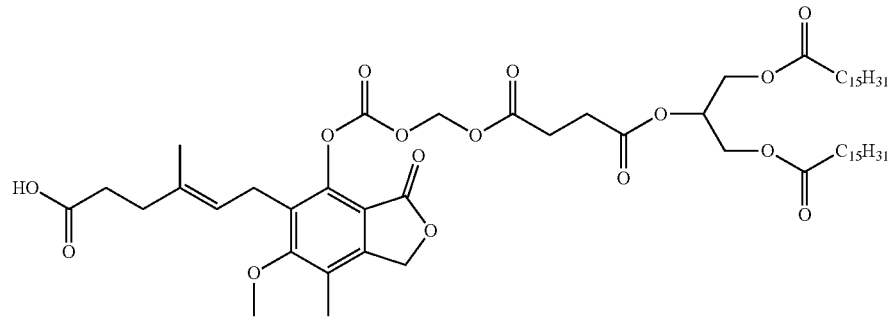
I-8
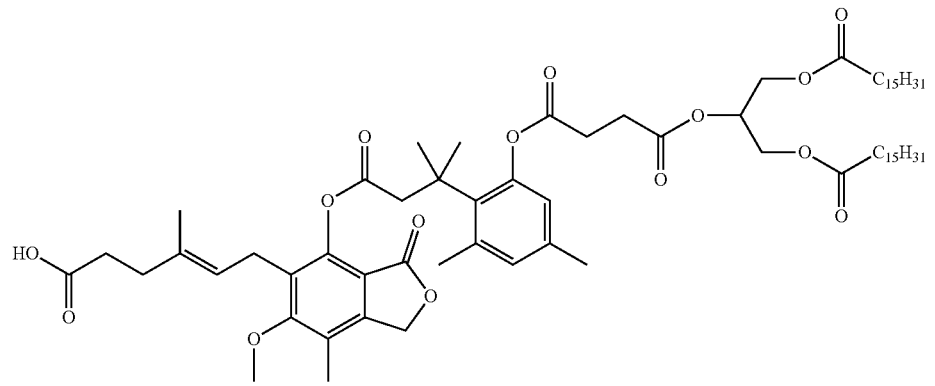

-continued
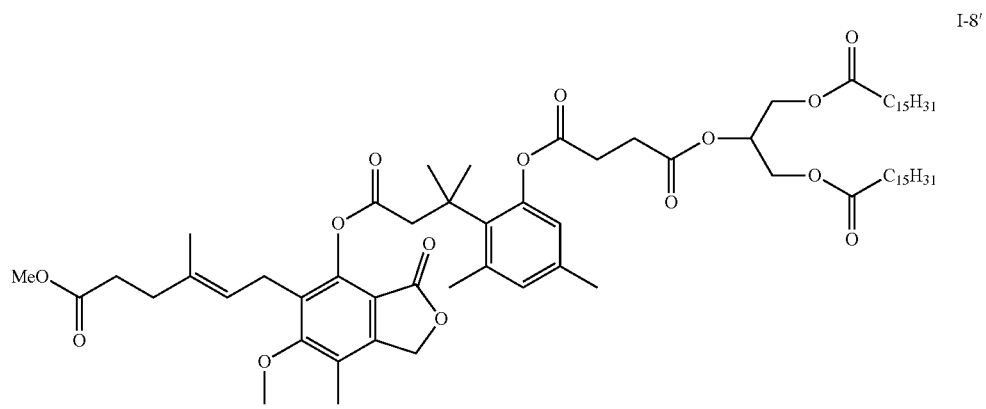
I-8'
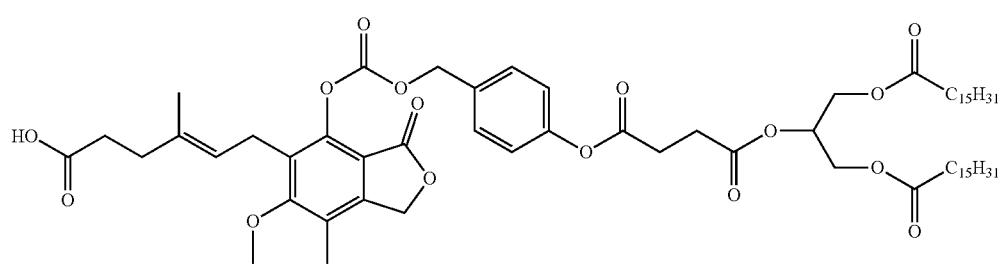
I-9
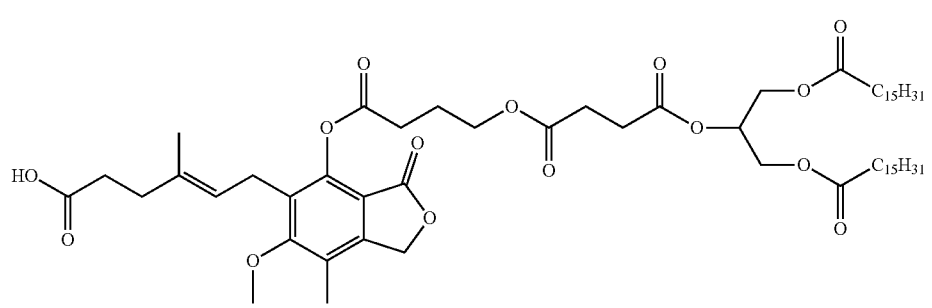
I-10
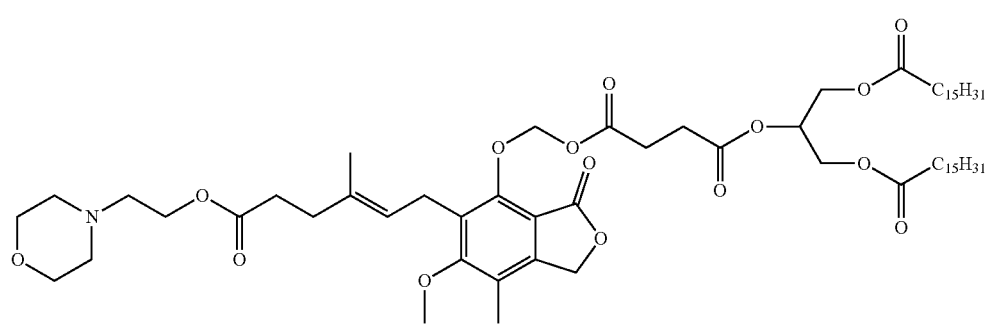
I-11
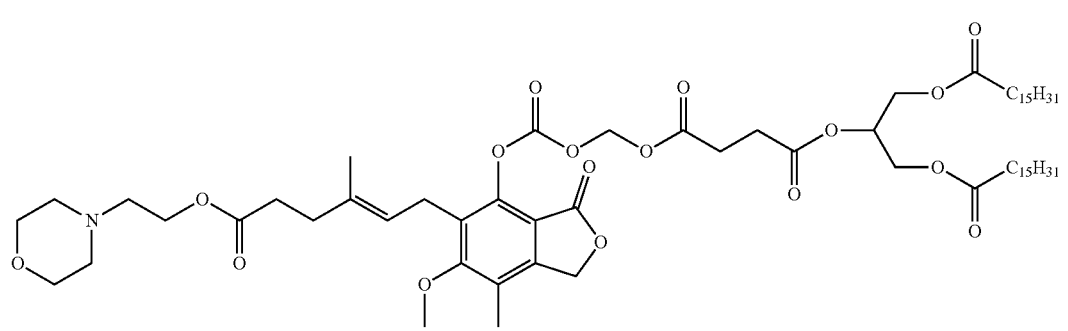
I-12

-continued
I-13
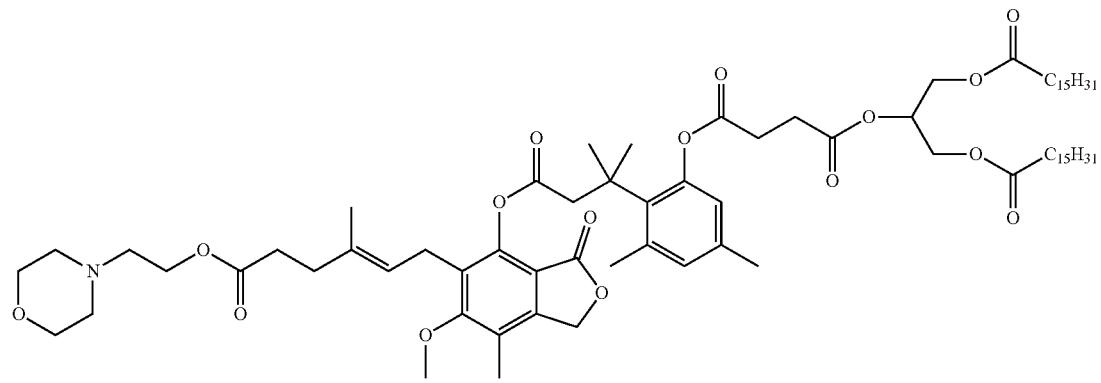
I-14
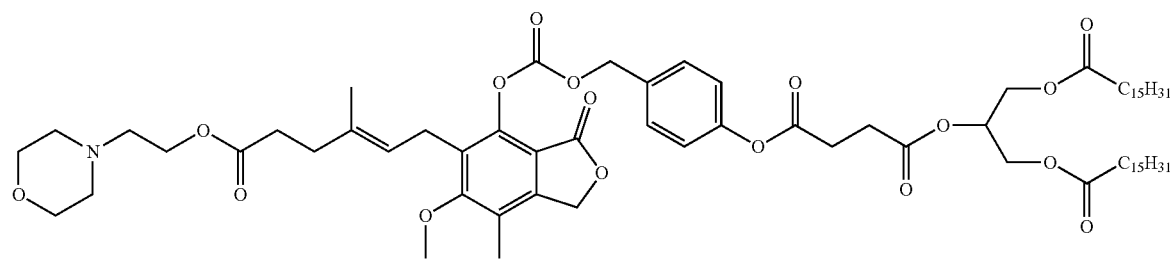
I-15
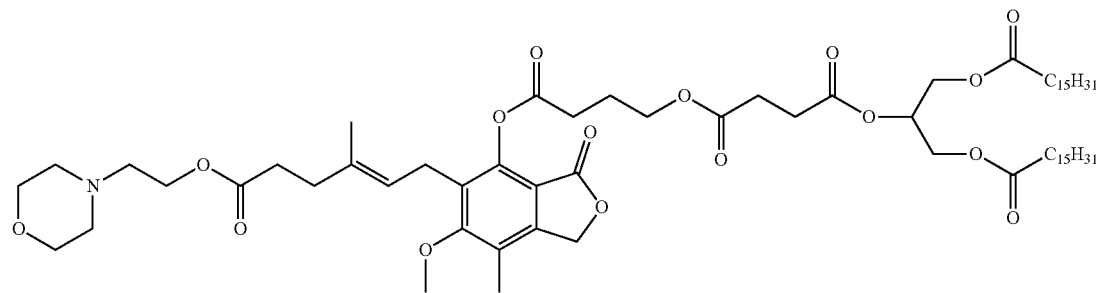
I-16
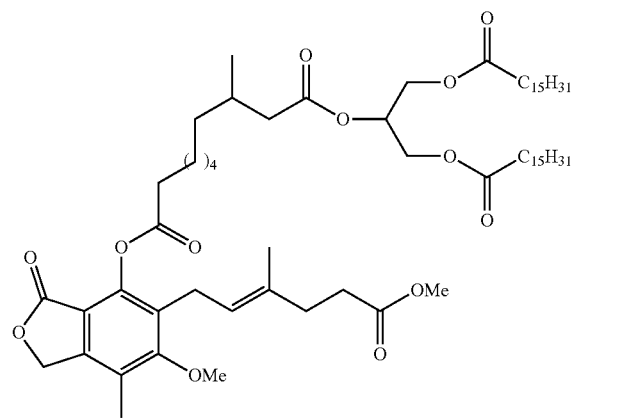
I-17
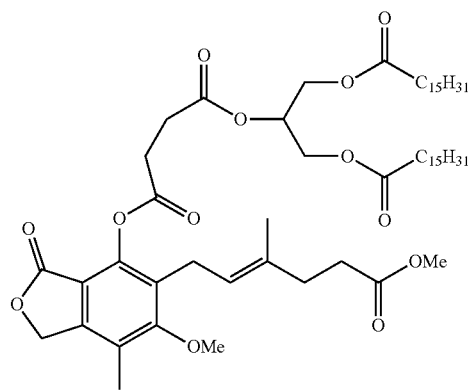

-continued
I-18
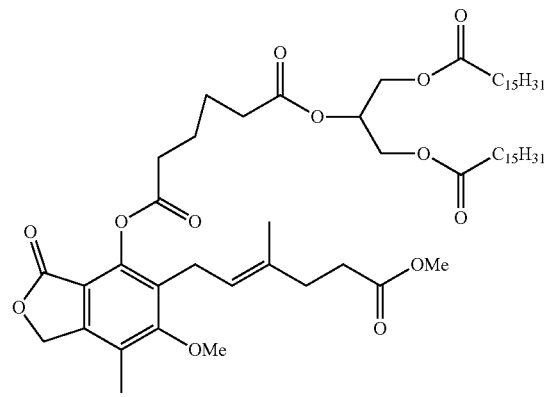
I-19
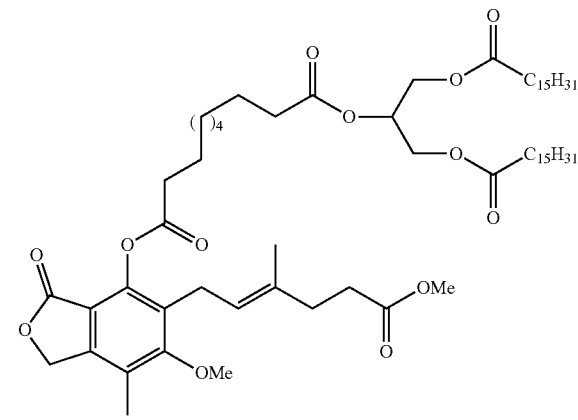
I-20
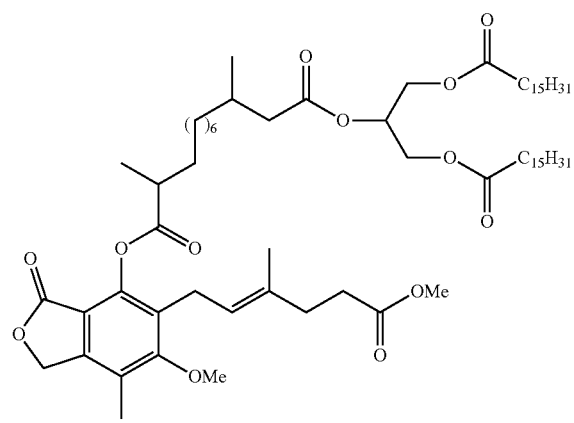
I-21
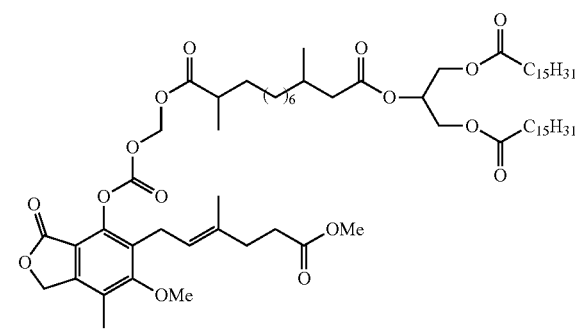
I-22
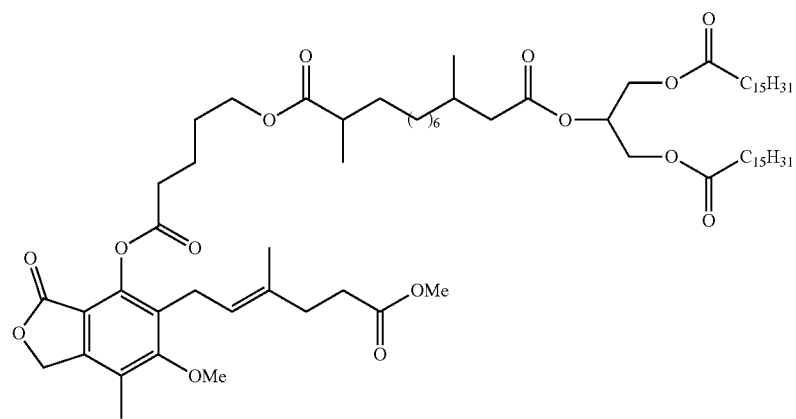
I-23
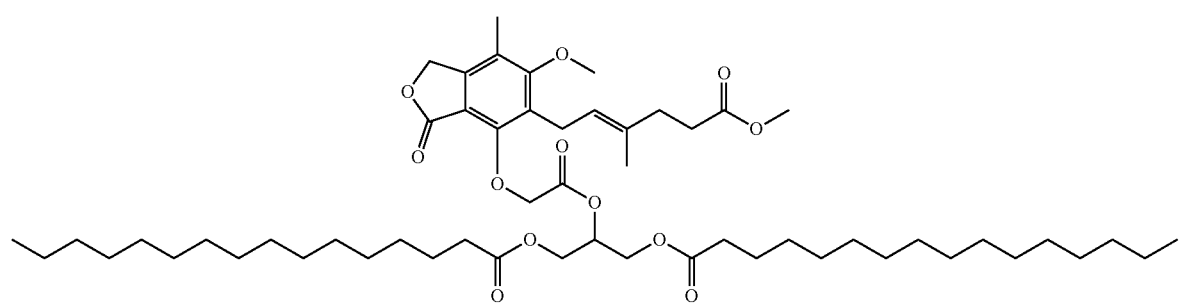

-continued
I-24
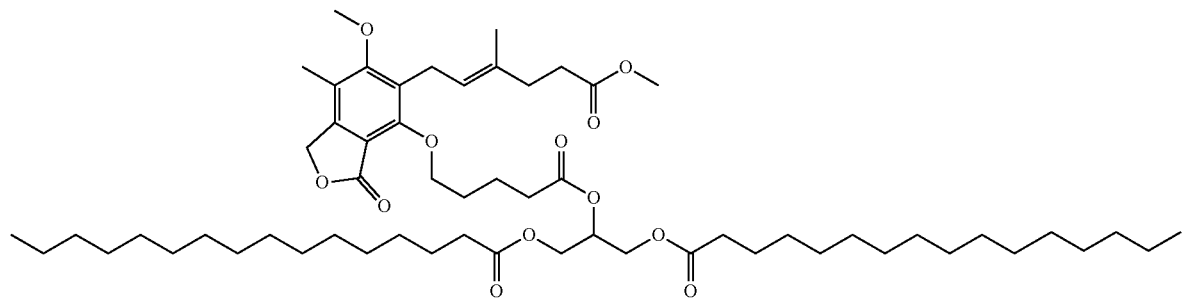
I-25
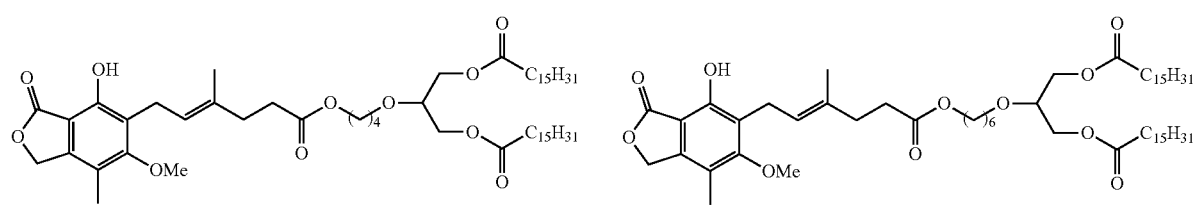
I-26
I-27
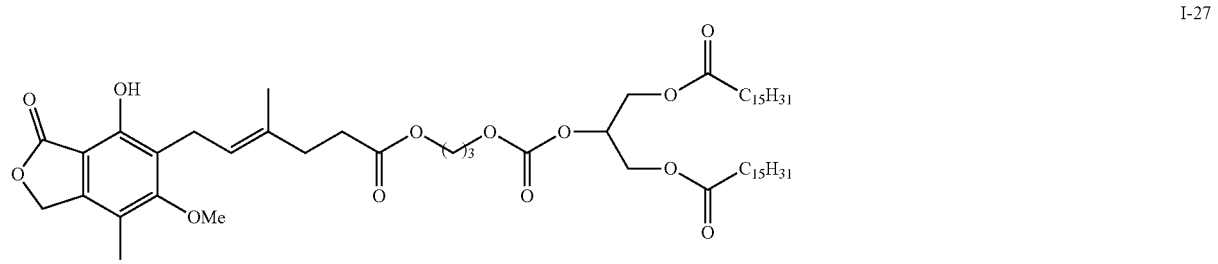
I-28
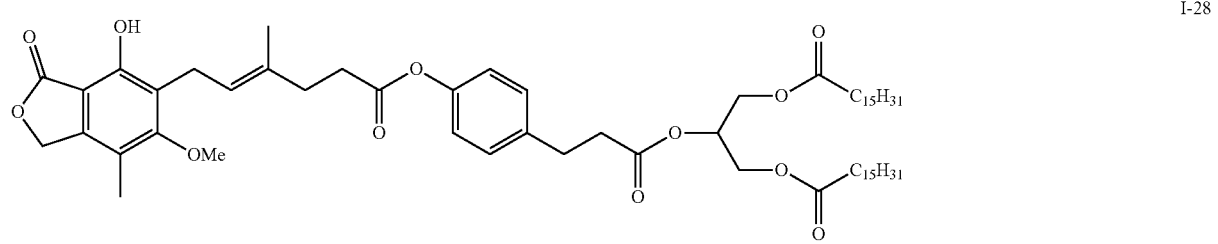
I-29
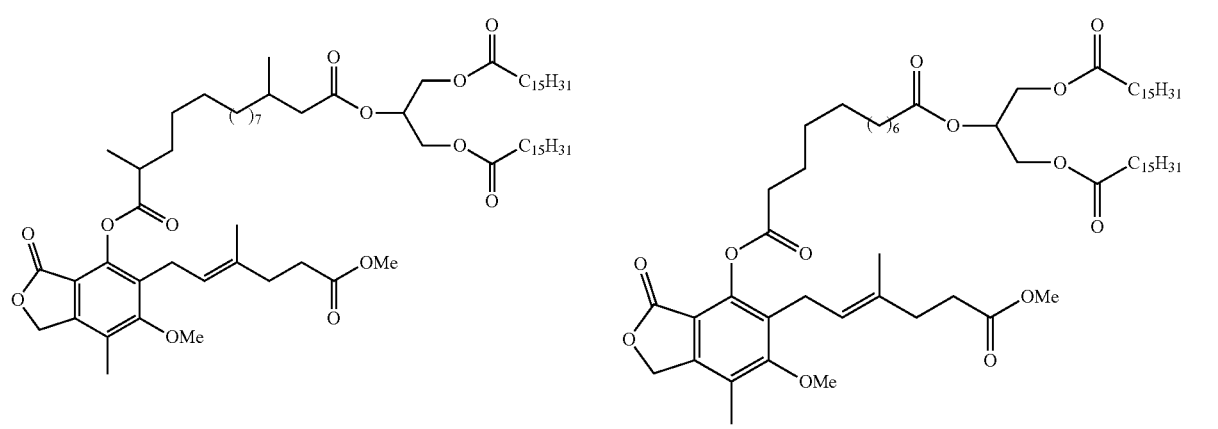
I-30

I-31
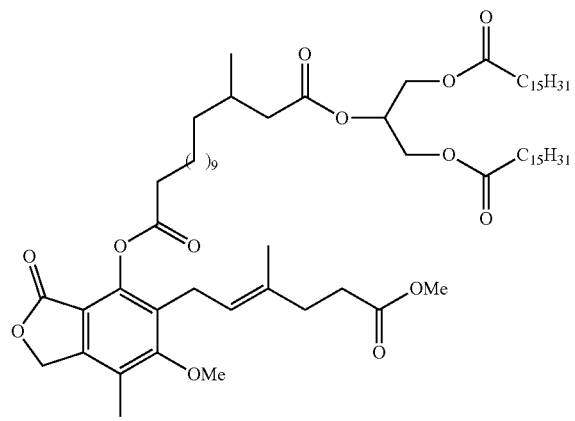
I-32
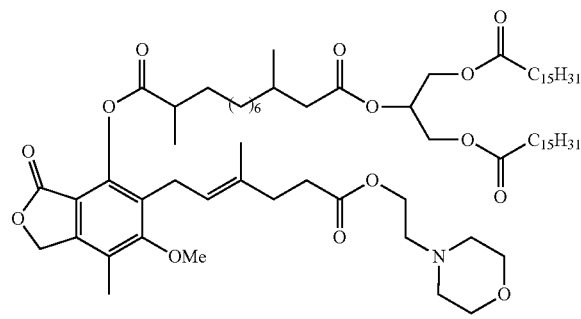
I-33
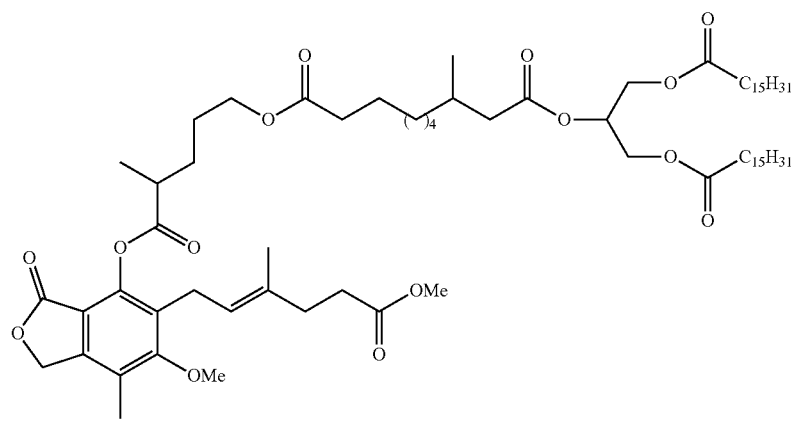
I-34
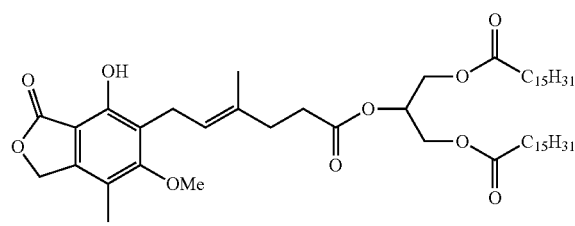
I-35
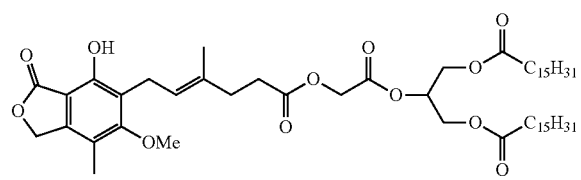
I-36
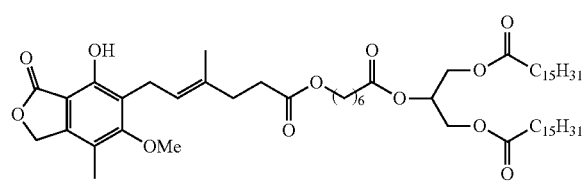
I-37
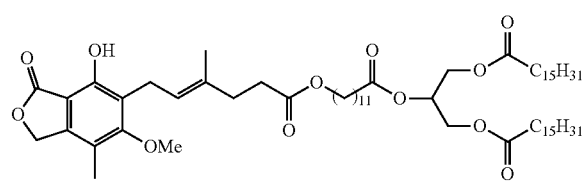
I-38
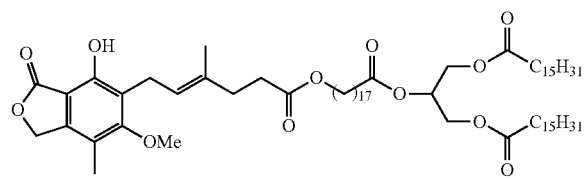
I-39
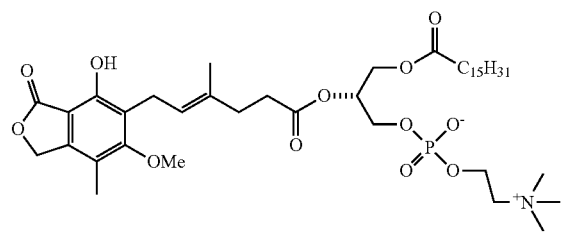

I-40
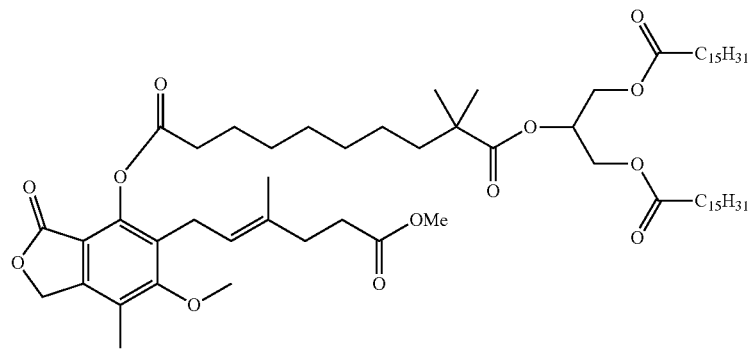
I-41
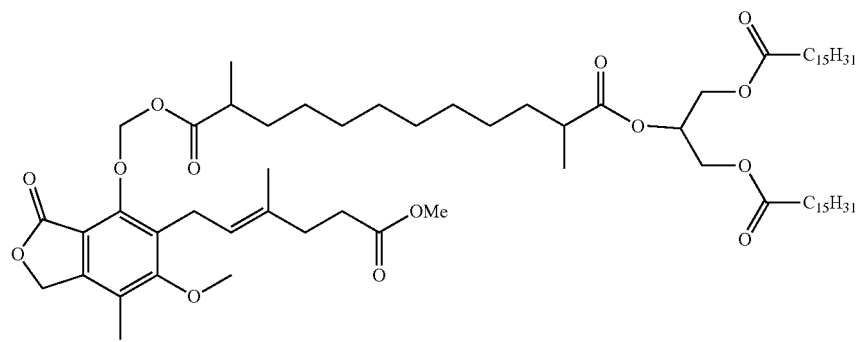
I-42
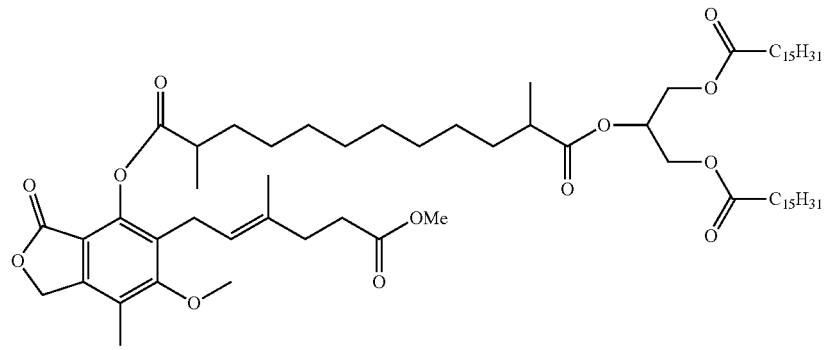
I-43
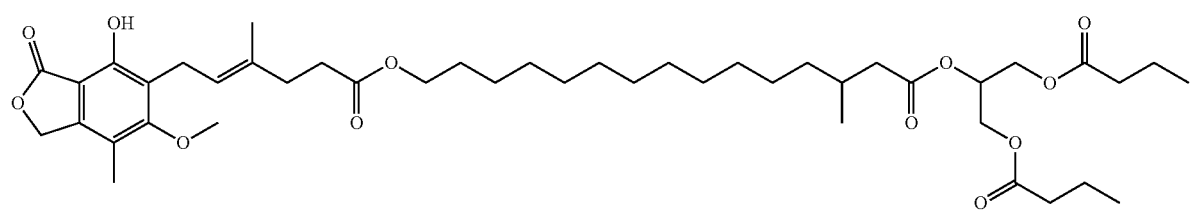
I-44
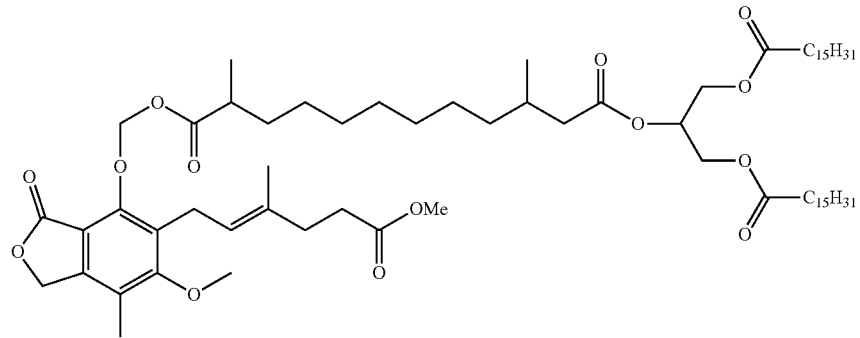

-continued
I-45
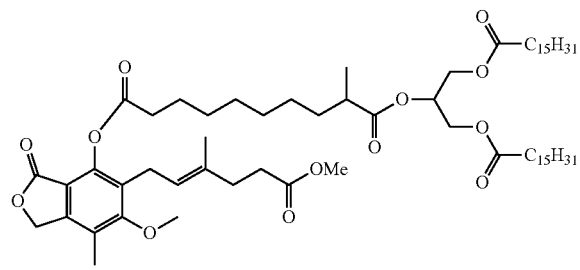
I-46
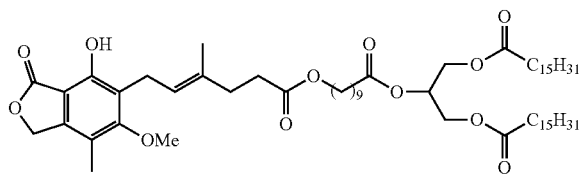
I-47
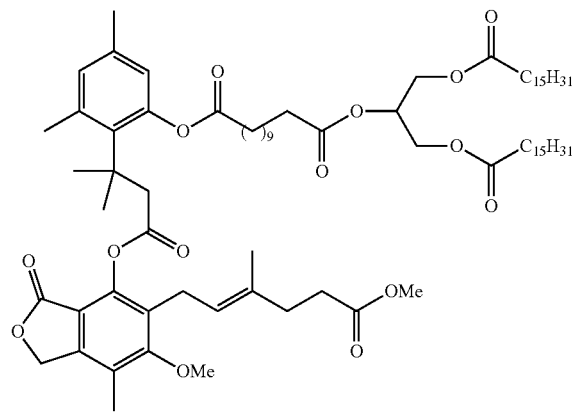
I-48
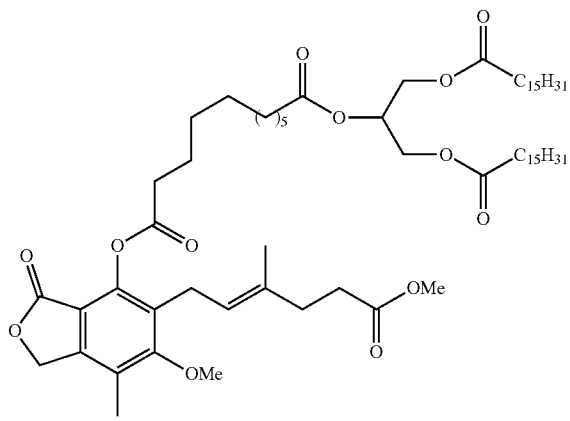
I-49
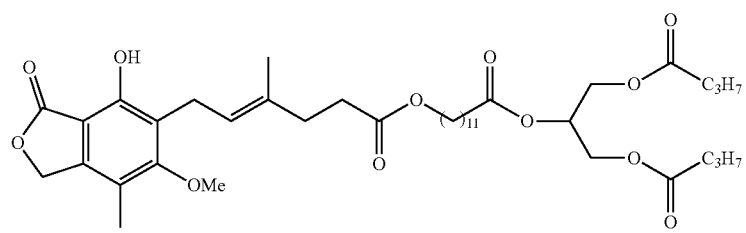
I-50
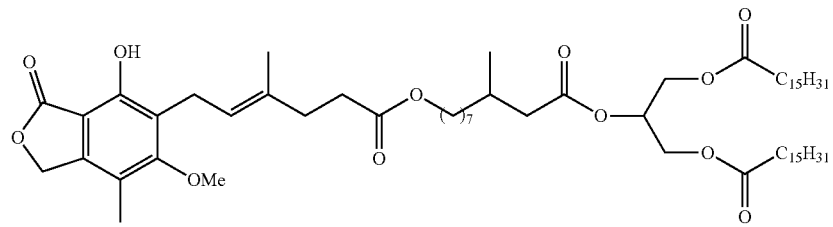
I-51
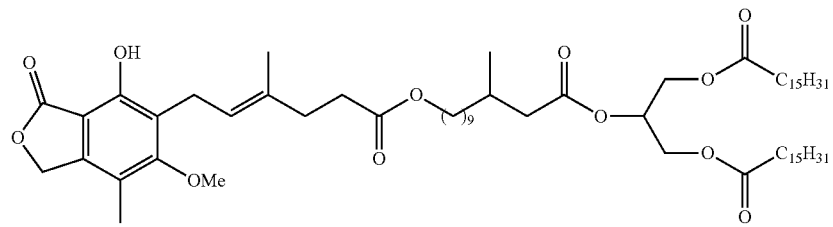

-continued
I-52
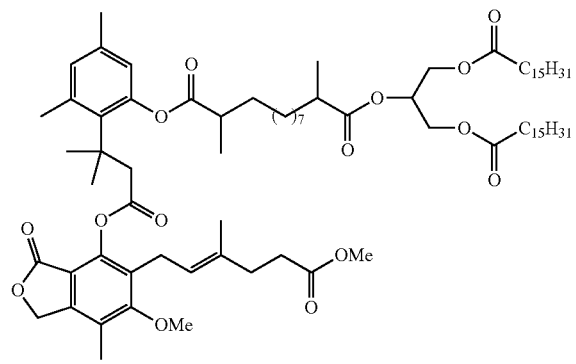
I-53
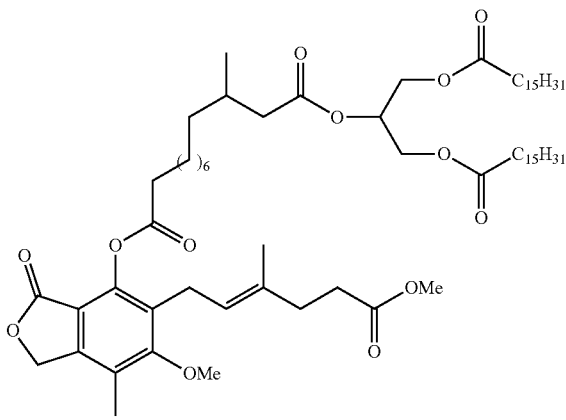
I-54
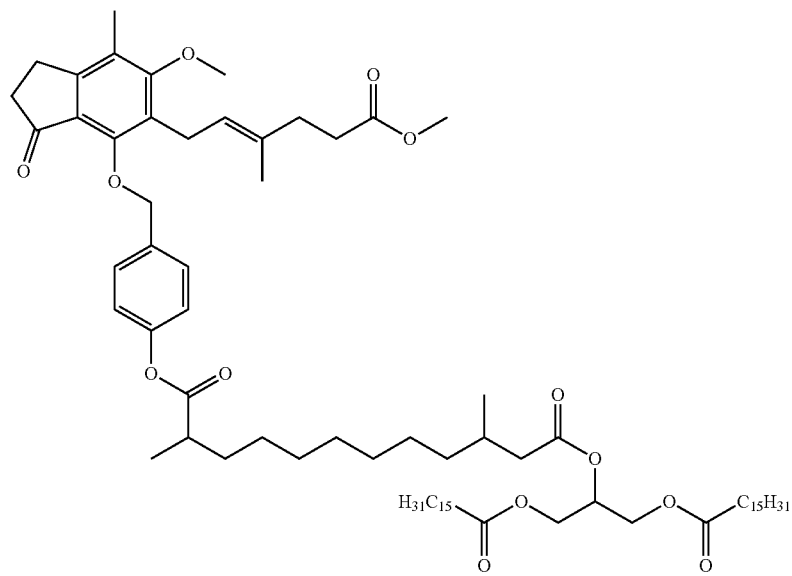
I-55
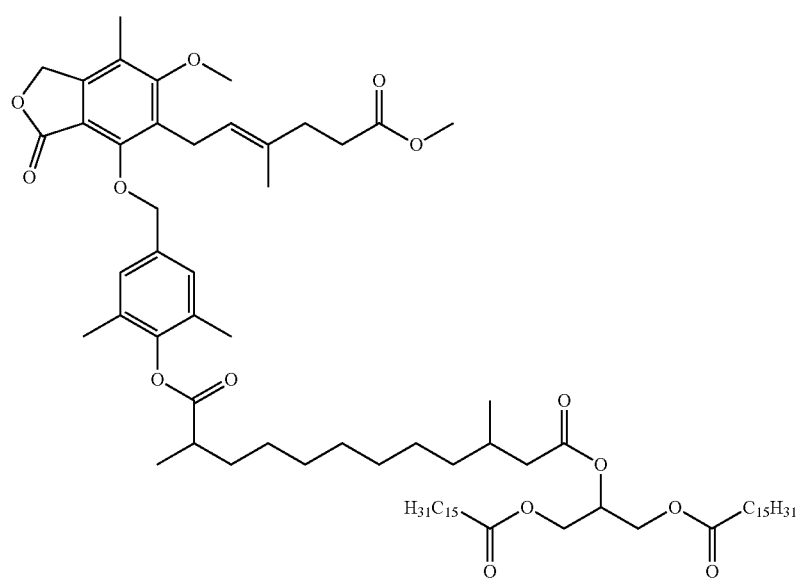

I-56
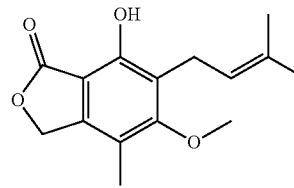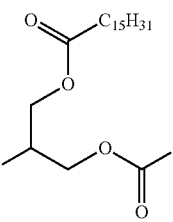
I-57
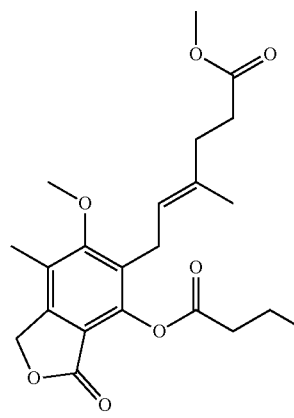
I-58
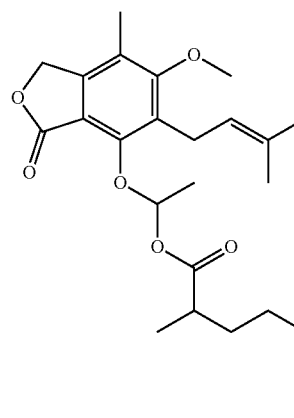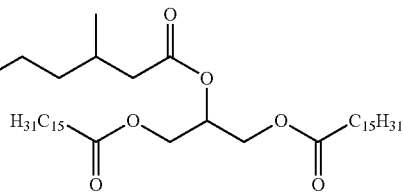
I-59
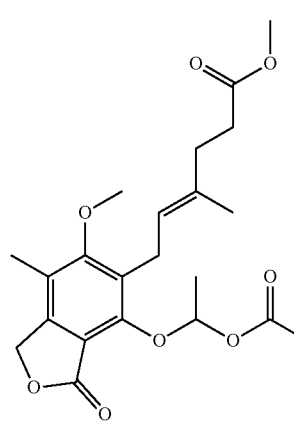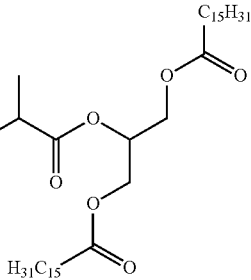

-continued
I-60
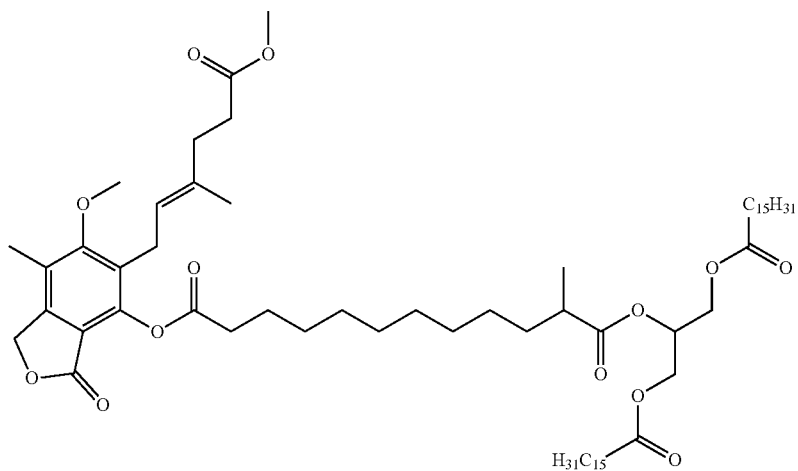
I-61
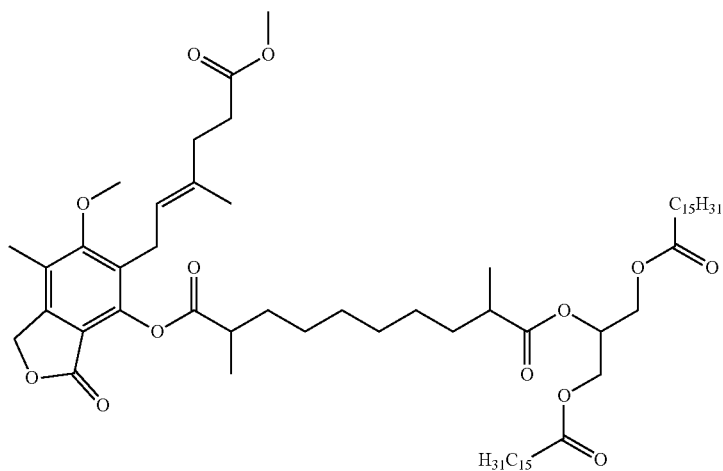
I-62
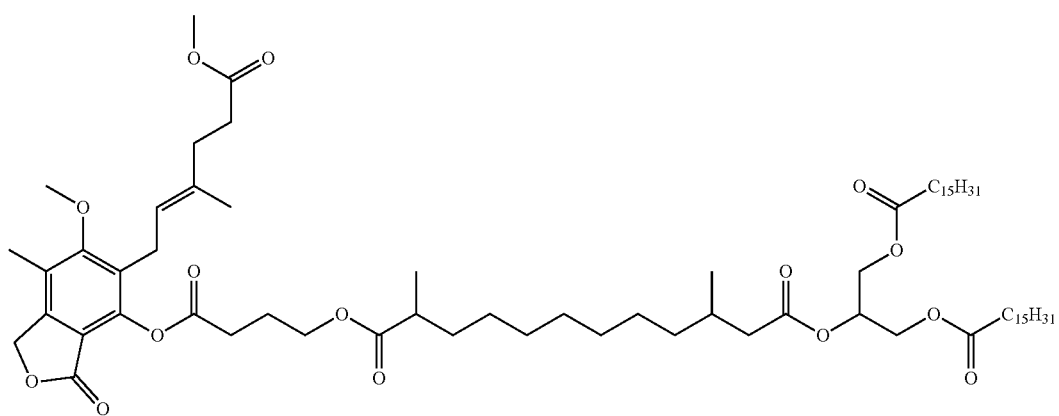

I-63
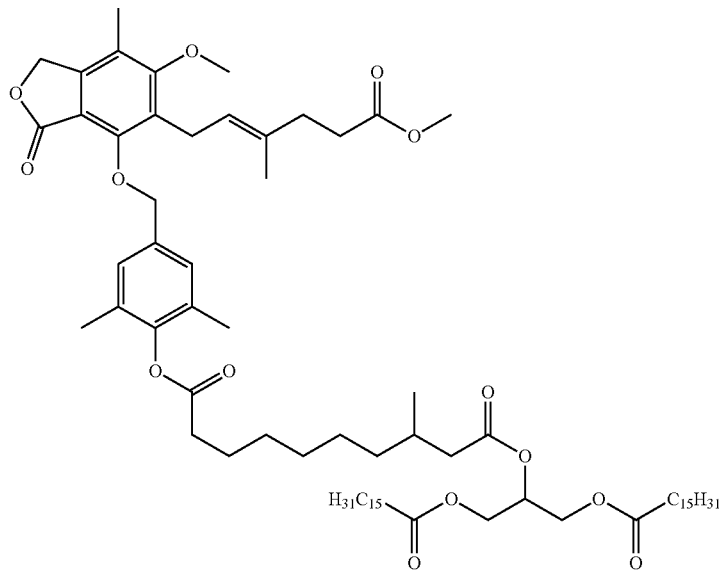
I-64
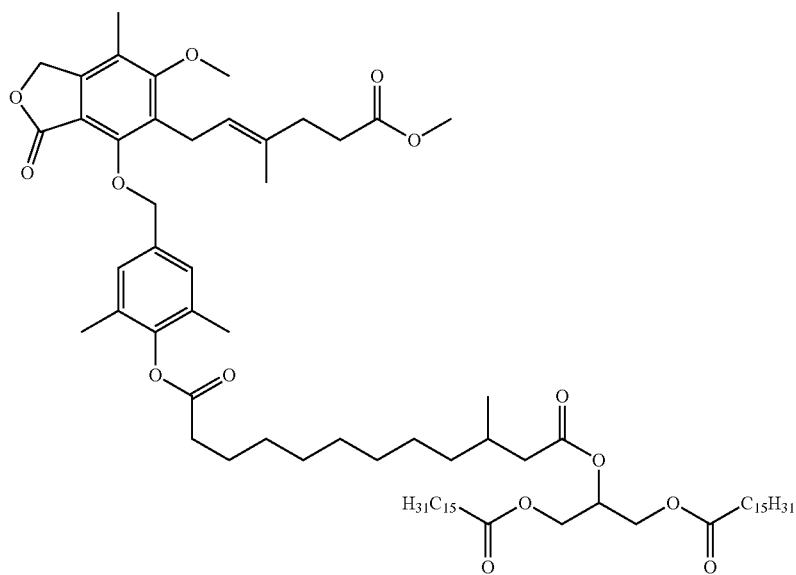
I-65
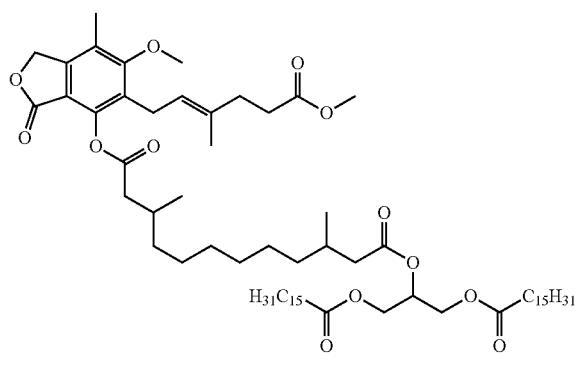
I-66
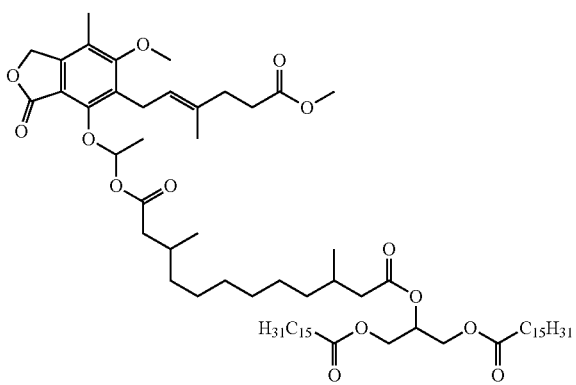

-continued
I-67
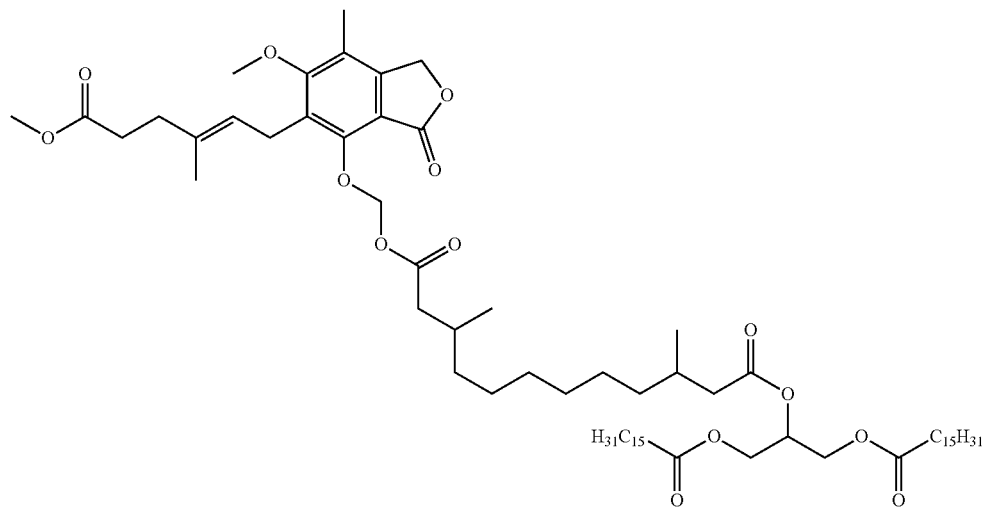
I-68
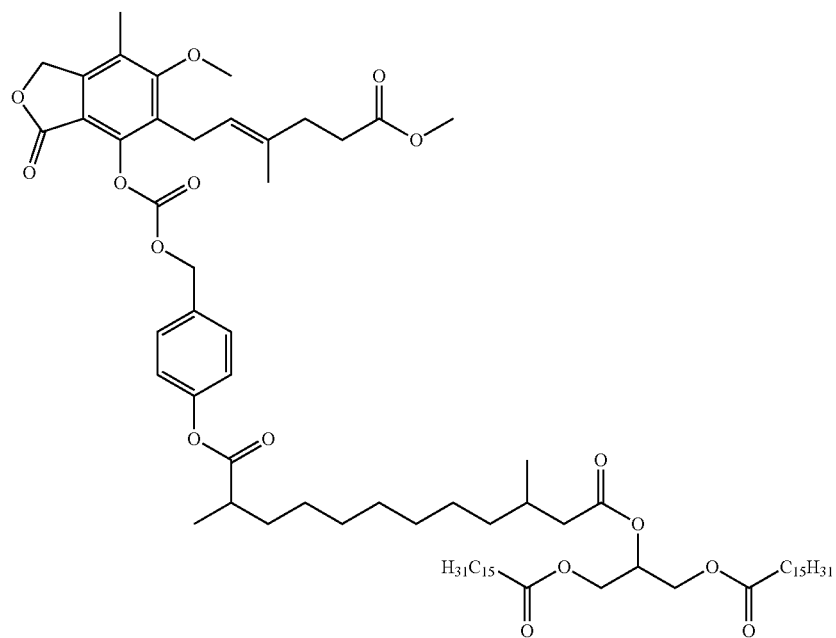
I-69
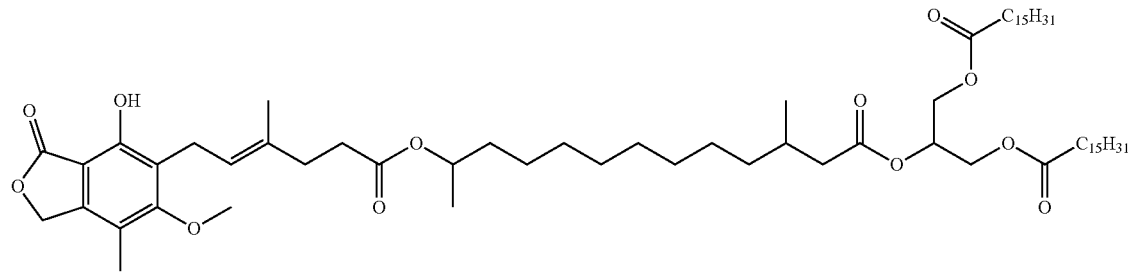

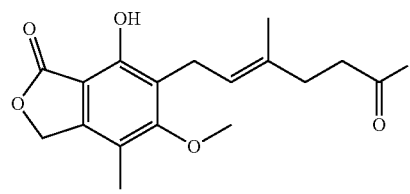
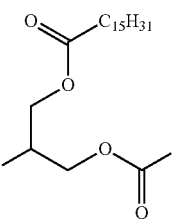
I-70
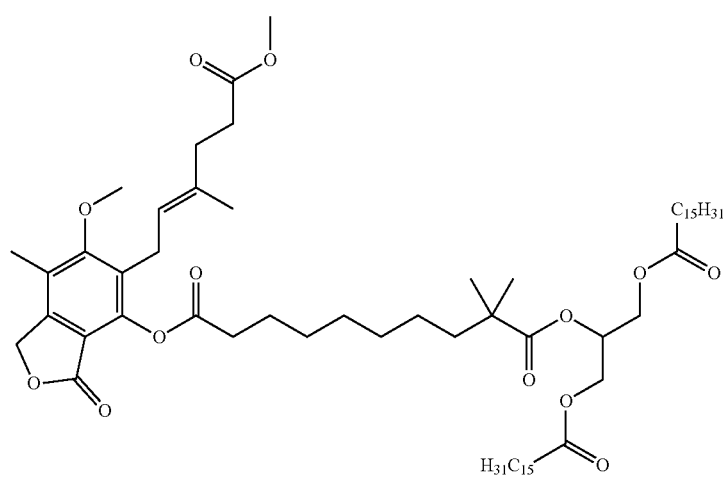
I-71
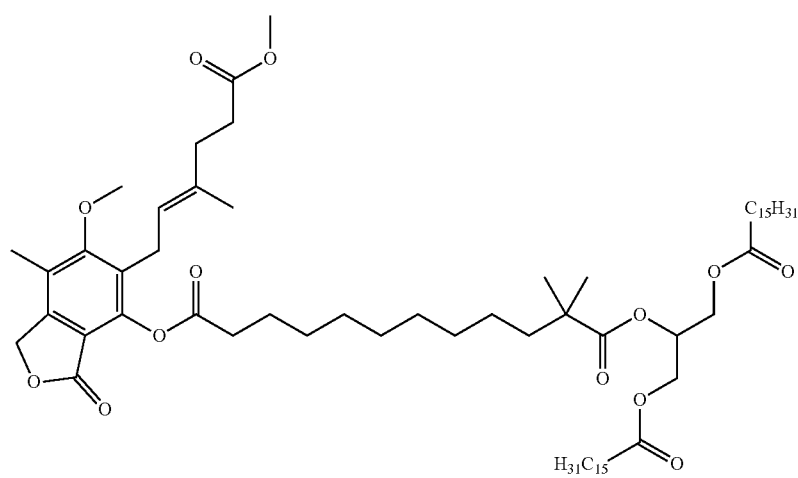
I-72
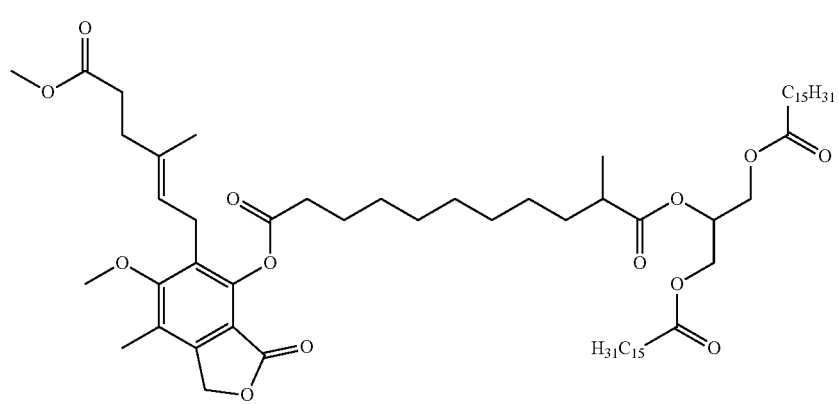
I-73

I-74
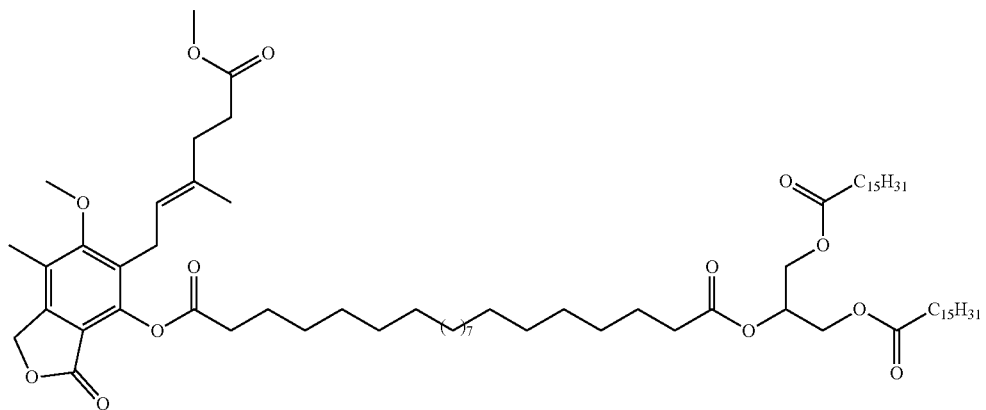
I-75
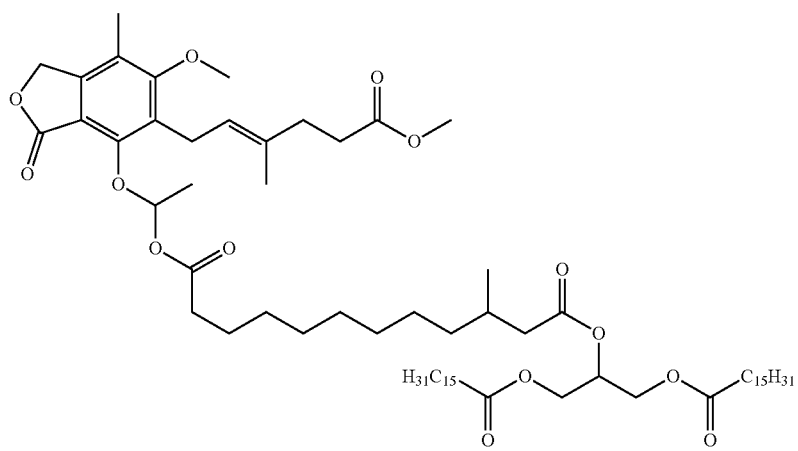
I-76
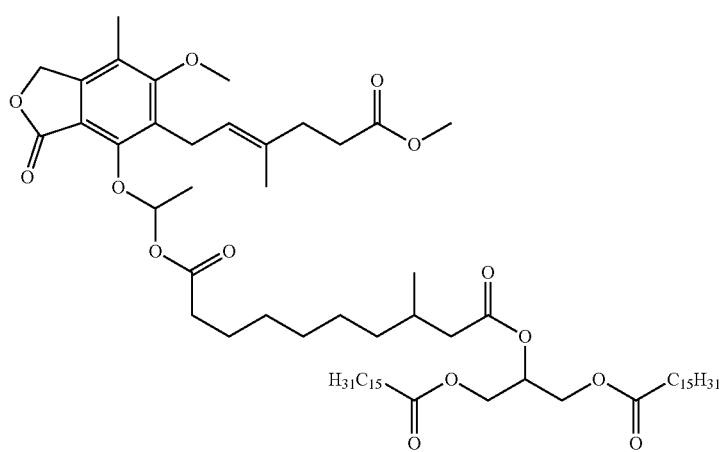

I-77
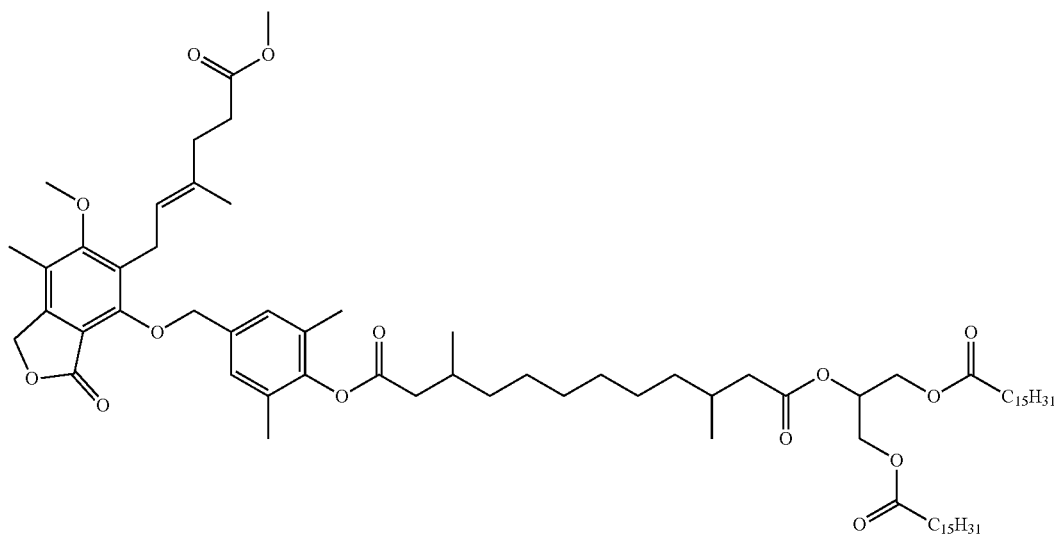
I-78
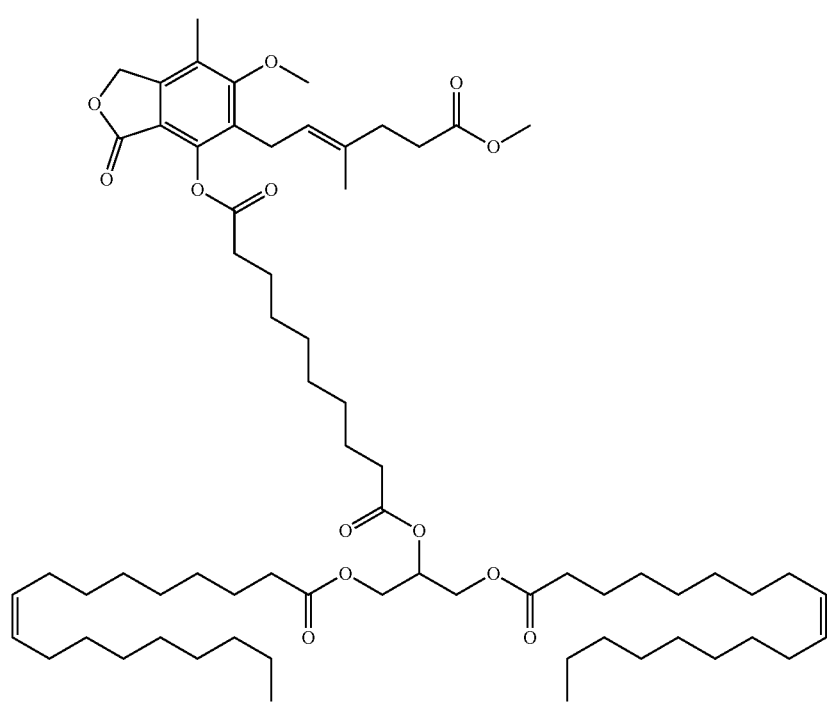

I-79
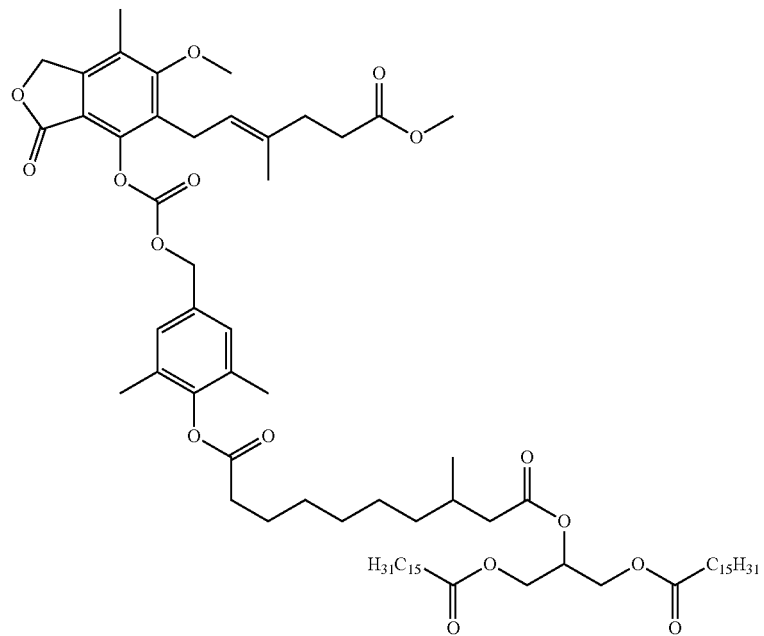
I-80
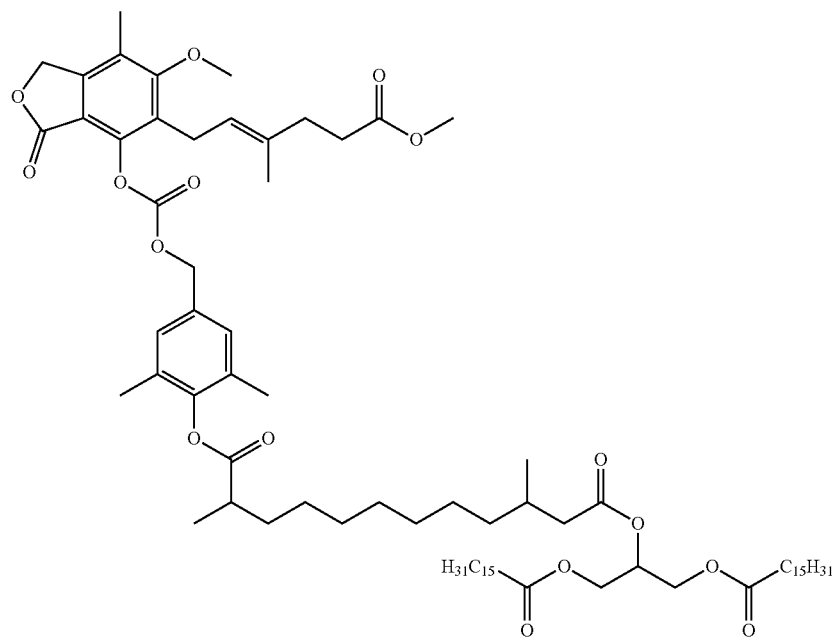

-continued
I-81
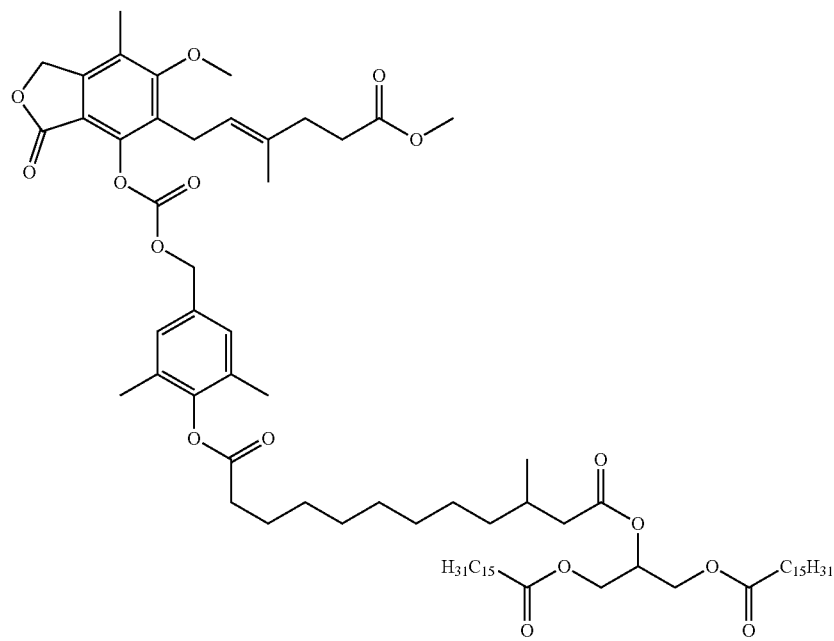
I-82
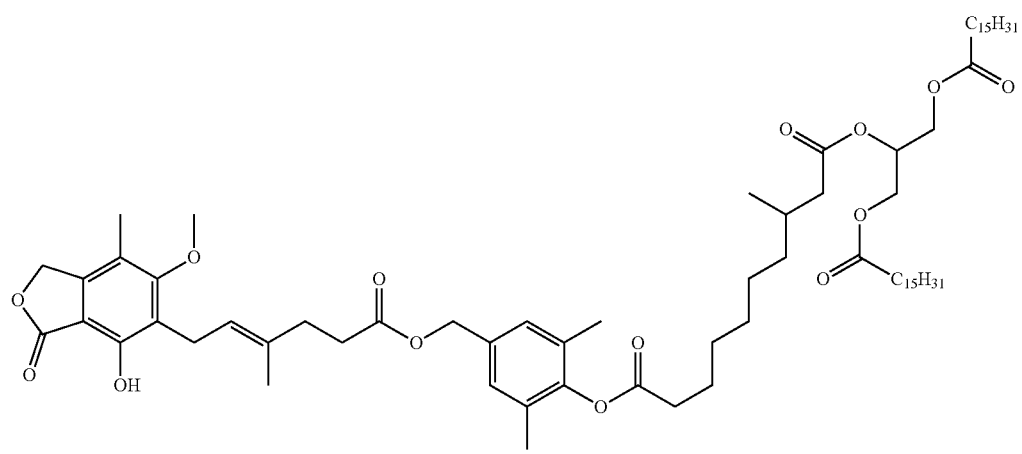
I-83
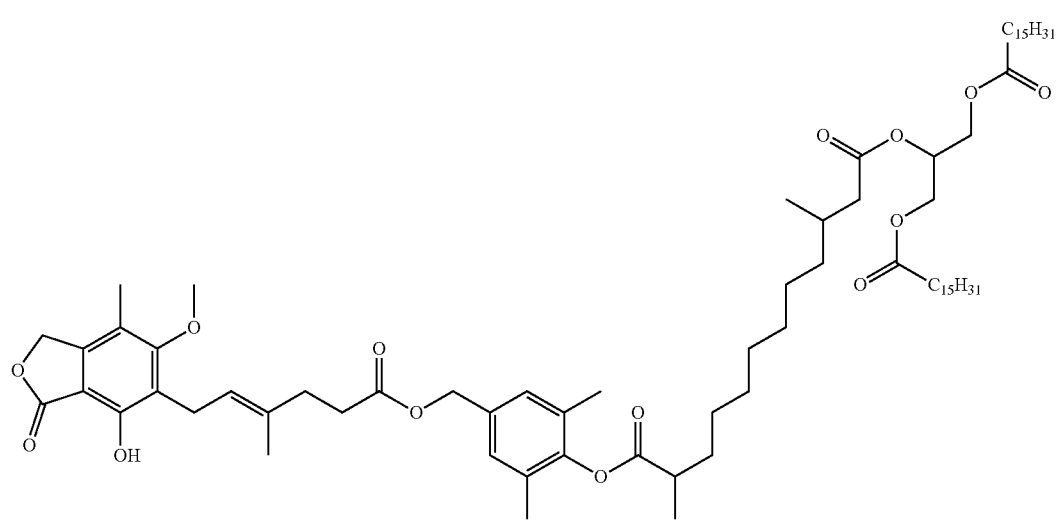

I-84

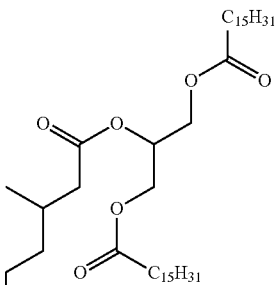
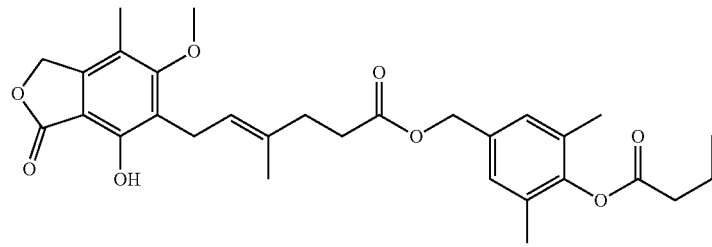

or a pharmaceutically acceptable salt thereof.

17. A pharmaceutically acceptable composition comprising a compound according to claim 1, and a pharmaceutically acceptable excipient, carrier, adjuvant, or vehicle.

18. A method of treating an autoimmune disease, disorder, or condition in a patient in need thereof, comprising administering to the patient an effective amount of a compound according to claim 1, or a pharmaceutically acceptable salt thereof.

19. A method of treating or preventing organ transplant rejection, graft-versus-host disease, or implant rejection in a patient in need thereof, comprising administering to the patient an effective amount of a compound according to claim 1, or a pharmaceutically acceptable salt thereof.

20. A method of treating a disease, disorder, or condition in a patient in need thereof, comprising administering to the patient an effective amount of a compound according to claim 1, or a pharmaceutically acceptable salt thereof, wherein the disease, disorder, or condition is selected from retroperitoneal fibrosis, idiopathic thrombocytopenic purpura (ITP), scleroderma (systemic sclerosis or SSc), pemphigus vulgaris, granulomatosis with polyangiitis, refractory incomplete systemic lupus erythematosus, inflammatory disease, Abdominal cavity inflammation, Peritonitis, Mesenteritis, Perihepatitis, Salpingoperitonitis, Autoinflammatory disease, Cryopyrin associated periodic syndrome, CINCA syndrome, Familial cold autoinflammatory syndrome, Muckle Wells syndrome, Cardiovascular inflammation, Carditis, Endocarditis, Bacterial endocarditis, Infectious endocarditis, Non infectious endocarditis, Thromboendocarditis, Pericarditis, Chylopericarditis, Dressler syndrome, Pleuropericarditis, Vasculitis, Arteritis, Aortitis, Takayasus arteritis, Endarteritis, HIV associated arteritis, Kawasaki disease, Periarteritis, Polyarteritis nodosa, Temporal arteritis, Extracranial temporal arteritis, Intracranial temporal arteritis, Churg- Strauss syndrome, Cutaneous vasculitis, Perivasculitis, Phlebitis, Lymphangiophlebitis, Thrombophlebitis, Mondor disease, Thromboangiitis, Thromboangiitis obliterans, Thrombophlebitis, Dermatitis, Acrodermatitis, Angiodermatitis, Drug eruption, Erythema multiforme, Serum sickness, Stevens Johnson syndrome, Toxic epidermal necrolysis, Intertrigo, Skin allergy, Atopic dermatitis, Contact dermatitis, Eczema, Fibrosis, Cicatrix, Tissue adhesions, Pulmonary fibrosis, Idiopathic pulmonary fibrosis, Renal fibrosis, Gastrointestinal inflammation, Anusitis, Biliary tract inflammation, Hepatocholangitis, Cholecystitis, Esophagitis, Eosinophilic esophagitis, Gastritis, Gastroduodenitis, Gastroenteritis, Hypertrophic gastritis, Hepatitis, Enterohepatitis, Hepatitis virus infection, Hepatitis A virus infection, Hepatitis B virus infection, Hepatitis C virus infection, Hepatitis D virus infection, Hepatitis E virus infection, Hepatitis F virus infection, Hepatitis G virus infection, Hepatocholangitis, Non-viral hepatitis, Alcoholic hepatitis, Autoimmune hepatitis, Perihepatitis, Steatohepatitis, Non-alcoholic steatohepatitis, Inflammatory bowel disease, Colitis, Diverticulitis, Meckel's diverticulitis, Enterocolitis, Acute enterocolitis, Necrotizing enterocolitis, Ileocecitis, Pseudomembranous colitis, Sigmoiditis, Rectosigmoiditis, Ulcerative colitis, Crohns disease, Enteritis, Enterocolitis, Acute enterocolitis, Necrotizing enterocolitis, Enterohepatitis, Hemorrhagic enteritis, Ileitis, Ileocecitis, Pouchitis, Jejunitis, Mucositis, Pancreatitis, Balser necrosis, Necrotizing acute pancreatitis, Peritonitis, Mesenteritis, Perihepatitis, Salpingoperitonitis, Proctitis, Rectosigmoiditis, Ulcerative proctitis, Genitourinary tract inflammation, Genital tract inflammation, Female genital tract inflammation, Endometriosis, Parametritis, Pelvic inflammatory disease, Salpingitis, Vaginitis, Atrophic vaginitis, Bartholinitis, Vulvovaginitis, Vulvitis, Vulvovaginitis, Male genital tract inflammation, Balanitis, Epididymitis, Epididymo-orchitis, Orchitis, Epididymo-orchitis, Periorchitis, Prostatitis, Urinary tract inflammation, Nephritis, Alport syndrome, Glomerulonephritis, Focal segmental glomerulosclerosis, IgA nephropathy, Membranoproliferative glomerulonephritis, Membranous glomerulonephritis, Wegener granulomatosis, Lupus nephritis, Pyelitis, Pyelocystitis, Pyelonephritis, Granulomatosis, Allergic granulomatosis, Sarcoidosis, Mastitis, Mouth inflammation, Gingivitis, Pericoronitis, Pharyngitis, Rhinopharyngitis, Sialadenitis, Musculoskeletal system inflammation, Arthritis, Behcets disease, Chondrocalcinosis, Gout, Infectious arthritis, Osteoarthritis, Periarthritis, Psoriatic arthritis, Reiter syndrome, Rheumatoid arthritis, Adult onset Stills disease, Felty syndrome, Juvenile rheumatoid arthritis, Bursitis, Dactylitis, Myositis, Dermatomyositis, Inclusion body myositis, Hereditary inclusion body myositis, Sporadic inclusion body myositis, Polymyositis, Pyomyositis, Nervous system inflammation, Meningitis, Arachnoiditis, Aseptic meningitis, Infectious meningitis, Bacterial meningitis, *Neisseria meningitidis* meningitis, Fungal meningitis, *Cryptococcus neoformans* meningitis, Parasitic meningitis, Viral meningitis, Neoplastic meningitis, Pachymeningitis, Neuritis, Neuromyelitis optica, Poliovirus infection, Postpoliomyelitis syndrome, Ocular and orbital inflammation, Ocular inflammation, Chorioretinitis, Conjunctivitis, Allergic conjunctivitis, Blepharoconjunctivitis, Keratoconjunctivitis, Infectious keratoconjunctivitis, Ophthalmia neonatorum, Trachoma, Uveitis, Intermediate uveitis, Pars planitis, Orbital inflammatory disease, Idiopathic orbital inflammation, Respiratory tract inflammation, Lower respiratory tract inflammation, Bronchitis, Lung inflammation, Asthma, Asthma attack, Exercise induced asthma, Nocturnal asthma, Occupational asthma, Status asthmaticus, Pleurisy, Upper respiratory tract inflammation, Pharyngitis, Rhinopharyngitis, Rhinitis, Allergic rhinitis, Perennial allergic rhinitis, Seasonal allergic rhinitis, Rhinopharyngitis, Sinusitis, Acute sinusitis, Chronic sinusitis, Ethmoiditis, Kartagener syndrome, Pansinusitis, Serositis, Familial mediterranean fever, Systemic inflammatory response syndrome, Immune disorder, Allergy, Delayed hypersensitivity, Contact dermatitis, Hypersensitivity, Immediate hypersensitivity, Food hypersensitivity, Egg hypersensitivity, Milk hypersensitivity, Oral allergy syndrome, Peanut hypersensitivity, Wheat hypersensitivity, Fungal allergy, Immune complex disease, Arthus reaction, Immediate type hypersensitivity, Respiratory tract allergy, Allergic rhinitis, Perennial allergic rhinitis, Seasonal allergic rhinitis, Asthma, Asthma attack, Exercise induced asthma, Nocturnal asthma, Occupational asthma, Status asthmaticus, Skin allergy, Contact dermatitis, eczema, autoimmune disease, antiphospholipid syndrome, Autoimmune hemolytic anemia, aplastic anemia, cold agglutinin disease, autoimmune hepatitis, autoimmune nervous system disease, autoimmune demyelinating nervous system disease, Stiff person syndrome, Lambert-Eaton syndrome, Behcet's disease, Crohn's disease, Cutaneous lupus erythematosus, Discoid lupus erythematosus, Evans syndrome, Goodpasture syndrome, Graves' disease, Guillain-Barre syndrome, Hashimoto's disease, Henoch Schonlein purpura, lupus nephritis, multiple sclerosis (MS), myasthenia gravis, paroxysmal nocturnal hemoglobinuria, primary biliary cirrhosis, painful bladder syndrome, psoriasis, Parapsoriasis, Psoriatic arthritis, rheumatoid arthritis, Adult onset Stills disease, Felty syndrome, Juvenile rheumatoid arthritis, Sjogren's syndrome, systemic lupus erythematosus (SLE), Temporal arteritis, Extracranial temporal arteritis, Intracranial temporal arteritis, ulcerative colitis, Vitiligo, Non segmental vitiligo, Segmental vitiligo, graft-versus-host disease, Transplant rejection, Bone marrow transplant rejection, Cell transplant rejection, Corneal transplant rejection, Heart transplant rejection, Kidney transplant rejection, Liver transplant rejection, Lung transplant rejection, organ transplant rejection, intestine transplantation, large intestine transplantation, small intestine transplantation, pancreas transplant rejection, islet cell transplant rejection, skin transplant rejection, tissue transplant rejection, immune deficiency, Agammaglobulinemia, Brutons disease, combined immunodeficiency, HIV, acquired immune deficiency syndrome (AIDS), AIDS related complex, Nezelof syndrome, severe combined immunodeficiency syndrome, adenosine deaminase deficiency, common variable immunodeficiency, DiGeorge syndrome, dysgammaglobulinemia, Immunoglobulin A deficiency, Immunoglobulin G deficiency, phagocyte bactericidal disorder, Chediak Higashi syndrome, chronic granulomatous disease, Job syndrome, Wiskott-Aldrich syndrome, immunoadsorption, lymphatic system disease, adenoid disease, adenoid hypertrophy, adenoid tumor, adenoiditis, lymphadenopathy, Kawasaki disease, lymphadenitis, lymphangiophlebitis, lymphangitis, lymphatic system tumor, Castleman's disease, lymphangioma, cystic hygroma, lymphangiomyoma, interstitial cystitis, a neuromyelitis optica spectrum disorder, juvenile neuronal ceroid lipofuscinosis, autoimmune bullous dermatose, nephrotic syndrome, idiopathic membranous nephropathy, congenital urological abnormality, chronic inflammatory demyelinating polyradiculopathy, immune thrombocytopenia, microscopic polyangiitis, MPO-ANCA vasculitis, Takayasu arteritis, hyperkalemia, Bronchiolitis Obliterans, polycystic liver disease, polyomavirus infection, amyotrophic lateral sclerosis (ALS), familial lipoprotein lipase deficiency, Hurler Syndrome, Fanconi Anemia, Glanzmann Thrombasthenia, severe congenital neutropenia, leukocyte adhesion deficiency, Shwachman-Diamond Syndrome, Diamond-Blackfan Anemia, Dyskeratosis-congenita, Chediak-Higashi Syndrome, histiocytosis, DOCK8 deficiency, uremia, Epidermolysis Bullosa, Amegakaryocytic Thrombocytopenia, Kostmann Syndrome, Lysosomal Storage Disease, Peroxisomal Disorder, mastocytosis, or Henoch-Schoenlein Purpura Nephritis.

\* \* \* \* \*